US008501194B2

(12) United States Patent
Spector et al.

(10) Patent No.: US 8,501,194 B2
(45) Date of Patent: Aug. 6, 2013

(54) VACCINE FOR VIRUSES THAT CAUSE PERSISTENT OR LATENT INFECTIONS

(75) Inventors: Deborah H. Spector, La Jolla, CA (US); Christopher S. Morello, Carlsbad, CA (US)

(73) Assignee: The Regents of the University of California, Oakland, CA (US)

( * ) Notice: Subject to any disclaimer, the term of this patent is extended or adjusted under 35 U.S.C. 154(b) by 615 days.

(21) Appl. No.: 12/282,123

(22) PCT Filed: Mar. 9, 2007

(86) PCT No.: PCT/US2007/006113
§ 371 (c)(1),
(2), (4) Date: Jul. 8, 2010

(87) PCT Pub. No.: WO2007/106404
PCT Pub. Date: Sep. 20, 2007

(65) Prior Publication Data
US 2010/0272752 A1    Oct. 28, 2010

Related U.S. Application Data

(60) Provisional application No. 60/781,123, filed on Mar. 10, 2006.

(51) Int. Cl.
*A61K 39/25* (2006.01)
*A61K 39/245* (2006.01)
*A61K 39/00* (2006.01)
*A61K 39/12* (2006.01)
*C07H 21/04* (2006.01)

(52) U.S. Cl.
USPC ...................................................... 424/230.1

(58) Field of Classification Search
None
See application file for complete search history.

(56) References Cited

PUBLICATIONS

Gallo RC. The end or the beginning of the drive to an HIV-perspective vaccine: a view from over 20 years. Lancet 2005, vol. 366, pp. 1894-1898.*
Levine AJ. Why do we not yet have a Human Immunodeficiency Virus Vaccine? Journal of Virology 2008, vol. 82, No. 24, pp. 11998-12000.*
Connick et al. CTL fail to accumulate at sites of HIV-1 replication in lymphoid tissue. Journal of Immunology 2007, vol. 178, pp. 6975-6983.*
Walker et al. Toward an AIDS Vaccine. Science 2008, vol. 320, pp. 760-764.*
Ou-Yang et al. Co-delivery of GM-CSF gene enhances the immune responses of Hepatitis C viral core protein-expressing DNA vaccine. Journal of Medical Virology 2002, vol. 66, pp. 320-328.*
Encke et al. Development of a heterologous, multigenotype vaccine against hepatitis C virus infection. European Journal of Clinical Investigation 2007, vol. 37, pp. 396-406.*
Bain et al. Effect of HCV viral dynamics on treatment design: lessons learned from HIV. The American Journal of Gastroenterology 2001, vol. 96, No. 10., pp. 2818-2828.*
Landolfo et al. The human cytomegalovirus. Pharmacology & Therapeutics 2003, vol. 98, p. 269-297.*
Adler, Stuart P. et al., "A canarypox vector expressing cytomegalovirus (CMV) glycoprotein B primes for antibody responses to a live attenuated CMV vaccine (Towne)", The Journal of Infectious Diseases 1999, 180: 843-6.
Aurelian, L. et al., "Vaccine potential of a herpes simplex virus type 2 mutant deleted in the PK domain of the large subunit of ribonucleotide reductase (ICP10)", Vaccine 1999, 17:1951-63.
Bourne, Nigel et al., "DNA immunization against experimental genital herpes simplex virus infection", JID, Apr. 1996, 173(4):800-7.
Bourne, Nigel et al., "Impact of immunization with glycoprotein D2/AS04 on herpes simplex virus type 2 shedding into the genital tract in guinea pigs that become infected", JID 2005, 192:2117-23.
Britt, William J. et al., "Human cytomegalovirus glycoproteins", Intervirology 39:401-412, 1996.
Dunn, Walter et al., "Functional profiling of a human cytomegalovirus genome", PNAS, Nov. 25, 2003, 100(24):14223-8.
Ebeling, Angelika et al., "Molecular cloning and physical mapping of murine cytomegalovirus DNA", Journal of Virology, Sep. 1983, 47(3):421-33.
Elkington, Rebecca et al., "Ex vivo profiling of CD8+-T-cell responses to human cytomegalovirus reveals broad and multispecific reactivities in healthy virus carriers", J. Virol., May 2003, 77(9):5226-40.
Endresz, Valeria et al., "Induction of human cytomegalovirus (HCMV)-glycoprotein B (gB)-specific neutralizing antibody and phosphoprotein 65 (pp65)-specific sytotoxic T lymphocyte responses by naked DNA immunization", Vaccine 1999, 17:50-8.
Eo, Seong Kug et al., "Prime-boost immunization with DNA vaccine: mucosal route of administration changes the rules", Journal of Immunology, 2001, 166:5473-9.
Haynes, Joel R. "Potent protective cellular immune responses generated by a DNA vaccine encoding HSV-2 ICP27 and the E. coli heat labile enterotoxin", Vaccine, 2006, 24:5016-26.
Koelle, David M. "CD8 CTL from genital herpes simplex lesions: recognition of viral tegument and immediate early proteins and lysis of infected cutaneous cells", Journal of Immunology, 2001, 166:4049-58.
Koelle, David M. et al. "Expression of cutaneous lymphocyte-associated antigen by CD8(+) T cells specific for a skin-tropic virus", J. Clin. Invest., Aug. 2002, 110(4):537-48.
Koelle, David M. et al., "Immunodominance among herpes simplex virus-specific CD8 T cells expressing a tissue-specific homing receptor", PNAS, Oct. 28, 2003, 100(22):1289-9904.
Manickan, Elanchezhiyan et al., "Vaccination with recombinant vaccinia viruses expressing ICP27 induces protective immunity against herpes simplex virus through CD4+ Th1+ T cells", Journal of Virology, Aug. 1995, 69(8):4711-6.

(Continued)

*Primary Examiner* — Louise Humphrey
(74) *Attorney, Agent, or Firm* — Kilpatrick Townsend & Stockton LLP

(57) ABSTRACT

The invention is in general directed to methods and compositions for preventing or treating infections by viruses involved in persistent and/or latent infections. The methods and compositions are directed toward the prevention and treatment of infections caused by viruses such as, for example, herpesviruses, retroviruses, hepatitis viruses, and papillomaviruses, including, for example, cytomegalovirus.

6 Claims, 49 Drawing Sheets

PUBLICATIONS

Manley, Thomas J. "Immune evasion proteins of human cytomegalovirus do not prevent a diverse CD8+ cytotoxic T-cell response in natural infection", Blood, Aug. 15, 2004, 104(4):1075-82.

Marshall, Beth C. et al., "Avidity maturation following immunization with two human cytomegalovirus (CMV) vaccines: a live attenuated vaccine (Towne) and a recombinant glycoprotein vaccine (gB/MF59)", Viral Immunology, 2003, 16(4):491-500.

McClements, William L. et al., "Immunization with DNA vaccines encoding glycoprotein D or glycoprotein B, alone or in combination, induces protective immunity in animal models of herpes simplex virus-2 disease", Proc. Natl. Acad. Sci. USA, Oct. 1996, 93:11414-20.

McClements, William L. et al., "The prophylactic effect of immunization with DNA encoding herpes simplex virus glycoproteins on HSV-induced disease in guinea pigs", Vaccine, 1997, 15(8):857-60.

McConkey, Samuel J. et al., "Enhanced T-cell immunogenicity of plasmid DNA vaccines boosted by recombinant modified vaccinia virus Ankara in humans", Nat. Med., Jun. 2003, 9(6):729-35.

McDermott, Mark R. et al., "Protection of mice against lethal challenge with herpes simplex virus by vaccination with an adenovirus vector expressing HSV glycoprotein B", Virology, 1989, 169:244-7.

Mercer, John A. et al., "Molecular cloning and restriction endonuclease mapping of the murine cytomegalovirus genome (Smith strain)", Virology, 1983, 129:94-106.

Meseda, Clement A. et al., "Prime-boost immunization with DNA and modified vaccinia virus ankara vectors expressing herpes simplex virus-2 glycoprotein D elicits greater specific antibody and cytokine responses than DNA vaccine alone", J. Infect. Dis., 2002, 186:1065-73.

Mester, Joseph C. et al., "Immunity induced by DNA immunization with herpes simplex virus type 2 glycoproteins B and C", Vaccine, 2000, 18:875-83.

Mikloska, Zorka et al., "Monophosphoryl lipid A and QS21 increase CD8 T lymphocyte cytotoxicity to herpes simplex virus-2 infected cell proteins 4 and 27 through IFN-gamma and IL-12 production", Journal of Immunology, 2000, 164:5167-76.

Morello, Christopher S. et al., "Development of a vaccine against murine cytomegalovirus (MCMV), consisting of plasmid DNA and formalin-inactivated MCMV, that provides long-term, complete protection against viral replication", Journal of Virology, 76(10):4822-35, 2002.

Morello, Christopher S. et al., "DNA immunization using highly conserved murine cytomegalovirus genes encoding homogols of human cytomegalovirus UL54 (DNA polymerase) and UL105 (Helicase) elicits strong CD8 T-cell responses and is protective against systemic challenge", Journal of Virology, Jul. 2007, 81(14):7766-75.

Morello, Christopher S. et al., "In vivo replication, latency, and immunogenicity of murine cytomegalovirus mutants with deletions in the M83 and M84 genes, the putative homologs of human cytomegalovirus pp65 (UL83)", Journal of Virology, Sep. 1999, 73(9):7678-93.

Morello, Christopher S. et al., "Suppression of murine cytomegalovirus (MCMV) replication with a DNA vaccine encoding the MCMV early nonstructural protein M84 (a homolog of human cytomegalovirus pp65)", Journal of Virology, Apr. 2000, 74:3696-3708.

Morello, Christopher S. et al., "Systemic priming-boosting immunization with a trivalent plasmid DNA and inactivated murine cytomegalovirus (MCMV) vaccine provides long-term protection against viral replication following systemic or mucosal MCMV challenge", Journal of Virology, Jan. 2005, 79(1):159-75.

Munks, Michael W. et al., "Genome-wide analysis reveals a highly diverse CD8 T cell response to murine cytomegalovirus", Journal of Immunology, 2006, 176:3760-6.

Natuk, Robert J. et al., "Recombinant vesicular stomatitis virus vectors expressing herpes simplex virus type 2 gD elicit robust CD4+ Th1 immune responses and are protective in mouse and guinea pig models of vaginal challenge", Journal of Virology, May 2006, 80(9):4447-57.

Pari, Gregory S. et al., "Eleven loci encoding trans-acting factors are required for transient complementation of human cytomegalovirus oriLyt-dependent DNA replication", Journal of Virology, Dec. 1993, 67(12):6979-88.

Prichard, Mark N. et al., "Evaluation of AD472, a live attenuated recombinant herpes simplex virus type 2 vaccine in guinea pigs", Vaccine, 2005, 23:5424-31.

Rawlinson, William D. et al., "Analysis of the complete DNA sequence of murine cytomegalovirus", Journal of Virology, Dec. 1996, 70(10):8833-49.

Scalzo, Anthony A. et al., "Genetic mapping of Cmv1 in the region of mouse chromosome 6 encoding the NK gene complex-associated loci Ly49 and musNKR-P1", Genomics, 1995, 27:435-41.

Strasser, J. E. et al., "Herpes simplex virus DNA vaccine efficacy: effect of glycoprotein D plasmid constructs", JID, 2000, 182:1304-10.

Sylwester, Andrew W. et al., "Broadly targeted human cytomegalovirus-specific CD4+ and CD8+ T cells dominate the memory compartments of exposed subjects", JEM, Sep. 6, 2005, 202(5):673-85.

Tigges, Michael A. et al., "Human CD8+ herpes simplex virus-specific cytotoxic T-lymphocyte clones recognize diverse virion protein antigens", Journal of Virology, Mar. 1992, 66:1622-34.

Tigges, Michael A. et al., "Human herpes simplex virus (HSV)-specific CD8+ CTL clones recognize HSV-2-infected fibroblasts after treatment with IFN-gamma or when virion host shutoff functions are disabled", Journal of Immunology, 1996, 156:3901-10.

Wang, Zhongde et al., "Recombinant modified vaccinia virus Ankara expressing a soluble form of glycoprotein B causes durable immunity and neutralizing antibodies against multiple strains of human cytomegalovirus", Journal of Virology, Apr. 2004, 78(8):3965-76.

Ye, Ming et al., "Multiple epitopes in the murine cytomegalovirus early gene product M84 are efficiently presented in infected primary macrophages and contribute to strong CD8+-T-lymphocyte responses and protection following DNA immunization", Journal of Virology, Oct. 2004, 78(20):11233-45.

Ye, Ming et al., "Strong CD8 T-cell responses following coimmunization with plasmids expressing the dominant pp89 and subdominant M84 antigens of murine cytomegalovirus correlate with long-term protection against subsequent viral challenge", Journal of Virology, Mar. 2002, 76(5):2100-12.

Yu, Dong et al., "Functional map of human cytomegalovirus AD169 defined by global mutational analysis", PNAS, Oct. 14, 2003, 100(21):12396-401.

Zaia, John A. et al., "Infrequent occurrence of natural mutations in the pp65(495-503) epitope sequence presented by the HLA A*0201 allele among human cytomegalovirus isolates", Journal of Virology, Mar. 2001, 75(5):2472-74.

International Search Report for International Application No. PCT/US2007/006113 dated Jan. 23, 2008, 1 page.

Supplementary European Search Report for EP Application No. EP07752789 dated Mar. 31, 2010, 2 pages.

* cited by examiner

FIG. 8A

```
SEQ         HCMV UL44
KEYWORD     PROTEIN
SEQ ID NO:  1

1    MDRKTRLSEP PTLALRLKPY KTAIQQLRSV IRALKEQTTV TFLPTPSLIL QTVRSHCVSK
 61    ITFWSSCLYI TKSFQFETI NNSTPLLGNF MYLTSGKDLT KFYVQDISQL SAKISHCAPD
121    PNMRFSSACV HGQDIVRESE NSAVEVDLDF GVVRDLLRWI GFRTRVKRNV RKAPCPTGTV
181    QILVRAGPPR IKFILTNGER LEFTANRVS FHGVKMMRIN VQLKNFYQTL LNCAVTKLPC
241    TIRIVTRSDT LLIYASPNGL FAVENFLTES PQKGSFFQK NYVGNSCKSR GGGGGGGSLS
301    SLARAGGLRD DGFGLDNDLM NFRGLGLG GGGGGGGKKH URGSGSGGT KRMSSGLGGG
361    DRDRGLSSKS KYSQSRKITSY LTSKQGSGGG QRGGGGGLQR NSSNYPNDAK RSNDSEQSVT
421    FSFVPNTKRQ KCG

KEYWORD     DNA  (NC_001347 REGION: 56142..57443)
SEQ ID NO:  2

1   ctagcgcaac tttgcatct tggtgttagg gacgaactcg aacgttacag aatcctcgct
   61   gtagctctcc tcttcgcgt cgttgaagta attgcggag ttgcgatcca aacgcagca
  121   tcctcctcct acgacgcga ccgatcgac tttggacgtc agtagctgc tgatcttgtg
  181   ctgctgtat ttttccttgg aggaaagacc gtggtcgtga tcacgccgc cgcacgatg
  241   gctcattttc tcgctacgg aaccaccgcc gacacgcgg tcgtgcttct tgccgccacc
  301   gccgccacct ctccagac gccgagacc catggcctcg ttcatgagat cgttatccag
  361   acccgggcg tgtcatgca gacgcagga attggccaga gaagagggc tccgccacc
  421   accgggtcg ccagcgact tgcagctgtt ccgacgtaa ttttgttga agggatcgaa
  481   acgctggaaa ggttcctcgg tgagaaaatt ctccacggcg aacagaccgt tgccgctggc
  541   cacgtacaac agcgtgtcgt gctccgtaac tatacgcaac gtgcacggca gtttggtgac
  601   ggccaattg agcagcgtct ggtagaagtt cttcagctgc acgtgatac gcatgttttt
  661   cacgccgtgg aaactgacga ggttattgg tgtgaattcc agtcgctgc cgttggtcag
  721   gatcaactg atggccggtg gaccgcgcgtg caccagaatc tgccagaatgc cgtagggcc
  781   gggcgttttt ttcaagttac gcttgacgcg ggtatgcgcc ccgatccact taagcaggtc
  841   ggccaccacg ccgaaatcta gatccacgtc caccgccgaa ttctcgcttt cgcgcacaat
  901   gcttggccg tgcacgcagg ccgagctgaa ctccatattg aaatagggcg cgcacatgga
  961   gatcttggcc gacaggtccg agatgtcctc caacgtagaac ttgtcaggt ccttgctgga
 1021   agtcaggtac atgaaattac ccagcagcgc cgtggaattg ttaatgctt ttgggctgaaa
 1081   cgacttgtca gtgatgtaga ggcatgagtc gttaaagtg attttgaca cgcagtgact
 1141   ggtaccgtt tgcaagataa gcgacggcgt gggcaagaag gtaacgtgg tgttctctt
 1201   gagcgcacgg atccagatc gcagctgctg gatagccgtc ttgtacggct tcagcgcag
 1261   cgcagcgtc ggggctccg agagcgcgt cttgcgatcc at

SEQ         HCMV UL50
KEYWORD     PROTEIN
SEQ ID NO:  3

1    MEMDRVLSQD LVQATPRILK LGFSELRVTD AGLICKNPNY SVCDAMLKTD TYYCVEILLS
 61    YWESPIDVP CYIFNNTGLA VSLCCFVERAP VKLVSPARHV GEFNVLKVNS SLIVTLKDIE
121    EIKPSAYGVL TKCVVRKSNS ASVENIELIA YGFBNSGRIK WLLRELYARK ARSTSLAVRS
181    SVTVSSHSGS GPSINRARMS AALTRTACKE SSRTASPPFP PRKPSCSPTS VAAGGRAAGP
241    RPPPPPRAAG SWRLCRCSRC WGRCCCASEG CADESEEELL ALAGECRAAA AAAGQDVGGS
301    ASRPLSEBVS RPRGVSTRER RPPSPPCAPS LERTGYRWAP SSWWRARSCP SRPQSGFWLP
361    ARPATLGFLV LALLLVLALL WRGHGQSSSP TRSARRD

KEYWORD     DNA  (NC_001347 REGION: 73000..74193)
SEQ ID NO:  4

1   tcagtcgcgg tgtgcgggagc gtgtcggaga cgacgactgg ccatgacgc ggccacagcag
   61   agcagcacc agcagaagag ccgcaccacg cggccagagc gtgcaagcg agcgggcag
  121   ccaggccccca gactgcggtc gcgatggcc ggagcgcgt cgccaccac atgacggtgc
  181   ccaagataa ccagtccgct ccaaggacgg cgcgacgga ggagacggcg gatgacggtg
```

FIG. 8B

```
 241 atgggtcgac accoctcgcc gacgactcac gtgctcctcc agaggccgac gcgggaccc
 301 tccgacgtcc tggcccgcg ctgccgctgc cgccttcct tctccggca gagccagcaa
 361 ctcctcctcc tcttcctcag cgtctcctc gcttgagcat ccgcatcgtc ccatacaggc
 421 ctcacaacga cacagccgcc acgacccgac cgccatgggt ggtggtggcg gtcgaggccc
 481 ggcagccgcc ccgccagcgg cgaccatggt gggagagcaa ctcggatgac gaggaggagg
 541 aggggagat ggggtccgag aggaccgctt tccgacgtt cgcgtaagcg cggccgacat
 601 gcgggcgcgc cacagggacg gaccgctgcc gctgtgactg cttacggtga cgtggttccg
 661 gaccgccaac gacgtcgacg cggcttcctt ggcgtacagc tcgcgcagca gattctcgta
 721 ctcgccctcg ttttcgggtc agaggcgat gagctcgatg ttgaagccg acgccgaatt
 781 ggattgcgc accacgcact tgtcagcac tcgctaggcc gagggcttga tctcctcgat
 841 gtccttgaga gtgacgacga gcgactcgtt cgacccgagc acattgaact caccctacgtg
 901 gcgccgccgc gaaacgagct tgaccgcgac tcgtacaaaa cagcagaggg agacggcgca
 961 gccagtgttt ttaaagatac aacaaggcac gtggtcgtg cggctctcc agtagctgag
1021 tcgataactcg acacaataga ccgtgtctgt cttgagcatg gcgtcgcaca ccgagtaatt
1081 ggggttttta cagatgaggc cggcatcggt gacgcgcagc tcgtcggac ccaacttgag
1141 gatccgccgc gtggcctgca ccagatcctg atggagaacc ttgttcatct caat
```

```
SEQ         HCMV UL51
KEYWORD     PROTEIN
SEQ ID NO:  5
  1    MSWAKQRVPF LDDDGREEE DVQDDVDSPV PTRPLVLDED AEPAAGTSGG LEGGGGDDED
 61    GEDGRALPDL DDDLLLQFEF MLPRVYDLLL PSLDARLSFV NAGQKYEAFL KYVHGOCATC
121    SHGEILREKT QLLTAIVSHL MDINGILEGK OESAPGK
```

```
KEYWORD     DNA (NC_001347 REGION: 74215..74688)
SEQ ID NO:  6

1 ttattttccc ggcgccgact cgtcttttcc ctccaggatt ccgttaatgt ccatgagctt
 61 gctgacgatc gccgttaata gttcgtcttc ctcaggagg atctctccgt gactgcaggt
121 ccgccagtcg ccgtcgcaagt acttgaggaa ggcggcgtac ttccgacccg cgttcacgac
181 atttaagcga gcgtccagag agggcagcaa cagatcgtag acgccggca gcatcggtc
241 gaactgtaat acagatcgt cgtccagatc gggtagccgc cgtccgcctt caccgtcctc
301 gtcgtcacca cctccccct cgagccgacc gctcgtacca gccgcgggct ccgcgtcctc
361 gtcgatcacc agggctcgcg tcgcacggg agaatccacg tcatcctgca gtcgtttctc
421 ctcctctccg tcgtcatcgt ccagaaacgg caccgctgc ttagccagg acat
```

```
SEQ         HCMV UL52
KEYWORD     PROTEIN
SEQ ID NO:  7
  1    MNPSTHVSSN GPTTPSHGFR TTFLPPTSPA PSTSSVAART LCSPQRQRVS RYSGWSTSYT
 61    QNRSDLTTEL LWHAHPRQVP MDEALAAAAA RSYQVNPQRP ANRVRHYEPQ TLSLGTSEVD
121    ELLNCCASET TCGGTQSTVL TRAFSTTSCG GAVAGSSNVG PAGASAACDL DRELAGLETS
181    AADFEQLARL CAPLAIDTRC NLCAIISICL KQDCDQSRLL EYSLLCFKCS YAPPAALSTL
241    IIMSEFTHLL QQRFSDLAID DLFRERVLTV FDPHLRFFIN RCFBKQVGDA VDSENVTLNM
301    LAVVRAMVMG EDTVPYSKPR RHPQQKQRNN PYRVEVPQEL IDNFLEHSSP SKDRFVQLLF
361    YMWAGTGVMS TTPLTELTHT KFARLGALST ASERECARNM IEEESEDEEG EKGGSDDPGRH
421    NGGGTSGGPS ESTLKKNVGP IYLCPVPRPF TKNQPSTVCL LCELMACSYY DNVVLARLYR
481    RVVSYCQNNV MVDRIQLWL ADLLRECTSF LGAAMEDVAR CGLEAPTSPS GDSDYNGLEG
541    VDGALAPPDP VFCRVLRQAG VTGIYRHFFC DPQCAGNIRV TNEAVLFGRL HPHNVQEVKL
601    AICRDNYYIS RLFGRVRLCI TLFKAPQITK RTYRGKVHLA PFMRDFTQLL ESCDIKLVDP
661    TYVISKYV
```

```
KEYWORD     DNA (NC_001347 REGION: 74727..76733)
SEQ ID NO:  8

1 atgaatccga gtacccacgt gagcagtaac ggccaacga ctccctca gggaccac
 61 accacgtttc ttcccgac cagccggcc ccgtcaaca gtcgtcga cgagtacc
121 tgtgaagtc cgcaaagaca ggcgttcg cgttacagcg cctggagcac cgagtacacc
181 cagtggcct cggactgac aactgagctg ctatggcac gccaccgcg tcaagtacct
241 atggacgaag cgctggccgc cgcggcggcc gcctcatacc aggtaaatcc tcaacacccc
301 gccaacgtt accgtcatta cgaattccag accgctcagcc tggcacctc cgaggtagac
```

FIG. 8C

```
 361 gaactgctca actgttgtgc ggaagaaacc acgtgcggcg gcacgcaatc cacegtacte
 421 accatgcga ccaacaccac tagctgcggc ggagccgtcg ccggcagtag caacgtagga
 481 ccggccgggg cttcggccgc ctgcgaccta gatgcagaac tgccggcct cgaaacctga
 541 gggccgact ttgaccaact gggcgactg tgccgcgcga tggccatcga cacgcgctgt
 601 aacctatgcg ccatcatcag catctgcctc aaacaggact ggaccagag ctggctcctc
 661 gagtacagct tgctgtgctt caaatgcagt tacgagccca gtgcgcgct caggacgctc
 721 atcatcatgt ccgagtttac gcatctgctg cagcagcact tttccgatcc gcgcatcgac
 781 gacctgcttc gacaccagt tctcacggtc ttcgatttcc aactgcactt tttcatcaat
 841 cgttgcttg aaaaacaagt gggagacgg gttgataacg cggatgtcac actgaaccat
 901 ctggcgtgg tcgggccat ggtcatgggt gaagacacgg tgccttacaa caagcctagg
 961 cgccaccgc aacagaagca aaaaaacaac cctatcacg tgaagtgcc gcaagaactg
1021 atgcaact tctagaaca cagctcacct agccgcgacc gttcgtgca gctgcttcc
1081 tatatgtggg acggaacgg cgtcatgagc accacgccac tcacggaact cacgcacact
1141 aagttcgcgc gactagacgc gttatccacg gcctcggaaa gagaagacgc aagatgatg
1201 atgaaagag aggaggatga agaaggagga gaaaaaggag gagacgatcc gggccgtcac
1261 aacggcggtg gcaccagcgg gggggttcagc gagcgcacgc taaaaaaaaa cgtgggtccc
1321 attacctat gtccgtacc cgcttttttt accaagaacc aaaccagtac cgtgtgtctg
1381 ctgtgcgaac tcatggcctg ctcctattac gataagtcg tcctgcgcga gctgtaccga
1441 cgcgtgtct cgtattgtca gaacaatgtg aagatggtgg accgcattca gctggtattg
1501 gccgatctgt tgccgaatg cacgtcgccg ctcgcgccg cacacggaga cgtggccgga
1561 tgtggactgg aagcaccac ctcgccgga ggcgactcgg actaccacgg cctgagcgg
1621 gtcgacggcg cactggcgcg accgaccccg gtatttgcc actactgcg ttaggcagga
1681 gtcacggca tctacaagca cttttctcgc gaccgcagt gcgcggcaa catccgcgtc
1741 accaacgagg acgtgctctt cggacgcctg cacccacc agtcagga ggtgaaactg
1801 gtcacctgtc acgacaatta atatataagt cgactccgc gacgtgtgtg gctttgcatc
1861 acactcttca aggcctttca gattacaaaa cgcaccaca aaggcaaagt gcacctggcg
1921 gacttatgc gcgatttcac gcagctgttg gagagttgcg acatcaagct ggtggaccc
1981 acgtacgtga tagacaagta tgtctag
```

SEQ     HCMV UL53  
KEYWORD PROTEIN  
SEQ ID NO: 9

```
  1 MSSVSGVRTP RERRSALRSL LRKRRQRELA SEVASTVRGA TSRENECEFF SPADARPRLT
 61 LHDLHDIPRE SPELELKYLN MRKMAITGKS SICLFFNEHS HRQNTCLCIS PYSMEQVSRI
121 ACTSCEDWRI LPTASGRMVA FINQTSNIMK NENFVSPCR SSELDKLSTN QPFIFQIYYL
181 LRARNHDIVP EMHAEDGRLR MRVIPENPDV RIPCQCITQM LTAAREDISV TLNIVRDHVV
241 ISVLCHAVSA SSVKIGVTIL QSKIDEMDIP NDVSESFERY KELIQELCQS SGRNLIEEAT
301 SSYAIRSPIT ASPLRVVSTN GCGFSESSQS TPPHLRPESQ ATQFHRYSRH QSQSQQHHRR
361 PQSPPPPLPL NSTRAP
```

KEYWORD DNA (NC_001347 REGION: 76726..77856)  
SEQ ID NO: 10

```
   1 atgtctagcg tgagcggcgt gcgcacgccg cgcgaacgac gctcggcctt gcgctccctg
  61 ctccgcaagc gccgccaacg gcgcgaactg gcgagctgcg agcgaagtgg cgtcgacggt
 121 acgtcggcca acaaccacgg cgaacagcg tgcaggcgca acgcgcgca gggcctcacg
 181 ctgcacgacc tgcacgacat cttccgcgag tcgccggaac tggagctcaa gtaccttaac
 241 atgatgaaga tggccatcac gggcaaagag tcatatgct tgccttcaa tttccactcg
 301 cacggcagc acacctgctt cgacatctcg ccgtacgga agagcaaagt ctgcgcatc
 361 gcctgctcc cgtcggaga caaccgcatc ctgccaacc acggcggcc catggtggcc
 421 ttcatcaatc agagtcaaa catcatgaaa aatgaaaact tttattaccg gttctgtaag
 481 agcagcgagc tactcaagct ctccacaac cagccgccca tcttccaaat ttattaccg
 541 ctgcacgccg ccaaccacga catcgtgccc tttatgcacg ccgaggacgg cggttgcac
 601 atgcacgtca tcttggaaaa cccgacgtg cacatccct ggactgcat cacgcagaty
 661 ctcacggcg cgcgcgaaga ctacagcgtc acgctcaaca tcgtgcgcga caacgtcgtt
 721 atcagcgtc tgtgtcacg cgtcgcggca agatcggca agatgggtac gactatttg
 781 caacgcaaga ttgacgagat ggacattcca acgacgtga gcgagtcctt tgagcgctac
 841 aaagagctga ttcaggagct gtgtcagtcc agggcaaca acctatacga ggaggcacg
 901 tgtctctacg cgatacggtc tcccttaacc gcgtagcgt tgacgtagt tttccaccaac
 961 ggctgagggc acctctcatc gtccagtcc acgccgatc atatacaacc gcgtcgcag
```

FIG. 8D

```
     1021 gcgacgcagc ccaaccacta ctctcaccac cagtctcagt ctcagcagca tcatcacogt
     1081 cccagtcacc cacogcogcc gctgtttctc aacagcattc gtgcgccttg a SEQ            HCMV UL54
KEYWORD        PROTEIN
SEQ ID NO:     11
       1       MFYNPYLSGG VTGGAVASGK RQRSQPGSAQ GSGKRPFQRQ FLQIVPSGVM PDKQTGLINK
      61       RTGRLPLMFY RSIKHLLSHD MVWPCPWRET LVGRVVGPIR FRTYQTDAV  LFPDSPENVS
     121       PRYRQRLVPS GSVLRFFGAT BKGYSICVNV FGQRSYFYCT YSDTDRLASV IASVGRLVPE
     181       PETPYAVSVT PATKTSIYGY GTRPVPDLQC VSISNWTMAK KIGEYLLSGG FFVYSVRVDP
     241       LTRLVIDKRI TFPGWCSVRK YDWRQQGRAS TCDIEVDCDV SDLVAVFDGS SWPRYRCLSF
     301       DIECMSGEGG FPCAERSDGI VIQISCVCKE TGGNTAVDGS IPSGNDGRGC FSESVIFSGG
     361       GLRLFTIGTC GQVGPDVDVI RFSSEYELLL GFNLFFQRYA PAFVTGYNIN SFDLKYILTR
     421       LEYLYPVDSQ RFCKLPTAQG GFFLHSPAV  GFFRQYAAAF PSASRHNPAS TATKVYIAG
     481       SVVIDMYPVC MAKTNGFNYR LNIMAEYLR  QRKDDLSYKD IPRCFVANRE GRAQVSPYCL
     541       QDAVILVRGLS WIINFRYEAG AIBNLAKIFL  RSVIFDGQGI SITSLLDEC  ACROFTILPNS
     601       YSKGTTVPET NSVAVSPNKA IISTAAVPGD  RGSVAAHFQM SPPLQSAPSS QDGVSPGSGS
     661       BSSSSVGVFS VGSERSGGVG VSNGNRGAGG TRAVSYQGAT VFBPEVGYYN GFVAVFDFAS
     721       LYFSIIMAHN LCYSTILVPG GEYPVDPADV YSVILENGVT SRFVRASVRV SVLGRLNSW
     781       VSQRREAVRDC MRECQDFVRE KLLDREQMAL KVTCNAFYGF TGVVNGRMPC LPIAASITRI
     841       GRCMLERTAR FIKDNFSEPC FLRHFINQED YVVGTREGDS HESSALPEGL STGSGGSNER
     901       RVEARVITGD TDSVFVRFRS LTPQRLVARG PSLAHVTAC  LFEVPKLSF  EKVFYSIMMI
     963       CKFRYIGKVE GASSLSMKGV DLVRKTACEF VRGVTRQVLS LLFEDKEVSK AAVRLSKLSL
    1021       DEVKKYGVPR GFWSILRELV QRKDDLYLRR VRVEDLVLSS VLSRKDISLYR QSNLPHIAVI
    1081       KSLAARSKEL RSVGDNVFYV LCAPGVRTAF QESSSNGDEV TRGVVSRSDA IDGTDGDAIG
    1141       SGVEESNRRG GEPACKRARK PPSAVCNYEV ARDPSYVRCH GVPIBADKYF SQVLRAVTNV
    1201       LSPVPFGGBT ARKDKFIBMV LPSRLHLSPA FLPYSVKAHS CC KEYWORD        DNA (NC_001347 REGION: 77834..81562)
SEQ ID NO:     12
        1      tcaacagcat tcgtgcgcct tgacactgta cggcagaaaa gcgcgctcca agtgcaagcg
       61      caggcgcagc accatgtgca aaaattgtc  cttgcgcgc  gttcgcage  cggaaagac
      121      gggcgacagc agttagtta  cagcttgag  aacctgctca aagtacttgt cggcgtgaat
      181      gcgcacgcgg tgctcgcgca cgtagctcga atcttcggct acctcgtagt tgcccacgga
      241      cgacgtggt  ttcagagcc  tctttcttgc cggctctcct actatcctgt tgctctccte
      301      tacccgcgcg gccgtcagcgt cgtgtccgt gccatcaatc gagtccgaca gggaaagcac
      361      gcggcaggtt acagaatcac cgttgtcgga ggaacccgta gggcgaagtcc ggacacaggg
      421      cgcgtcaga  acgtaaagga aacgatcaca gaacgaggtg agctcctcag aacggcgaa
      481      caatcgcaga atgcggcaa  tgtgcagcgg gttagatga  cggtacaggg agatgtcctt
      541      agagagcacc gacgaaagca ccagtcctc  gacacgcaca cggtgcaggt acagatcgta
      601      gcgggcctgc accaagcgc  gtaagatacg ccagaaactg cgtggcacgc cgtacttatt
      661      gacttcatcg agtcagacga gcgacaggcg cacggctgct tcgagacct  cgcgatccta
      721      aaagcgcagc gagagcacgt cacgcgtgac gcctgatcg  aactacggca cgtcttgcg
      781      caccagatcc acgacttca  tgctcagacc cgaggcgacc tccattttgc agatgtaacg
      841      ttccttgcag atcatcatca gagagacgaa gacctttttca aactaccagt tgacgggtc
      901      cacaaaaaga caggcacgcca cgtagtgcgc caggctggga ccacgcgcaca ccagagctg
      961      cggcgtcagg ccacgaaaga ggacaaacac gctgtccgtg tcccgtaga  tgaacgcga
     1021      ctcacccga  agttgttcg  agcacctga  cgatgtttcag agcacctcgg gtaacgcgct
     1081      gctctcctcg gaatcccct  ccgggttcc  cactacatag tcttcctgat taaaaaaatt
     1141      gtgcaaaaaa cacggctcctg aaagttgta  tttgatgaac cgacgcgtga gctctagcat
     1201      gtcgcacgg  atgcgctga  tgctgcggga gatgggaaga cacggcatca taccgttgac
     1261      cacgcggtta aaacgtaga  aagcgttgaa cgttactctg agcgacatct gttccttgtc
     1321      gagcaccata cggcgcacag ggtcttgaca ctcgcgcatg catcgcaga  aggcgcgcg
     1381      ctgcgaaacc cacttgttga gcgcttcga  gagcacgag  acgccacog  aagcacgcac
     1441      aaagcgcgtgg gtcacgacgt tctctagcgt gacgctgtat acgtaggcg  ggtccacagg
     1501      gtactcgcca ccgggcaaca gcgggtcaa  gtagcagagg tttgtggcca tgatgatgca
     1561      agggtagtcg ctggcaaagt cgacacgcag acgcagtaga ttgtagtaga ccactcggg
     1621      ctcaaacacc gtgcgcgct  ggtacgaaac cgcacgagta acgccgcage cgtcgattgtc
     1681      gttggaaacg ccgacgcgc  cactactgcc ggacggacg  ctgaaaacgc cgacgatgct
     1741      actactgtta ctgccggago cgggtgaaac gcgtcctga  ctgacggcg  cagattgcaa
```

FIG. 8E

```
1801  ggggggcgac  atctgaaaca  tagccgccac  agaacccgcg  tcgccgggca  cagcggcggt
1861  agagatgata  gaagcgttag  gtgacacagc  aacgctattc  gttcggcca   ccgtcgtacc
1921  tttgctgtag  tgttgggca   ggataaaatc  gcggcaggcg  cactcgtcca  gcacgcaggt
1981  gtagatacgg  atctgctgtc  cgtcaaagat  gacacgcgga  aacggaattt  tagccagccg
2041  cgcgatggcc  ccggcctcgt  agtgaaaatt  aatggtgttg  aacagatacg  gaaccaatac
2101  ggcgtcctgc  agacagtaac  ggctaccctg  gcgcggcgcc  tcggcattag  ccacgaaaca
2161  acgcgggatg  tccttgtaag  acaggtcatc  cttgcgttgc  cgcaggtaaa  gctcggccat
2221  agtgttgagc  ttatagtcgg  gcgagttagt  ctggccatg   catacagggt  acatgtcgat
2281  aaccaccgaa  cccgcaatat  acaccttgt   ggcggcgtg   ctggccggat  tgttgtgaga
2341  agccgaggga  aaagcgggcg  cgtactgcg   cttaaaaccc  aggcgggga   tgtgtaaaaa
2401  gaaacggccg  ccctgcgtca  taggcaactt  gcagaagcgc  tgcgagtcca  acttatacag
2461  gtactcgaga  cgcgtgagga  tgtacttcaa  gtcaaagag   ttgatgttgt  aaccggtcac
2521  aaaggccggc  gcgtaccgtt  gaaagaaaag  cataaagccc  agcacgcagct  cgtattcga
2581  agggaactcg  tagacgtcca  cgtctgggcc  cacctgccg   caggtgccga  tcgtaaagag
2641  atgaagaccc  gagtgcccaa  agatcacacc  atcgaagtg   cagcccgac   catgttcca
2701  gttggggatc  cctgatcca   cggcctgtt   tcccccgtc   tgtagcaca   cgcacgagat
2761  ctgaatgaca  atgtcatgg   acttctcgga  gcaggaaaa   ccacctcgc   cgctcatgca
2821  ctcgtatcg   aaggacaggc  atcgatagcg  cggccacgag  ctgtgtcgg   gaacagcac
2881  caggtcagag  acatcgcagt  ctacctcgat  atcacaagtc  gacgcgcgac  cctgctgcg
2941  ccagtcgtaa  cgattcaagg  agcaccagcc  gaacgtggtg  atcgccgat   cgatgaccaa
3001  acgcgtcagc  ggatccacac  ggacctgta   cacgggaaaa  ccctgctcca  gaagatactc
3061  gccgatttt   ctggccatgg  tccagttgct  gatagacaca  cactgcaaat  cggccacggg
3121  tcgcgtcccg  taccataga   tggagtctt   ggtggcacgg  gtgacagaca  aggcgtatgg
3181  cgtccgcggt  tcgggcacta  gttcgcccac  gctgcaatg   acctcacgca  gcctatacgt
3241  gtcgctgtac  tcacagtaaa  agtagctgcg  ctgccgaaa   acgttgacgc  agatactgta
3301  gcgcgttct   gtgccccga   agaaacgcaa  cacgttccc   gaaggtacca  gatgctgacg
3361  atagcgnggc  gacacgtttt  cggcgagtc   gaagaagagc  acggagtcg   tctgatcgta
3421  ggtgtgaaaa  cgaataggtc  ccacccacgcg  accaccagg   gtctcgcgcc  aaggacacgg
3481  ccaaaccatg  tcatgantca  acaaatgttt  aatctctga   tagaacatga  gaggcagccg
3541  tcccgtctta  tgcttgatca  acccgtctg   acgtcgaac   atgcacgctc  gcggacgat
3601  ctgcaaaaac  tgtttctgtg  ggggccgctt  gccgagccc   tgcgcgagc   cgggctgcga
3661  acgctgacgc  cggccaccg   cgaccgcacc  gccggtcacg  ccgccgatca  gatacgggtt
3721  gaaaaacat
```

```
SEQ            HCMV UL55 (gb)
KEYWORD        PROTEIN
SEQ ID NO:     13
1       MESRIWCLVV  CVNLCIVCLG  AAVSSSTSH   ATSSTHNGSH  TSRTTSAQTR  SVYSQHVTSS
61      EAVSHRANET  IYNTTLKYGD  VVGVNTTKYP  YRVCSMAQGT  OLIFTERNII  CTSMKPINED
121     LDEGIMVVYK  RNIVASTFKV  RVYQSVLTFR  RSYAYIYTTY  LLGSNTEYVA  EPMWEIRHIN
181     KFAQCYSTS   RVIGSTVFVA  YHRDSYKRKT  MQLIPDDYSN  THSTRYVTVK  DQWHSRGSTW
241     LYRETCNLNC  MLTITTARSK  YPYHFFATST  GDVVYISPFY  NSTSRNASYF  GENADKFFIF
301     PNYTIVSDFG  RPNAAFETHR  LVAFLSEADS  VISWDIQDEK  NVTCQLTFWE  ASERTTRSEA
361     EDSYHFSSAK  MTAFFLSKKQ  EVNMSDSALD  CVRDEAINKL  QQIFNTSYNQ  TYEKYGNVSV
421     FETSGGLVVF  WQGIKQKSLV  ELERLANRSS  LNITERTRRS  TSDNNTTHLS  SMESVRNLVY
481     AQLQFTYDTL  RGYINRALAQ  IAERWCVDQR  RTLEVFKELS  KINPSAYLSA  IYNKPIAARF
541     MGDVLGLASC  VTINQTSVKV  LRDMSVKESP  GBCYSRPVVI  FDFANSSYVQ  YGQLGEDNEI
601     LLGNHRTEEC  QLPSLKIPIA  GNSAYEYVDY  LFKRMIDLSS  ISTVDSMIAL  DIDFLENTDF
661     RVLELYSQKE  LRSSNVFDLE  EIMREFNSYK  QRVKYVEDKV  VDPLPPYLKG  LDDLMSGLGA
721     AGKAVGVAIG  AVGGAVASVV  EGVATFLRNP  FGAFTILVA   IAVVIITYLI  YTRQRRLCTQ
781     PLQNLFPYLV  SADGTTVTSG  STRDTSLQAP  PSYEESVYNS  GRKGPGPFSS  DASTAAPPYT
841     NEQAYQWLLA  LARLQAEQRA  QQNGTDSLDG  QTSTQDKGQK  PNLLDRLRHR  RNGTRHLKDS
901     QEKEDV
```

```
KEYWORD     DNA (NC_001347 REGION: 81703..84423)
SEQ ID NO:  14

1    tcagacgttc  tcttcttcgt  cggagtcttt  caagtgtctg  tagccgtttt  tggatgtcg
61   cagcgggtct  agaaggttag  ggttctgtcc  cttgtcctgc  gtgccagtct  gtccgtccaa
121  agaatctgta  ccgttctgct  gcgctcgctg  ctctcagtcc  agacgggca   gggccagaag
181  catctggtaa  ggctgctcgt  tggtgtaagg  cggagccgcc  gtggatgcat  cagacgacgg
```

FIG. 8F

```
 241 tggtccggt ccttggcgac cagaattata aacacttcc tcgtaggaag gggagcctg
 301 taacgacgtg tcttggtgc tgccgacgt caggtggtc ccgtcggcgg acaccagata
 361 gggaagagg tctgcaagcg gctggtgca cagacgcgc tgtcgagtat agatcaaata
 421 agtgataatg actacggcta tggccatgag gatgatggtg aaggtccga agggttttt
 481 gaggaaggtg gcaacgcctt cgaccacgga ggccacgcg acaccacgg cccaatggc
 541 tacgccacg gccttaccg caggcgccag gccgctcatg aggtcgtcca gaccttgag
 601 gtaggcacgt agcgggtcga ctaccttgtc ctccacgtac tttaccgct gcttgtacga
 661 gttgaattcg cgcatgatct cttcgaggtc aaaaacgttc tggaacgca gtctttctg
 721 cgagtaaagt tccagtaccc tgaagtcggt atttccagc gggtcgatat ccaggcgat
 781 catgctgtcg acggtggaga tactgctgag gtcaatcatg cgttgaaga ggtagtccac
 841 gtactcgtag gccgagttcc cggcgatgaa gatcttgagg ctggaagct gacattcctc
 901 agtgcggtgg ttgccaaaca ggattcgtt gtcctcgacc agtgacgt actgaacgta
 961 cgagctgttg gcgaaattaa agatgaccac gggtcgtgag tagcacgcgt ctggcgattc
1021 cttcaagttc atatcaagca gcaccttgac gctggttcgg ttgatggtca cgcagctggc
1081 caggcccaag acatcaacca tgaaacgcgc ggcaatcggt ttgttgtaaa tggccgagag
1141 aatggctgac tggttgatct tgctgagttc cttgaagacc tctaggtgc gccgttgatc
1201 cacacacag gttctgaga ttttcgccaa cgccggttg atgtaacgc gcaacgtgtc
1261 atcgtgaac tgcagtggg cgtagaacag attgtgaacc gattcctcg tggacaaatg
1321 agttgtatta tgtcactcg tacttcttct ggtcctatga gtgatatca gactggatcg
1381 attggccaaa cgttccaatt ccaccaaaga ttttgcttg atgccttgcc agaaccacga
1441 cagaccgcg ctggtttcga agacggacac gtttcgtat tttcatatg tttgattgta
1501 tgaagtattg aaaaatcgct gtaacttatt tatagcctca tcacgtaccgc agtccagcga
1561 ggagtcggac atgttcactt cttgttctt agacagaaaa gttgcagtca tttggcagaa
1621 agaaacggaa tacgacgctt aggcttcgga acggatgta cgtccgtagg cttcccagaa
1681 ggtgagctgg caggtgcat tcttctcgtc ctgtatacc caagagatca ccgagtcgg
1741 acgttcgaga aaagccaacc acctatggt tcctggcgca gcgttgggtc ttccaagtc
1801 ggaaacgatg gtgtagttcg ggaaatgaa aaactgtcg gggttttctc caaagtagct
1861 ggcattgaga ttggttccgt tgtagaaggg agaaatgtaa accacatcac ccgtggaagt
1921 tgcaaaaaa tgataagat acttgatgcg ggactgggcag atgtgaaca tacagttcag
1981 attacaggtc tcacgataga gccaggtgct gccgaggctg tgccactgat ccttgaccgt
2041 cacgtaacgg gtactgtggg tgttggaata atcgtcggga attaattgca tggttttgtt
2101 ttcataactg tccctatgat atgccacgaa aacgtgcct cctataacgc ggctgtagga
2161 actgtagcat tgaacaaact tgttgatgtg atgaatctcc cacataggag gcgccacgta
2221 ttacgtattg ctgcccagca gataagtggt gtagatgtaa gggtagctac gacgaaacgt
2281 caaaaacttt tggtagacc gtacccttaaa cgtagtcgcc aacgattgc gcttgtagac
2341 caccatgatg ccctcatcca agtcttcatt gataggcttc atcgagggtgc agatgatatt
2401 acgttcaaag cgaataagat ccgtaccctg gccatagaa cacacgcgat aggggtactt
2461 ggtagtgttg actcccacca catctccgta cttgagggta gtgttgtaga tagtctggtt
2521 ggctctatga ctgacggctt cagaagacgt tacgtgtga gaatagactg acgggttgg
2581 agcagacgtc gtacgagaag targgcttcc attgtagta gaagaagttg catggaagt
2641 actcagaacg gaaacgcag caccagaca gacgatacac aggttaacgc agactaccag
2701 gcacacgac ctggattcaa t
```

```
SEQ         HCMV UL56
KEYWORD     PROTEIN
SEQ ID NO:  15
  1         MEMSLLQKLC VVCSKCNGYA MSLRCLRYCG PNVLLAKSTP FKRNAAAIVY LYRKIYPKVV
 61         AQNRTQSSLS TLYLEMLLKA LREDTALLGR ALMATSRQPD RAAFYPTVLR LDRCDRNRTV
121         SLQFTDNVRF SVSLATLGGI KRFLCKMNTV YSILAPERGL EVCAQLLELL RRLCGISPVA
181         RQEVYVSGTT CAQCYEELTI IPHQGRSLNK RLQGILCNHI AVRRPSSQSD VSIQTVEQSL
241         LDLTTRIPHL AGVLSALKSL FGSSSAYHSY IQSAEEALRE YNLFTUIPER IYSLSDFYTW

301         SPTSEVIVKR VGITIQQLRV YEQLCRAIMN GISRHLYGRD VEDIFVLGRK ALDQKEEMFV
361         GSVFAAFNRI IDLITSLSIQ AFEDNPVFNK LRESNRMYTK IKRILSEIFR FLPDGTSGDS
421         FEGEAIRLSG REAMSGTGFT IRTANSNSNS STREQRNEGG GGSARGGGRK VVGGSVSQQD
481         GGSSENGLRV RNCDERBALD LVDARSRISM VTREVNVREK AYLQKVSEVS YGKVIRCIKT
541         QERLTSKLID VNLVGPLCLD FISKLNBGFL YRSGYSQDQD VVDVGDQFTY DERLYVVNRL
601         ISKSLPVESL PLLGQQIYSL CNGFLFTECT DRYPLSRNVD MAYACDRAGV LPRVKDDLVK
```

FIG. 8G

```
661     CRESTVYPSE RMVYXYNGFF BFSDQQDLNV LQKEMWNHVR RLVLSVALKN RTFGRQLSIR
721     CLRDELRPDR SVILTYNSEW FLLRBEGSL YRKDLYLIL YRHLSRPDES GGVPTSPVAR
781     PSTLTAAAAV SGVFREPDRP WLFSPYPSSS TAGVSRRVRA TRKRPRRASS LLCLARDEHG
843     IQDLVPGSLR

KEYWORD     DNA (NC_001347 REGION: 84386..86938)
SEQ ID NO:  16

1    ttaacgcaga  ctaccaggca  ccagatcctg  gattccatgt  tcgtcgcggg  ccaaatccag
  61    cagcgatgag  gcgcgtcgtg  gtctcttgcg  tgtcgcgcgg  accctccggg  aaacaccgc
 121    agtcgaggag  gagggataca  gacttgccag  ccaagtcgg  tccggctcca  tgaagacacc
 181    cgacgcc     gcggcggcg   tcaggtgga   gggcttggac  acggagctg   ttgcacgtc
 241    gccactctca  tccggtctgg  acagatgct   gtagaggagg  agatatagat  ctttggactt
 301    ataaagactt  ccttcgtgac  gaagcagcaa  cggccactct  ttgttatacg  tgagaatcac
 361    atctctgtcc  gggtgcagtt  cgtcgcgcag  gacgcgatc   gagagttgtt  tccgaaagt
 421    ttcattatat  agtgcgacgg  agagcacgag  ctccgcacg   tgcatcaaca  tctcttctg
 481    cagcacgttt  aggtcctgac  agtccgaaaa  attgaaaaaa  ccatatact   tcaccaccat
 541    ccatctactg  ggatacacgg  tacctcccga  gcatttgcc   aaatagtcct  tgacgtgggg
 601    tagtacgccc  gcgttgtcga  aggcatcggc  catgtccaca  ttgtgagaga  ggggataacg
 661    atcggtcgca  tgggtgaaga  gggcacgtt   acacaactcg  tagatctgct  gaccagtag
 721    aggagggat   tccacagtca  gactcttgt   gatcaggtta  ttgaccacat  acaggtgctc
 781    atcgtaggtg  aactgatcac  ccacgtccac  cacgtcttgg  tcctggtggt  attgctgcg
 841    gtacagaaac  ccattcatga  gcttagagat  aaagtccaga  cacaagggc   ccactagatt
 901    gacatcgatg  agcttgctag  tcagacgatc  ctggtttg    atgcaacgga  tcaccttgcc
 961    atagccacc   tccagacct   tatgcaggta  ggcgcgtttg  cgcacgttca  cctcgcgagt
1021    gacgttgtg   atgcgggagc  gcgcgtcaa   caagtcgaga  gcatcgtgtt  cgtcgcagtt
1081    gcgcaccgt   aagcgttct   cgctgccgtc  gccgtcctga  ccattcacac  ctccacctac
1141    cacttttcttg cctcctcac   gagcacggcc  gcgcaccg    ttattcctct  gactgtgagt
1201    actgctgttc  ctgctgttgc  tggcgtcat   caagtcgta   cacgtccacg  acatcgcctc
1261    ccgtccacgc  aggtgaatag  actcgccctc  ggggcgtcg   ccccacgtgc  catctggcag
1321    aggacgtcga  atctcctcga  gaatatgctc  gatttgtg    tacatctcgt  tgctttcgtg
1381    gagcttgttc  aaacacgggt  tgtcctcgaa  agcttgaatg  ctgagcgatg  tgatgaggtc
1441    gatgatcctg  ttggggtcgg  caaagaccga  cccccagaac  atgcgctcct  cccgtccaa
1501    cgctttttcc  ccgagcaaga  agatgtcctc  caagtccttc  acgtacagat  ggcgactgat
1561    gccgttcatg  agcgccggc   acagctggtg  atacacattt  agctgctgga  tggtatgcc
1621    ccccgcttg   acgataacct  ccgaggtacg  ggaccagtag  gtaaatccg   acaaggaata
1681    tattcgttcc  ggtctatccg  tcaacaggtt  gtactccctc  agcgcctcct  acgactactg
1741    gatgtagctc  tggtaggcct  atgaagaaga  gaatacggctt ttgagggccg  aaaggactcc
1801    agccaagtgg  gggatgcgcg  ttgtcaggtc  caggaggtcc  tgctccacg   tctggatatt
1861    cacatggac   tggcttgacg  gacgcttgac  cgctatatgg  ttgcacagca  agcactgcag
1921    ccgcttgttc  agagagggc   cctgattcgg  gatgatggtc  agctcctcgt  agcattggcc
1981    gcatgtcata  ccttcagacgt acacttcctg  agcgccacc   gcgagatgc   cgcatcgcg
2041    acggaggage  tccaggaact  gcgcgaagca  ctccaggccg  gcctccggcg  ccaggatccc
2101    gtacaagtag  ttcattttgc  acaggaagcg  ctcgatgtcg  ttgagtgtgg  ccagactgac
2161    gctgaaacgg  acgttgtccg  taaactggag  ctccaggtg   tgatggcgat  cgcagcgatc
2221    caaacggagg  acggtacggt  agaaggcgc   caggtcggc   tggcgcagt   aggcatcag
2281    cgccgatcc   agcaaagccg  tatcctcgtg  cagcgcctta  agcagcatcc  ccaggtagag
2341    cgtcagcaac  gaactctgcc  tacgattcttg ctgcagcc    tccgggtaga  tcttccggta
2401    cagatacact  atagccgccg  cgtttatctt  gaccggcgtg  gactccgcca  gtaacacgtt
2461    cggatcgcag  tacttcagac  actccagctc  catggagtat  tcgttgcatt  ttgaacacac
2521    tacgcatagt  ttcgtaacca  aattcatcc   cat SEQ         HCMV OL57
KEYWORD     PROTEIN
SEQ ID NO:  17
  1     MSHEELTALA FVGPRAFLYF SRINARTQEI IATLSLCDRS SSVVIAFLLA GLTVEADFGV
 61     SVRTFVLCYD GGVLTKVTSF CPEALYFRHT QGIVAFTEDR GDVHRLCEDA RQKYALEAYM
121     FEADRVPTDL AALCAAVSCQ ASETTYHVVV GNGLKEFLER GQLIPCVEEA TTVRLSGGEA
181     VRVFLYPFTL FNSLQLDAEA DKVSLDARSA FVRARGLYVP AVSETLFYYV YTSWCQSLRF
241     SKPRVLIEAA LSQFVRDSQE SVKLAPHKRY LGYNSQRLSS LEKDHIMLSD AVVCELAFSF
301     ASVFFDSAYQ PAESMLFSEW PLVTNATDER DLIRALFELK LRLSTHVAAL VFSANSVLYQ
361     HRLVYLQSSA RHFSAGGTAS QETLKAIQF  TNGLSAACED VYNDARKVLR FQGAPLKDER
```

FIG. 8H

```
 421    YGPQHLALVC  STCPQLVSGF  VWYLNRVSVY  STGLSQSSTL  TSRLVGCAAG  LCEACRGTCC
 481    HTCYQTAFVR  VRTRLPVVSK  QPKEEPCVIT  VQSRFLNDVD  ILGSFGRRYN  VDAKLGGLLG
 541    RGDXGVPGSG  AGGGGGRDVS  GSPSDGLGSG  RGGGSGDSG   GMSKSSGRML  GASVDRTYRL
 601    NRILDYCRHN  RLIDPVYGED  TPSANGKSGP  VAVFSALEKF  VDGSALGPVS  EVRLESSRDE
 661    VAGATQAFNL  DLNSYAVAFQ  PLLAYAYPRS  VPYVIQSVAL  ITATPSYIVDN  PLTTNLVSKN
 721    MTQRFQSIEG  AFSTTSSRKG  FLPTKQIKSS  KNSDHDRLLD  FRLYAQQTTA  VVPMEIKLSS
 781    LSVPTLIRVR  VENRPIYRAS  KGNAGGVFTR  RDHVPRRRSA  KGCLSPLLYR  RHERLSPECG
 841    LPCLQFWQKV  CSRALFKNVP  IGDMGEFNAF  VRFLVAVTAG  YQSRDLLDVA  PDCVLSYVES
 901    KFNKFLCIY   GFKDYIGSLN  GLTTRLTTQS  HAQFFHVLGA  SPRFSSPAEF  ALHVKGLKEA
 961    GVPAPMAHTV  ARRSLVRSVF  RHRSLVTVPV  SVEKYAGINN  SKEIYQFGQI  GVFSGNQVEK
1021    SLNVSSNSSQ  DYRFMRQRYL  LATRLADVLI  KRSRKENVIF  DADLIKNAVM  LALGRENLDC
1081    DFEVSAVYEI  LSVEEEIPAS  DDVLFFYDGC  EALAASLMDK  FAALQEGGVS  DPSLENLREV
1141    LQACAQRLTD  AAGGEVRDLS  ALFAPSGVGA  ASGVGGSGLL  LGRSVAGRSI  CPGVPGETGG
1201    GCFLVGAGED  EAGSVGGSGG  GGGGSSLLPA  KRSRL
```

KEYWORD    DNA (NC_001347 REGION: 87505..91212)
SEQ ID NO: 18

```
   1    ttacaacgg   gtgcgtttgg  cggcaataa   ccgctgccc   cgccgccc    cgctgctcc
  61    gacgacgcg   ccagcctcgt  cttcgcgga   gttcacgaga  aagcagccac  ctccgtctc
 121    gccggacacg   ccgaagcaaa  tggagttgtc  cgcgacgac   tcgccgagaa  gaagaccgcc
 181    acgccgacg   ccggacgcg   cgccgacgcc  actgggcgcg  aagagcgcag  acaggtcgtg
 241    cacctccccc   ccggacgcgt  cgttaacgc   atgggcgtg   ggctcaagca  acgtcgaca
 301    gttcctcaga  gaaagtcct   ccagcactg   ctcctgcaac  gcgcaaact   tgtccatcag
 361    cgacgcggct  agcgcctcgc  agccatcaca  gaagaagagc  acatcgtcgg  accgcgggat
 421    ctcctcgtgc  acgctcagaa  tctcgtacac  ggccatcact  tcggggtcgc  aatcccaagtt
 481    ctcggcgtcc  agcgccagca  tgacgcggtt  ttttataaga  tccgcgtcaa  aagcagtt
 541    ctccggcgca  gacgttcga   tgacgacgtc  ggcagacgc   gtagcaaga   ggtagcgtg
 601    gcgcatgaaa  cgataatctt  ggccgtcat   agagctcacg  ttaaggctgc  gttccacac
 661    gtgcccgaa   aagtagccga  tctgccaaa   ctgatagatc  tacttgctgt  tgttgataac
 721    cgcatatttt  tccacgctca  cgggcacggt  caccaaggaa  cgatgcttcaa  aaacgctcg
 781    taccaaacgat  tcacgcgcca  cagtgacggc  catgggcgcc  ggcagcctg   cggtcttcaa
 841    gccccttgaa  tgcaacgcaa  attcgcgagac  ccgcgacgac  acgggactag  cacctaacac
 901    gtgaggaaac  tgcccgtggc  tctgcgtcgt  taagcgctcc  gtcaaccgt   gcacgcgagcc
 961    gatgtagtct  ttgaagtcat  aatagcagag  gaattgtta   tggaaacggc  gttccacgta
1021    actcagcaca  cagtctggcg  ccaatccag   cagatcgtgc  tccgtatagt  cagccgtcac
1081    agccaccaga  aatttgaagc  aagcattgaa  actgccctag  tcacctatgg  tgcatatctt
1141    gggcaaacgg  ttggaaccaga  cctcctgcca  aaactgtaag  caggggacag  cacattcagg
1201    aaagagtcgc  tcgtcgatgtc  gatacagcag  aaatccaag   cagccttag   ccggattacg
1261    acgagggaacg  tgataggcggc  gaaaaaacac  gctaaacgc   ttgcctttgac  ccgcgcggta
1321    gatgggtcgg  ttttcaccc   gaccatgat   caacgtcggt  accgacaggca  gagacgctt
1381    gatctccatcg  ggcaccacag  cgtacgtgca  ctgcttcagc  agccttcaagc  ccagcaggcg
1441    gtcgtgatcc  gaattcttgg  acgactggat  ctgcttgtg   aagagaaagc  acttgcgcga
1501    cgacgttggtg  gagaacgcgc  cgtgaatgga  ttgaaaatgc  tgcgtcaatcc  atttggatac
1561    caagttggtg  gtcaacggat  tgtccacaat  gtatgaggta  gcggtaataac  gcgcacgtt
1621    ctggatcacg  taaagacgg   atatgaaata  agcgtaggt   agcagcgget  ggaagcaac
1681    ggcctaggga  ttcagatcca  ggttgaagc   ctgcgtgagc  ctgccgacct  cgtcgcggct
1741    gctcttgagg  cgcacctccg  aaacgaaacc  caggggctcg  tcgtccacaa  acttgttgag
1801    cgccgaaaag  acggccacaa  agtcgcttttt  gccgtcgcga  ctaaagttat  cctcgcccgt
1861    cacgggtcg   atgagcgca   tcttcgcgca  gtaatccaag  atcgattga   gcggataggt
1921    acggtccacg  ctagcgccca  acatgcgacc  gcgcgccc   atcattccc   cggaatccca
1981    accaccaccc  ccacaccgag  tgccaccacg  acgtcgctca  accccgtcg   tcaccttgc  cgtccaacc
2041    tccaaccaccc  ccgccagcac  cgccgccagg  acccgtcg   tcaccttga   cgtccaacc
2101    cccgtccttg  gcgtcgacgt  tgtacgcgca  acgagctg   cccaaaatat  ccagtcgtt
2161    gagaaaacgc  gactgacggg  tgatacgca   gggctcattc  ttgggctgct  tggcaccac
2221    gggcaagcgg  gtgcgcacca  gccgaaggc   cgtctgatca  caccgtgtgc  aacaagtacc
2291    cccaccaccg  tgcacagcc   acgcgggcc   cacaaccagg  tgattcgtga  gcgtcgacga
2341    accgacaag   ccgtcgttgt  acaccgcgag  acgattcaga  taccagacga  agccgaaac
2401    tagctgcgga  cacgtcccc   acaccaacgc  caaatgctgt  ggccataga   gttcgtcctt
2461    gagcgggcgc  ccctgaaact  tgacgccctt  gcgcgcgtcg  ttgtagacgt  cttcgcaggc
2521    cgcgacaac   ccgttgtgac  actgaataga  cttgagcaac  gtctcctgac  tggccgtacc
2581    gccggcgctg  ggatgcgcg   ccgacgactg  gagatacacc  agcctgtgat  ggtagagcac
```

FIG. 8I

```
2641 cgaattagcg ctgaagacca aggcggcac gtgcgtcgag agatgcaact tgagctggt
2701 cagcgcgcgg atcagatcgc ggtgatcggt tgcgttggtc actaaaggcc actcggaaaa
2761 gagcatagat tcggcaggtt ggtaagcgga atcgaaaaat accgaggcaa aactgaagga
2821 caactcggaa accaccggt cactcagatcc ttttccagac tgctgagtcg
2881 ctggctcatg taccccaagt agcgcttatg tggcgtcagc ttaccgact gctgactgtc
2941 gtgcacaaac tgccgcaacg ccgctagat cagcacacg ggctccgaga agcgagcga
3001 ttgacaccat gacgtgtaca cgtagtagaa aagcgtctcg cttacggccg gcacgtagag
3061 acctcgcgcc tccacaaaag cgctgcgcg atcagcgag aactcgtcgg cttcggcgtc
3121 aagctgcgac gaattaaaga gcgtaggggg gtacaacgga agcgcacgg cctcgccgcc
3181 gtgcagtcgc accgtggtcg cctcctcac gcatgaatc agctgaccgg caaagagaaa
3241 ctccttcaag ccgttgccca ccaccgctg cacagtcgtc tggacgcct gacagccac
3301 cgccgcgcac aacgccgcca gatcggtagg cacgcgatcc gctcgggca tgtaagcctc
3361 caacgcgtac ttctggaggg cgtcctcgca cagcgatgc acgtctccgt gatactcggt
3421 aaaagccacg atgcttgcg tatgatgaac gtcacgccga aaggacaga aggacgtgac
3481 tttcgtgagc acccgccgt cgtaacaaag cacaggcgtg cgcacagaga cgccgaaatc
3541 cgcctccaca gtgagccccg ccacaaaggt agcgatcacc acgctcgagg aacgtcgca
3601 tagcagaga gtggccagaa tctcctgcgt ttctgcgtc aacctgctga agtagagaaa
3661 agccgcgggc ccaccggcg ctagcgcggt tagtctcatag tggctcat
```

```
SEQ        HCMV UL70
KEYWORD    PROTEIN
SEQ ID NO: 19
  1.       MTLVLPATEV DSAHIVANVL SQTPIDHCVF FLLVEHQVSE RVYFCLQTQR CSDSRRVAFV
 61.       FAVMMETLQL SRYLAARQPI PLSALIRSLD EAETQPLYRN LSRTPVLSPE NGGEVRSFKS
121.       LVYPNSARVL RHLNQVSLCP TSPSWFISVF GRTESQVLLS MAYYLFEQQV STISPVSEYV
181.       RSPCTRDLCT IIPTRASMSG FARLLLGSFF RQRVSAPVAY AVAPNHRDYT RLEQVPTQIN
241.       AFPERASRPD TVCVRYVYLA YRTALASARL LEYRFVYAYD ADAAPEAQCT REPGPLGERL
301.       STELLDVMQK YFSLDNFLRQ YVETHLLSLD ESPHSATSPR GLGLAGYGGR IDGTRLAGFF
361.       GTSTQLAEQL ERINTLSESV FSPLERSLSG LLRLCASLRT AQTYTTGTLT RYSQRKYLLP
421.       SPALAPLLER FLPVYRVLFP NQQSVFCAVA SSTWERSLFP RDLLSRVBDS RFSEBALTST
481.       VWLRDQQVAS TSFETQFYYT RHCVERERLP YPNFVADFDL RLRDGVSGLA RRTVFKLCRG
541.       LRRVWGTVWA SLFGYTRFDK HPVYFFKSAC PFNGVPVDAA GAPFDGDDYL DYRDERDTRE
601.       DEDGEREDRNN VFDNGVFQKT TSSVDTSPFY CRCKGKLGLS IITPPPACTV AVHFSVLRAV
661.       AQVLNEAVCL DAELEYLLDF ISHPESSLDT GTYRNGRSYR LFYMYKNDQD DGYFMNRSLL
721.       FLFIVPDAYR EHPLSPVPAQ LDLRNLLERK FPHDLFALFL SPFPRVILSV RDKTCPSTEA
781.       NPIETRGLNV TRYRSRGLTE VLAYRLYGGD GATAAAISDT RLQRLPVTRV WPFLLERLTQ
841.       RYEFRVSEQF TAPRVLLFQP HCACCVAVRR RDGARTRDFR CLNYTRPNPQ ETVQVFIDLS
901.       TERSYALWAS LWQRGFTFKC KSNAPNVRLS IRERPFDAPV PPATAV

KEYWORD    DNA (NC_001347 REGION: 103464..104304)
SEQ ID NO: 20
```

```
  1 tcagacgggcg gtgcgggcg gcaaggagc gtgggcggt ctgatttga tggaaatgtg
 61 gacgttttttg gggttggagt gacactttt ggtgaaacag cggctccaga ggctggccca
121 gagcgcgtag ctgtgctcgg tgcgcaggtc gatgaacacc tgcacggtct cttgcgggtt
181 gcgctgcgtg tagttgagac agcgaaaatc cccgcgtcgc gcgccgtcgc gccgcttgac
241 ggccacgacg caggagcgt gggcgtgaaa gaggcgacg tggcgagcg taaactgtc
301 gctgacgtgc ggttcgtagt gttgcgtgag gtgctcgagc agcgcggcc acacgcggt
361 gacgacgagc cgctgcaagt ccgtgtcgga aatcgcagcg gcagtggcgc cgtcgccacc
421 gtacacggtg taggcgagca cctcggtgag accgaggcgt agataacgg tcacgttaag
481 cgacgcgtc tcgataaagt tgggcttcgt cgagcgggcag attttgtcgc gtcgcgtgag
541 aatgacgcgt ggcgggcgc acaggggcaa cgcgggagg tgtcgaggag gtgctgtgtg
601 aagcaggttca cgagatcca gttgggcgcg cacaaagcct agcgggtgtt cgcgttagc
661 gtccgcgaca atgaacagcg gcaacacgca gcgatcgctg aaatagccgt cgtcttggtc
721 cattttatac atgtaggcga gacgtacaga gcgtccatcg tggtagatgc ctgtgtcaag
781 gctgctctcg ggatgcgaga tcgggtccag cagcgtgtgc agtcggcgt cgagacagac
841 ggcgtgattg agcactcgcg ccaggcgcg taaaagctg ggtgtacgg cgacgtgca
901 ggcggggaac tgcgtgatga tgcgagcca cagtttgcc ttgcagcgcg agtaagggg
961 tgacgtgtca acggaggacg ctgtttttg gaaaacgcg ttatcggga cgttattttt
1021 atcctctttc ccgtcttcgt ctccctcgt gtcgcgctag tcccggtaat agagatagtc
```

FIG. 8J

```
1081 gtcgtcatcg aaagcgcgc cggccgcgtc caggggcaag ctgttgggtg ggcacgcgct
1141 tttgacgaaa tagaccgggt gccggtcggg gtgcgtgtag ccaaagaggc tgccccatac
1201 ggtcatccag acggtcgta gtccgcgaca tagctcaaag acggtgtgtc cgccagacc
1261 ggagacgccg tcgccgagcc gtaaatcaaa gtcggccaca aaattgaaga cgggcagacg
1321 ttcgttgaag acttcgtgtc gcgtgtagta gaactgtgtc tcgggctgg tgctggccac
1381 gtcgtcgtag tgtagccaca cggtctcggt caggcctcg tccgagaaac ggctgtcggg
1441 tacgtgacgg agcaggtcac gcggaagag gctgcgatgc caggtttcgg aggccacggc
1501 gcagaagacg tgctggtcat tgggcaggtg tacgcggtag acgggcagcg gtgctccag
1561 caggcgtgcc agcgcgggct cggtagcag gtagcgacgt tgcgagtaac gcgttagcgt
1621 gccggtggtg caagtctggg ctgtgcgtag cgagcggcat agacgtaaca agccggacag
1681 ggagcgttcc agcggggaga agacagactc cgaaagagtg ttgatgcgt cgagctggcg
1741 cgccagctgc gtggaggtgc cgaagaagcc cgccagtgc gtgcgtga tgcgcgcc
1801 gtagccggcc agcctcaagc cgtgcgggct ggtgccgag tggggatt cgtcgagcg
1861 cagtaggtgc gtctccagt agtcgtgtag aaagttgtcg agcgagaagt attttgcat
1921 gacgtccagc agctcggtgg aaagccggcg gccccagcga ccccggttcga gcgtgcactg
1981 cgcttcaagc gccagctcag cgtcgtactca cggtactcga gcaaccgcga gcaaccgcag
2041 gcgtgccagc gccgtgcgt aggccaggta gacgtagtgc acgcagacg tgtccggcag
2101 acgcgcacgt tcgcgaacg cgttgatctg cgtgtccaca tgctctagct cggtgtagtc
2161 gccgcggttg cgcgcgacg cgtacgccac gaaagcggac acgcgtgac ggaagggcga
2221 gcccagtagc agcgcgcgca actcgcccat ggagcgtgca gtgggatga tggtgccag
2281 gtccgcgtg cagaagctgc gcacgactc ctccacgtg gagcgtgtgc tgtactggca
2341 ctcgaatcgg tagtcggcca tggtcagcac cacctggcac tcggtgtgca cgaagacgct
2401 gatgaaccac gagggcgaag tgggcagag gaagacctgg ttgagtgac gtagcacggc
2461 cgcgtggtga aagtacacca ggtgcttgaa ttgcgcacc tcgccgtcgt gttcgggcga
2521 gagcagggc gtgcggaaaa gatgccggta gagcggttgc gtctcggcct cgtccagact
2581 ggcgatgagc gccgagaggg ggatgggctg gagcgcggcc aggtagagcg agagctgcag
2641 cgtttcgttg ttcaaccgga agacgccggc gagtccgagc acttttgcgt
2701 atgtaggcag aagtaaacac gtcgcgagac ctgcgtgttg accagcaggg ggaagacgca
2761 gtcgtccgtc ggtgtctgcg agagtacgtt ggcgactata tgagcagaat catactctgt
2821 tcgaacaga acgagcgtca t
```

SEQ HCMV UL71
KEYWORD PROTEIN
SEQ ID NO: 21
```
1     MQLAQRLCEL LMCRRKAAPV ADYVLLQPSE DVELRELQAF LDERFKQLEI TPADLKTFSR
61    DTDVVNHLLK LLPLYRQCQS KCAFLKGYLS EGCLPHTRPA AEVECEKSQR ILEALDILIL
121   KLVVGSFANS EADSLEMLLD KFSTQQASLV EVQRVMSLVD MDCEKQAYML EAGAAATVAP
181   LTPPAVVQGE SCVREDSBTV AAVSAPACFS VSDSLIFERT GVTRPMSLA HINTVSCPTV
241   MRFTQRLLEE GDERFDEVTM SPSFEPVQQQ PPVEPVQQQP QGRGSRRBRY KESAPQETLP
301   TNHERSILDL MRHSPDVPRE AVMSFTRVTI PPPQTFFVGS ARSLRQVKKX RPTAAALLSS
361   &
```

KEYWORD DNA (NC_001347 REGION: 104320..105405)
SEQ ID NO: 22
```
1    atgcagctgg cccagcgcct gtgcgagctg ctgatgtgcc gtgccaagc cgcgcctgtg
61   gccgattacg tgctgctgca gcctagcgag gacgtggagc tcgcgagct gcaggcgttt
121  ctggacgaga actttaagca gctggagatc accccggcg actgcgaac cttttctcgc
181  gacacggacg tggtgaacca cctgctgaag ctgctgccgc tctatcggca atccagaagc
241  aagtgcgcgt tcctcaaggg ctatctctcg gagggctgtt tgcctcacac gcggccgcg
301  gccgaggtgg agtgcaagaa atgcagcgt atcctagagg ccctggacat tctcatcctg
361  aaactggtgg tgggcagttt tgccaatgtc gaggcgaaca gctggagat gttgctggac
421  aagttctcca aggatcagg ctgctggtg gaggtgcag gagttatggg cctggtggac
481  atggactgcg agaaaagcgc gtacatgctc gaggccgcg cggctgagac ggttgcgcca
541  ctgacgccac cggcggtggt tcaggggag cagaggtca gcagggaga gcgaggacgg gaaaacggtt
601  gccgccgtgt cggccttgc ctgtcctcg gttcggact cgtgatcc cgagaaacg
661  ggcgtcagc gtcctatgat gagttggct cacattaaca acgtctcctg tcctaccgtt
721  atgaggttcg accagcgct gctggaagag ggcgacgag aggatgaagt gaccgtgatg
781  tcgccgtcac ccagccgt gcaacagcag ccgccggtcg agcccgtgca gcagcagccc
841  caggcgagcg ggtctcacg tcggcctgc aaggagtcgg cgcggcaaga gactgctgct
901  acgaatcacg aacgcgagat ttgcgacata atgctctaca gccccgacgt gcctcgggag
961  gcggtgatgt cacggaccat ggtcaccata cctcctccc agataccctt tgtgggttcc
```

FIG. 8K

```
     1021 gcgcgtgaac tcagggcgt gaagaaaag aaacccacgg cggcggcttc gctgtcctcc
     1081 gcgtga SEQ           HCMV UL77
KEYWORD       PROTEIN
SEQ ID NO:    23
        1     MSLLRTFWRL PVAVFFFPHE ENVLRCPERV LRRLLECKAV TMRGCGWRED VLMDRVRKRY
       61     LRQELRDLGR RVQTYCEDLS SRVSEAEALL NQCCELDKGP SPETLLQPPC RPESSSPGTG
      121     VAGRSAVPRC LYSRHDAITG FAAAPSDVVA PSDRVAASAA AGASSTWLAQ CRERFLPGPV
      181     PRYPGITQND PFIRFHTDFR GEVVHTRFEN ASTWTFSFGI WYFRLRRGLF TQPRWERVYR
      241     LAQMDNFSIS QEILLGVVNA LENYTVYPTY DCVLSDLEAA ACLLAAYGHA LDESRQPPDS
      301     VATVLGELPQ LLPRLADDVS RETAAWEGPV AAGNWYAYR DSPCLRYYMP LSGGRRYHPG
      361     TFDREVLVRL FHRAGVIQHL PGYGTITEEL VQERLSGQVR DDVLSLWSPR LLVGRLGRDV
      421     PYFVHBQQYL RSSLTCLAGL LLLMHVTNAD SVFAPRTCKF TLADLLGSHA VAGGGLPSGR
      481     AGGEEESTGG RHGRVRNFEF LVRNYIGPWY ARDPAVTLSQ LFPGLALLAV TESVRSSWDP
      541     SRREDGAGGS DGGRAVLMQL SKSNPVADYM FAQSSRQYGD LRRLEVRDAL LFHYERGLGR
      601     LLSVTLFRHR VSTLGDSLPN VWDIYELLIF LVLGFLPSVA VL KEYWORD       DNA  (NC_001347 REGION: 111838..113766)
SEQ ID NO:    24
        1     atgagtctgt tgcacactt tggcggcta ccgtacgcg tattcttcga accgcacgag
       61     gaaaacgtgc tgcgctgccc cgagcgcgtg cttcgggcgt tgctggagga cgcgcgcgtg
      121     acaatgcgcg gcggggcggtg gcgcaggac gtgctcatgg acgggtgcg caaacggtat
      181     ctgcgtcagg agctcaggga tctggtcac agggtgcaga cttactgacg ggatctgaa
      241     gggcacgtgt ccgaggcgca gcgctgttg aaccagcagt gcgagctcga cgaaggcccg
      301     tcgccgagga cgctgctaca accacgtgt cgtccgcgtt cttgtcccc aggacggc
      361     gtggcaggag cttctgcgt cccaccgt ctttatagtc ggcacgatgc catcacggga
      421     ccgacgccg cccgtctga cgtggtcgcc cgtctgacg cggtcgcacgc gtcagcggcc
      481     gccggtgctt cttctaccctg gctggcgcag tgccgcgagc ggccgttgcc cgggacgta
      541     cctagctact tggaatcac gcagacgat cctttctac gattcacac cgatttcgc
      601     ggcgagtgg tcaacaccat gtcgagat gcctctactt ggactttctc ctttggtatc
      661     tggtactaca ggctcaagcg ggggttgtac acgcaaccac ggtggaaacg agtgtaccat
      721     ctggcgcaga tggacacttt ttccatttcg caggactga tgctcggcgt ggtcaacgct
      781     ttggaaacg tgacggtgta tccgacgtac gactgtgtac tctccgattt ggagcccgcc
      841     gcctgtgcta tggcgcctta cggacatgc cttggggag gccgagatcc gccggactcc
      901     gtggcgacg tgttgggtga gatccctcag ctgttgcgg gtctggccga cgagtgagt
      961     cgtgagattg ccgcttggga aggccccgtc gccgagggta acaatacta cgcgtatcgc
     1021     gactcgcccg atctacgcta ctacatgccc ctaagcgggtg gtcgtcacta tcaccccggc
     1081     accttgatc gtcacgtgct ggtgcggctt ttccacaaac cggggtat tcagcattgg
     1141     ccggatacgg ggacgataac ggaggagttg gtgcaaggga gtctgtcggg ccaggtgcgc
     1201     gacgacgtgc tttctctctg gagtcgacgt ctgctgtcg gcaagctggg tcgcagcgtg
     1261     ccgtctttg tgcacgaaca gcaatatctg cgttcgggac tgcctgcct ggctggctg
     1321     ctgtgttgt ggaaggtgac caacgcggat agcgtcttcg ctccgcgcac gggcaaattt
     1381     acgttggcg acctgctgg ttcggatgcc gtagccggcg gcgggttgcc cggggcgc
     1441     gccgggagc aagaggagg ctaccggga cggcaccgga gggttcgtaa ctttgagttt
     1501     ctggtacgt actacatgg gccgtgtac gcgcgcgacc ccgagtaccc gctgtcgcag
     1561     ctctttccg gcctgctcct gctggcgtc accgagagcg tgcgaagcg ctgggatccc
     1621     tcacgtcgcg aggacagcgc cggaggtggc gacggcggc gcgcgtgct catgcagctc
     1681     agcaagagca accccgtggc cgactacatg ttcgcgcaga gtccaaaaca gtaggcgat
     1741     ttacgtcag tagaggtacc cgatgcctg ctctttcact acgaacggg gctaggggg
     1801     ctgttgtcag tgaccctgcc gcgtcacgt gtccacctc tgggctgtc cctctttaac
     1861     gtcaangata tttacgaact gttgtacttt tagtgttgg ggttattcc gagcgtggcg
     1921     ggtggtaa SEQ           HCMV UL79
KEYWORD       PROTEIN
SEQ ID NO:    25
        1     MRARSEENPA VPRVRTGKFS FTCANHLILQ ISEKMSRGQP LSSLRLESLK IVRLICVLLF
       61     SRGLETLLLR ETMRNLGVSD HAVLSRRTPQ PYPRLYREL RQAFPGLUFS AAVFDETFAA
      121     RLSQRLCHFR LSGGLLFRFV QRHTGLPVVF FSDLARRGHI LFSLGTLYGH RLFRLAAFYT
      181     RHWGARAYEF LIRHICQRMV YFYLIGTGKW RITPDAFSIQ RSRHETCIFT FIMEDYKYFA
```

FIG. 8L

```
241       GILSRHPSRP SPQQQQHRHP GPPRPPLSRP ASSCLSPEAV LAARALHMST LANDV

KEYWORD      DNA (NC_001347 REGION: 115205..116092)
SEQ ID NO:   26

1 tcacacgtcg ttagctagcg tcggcatatg aagggcgcgg gcggccagta cggcctctgg
    61 gctgagacag gacgaggcag ggtgagaaag aggaggatgg gggggacggg ggtggtggtg
   121 ctgctgccgt tgtgggtgcg gacggtgcgg gtgccgggac agcgtgccgg cgaacgttct
   181 gtaatcttcc ataataaaag taaaaatgcc cgtctcgtgt cgactccgct ggatctcgaa
   241 gggtcgggg gtaatgcgca tcttgccggt gccgatgaga taaaagtacc acattttttg
   301 acagatgatg cgaatcaagg gttcgtacgc ttcggcaccc cagtggcgcg tgaagaaggc
   361 cgccagacga aacaagcggt gtccgtagag cgtgcctagg gagaagagga tgttgccgtt
   421 gcgcgccagg tcttcgggga aaacgaccgg caggccggtg tggcgctgca caaagcgcgt
   481 cagcagtccg ccgctcaagc gcgggtgaca caggcgctgg ctgagaaggg cggcgcgcgt
   541 ttcatcgaac acggccgcct caaagtccag cccgggaag gcctggcgca gttcgcggta
   601 cagatgaggc cagtagggtt gcggcgtctt gcgactaagc acgggcgtggt ccgagacacc
   661 caggttgttc atggtttcgc gcagtagcag cgtttcgaga ccgcggtgaa agaggaggac
   721 gcagatgagg cgtacgatct tgagttcttc caaacgcagc gagctcagcg gctgtccgcg
   781 cgacatcttc tcgctaatct gtaatattag atgattggcg caagtaaagg agaatttgcc
   841 cgtgcggacc cgcgggacgg cggggttctc ttcgtcgcgg gccatcat SEQ          HCMV UL37
KEYWORD      PROTEIN
SEQ ID NO:   27
1         MAGRAPRRLG CDALIVVGSS ANPRRVLHVF VHVRACNLTQ ELSTGEDARF CRFREVNVER
61        VRAVFRALYR ACPIHVRTEP ERVKLVLGRL LLGPVAVPCF CDGRVEGHGE SLVPTTQFCR
121       GPLLYVHRRC CCGSVTAGRA LSYHVLENRV ATHVLRGLLS LTEWNRELPS LFCDCPGGGS
181       ASGTEERYAM ACLPRDLSLH LDDYPYLMVE IGRVLSVSEV DDYVTAVSGY LGEAAAPRIQ
241       VHXKLLEGLN VRPQAPCALD ATKDFFLLEL QKLWIAVEYH HEVTSRFFGR VLAQLHRDRA
301       RVMRALHLPE QTVCHLSTFV LSRFKRQVLY FKLQVSYGKC RTGHAGRSGG GGNCGNQGRH
361       RLLCYRRLSV TFADTDTVWR NLFYVYYELA RDLGSHGYEG RPVSRGYGVS CASRTSRLSP
421       SESTVVSAGG HALGSTALPT TSAGRKLGLF RDPAADRVRR YVCIISRLMY ARYGERWRKH
481       CQSRSETGER EEETLESGE TDATPPPDPT GQQLARAYQE HNRRKHLAVQ RYARCRKKLI
541       SGMEFREVTG VSLDRIAVSA FNTNRVINMK AALSSIAASG LGVRAPRLPK SMIHSFVMYR
601       HTPKEPACTV STFVGNDAVY IRSLNVRISG SYEEPLYSLG VYRLHVNIDH FFLPAVVCNS
661       NSSLDVHGLE DQAVIRSERS KVYWTTNFPC MISHTNNVNV GRFKAATAIV PRVSGADLEA
721       ILLKELSCIK NMRDVCIDYG LHRVFTQLEL RNSYQIPFLA KQLVLFLRAC LLKLHGREKR
781       LQLDRLVFEA KQRGLFDYSK NLTARTKIRH TCALIGSRLA NNVPKILARN RKVRLDHLGR
841       NANVLTVCNR VEAHKIPRTR LKVLVEVLSA LGSISSTPST REVIHQTLFR LCSARAATSG
901       LCSSPPPLCV SSSSSVPSVP TSVSVDGSSE PTSPRARPAS R

KEYWORD      DNA (NC_001347 REGION: 129286..132111)
SEQ ID NO:   28

1 atggccggcg ctgcggcgcg ccgccctggc tgtgacgctc taatcgtcgt tggcggctcc
    61 gctatgccgc gccgggtttt acacgtcccc gtgcacgttc gcgcctgcaa cctcacccaa
   121 gagctatcga cgggcgagga cgcccgcttt tgtcgtcccgc gacccgttaa cgtcgaacgg
   181 gtgcgcgctg tttttgcggc tctctacccgt gcctgtcccga tacacgtgag gacccgagccc
   241 gagcgtgtca agctggtact gggtcgtctg ttactgggac ccgtggccgt acccctgtttt
   301 tgcgacggtg aagtggaggg ccacggtgaa catctggtac ctacgacgca gtttttgtcgc
   361 gggccgctgc tctacgtgca ccgacgttgt tgttgcggat ccgtgacgc cgggcgcgcg
   421 ctgtccctacc acgttctcga aaaccacgtg gccacgcatg tgctacgcgg attgctctcg
   481 ctgacggaat ggaatcgaga attgccgagc ctcttttgcg actgtcctgg cggcggtggc
   541 gcctcgggaa ccgaggaacg ctacgctatg gcctgcctgc cgcgcgacct cagcctgcac
   601 ctggacgact atcccttacct gatggtggaa atcggacgcg tactcagtgt cagcgaggta
   661 gacgactacg taaccgccgt ctccggctac ctgggcgagg ccgcggcgcc gcgcatccag
   721 gttcactaca agctgctctt tggactcaac gtgcgtccgc aagcgccgtg cgcgttggac
   781 gctacacgcg acttttttct gctggagctg caaaagcttt ggctgggcgt tgaatatcac
   841 cacgaagtca cgtcgcgagtt tttcggtcgc gtactggctc agctgcatcg cgaccgcgcc
   901 cgcgtcatga tgcgcgcttcg cttgcccgag cagaccgtgt gccacctgag caccttcgtt
   961 ctcagtcgct tcaagcgaca ggtactgtac ttcaagctac aggtgagcta cggcaagtgc
  1021 cggactggtc acgctgacag aagtgggggga gggggaacg gtggaaatca gggacaccac
```

FIG. 8M

```
1081 aacctactgt gttatcgacg cctagcgtc acatttgccg acacagacac ggtgtggaga
1141 aactttct aagtttatta cgaactagct cgggatctgg ggtccatgg gacggaggac
1201 cgaccgtaa gccgcggtta cggtgtttct tgcgcttcga ggacgtcgcg actgtcaccg
1261 tcagaatcga cggtggtttc gggaacggaa aacgcgcgt attccacga gtccccgacg
1321 agagcgcgg gtcaacagct gtcactgcg cgcgaccggg ccgcagtcg cgttcgacgt
1381 tacgtatgca ttatctgcg tctcatgtac gctcggtacg gggagagatg gcgtaaacac
1441 tgtcaacggc ggtcggagac gggagaagag gaggaggaag agacgctgga atcgggggag
1501 actgacgcca cgccgccatt tgactttacg gggcagcagc tgccccggc ctatcaggaa
1561 cacgacgtc gtaaacatct agccgtgcag cgttacgcgc cgtgccgtcg taagctcatc
1621 ggcgggatgg agtttgccga ggtgacggga gtgagtctga accgcatgca cgtcaaacgct
1681 ttcaacacca accgcgttat caatatgaag gctgcgctct cgtccatcgc cgcgtcggt
1741 ctgggtac gagcgcgcg gcttcccaag aacatgaccc acagtttgt gatgtacaag
1801 cacaccttta aggagcccg ttgcacgtc agcactttg tttccaacga cgccgtctcc
1861 atcaactgc tcaagtcaa tattcgcggt tcctaccccg agtttctgta ctcgctgggc
1921 gtgtaccggc tgcacgttaa tatcgatcac tttttctgc cggccgtggt gtgcaacagc
1981 aactcctcgc tgcacgtgca tggctggag gacaggcgg tgattcgctc ggagcgcagc
2041 aagtgtact ggacacccaa ctttccgtgc atgatctcgc atactaacaa cgtcaacgtg
2101 ggctggttca aagggctacc ggccattgtg ccgcgcgtct cggcgcgca cctggaagcc
2161 attctgctca aagactcct cgtcatcaag aacatgcgcg acgtgtcat cgattacggt
2221 ctgcacgtg ttttcacgca actagagctg cgcaattcgt accagatccc cttcctggcc
2281 aagcagttag tgctgtttct gcgtgcttgc ctgctcaagc tgcacggtcg agagaagcgg
2341 ctgcagttgg acgcctagt atttgaggcg gcacagacgg gtctctttga ctacagcaag
2401 aacctcacgg cgcacaccaa gatcaagcac acttgtgcgc tcatcggcag tcgtctagcc
2461 aacaagtgc ccaagatcct ggcccgaaac aaaaagtca aattggatca cctggacggg
2521 aacgccaacg tgctgacggt gtgtcggcac gtggaagccc acaagatccc tgcacgcgc
2581 ctcaaagtgt tagtcgaggt gctgggcgcg ttgcagagta tcagcggtac gccgcacacg
2641 acgcaagtga tcaccagat gttgtttcga ttgtgctcgg aggacgcaga cacatcgggc
2701 ctgtgttcat ccccctcacc attgtgtgtg tcctcatctt cctccgtccc ttctgtccca
2761 acctccgtca gcgttgacgg cagttctgaa cccacgtcgc cgcgagcgcg gtttgcatca
2821 cgatga
```

```
SEQ          HCMV UL89
KEYWORD      PROTEIN
SEQ ID NO:   29
  1    MLRGDSAAKI QERYAELQKR KSHPTSCIST AFTPVATLCR KRYQMMHPEL GLAHSCNEAF
 61    LPLMAFCGRH RDYNSPEESQ RELLFHERLK SALDKLFFRP CSEEQRASYQ KLDALTELYR
121    DRQFQQIRNF WYDFKKWLDG GFSTAVEGGA RAIRLEPFQK NLLIRVIFFI AVTKIPVLAN
181    RVLQYLIRAF QIDFLSQTSI DIFRQKATVF LVFRRMGKTW PTIPIISFLL KHNIGISIGY
241    VARQKRVSQF VLKEVEPRCR HTFAEDYVVE NKDNVISIDH RGAKSTALFA SCYNTNSIPG
301    QNFRLLLVDS AHFYKKEAFY TILGFLAQNT TKIIFISSTN TTSDSTCFLF RLNRRAFFDML
361    BVVSYVCEHH LHSTTEKGOA TACPCYBLHK FTFIZLNSQV BRTANMFNFG AFMDEIIGGT
421    NKISQNTVLI TDQSKEEFDI LRYSTLNTRA YDYFGKTLYV YLDPAFTTER KASGTGVAAV
481    GAYBHQFLIY GLEHFYLBDL SESSEVAIES CAASMIISVL SLHPYLDELR IAVEGNTHQA
541    AAVRIACLIR QSVQSSTLIR VLFYHTPDQN HIDQFFYLMG RDKALAVEQF ISRFNSGYIK
601    ASQELVSYTI KLSHDFIEYL LEQIQNLHPV TLASGTTAKY SAFRQDRISQ DLITAVIMAT
661    YLCDOTHAIR FRVS

KEYWORD      DNA (NC_001347 REGION: 133394..139320)
SEQ ID NO:   30

1    ctagctgacc ctgaaacgga tggcgtgtat atgtcacac aggtaggtgg ccatgatgac
 61    ggcgatgata agatgtccg agatacgatt ctggcgttg gccgagtaac gcgccgtcgt
121    gcttcgca agcgtgaacgc ggtcaggtt gtgaatctgc tccagaaagat actcgatggg
181    gtgctggctc agcttgatgg tgtaggagac gagctcttgc gaggcttga tgtagccga
241    gttgaaacgc gagatgaact gttcaacggc aagcgccttg tcgggccca tgaggtagaa
301    gggctgttcg atgtgttct ggtcgggtgt gtggtagaag agcaacggga tgagcgtgct
361    gccctgcacg ctctgtggga tgaggcaggc gatgcgcacg gccgccgct ggttggtgtt
421    gcctcaccg gcgatgccga gttcgtccag gtaagggtgc aggtcagca ccgagatgat
481    catgtcgcga gggcactgg cgatggctac ctcagaactc tggagaggt cgcgcaaaa
541    gaaatgctct aggccgtaaa tgagaaactg gtgtggtag gcgcctacgg ccgccacgcc
```

```
 431  gtcgagctct tccagttgct ggaaaaggaa tcgcgcggac agtcgcgcaa ctcggtgtgg
 481  catctgttgc gtatggacac ggtctcggcc accaagttct acgaggcttt cgtcagcggc
 541  tgtctgcagg gcgccgaggc cgcggacggt tcgggtggcg gcggctgcac ctacacgggt
 601  tcgcgcgacg gcgtctcgcc gggcatccag ttcggtatca aacacgaggg cttagtcaaa
 661  acgctggtgg aatgttacgt gatgcacgca ctgcagacgg tgcgcgacgg cctcggtctg
 721  ctcatgacc ccacgtgggg gctgctgggc gcttccatgg aactgtgctt cggcgtgctc
 781  aagcagggta gcggtcgcac cttgctcgtg gaacgcgtg cgcgcgtcta cgagatcaag
 841  tgccgctaca aatattgcg caaaaggag gaccccttg tcagaaagt gctgcggagg
 901  cacgacgcgg cggccgtgga ctcgctgttg cagtcacacc cggtgccgga cgtggagttt
 961  cgcggtgaac gcgagaccc gtcggcacgc gagtttatgc cttccgcacga cgcggcgtcg
1021  ttcaggcaa cgctcaagag cgcgcgcacg ctcaagccgc ccgaacgct cgccgagtac
1081  ctgccgatc tgctgtatct caataaggcc gagtgttcgg aagtgatcgt gtttgacgcc
1141  aagcacctga gtgacgacaa cagcgacggg gacgtccacga tcactattca cggcgagtctc
1201  ggctagccg cgggcgacgg cgctggcggc ggcgctgatc accactgag gggcagccg
1261  gcgcattcga cgccgcgat acctttcgag gacgaaaaca cgcccgagct gctgggccgg
1321  ctcaacgtgt acgaggtagc gcgcttttca ctgcgcggctt ttgtcaatcc gcgtcaccag
1381  tattactttc agatgctcat tcagcagtac gtgctcagcc aatactatat aaagaagcat
1441  ccggaccgg agcggatcga tttcgcgac ctgctacgc tctacctggt ctcggccatc
1501  ttccgcagc gcgaggaaag cgaactgggc tgcgagttgc tgccaggcga tcgcgttttc
1561  cactgcgac acatccgct cctgctcatc gtcacgcccg tggtcttgga acctcagttt
1621  acggcatg ccgtctctac cgtgctagaa cgttggagtc gcgacctgtc ccgcaagacg
1681  aaccctacga tatgggtgcc gaactctgca aacgaatatg ttgtgagttc ggtccaacga
1741  caggtgagcc cctga
```

```
SEQ         HCMV UL100
KEYWORD     PROTEIN
SEQ ID NO:  37
   1        MRPSHVDKVN TRTWSAGIVF MVITFVNVSV RLVLSSFPHL GYPCVYYRVV DFERLSMEAY
  61        NVMHLSTPML FLDSVQLVCI AVFMQLVFLA VTIYILRCWI KISMRKDKSM SLNOSTROIS
 121        YMGQSLTAFL FILSMDTFQL FTLTMSFXLF SWIAFMAAVK FFCLTIFNVS NVTQYRSYKR
 181        SLFFFSRLRP SLKGTVQFRT LIVMLVEVAL GFNTTVVAMA LCXGFGNWFF VRTGRMVLAV
 241        FVVYAIISII YFLLIEAVFF QYVKVQFGYR LGAFFSLCGL IYFIVQYDFF LSNBYRFGIS
 301        WSFSMLFFIW AMFTTCRAVK YFRGRGSGSV KTQAIATASS ESVAVLSNHD SLESKRLPES
 361        EDDDDDEDFE DA
```

```
KEYWORD     DNA (NC_001347 REGION: 146157..147275)
SEQ ID NO:  38
```

```
   1        ttaagcgtcc tcgaagtctt catcatcgtc gtagtcctcc tcttcgagga ggcgacggct
  61        ttccagcttg tgtggtgac tgagcacagc gacttcttg ccggaggtg tggccagcgc
 121        ctgtacttg acactgccgc tacgcgtgcc gcgaagtagc cggacggcgc gacacgtcgt
 181        aaccatgccc catatgaaaa agagcatgcc agcgagcaca ctgtgcgcg tgggtattc
 241        gttgctgagg aagtatcgt actgcacgat ggggtagatg aggccgcaga gtccaagaa
 301        gcgcgcagg tgtagccga attgcaactt gacgtattga aaaagacgg cctcgatcag
 361        taaaagtag atgatgaga tgatagcgta gaccacgaag acggctcaca ccatgtggcc
 421        tgtacgcacg aaaaagttgt ttccgaagcc gtagcacagg gccatggta caacgtggt
 481        gttgaacaca agcgtacct ctaccggtt gacgctgagc gtgcggaact gcacgtacc
 541        tttgagcttg gggtccagac gcgagaagca aaagagtgag cgttttgtag tggggtactg
 601        cgtgaccatg ctcacgttga aatggtcag gcagaaaaag tgcacggagc ccatgaaggc
 661        gatcatgctg ggcagccgaa atgacatggt cagtgtgaat agttggaacg tgtccatgct
 721        gagaatgaag aggaaggtg tgaggctgtc gccatgtca gaatgtcga gtgtcgacta
 781        gttaggctc atgccttgt ccttcagcat gctgatcttc atccagcata acaggtagta
 841        gatggtaacg gctaaaaga cgagctgcat gaacacggcg tagcacacca actgcacga
 901        gtctaagaaa agcataggcg tgtcaggtg aattacgttg taggccgaca tgttgagcct
 961        ttcaaagtcc acgacgtgat agtagacgca gggtagccc aggtgcggaa aattgctcag
1021        cactagatgc acgtgacgt tgacaaaagt cagcaccatg aaaacgatag aagcgctcca
1081        tgtccgtgta ttcaccttac acacgtgcga gggggccat
```

```
SEQ         HCMV UL102
```

FIG. 8R

```
KEYWORD    PROTEIN

SEQ ID NO:  39
  1        MTAQPPLHRR RHPYTLFCTS CRLSWYGLLE ASVPIVQCLF LDLSGGRASP RLMTFVVRGD
 61        RLPFAEVPAV HRASYAALAS AVITDADERR RGLEQRSAVL ARVLLEGRAL IRVLAPTTTF
121        VQIQTDASSY EILEAAPAIG VETRALSRAL SLPHVAKLVV IGSYPEVHRP RVVTSYACKV
181        SERYSTHAHK RLRSGYYAYD LAMSFRVGTH KYVLERDDEA VLARLFEVRE VCFLRTCLRL
241        VTPVGFVAVA VTDEQCCLLL QSANTRLYDV LFRGPAGQPP LRDYLGPDLF ETGRARSPFF
301        PGFPPVPVTA VHGLHTLNEE TALDAAAEVL SWCGLPDIVG SAGRLEVEPC ALRLGVPEDK
361        WQVEGTRASG GAVRLNATAF RERPAGGORR WLLYPLPRDD GDGEONVVEV SSSTGGARPF
421        SDDATFTVHV RDATLHRVLT VDLVRVLAR CVRARDFNPY VKYSERLRTY AVCEKFIERL
481        RFRSRHAFWQ IQSLLGYISE RVTSACASAG LLRVLSRGHR EFYVIDSYSG HGPVSAEVCV
541        RTVVPCYWRK LPGGDDPGPT CRVQESAPGV LLVWGDERLV GPFRFFYGRG GAGGSPLHGV
601        VSGFRAGHCG GACCGRGCVVT HRESGGGGGS GVGDADHASG GGLDAAAGSG HRGGSSDRVSP
661        STPPAALGGC CCAACGGWLS AVSHVLGRLP ALLSERVSVS ELSAVYRSLL FRFVARRNDV
721        CFWLLRFQPG SHEVPRHAGV IDCAPFHGVW ASQGGIIVQS RDTALAADIG YGVYVCKAFA
781        HLTACVEVWA RELLSSSTAS TTACSSSSVL SSALFGVTSG GSGCATVSPP SCGSSSATWL
841        SSRCRWVRSL AVDAQHAAKR VRSKGLRFPR LAA

KEYWORD    DNA (NC_001347 REGION: 147453..150074)
SEQ ID NO:  40
```

FIG. 8S

```
2401 accacegett gtetettta tteagttata tactacgact tgaagtcagt aacttagtaa
2461 tattcaggaa cggagacggt gtchactacg tattgttatt cttegtagga gacttggcta
2521 gaggagagag aagagtgggt gagetagatg gaggttgacg agaacacga tgctaagcgg
2581 gtggattcag aggggactgag gttttttcgg ctcaacgett aa
```

SEQ          HCMV UL104
KEYWORD      PROTEIN
SEQ ID NO:   41

```
  1    MEKNHWNEKS SGAKKSKEKD LTLSTIRSIL AADERLSIKA SSYLGVSRGV DDEAVIDIFP
 61    TGQTKSFLRL LRGPLGTCRG QSMKQVLRDP CVLRKQLLYG VCKTLFDTIT VRRVAEEWKL
121    BAALFPYPAL DEEOLEQYLL VWSAELSQSV QTEVILGELRD IILYQYADNOD YSLMVDRCVT
181    VELVPILDVR TKPSELAERA QFVERAVQRA TETKPLRQDL LQANLALLIQ VAERLGAVRV
241    ARAPEVRVFK KVRSERLEAQ LRGKRLRLYV AAEPLAYERD KLFTTPVAH LKGEILRVDG
301    LCRHQKICQL LNTFPVKVVT ASSRELNEKR LVEMMEQHDP GSDAKKSIMK PLLNVSDSKS
361    EIGIEDSVDS FLQDLTPSLV DQNRILSPARG PGGPGYGPG GAVVGSPAGS VGLLPPPGP
421    AAPERDIRDL FRKQVIKCLS EQIQSQVDSI QRLATLRQTW KRRVREKRDL LTPYASRERD
481    SRELGARDAE LYRLPVLRAV EKARDAAPPR FLAVEDNRLV ANSPFSQFVF GIESLERFLT
541    QLRERSEYFRT FRLRRLVTRQ GAERAIVISR YTVERVTLFV LCRILALGTL DPVPERYLQL
601    SFGKEIVARAY ODSKFCRYVE LICSREKARR ROWSPERAGG VPERGTAGSG SPSTLERSAP
661    RPLITAGSER RGFSRVGSFN NGSFDDPREA GSFYGPR
```

KEYWORD      DNA (NC_001347 REGION: 150936..153029)
SEQ ID NO:   42

```
   1    ctagtgaaat cogtatggac ctocagcaag cogaggatca tcaggcactc cattcgaaa
  61    taggccgaca cgctctggcc cgcagcgctc ctctctgccc gtgatcaaga ggcgcggcgc
 121    gggaccttttca agtgtcectg cgccgcgct cgagtcagtt ccctttctg gcactccgca
 181    cgccgcttgc cggatcacttt gtccgcgacg cgccttctcg cggctgcaaa tcagctccac
 241    gtatccgcaa aacttgctgt ctgtcctagga ggcgcacg atctgccgga aggagagctg
 301    caggtaggcc tcgggtactg ggtcacgct gccagcgcg aggatgtgac acagataggg
 361    caggtcagg cgtctacgc tgtaattgga gtagacgatg gatctttcgg cacttgatg
 421    cgtgaccaga cgccgtagga gaaaggtacg gaaatactcg tttccacaa actgcgtgag
 481    gaaagcgttcc agegactcgg tgccgggcaa gaactgagag aagagctgt tgccactag
 541    gggtgtggct tccaccgcca gcgacgaa gggcgcagcg tcgacgcc tgcgaacgc
 601    ctccaacacg ggcaggtgt agagttcgga gtacgcgcg cccaggctca tggagtacta
 661    gcgcagagag gcgtacagcg tgagcaggta gcagcagttcg agcacgaat tctccagggt
 721    ctggttaagc gtgcgcaggt cctggatctc gtccactga gactgatctc gctcctcag
 781    gcacttgata acctgcttct taaacaggtc gaggatgca cgctcagacg cagacggcta
 841    gggtgacga ggcagaccgc cgacgtgcc cgcacgcgag aagcccggcg cgcgcaggg
 901    tccaccacg acgggtcagc ccggccacg tgcggtagt agaacgttt ggtccacag
 961    cgaggggtc aggtactgca gaaaggactc gacgctgcc tcgatgcgga tgcagattu
1021    gctgtcgag acgttaagca aaaacttcat aatggactu ttggcgtaga tgccccggtc
1081    gtgtgtcca atcatctca caggcttctt gagttgaga tccggcgcgg tggcggtaaa
1141    cacttttcaca ggaaggtat tgagcaactg gcagatcttt tgctggggga agagaccgtc
1201    gtcgcgcaga atctcctcgt gcagtgtgc caacgccgtg gtgaacagca gcttgtcgcg
1261    ctcataagcc agggttcgg acgccagta cagcggaty tgcttcagc gcagctgca
1321    ctccagcgc tccgagcca acttatttgaa gaccgtaccc tcggcgcgt tggctacgcg
1381    cacgcgacag aggacgctgg ccaactgcag aacgacgcag aggttagact gcagacggtc
1441    ctggaccagc gggtgtgtct aggtggccg ctgcacggcc gcgcgtacaa attgcgcgcg
1501    ctcggacgca tccacggct tgtcctcac gtccagcagt ggtcaacgtc ccaacgttac
1561    gaaccaatcc acgtagagac catagtcgtc gttatcggag tactgatata aaatgtcgcg
1621    gaggccgcca agcacgccg tttgcaagct ctgcgcaaa gaggcgctca acaccacacag
1681    atactgctcc agtccatatt cgtcagcgcg gggtaggga actcgcgcca cgtgcaactt
1741    ccactcctcg gccaagcgcc gcacccgtat ggtgtcaaag agcgttttgc acactccgta
1801    gagcgcctgc ttgccgcacca cgcacgggtc gcgcagcaca tgtgcatgta ttggacgcg
1861    acacgtccca agaaagccgt gcagcaaccg caggaagctc atgtctgcc ccgtcgggaa
1921    aatgtcgatg acggctcgt catcaagcc gcggccacg cccagtacg acgacgctt
1981    gatccaaac ctccgtcgg cogcaaggtt agaaggatc gtcgacaagg taagtcct
2041    ctagacgag cgcttcgcg ccgaggattt ttgcttccag tggttcgct aact
```

SEQ          HCMV UL105

FIG. 8T

```
KEYWORD    PROTEIN
SEQ ID NO:  43

1        MSMTASGTP  RPTPKYDDAL  IINLSSAAKI  ERIVDKVKSL  SRERPAPEDF  SFQRFPGISR
 61        VERTTDNNPS  AATTAAATTT  VHSSASSSAA  AAASSERGGT  RVPCVDRSPP  PPFRALLVTS
121        TAGAGKTSSI  QVLAASLDCV  ITGTFVIRAQ  NLSAILGRTS  SAQVKTIYPV  PGPVSKSVPL
181        ADGAVSRETL  ERYKVCRPSE  RTTIQRLQIN  DILAYRSFVLA  DIVDKCLNSW  SRKASASASA
241        KARAACKDLS  RLCRSNIIVI  DECRLMLRKN  LQVVVPFYYF  YNALGDTRLY  RERRVPCIIC
301        VGSPTQTRAL  ESRYDRYTQN  KSVRKGVDVL  SALIQREVLI  NYCDIADNRV  NFIBNKRCTD
361        LDFGRLLKYN  KFGIPLKESR  VAYVDRPVSP  PSSIRNPSYR  REMTRLFLSH  VEVQAFFKRL
421        REQIRLSERH  RLFDLPVYCV  VWNRAYQELC  ELADPLGGSP  QPVELNFRQN  LARIINTSQF
481        VDRNLSGSIT  REALSPAAPV  VATNESSVQA  RGGGSSVIGS  TGSRDETAFF  QDDQTTTAPG
541        SRETLLTLRI  YYIKGSSVGV  NSKVSACVIS  TQSTVERFVD  ILQKDTFIER  TFCEQAAYAY
601        SLVSGLLPSA  WYYPYVSPYT  TEERLRELAR  VSLPDVSSLC  AAAAATAAAF  AWSGGERPIR
661        NRVDADRSQS  GQSVPVSQRN  RHGQERTRDI  PCLENRRDQS  DAITDAELMD  RTSLYADPFF
721        LRYVKPFSLA  LLSFEETVRN  YYTFRDIFLK  RYQLMQRLTC  GRFATLPLVT  YNPRRVVFKA
781        RGQISSQTES  PVGMLSNVSP  AQFYTLEGYT  SDNVLSLPSD  RRKISPSVVQ  RGLSRLVLRQ
841        ALGFLFYLCV  NVSRPVESAQ  GKSLSVGTTV  DYBLPSRTAN  TIRKSQSDSL  DKVAVGFGGR
901        PKSLKESHIY  VAMSRVTDPR  RLMNNVNFLR  LPYEKNTAIT  FYTCSRALKDK  RTTLIF
```

```
KEYWORD    DNA (BC_001347 REGION:  152857..156727)
SEQ ID NO:  44

1  atgtcgatga  gggctcgtc   atacacgccg   cggccaagc   ccaagtacga  cgacgcttg
  61  atcctcaacc  tctcgtcggc  cgccaagata  gaaaggatcg  tggacaaggt  caagtcccta
 121  tcgcgcgagc  gatttgcgcc  cgaggatttt  tcgttccagt  ggtttcgtc   catcagtcga
 181  gttgaacgaa  cgacagataa  caaccactct  gtcggaacta  cdgccgcggc  aacgacgacc
 241  gttcactcct  ccgcctactc  tatcgccgac  gctgcgcct   cgtcggcgac  gtccggcacg
 301  cgcgtgcct   ggtcgacccg  ttggccttca  ttccctcc    gccgctcgt   cgtcactccga
 361  aggcgggcg   cggcaagac   tcaagcata   caagtgctgg  cggcaatct   agattcgtg
 421  atcacggta   ccaccgtgat  agacgcagc   aacctaggcg  cgatcctcaa  ccgactcga
 481  tcggagccagg  tcaagacctat  ctacgggta  ttcggcttcg  tcagccagca  cgtcgacgtg
 541  gctgcaaggcg  ccgttagcca  cgagacgcag  gaacgctcac  gcgtgtccga  gccgcacgag
 601  gagaccacca  tccagcgcct  gcagatcaac  gatctgctcg  cctactgcc   ggtcatcgcc
 661  gacatctgg   acaaatgctt  aaatatgtgg  gagcaaagg   cgcttcgga   ctccgccgcg
 721  gccgcagccg  acgcctgcga  ggacctctcg  gagtgtgcg   agagcaatat  catgtcatc
 781  gacgagtgcg  gccttatgct  gcgctacatg  ctgcaggtgg  tggtgttttt  ttactacttt
 841  tacaacgca   tgggcaagcca  cgcacttac   cgacagttga  cgttgcacga  catcactcga
 901  gtcggttcgc  ccacgacgac  cgaggcgctg  gagccgct    acgaccacta  cacgcaaaac
 961  aagagcgtga  gcaagggct   tgacgtgctc  tcgcgcgtga  ttcgaacga   ggtgctcatc
1021  aactactgcg  acatcgccga  caactgggta  atgtttattc  acaacaagcg  ttgcacggac
1081  ctggactttg  gcgacatgct  caagtacatg  ggcttggta   tccgctcaa   ggaggagcac
1141  gtggctacga  tggatatgtt  cgtgcggga   ccngctcca   tcaagtcga   cctagtacga
1201  gccgagatga  cgggcttt    tctctcacga  gtcgaggtgc  aggttacct   caagcggtg
1261  caggagaga   tcgcctgag   cgacgcaac   cgtctcttg   atctgccgt   ctactcgtg
1321  gtcaacacc   gagcgtacca  ggagctctgc  gagctggccg  acccgctggg  cggctcgcg
1381  cagccgtcg   agctctggtt  cgcagaaa    ttggcgcga   tcattaacta  ctcgcagttt
1441  gtgaccaaca  acctctccag  cgagatcacc  aaggaggcga  tccgccgc    ggcggaccgtc
1501  gttgcaacca  acaactcct   cgtccaggct  cacggaggcg  aggatctgt   aatcggagc
1561  acgcgcgca   acgacgaga   gggtttttt   caggagatg   atacacaca   tgcgcccgat
1621  agcctgaga   cgctgctcac  cttgcgcatt  acctactca   aggccgttc   ggtggagta
1681  aactctaagg  tgcgggctg   tgtatcgga   taccagggca  cggtcgaacg  tttcgtggac
1741  atattgcaaa  aggacacgtt  tatcgagcga  acgcattgca  gacaggctac  ctacgctac
1801  tcgttagttt  cgggcctgct  cttcagcgc   atgtactact  tctacgtgtc  gccctacacg
1861  acgagagaa   cgttgcgtga  gctggcgcga  gttgagtgc   cacacgtgag  ttcgctcgc
1921  gcggctgcg   acgccacgg   cgcgctcca   gcttggagcg  gggagagaa   tcggataaat
1981  aatcagtcg   acgcggattc  ttctcaggg   ggccagagcg  tgccggtata  tcaacggatc
2041  gaacagccgc  aagaggagac  acacgacaca  ccctgcctgt  ccaacaaca   tgacgactcg
2101  gacgtcatca  aggacgccga  actcatggat  caaccagtc   tgtacggga   tccctttttt
2161  ctcaaatacg  tcaagccact  tagcctggcg  ctgcttctt   tcgaggagac  ggtgcacatg
2221  tacaactact  tccgcgacat  ttttctcaag  cgctaccaga  tcatgcagcg  tctcaccggga
2281  ggtcgttcg   cgaagttgcc  gctcgttacc  tacaatccgc  gtaacgtggt  gttcaaggcc
```

FIG. 8U

```
2341 aactgtcaga tcagctcgca gaccggctcc ttcgtgggca tgcttcgca tgtgtcgccg
2401 gcgcagaagt acacgctcga gggctacaca agcacgaacg tgctcagtct gcccagtgac
2461 cgccaccgca tccaccccga ggtggtgcag cgcggcttt cgcggctggt gctacgcgat
2521 gagcttcggt tcctctttgt gctcgacgtt aacgttcgcg gcttcgtcga gtcggcgcag
2581 ggcaagagtc tgcacgtgtg caccaccgtg gactacggc tcacttcgcg cacggccatg
2641 accatcgcca agagtcaggg actgtcgatc gagcaggtgg ccgtggactt tgggaccat
2701 cccagaaacc tcaagatgag ccacatctac gtggccatgt cgcgagcac ggacccgaa
2761 cacctcatga tgaacgttaa ccgttgcga ctgctctatg agaagaacac cgtatccacc
2821 ccatatatct gtgcgcgct caaagacaaa cgcacacgc ttattttttg a
```

```
SEQ         HCBV CL114
KEYWORD     PROTEIN
SEQ ID NO:  46
1           MALEQNMLAN IADNKGSLIT PUEQARVFCL SADWIRFLSL PDHGTVLLRQ TVAAVGGARQ
61          LENVYFAFEN VHNSYLCFF EQVRVVIVGQ UFKCCGSASG IAFGTLAGHF FPFSLNGVFR
121         ELARTVCGFQ RFASGCLOAW AEROVLLLNT VFTVVKGQEG SHRHLGWQTL SNHVISKLSS
181         RKEHLVFMLS GADAHTCEYL IGRRHLVLK SCRFSPRGTT RAFVGSDHFI LASAYLDTHY
241         SETMDWSLCG
```

```
KEYWORD     DNA (NC_001347 REGION: 163901..164653)
SEQ ID NO:  46

1           tcacccacag agtcgccagt ccatggtctc taggtactgc gtgtccagat acgagttggc
61          cagtataaaa tggtcgttgc ccacgaagga gcgctggtg ttgcgcgca acgggtgcca
121         ggacttgagt accaagtcc gccgtcgtc gatcaggtac tcgcaggtgt gcgcgtcgge
181         gccccaccgc atgaaccaca gatgtcacg gcgctctgac agcctcgga tcacatggtt
241         actcacgcgtc tgccagccta agtgacggtg agatccaggc tgtcctgca ccaggtgaa
301         cacgtgttg agcagcagca cgcagcgtcg cgcccaggcg tccagcaaa cgaggcgg
361         acgctgaaac cgtccaccg tacggacag ttcgagaaac acgttgttga gggagggcg
421         cggagtcgg ccgccagcg tgccgaaggc caggcagctg gcgctgcgt cgccgtacgg
481         gtcctggcc acgatcacca cgcgcacctg ctcggcgga cacagatga tccacggtg
541         tacgtgctcg ggtgccgggt acaccatcta gagttgccgc gagccctcca acgacgcac
601         cgtgtgcgc agcagccgg tgtacgtgta gggaagctg aggagcgga tccagtcgge
661         gtcagacaaa aacacggag actgctcgta gggggttaac agagagcctt tattatcagc
721         aatgttagcg agcatccact gcttgagggc cat
```

```
SEQ         MCMV M44
KEYWORD     PROTEIN
SEQ ID NO:  46
1           MKCGRKVKEH EPPTLAFRLK GVKTBIQQLK GVVASLKENT TVSFLFTFSL IVQTVKRQFI
61          AKIVFNSGCL YITOKSFSAK TINNSIPLLG NLMYNTSSRD LTKFTVQDTS DLSAKVCMSA
121         FDVSMSFSGA CVENQDTIHE TGDSAARVGL DSAVVGELLR WIAPNIRFKE WSRKQSTGSS
181         TVQITLHANF FTVKFSLGCN SELEFTASNR IAFREVKNLE ITVQAKNLHQ ALCNCVVTKL
241         ACTLRVMFDK STMLYVASKN AFFTIRHFLS ESFPVKCGDVG FDRMFVANSN NYQMSSSSAG
301         DCFRACVDGV IGNCYKKREER VSREAGGGGS SGGGVVSDD RGGGSSCKD SKYIEQHKITS
361         FNVSKGBVGG CAGGGGSURG GYFNDTKESS DSEDSVTFEF TPNTEKQKCA A
```

```
SEQ         MCMV M50
KEYWORD     PROTEIN
SEQ ID NO:  47
1           MEIDKNVGAD LIENTRRILS LDEREIRITD TALICKNPNY SLCDAMLTTD IVYPVEYLLS
61          TWECRSGFTA CEVFNNTGCR VSLSCYIGFF BRLKDLKRVC DENFLSVREA LVVTLADIER
121         IKFCOKGVLT NCVVRKSNSG NSTNIEVVRF GPDNRACYQA LLRDIYARRM TSVPTDCSSL
181         ICRKAFCLAA APERRFFPPF SFMQRSGSLR KHGPVLTFRI AGOGKAAENQ PAAASPTSYS
241         TSSPAAPSRD QDQTQRPPPA SDTNVTAART TYGSRTISFL TRNANAIKCA LILAAKIALV
301         LLNLLYNRAA RSAGRF
```

FIG. 8V

```
SEQ          MCMV M51
KEYWORD      PROTEIN
SEQ ID NO:   48
1            MLTIAHRLQR  ESISSGRHSS  RISAVFSSPI  RASSESRSQH  AASSSSSIVS  RPESVDEDEE
61           EDGVRPSVTS  GGVLVGCACS  NSSLTRNESI  VVSEGSQALY  IASAATANNG  DSVRRRGGDA
121          PDDDEAAGAA  PVFAEECNLD  ALFERFFGDG  GADAIRFEPM  LPSVYELTLP  SIDSRLNFID
181          VGRRHAAFLR  HVYGGCDRCE  RAAVLNERMK  LPTAVIFELL  DVNGILERRE  TTD

SEQ          MCMV M52
KEYWORD      PROTEIN
SEQ ID NO:   49
1            MYRAWDPSLF  TIDSFLVNEL  LLHAHPTKTP  PSVTECQTPS  SSSSSSTDSG  RETMLEEEEA
61           ACCDLDSELA  RIGDENTAEI  RELCLPLEID  SPQNLCAIVS  ICLARDPQQK  WLLDYCFLCE
121          KCAAAPRTAM  ATLIVATEFL  HLMKLHFRDI  AFDNIPKERI  VTIFDFRAHF  FINRCYTQRD
181          EHPVMVERIT  LARMAVTRAL  LTEDDAVPYT  KRRKIQYKLP  KRPAFARFEE  LRLLDKYRRA
241          TEGSFARVLF  YIWSGTNVMF  NTTLTDLAIK  KSKALKALRT  RQSEIEPSVG  PVFLSPIPTF
301          RLRNATTTVC  LLCELMACSY  RDNVFLQQLR  ERIPNYSRNN  LKIIDRFQLT  MAEILSRGRN
361          SEFPQQLKNK  DVSIYVTSSF  ETLAAASRPG  TERPFELSAL  TYLVLRQVGY  IGVYRHLFAD
421          PLCAANMRST  DPNILFFDVP  NEYLNEAKLA  ICSTNAYPSR  VERDFWLYAH  MFKAFQIIKR
481          NEKTKIQLSD  FLRDFSQVLE  SHDFSLVDPS  PIVEKYV

SEQ          MCMV M53
KEYWORD      PROTEIN
SEQ ID NO:   50
1            MFRSPEGEER  DAADREEEEG  GEARRESRMM  NGPRRVKRAR  ERPAGGGLRT  PLRSPSACRC
61           SSPSPSRQWQ  QRRRAEKRST  TPTDPPPPSK  RSAASARAGA  AAPESEYLNV  KLSELHDVFQ
121          RHPDLEQKYL  KIMKLFITGK  ESIRLPFDFK  SHRQHTCLDL  SPYGNDQVSR  SACTTCKETT
181          RLPTASDSNV  AFINQTSNVM  KRRKFYFGFR  KNMELLRMAA  NQPQLFQIYY  IVQSCVQSIV
241          PLITYDREMA  HNQLIFEKET  VHIFSQCIEQ  ILTVAKDAYG  VSLDIAHQRI  TLTARCLRLE
301          SSSLRIDVLM  LQRKVDELEI  PNETMERFES  YSL

SEQ          MCMV M54
KEYWORD      PROTEIN
SEQ ID NO:   51
1            MDTCVETFFN  PYLERKPRRD  WRRCEDWNKN  FLQVVPRGVL  YDGATGLIKV  QSGREPRMFY
61           AEKEYVLNPD  KPWPTLRTRG  WCRGPYSDEL  RFHTYDQVVM  LVLADSDEQI  SPRNKRHVVE
121          AGNVIRMFGA  TDEGVSVCVR  VFGQKAYFYC  ERMQSEDIKS  TYYDIADKVF  EPCSPFSVSI
181          SPVTKSSFYG  YGLGHIPNLY  RLSFMNWNNC  RKIGKRMLEE  GRKVYELGVD  PLANFLIDRK
241          IPSFGWCLAR  RYSVRAAGYV  SRAQLEIDCD  VADILPIEEQ  SNWPFYRCLS  FDIECMSGTG
301          APPAAENVDD  IIIQISCVCF  GVGEMVRHAY  DVRADLSTPA  VPSNHIFTIG  PCAFIPDVKI
361          YTFFSSYEML  RGFFIPLSWY  SPEFITGYNI  NGPDIKYILT  RAEKLYKMDV  GQFTKLRRGS
421          RMFVFSPEKG  KAGFGTGNTV  KVFRSGGIVL  DMTPVCTAKA  SSPNYKLDTM  AEIYLKKKKD
481          DLSYKEIPVQ  FRAGDEGRAR  VGKYCLQDAV  LVRELFEMLA  FRFEAAAIAR  LARIPLRKVI
541          FDGQQIRIYT  CLLEECSGRD  MILPNMFSLG  REAAAATEEA  AAGGEGDETS  EGENSNNSRT
601          VGYQGATVLE  FECGFREVPV  CVFDFASLYP  SIIMSNNLCY  STLLVEGSPE  VPEKDVLRVE
661          IGSQCHRFVR  ENVHRSLLAE  LLVRWLTQRK  LVRSAMKQCT  NEMQRMIMQK  QQLALKVTCR
721          AFYGFTGVAA  GNLFCLPIAA  SITKIGRDML  LATACHSIEDR  CSRPDFLSTV  LGLFPEAIDP
781          EALRVKIIYS  DTDSVFAAFY  GIDKEALLKA  VGALAANVTN  ALFKEPVRLE  FERMFVSIME
841          ICKRRYIGKV  HGSQMLSMKG  VDIVRRTACS  FVKAVVSDVL  HMVFWDETYS  EGTMKLSRMT
901          FDDLKKHGIP  CEFGPVVSRL  CRARDDLRLR  KVPVFEITLS  SVLSQEISCY  RQKNLPHLAV
961          IRRLAARKEE  LPAVGDRVEY  VLTLPDGCRK  NVPNYEIASD  PRSVVEAKLS  INAEKYYEQV
1021         VKAVTNTLMF  VFPROMPKRE  KFFSLVVPQR  IYIPDQFLHL  CGNVNELARG  GDDSDGGDSE
1081         KENMDTERSS  SHEAMET
```

FIG. 8W

```
SEQ           MCMV M55 (gB)
KEYWORD       PROTEIN
SEQ ID NO:    52

1    MSRRNERGCR  GGSWIAMSTA  LAVTIWCLLA  CTSEVIAAAS  TPGTTPKANT  DTSSETASAE
 61    TETATSGAAF  QKKEATPTQA  SKITGTTIVP  FVNETERMYS  VOIDKYPYRV  CMSVSTDLVR
121    PGKSIDCISK  TPRTPVQEGI  MIVYKQSIVA  HTFBVITYHK  DAIFQRSYAD  TTTNYYLGTS
181    VTKMAFPVWB  LDEVNRNWRC  YSAASBILNG  EVYVAYHEDS  IRNYTNVLVE  DDYBSKNSKR
241    YVTTKSRYEK  GAWTNRYTES  CNMBCVVVVT  KARSNTPYEF  FVLSSCEVVE  ISPFYDGERS
301    RPFEDYRNF  WIRKNYTMRT  YFGELAAPRK  VVELMAFLER  BIMSTIGWRIF  PRQNVTCDWK
361    KWQTVSRAIR  TDTNTSYBFV  SKBLTRTFVA  SENKIDYNTT  TEGKWYNTFR  CVYDEFVESV
421    BRVFEDRYNB  TRVKDGELEM  YPTTGGLIVL  WQGLKAKSLB  BLEKTRALMN  VSVGTVSPPV
481    TSAFENGTIA  ASVAARRKKS  LDNIDPVVTG  ITYAQLQFTY  DVLKDYIRDA  LBNIMDAWCR
541    DQKRTBFMLR  ELSKINPSNI  LSAIYERPVT  AKLAGDVIAM  SECVKVDQSS  VKVLKDNRIF
601    QDGKVVDCYS  RPLVVPQFIM  STRLSSQQLG  ENDEIMLGTF  BTESCDTNSR  KIPVVGTVGY
661    EYBDYRFRBV  TSLBNIQLVD  TLIGLDIKPL  ENTDPKVLEL  YSRSBLRASN  VFSLDCIMRK
721    YNSQKQBIRT  LGAKVNDNTP  STILQLDTYM  QSLGVAGHGI  GVRIGAVGBA  VSSYVNAVTG
781    FLTNPPGGFT  TILLVIGVLA  VVYLIFTRQR  BAARFPVEYF  FPYATQTAVQ  YAFFGGABGG
841    LESGPPGAPG  LRRKVNAGGS  DDSGRAWTSD  RKGLSRTYTE  QDALLIIRAL  RQLDDSQRTR
901    KAQQKATRLF  TGILDRLKGN  DTSGYQRLPA  RDSDFEY

SEQ           MCMV M56
KEYWORD       PROTEIN
SEQ ID NO:    53

1    NANWTLQKLC  VVCSKCNECA  NDVECLKYCD  PNIVSMDSTA  PRRNGVMVIH  LYRTLYPALV
 61    SQNRVQTSVL  TLYMEMLLQG  LYDTMREIDM  ALTDFGTHRD  RQRYTRRVLK  LDSCNRHESI
121    TFTFAPELAL  TIDLATLNDV  BRLLCKINCV  YGAVDASQGV  AVCKRLLSLI  ARLCDICPVA
181    GPETYRETVT  CFQCYEELNA  VFSQRSEIOR  RMQGLLCDHI  TERKVLVQLD  NDAQYVEQDN
241    GDIAIPAPSV  KSIIRAIKSL  AGFSPASYAY  IDDASERLAG  YPLFSEIPDR  IYSLSDKTTW
301    SRTSSAIVRN  VGITMRQLNV  SHBLWRTLRT  ELSRYRYGED  LEDVFTLGRG  BFYGQERIYV
361    GSIFRAPSKV  YDMITSMSIR  BFENNPLFNR  LRESWEITAR  IKSLIEBIRG  VGOGPAAGAA
421    ASRAEAASGA  GAGGGEGAGA  AAGRGNTGGD  RGASTTTAMS  SALBCGDPLL  RVHDVNKSVR
481    VBKRAYLEKV  SEMGYEKVMA  CIRNQBRLVT  KLVDVNLVGT  VCLEAVGKIM  NGFLSRQRSI
541    TERETYPDVA  QSLGYDEHLY  VINNLVHKRL  FSELLPQLEQ  QIYRFINGPM  PTHYLDRRPL
601    FYNVMAYAC  DGAGILFHVK  EDLVRCAQGF  VVFSUWMTVG  EMSFFAFADI  RELMDLQMMV
661    WAHIRBLVLS  VALYNEBTGK  QLALWRVEEG  DBISDGIILT  YNPESPLILR  RGDRBYRSRD
721    LYLLLYKHLS  VDSETIADAG  SRASVADLCQ  VERPGPIAEQ  RSSTQNVKKK  PKRMSLLELV
781    RDVDGAGSDD  LVPPCLYK

SEQ           MCMV M57
KEYWORD       PROTEIN
SEQ ID NO:    54

1    MADDDLSSLA  PVAPAVWMFF  LRKTRELADI  VAAMSLCDKA  TPVVIAPLLI  DLTVDRDFCG
 61    AVRTPNGTYE  GGVLRKVTSF  CPFAFFPRNT  DEILDVVSDH  GLVVRLCDDA  RRRPGVQAFR
121    FLANRDRTGV  DVLCDELGIA  PAEYTGRVVC  GNGLMRLLYA  GQLIPCPPES  VKVQVGAVDG
181    VKVPLYPYTL  PDGGADABBA  DGASSAVACD  DPWVLEHGPY  DFRLSEALFY  PMFTSWGQSL
241    RVCETSRLIE  AGLQQFVEDT  QQTVKLTPFK  KYRGYTSQKL  TAVEROQIMT  VDAVCSELAF
301    SYRSIYLDSV  YRFSTASRFL  SWPLVRNART  RADILONLRD  FQLRLARHIA  ALIPSSNSIL
361    YQTRIVFVPS  AGKGABENPS  AQDSLLKSIR  FFNGLTGMYD  DILRDAKKTI  RFEGAVGRDE
421    RYSPHRLAYF  CSTSPQLFST  LSWFPNRMSI  YSTCVTSGDT  VFSHIVNRGS  KLCGACGGRC
481    CRTCYATSFI  AVNTRLPGIF  KQIKKEFVVV  TLLSRAFADA  DALGNYCKRV  GLESREAGGG
541    GGGGAGSRTD  EVAAGPPAGG  AGGLNFVSVD  RMKYLGQVLD  YCKKRSLIDA  ITGEDIINVR
601    SKRDFVATVT  ALNQTIDDAV  CRFANDVPRS  GBGREDEISGS  TQSFNLDLSP  YATAFSPVLS
661    FQYYRTMFSI  IQNLALINAA  SYVVBMPLIT  AGISBWVALE  FQSICDARFT  TPLRKGFINV
721    RDTRNLESVE  FERIMDFRSF  QETSRYRKIS  TBIKSCKMSV  QSLKSCKIRN  RFISKFPQSS
781    VFFKKGALQR  KDPIKGCLSF  LLFRCHEKLF  PACGLSCLEF  WQRVLQDSIP  RSVSVGKVED
```

FIG. 8X

```
841        FTNLVRFLLT  VTDDYDESDV  VDIQPDCLLS  YVRWRFHRKF  LYMPGFRDYM  STIQGMSTRL
901        TPQNHSQFPC  LLKDAPKPVS  IAEYVLHFKK  MKLTGVKAPQ  VATIPREFVL  RNVFDGRSLV
961        SVSFAVEKYS  SSMGTRDVFQ  FGQIGYYVGS  GVDRSLNTGS  MSTQDYRFMR  YRYIIATKLV
1021       DVLIRASERE  NVMYDADVVR  SPYLAALDST  GLDVDPELAA  IAEIMEGRDE  GDIPEIDDTL
1081       FYVDQQEYIA  RSMYRSMRSL  ARPGVTDFSL  ASLPRATATN  ATAAGSAAGQ  GSSATEGGGS
1141       AAAADRSGPM  YDFSALFSRP  DEARDVNAGL  INGDDVRGDD  EFSLPSRRSR  L
```

```
SEQ            MCMV M70
KEYWORD        PROTEIN
SEQ ID NO:     55
1          MTVVLFATEY  DTPNIVVNML  SETPTERRLF  PLMIKYKPSN  RIEFVLQTQR  CPDSTRVRPV
61         FICDARRLSL  SEYVSTNTPL  PARVICAGID  ADATRELYSH  LFDRKKDETG  RDSENGSAGG
121        DLFSCLYSTL  KCLVHYNRSA  ILRYLWNTFL  SPTSPSWFLS  TYGTRROTLI  LYMSYYLFER
181        QYSTIQPTRD  YTRCFTADPG  RNLFTYINMR  DFMAPMNGSR  FRKQTARFAA  FAKARNARDR
241        RELEYVDAKI  NAPREESRLA  ADSCVYYYTL  AYRTALCREK  FLQYCERTAY  DRNLPDDQQC
301        ARENYLGRS  LDRELLISNN  TYFSVECYFQ  SYINVDRAKL  SPPRSYRGYD  WNTEADTNVG
361        YSSTATNLAI  SLRKLRSTCE  SLFSPLFPTL  MGLLRLCASD  RYVPPAEKSR  KRTSGGREKE
421        CETRVCRRNT  LLRDTSRPTG  PMPVPRVEMP  EKRRVFCRVS  AENWTERLLP  KDLMKNLPSE
481        YVSDECLTDA  VWLSEEDIAAS  CEVGEQLYRT  PRENFRENLP  VFNFVGDVDL  MLAEDLQGLS
541        RQEVFDLCRA  LRRTLIGAWR  HLFPEVGPDS  RPVFFFRSAC  PQNAAGAADE  AMLYGGOGYD
601        EDDDFRPERA  AAVVDYGDAV  RRPPFCVRR  KLGLRVIIFF  PFRTAAICAQ  TLKRLAGILG
661        HTLCLORELV  CKLNAISHPG  SCPDTGIYSH  CRSIRMPLWY  KLDKASGLML  HSRLNPIPIV
721        PAGYRDRPAS  FVLQQLCPQN  LTHBGRPPKR  DCSADQLTEV  VLEITDRACA  DSDGNFLQSR
781        ARPAMSPPRL  PLGPLLRAHL  SLESCQSAPS  LPTLVGPGGG  GGGGASSDYE  EERAVGSDEE
841        EDDDDVENLQ  AFARRIAWPA  LLRRTRNNYB  EEVQQQLEAA  TVFFAVGRTC  VAVRKGLYGR
901        ARDFSCLARE  NYTRQETVQV  FLDIRSDQKR  NVWATLNSRC  FTRRCNSNAK  QTRKLSLKISL
961        PSQY
```

```
SEQ            MCMV M71
KEYWORD        PROTEIN
SEQ ID NO:     56
1          MMMTDFGGGS  TGTSNARGGV  GGAIAAADDD  AGAAPPSCWR  RMLDFALCRR  TIROGSSYIV
61         LRADEDVDMA  ELGGFLMDNF  GNLGVSSADL  SETDRESBVT  KRLLRALLPVT  KRCVRRQTRL
121        DRLIANQCRP  RLRRAARIEC  QKSKRVMQAL  DIVILRILVG  RFTLSDECSV  EXILEKFSVD
181        QSTLCEVGRI  VRLIDMDREN  TQRLVDGREE  PAPPLCDING  VPSSSDLESQR  AATTYICSAS
241        DLIILRELDNA  PAAFDHLFGS  IDEILLRDEA  TSGTGRLHNV  GRRRDLERQK  QQHSQQMAAL
```

```
SEQ            MCMV M77
KEYWORD        PROTEIN
SEQ ID NO:     57
1          MSRLKTFRDV  PCIVAFEAHR  RNVLVFPREK  LARLRDESRL  RLRQYADDLG  RDARLRRRAS
61         EDLESLGREL  PNECERFRGR  IDQARQLLSG  PMSDILGQGS  GTEVAGTRGD  GGSVDNASQR
121        NKRMKAGGGA  SASSCSATGD  GGSRGVGDDD  DSRQQCHWVT  PNDPPISYST  DPRGSLVPFI
181        FNVSQANTFS  FGSWYYELKR  WLTNQPPKAB  VYRLTQIESL  SVSQELLWGV  LNAVSQVTVY
241        PGHDTVVSDL  EVAACLLAAY  QRALDPRAAV  PTTVEGVLRO  SGRVLRRALSD  QIAAESIAHSF
301        SGGRAFAYKD  PPSLRFYAPV  QQERRYAAGT  FDSNALVAVL  LRRGAIAQVP  GGATGVARAA
361        SGGPGDSAAA  AVASREVMSR  LSGAVSDDVL  ALWTLRLPGK  RLSCVVPNLL  QEQRYLRSGL
421        TAVLCLHFLR  KLLSSESVFS  GRAGKFSLRD  VFFDLCSGRD  APPPVEREIG  FAGGCVRNPE
481        FRMERYVVPW  TSRDPAVTVS  QLWPGLVLLL  YCESHRSGWD  LSRRPFERAT  ADGVSSAAGV
541        LWVQASRFMP  LVDYMLLQQT  AAFQKDVDRL  AAHDFALFRC  SNGIGRLLSI  TLPKSPVLTL
601        GQQFPNLQSV  YDSMYFPVLG  FLPVVSVT
```

FIG. 8Y

```
SEQ         MCMV M79
KEYWORD     PROTEIN
SEQ ID NO:  58
1           MYKTIRVGKF LHLSDDNHLI LHITTKLLGG QFLGSMRLES LKIIRLACLL TLGRGIELLI
61          LPETVANNGV SDNTILRRKI SPEFWRHMYS AMRARVPTET LHRAFSERSA AALGVSITGS
121         RACRALVSHL IPTETGLALS LFDKLLSDGN IFFSLGTVIG HRLFKLLKFF NRHWGKEAHE
181         PHIRTICQAV WFYLIAWKK LTVSPEAFSV QRSDHEIGIF SFLIQQYLTF TGTLARSTPF
241         MDKKEEGVIA DLLSGALE

SEQ         MCMV M87
KEYWORD     PROTEIN
SEQ ID NO:  59
1           MNSASDGSPA SLSCLDPALI VKSPTAPVKS APVCVNSFNL TREISPFEDS RLSQAVTVDE
61          EHISSIERTL MAAGPDPGAT DEDKARVVLC RLLMGPVAVP CYCDEWDVDQ YLAKCAYRCS
121         CPALYVSRSA CRCGAEGGGT MFTLIHDRYT THVSRGLLSY SEWNVRLTDV FCRCNAPRSQ
181         RYVMAVLPRH QSVFIEYYPY FLVCLARYLT VPEIDDCARS MTAHLGPAIA ARVGVRYRSL
241         PGANARPDPV TEVARRANYD LPLLELQKLR LNVSYRSAVT RDPFETVFSR PRRETCRVML
301         ALRSPGRQFL FPRWISMSRF RKQVLVFELS VRCTKSRKDS LKNALIFRKT SVLFACSDVI
361         WSNLFYTTYA WCAHRGPGGE SRLWGPSSSG GGARTESERG SGVRGRDQAT YASAAAAAS
421         TCQDASASAT BSGVAYSAPA RAATSARKAR PHAPAAFTVV GSGQSTAVSS TATQKYVRIV
461         DRLALVRLNF RERKLAAERA VGSGKGSVEG AVAGGTSGVQ TCVKAGEPVA VRSFDFCPYR
541         CLVRNRAAEG VRREGEGSVY GARKIGGRR FSRMTAVSLN NVAVNAFNTN RVISLKATIV
601         QTPRLSAFTV PRNMFHSFYM YKRFFESPPY TVSTFVSNDA ARTRSLRVNI RGSYQSFLYA
661         LSVYKLVVNI SNFYLPASVC NSNSSLDVHG IEDQGVIRSE RDKVYWTTNF PCMISNTDRI
721         NVGWFKAATA IIFKVSGVAL ENVLLKELAY VTSIDQLCVD YTLHRVFTVL STRNCKQIFF
781         LSKQFILFVR IMMLRICGLS HRLAVDRLIF RAIRQGVFDY SKNTVASCRI KRPCALVGIR
841         LAHKVFKVIV KRKKIKLDVL GRNAHHLTLC RHVDHACVDA SRLEALISVL DCLEKLTSID
901         RTKRALTRAR VRLCGGYRPR AATSRR

SEQ         MCMV M89 Ex2
KEYWORD     PROTEIN
SEQ ID NO:  60
1           MSIRGQNFWL LIVDEASFIK KEAFNTILGF LAQHTTKIIF ISSTHTTSDS TCFLTRLTSA
61          PSIMLNVVST VCEESHIQAFS EHGDATACPC YRLHKPTFTT LNSDVRKTRN MFMPCDSPNDC
121         INGGTNKINS ETVLITDESR EEFDLSRYST TNPQPHPHLG AILSYYVDFA FTSNRRASCI
181         GVAAVGTYRD QFIVGSLEHY FLKDLLCDSSE TSIADCVSRM LLSILRLSPF LSQVRVTIEG
241         NSNQAAAVRI ACHIKHNLLS AHAETLFYRS PDQNEIQQPF YIMNRDKRLA VEDFIAKPNS
301         SYIKASQELI SHTIKLSYDP VEYLLDQLRE IQRITLNEYV TYSAKRNNQS DDLVVALIRA
361         VIMCSPERST NFKFI

SEQ         MCMV M92
KEYWORD     PROTEIN
SEQ ID NO:  61
1           MFSSGRDPST GRPISRAGAR AHARGRGSCR CLRGGGCOMP NLCNPLTQEL NLRRMYVCVR
61          CRRTRICGLR RDCVVVRTQD GSVCIKTGLF YGSVFPGGCV SALRPVTRPR VGRINVVGVI
121         MSYVTYVLTA NADRYAGVIG GVIRGGWFRR PTRNAIYFTF NRVFRQRHAL QSVPISVIGQ
181         LFVQLVIGVR RKVTKYDSTV IRVSRRKRSD GLLKRMRFEY GNAFSFRTGR

SEQ         MCMV M95
KEYWORD     PROTEIN
SEQ ID NO:  62
1           MATAAGGVYA GGRDQQQQRP RATDVSTALC DVERALAAVER GRVSRADVRR YRRAVDAALI
61          DCEASSPRDR FRLIRTAGGN FLIVTNALFK DRTEQQPFCV LEGGGRASSR NRYEGIGTFS
121         AGSGHAFDGL LALERGTSGG GLITVPSAP GYVAKSVNTL SYDGRLLSRS YVLYFKQLR
```

FIG. 8Z

```
181        KSLSPDKRAI  VERILKFVDF  PSILDNNVQ  DVEKVLWLLF  CGPQSVCQNP  TCFGRDKECE
241        VSYPVLLPPV  FYOPITDYSA  YINLAELYVY  VWYRNYDFDS  EPTRCYKLGT  VAMDRVKKYL
301        QSVRQRFSDR  SVPVWPVSSR  TCVFCALYNQ  NRVCLELAKS  DVDVTSYSFI  IIKDCRDAAT
361        NVTLSHVLPS  QRVASLFPVY  SIGTLLRALC  DSNDGEERRK  RMRSTIDSAL  STTDDAV

SEQ            MCMV M98
KEYWORD        PROTEIN
SEQ ID NO:     63
1          MATTVLPPEA  TANTTIFRRI  VEDVVVDKSG  SFVTRNIESA  FGSSERNECL  VFDQSEQCLA
61         RVFDGLSSES  FDIYCLYNLL  DIKERVSSVP  VCALRLAYFR  SVFNKIGLTH  DGSPGLAINFL
121        SIVDREVSNA  GGESTVRDAV  GGVEGAQFAL  SRAIFKRLPAR  RLLEVMKAIS  RDSRGQAANF
181        VWHALRVDTV  SATRFHDVLA  TRKTAFRKDL  SVRHSSEAVR  FGMQCESAIA  QVLREFVAEG
241        RGGVSDIGLL  LDPASGVLGA  SLDFCSGLSR  DDDGLLVVAP  GAAIFEIKCS  FKYLRSBCDR
301        AVQGLLDDFG  LQSPADFILD  HSTPAVEFSH  QGQLPTSREC  LVSYDRVFRQ  SCKRERTGVV
361        SESIRLWIDG  LIKENSEVLS  TVFVFDANAA  EGSTSAATCV  SDDBEDFILS  AERPPLYLDL
421        FLFAAFAAFV  FANFRHSYYC  QTLVQRYVLS  QYYINARRDP  ERMSPDELFS  VYLVSAILRK
481        RDFSERGRVI  RINGHRSDCD  EVPLCVVVTP  VRLDPHEARD  AVSSVLDVNE  GDIGKRTGLA
541        LRVQSAVNSY  VAACIPTPRT  F

SEQ            MCMV M100

KEYWORD        PROTEIN
SEQ ID NO:     64
1          MLSLFDPPRH  PRTRDTCTMA  KAGVMTLSRV  DRMWLRTWTR  AIACCLLSFV  NIVVFSVAAH
61         FPGIGFPCYY  PRIIDFDNMS  LTMYRAIHRL  TPQLFLDPVQ  LIVYVIFTEL  IFFCVLSYYI
121        VCRVQIYFRS  ERGTQVNQST  RDINFNGDSA  TCFTFVLRND  TPQIFLLSLS  FRLPSMVAFS
181        KCMYFMCLTA  FVVTLVTRYE  SRERSAFALS  KIHPKLQSTI  RIRTAVVNLT  QLIIGFATNV
241        LAWSLALGFG  NSFFVKTAHV  VFGAMVAFAI  VACVYFSITE  SVLSRYMKVQ  FGYRISTILS
301        VCGAMYPIIR  YEALNASSYA  RDINIGITVL  LLLCVAFSVI  STVRFILBRN  KRYRAIALON
361        EEIRALRSDA  E

SEQ            MCMV M102
KEYWORD        PROTEIN
SEQ ID NO:     65
1          MERPWRRGLF  VHLSIYAFLF  EEDQAILQCF  FCEVADGDPV  VTRLFVFPVN  IPAEGELRTY
61         LLANYTSAIV  SSSLDTIFDS  TTAANSSGVG  GEVGSSGGSG  DECADRVARE  SSALAQIIWS
121        VGPDFEPLTR  FFTPVEIFSD  GVEILGSRRN  ENVRGIYRSI  LQTLAALTVG  RIRAIGSTHQ
181        MADAVSIETS  TAIQSITAEG  ATTEDAEDEC  RYRNTRAYRR  LSRGFVSRDI  TPFSIRIGNKR
241        FMLSEPSAVG  AKFSVSDVFV  IQDVKWRGKK  LRLCFPREFL  AFVFSDDQCL  VLLRDAMQRL
301        FKEVVGGFSG  LYPVFDFFCP  NMLASGGEPS  VFPFGFYAVA  VYSVPNRYDM  RPENGADAIN
361        BIRSLVGLPD  IYGVAGKVPL  VFEFGNAVDT  IDAVRMYDID  LHYADSRHFR  ISARLCVTHD
421        MGDAALDDES  SVARIYVGVS  GVCRISIVDL  RFAVLAMCLP  GPEFEFVLSD  VABRVDSMMI
481        DAFLQRLARS  SFRIFRRVKS  LEWYICKRVM  DACEDEGYPW  ILVRDDCEIF  VRRPVDCDQV
541        NFDTIVKRNL  APVWAELFGL  QYLCPVCRIT  VAMSGVLFAT  GNYLLSGFRD  EQKYSPTPGN
601        VGATGRLLSE  AVFCAFQSFD  NGAKDRIIRF  NATRHLRLSA  RRHETRFWAQ  RFAPGRSRVQ
661        QHDGVNDANE  FCGIRVCGRM  VAVQPLDGAL  HDNICYNDVV  KRTFBVLRVT  LEKVIIVLSQ
721        DQTNTAVVNH  STGEIDCVAI  RQEVTDDATV  SDTTGSDELD  AALRALREIT  ANTVSRVVES
781        TDTHNLIEEF  NDVFQQTMDF  VVERYSAFFS  MN

SEQ            MCMV M104
KEYWORD        PROTEIN
SEQ ID NO:     66
```

FIG. 8AA

```
1       MWRNQSLYRD  SKEURFKASD  LTRSTIRSIF  KADDIFRTKM  LSYLDNPPEP  PSDPLFFTDS
61      SLDLFSMING  TEGACIGQTI  SQILRDPSVF  RKQIFYAMMR  FLLNGISVGE  LSTAWASHKR
121     RFVPAEDGGG  AALEQFEIWA  DALRNTIVDS  IAALLEKLIY  TIAADDRYCR  YVDWIVSVGV
181     VPIAEVRTAE  REKAVDAAQR  RFLAEVAECK  LLCRPDPLRA  RTLEACVSAL  MTREVPNVPD
241     IRIHRLKSNG  SIECPSSKRR  LKRFIYAEPT  ILEEERLILT  TPLARTRYER  KRHMELRIHK
301     KICQLLNTNP  IKVVTTSRND  MNTKRIVELM  EKRDRQVDAR  TSIVKFLIRV  SDSKSEIGLS
361     DSVESFLQDL  TPSVDQAKLL  FSPAPLIQPA  PSCSGAQDIR  BLFRRQVIBC  LEDQIQDRVE
421     BIENLRLLNK  TWESKTPELR  DALDRYRSEG  RRRBGPFAFD  LQTLDTVNAL  RRVQGLPTAP
481     VTVDDNRVVC  NSFFSQFVFD  ERESDERLSR  LWEQBYPRCF  KPRRNVTNQG  AEDSISYSNY
541     TIERVLLPFL  TAVIEFRMLD  AIPERYLFLS  LSELANVIYE  PSKLQRYTDY  IRYRETIRVQ
601     AFLEREQAFA  AAAAAAGAAT  AAAPSERIGR  AFGQVSGPPT  KIRRLDETTP  GTANYRPQQK
661     TIVTTTPIGL  DFPSSPAPEV  SPSFRSPQQK  LETLRDRNVQ  RLNG
```

```
SEQ          MCMV M105
KEYWORD      PROTEIN
SEQ ID NO:   67
1       MEKRSSDESV  GNKGSDGGSG  GLSRYDNIFV  LNMSSASKIS  RIVDRVKSLA  LKRFSRESLY
61      KDWFRHMLDP  CAGLVAPELG  DDGSSEGKSN  AAMIVGDBEL  ARAPPFLSFS  CLLITGTAGA
121     GKTSSVQVLA  ANLDCVITGS  TVISSQALSS  ALNRSRSAQI  KTIFRYEGFN  SRHVALADRV
181     HLRRBDDVAF  DGDVDFICQQ  QNRDLSTYWF  VVSDIAIRAL  DGGKGRKDTD  DLCRSNIIVI
241     DECGVILRKM  LRVVVFFYTF  TRALRDSELY  RQRAAPCIVC  VGSPTQSEAL  ESRYDHRTQN
301     RDVQRGMDVL  SALISDFVLS  EYCDVAHNMV  MFINNKRCLD  LEFGDLLMRI  SFGLPLESER
361     VEYLRKFVRP  AGLIRDPARA  IDVTRLPISH  AEVKRYFTAL  BDRVRIYSQR  LIFEVEVYCV
421     LNNSAFREYC  ASMCTGEPTF  RFSTWFRKNL  ARISNYSQFT  DRNLSEDIQV  EELAQSCGGG
481     GAGGDDDGFO  LEGEMINSTL  LTRRITFIRD  GAVGVTAKTK  ACVVGYTGTF  DCFAEIIQKD
541     LFIERTPCEQ  AVYAYSLISG  LLFSAMYLPY  SSPLTTPEIL  RDLSRIPLPD  IPTLVIGANG
601     GDGARDSDDN  DSYESDLESG  GCPDRVSRGG  SSNGGGERYR  RRLTSDDEDD  FYDLSYVDRG
661     RQFBPFQLQP  FPQPQPQPRL  TMSAALPPRQ  IDERISDVEM  LCYSDIITDE  FFLRYSIPPP
721     VSSISFEEIV  RIYYIFRDIF  LARYRIMQRH  EMGAFGKTRL  VTYNRRUVWR  RRNCEIESQT
781     GSFVGMLTFV  SPSBNYVLEG  FSNHUVSIMD  AERNRIHRRI  LEKGLPRLIV  RDACGFLLIL
841     DYNVSKPSDV  IDGKSVALLT  MVDYGVTSRM  AMTIAKSQGI  GLESVAIDFQ  DNPKNLRMSQ
901     IYVGISRVVD  PDRLVLNTNF  VRNTYRRNTF  ITPFIRRALQ  NRDTILVF
```

```
SEQ          MCMV M114
KEYWORD      PROTEIN
SEQ ID NO:   68
1       MALRQWMLRH  IRVHDVGAAA  AGRDVSADVI  HQQAPALSIH  EAWMSELKLS  ATQASQLVRI
61      TDRVDQERRM  CTIYFEKSDV  HRWSRLCFPY  DVRVVILGQD  PYHDGSACGL  AFGTVRDRPA
121     FFSLVTVFKE  LRRSIPEFSW  PKCGCLDAWC  REGVLLINTV  FTVVKGQPGS  REALGWQILS
181     DRVLQALSEQ  REGLVELLWG  IQRQKKEYLI  DFRKNLILRS  SBFSFRAQGA  RSPFVGDWHF
241     VLANSYLSPR  GERVDWNVLC  SK
```

FIG. 9A

```
SEQ         HSV-2 UL5
KEYWORD     PROTEIN
SEQ ID No:  69

1    MEASGGEGSR DVEAPGFPPQ QPCARPAVDF REEAFLNFTS NHGVQPIIAR IRELSQQQLD
 61    VTCVRRLQWF RDVAALDVPT GLPLREPPFA AYLITGPAGS GKSTCVQTLN EVLDCVVTGA
121    TRIRAQHMYV KLSGAFLSRP INTIFHEFGF RGNHVQAQLG QSPYTLASSP ASLEDLQRRD
181    LTYYREVILD ITKPALAAEG GEDARNEFKA LTALEQTIGL GQGALTRLAS VTREALPAFT
241    SSNIIVIDEA GLLGRRLLTT VVYCNNGINA LYHTPQYSER LRPVLVCVGS PTQTASLEST
301    FEROKLRCSV RQSENVLTKL ICNRTLREYT RLSHSKAIFI HNKRCVSNDF GNIAKVLEYG
361    LPITESHMQF VDRFVVPESY ITNPANLPSW PRLFSSHREV SATMAKLHAY LKVTREGEFV
421    VPTLPVLTFV SVEKFDKYRR LTQQPTLTME KWITAEASRI TNYSQSQDQD AGHVRCEVRS
481    KQQLVVARNS ITYVLNSQVA VTARLRENVF GFDKTFRTFS AVLRDQSFVK TQGETSVEFA
541    YRFLSRLMFG GLIRFYNFLQ RPGLDATQRT LAYGRLGELT AELLSLRRDA AGASATRAAD
601    TSDRSFGERA FNFKRLGFRD GGFDDFFDDD LQVIFAGLDE QQLDVFYCBY ALEKPETTAA
661    VEAQFGLLER APLGSYLIIR ELFGEVFESA RFSTYVDKVI FRGCELITGS PRGGIMSVRL
721    QTDNYTLMGY TYTRVPAPAE SLRENHATAG VAEFLDESPL PTIVLRDQHG PMXVVNTDIS
781    SFVESIDSTE LAMAINADYG ISSKLAMTIT RSQGLSLDKY AICFTPSBLR LNSAYVAMSR
841    TTSSSFLFMS LNFLRENRR CDVISEHILS ALRDPDVVIY Y

KEYWORD     DNA (NC_001798 REGION: 11846..15249)
SEQ ID No:  70

1   ttatattgac gttcgttcgc ccggcgggtg cgtcgcgcg gcgagggga atatgcaacc
  61   gggcggggtg gggaggaaag aaggtttcag gttccggggg ttggtctgc gtcgtccagg
 121   gtggggctga tctgaattto cdgcagaacn tcgaccagta ggtctgttgt gcttgctggg
 181   aactcgccog ccgttgggga tacgggggcg gggggtgtgg tcgggcggac gtccaggggt
 243   gggttatcg accccgcgc cgcctcggggg gccgtccgt agatcgttgc ggtgatgtag
 301   atggtgtcgc gggtccacac cacgtcagg atgccggccg tgcacteacg gacgctttcg
 361   ccgtgcgatc agctgaccca ggagtcaaag gggtacgcgt acatatgggc gtccaaccag
 421   cgctccagcc tctggtact agccgtcct ataaggggt atgcgcaaaa ttcggcacga
 481   cagtcgataa tcaccagcag ccgatgggg gtgtgttgta teaccacgcc tcgcggggc
 541   aggcggtcct ggcgcgctcg accccgcgtc agaacgcgc ggtccctga ctcaacacg
 601   tgcaccacct gtccgcgtc cggacggga ctcgttagcg acgccctcga gtgatggag
 661   ctgtacgcga tggtcgtctg gggttcccc atgtctcggg ggggtggggg tgaatgtcac
 721   cgggccggg tcggtggga acgcaggga atggaggtt aatagacaat gacacacta
 781   ggatcgcgta gacgacgat tatgtgctog ctastgacgt cctcgcgtto gtggcgcco
 841   aggacgggt ttagattcat gtgcaggaac tggatgagg tggtcgggca catggctacg
 901   tacgocgtgt ttaggcgcga gttccggga gtgaagcata tggcgcatc gtccagacto
 961   agccctggg agcgtgat gtcatcgcg agtttggagc tgatccgta gtcggccttg
1021   atggccatgg ccagtcgct ggagtcgatc gactcgaaa actcactgat gttggtattg
1081   acgacagaca tgaagccgtg ctggtcccgc aggacgatgt gggcaggg ggactctcg
1141   aggaacgtcg cccacgcca cgtcgtctga cgccgcgca gctactccg gaacgcgaac
1201   aaccgggtgt acgtgtacco aatcagcgta tagttgtccg tctgcaggc caggacatc
1261   agacgcccga gcagcgacca ggtcagcaga tccagccca ggaaatgac attgtccacg
1321   taggtgctga agggggcgct ctcaaacacc tcccgaaga gtccgtag gataaggtat
1381   cgccccagaa aggccctctt caggagcca aactggggt ggacggcgc ggtggtctca
1441   ggctcctaga gggcgtagtg gcagtaccag acgtcccagct gctgttcgt cagcccggga
1501   aagataacgt caaggtcgtc gtcgggaag tgtcaggn ccccgtccg caggccagg
1561   tgcttaaaat tgaacgcaag ctccccgga gagcggtcgc tggtgtcggc ggccatggtt
1621   gccgatgcgc cggcggtgc cggcgtago gacaggagtt ctgccgtcag ctccctagg
1681   cggcgtagg ccagggtcct ctggtcgcg tccaggccg ggcgctggag aagttgtaa
1741   aagtgaactca gccccgaa catcaggcga gacaggaaa gttaggcgaa ctccacccga
1801   gtctcccct gggtattcac gaagctgtcg tcgcgcagca cagactgaa ggtccgaaac
1861   gtccgtcgca accccacaac catcttoggg aggcgcggg tcaccogac ctggcgttg
1921   aggagtacg tgatgtcgtt coggcacg actagctgt gcttgctgtg caccteacag
1981   cgcacgtgcc acggtctg gtactgactc tgggagtagt tggtgatgcg actggcgttg
2041   gccgtgatcc actttccat ggtcagcgtg ggttgctcg tgacgcgtcg atactcgtca
2101   aactctttga ccgacacaaa cgtgagcacg gggagggtaa acacaacaaa ctccccctcg
```

FIG. 9B

```
2161 cgagtcaact ttaggtaggc gtggagcttg gccatgtacg cgctgacctc cttgtgggac
2221 gagaacagcc gcgtccaccc cggaaggttg gccgggttgg tgatgtaact ttccgggacg
2281 acaaagaggt ccacaaactg catgtgctcc tcggtgatgg gaaggccgta ctccagcacc
2341 ttcatgccaq tccggaactc gtgctccaca catcgttgt tgttaatgaa aatggccag
2401 ctgtcgaga gcgcgtgta ctgcgtagg gtgggttgc agatgaggta cctgagcacq
2461 ttttcgctct gccggacgga gcatcgacqt ttttggtgtt cgaagtgga ctccagcgag
2521 gcgtctggg tcgcgaccc cacgcacacc agcaacggcc gcaggcggcc cgcgtactgg
2581 gggtgtgt acagggcgtt aatcatccac cagcaataca ccacggtcgt gagtaggtgc
2641 cgcccagga gccggcctc gtcgatgcaa ataatgttgc tgcggtgaa agccgcaga
2701 gccccgtgtg tgaccgaggc caggcgcgtg agggcaccct ggcccagcc caaagtctgc
2761 tctagggcgg tgagggcgtg gaactcgttt cgcgcgtctt cgcccccgt cgcgccagg
2821 gcccgattgg tgatgtcgag gatcacctcc cagtagtacg tcaggtctcg ccgctgcagg
2881 tcctccagcg aggccgggct gctggccagg gtgtacgggt gctgcccag ctggcctgg
2941 acgtgattcc cgcgaaaccc gaactgggtga aagatggtgt tgatgggtcg actcagaaac
3001 gccccgaga gcttaacgta catgttctgc gcgcgattc ggtgggcgca cgtgaccagc
3061 cagtccagga cctcgttgag ggtctgcacg cacgtactct ttccggatcc ggcgttgccg
3121 gtgatgagat acgcgcgaa cggaaactcc cggagcggca ggccgtcgg gacctccag
3181 gcgcccacgt cccggaacca ctgcaggcgc ggcaccctgcg tgacgtcgag ctgctgctgc
3241 gagagctctc cgatgcgtgc gatgattggt tggaccgt gcatgtcgt aaaattaaa
3301 aacgcctcgt ccctgaaacg caaggcgggt ctggtccgg gctgctgtgg gggcggacct
3361 ggtgccagga agtccgcga gcctccccg caggacgccg ccat
```

SEQ                 RSV-2 UL6
KEYWORD             PROTEIN
SEQ ID No:          71

```
  1    MAAQKARAPA MRTPGGDAAL CAPEDCNVRV RPTPGTMLFR EILLGQMGTT EGQGVYNVVR
 61    SSEAATRQLQ AAIFHAVLRA TTYRDLEEDW RPHVVARGLQ FQELVRRYPN AREGDIAGVA
121    ERVFDWRCT LRTTLLDFAR GVVDCFAPGS PSGPTSFPKY IDWLTCLGLV PILRKTREGE
181    ATQRLGAFLR QHTLPRQLAT VAGAASPAGP GLLDLAVAPD STRMAEYDRV NITYNRRGE
241    WLVRDPVSGQ RGBCLVLCPP LWTGDRLVFD SPVQRLCPEI VACHALREHA RICRLRNTAS
301    VRVLLGRKSD SERGVAGAAR VVNKALCEDD ETRAGSAASR LVSLIINMKG MREVGDINDT
361    VRAYLDRAGG RLIDTFAVDK TLFGPCKGGT GRGGRPQDPG ARFQQLRQAF QIAVVRNING
421    PLEGTINNLF GTIERLRETN AGLATQLQAR DPRLRPAQRG ALEREQRAAD RAAGCGAGRF
481    AEAQLLRADY DIIDVSKSMD DDTYVARSFQ KQYIPATYGQD DERLSKWLER ELVRCFKILR
541    RRHKQGQETS ISYSSGAIAS FVAPIFRIVL RAFHAGRLIT GSDVILGREE LWEAVFKKTS
601    LQTYLTDVAA LPVADVGRAA LPRPPSFTPA DFRASASPRG GSRSRTRTRS RSPGRTPRGA
661    PDQGNGVERR DGFFHARR
```

KEYWORD             DNA(NC_001738 REGION: 15248..18163)
SEQ ID No:          72

```
   1   atggcgcac agcgcgagcg ggcgcggcg atgggacgc gggcggcga cgggcgcta
  61   tgacgcgga aggacggctg ggtgaaggtt cacccaccc ccggacgat gttgttcgc
 121   gagattctcc tcgggcagat ggggtcagg gggtcagg gggtcacaa cgtcgtcgg
 181   tccagcgagg cagccaccg acagctgcag gcgcgatct tccacgcgt cctcaacgcc
 241   atgacgtacc gggacctgga gtaggactgg cgcgccacg tggtggcg aggcctcag
 301   ccgaggcgc tggttcgag gtacggaac gcccggagg gcgatatcg cggggtggcc
 361   gagcgggtgt tcgaccgtg gcgatgcacg ctcaggacga cgtgctgga cttgccac
 421   gggttcgtag actgcttgc gccggacggc ccacgggggc cgacccgct cccaaatat
 481   atgactgga tgacgtgct gggctggtt cccatattgc gcaagacgcg cgaggggggag
 541   gcgacgcaga gctggggc gtttctcagg cagcacagc tgcccgca gtgggccacg
 601   gtcgccggg ccggagcg cgccgccg gggcttctgg atctggccgt cgcgttcgac
 661   tccacgcgca tgggggaata cgaccgtg cacatctact acaacctcg acggggggag
 721   tgggtgcgc gaccccgtgt cagcgcgag cgcgcgagt gcctcgtgct gtgcccccc
 781   ctgtggacg gagacgcct ggtcttcgat tcgccgttc agggctgtg cccagatc
 841   gtcgcgtgcc acgccctcg ggaaccgca cacatctgcc gtctgcgcaa cacgcgtcc
 901   gtcaaggtga tgttggggcg caagagagac agagcgcg ggtgcctgg cgcgcgagg
 961   gtcgtcaata aggcgctggg ggaggatgac gagacgaagg ccggctggga cgctcgcgt
1021   ctcgtgcggc tcatcatcaa catgaagggc atgcgcgaca cgggcgacat caagacacg
1081   gtacgagcct actggagcga ggcgggggg cacctgatcg acaccccgc cgtcgaccac
```

FIG. 9C

```
1141 accctccctg ggttcggcaa gggaggcacc ggcagcgggt cgcgccctca ggaccggggg
1201 gcgcgaccgc agcagcttcg ccaggcgttt cagacggccg tggtcaacaa catcaacggc
1261 atgctggagg gctatatcaa taatctcttt ggaaccatag aacgcctgcg agagacgaac
1321 gcgggtctgg cgaccagct gcaggagcgc gacgcgagc tgcggcgcgc ccaggagggg
1381 gcgctggagc gggagcagcg cgcggcggac cggcggcgg ggggaggcga gggcgcccg
1441 ggggaggcgg atcttctccg ggccgactac gacattatcg acgtcagcaa gtccatggac
1501 gacgacagt acgtggccaa cagtttccag cacagtaca tcccgcgta cggccaggac
1561 ctgagcgcc tgtcgcgcct ctggagcac gagctggtgc gcgcttcaa gattctgcgc
1621 cacgcaaca agcaggcgca ggaaacgtcg atctcgtact ctagcgcccg gatcgcctca
1681 ttcgtggcca cgtattcga gtacgtgctt cgcgccccca gagcgggcgc gctcatcaca
1741 ggctcgatg tcatcctagg ggaggaggag ttatggagg cggtcttaa gaaaaccgc
1801 ctgcagacgt acctgacaga agtcgcggca ctgttcgtgg cggacgtaca gcagcggct
1861 ctgccccggc ccccctcccc aaacccagcc gatttccggg cgagcgcgtc ccgcagggac
1921 gggtcccggt ccaggaccg gacccgatcc cggtcgcccg ggagacgca gagggtgcg
1981 cggaccaggt gctggggcgt cgaccgcagg gatggccgac cccacgccg ccgatgaggc
2041 aacggccgcc gccatcctca aacaggccat cgccgggac cgcagtctgg tcgaggtggc
2101 ggagcggatc agcaaccagg cgctgctgcc catggctgc gaggtgcgcc aggtcagcga
2161 tcgccagcgc cggtttaccg cgacagcgt cctgcgcgtt gacgtcaccc ccaggggggcg
2221 gttgcggtt gtctggacg ggagttccga cgacgctac gtggcgtgcg aggattactt
2281 taagcggcca ggggaccag cgacgtatcg cggtttgcg gtcgtcgtcc tcacggacaa
2341 cgaggaccac gtgcacagcc tggccgtgca cccctcgtt atgctgcaca ggctctcctt
2401 gtttcgcccc acggacctcc gggacttcga gtcgctcgc ctgctgatgt acctggagaa
2461 ctgtccccgg agccacgcca cgccctgct gttcgtcaag gtgtcggcgt ggttggggt
2521 cgtggccgga cacgcgtctc ccttcgagcg cgtccgctgc cttctccctc gcagctgcca
2581 ctggatcctg aacacgtaa tgtgcatggc gggcgtgaag cccttcgacg acgagctagt
2641 cctgcccgac tggtacatgg cccactacct gctggccac aatccgccca ccgtcctctc
2701 gccctgttt tggccaccc cgcagagctc tgcgttgcag tgcccgggc cgtccccg
2761 caaggactgt gtggcctata accggccgg cgtcatggga agctgctgga atccaaagga
2821 actgcgttcg gctctggtgt actggtggct ttcgggggagc cccaaacgac ggacctcgtc
2881 gctttttatt cggttttgct aactcaggaa aataaa
```

| SEQ | RSV2 UL8 |
|---|---|
| KEYWORD | PROTEIN |
| SEQ ID No: | 73 |

```
  1 MEAPGIVNVE SSVSAITLYA VWLPPRTRDC LHALLYLVCR DAAGPARARF AEVSVGSSDL
 61 QDFYGSPDVS APGAVAAARA ATAPAASFLE PLSGPTLWRA LYACVLAALS RQTGRWALFV
121 PLRLGWDPQT GLVVEVERAS WGPRAAPRAA LLDVEAKVDV DPLALSARVA EHPGARLAWA
181 RLAAIRDSPQ CASSASLAYT ITRTARFAR SYTTLAFPPT SKEGAFADLV EVCEVGLRPR
241 GRPQRVTARV LLPRGYDYFV SAGDGFSAFA LVALFRQWST TVRAPGALA PVFRPLGPGF
301 EVRGGPVQYF AVLGFPGWPT FTVPAAAAE SARDLVRGAA ATHAACLGRW PAVGARVVLP
361 PRAWPAVASE AAGRLLPATR EAVAEWHFTA TTIQLLDPPA AVGFVWIARF CFSGLQAQLL
421 AALAGLGEAG LPEARGRACL ERLDALVAAA PSEPWARAVL BRLVPDACDA CFALRQLIGG
481 VMAAVCLQIE QTASSVKFAV CSGTGAAFWG LFRVDPGDAD AARGAIQDAR RALEASVRAV
541 LSKNGIRFRL APSLAPEGVT TRVVTWSQTG AWFWNSRDDT DFLQGFPLRG AAYAAAAEVM
601 RDALRRILRR PRAGPFEEAV CRARGVREDA CDRFVLDAFS RRLGREYWSV LPPPGEADDF
661 LPQTAERGGA LLDAEQTWRR VVRVCPGGGE SVGVPVDLYP RPLVLPPVDC AHRLREILRS
721 IQLVFTGVLE GVWGEGGSFV YFPDERIRFL FP
```

| KEYWORD | DNA(NC_001798 REGION: 18393..20665) |
|---|---|
| SEQ ID No: | 74 |

```
  1 tttattgacc aaattcaggg aaacagaaac cgaatctttc catcgaaagg gtacacaaag
 61 ctcccgcct aaccccacac ggcttccaga accccgtaa acaacagttg aatctcgcga
121 aggatctcgc gcaggtgatg gggccagtcc acggggggga gcaccaaggc ccgcagggtac
181 agatccaggg ggacgcgac cgactcccc cccccggac atacgcgac gacgcgtcta
241 cagtattgct ccgggtccag cagggcgcct ccgcggaagg cgtttgggg caggggtcg
301 tcggcctgc ctggggggt cagaacgtc cagtactccg cgtccagacg cctccgaag
361 gcatccagga caaagcggtc acaggcgtcc tcatgacgc ccgggcgc gacacggcc
421 tcctcaggcg tgggggcgc cggcgcgg aggattcgtc tcagcgtc gtgcataaac
481 tcggccgcg cgggtacgc ggcccgcgg agaggaaatc cctgcaggaa gtcggtgtca
```

FIG. 9D

```
 541 tgcgggagt tccagaacca cgcccggtc tggctccagg tgagctacg ggtgtagacg
 601 ccctctggcg ccagggaggg ggcgagcgc gggcgtatgc cgttggccga aagtacgcg
 661 cgcacggacg cctcgagggc cggcggggcg tcctggatcg agccgtgcgc gggtccgcg
 721 tcccggggt ccacgttgaa cagcccccag aagcagccc cggtgccgc gcagaccgca
 781 aacttcacg agctggccgt atgtctgatc tgcaggcaga cggggccat gacccgcg
 841 agcagctgcc cgacgcgggg gcaggcgtcg caccgctcg cgaccaggcg ctccagcacg
 901 gccgccccc agggctccga gagcccagcg gccccagcc agtccagcct ttccaggccc
 961 gcccgcccc gggcttccgg cagcccggcc tcccgaggc cagcgaggc ggcaggagc
1021 tgggctgga gccggagaa acaaaaccga gccgtccaga ccggccgac ggccgccggg
1081 gggtcgagta gttggatggt ggtggcgtg gggtgccacc gcgcgaccgc ttccgaaag
1141 gcgggcagga ggcggccggc cgcctcgag gccacggccg gccatgcccg cggggcagg
1201 acgaccctgc cgcccaccgc gggccaggcc cccaggcacg cggcatggct ggccgcggcg
1261 cccgccacca ggtcacgcgc cgactcggcg ggggccgcgg ccggcacggt aaacgtggc
1321 cagccggaa atcccagcac ggcaaagtat tggacgggcc ctcccaggac ctcaaaccg
1381 gccccagaa aagcgaagac ggggcaggg gtccggggg cggcgtggac cgtggtatgc
1441 cactgccgga agagggcgac cagcgccggg gcggagaacc cgtcgccggc gctcacgaag
1501 tagtcgtagc cgcgcgcag cagcaccgcc gccgtgccc gctgcgggtg tccgcgaggc
1561 cgcaggccga cctcgcacac ctcgaccagg tccgcgagg cgccctcctt cctggtcggc
1621 ggaaacgcca gggtggtgta ttcgcgcgca aaacgcgggg tactcgtcgt gatggtgacg
1681 gcgagcgagg ccgaggacgc gcactgggg ctgtcgcgaa tgcggccag gcgcgcccac
1741 gccaaccgcg agccggggtg ctcggccacg cgcgggaca gggacaggg gtcgacgtcg
1801 accttggcct ccacgtccag gaggcggcg cgaggagcgg ccgggggcc ccacgacgcc
1861 ctttcgaccc tcacgaccac accgtatgc gggtccaagc ccaggcgcag cgggacgagg
1921 agggccacc ggccgtctg gcgtcagg gccgccagaa cgcacgcata cagcgccgc
1981 cacagggtcg ggtccacag gggctccaga gggaagcgg caggcggt cgcggcgcg
2041 gcggccgcga aggccccggg ggccgagacg tcggggagc cgtagaagtc ctgcaggtcg
2101 gacgaccaa cggacacctc cgcgaagcgc gcgcgccct ccccgcggc gtcgcgacag
2161 accagataca gcaggcgtg gaggcagtcg ccgtgcgcg gggcagcca taccgcgtat
2221 agggtaatgg cgctgacgct ctcctccacc caaacgatgc cggggcttc cat
```

```
SEQ       RSV2 OL15
KEYWORD   PROTEIN
SEQ ID No:  75

1  MFGQQLASDV QQYLERLEKQ ROQKVGVDRA SAGLTLGGDA LRVPFLCFAT ATPKRHQTVV
 61  PGVSTLRDCC SHSPLFSAVA RRLLPNSLVP AQLAGRDFGS DHTAKLEYLA PELVRAVKRL
121  RFRECAPEDA VPQRRAYYSV LNTFQALHRS EAFRQLVHFV SDPAQLLRYS FRASSLAKTT
181  GPFKNRARVD VATRGQTYST LELFQRMILM KATYFLARVL LGDBAEQVST FLRGVFKIPL
241  FSDTRVRHPR QRATVFLVER RRGKTWFLVP LIALSLASFR GIKIGYTARI RRAFPFVFDE
301  IDACLRGWEG SSRVDHVKGE TISPSPDGS RSTIVFASSH NTNGIRGQDF NLLFVDEARF
361  IRPCAVQTIM GFLNQANCKI IPVSSTHTEK ASTSPLYNLR GAADELLMVV TYICDDSMPR
421  VVTNMNATAC SCYILNKPVP ITWDESAVRNT ADLFLPGSFM QEFIGGQARE TGDDRPVLTK
481  SAGGRELIHR PSTTYNSGLM APELEYIVDP RPTANTRASG TGIAVVCRYR DDFIIFALES
541  PFLRALTGSA RADIARCVVR SLAQVLALHP GAFRSVRVAV EGNSSQDSAV ATATRVRTEM
601  HSTLASAGRN GSGPELLFYR CSPEGCAVLY PFTLNKQKT PAFEYFIRKF NSGGVMASQE
661  LVSVTVRLQT DPVEYLSEQL PNLIETVSPN TDVEMYSGRR RGAADDLMVA VIMAIYLAAP
721  TGIPFAFFFI TRTS

KEYWORD   DNA(NC_001798 REGION: 28969..34828)
SEQ ID No:  76
```

```
  1 atgtttggcc agcagctggc gtccgacgtg cagcagtacc tggagcgcct ggagaaacag
 61 agacaaacaga aggtgggggt cgacgaggcg tcggggggc tgaccctcgg cggggatgcg
121 ctgcgcgtgc cttttctgga tttgccacc gcgaccgcca agcgccacca gaccgtggtc
181 ccggcgtcg ggacgctcca cgactgctgc gagcactgc gctcttctc ggcgtgcg
241 aggcgttgc tgtttaatag cctggtgccg gcgcaactca ggggcgtga cttgggggc
301 gaccaacggg ccaagctgga gttcctggcc ccgagctgg tgcgggcggt ggcgcgcctg
361 cggttccggg agtgcgcgcc ggaggaccgca gtgcccagc gaagcgccta ctacagcgtc
421 ctgaacacgt ttcaggcct gcaccgctcc gagccctttc ggcagttggt tcacttcgtg
481 cgggacttcg ccagttgtt gaaacctcg ttcgggcct ctagtatcgc ggagactacg
541 ggccccga agaaacgggc caaggtggac gtggcaaccc agggcagac gtacggcacc
```

FIG. 9E

```
 601 ttggagctct tcagaaaat gatactaatg cacgagcct actttctggc cgccgtgctg
 661 ctcggggacc acgcggagca ggtcaacacg ttcctgcgga tcgtgttcga gatcccctg
 721 tttagcgaca cggccgtgcg gcacttcgc cagcgcgcca ccgtgtttct agtcccagg
 781 cgccacggaa agacctggtt tttggtgacc ctcatcgcgc tgtcgctcga gtccttcgg
 841 gggatcaaga taggctacac ggccacatc cgcaaggcga ccgagcccgt gtttgatgag
 901 atcgacgcct gcctgcgggg ctggtttggc tcgtcccgg tggaccacgt caaggggaa
 961 acatctcgt tctcgttccc ggacggctcg ccgagcacga tcgtgttgc ctccagccac
1021 aacacgaacg tcagtacgcc ttcctcccgc ggtgcctgtt tcccggtgc cgccctcccc
1081 gagatcgacc gacagacaaa cacgccaga cgcgagtgtg ggacgacag ccgcagccc
1141 cccccccgcc atggcggggg ggaagcctta ctgtttattt gtaatcggac gatgaggctc
1201 tggccacggc ccgcgcacc gcgggcaga tcgttgcaaa caggcgggtg gtatacgatg
1261 acagaacgca gaggcgccac ccgcgctgg tccggcggat gacgctttcc gcgtcgtccc
1321 ggccacgac gacctcgtgc agtgggccg tgatgcgcgg ccgcgggtc gcctgccgca
1381 ggataaccgc gtccacgggg tcccgaaga ggagctgaca caggctcgag tccccccgga
1441 cggccaggt gcgctggcc atattggacc acatgcacgg gcgacgcag ggacaggcct
1501 ccgccacggc ggtggcgcgc cacgccgcgt tggcggaatc gatgtcggcc gtcgggcgc
1561 aggcgacgcc tcctcccgg gggtcggtaa tcctggatag cagccatcct aaatgccggg
1621 ccggctgcc ccggggacag agcgacccca ggtcatcatc catggccag cagtatatgc
1681 ggcgccgtca gaggtgcacc caggacccag gacacaggc acagcacgcc ccggattcgg
1741 gggccgtgtc cgtgggtacc aagtaggcgc cgtcgagctc gtgggccacg ggctcgtccg
1801 cgagctcttc ggccgcgggg tcggggttt actccggggg ggaggcagct tccaggtggc
1861 cgaaggctag ggtcaacaga agcggggtcc gggggtcgtc tacgctcgcg aggtgacgg
1921 tgcgcagtca gcgggctcg cgttaaaga agaaaatggc aaagaacgtg ttcgaaggca
1981 ggcgacgcgc cttggcgcgg gtcaggtaca ggaagatctc gcagaaaagg gcacgctgg
2041 ggtcgggtc cggaagggcc acctggcaca gcggctcggt gaggaccgtg aggcacccga
2101 aaatcttaag acgctcgtcc cccgaacga cccgccacac gaagacagag ttgtcgatgc
2161 gcgcgacgag gtcggattcg ggcacccggt acgggcgcg ccgtcgggg ggccgcccc
2221 ggtgacccgg ccggggccgc gctccacggg ggcctggcgt cgcctggga cgccagagtg
2281 cccgatgtgc caggttgtc gtcggggagg gacccggagac gcaccaaaag cagaggggcc
2341 acgcgtgta tgagttgggg ggggggttgg tgacgggtga aacaaaagca cgctcagcg
2401 gacaaggcg ggtccagtag ccgcccccgcg acagaaccgg agtccgacgg cacgccgac
2461 gggctgcg aggctgaggt acgccgcgt gttaatggta aacgcaaaga ctcccggaaa
2521 gaccactaga ccgcagagg ggcgattgaa cccaaggcag aggtacgcgt agctctctcc
2581 cggaaggtat tgctcgcaga ccctgtgtgg ggcagtggag gggctgcct ccatgaagcg
2641 acatttactc tgctcgcgtc cattgacgtc accgtcaatc accactgcga ttggacggtt
2701 ggtgacggcc agcgtgtctc cgctggtgct gtagtagtca aacggtagt gggggtcgga
2761 gtcgggcaag ggggcggga tgtcgtcgct gagagggacg agccgtcggc gccgcaccg
2821 accgccctg ccgcccagat gcgcccagcac ggccagggcg tacgggtgt gaagaacgc
2881 gtcgggggcg gtccctcga ggggcgcat cagttctcc aggagccagg ggaagcgcg
2941 cgtcacctcc cctagccact cgctctggtg ggggccaaag tcgtagcgca gggctggaa
3001 gatgcgcggg ccgccttgga gcgcggccgg gatagagtgg cccaggggcc gcagacacgc
3061 gatctggatg cgcggacga agggcaggtc ggccgcgatg tcaaagggct ggagcacggg
3121 gcgcgtggc gcagggtc cctgagcgc gggaaagcga cgcagcacgc ccgtctggc
3181 cgcggggac agctggtggg ggcgcacgac gagctggcg gcacaggct ccgtcaggc
3241 cgtggccagc tggaggaca gccgcgggg gcgggcgtg cgccccgccc acgaacccga
3301 attctcgtag gagacgacga cgaagcgctg cttggtcccg tagtgatggc gcaggaccac
3361 gggatggag cgaccgctcc acagccagtc gggccggtcg ccgccggcca gagcttcca
3421 ccgccgtca agccactcga ccagcatcg cggcttggcg gtccggggca cgaggggtgag
3481 cacgtcgttg aggacgtcct cgccgcgcg ccggggccc caccggtgg caaagccca
3541 ccgccccggg ggatccaggc ccgccagcac cgcatccgag tcgacgcgc ccagggtca
3601 cacgctgacg gcctgtgga ccagggcgcc ctggcggagc ccgaggcga agcggaggc
3661 cgcgtgttg ggcgcgcgc ggaccgggtg gggcgggtg acgtactgca cggacccgtg
3721 cgcaccggcc aggatctcct cgttctcttg cgtgatggac agtcctcca cggtggccgt
3781 gtgcctccc ggggcgtga gctgctcctc cgggagatg cggggcgtg gggtgacgac
3841 aacggccgga ccgccccga ccgagaccga ggacgcctgg ggagtgggg tgccgcttta
3901 cccatccc agggacaggt gggccgcgc ctagtcggg gcgcggggag ccggggcccc
3961 cagccgcgcg aagtagcgac aaaagtggcg acagagggcgc atgaggcgcg cgccgtcggc
4021 cggttatcga gtgttgggc ggacgagctc gtcgtaacg aacaggagca ccggggcaca
4081 ggtcgccac ggcgcgacg ccaggcgcag ccgccgcaca gtgtacggt cgtacacgc
4141 ttggcgctcg cacgcgaccg ccaggcccc gaacaccgcc ccggcctcg tgacgccggg
4201 caggaggtcc ggtgccgcg agatgacggg ggctaggatc gccccaccg catccgccgg
4261 cagtaggcg gcaaacgccg aacgccacgg ggtgcagtcg ccggtcgcgt gggcccgggt
```

FIG. 9F

```
4321 ctgggtttcg accggaagt tcgaggcgg cccaccgtcg gggggcagc gaacgaggc
4381 gaacagggg acccccgcg cagccaggca ctcgctggag atgatgacgt gaatcagcga
4441 gcgggggctg ctgggtccc gggtgagatc gtattggacc tcgttggcaa agtgcgcgtt
4501 catggccgg ccggcggtgc gcgaccttcc cggtgccgga aggggcgtgg gtgggggtg
4561 cgtgtgcgcg tcctcgggc ccgcgggcgc acgtgcgctt atacgctgtg tgtttcgtct
4621 gtcccaggg aatccgggcc caggacttta acctgcttt cgtcgacgag gccaactta
4681 ttcgcccgga tcgggtcaag acgattatgg gcttctcaa tcaggccaac tgcaagatca
4741 tcttcgtctc gtcgaccaac accgggaggg ccagcacgag cttttttgtac aacctccgcg
4801 gggtcgtcga cgagctgcta aacgtggtca cctatatatg cgacgaccac atgccgcggg
4861 tggtgacgca caccaacgcc acggcctgtt cctgctatat cctgaacaaa cccgtgctta
4921 tcacgatgca cggagccgtt cgcaggaggg acgatctgtt tctgccgac tccttcatgc
4981 aggagatcat cggcgaccag gcccgcgaga ccgcgacga ccggccgtc ctaaacaagt
5041 agggggggga gcggttctg ctgtacgcc cctccaccac caccaacgag ggcctccgca
5101 cccccgagct gtacgtgtac gtggaccgg agttcacggc caacacgagc gcctccggca
5161 ccggaatcgc ggtcgtcggg aggtaccgcg acgattccat tatcttcgcc ctggagcact
5221 tttcctccgg cgcgctcacg gggatcggcc ccgggacat cgccgctgc gtcgtgcaca
5281 gcctcgccc ggtgctggcg ctgaccccg gggagttgcg cagcgttgcg gtggcggtcg
5341 aggcgcaacg cagccgaggac tccggccgag cccatccaac acacgtgcat accgacatgc
5401 accgcatcct ggcctcggcg gggggcaaag gccggggcc cgagctcctc ttctatcact
5461 gcgagccgcc cggagcgcg gtattgtacc cctctatttct gctcaacaca cagaagaacgc
5521 ccgccttcga atacttatc aaaaagttca actccgcggg cgtcatgcgc tcccaggacc
5581 tcgtctccgt gaacgtgcgc ctgcagaccg accccggcga gtatctgtcc gagcagctca
5641 acaacctcat cgaaaccgtc tctcccaacc acgacgtccg catgtactcc ggaaaacgca
5701 aacgtgcgc ggacgaccta atggtcgcgg tcattactgc cacttacctg gcggcccgca
5761 acggcgatcc ccccggcctt tttccgatcc ccgcccagtc ttgagtcttt ctgccgttt
5821 ctttttgtttc tcttcttca ccccctctc tccgccataa a
```

```
SEQ             HSV-2 UL17
KEYWORD         PROTEIN
SEQ ID No:      77

1    MSARFANSVQ  YQLTRDFSSP  ASLIRVISS   ECLAARGVPL  SALVRGRPDG  GAAANFRVET
 61    QTRAHATGDC  TPWRSAFAAY  VPADAVGAIL  APVIPAHPDL  LPRVPGASGL  PVSLPVACDA
121    QSVYDFYTVA  ALRLAWGPWR  TQARVLLFSY  DELVEPNTRY  AADGARLMRL  CRRFCRYVAR
181    LGAAAPAAAT  RAAARISLGM  GESGTPTPQA  SSVGGSAGPA  VVSTPDFPIS  PEQLTAPGG
241    STATAEDVSI  TQENEEILAL  VQRAVQDVTR  RHPVRARPER  AASGVASGLR  QGALVHQAVS
301    GSALGASOAE  AVLAGLEPFG  GGRFAGRGGP  RAAGEDVIMD  VLTLVPGTAK  FRSLVEWLDR
361    GWEALGSGQR  PDWLSGRRSI  SVVLRRRYCT  KQRFVVSYK   HSVAWGGRSA  RPPRLSSEIA
421    TALTERCARE  RVVRPHQLSP  AAQTALLARF  PALEGCPLRRP  RPVLQPFDIA  ASVRFVARIQ
481    IACLRALGRS  IRAALQGCFR  IFQRIRYDFG  PHQSEMLGEV  TRRFPVLLEN  LMRALEGTAP
541    DAFFTRTAYAL  AVLABLGGQG  GRGRRRKRLVF  LSLDIFARFA  DSDNHYAFDY  YSTSGDFLRL
601    TNRPIAVVID  CDVNGREQSK  CRPMECSPST  APHRVCEQYL  PGESYAHLCL  SPNRRLCGLV
661    VFPGGPAFTI  STAAYLSLAD  PVARAVGLRF  CRSAATGPGL  VR
```

```
KEYWORD         DNA(NC_001798 REGION: 30142..33471)
SEQ ID No:      78

1    tttattgta  atcggacgat  gagggctgg   ccaggccg    cggacggg    gggcagctcg
 61    ttgcaaacag  gggtggta    tacgatgaca  gaacgcagag  gcgccaccg   gcgctggtcg
121    gggggatgac  gcttccgcg   ccgtccggga  ccacgacgac  ctcgtcagg   tgggccgtga
181    tgcgcggcg   gcgggtcgcc  tgccgcagga  taacccgtc   ccacgggtgc  ccgaagagga
241    gatgacacag  gctcgcgtac  cccgggacgg  ccaggggtcg  ctggccata   ttggaccaca
301    gcgggggcg   gacgcaggca  caggcctcgg  ccagcgcggg  ggcgcgccac  agcgcgttgg
361    cggaatcgat  gtggccgtc   gggccgcagg  cgcgccgtca  tccggggggy  tcggtaatcc
421    tggatagcag  ccatcctaaa  tggcgggacc  ggctgccagg  gggacagagc  gacccaggt
481    catcatccat  ggcccagcag  tatatgcggc  cgccgcggag  gtgccaccag  gcccccggac
541    ccagggcaca  gcacgcacag  gattcggggg  ccgtgtccgt  ggtaccagg   taggcgccgt
601    cgagctcgtg  ggccacggga  tcgtacgaga  gctgttcggc  gggggtcg    gggtttcct
661    cggggggga   gcgctcttcc  aggtgccga   aggtagggt   gcacgcaga   gggtccggg
721    ggtgcgttac  gctgcggagg  tggacggtgg  cgcagtcgga  gcgctgcgy   ttaaayaaga
781    aaatggcaaa  gaacgtgttc  gaaggcaggc  gcagcgcatt  gggcgcgtc   aggtacagga
```

FIG. 9G

```
 841 agatctgca gaaagggca cgctcgggt cgggtcgg aagggccac tggcacagcg
 901 gctcggtgag gacggtgagg cacggaaaaa tcttaagcgg ctcgtcccc cgaacgacgc
 961 gccacgaa gacagagttg gcgatgcgcg cgacgaggtc ggcttcgggc ccgggtcgg
1021 gggcgcgc gtcggggggg gcgcccggt gaccggggg ggcgcggct cccgggggc
1081 ctggcgtcgc ctggggacgc cagagtgccc gctgtgccag gttggtgctg ggaaaggac
1141 cggagacgca ccaaaagcag agggacagc ggtgtatga gttgggggag gggtggtga
1201 gcggtggaac aaaagcagc gtcagcggac aaggacgggt ccgtagccg cccgcgaca
1261 gaaccgggagt cggacggac gcgcgacgg gtctgcgagg gtgagggtacg ccgcgggtgtt
1321 aatggtaaac gcaaagcctc ccgtaaagac cactagcccg cagaggcgg gattgaaccc
1381 aaggcagagg tacgagtagc tctctcccgg aaggtattgc tgcagacc tgtgtggggc
1441 agtggagggg ctgcctcca tgaagcgaca tttactctga tcgcgtccat tgacgtcacc
1501 gtcaatcacc actgcgattg gacggttggt gaggcgcagc gtgtctccgc tgtgtctgta
1561 gtagtcaaac gcgtagtggg cgtcggagtc ggcgaagcgg gcggggatgt cgtcgctgag
1621 agggacgagc cgcccgccga gccctgaccg gccctgaccg cccatgatgcg cccatgatgcg ccagcaccgg
1681 cagggggtac gcgggtgtga agaacgcgtc gggggcggtc cctcgaggg cgcgcatcag
1741 gttctccagg agcacggga agcgccgcgt cacctccct agcacctcgc tctgtgcgg
1801 gccaagtcg tagcgcaggc gctggaagat gcgcgggcg cttggagcg cggcccggat
1861 agagtggcca aggggccgca gaacgcgat ctggatgcgc gcgacgaagg ccacctggc
1921 cgcgatgtca aagggctgca gcacggggcg cggtggcgc agggtcct cgacgcgggg
1981 aaagcgacgc agccagccc tctgggacag tgtgggggga gcacgacgg
2041 ctggggcca caggcctcg tcagggccgt ggcagctcg gaggacagc gccgggggc
2101 ggcgcgtcgc ccgccacacg ccacggaatt ctcgtaggag acgatgacga agcgatgctt
2161 ggtccgtag tgatggcgca ggaccacgga gatggagcga cggctccaca gccagtcggg
2221 ccggtgccg ccggccagag cttcccaccc gggtccagc cactcgacca gcgatcgcgg
2281 cttgcggta ccaggcacga gggtgagcac gtcgttgagg acgtcctgc ccgcggccg
2341 gggccagca cgccctggcaa agcgccgcca gccaggccga tcagggccag ccagcaacgg
2401 ctccgcgtcc gaccgcgcca gggctcaac gctgacggct tggtggacca gggcgccctg
2461 gcggagccc gaggcgacgc cggaggccgt gtgcttggga cgcgcgcgga acgggtggcg
2521 gcgggtgacg tcctgcacgg ccgatggac cagcgcgagg atctcctgt tctcttgcgt
2581 gatggacacg tcctccgggg tggccgtgtc gcctccgggg gcggtgagct gctcctcgg
2641 ggagtgggg gggtctggg tgccgacaac ggccggcccg gcccgccg agaccgagga
2701 cgcctgggga gtggggtga cgcttccaac catcccaga gacaggtggg ccgccgcctc
2761 cgtcgcggcg gcgggagcg cggcccccaa cccgcccgacg tagcgacaaa agtgcgacga
2821 gaggcgcatg aggcgcgcgc cgtaggccgc gtatcgcgtg ttcggcggggga cgagtcgtc
2881 gtaactgaac aggagcacgc gggcacaggt cgccacgggg ccncaacgca ggcgcagcgc
2941 cgcgaccgtg tacggggtcgt acacggcttg gcgtcgcac gcgaccggca gggagacgaa
3001 cagccgccgc gcgtgggga cgcgcggcag gaggtccggg tcgccggga tgacggggc
3061 taggatcgcc gccaacgat ggcaggcgca gtaggcgca gacgccaacg gccaaggggt
3121 gcagtcgccg gtcgcgtggg ccgggtctg ggtttcgacc cggaagttcg cggccgccc
3181 accgtcgggg cggcgcgca cgaggcgga cagcgggacc ccgccgccg caggcacta
3241 gctggagatg atgacgtgaa tcagcgagg ggggctgctc gggtccgggg tgagatcgta
3301 ttggaccctg ttggcaaagt gcgcgttcat
```

```
SEQ         HSV2 UL29
KEYWORD     PROTEIN
SEQ ID No:  79
```

```
  1 MDIRKRTTT VKVPPGPMGY VYGRACPAEG LELLSLLGAR SGDADVAVAP LIVGLTVESG
 61 FEANVAAVVG SRTTGLAGTA VSLKIMPSHY SFSVYVFMSG RHLAPSTQAP NLTRLCERAR
121 PHFGFADYAP KPCDLRSETT GDRLCERLGL DPDRALLVIV ITEGFSEAVC ISNTFLHLGS
181 MDKVTIGDAE VHRIPVYPLQ MPMPDPSRVI ADFFNCNRS IGENPNYPLF FPNKPLARLL
241 FEAVVGPRAV ALRARNVDAV ARAAARLAFD SRHEGAALPA DITFTAPFAS QGKPQRGARD
301 AGNRSPACGS EQRLASVMKG DAALALESIV SMAVFDEPPP DITTWSLLEG QSFPAARACA
361 VGAYLARAAG LVGAMVFSTN SALRLTEVDD AGFRDFKDHS KPSFYSRFEIV FGTRVEANPQ
421 LDRKSRVVPS TEGRPTAFLV GGTQRFBGEH LAMLCGFSPA LLARMLPYLE PCDGGVIVGR
481 QEMDVFRYVA DSGQTDVPCN LCTFETREAC AHTTLMSLRA RHPKFASAAR SAIGVPGFWN
541 SAVSDCDVLG NYAAFGALKR ADGSENTKTI MQETYRAATE RVMAELEALQ SVDQAVPTAL
601 GRLCTIIGNR EALRTVNNI RQLVDREVEQ LMRNLIEGEN FKFRDGLAEA SRAMSLSLDP
661 YTCSPCPLLQ LLARRSNLAV YQDLALSQCR GVSAGQSVEG RRFSNQFQPV LRRRVMDLPN
721 NGFLSAKTLT VRLSEGAAIC APSLTAGQTA PAESSFEGDV ARVTLGPPRE LRVKDRVLFA
781 GASANAGEAA RARVASLQSA YQKPDKRVDI LLGFLGFLLK QFHAVIFPNG KFPGSNQPNF
841 QWFWTALQRN QLFARLLGKE QIETIAFIRR FSLDYGAINF INLAPNNVSE LAMYYNANQI
```

FIG. 9H

```
 901    LRYCDRSTYF INIIIAVIAS SRRPPSVQAA ARWARQSGAG LRAGARALMD SLGRRPGANT
 961    SMFASCNLLR PVMAARPMVV LGLSISKYYG MASWDRVFQA GNWASLLGGK NACPLLIFDR
1021    TRKFVLACFR AGPVCAASSL GGGAHRHSIC EQLRGIIAES GAAVASSVFV ATVRSLGPRT
1081    QQLQISDWLA LLEDKYLSEE MMSPTTRALE RGRGKWSTDA ALEVANRARA LVSQLGRAGE
1141    VFNFGDFGDE DDRAASFGGL AAAAGAAGVA RRRAFHGDDP FGEGPPERKD ITLGML
```

KEYWORD DNA(NC_001798 REGION: 58805..62447)
SEQ ID No: 80

```
   1    tttattttat acacaacacc aactttctt tgacccacc cgaccccgc cctagagca
  61    tatccaacgt caggtccttt ttctccggtg gtcctccc aaacggatcg tgtcgtgaa
 121    aagccgctt tcgggacg ccggcagcca ccgcgccgc cgccaaccgc ccgaacgacg
 181    ccgctggta atcctcgtcg cggaatccc caaagttaaa cacctccag gggcgccga
 241    gctggctgac cagggcctcc gctcgtggg ccactccag ggccgcgtcg gtcgaccact
 301    cgccatgcc gcgctccagg gcgcgggtgg taaactccat catttcctcg ctcaggtact
 361    cgtcctccag cagcgccagc cagtcctcga tgtcaagctg ctgggtcgg gggccaggaa
 421    tcttgacggt cgcacaaaa acgctgctgg cgaccgacga ccgccctcc gcaatgatgc
 481    ccggagctg ctcgcacagc gaatgctgt gggccagcc cccgagact gacgccgcgc
 541    acacaaacca ggcctgggg caggccagga caaactgcg ggtgaggtca aagatcagca
 601    ggggcacgc gttttgccgc cacagcagg tggccagtt cccggctga aacacggt
 661    cgttgacgc catgcgtag tatttgcta tgctgcacat cagcacgaca atcgggcgc
 721    cggccatcac gggccgcagc aggttccagc tcgcgaacat ggacgtccag cgcgccgggt
 781    gcgcgtgag ggagtccatc agcgcgcggg cccaggcctc caggccgcg ccgcctgcg
 841    gggcccagga cgccgcgcc tgcacgctgg gggacggcg ggaccccgcg atgacggcg
 901    tgagggtgtt tatgaagtac gtcgagtggt cgaagtacct caagatctgg ttggccatgt
 961    agtacatgga cagttcgtc acgttattgg gggccaggtt gataaagtta atcgcccgt
1021    agtccggga gaacctctta atgaacgaga tggtctctat gtcctcgcg gacaagacc
1081    gggcggggag ctggttgcgc tggagggcgg tccagaacca ctgcgggttc ggctggttcg
1141    accccggggg cttgcgttg ggaaagatga cccgtagaa ctgcttcagc aggaagccca
1201    gcggtccgag gaggatgtcc acgcgcttgt cgggcttctg gtaggcgctc tggaggctgg
1261    cgaccgccgc cttggaggcc tggacgcgt tggcgctcga gcccgcgaac aacacgcggc
1321    tcttgacgtg cagttccttg ggaaaccaa gggtcacgcg ggcaacgtcg cgctcgaagc
1381    tgctctcggg ggggccgtc tggcccggcg ttaggctcgg cgcgcagata cgcgcccct
1441    ccgagagcgc gaccgtcagc gtcttcgccg acaggaaccc gttgtgaac aggtccatga
1501    cgcgccgcgc cagcacggt tggaattgat tgcgaagtt gcgcccctcg acggactgcc
1561    cggcgaacac ccgtggcac tggtcaggy ccaggtcctg gtacccgcg aggttggacc
1621    gccgcgcgag gagctgcagc aggggcgacg gccgcaggt gtacggtcc agcgacagcg
1681    acatgcggta gtgcgcctcg gccagacgt ccgcgaactt aaagttgcgc ncctcgatca
1741    cgttgcgcat cagctgttcc acctgcgcgat ccaccagctg cttgatgttg ttcaccacg
1801    tgtccaggga ctgcggttgc ccgataatcg tctccagcct cccagggcc gtgggcacgt
1861    cctggtccag gtactggcag gcctcgagct cggccatgac gcgctcggtg gccgcgcgt
1921    acgtctcctg catgatggtc cgggtgttct cgggaccgtc cgcgcgcttc agggcgagga
1981    aggcggcgta gttccacagc acgtcgagt cgatgtaccgc gctgttcatc gttccgaaga
2041    ccccaatgac cccccgggg cgcgtccgga actggggtg ggggcgccg agncgcatca
2101    gactcgtgtg cgcgcaggcg tggcggtct cgaaggtaca caggttgcag ggtacgtggg
2161    tctgccccga gtcgcgacg tagcgaaaca cgtccatctc ctggcgccg acgtcgactc
2221    cgccgtgca gcgctccagg taaaacagca tcttggccag caggccgga gagaaccgc
2281    acagcatggc caggtgctcg ccgcgaact cctggttcc gccgacgagg ggccgcgtgg
2341    ggcgccctc gtaccggga accacgtggc cctgcggtc cagctgggg ttgccgcca
2401    cgtcgctgcc cggcacgaga aagaacggt aaaaggaggg cttgctgtg tccttgggt
2461    ccgccgtgcc gggtcgtcc aactcggtca gtgaggc cgaattgtc ctgaacaca
2521    tggccacaa caggccgcg gcgcgcgca ggtacgcca caccgcgcg gcgcggccg
2581    cggcgtttta ctggcatca agcagggcc acgtggtgat gtcggggcc ggctcgtcaa
2641    agacgcat cgaacgatg gactccaggg ccagggcgga gtgccgcgc atcacgagg
2701    ccaggcgtg ctcaaacgc ccgcacggc cccgttcacc gggctgcgc gcgcccgct
2761    gggcttacc ctggctgcc tcgaaggcg tgaacgtaat gtcggggg agggccgcc
2821    cctgtggct ttcgtcgaac gccaggtggg cggcgcgcg ggccaggcg tcaacgttac
2881    gggccacgag gccacggcg gggcccga cgaccgcctc gaacacgcg cgggcgaggg
2941    ggggttgaa aaacggaagg gggtagttga aattctccc gatcgatcgg tggttgcagt
3001    taaagggatc gggcatgacc cggctaaaat ccggaataaa catctgcagc ggatacacgg
3061    ggatggggtg aacctcagga tcccgatgg ttaccttgtc catccgccc agatgcagga
```

FIG. 9I

```
    3121 aggtgttgct gatgacaacg gcctccggga agccctccgt gatcaccaga tacagcaagg
    3181 acggtccgg gtccagtccg agccgctcgc acagagcgtc cccgtcgtc tcgtgcttta
    3241 ggtcgcaggg acgggcgcg tagtccgcga agccaaaatg cgggcgcgcc cgctcgcaga
    3301 gctgcgtcag gttggggcc tggtgctgc gcgccaggtg gcggccgcg tgaaagacgt
    3361 aaacggacgg gctgtagtgc gagggcataa gcttgaggga cacgcggtc ccaccaggc
    3421 ccgtcgtgcg ggaccgacg acgcggcca cgttggccatc aaacccgtc tccacgtca
    3481 gccgacgat gaggagcgcg acggcgacgt cacgtcgcc gctgcgcgcc gacgtagcg
    3541 aaagcagctc caggccttcg gcggacacgg cgcggccata caccgtaccc atcgggccg
    3601 gaggaacctt gacggtggtc gtcgtcttgg gcttggtgtc cat
```

SEQ         HSV-2 UL30
KEYWORD     PROTEIN
SEQ ID No:  81

```
    1    MPCAAGGPAS PGGKPAARAA SGFFAFHGFR GAPQTAPPPC SRQNFTNPHL AQTGTQPEAL
    61   GPAQRHTYYS XCCBFRFIAP RSLDKDAFAE QSTGVHDORL REAPKVYCSG DKRDVLRVGF
    121  SGFWPRRLRL WGCADHAPSG FDFTVTVFNV YCILSKVSHA YSMRAAQLSE RFMDAITPAG
    181  TVITLLGLCF SGHRVAVHVI GTRQYFYMNK AEVDRHLQCR APRDLCERIA SALRESPGAS
    241  FRGIEADRFS KEVVERADVY YYSTRPFLYY RVFVBSGKAL AYLCDNPCPA IREYEGGVDA
    301  STRFILDNPG FVTPGWYRLK FGRGNAPAQF RSPTAPGTSS DVEFNCTADN LAVEGAMCDL
    361  PAIKLNCFDI ECKAGGRDEL AFPVAERPED LVIQISCLLY DLSTTALSHI LLFSLGSDDL
    421  PESHLSDLAS RGLPAPVVLX FDSKFEMLLA PMTFVKQYGF SFYTGYNIIN FDWPFVLTKL
    481  TKIYNFVFLGG YGRMBGRGVF RVWDIGQSHF QHRSHIKVNS MVNIOMYGII TKRVKLSSYK
    541  LNAVAEAVLK DKRQLSYRQ IRAYYASGFA QRSVIESYCV QDSILVGQLF FFFLPHLSLS
    601  AVERLAGHNI TRTIIDEQQI RVFTCLLALA GQRGFILPDT QQRYFRGLGKS APKRFKVFFS
    661  EGERPSDGNG DEDRGDGKDG GRDGDERCEV ARETGSRNVG YQSARVLDPT SGPNVGPVVV
    721  FDFASLYFSI IQAHNLCFST LSLRPEAVAH LEARDKDYLEI KVGGRRLFFV KAHVRESLLS
    781  ILLROWLANR KQIPSRIPQS TFEEAVLLCK QQAAIKVVCS SVYGFTCVQR GLLPCLSVAR
    841  TVTTIGREML LATRAYVBAR WREFDQLIAD FREAAGMRAP GPYSMRIIYG DTDSIFVLCR
    901  GLTAAGLVAN GGKMASHISK ALFLFPIKLE GERTFTKLLL IAKKRYISVI CGGRMLIKGV
    961  DLVEKNNCAF INETSSALVD LLFYDDTVSG AAAALAERPA KEWLAKPLFS GLQAFGAVLV
    1021 DAHRRITDPE KCIQDFVLTA ELSRRHPRAYT NKRLASLTVI TKLWARRAQV PSIKDSIPYV
    1081 IVAQTRSVES TVARLAALRE LDAAAPGLSP APPAALFSPA KRFRETPSRA DPPGGASKPR
    1141 KLLVSELAKD FGYAIARGVF LNTDYIFSHL LGAACVTPKA LPGNNAKITE SLLKRFIPKT
    1201 WRPPDIVAAR LRAAGPGPAG AGATAKETRK KLSRAFDTIA
```

KEYWORD     DNA(NC_001798 REGION: 63268..67026)
SEQ ID No:  82

```
    1    atgttctgtg ccgagggggg gccggcttcc ccgggggga agccggggc tcgggggcg
    61   tctgggtttt ttgccccca caaccccgg ggagccacca agacggcaac gccggcttgc
    121  cgcaggaaga acttctacaa cccgcactc gatcagccg gaacgcagcc aaaggcccta
    181  ggcgcggctc agcggcatac gtactacagc gagtgcgacg aattcgcgacg tatcgccccg
    241  cgttcgctcg acgaggacgc cccgcggag cagcgcaccg ggtccaccga cggcagcgtc
    301  cgcgcgcgcc ctaaggtgta ctgcggggg gacgagcgcg acgtcctcag cgtcggcgcc
    361  gaggcttct ggcagtcg attgcgcctg tgggcgggtg cggaccatgc accgagcggg
    421  ttcgacccca ccgtcaccgt cttccacgtg tacgacatcc tggagcgt ggaacacgcg
    481  tacagcatgc gcgccgcgcc gctcacgag gatttatgg acgccatcac gcccgcaggg
    541  acgtcatcca cgttctggg tctgctccat gaaggccatc ggtgcgcgt tcacgtctac
    601  ggcacgcgg agtacttta tatgaacaag ggggagtgg atggcacct gcagtgcgt
    661  gccccgcgcg atcctctgga gagcctgcg gcgggcctga gcagtcgcc tggggcgtgg
    721  ttccgggca tccgcggga ccattcgag gcggaggtgg tgcgcgcgc agcgtgtac
    781  tattacgaaa cgcgcccgac cctgtactac cgagtcttcg tcgaagcgg gcgcgacgt
    841  gcctaccgct gcgacaactt tgccccgac atcagaaagt accggcgcgg cgtcgacgcc
    901  accaaccgtt tatcctgga caaccggg tttgtcacct tggctggta ccgcctcaag
    961  ccggcccgcg ggaacgcgcc cgcccaccgc cgccccccga cgggttcgg aacctcgagc
    1021 gacgtcgagt tgactgcac ggcggacaac ctggccgtcg aggggcat gtgtgacctg
    1081 ccggctaca agtcatgtg cttcgatatc gaatgcaagg ccggggga gggacgagctg
    1141 gccttccggg tcgcggaacg cccggaagac ctgcctcca agatatctg tctgctctac
    1201 gacctgtcca ccaccgcct cgagcacatc ctcctgtttt cgctcggata ctgcgacctc
```

FIG. 9J

```
1261 ccggagtccc acctcagcga tctcgcctcc aggggcctgc cggcccagt cgtcctggag
1321 tttgacagcg aattcgagat gctgctggcc ttcatgacct tgtcaagca gtacggcccc
1381 gagttcgtga ccgggtacaa catcatcaac ttgactgga cctcgtcct gaccaagctg
1441 acggagatct acaaggtccc gctcgacggg tacgagcgca tgaacgccg gggtgtgttc
1501 cgcgtgtggg acatcggcca gagccacttt cagaagcgca gcaagatcaa ggtgaacggg
1561 atggtgaaca tcgacatgta cggcatcatc accgacaagg tcaaactctc cagctacaag
1621 ctgaacgccg tgccgaggc cgtcttgaag gacaagacga aggatctgag ctaccgcgac
1681 atcccgcct actaccctc cggcccgcc caggcgggg tgatcgcgga gtattgtgtg
1741 caggactcga tgctggtcgg gcagcgttc ttcaagttc tgccgcctt ggagctttcc
1801 gccgtcgcgc gctggaggg catcaacat acacgtacca tctacgacgg ccagcagatc
1861 cgcgtcttca cgtgcctcct ggccttgcg ggcagaagg gttcatcct gccgacccc
1921 cagggccgt tgggggcct cgacaaggag gcgcccaagc gcccggcgt gcctcggggg
1981 gaaggggag ggccggggga cggaacggg gacgaggta aggacgacga cgaggacggg
2041 gacgaggacg gggacgagcg cgaggagtc gcgcgcgaga ccggggcg gcacgttggg
2101 tacggagtcct cgcccdccac tacggttc agtcgaacc agtggtggtg
2161 tttgactttg ccagcctgta ccacagcatc atccaggcc acaacctgtg ctcagtcg
2321 ctctccctgc ggccgaggc cgtcgcgcac ctggagcgg acgggacta actggagatc
2281 gaggtggggg gcgacggct gttcttgtg aaggcccacg tacgagag cctgctgagc
2341 atcctgctgc gcgactggct ggccatgcga aagcagatcc gtcgaggat ccccgagac
2401 accccgagg aggccgtcct cctgacaag caacaggccg ccatcaaggt ggtgtgcaac
2461 tgggtgtacg ggttcaccgg ggtgcagac gtcttctgc cctgactgca cgtggccgcc
2521 acgtggtgc ccatcggccg cgagatgctc ctcggcgac ggcgtacgt gcacggcgc
2581 acgtggggagt tgatcagct gctggcgac tttcggagg cggccggcat gcgcgcccca
2641 ggtccgtact ccatgcgcat catctaacgg gacaggact ccattttgt tttgtgcgc
2701 ggcctcaacg ccgtgggcct ggtggccatg ggcgacaaga tggcgagcc catctgcgc
2761 gcgtgttcc tccccccgat caagctagag tgcgaaaaaa agttcaccaa gctgctgctc
2821 atgccaaga aaagtacat cgggtcatc tgcggagca agatgctcat caagggcgtg
2881 gatctggtgc gcaaaaacaa ctgcgcgttt atgaaccgca cctccagggc cctgtgtgac
2941 atgctgtttt acgagtac cgtatcccga ggactgcagg cgttcgggc cgtcctcgta
3001 gaggagtggc tgcgcgaccc cctgcccgag ggactgcagg cgttcgggc cgtcctcgta
3061 gacgccccatc ggccatcc cgaccggag aggcacatcc aggacttgt cctcaccgc
3121 gaactgagcc gacaaccgcg acgtacacc aacaagcgcc tggcccacct gacggtgtat
3181 tacaagctca tgccccgcg cgcgcaggtc cgtccatca aggacgcat ccgtccgtg
3241 atgtggcccc agacccgcg ggtagaggag acggtgcgc ggctggccgc catccgcgag
3301 ctagacgccg acgccccagg ggagagccc gccccaag aggcctgcc ctccccggc
3361 aagctgcccc gggatgcc gtgcatgcc aagcatcgc gaggagcgtc aagccccgc
3421 aagctgctgg tgtccgagct gcggggagat ccggggtacg cactgccgc gggcgttcg
3481 ctcaacaggg actattactt ctgccacctg ctggggcgg cctggtgac gttcaaggcc
3541 ctgttggaa ataacgccaa gatcaccgag agtctgttaa agaggtttat tccgagacg
3601 tggcacccc cggaagacgt ggccgagcg ctcagggcg cgggttcgg gccggcggg
3661 gccggcgta cggggagga aactcgtcga atgttgcata gagcctttga tactctagca
3721 tgagcccca gtcgaagctg atgtccgca tcttgcaata aa
```

```
SEQ                 HSV-2 UL32
KEYWORD             PROTEIN
SEQ ID No:          83

1     MATSAPGVPS  SRAVRBESPG  SSWKBGAFER  PYVAFDPDLL  AINEALCAEL  LAACHVGVP
 61     PAGALDEDVE  SDVAPAPPRF  RGAAREASSG  RGPOSARGEP  ADPTAEGLLD  TGPFAAASVD
121     TFALDRPCLV  CRTIELYKQA  YRLSPQWVAD  YAFLCAKCLG  AFRCAASIPV  AAFRFVYVMD
181     HRFLRNTKKAI  LVGSFARFAL  TINDIRHFP   LRCCFRTDGG  VPGRHAQKQP  RPTPSPGAAK
241     VQYSNYSFLA  QSATBALIGT  LASGGDDGAG  AGAGGGSCTQ  PSLTTALMNN  KDCARLLDCT
301     EGKRGGGDSC  CTRAAARKNGP  FEAAAGALAQ  GGEFETWAYA  DLILILLAGT  PAVWESSPRL
361     RAAADAHRAA  VSESWEAHRG  ARMRDAAPRF  AQFAEPQFQP  DLDLGPLMAT  VLKHGRGKGR
421     TGGECLLCRL  LLVRHYNLAM  RRLPASVVRY  SENNTSLPDC  IVPVVDQLER  DPEAQPGDGG
481     RFVSLLARAG  PEAIFRHMFC  DPMCAITENE  VDFNVIRGHF  RADRKPELQL  HKARLACGWK
541     FEGRVCTALR  ALIYTFRTYQ  VFVPKPTALA  TFVRACAGLL  RRESISLLSL  SRPLCTYV

KEYWORD             DNA(NC_001798 REGION: 66850..69638)
SEQ ID No:          84
```

FIG. 9K

```
   1 tttattcccg agacgtggca cccccggac gacgtggcg cgcggctcag ggccgcggg
  61 ttcggccgg aggggccgg cgctcggcg gaggcaactc gtcgatgtt gcatagagcc
 121 tttgatactc tagcatgagc cccccgtcga agctgatgtc ccgcatcttg caataaatgt
 181 atgccggcga cacggtcgga atttccgcgt ccgctggttt ctctgcgttg cgtctgacaa
 241 cgagccgaaa cgtgctgcgc cacacgtggg cggcgaacgc gtacgcgggc cacgcggtca
 301 gcatccgatc gatgagccgg tagtgcaggt gggcgacgt gccggggaag atgacgtaca
 361 gcatgtggcc cccgtacgtg gggtcagggt aaacaagaac ccgggggtcg cacgccccc
 421 ctccgcgcag gatcgtgtgc acgaaaaaga gctcgggctg gccgagcgta tcggccagga
 481 ggtcctggag ggggtgctg tggcggtcgg ccagcacgac cagggaggcc agaaaggtgc
 541 ggtgctcaaa gatcgtattg atctgctgca cgaaggccag gatgagggcc tacggctga
 601 cggtccgcaa ccgcccgtcg ccagcgtga acgcgggca gcagccccg atcccaggt
 661 agtagccat gccgagagg gtccggcagt tgtcggccac ggtctggtcc aggctgaagg
 721 ggagcgacac gggggtcgtc ttcaccaggg gcacggagag cgagcgcacg atgcgatct
 781 cctcggaggg cgtctggtcg aggcggcga agaagccgcg gtacgacgc cgctcgtgca
 841 ggcagagctc cagcctcgcc gcgtcgcacg gcaaggctatt gcgggaggca cggcgctcca
 901 cgccgggtt ccggcgcgc gaaaagcgcg acgacgcg ggtcttgtcg cggccggcc
 961 cgggccggga gcggagacga cgggggcga tgtcataacat aggtacagag ggtgtgctcc
1021 agggacaggg gagagatcga gtgtcgtctg agcagcgcgc cggcctcgcg gacaaatgtg
1081 gccagccgcg tggcttcgg cacaataca tggtacgtct tgaaggtgta gatgagggcc
1141 cgcagggcta tacagaccgc cccctcgaac tcgttgccgc aggccaactt ggccttgtga
1201 agctgcagct cgtcgcgatg gtcgcgcgg gggtggcaa acaggaccca gggtcgact
1261 tacatctccg tgatgggca catggatcg cagaacatgt gctgaaagt ggctcagggg
1321 cccgcggccc gaagcaggct catgaacagg cacagtacc cgggctgcgc ctcggggtcc
1381 gctcagagct ggtccacgac cggcactatg cagtcgaaga ggctgtgtt gttctccgag
1441 tagcggacga cggacgcctc cagcgtcgc atggccagcc agtagcccg caccagcaac
1501 agattgcaca gcaggcattc cccgccggtg cgcacgcgcc cccggccgtg cttcagcacg
1561 gtggccatca gcgggccag gtccaggtcg ggctggggct ggggctagga gaactgcgca
1621 aaacgcgggg ccgcgtcgcg catgcgcgcc ccgggtgcg cttccagga ctgctgacc
1681 gcgggggg gggcgtccgc gccggcgcgc agccgggcc ccgactcca gacggcggg
1741 gtgccgaagc gcagcagcag gatcacgtcg gccgtacgcc acgtctccgg tctcaddccc
1801 tgcgccagcg ccccgcggggg ggcctcgaac tcccgtgc gtggggcggg gcgagtgcag
1861 cagctgtatc cgccccgcg cttgccctcg gtgcagtcga gcaggcggc gaagtacttc
1921 cagttcatca gggcggtggt gagggaggt tgcgttccg agccccccgc cgcccccgcc
1981 cccgcccgt catcgcccc ggagggcagg gtccgatga gggcccggt tgcggactgc
2041 gagaggaagg aatagttgga gtactgcacc ttgcggcgc ccgggaggg cgtcggcctg
2101 ggttgcttct ggggctgcg cccggccace cacgcctcgg tccagaagca gcagtggaga
2161 aagaaatgcc cgtggatgtc gttgatggtc agcgcgaagc gctcgaagga cacgacaagg
2221 gtcgcattct tgctgcgcag gaagtggtgg tcatgacgt agacaactc gaaggcggcc
2281 acgaagatgc tcgcggcca gtgggcgcg cccggcact tggcgcagag gaacggtaa
2341 tcggccaccc actgggcgca gaggcggtag gcctgctgt acagctcgat ggtgcggcag
2401 accagacagg gcggtccag cgcgaaggtg tcgccggacg ccggggcgaa gggccccgtg
2461 tccaaggcta cctatgcgt ggttgccgc ggtgtcgcg gggcgagcc aggccccgc
2521 cccccgaag catcgagc ggaccgcgcg cggccgggg gggcggcgc gagctcgtc
2581 tccacgtgct cgtagagcgc gctcgcgggc ggacgccta ccacgtcaca ggcggccagg
2641 agctccgcgc acaggcctc gttaagagcc agaaggtggg gatcgaaggc cacataccga
2701 cgctcgaacg cgccctacct tccagtcgctg cccggcgact cttcgcgcaa ggcggagctc
2761 gaccgcaccc acggggcgga cgtcgccat
```

SEQ     HSV-2 UL33
KEYWORD PROTEIN
SEQ ID No: 85

1     MAGRAGRTRP RTLRDRIFDC ALRSQTLRSL DARYVSRDGA GDAAVWFEIM TPAELEVIFF
61    TTDAKLNYLS RTQRLASLLT YAGPIKAPDG PAAPHTQQTA CVHGELLARK SERFAAVINR
121   FLDLRQILRG

KEYWORD DNA(NC_001798 REGION: 69637..71469)
SEQ ID No: 86

1 atggccggtc gagcgggcg cacgcgtccg cgaacgttac gggacagat ccgagctgc

FIG. 9L

```
  61 gggctgcggt cccagaccct ggaaagtcta gacgcgcgct acgtctcgcg agacggcgcg
 121 ggggacgcgg ccgtctggtt cgaggacatg acccccgccg aactagaggt tatattcccg
 181 accaggacg ccaagctgaa ctacctctcg cggacgcagc ggctggcctc cctcctgacg
 241 tacgacggc ctataaaaga gccgacggc acgptcgcc cacatacgca ggacacgcg
 301 tgcgtgcacg gcgagctgct cgccgaaagc cgcgaaaggt tcgcggcggt cattasccgg
 361 ttcctggacc tgcaccagat cctgcgggc tgacgcgcgc ttcgcgggg cacggcacc
 421 gggacgact tgtttacat aacagtaggg ggtggggga cgcgcacct tgccccgtcg
 481 cgatggcggg gatgggaag ccctacggcg gcgccccggg ggacgcgttc gagggtctcg
 541 ttcagcgcat caggctcatt gttcccgaca cgctgcgcgg cgggtgcgg gagtcgggcc
 601 actactcgcc atccaaccgg ccctcgagat gtgcttcca gttccacggg caggatgggt
 661 ccgacgaggc cttcccgatc gagtacgtcc tgcggctcat gaacgactgg gccgatgtgc
 721 cctgcaaccc ctactcgcg gtgcagaaca cggccgttc ggtgctgttt caggggtttt
 781 ttaacaggc ccaaggcgc ccgggggcg cgatccacgg ggagcagac aacgtgattc
 841 tgcactccac cgagacgacg ggactgtcca tcgagccct ggacgacgtc aaggggcgcc
 901 taggcctgt cgcccgggcg atgatggcca gcatgtggat cagctgcttt gtgcgcatgc
 961 ccggggtgca gatgcgtttc cggtcatgg gcccggagga cgccgttcga acgcggcgga
1021 tactgtgtcg cgcggcggag caggcctcg ccgctgcgc ccggtccagg cggtccagg
1081 atgactacgg ggccgtcgtg gtgccgcgg agcaccactc ttccggagcg cccgggccgg
1141 gggtccgcg ctcgggccgg ccagcgccgc ccggacgggg accggccccgt ccgtggccc
1201 aggccgtgca gtttgtcagg gcccccagtc cgcgccccc ggcgttctg ttgctgcgg
1261 cgggcgtgtt tctggggcc gctatcggt gggcgttgg cgcgccgca tgaaagggcg
1321 cgagccaccg tccccgccgc cagtgcatcc cagacgcccg cgagcagcac atccctccg
1381 ctcccgctc cggcccgatt cttacgggcg gacccaagct ccgatggcc gccccgcagt
1441 ttcacgccc caagaccatt acgccgaca agtcagggc gctcggcatg cgcgggctcg
1501 tgttggccac caacaaacgct cagttcatca tggataacag ctaccgcat ccgcacggaa
1561 cgcaaggtgc ggtgcgagag tttattcgcg gcaaggccgc gggctgaca gacctggcg
1621 tgaccaaccgc caacaacacg ttcgccccgc agcctatgtt cgccgcgcac gccgccgcg
1681 aatggctgcg gccctgttc ggtcttaaagc gcacgtattc ccctttgtc gttcgcgacc
1741 ccaagacccc cagcacccgg tgactcctcg gcgggtcct ccgcggccgt ctctcgttgc
1801 ccccctttcc ccctccccgg gtggttcatt aaa
```

```
SEQ         HSV-2 UL34
KEYWORD     PROTEIN
SEQ ID No:  87

1    MAQMSPPYCG RFGDRFEGLV QRTPLIVFAT LRGCGCESCF YSFSHPPSRC AFQFHGQDGS
 61    DEAFPIEYVL RLMNDWADVP CNPYLRVQNT GVSVLFQGFF NRPHSAPCGA ITAEQTNVIL
121    HSTETTGLSI CHLGDVKGRL GLGRRRMMAS MMISCFVRMP RVQLAFRFMG PEDAVRTSRI
181    ICRAAEQALA RRRRSRSQD DYGAVVVAAK HHSRCPCPG VAASPPAPP GRGPARFWRQ
241    AVQLFRAPRF GPPALLLLAA GLFLGAAIWW AVGARL
```

```
KEYWORD     DNA(NC_001798 REGION: 70119..71469)
SEQ ID No:  88

1 atgccgggga tgggaagcc ctaggcggc cgccggggg acgcgttcga gggtctcgtt
 61 cagcgcatca ggctcattgt tcccgacacg ctgcgcgcg gggtgcggga gtcgggccac
121 tactcgcat ccaaccggc ctcgagatg gcttccagt tccacgggca ggatgggtcc
181 gacgaggcct tcccgatcga gtacgtcctg cggctcatga acgactggg cgatgtgccc
241 tgcaacccct actcgcgcgt gcagaacacc ggcgttcgg tgctgttca ggggtttttt
301 aacggccc aaggcgcccc ggggggcgcg atcaccgcgg agcagacaa cgtgattctg
361 cactccacg agacgacgg actgtcctc ggagccctgg acgacgtcaa ggggcgcctc
421 ggcctgtacg agccgcgcgat gatggcca gcatgtggatc agctgcttt gtgcgcatgc
481 cggtgcagc tgcgtttcg gttcatggc ccgaggacg cggttcgac gcgggcggatc
541 ctgtgtcgcg cggcggagca ggcctcgcc cgtcgcccc ggtccaggaa gtcccaggat
601 gactacgggg ccgtggtggt gggcgggcg cacccctctt ccggagcgcc cgggcggggg
661 gtccgcgcct cggggccgcc agcgcgccc ggaagggac cggccgtcc gtggccatcag
721 gccgtgcagt tgttcaggc cccgaggttc ggccgcccgg cgcttctgct gctgcgggcg
781 gggctgttt ctgggggcgg tatctggtgg ggggttggag cgcgcatatg aaaggggcgc
841 agccaccgtc ccccgccgca gtgcatccca gacgcccgcg agcagcacat ccctccgct
901 cccgcctcgg gcccgattct taccgcgcga gaccaagtcc ggatggccga ccccgcagttt
```

FIG. 9M

```
 961 cacegeeca geaccattac egcegacaac gteggggaga teggcatgeg egggetegtg
1021 ttggcaaca acaacgetca gttcataatg gataacagct acccgcatcc gcacggaacg
1081 cagggtgcgg tgcgagagtt tcttcgcggg caggcgcgg cgctgacgga cctagggtg
1141 acccacgcca acaacacgtt cgccacgcag catatgttcg cgggcgacgc gcggcgaa
1201 tggctgggc cctcgttcgg tcttaagcgc acgtattcc cctttgtcgt tgcgaccca
1261 aagacccaa gaacccgtg agtcctcgga gggtccctac ggggccgtct ctcgttgccc
1321 ccctttcccc cttccgggt ggttcaataa a
```

SEQ        HSV-2 UL42
KEYWORD    PROTEIN
SEQ ID No: 89

```
  1   MAHLFGGAAA APLSEDAIPS PRESTEDWPP CQIVLQGAEL NGILQAFAPL RTSLLDSLLV
 61   VSDAGILVHR AIFGEQVFLP LDESQFSRYR WGSPTAAFLS LVDQKAGLLS VFRANQYPDL
121   RRVELTVTGQ APPRTLVQRI YTTASDGEAV ELASETLMKR ELTSFAVLLP QGDPDVQLRL
181   TKPGLTKVVR AVGDETAKPT TFELGFDNOKF SVFNARTCVT FPARSEGASS STGAQVCILT
241   SALKKAGQAA ANAKTVYGEN THRTFSVVVD DCSMRAVLAR LQVCGGTLMF FLTADVPSVC
301   VTATGPNAVS AVFLLKPQRV CLRWLGRSPG SSTSSLASQD SRAGPTDSQD SSSEFDAGOR
361   GAPEEEGLEG QARVPPAFPE PPGTKRRHPG AEVVPADDAT KRPKTGVPAA PTKAESPPLS
421   ARYGPAAESG GGDEGAYACY FRDLQTGDAS FSPLGAFRGP QRPPYGFSLP
```

KEYWORD    DNA(NC_001798 REGION: 93769..95255)
SEQ ID No: 90

```
   1  atggctcatc ttcccggcgg tgcggacgcc gcccccttt cggaggacga gatcccgtcg
  61  ccgcgcgagt ggacggaaga ctgccaggcc tgccagatag tgctgcaggg cgccgagctg
 121  aacgggatcc tgcaggcctt cgccgcgctt cgcacgagcc ttttggacc gctcctggta
 181  gtggtgcgacc gaggcatcct tgtacacaac gcgatttccg gcgagcaggt tttctgccc
 241  ctgaccatt cgcagttcag tcgctatcga tgggggagac ccacgcgga gttcctgtct
 301  ctcgtggacc agaagcgatc cctgctgage gtgtttcgcg caaaccagta acctgacctg
 361  cgggggtgg agctgacggt cacgggccaa gcccgcttc gcacgctgt gcagcgcata
 421  tgcgcgaccg cgtccgacgg agaggccgtg gagcttgcca gcgagacgct catgaaacgc
 481  gagttgacga gcttcgcggt actactccca caggggagac ccgacgtcca gctgcgctc
 541  acgaagccc agctcacgaa ggtggtgaac gcggtcgggg acgagacgcc caaacccacc
 601  acgttcgagc tcggcccaa cggcaagttt tccgtgttta acgcgcgcac ctgcgtcacc
 661  tttccagcgc gcgaggaggg cgcctagtcc agcaccggcg cccagtcca gattctgacc
 721  agcgcgctga gaagggcggg caagcggcc gccacgcca agacggtcta cgggaaaac
 781  acacacgca cattctcggt ggtcgtcgac gactgcagca tgggcggt cctcgggcgg
 841  ctgcaggtcg gcgggggcac cctcaagtca tttcctcacg gcgacgtcc cagcgtgtgt
 901  gtcacgcca ccggcccaa cgcggtgtcg gggtgtctc ttttcaaaac ccaggggtc
 961  tgcctgagcg gcgcgaccga cagcaggac tcctcctag agcggacgc ggggacgc
1021 tctcgggcg gcccgaccga cagcaggac tcctcctag agcggacgc ggggacgc
1081 ggcgcccag aagaagaagg cctcgaggga caggccgggg tacggccga gttccggaa
1141 ccgcgggaa ccaagcggag gcacccggg gcggagttg tcccgcgga cgacgccacc
1201 aagcgtcga gacgggcgt gccgccgcc ccacgcgag ccgagtgcc ccccctctcc
1261 gcgcgatacg gaccggagtc gggaggggt ggtggcccgta cgggtgctac
1321 tttcggcacc tccagacggg cgacgcgaga cccagccccc tctccgcttc cgggtgtcc
1381 caagacccc catacggctt tggttgccc tgacgaaac gggtggtgga agaacgcta
1441 acgcgcgcg ggcacgcggg gtgcgttgtg ttaaaaaaat aaataaa
```

SEQ        HSV2 UL52
KEYWORD    PROTEIN
SEQ ID No: 91

```
  1   MSTEDCORHG RSVAAPYEVT ALVATEGCVI TGSLALLTNG LLGAEPLYIF SYDAYRSDAP
 61   NGFTGAPTEQ SRFGSSRALY NDAQGLNGDS FRVTPCLLST EVGVTHHPKG RTRPNFVCPF
121   ERAUDDVAYLQ DRLGRSTFLL PAHVTATLDL EATFALHANI IMALTVAIVE NAPARISSGS
181   TAPLYEPGRS NRSVVGRMSL GQRGITTLPV HREARVLGAY ARAYTGSAQS PFWFLSHTGP
241   DEKSLVLAAR YYLLQAFRLG GAGATYDLQA VKDICATYAI PHOPRFDTLS AAGLTSFRAI
```

FIG. 9N

```
 301    TRFCDTSQYS  RGAAAAGFPL  YVERSIRADV  RETGALEKFI  ARDRSCLRVS  DREFITYIYL
 361    AHFRCFSFPK  LAIHLRAVIT  RDFSEAASTE  QPSFLGREAV  SQFFREVRAQ  LSISEYVKQN
 421    VTPRETALAG  DRAAAYLRAR  TYAPAALTPA  PAYGGVADGS  TRMMGRLAEA  ERLLVPHQWP
 481    AFAPTTPGDD  AGGGTAAPQT  CGIVKRLLKL  AATEQQGTFP  PAIAALMQIA  SVQTPLPVYR
 541    ITMSPTGQAF  AAAAKDDWAR  VTRGARPFRA  TVVADAAAAF  EPGALGSRLT  SRICARGPAL
 601    PPGGLAVGGQ  MYVNARSIFR  AALAVTNIIL  DLDIALKEFV  PFPFRIHERLG  KFRRAGALARV
 661    QLLFPAAAVD  PDAYPCYFYK  SACKPRAPPV  CAGDGPGADGG  DGGDGDWFPD  AGGPGDSEWR
 721    EDTDPMDTYR  GPLPDDEAAY  LDLLREQIPA  ATPSEFPDSVV  CSCADKIGLR  VCLPVPAGYV
 781    VHGELTMRGV  ARVIQQAVLL  DRDPVEAVGS  RVKNFLLIDF  GVTARGHSLR  LFYFAKIGPD
 841    GSACGRLLFV  FVLPFACEOV  FAFVAAHADP  RRFHFRAPFM  FSAAFRELRV  LRSLGSDYVS
 901    FFRKEASRNA  LEHFGRRETL  TEVLGRPYDVR  PDAGRTVEGP  ASELLGRIVA  CIEAHFPERA
 961    RRYQRVSVAR  AVIKGRWVIL  QLIPGRGAIN  QSLSCLRFRN  GPASRATART  PIALSVGTNS
1021    RLCASLCQQC  PATKCONGRL  RTLPTVGAGT  PCGRSRAPPST  SRFSSS
```

KEYWORD     DNA(NC_001798 REGION: 109878..114314)
SEQ ID No: 92

```
    1  atggggacgg  aagactgcga  tcacgaaggg  cggtcggttg  cggctcccgt  ggaggttacg
   61  gcgctgtatg  cgaccgacgg  gtgcgttatc  acctcctcgt  tgcgcctcct  cacaaactgc
  121  ctgctggggg  ccgagccgtt  gtatatattc  agatacgacg  cgtacgggtc  cgatgcgccc
  181  aatggcccca  cggcgcgcgc  caccgaacag  gagaggttcg  agggagacgg  ggcgtctac
  241  cgggatgcgg  ggcggctaaa  tggcgattca  ttccggtga   catttttgtt  atgggacg
  301  gaagtggcc   tgacccacca  ccgaaaggc   cgcaccaggc  ccatgttcgt  gtgccgcttc
  361  gagcgagcgc  acgacgtcgc  cgtgctccaa  gacgccctgg  gccgcgggac  ccattgatc
  421  ccggccacg   tcacagcaat  tctggacttg  gaggcgaagt  ttgcgctcca  cgtaacatc
  481  atcatggctc  tcaccgtggc  catcgtccac  aagcccccg   ccgcatcgg   cagcggcagc
  541  accgccacc   tgtatgagcc  cggcgaatcg  atgcgctagg  tcgtcgggcg  catgtcctg
  601  gggaagcgcg  gcctcaacac  gctgttcgtg  caccacgagg  cgcgcgggt   ggggggtac
  661  cgccgggcgt  attatgggag  cgcccaaagc  ccttttttggt  ttctgagcaa  attggccg
  721  gacgaaagaa  gctggtgct   gcgcgctagg  tactacctac  tccaggctcc  gcgcttgggg
  781  gggccggag   cacgtacga   tctgcaggcc  gtgaaagaca  tctgcgcgac  ctacgcaatc
  843  ccccacgacc  cacgacccga  cacctcagt   gcgcgctcct  tgacctagtt  cgccgccatc
  901  actgcttct   gttgcacgag  ccagtaccac  cggagcgatgy  cgccccgtgy  gtttccgatg
  963  tatgtggagc  gccgcatcgc  cgccgacgta  cgcgagaccg  gcgcgctgga  gaagttcatc
 1021  gcccacgatc  gcacgtgcct  gcgcgtgtcc  gacccgggaat  tcattacgta  catctacctg
 1081  gaacactttg  agtgcttcag  cccccagage  ctggccacgc  atctccggga  cgtgaccacc
 1141  aacgacccca  gcccgcgcgg  cagcacggag  cagccctcgc  cactggtcg   gaggggt
 1201  gaacagttct  tcggcgacgt  cgcgcaacatcc  gcgagtacgt  aaagcaaaag
 1261  gtcaccccca  gggaaaccg   actggcggga  gacgcgccg   ccgcctacct  gcgcgcgcgc
 1321  aagtatgcca  cggcggccct  caccgccgca  ccgcgctacct  gcgggtgcg   agactcgtcc
 1381  accaaatgza  tggaacgtct  gccggaagca  gaaaggatcc  tagtccccca  cggctggccc
 1441  gcgttcgcac  caacaactct  cgggacgac   gcggggggcg  gcactgcga   cccccgacc
 1501  tgccgaatcg  tcaagcgcct  cctcaagcg   agcagcaggc  aggacgcgc   cacgacgcgc
 1561  accgcgatcg  cggctctcat  gcaggacgcg  tggtccaaa   cccccctgcc  cgtgtacagg
 1621  attaccatgt  ccacgaccgg  ccaggggttt  gcgcggcagg  cgcgggacga  ctgggccga
 1681  gtgacgcggg  acgcgcgcc   gcggaagcg   acgtgtcag   aggacgcgga  gcggcgcc
 1741  gagccggcg   cgctggcag   acgactcacg  cgcgaattt   gcgccgggg   ccccgcgtc
 1801  ccccggcgc   gctcgacgt   cggggccag   atgtacgtga  acgcaacga   gatcttcaa
 1861  gccgcgtgg   ccgttacgaa  cetcatcctg  gatctggaca  tcgcctcgaa  ggagccgtc
 1921  ccttcccca   ggctcaaga   ggcctggt    cactttagc   gcgggggcgt  ggcggcggtt
 1981  cagatgttgt  ttcagcggc   cggtcgag    ccgacgcct   atcctgtta   tttttaaaa
 2041  agagctgtc   ggccacgcgc  gcgccggtc   tgtgagggcg  acgggacctc  ggccggtggc
 2103  gacgcagcga  acggggactg  gtttccacgac  gctgtgttc   ccgcgacga   ggagtcggag
 2161  gaggacacgg  accccatgga  cagacgaagg  ggccacgtcc  aggacggga   cgcgcgtac
 2221  ctgacctgc   tacacgaaca  gataccagcg  gcgcgagcca  ggaacgga    ctcgtcgtg
 2281  tgttcctgag  ccgacaagat  cgggctgcgc  gtgtgcctac  cggtccccga  ccgtacgtt
 2341  gtgcacggct  ccctgacgat  gcgtgggtg   gcgagggtga  tccagcaggc  ggtgctgttg
 2401  gaccggagt   tcgtggaggc  agtagggagc  cacgtaaaga  acttttttgct  gatcgataog
 2461  gcgctatacg  cccacggcca  cagccgtac   ttcgctatt   tcgcaaagat  cggccgac
 2521  ggctccggct  gcgccgtt    attgccgtc   ttcgtgatcc  cccacgtg    cgagacgtt
 2581  cggggtcag   tcgcgcgca   cgcgaccg    aggctttcc   actttacgc   ccgacatg
```

FIG. 9O

```
2641 ttttccgcgg cccgcggga gatccgcgtc ctccacagcc tgggcggga ctatgtcagc
2701 ttttcgaga agaaggcgtc gcgcaacgcc ctggagcact ttgggcgacg cgagaccctg
2761 acggaggttc tgggccgcta cgatgtgcgg cccgacgccg gggagacgt ggagggcttc
2821 ggtccagaac tgctggggcg aatagtcgcg tgcatcgagg ctcacttcc cgagcacgcg
2881 cgggaatatc aggccgtgtc cgttcgccgg gccgtccatta aggacgactg ggtcctgctg
2941 cagatgatcc acggccgcgg cgccctgaac caaagcctct cgtgtctgcg cttcaagcac
3001 gcagggcaa gtgcgcgac ggccaggacc tttctcgcgc tgagcgtcgg gaccaacaac
3061 cgcctatgcg cgtccctgtg tcagcagtgc tttgccacta aatgcgataa caaccgcctg
3121 cacacgctgt ttaccgtcga tgcgggcacg ccatgctcgc ggtccgctcc ctccagcacc
3181 tcacgaccgt catcttcata aggcctacg gcctcgtgct cgcgtggtac atcgtctttg
3241 gtgccagtcc gctccaccga tgtatttacg cggtgcgcc cgccggggcg cacacgata
3301 ccgccctgt gtggatgaag ataaaccaga cgtgttgtt tctgggccg ccgaccgcc
3361 cccccggcgg ggcatggaca ccccaccgcc gcgtctgcta cgccaatata atcgaaggtc
3421 gggccgtgtc cctccggcc atccccggcg ccatgagccg ccgggtcatg aacgtgcacg
3481 aggccgtaaa ctgcttggag gcccctctggg acaccagat gcggcctggtg gtcgtcggtt
3541 ggtttctgta tctagcgttc gtcgccattc accaacgacg atgcatgttc gggctcgtga
3601 gtccggcga cagcatggtg gcccggcga cctatctttt gaactacgcc ggcgcatag
3661 tgtcgagcgt gttcttgcaa taccctaca cgaaaatcac cgcctcctc tgcgagctat
3721 ccgttcaacg ccagaccctg gtgcagctgt tgaggcgga tccgtcaca ttcttgtacc
3781 accgccggc cattggcgtc atcgtgggct gcgagctgct gctccgcttc gtggccctcg
3841 gtctcatcgt cggcaccgct atcatctacc ggcgcgctg ccgatcaca cacccctgt
3901 ttctaacaat caccacctgg tgttctgtgt ccatcatcgc cctgacggag ctgtatttca
3961 tcctgcgcg gggatcggcc cccaaaacg cggaccagc ggcccccagg gggcgctcca
4021 aagggtggtc gggcgtctgc gggcgctgct gttccatcat cctctcaggt atgccgtgc
4081 gactgtgcta tatcgcagtc gtggccggg tggtgctgt ggccttcgc tacgaacagg
4141 agattcagcg gcgcctgttt gatctgtcac gtaacgccta ttccgtggga agaggcggac
4201 ccagtcgacc atacaaatta aatacacgac ccgcctgggg cctacgcacc ctgcaagtc
4261 gcatgcaaat taaaatcgtg cacagagccg atccggctc gggtctgctt gccctccc
4321 cggcccagca caggcaggct cgtccgactt ccgcatacac cccaccctac cgtgtgcttc
4381 cgccaccccg cctacgcgtg tacgcgaagg cggacccaga cctgccgtat gctaattaaa
```

VACCINE FOR VIRUSES THAT CAUSE PERSISTENT OR LATENT INFECTIONS

PRIORITY

Priority is claimed to U.S. Provisional Application Ser. No. 60/781,123, filed Mar. 10, 2006, and entitled Vaccine for Human Cytomegalovirus, which is referred to and incorporated herein by reference in its entirety.

STATEMENT OF FEDERALLY SPONSORED RESEARCH

This invention was made with Government support under Grant Number R01A1051551 by the National Institute of Health. The Government may have certain rights in this invention.

FIELD OF THE INVENTION

The invention is in general directed to methods and compositions for preventing or treating infections by viruses involved in persistent and/or latent infections.

BACKGROUND

Most current vaccines target diseases that cause acute infections and are then cleared by the immune system. In vaccine development, a significant inclusion criterion has been the extent to which a given immunogen is able to generate a strong T-cell response. However, this strategy has not been optimal for persistent, or latent infections, such as those caused by human cytomegalovirus (HCMV). In fact, some immunogens generate very strong T-cell responses, but are ineffective as vaccines against viruses that cause persistent or latent infections.

Vaccines are often targeted against immunodominant proteins of the virus. That is, vaccines often use the same antigens that are recognized and targeted by the immune system of a healthy host. HCMV candidate vaccines in preclinical and clinical testing are focused on eliciting CD8+ T cell or neutralizing antibody responses toward HCMV proteins that are known to be targeted during HCMV infection of the immunocompetent, healthy host. The HCMV targets for CD8+ T cell-mediated immunity being tested are most commonly the immunodominant UL83-pp 65 and IE1-pp72 proteins. While CD8+ T cells specific for these viral proteins are believed to be protective, recent results in an animal model suggest that CD8+ T cells against immunodominant CMV antigens may not provide any protection despite their high numbers in the infected host.

In the United States, approximately 40,000 newborns are congenitally infected with human cytomegalovirus (HCMV) annually. For many years, it has been recognized that human cytomegalovirus (HCMV) is efficiently transmitted to the fetus during pregnancy, with 0.5 to 2.5% of all newborns showing evidence of congenital infection. Unfortunately, the in utero infection is not benign, and 5 to 10% of the congenitally infected infants will be symptomatic at birth, with serious neurological defects. (for review, see (67)). Of the 5% to 10% that are symptomatic at birth, most develop sequelae such as microcephaly, sensorineural hearing loss, optic atrophy and chorioretinitis, and motor disabilities. Even the infected children who appear asymptomatic at birth are at high risk, as 10 to 15% of these children will show varying degrees of neurological damage later in life. The problem is intensified by the large increase in the number of young children in day care centers as the transmission rate of HCMV among children in these centers is high, and these children will frequently transmit the virus to their seronegative mothers or day care providers. The annual seroconversion rate for women with infected children is 30% as compared to a 3% rate for women with uninfected children. Moreover, immunization with the Towne strain of HCMV, which has been tested as a potential vaccine, did not significantly decrease the transmission rate. Since it is this group of women who most commonly will be pregnant, the risk to the newborn is significant. While the serological status of the mother positively correlates with protection of the newborn from disease, recent evidence strongly suggests that prior maternal immunity is not completely protective against neonatal disease from recurrent infection or infection with a different HCMV strain (4, 21). The devastating consequences of in utero infection make it imperative to develop an effective and safe vaccine that will prevent both acute infection and the establishment of latency. In addition to the effect in newborns, HCMV disease in other populations, such as, for example, transplant recipients, including both solid tissue and bone marrow transplants, can be quite severe, and has gained greater attention as the number of transplants has significantly increased.

Recovery from HCMV disease correlates with a cellular immune response rather than the presence of CMV-neutralizing antibodies (59, 70). Initially, it appeared that most of the HCMV-specific CTLs were directed against the HCMV UL83 (pp 65) matrix phosphoprotein with relatively low levels of CTLs specific for the HCMV IE1 72-kDa protein (a functional homolog of the MCMV gB) and the structural glycoprotein B (1, 5, 23, 28, 55, 78). Subsequently, it was found that the frequency of CD8+ CTLs directed against IE1 is similar to that against pp 65 (30, 43), and that multiple HCMV proteins are potential targets for CD8 T cells (14, 50).

An effective vaccine against HCMV disease has been an elusive goal for many years, even though many of the antigenic targets of the neutralizing antibody and CD8+ T cell responses have been identified (for reviews, see (26, 67)). Clinical trials using the tissue culture-passaged Towne strain was found to induce both neutralizing antibodies and CTLs and provided limited protection against severe disease in transplant recipients and in volunteers given a low dose HCMV challenge, but failed to prevent infection in women exposed to young children shedding HCMV. The envelope glycoprotein B (gB) has been the basis for virus neutralizing antibody inducing vaccines, both as a subunit vaccine (adjuvanted with MF59) as well as a recombinant replication deficient canarypox vector ALVAC-CMV (gB). Both vaccines were found in clinical trials to be well tolerated, and although the subunit gB vaccine was found to elicit high levels of HCMV neutralizing antibodies in seronegative volunteers, ALVAC-CMV (gB) was only able to elicit neutralizing antibodies after subsequent boosting with Towne. Preliminary results have been obtained following vaccination of seronegative subjects with the pp 65 expressing ALVAC-CMV (pp 65) vector, as strong pp 65-specific CTL levels were elicited as well as CTL precursor frequencies similar to those found in HCMV seropositive subjects. Other vaccination approaches that have undergone preclinical testing in mice include plasmid DNA (pDNA) encoding gB or pp 65, a peptide of the conserved CD8+ T cell epitope of pp 65, dense bodies, and more recently a recombinant vaccinia virus Ankara that expresses gB (2, 16, 17, 46, 69, 91). The key question; however, is whether they will protect against infection in seronegative individuals.

There is a need for an HCMV vaccine that can prevent HCMV infection, and that could limit HCMV replication, and possibly vertical transmission from mother to fetus or viral dissemination and disease in the transplant recipient.

Herpes simplex virus type 2 (HSV-2) is a medically important pathogen worldwide, with a seroprevalence rate that has been increasing in the US over the last two decades. HSV-2 infects between 10 and 50% of the population worldwide, and in the US, it is estimated that 20% of the population is infected (for review, see (92)). A unique property of the herpesviruses is that they can enter latency, a state characterized by the absence of infectious virus and limited viral gene expression. In response to various stimuli, the virus reactivates, replicates, and produces infectious virions. HSV-2 infection is usually initiated following sexual contact of a seronegative individual with someone who is shedding infectious virus. The primary infection of genital, perigenital, or anal mucosal skin sites is followed by transmission most commonly to the sacral ganglia where the virus establishes latency. Reactivation from the ganglia then leads to infection and viral shedding in the vagina or skin of the penis. The frequent reactivation of genital herpes not only is a source of physical discomfort and psychological stress, but also can cause serious disease in the newborn, which often leads to death. A major problem in controlling sexual transmission is that shedding of virus may be asymptomatic, and the incidence of HSV-2 infections continues to increase. Although antivirals are available, the lifelong persistence of this virus provides a strong impetus for the development of a vaccine that will prevent infection and the establishment of latency.

There is a need for the development of an effective vaccine that prevents infection and the establishment of latency, thus eliminating the possibility of recurrence. While most vaccine strategies to date have failed in human clinical trials, the immunological data gained over the years have shown that HSV-2 infection is controlled by both innate and adaptive immune responses, with CD8 and CD4 T cells playing a major role in viral clearance from the lesion. To provide the basis for a protective T cell based vaccine, recent work has identified many of the HSV-2 proteins that are primed by infection. However, the cellular and antibody responses to HSV-2 infection are not sufficient to provide sterilizing immunity and protection against recurrent infection and viral shedding. Thus, immune responses generated by a successful vaccine must be more effective than natural immunity.

SUMMARY

The invention is in general directed to methods and compositions for preventing or treating infections by viruses involved in persistent and/or latent infections. The methods and compositions are directed toward the prevention and treatment of infections caused by viruses such as, for example, herpesviruses, retroviruses, hepatitis viruses, and papillomaviruses, including, for example, cytomegalovirus.

BRIEF DESCRIPTION OF THE DRAWINGS

FIGS. 8A-8AA: Amino Acid and Nucleotide Sequences of 23 Conserved, Essential Genes of HCMV (Strain AD169) and Amino Acid Sequences of Their MCMV (Strain Smith) Homologs.

FIGS. 9A-9O: Amino Acid Sequences of 12 Essential Genes of Herpes Simplex Virus Type 2 (Strain HG52) That Are Highly Conserved with HCMV (Strain AD169), and corresponding nucleotide sequences.

DETAILED DESCRIPTION

Figure 1:
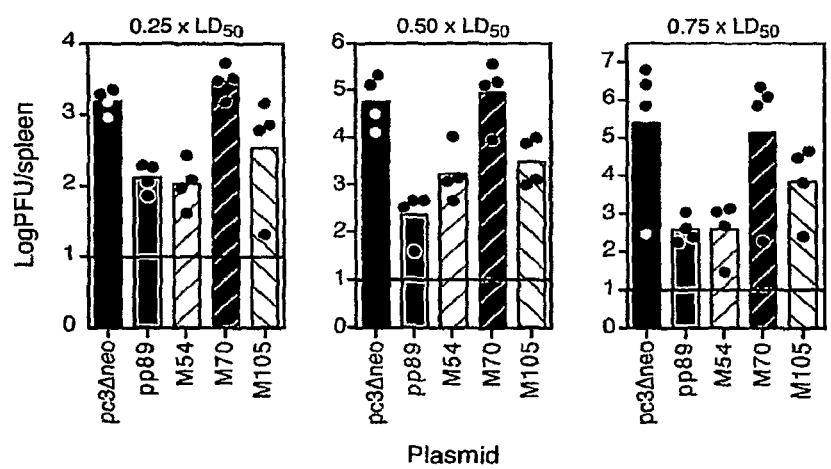
FIG. 1 is a graphical depiction of the results of DNA immunization of mice with M54 (DNA polymerase) or M105 (helicase) showing consistent protection against challenge virus replication in the spleen. Four BALB/c mice per group were i.d. immunized 3 times in 2 weeks with either empty vector DNA (pc36Δneo) or DNAs encoding IE1, M54, M70, or M105. Two weeks after the last immunization, mice were i.p. challenged with 1 of the 3 $LD_{50}$ doses of SG-MCMV shown. On day 6 postchallenge, spleens were removed and homogenized for MCMV titer determination. Bars and circles represent the group means and individual $Log_{10}$ of the virus titers for each of the spleens, respectively. The horizontal lines indicate the limits of detection for the highly sensitive plaque assay.

It has been found, surprisingly, that a strong immune response against a virus that causes persistent or latent infections may be achieved by immunizing with DNA derived from a highly conserved gene, or encoding a highly conserved gene product. In contrast to traditional vaccines, which usually target proteins that are immunodominant, an effective response against a persistent or latent infection may be achieved by vaccines that target proteins that are otherwise not targeted by a natural immune response. The present invention also provides a new method for inducing an effective immune response against a virus that causes persistent or latent infections by, for example administering a DNA vaccine encoding essential viral genes in a priming step, and a killed virus or attenuated live virus in a boosting step. The present invention may be used to generate effective immunity against persistent or latent infection-associated viruses including, for example, herpesviruses, retroviruses, hepatitis viruses, and papillomaviruses, including, for example, cytomegalovirus.

One benefit of using highly conserved viral proteins as vaccine targets is that the virus must express the targeted gene products in order to replicate and thus cannot escape immune detection by abrogating their expression. Another is that viral mutants that could otherwise escape CD8+ T cells specific for these genes would be less likely to arise due to the necessity for conservation in these genes to maintain the enzymatic activities of their encoded proteins.

In one embodiment of the invention, the vaccine consists of delivery of the plasmid DNA encoding essential, conserved viral genes and the killed virus or attenuated live virus preparation in priming and boosting steps. Those of ordinary skill in the art may determine the order and method of delivery. For example, the plasmid DNA is delivered to elicit specific CD8+ T cell responses against the conserved, essential proteins of the virus. Upon subsequent infection with HCMV, these CD8+ T cells can recognize and destroy virally infected cells within the host to limit the replication of the virus in target organs and prevent disease.

The priming arm of the immunization procedure consists of delivering purified plasmid DNA that expresses viral gene targets that elicit protective CD8+ T lymphocyte responses, while the boosting arm of the vaccine consists of delivering chemically killed or attenuated live HCMV to elicit virus neutralizing antibodies that help limit the dissemination of virus. Targeting antiviral CD8+ T cell immunity against the highly conserved, essential genes of HCMV is of particular importance because 1) the virus must express the targeted gene products in order to replicate and thus cannot escape immune detection by abrogating their expression, 2) viral mutants that could otherwise escape CD8+ T cells specific for these genes would be less likely to arise due to the necessity for conservation in these genes to maintain the enzymatic activities of their encoded proteins, 3) the CD8+ T responses to these gene products during HCMV infection have been found to be low overall, and thus plasmid DNA primed CD8+ T cells to these gene products could provide qualitatively better protection than the ultimately incomplete protection elicited by viral infection, and 4) the high level of conservation between HCMV and the CMVs that infect model animals provides for efficacy data in the animal models to Phase I clinical testing in human subjects.

The vaccine may be used to immunize any individual. By "individual" is meant any animal, for example, a mammal, or, for example, a human, including, for example, patients in need of treatment. An FDA-approved, commercially licensed HCMV vaccine could, depending on its protective ability, be sold and administered by physicians or clinics to either specific at risk populations or possibly to all children as part of childhood immunization. By "at risk" population is meant any individual at risk for diseases caused by HCMV, or that may carry HCMV infection to others including, for example, women before their child-bearing years, children, children under age one, day care providers, and transplant recipients or transplant donors. By treating transplant donors, for example, before the transplant is donated, infection of the recipient may be avoided. Transplants may include, for example, hematopoietic stem cell and solid organ transplants.

Diseases

Diseases or conditions that may be treated, prevented, or exhibit an alleviation of symptoms according to the present invention include any disease or condition that involves the acute or latent infection by viruses that causes persistent or latent infections. These include, for example, diseases involving infection by herpesviruses, retroviruses, hepatitis viruses, and papillomaviruses, including, for example, cytomegalovirus. It will be appreciated by those skilled in the art that reference herein to treatment extends to prophylaxis as well as the treatment of established infections or symptoms.

DNA Vaccination

The direct inoculation of pDNA ("Naked DNA" or "DNA Immunization") into animal tissues has become a widely used approach to vaccination as it overcomes many of the dangers and limitations associated with traditional immunization methods (for review, see (29)). DNA immunization has been shown to generate protective humoral and cell-mediated responses in a variety of infectious disease models, but its ability to present antigen-derived peptides on MHC class I complexes and generate anti-viral CD8+ T lymphocytes is the key correlate for protection against CMV disease (see above). This is in contrast to older protein-based immunization methods that induce primarily MHC class II-mediated responses and themselves are poor stimulators of CD8+ T lymphocyte responses. In addition, several methods for delivering pDNA have been developed to effectively generate immune responses, including biolistic (gene gun) delivery using microprojectiles, intramuscular (i.m.) and intradermal (i.d.) injections (administered by needle or Bioject needleless jet injection), and mucosal delivery (22, 72, 80, 84). Although i.d. DNA injections provide protection against systemic MCMV challenge (27, 62, 64), other approaches may be necessary for CMV immunization to achieve mucosal immunity. An additional approach, heterologous prime-boost using DNA as the priming step, is emerging as an effective means for vaccination against such pathogens as HIV, herpes simplex virus, hepatitis viruses B and C, *Mycobacterium tuberculosis*, and the malaria causing *Plasmodium* parasites, with clinical trials already underway in some cases (for review, see (87)). Heterologous DNA prime-boost been shown to elicit synergistic levels of T cell and antibody immunity that are not observed with repeated boosts with the same antigen delivery system, and the mechanisms underlying this synergism are beginning to be defined (20, 54). Coupled with their ability to generate high levels of protective antibodies, heterologous prime-boost vaccination may provide the long awaited tool for vaccination against pathogens recalcitrant to control using the traditional vaccination strategies.

The DNA vaccine may be administered using any appropriate method, including, for example using a replicating or a non-replicating viral vector, such as, for example, an adenovirus or vaccinia virus vector, a purified plasmid vector, or other form of DNA vaccine known to those of ordinary skill in the art.

By "derived from a highly conserved gene" is meant that the DNA encodes either part or all of a protein that is highly conserved, or the DNA sequence is the same as either part, or all of a highly conserved gene." By "part" is meant at least 20, 30, 40, 50, 60, 70, 80, or 90% of a protein or gene sequence. One method to determine whether a gene is highly conserved is to determine its % FastA aa identity, guidance for this determination may be found, for example, in the present application, including, for example, in Table 1.

Although many examples of the present application discuss the use of mouse CMV, it is understood by those of ordinary skill in the art that the present methods may comprise the use of human CMV, and human CMV genes and proteins. For example, DNA encoding for highly conserved proteins may comprise protein-coding segments from HCMV, such as HCMV having the DNA sequence provided in GenBank accession number G1128373214 (NC001347).

Murine Model of HCMV Infection

The serious problems associated with HCMV infection have made it imperative to understand the pathogenesis and immunology of this virus in order to develop strategies for its prevention and treatment. However, progress with the human virus has been slow primarily because the strict species-specificity of the virus has precluded studies in animal models. As an alternative, many in vivo studies have utilized as a model murine CMV (MCMV) infection of mice, which greatly resembles its human counterpart with respect to acute infection, viral gene expression, establishment of latency, host immune response to the viral gene products, and reactivation after immunosuppression. These similarities coupled with the ease of performing experiments with large numbers of mice, the availability of many genetically-defined inbred strains, and the vast body of knowledge on murine immunobiology has made this model system extremely attractive. One of the greatest values of this model is that a large amount of information can be obtained at a relatively low cost and in a reasonable period of time. This knowledge can then be used to efficiently design and prioritize the far more complicated and expensive studies for the development and testing of a human vaccine.

The molecular organization of the CMV genome, the transcriptional patterns during the permissive infection, the mechanisms involved in viral DNA replication, and the in vivo pathogenesis of the virus during acute and latent infection has been defined (51-53, 56, 57). MCMV homologues of HCMV DNA polymerase, glycoprotein B, and matrix proteins have been identified (10, 11, 15). Efforts have been made to develop a vaccine using this mouse model. ((27, 61, 62, 64, 88, 89, 93).

The MCMV genome is ~230 kbp in length and encodes at least 170 open reading frames (13, 56, 71). During the permissive infection, there are at least 3 distinguishable phases of gene expression (for review, see (60)). The IE gene products are those synthesized immediately upon infection and rely primarily on host factors for their expression. Early RNA and protein synthesis precedes viral DNA replication and is dependent on the prior expression of one or more IE genes. Finally the late genes are transcribed after the initiation of viral DNA synthesis.

MCMV infection is controlled by both innate and adaptive immune responses. The innate response, consisting of NK cells, macrophages, and the cytokines IFN-gamma, TNF-alpha, IL-12 and IFN alpha/beta, plays a central role in the initial resistance to infection (8, 31, 49, 65, 66, 68, 81). In addition, a cellular gene designated cmv1 controls the early splenic replication of MCMV and confers NK-cell mediated resistance (79). This gene has been identified as the killer cell receptor Ly49h, which activates NK cells against virally infected targets (7, 47).

Studies of HCMV immunity and disease in transplant recipients have shown the importance of cell-mediated immunity in protecting against HCMV disease (3, 77), and work in animal models, such as the MCMV model, has allowed for elucidating the protective roles of specific leukocyte subsets (74). The necessity of the adaptive component of cell-mediated immunity, the CD8+ and CD4+ T lymphocytes, to limit the acute, persistent, latent, and reactivating infections has been documented through depletion and adoptive transfer studies (reviewed in (73)). Immune reconstitution of immunoablated mice with MCMV-specific CD8+ T lymphocytes has been shown to reduce the viral load in the spleen, lungs, liver, and adrenals, while long-term depletion of CD4+ T lymphocytes in infected mice results in persistent infection in the salivary glands (41). The identity of the specificities of the antiviral CD8+ T cells has long been a subject of interest as the findings have strong implications for choosing viral antigens to use in antiviral cytoimmunotherapies and vaccines. While the identity of the immunodominant peptide of the immediate early 1 (IE1) gene product and the protective ability of IE1-specific CD8+ T cells in BALB/c mice have long been known (74), there had also been strong evidence pointing to the existence of CD8+ T cells that were generated against unidentified viral early (E) and late (L) gene products (75). With the advent of more reliable methods for the detection and quantification of specific CD8+ T cells, the identities of additional CD8+ T cells specificities have been revealed. These include the HCMV UL83-pp 65 homologs M83-pp105 and M84-p65, the antiapoptotic gene product M45, the MCMV immunoevasin gene product m04 (gp34), and two additional genes unique to MCMV, m164 and m18 (24, 34-40). One common feature of these MCMV genes is their expression at either E or E/L times of infection.

The identification of these E and E/L gene products as CD8+ T cell targets was initially paradoxical due to the known expression of immunoevasin E genes that encode glycoproteins that block cell surface presentation or recognition of virus derived antigenic peptides on MHC Class I complexes (73). The MCMV m152 gene product gp37/40 retains peptide loaded Class I complexes in the ER-cis-Golgi intermediate compartment, and the m06-gp48 reroutes these complexes to the lysosome for degradation (24, 45, 48, 76, 92). The m04 gene product gp34 binds to MHC Class I complexes without hindering their transport to the cell surface, but appears to prevent recognition of the complex by CD8+ T cells (44). Mutational analysis of MCMV has demonstrated the relative roles of the known immunoevasins in MHC Class I downregulation as well as some of the cooperative and competitive interactions among the immunoevasins (42, 85). In addition, the m152 deletion mutant was demonstrated to be attenuated in T cell competent mice (45), and cells infected with wild type, but not m152 deleted, MCMV are not recognized by M45-specific CD8+ T lymphocytes (24, 37). This is a significant result, as M45 has been shown to be a dominant antigen during the acute and memory response in C57BL/6 mice. It also has important ramifications for vaccine design, as cytoimmunotherapy with a specific CTL line for this dominant antigen was not effective in limiting viral replication (37).

The murine model has been used to test a prime-boost approach consisting of intradermal (i.d.) DNA immunization with a pool of 13 plasmids expressing MCMV proteins followed by intraperitoneal (i.p.) vaccination with formalin-inactivated MCMV (FI-MCMV) generated strong neutralizing Ab as well as antigen-specific CD8 T cells and confers complete short-term protection against infection in BALB/c mice following systemic challenge with highly virulent virus (64, 89). Sterilizing immunity had been achieved, as there was no detectable virus in either the spleen or salivary glands. Neither intradermal DNA immunization nor vaccination with formalin-inactivated MCMV alone provided complete protection. Further research investigated protection against an intranasal (i.n.) mucosal challenge and whether the protection was long-term. It was found that the viral titers in the spleens and lungs and in the majority of the salivary glands were below the limits of detection at all time points following systemic challenge. Following mucosal challenge, although complete sterilizing immunity was not achieved, viral titers in the lungs and spleen were reduced 1,000 to 10,000 fold, and titers in the salivary glands were reduced 10,000 fold at times corresponding to the peak of replication in the unimmunized controls.

Using the mouse CMV (MCMV) model of infection, immunization of mice with plasmid DNAs encoding conserved, essential genes of MCMV is able to provide protective immunity against subsequent MCMV replication in the spleen of the vaccinated mice. Delivery of the whole, killed MCMV virus or attenuated live virus particles elicits antibody responses against the glycoproteins in the viral envelope that can neutralize the virus and help to limit the spread of the virus from organ to organ.

A prime-boost approach consisting of DNA immunization with a pool of 13 plasmids expressing murine cytomegalovirus (MCMV) proteins followed by vaccination with formalin-inactivated MCMV (FI-MCMV) generates strong neutralizing Ab as well as antigen-specific CD8 T cells and confers complete short-term protection against infection in BALB/c mice following systemic challenge with highly virulent virus. As detailed in the examples, a smaller pool of plasmids may be used to generate an immune response. A smaller pool may include DNA plasmids expressing at least two, at least three, at least four, at least five, or at least six MCMV proteins. As shown in the examples, this pool may include, for example, DNA that encodes all or part of gB, M54, and M105. Each DNA sequence may be included on a separate plasmid, or one plasmid may include more than one DNA sequence. In other protocols, the three MCMV DNA plasmids (one of which was not in the original 13) were injected followed by immunization with formalin-inactivated MCMV. The most important finding was that this dual immunization protocol generated long-term sterilizing immunity in the lungs, spleen, and salivary glands of all BALB/c mice challenged systemically.

Boosting Vaccines

Either inactivated or attenuated live virus may be used in the boosting step of the present invention. Virus may be inactivated by, for example, chemical means known to those of ordinary skill in the art, including, for example, chemical treatment, or treatment with extreme temperatures, such as heat. Formalin treatment, for example, is one method of inactivating live virus. In other embodiments, attenuated live virus is used in the boosting step. The attenuated live virus may, for example, be the Towne strain of HCMV. In exemplary embodiments, for treatment of humans, the Towne strain of HCMV is used in the boosting step.

Herpes Simplex Virus 2 Infection

A. HSV-2 Genome Organization and Growth Cycle

The HSV-2 genome is ~154 kbp in length and encodes at least 84 open reading frames (ORFs). During the permissive infection, there are at least 3 phases of gene expression, immediate early (IE), (E), and late (L) (70, as referenced in Example 16). The IE gene products are synthesized immediately upon infection and rely primarily on host factors and at least one input virion protein (VP16) for expression. Early RNA and protein synthesis precedes viral DNA replication and is dependent on the prior expression of one or more IE genes. Finally the late genes are transcribed after the initiation of viral DNA synthesis.

B. Immune Responses to HSV-2 Infections

HSV-2 infection is controlled by both innate and adaptive immune responses (41, 67 as referenced in Example 16). The adaptive immunity involves neutralizing and non-neutralizing antibodies and specific cell-mediated immune responses, with both CD8 and CD4 T cells having a major role. These immune responses modulate the infection, but do not prevent recurrent infection or infection with another HSV-2 isolate. Their importance, however, is highlighted by the more frequent recurrences and increased disease severity seen in immunocompromised individuals. Analysis of recurrent HSV-2 genital lesions has also shown that infiltration of cytotoxic T lymphocytes (CTLs: CD4+ and CD8+) correlates with the clearance of virus from the lesion (44 as referenced in Example 16).

Neutralizing antibodies in HSV-2 infected individuals are primarily directed against gB and gD. Early work indicated that in humans, the CD8 T cell responses to HSV-2 proteins were relatively narrow, with the following ORFs detected: gB2, gD2, gE2, UL46, UL47, UL49, ICP0, ICP4, ICP22, ICP27, UL7, and UL25 (40, 42, 43, 58, 86, 87 as referenced in Example 16). Recently, an extensive analysis with peptides representing 48 HSV-2 ORFs, showed that the CD8 T cell responses were broader (35 as referenced in Example 16). All 48 ORFs were detected, and there was significant diversity in the pattern of responses between different individuals. The greatest frequency of responses were specific for ORFs UL39, UL25, UL27, ICP0, UL46, and UL47. It should be noted, however, the ORFs analyzed were primarily IE and viral structural proteins.

The herpesviruses are proficient at immune evasion, and HSV-2 is no exception. HSV-1 and HSV-2 down-regulate MI-IC class I presentation of viral antigen by a mechanism that involves interaction of the viral protein ICP47 with the transporter protein associated with antigen presentation (TAP) (24, 32, 88 as referenced in Example 16). This interaction prevents TAP from transporting viral peptides into the lumen of the endoplasmic reticulum, where they would form a complex with MHC class I molecules and be transported to the surface of the cell for recognition by CD8+ CTLs. Another mechanism of immune evasion involves viral effects on dendritic cells, the professional antigen presenting cells (APCs). HSV-2 impairs the function of murine dendritic cells and can induce cell death (37 as referenced in Example 16). In particular, HSV-2 infection of bone marrow-derived dendritic cells impairs their allostimulatory ability and production of IL-12, and hence may inhibit the priming of naïve T cells against HSV-2 infection. A study of the mechanisms governing the initiation of protective Th1-directed T cell immunity following intravaginal inoculation of HSV-2 in mice indicated that there was a rapid recruitment of submucosal dendritic cells to the infected epithelium (96 as referenced in Example 16). These cells remained uninfected but did acquire viral antigen and presumably traveled to the lymph nodes where they presented the viral antigen in the context of MI-IC class II molecules to CD4+ T cells. Recently, it has been found that HSV-2 infection of human monocyte-derived dendritic cells also results in apoptosis, but uninfected dendritic cells can phagocytose cell fragments from the dying cells and cross-present the antigens (8 as referenced in Example 16). Thus, the host may counter the viral effects on dendritic cells by priming T cells in the lymph nodes via cross-presentation of viral antigens by uninfected dendritic cells.

C. HSV-2 Vaccine Trials

Many approaches have been taken to develop a vaccine against HSV-1 or HSV-2 (for review, see (36, 41, 78 as referenced in Example 16)). Almost all have shown some level of protective efficacy in animal models, but have failed in human clinical trials, despite their ability to elicit strong neutralizing antibody responses. An approach used in the 1980s was to develop vaccines that consisted of inactivated HSV viral preparations. One included formalin inactivated fractions of HSV-1 proteins from infected cells, and this was tested in HSV discordant couples to prevent genital disease (74-76 as referenced in Example 16). Heat inactivated HSV-2 and HSV-1 virion preparations were also tested in Italy (49 as referenced in Example 16). Unfortunately, the studies were not performed in double blind, randomized, clinical trials, making interpretation of the results difficult. Another vaccine utilized preparations of detergent-dissociated viral glycoproteins. Although this vaccine protected against acute infection and central nervous system disease in animal models, and elicited an immune response in humans, it showed no protection in clinical trials (2, 15, 54, 79 as referenced in Example 16).

Various live-attenuated HSV vaccines have been tested, as it was believed that they would generate a much broader immune response. These vaccines have been produced either by multiple passages of the virus in tissue culture or by mutation of specific viral genes. A problem with these vaccines is that a balance of high immunogenicity and reduced virulence must be achieved. One live-attenuated vaccine against HSV-2 currently being developed consists of HSV-2 with a deletion of the protein kinase domain of the large subunit of ribonucleotide reductase ICP10 (4 as referenced in Example 16 as referenced in Example 16). This domain has polarizing Th2 activity and is required for efficient viral replication and latency reactivation. The vaccine (ICP10DPK) generates protection in animal models, and results of the initial trials indicate that this vaccine has some therapeutic efficacy (3, 16 as referenced in Example 16). Another live attenuated HSV-2 vaccine was derived by deleting both copies of the $\gamma_1$34.5 gene, UL55-56, UL43.5 and the US10-12 (69 as referenced in Example 16). Although this vaccine was immunogenic and could protect guinea pigs from disease, it did not protect against infection.

An alternative to a live-attenuated HSV vaccine is one that contains replication-impaired HSV. One approach consisted of either HSV-1 or HSV-2 that had a deletion of gH, and hence the virus could only undergo one round of replication (13, 22 as referenced in Example 16). These vaccines were protective in animal models, but the gH negative HSV-2 viral vaccine showed no protection against recurrence when tested for therapeutic efficacy in humans (14 as referenced in Example 16). A second approach has been to derive replication defective HSV-1 and HSV-2 viruses that do not express ICP8 (UL29) and one of the proteins (UL5) of the helicase-primase complex (for review, see (19 as referenced in Example 16). The dl5-29 HSV-2 vaccine was protective against lethal viral infection in mice, and showed protective efficacy when used as a prophylactic or therapeutic vaccine in guinea pigs. A major advantage of this vaccine is that it does not establish latency. Clinical trials with this vaccine are planned.

As another approach, vaccines with recombinant HSV glycoproteins, primarily gB and gD, were developed. A vaccine developed by Chiron, consisted of gD and gB from HSV-2 with the adjuvant MF59 (17 as referenced in Example 16). Another vaccine, developed by GlaxoSmithKline, contained HSV-2 gD along with the adjuvant alum and deacylated monophosphoryl lipid A (82 as referenced in Example 16). Both vaccines were tested in HSV-2 serodiscordant couples. Although the Chiron vaccine did not yield statistically significant protection against HSV-2 infection, the GlaxoSmithKline vaccine showed a significant protective effect against disease specifically in women (but not in men) who were seronegative for both HSV-1 and HSV-2. Interestingly, in this latter study, it appeared that prior infection with HSV-1 also conferred some protection against HSV-2 disease, although the vaccine did not augment the level of protection. Peptide vaccines have also been considered as an alternative approach, but the difficulty is finding the right combination of immunogenic peptides that will be protective in individuals with different HLA genes (7, 26 as referenced in Example 16).

Several viral vectors that can express HSV antigens, usually gD, have also been tested: vaccinia virus, adenovirus, Oka varicella zoster virus, and vesicular stomatitis virus (VSV) (1, 5, 6, 23, 25, 53, 64 as referenced in Example 16). Although these vaccines showed protection in animal models, they have not yet been transferred to human clinical trials. These vaccines, with the exception of VSV, have the disadvantage of potentially reduced efficacy in individuals with prior immunity to the vectors.

Formulation

While the compositions and methods of the present invention will typically be used in therapy for human patients, they may also be used in veterinary medicine to treat similar or identical diseases. The compositions may, for example, be used to treat mammals, including, but not limited to, primates and domesticated mammals. The compositions may, for example be used to treat herbivores. The compositions of the present invention include geometric and optical isomers.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

The exact dosage will depend upon the route of administration, the form in which the composition is administered, the subject to be treated, the age, body weight/height of the subject to be treated, and the preference and experience of the attending physician.

The compositions of the present invention may include pharmaceutically acceptable salts. Pharmaceutically acceptable salts are generally well known to those of ordinary skill in the art and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20.sup.th ed.) Lippincott, Williams & Wilkins (2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Administration of pharmaceutically acceptable salts of the DNA molecules described herein is included within the scope of the invention. For example, pharmaceutically acceptable salts may be prepared from non-toxic bases including organic bases and inorganic bases. Salts derived from inorganic bases include sodium, potassium, lithium, ammonium, calcium, magnesium, and the like. Salts derived from pharmaceutically acceptable organic nontoxic bases include salts of primary, secondary, and tertiary amines, basic amino acids, and the like. Pharmaceutically acceptable salts may be found in, for example, S. M. Berge et al., Journal of Pharmaceutical Sciences 66:1-19 (1977).

Methods of delivering DNA vaccines, as well as formulations and methods of administration may be found in, for example, U.S. Pat. Nos. 6,806,084 and 5,580,859. The DNA vaccine may, for example, be formulated to include transfection-facilitating proteins, viral particles, gold particles, liposomal formulations, charged lipids and calcium phosphate precipitating agents, or it may not include these components. Those of ordinary skill in the art may determine the appropriate formulation, considering factors such as the route of administration, for example, intradermal, intramuscular, or intranasal. Methods of administration may comprise the use of replicating or non-replicating vector.

In addition to the active ingredients, these pharmaceutical compositions may contain suitable pharmaceutically acceptable carriers comprising excipients and auxiliaries.

Kits

The present invention further provides kits comprising vaccine compositions or components that may be used to prepare vaccine compositions. For example, such kits may comprise DNA molecules of the present invention, such DNA molecules may be, for example, formulated for vaccine delivery. Such kits may further comprise a second vaccine composition, comprising, for example, an attenuated live or an inactivated virus. Or, for example, such kits may provide chemicals that may be used to inactivate viruses, such as, for example formalin; such kits may further comprise virus that has not yet been chemically inactivated.

Kits may also include instructions, and other components needed for immunization, such as, for example, nasal, muscular, or dermal delivery systems, such as, for example, needles, syringes, and inhalation or misting devices.

EXAMPLES

Figure 8N:
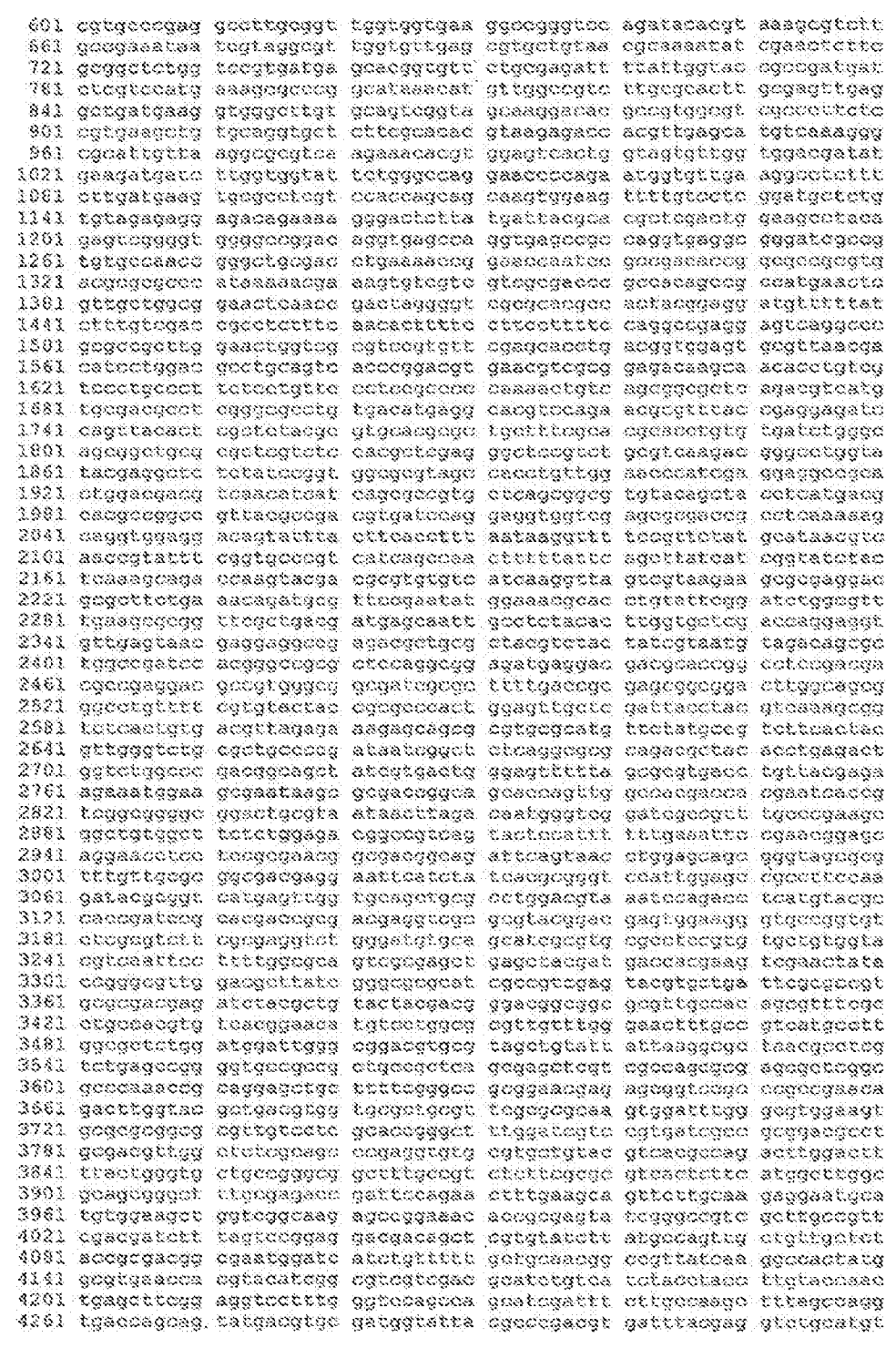
Figure 8O:
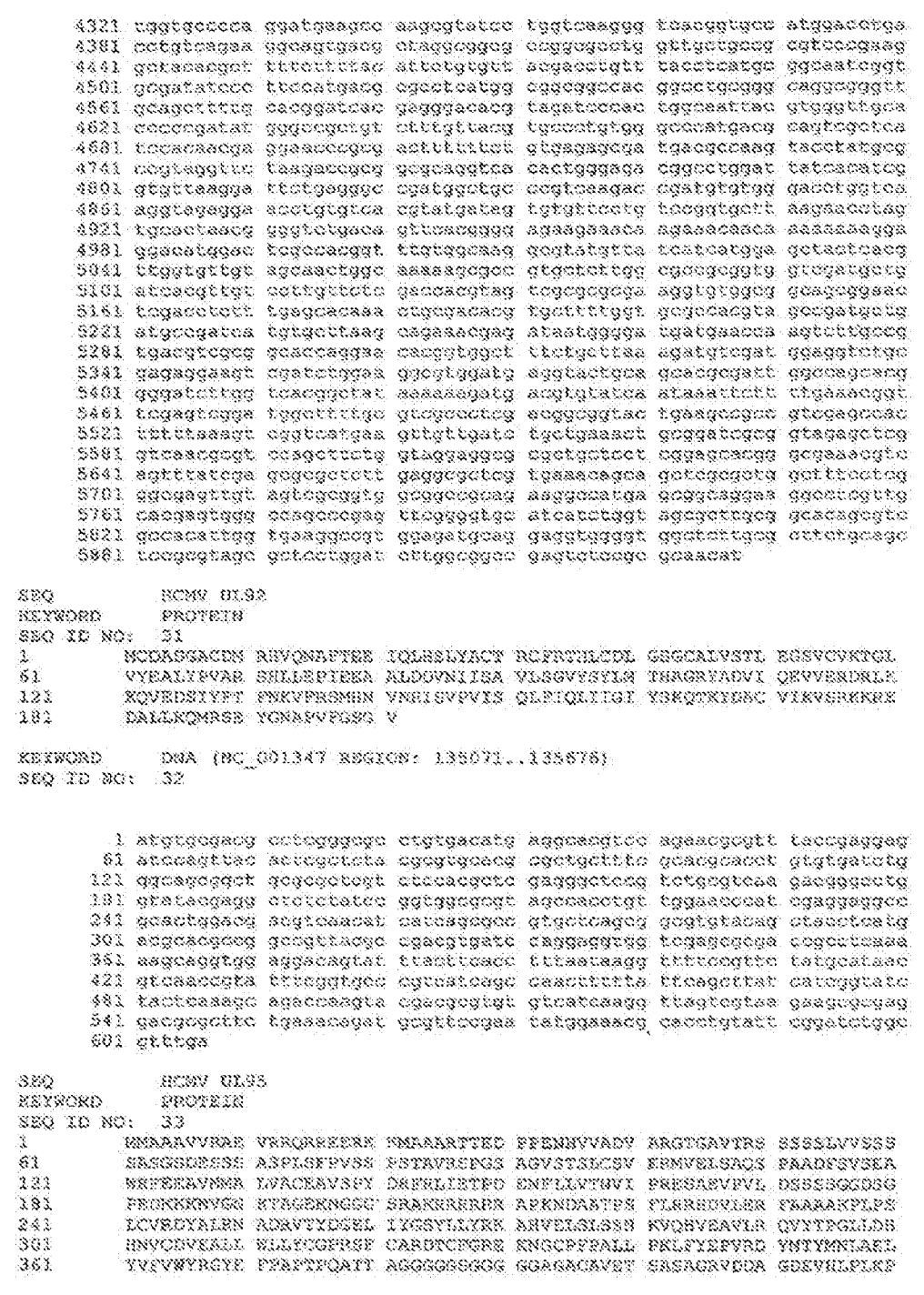
Figure 8P:
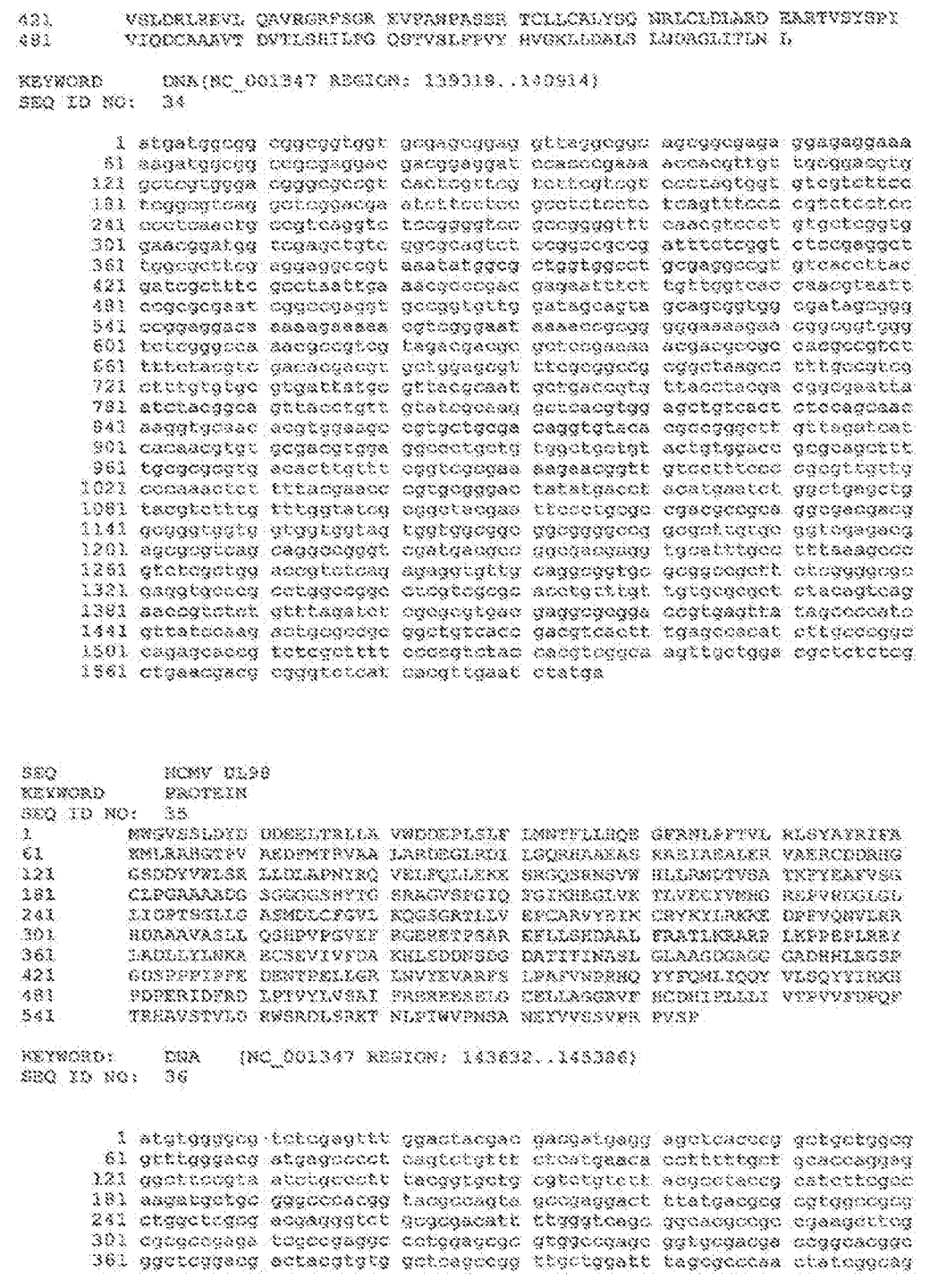

While the examples presented below discuss studies in MCMV, these examples are illustrative of methods that may be used with other persistent or latent viruses. Thus, examples that, for example, present methods of determining appropriate DNA sequence, or delivery method to use in the immunization protocol, are illustrative of methods that may be used in other viruses to determine the appropriate DNA sequence or delivery method. Amino acid sequences of exemplary HCMV conserved genes are presented in FIGS. 8A-8AA, along with corresponding nucleotide sequences. In some instances, the nucleotide sequence presented encodes a longer protein than the amino acid sequence in the Figure; those of ordinary skill in the art may determine whether the full length, or a truncated version of the nucleotide sequence is appropriate. Those of ordinary skill in the art would also recognize where the nucleotide sequence may vary from the nucleotide sequence encoding the corresponding protein, for example, where the nucleotide sequence is the complement of the coding sequence. In addition, although a particular strain of HCMV, AD169, is used in FIGS. 8A-8AA, those of ordinary skill in the art recognize that other strains, and related viruses, may also be used.

Example 1

Long-Term Protection (31 weeks) Against Systemic and Mucosal Challenge Following Dual Vaccination of Mice with Three MCMV Plasmids (Encoding IE1, M84, and gB) and Formalin-Inactivated Virus Three MCMV plasmids were given i.d. followed by injection of FI-MCMV. The choice of plasmids was based on previous results that showed that the plasmids expressing IE1 and M84 were highly protective but together they did not generate sterilizing immunity even when the DNA immunization was followed by injection of FI-MCMV. Therefore a plasmid that expressed glycoprotein B, which is the major target of neutralizing antibody during the natural infection, was added. At week 30, one group of mice was challenged mucosally with tissue culture derived virus and at week 31, a second group was challenged systemically with salivary gland derived virus. Organs (spleen, liver, lungs, and salivary glands) were harvested at days 6, 10, 14, 18, 24 and 32 postchallenge to determine viral titers. In the lungs of mice challenged mucosally, the viral titers were somewhat reduced in the mice that had received the MCMV plasmids alone and markedly reduced in the mice that had received the MCMV plasmids and FI-MCMV; by day 32 postchallenge, no virus could be detected in the lungs of the dually immunized mice. In the salivary glands of mice challenged mucosally, the reduction in titer in the dually immunized mice was even more striking, and for most mice, the titer was below the limits of detection. The most important finding was that this dual immunization protocol generated long-term sterilizing immunity in the lungs, spleen, and salivary glands of mice challenged systemically. (93)

Example 2

Multiple Epitopes in the MCMV Early Gene Product M84 Are Efficiently Presented in Infected Primary Macrophages and Contribute to Strong CD8+ T-Lymphocyte Responses and Protection Following DNA Immunization Following DNA vaccination of BALB/c mice with MCMV IE1 or M84, a similar level of protection against MCMV infection was achieved (89). However, the percentage of antigen specific CD8+ T cells elicited by IE1 was higher than that by M84 as measured by intracellular cytokine staining (ICCS) when splenocytes were stimulated with an epitope peptide. These results raised the question of why there were major differences in the CTL responses between the two vaccines while both displayed similar protective effects against a MCMV challenge. To further investigate the M84 specific CTL response following i.d. DNA immunization, a modified ICCS assay was developed in which antigen-presenting cells (APCs) expressing full-length M84 were used as a stimulator. Using this modified ICCS assay, a much higher percentage of M84 specific CD8+ T cells were detected when compared to the response to the single defined epitope. By immunizing mice with plasmids expressing subfragments of the M84 gene, at least two additional CD8+ T cell epitopes were demonstrated in M84. These results provide an explanation for the correlation between the strength of immune responses and the viral protection following DNA based vaccine immunization. The IE1 and M84 specific CD8+ T cell responses following MCMV infection of BALB/c mice with the modified ICCS assay was also further investigated. Only a modest increase in the percentage of M84 specific CD8+ T cells was detected when the additional epitopes were used in the assay. These results highlight the importance of keeping in mind that antigens that do not elicit a protective response during the infection may be highly protective when administered by DNA vaccine. (88).

Example 3

CD8 T Responses to IE1, M84, and gB in BALB/c Mice Immunized with the 3 MCMV Plasmids Encoding IE1, M84, and gB or gB pDNA Alone Groups of BALB/c mice were i.d. immunized with either 1) pc3 Δneo vector alone, 2) gB pDNA alone, or 3) a pool of IE1, gB, and M84. Another group of mice was i.p. infected with TC-MCMV. Nine days after the last pDNA immunization or MCMV infection, splenocytes were harvested for CD8 T cell quantification by ICS assay. Splenocytes were stimulated in vitro with either the dominant IE1 nonapeptide or with J774 (H-2d) macrophages infected with recombinant vaccinia viruses expressing either gB or M84.

Stimulation of the splenocytes from the vector alone-immunized mice using the gB-expressing J774 cells resulted in a low background staining level of 0.08%. In contrast, mice i.d. immunized with the gB pDNA alone had a mean of 1.84% of gB-specific CD8 T cells, and mice immunized with the IE1, gB, and M84 pDNA pool had a mean of 0.32%. Infection with MCMV elicited gB-specific CD8+ T cells to a mean level of 0.66%. Splenocytes were also stimulated with J774 cells expressing M84 as well as the IE1 peptide to document that CD8 T responses were generated against these antigens in the IE1, gB, and M84 group. Taken together, these results demonstrate that MCMV gB contains H-2d restricted MHC Class I epitopes and that both pDNA immunization and MCMV infection prime gB-specific CD8+ T cells in BALB/c mice. It is suspected that the CD8+ T cells themselves do not confer significant protection as several experiments have indicated that there is no significant decrease in MCMV titers in the spleens of gB pDNA immunized mice following short-term intraperitoneal (i.p.) challenge.

Example 4

Identification of ORFs that Augment the Protection Against Mucosal Challenge in BALB/c Mice—Protection Against Short-Term and Long-Term Systemic or Mucosal Challenge Following Immunization with gB and/or gH/gL Plasmids and FI-MCMV One approach to improve protection against mucosal challenge is to include a vector encoding the virus neutralizing antibody target glycoprotein H (gH). Previous studies have shown that MCMV gH is able to elicit complement independent virus neutralizing antibodies in mice following immunization with soluble gH protein. In HCMV infected cells, trafficking of gH to the cell surface requires the formation of a gH/gL/gO complex by disulfide linkage of gH to gL followed by interaction with gO. Because the proper trafficking and glycosylation pattern, and possibly native immunogenicity, of gH may require the coexpression of the accessory glycoproteins, a vector was constructed that coexpresses MCMV gH and gL (MCMV lacks an obvious gO homolog) to use in the DNA pool to increase the levels or longevity of viral neutralizing antibody responses. A plasmid was also constructed that expresses a truncated version of gB, which will be secreted and thus may prime for a higher level of neutralizing antibody.

Groups of mice were immunized with: 1) DNA vector plus PBS in alum; 2) DNA vector plus FI-MCMV in alum; 3) gB plasmid plus PBS in alum; 4) gB plasmid plus FI-MCMV in alum; 5) gB truncated plasmid plus PBS in alum; 6) gB truncated plasmid plus FI-MCMV in alum; 7) gB plus gH/gL plus PBS in alum; 8) gB truncated plasmid plus gH/gL plus PBS in alum; and 9) as a repeat of the above, gB plus IE1 plus M84 plus FI-MCMV in alum. DNA injections were i.d., while all injections of FI-MCMV or PBS in alum were i.p. Blood samples were collected pre-challenge and tested for neutralization antibody. All mice that received the FI-MCMV acquired neutralizing antibody prior to mucosal or systemic challenge, and although preliminary, one interesting finding is that groups that received the truncated gB plasmid plus PBS in alum showed a rapid rise in neutralizing titer after both mucosal and systemic challenge while the groups that received gB plasmid plus PBS in alum only showed a rapid rise in neutralizing titer after systemic challenge.

As a complement to the above experiment, groups of mice were immunized by priming with combinations of the gB and gH/gL DNAs and subsequent boosting with FI-MCMV in order to carefully evaluate the antibody and protective responses primed by the viral glycoprotein DNAs and to determine whether the priming provides additional protection from long-term mucosal or systemic challenge. In this experiment, the focus is on the immunization groups that receive FI-MCMV boosts so that the immunity and protection in the various DNA prime groups can be directly compared to the group that only received the FI-MCMV boosts. Groups of mice were immunized as above with the following: 1) vector DNA plus PBS/alum, 2) vector DNA, 3) gB DNA plus FI-MCMV/alum, 4) gH/gL DNA plus FI-MCMV/alum, 5) gB+gH/gL DNAs plus FI-MCMV/alum, or 6) gB+gH/gL+

IE1+M84 DNAs plus FI-MCMV/alum. As a positive control for antibody responses, another group of mice was i.p. infected with live MCMV. Blood samples were collected prior to i.p. or i.n. challenge, and on day 14 postchallenge, target organs were harvested for MCMV titer determination. Additionally, half of the mice were left unchallenged for later determination of long-term protection levels.

Prechallenge virion-specific serum IgG was quantified by ELISA. Prior to the first FI-MCMV boost, priming with gB pDNA either alone or together with gH/gL or gH/gL+IE1+M84 resulted in low-level seroconversion in 2 of 4 mice per group, whereas none of the gH/gL alone primed mice had seroconverted. Three weeks after the first boost, all of the mice except for the PBS/alum boosted mice had seroconverted. Compared with the mean ELISA titer of the vector+FI-MCMV group, the other groups had slightly higher ELISA titers, suggesting that the pDNA priming with the gB or gH/gL pDNAs provided measurable B cell priming. Three weeks after the second FI-MCMV boost, the mice primed with gH/gL either alone or in combination with the other plasmids (gB or gB+IE1+M84) had ELISA titers approximately 2-fold higher than those in the mice primed with vector and boosted with FI-MCMV and similar to those in the mice infected with live SG-MCMV. The mice primed with gB alone and boosted with FI-MCMV had similar ELISA titers as those primed with vector alone and boosted with FI-MCMV. With the caution that there is variability inherent in the use of endpoint titers, these data suggest that at the time of challenge there was a trend towards higher ELISA titers in the three mouse groups primed with gH/gL compared with those primed with the vector or gB pDNA alone.

Example 5

Salivary IgA Responses and Protection in BALB/c Mice Mucosally (Intranasally) Immunized with FI-MCMV with or without Mucosal Adjuvants As discussed above, i.d. pDNA priming followed by i.p. FI-MCMV boosting appears to confer complete protection against viral replication in the spleen, salivary glands, lungs, and liver following i.p. challenge. In addition, this parenteral prime/boost vaccine was able to provide complete protection of the spleen, salivary glands, and liver in the majority mice following i.n. challenge. However, in the lungs of the i.n. challenged mice, virus was detectable in the majority of the mice, though at reduced levels when compared to the vehicle only immunized controls. Therefore it was sought to determine whether i.n. delivery of the FI-MCMV could increase the mucosal protection against MCMV at the initial site of replication following i.n. challenge. Because mucosal responses are generally poor to protein antigens following i.n. immunization, the ability of two commonly used experimental mucosal adjuvants, cholera toxin (CT) and immunostimulatory CpG DNA (CpG), to elicit enhanced levels of mucosal immunity and protection was also tested.

In the lungs following i.n. challenge, all of the mice immunized i.n. with either PBS or FI-MCMV together with CT, CpG, or both had MCMV titers similar to those in the control group that received PBS+alum i.p. In contrast, the mice that were i.n. immunized with FI-MCMV alone or were i.p. immunized with FI-MCMV alone had a mean titer in the lungs that was reduced 35-fold below controls. However, the protection provided by i.n. immunization with FI-MCMV alone was lower in the salivary glands, with a mean titer reduction of only 4-fold below controls. In contrast, i.p. immunization with FI-MCMV either alone or with alum provided mean titer reductions of approximately 40-fold. Finally, following i.p. challenge, i.n. immunization with FI-MCMV alone did not provide protection in the lungs, liver, or salivary glands when compared with controls. This was in sharp contrast to the high level of protection to i.p. challenge that was conferred by i.p. immunization.

Intranasal immunization with FI-MCMV together with CT or CT+CpG resulted in the deaths of some mice following i.p. or i.n. MCMV challenge. This did not occur in control mice that were i.n. immunized with the adjuvants alone, indicating that the deaths were not caused merely by CT toxicity. These results suggest that there may be a deleterious interaction between the antigen and adjuvants. The virus titers in the PBS+adjuvant controls were comparable to those in the control mice immunized i.p. with PBS+alum. However, following i.p. challenge, the mice that were i.n. immunized with FI-MCMV+CpG had virus titers in the liver and lungs that were 50 to 100-fold higher than controls.

This study may indicate that there may not be an advantage to i.n. immunization with FI-MCMV; and that it is difficult to extrapolate effects of adjuvants from experiments that use different antigens for immunization.

Example 6

Assay of Protection Provided by Dual Immunization in Other Strains of Mice

A pilot study was conducted to test the efficacy of the dual immunization protocol in a mouse strain other than the BALB/c. C57BL/6 (H-2b) mice were immunized with: 1) DNA vector alone; 2) DNA vector plus PBS in alum; 3) DNA vector plus FI-MCMV in alum; 4) 13 MCMV DNA plasmids alone; 5) 13 MCMV DNA plasmids plus PBS in alum; or 6) 13 MCMV DNA plasmids plus FI-MCMV in alum. All DNA injections were i.d., while all injections of FI-MCMV or PBS in alum were i.p. Blood samples were collected pre-challenge, all of the FI-MCMV immunized mice acquired neutralizing antibody. Twenty-six weeks after the last FI-MCMV boost, mice were i.p. challenged. Six and 10 days following challenge, spleens and salivary glands, respectively, were harvested for MCMV titer determination.

Mice immunized with the 13 MCMV DNA plasmids alone or with the 13 MCMV DNA plasmids plus PBS in alum did not show significant protection in any organ. Although this result was expected for the salivary glands, the lack of protection in the spleen indicated that DNA immunization with these MCMV plasmids alone was not able to elicit protective CD8+ T cell responses. However, the titers in the spleens of the DNA vector plus FI-MCMV in alum immunized mice were 45-fold lower than those in the DNA vector alone immunized mice. Importantly, the viral titers in the spleens of mice immunized with the 13 MCMV DNAs plus FI-MCMV immunized mice were below the limit of detection for 3 of 4 mice tested. In addition, the salivary glands of 3 of 4 of the mice immunized with DNA vector plus FI-MCMV in alum had undetectable levels of MCMV. Most significantly, all 4 of the mice immunized with 13 MCMV DNA plasmids plus FI-MCMV had undetectable levels of MCMV in their salivary glands. Although the numbers were small, these results showed that the immunization of an H-2b mouse strain with FI-MCMV is effective in providing long-term protection against viral replication in both the spleen and salivary glands following systemic challenge. They also indicated that sequential immunization with the 13 MCMV DNA plasmids plus FI MCMV provides additional protection.

Example 7

DNA Immunization with the MCMV Homologs of the Highly Conserved HCMV DNA Polymerase (M54) or Helicase (M105) Genes Elicits a Protective Response MCMV (strain Smith) genes that are essential for viral DNA replication (71): M54 (DNA polymerase—50% FastA identity over 415 amino acids to HCMV UL54); M105 (helicase—43% FastA identity over 861 amino acids to HCMV UL 105); and M70 (primase—36% FastA identity over 982 amino acids to HCMV UL70) were tested for their ability to confer immunity.

Four BALB/c mice per group were intradermally immunized 3 times within 2 weeks with either the vector plasmid alone (pc3 Δneo) or this plasmid expressing the MCMV IE1 gene or the conserved, essential genes M54, M70, or M 105. Two weeks after the last immunization, mice were intraperitoneally challenged with virulent MCMV at one of three doses, 0.25×, 0.50×, or 0.75× the 50% lethal dose ($LD_{50}$), and 6 days following challenge, spleens were harvested and homogenized for measurement of the load of infectious challenge virus. Results in FIG. 1 are shown as the log 10 of plaque forming units (PFU) of virus per spleen, with bars representing group means and circles representing values from individual mice. In addition to the positive control IE1 pDNA, the pDNAs encoding M54, and M105 were protective against viral replication in the spleen following all of the i.p. challenge doses. (FIG. 1) Following challenge with the low dose of MCMV, the reductions in titer provided by immunization with the M54 and M105 pDNAs were comparable to that in the IE1 group. While the virus titer reductions in the spleens of the M54 and M105 immunized mice were not as high as those in the IE1 immunized mice following the intermediate challenge dose, following the high challenge dose, both IE1 and M54 immunization resulted in greater than 600-fold reductions in viral titers, and M105 resulted in a 60-fold reduction. M70 pDNA, which interestingly has the lowest percent aa identity to its HCMV homolog, was not protective.

Example 8

Identification of MCMV ORFs that are Protective Across Different Mouse Strains Other combinations of genes that may generate a more vigorous protective mucosal response in BALB/c mice may be identified. The related homologous human CMV genes may then be useful for more protective mucosal responses in humans. There may also be a different subset of genes that are required for protection in animals with a different H-2 haplotype.

Immunity established following natural CMV infection may suppress dissemination of the virus and disease, but if the virus persists; latency is established, the virus can reactivate, and individuals can be reinfected with a different strain of CMV. Thus, immunization must be more effective than natural infection. The most visible populations of CD8 T cells (as well as CD4 T cells and antibodies) in seropositive individuals may be immunodominant, but not immunoprotective. Highly conserved, essential nonstructural proteins may be excellent targets in infected cells for "primed" CD8 T cells, but during the natural infection there are still to be discovered immunoevasive mechanisms that prevent naïve T cells from being primed against these antigens. However, delivery of these antigens by DNA immunization might elicit the protective response.

Recent work characterizing the CD8+ T cell responses to the CMVs strongly suggests that while the CD8+ T cell repertoire that is primed by infection is not significantly affected by the known viral immunoevasins (24, 25, 50), the immunoevasins can inhibit primed CD8+ T cells from reducing the level of viral replication. For example, it has been shown that MCMV infection of C57BL/6 mice primes high levels of M45-specific CD8+ T cells. However, following adoptive transfer of these cells into irradiated recipients, expression of immunoevasins in the tissues infected with wild-type, but not mutant, virus inhibits the presentation of viral peptides and prevents the M45-specific CD8+ T cells from controlling viral replication (37). These findings have at least two important implications for rational vaccine design. First, while immunological assays can characterize the CD8+ T cell repertoire elicited by CMV infection, the ability of each specific CD8+ T cell subset to provide control of viral replication must be directly assessed by a protection assay. Secondly, since previous infection with the CMVs does not provide complete protection against reinfection or reactivation and in utero transmission of virus, the CMV infection may skew the CD8+ T cell repertoire so that the virus can establish and maintain persistent and latent infection in the midst of high numbers of primed, but ineffective, CD8+ T cells. During the infection, it is possible that naïve CD8 T cells are not primed against conserved nonstructural essential proteins (see Table 1), as the virus cannot sustain mutations in these proteins to evade the immune responses. Therefore, in order for a CMV vaccine to provide sterilizing immunity, the vaccine induced CD8+ T cell responses may need to include specificities to essential viral proteins that do not prime the CD8 T cells in the context of the viral infection.

One approach to increase the breadth of the immune response generated by the DNA vectors already being used and to identify additional MCMV genes that elicit protection is to use a DNA expression library constructed from the known MCMV ORFs for DNA vaccination. To determine additional MCMV ORFs that are protective in the 3 mouse haplotypes, MCMV genes that are highly conserved with their respective HCMV homologs (see table 1) are cloned and tested (71). Many of these are early genes that encode proteins that contribute to viral DNA synthesis and are conserved with other herpesviruses. In addition, with the exception of M114, all of the HCMV homologs have been shown to be essential for virus replication in primary fibroblasts (12, 90). As described above, M54 and M105 genes are protective in the spleens of BALB/c mice following i.p. challenge. Interestingly, the nonprotective M70 has the least amino acid identity to the HCMV UL70. The PCR products of these genes are ligated into an eukaryotic expression vector (i.e. pcDNA3) such that a carboxyterminal Flag tag is added to facilitate protein detection. Resultant transformants are be screened for the presence of insert in the correct orientation by restriction analysis, and the 5' and 3' ends of each ORF are sequenced. Expression of each protein is demonstrated in an in vitro transcription/translation reaction or in an in vivo transient expression assay. In the initial screening experiments, for example, 12 mice per group are i.d. immunized 3 times in 2 weeks with pools of 5 or 6 of the genes in the table that have not yet been tested in a particular mouse strain. As a negative control, a group of mice is immunized with the empty plasmid vector. Two weeks after the last injection, mice are i.p. challenged with 1 of 3 sublethal challenge doses of virulent SG-MCMV, to improve the interpretation of the data, multiple doses are given. Spleens are harvested on day 6 postchallenge for MCMV titer determination. In order for a DNA pool to be considered protective, there is a spleen titer reduction of at least 5-fold relative to the vector immunized group in at least two of the challenge groups. To test for the protective ability of the DNA pools in mice of differing MHC haplotypes, the pools are screened in the CMV sensitive BALB/c (H-$2^d$), CBA (H-$2^k$), and 129/J (H-$2^b$) strains. The goal is to construct a minimal DNA pool that contains the fewest number of the conserved essential MCMV genes needed to protect across all 3 mouse haplotypes.

TABLE 1

Highly Conserved Proteins of HCMV and MCMV

| MCMV gene | (HCMV functional homolog) | % FastA aa Identity with HCMV (aa Overlap length) | |
|---|---|---|---|
| M44 | (DNA pol processivity subunit) | 59 (351) | UL44 |
| M50 | (Egress) | 46 (252) | UL50 |
| M51 | (DNA packaging/cleavage) | 55 (78) | UL51 |
| M52 | (DNA packaging/cleavage) | 44 (250) | UL52 |
| M53 | (Egress) | 49 (280) | UL53 |
| M54 | (DNA polymerase) | 50 (415) | UL54 |
| M55 | (Glycoprotein B) (gB) | 44 (929) | UL55 |
| M56 | (DNA packaging/cleavage) | 42 (696) | UL56 |
| M57 | (ss DNA binding protein) | 51 (597) | UL57 |
| M70 | (DNA primase) | 36 (982) | UL70 |
| M71 | (unknown) | 41 (201) | UL71 |
| M77 | (Pyruvoyl decarboxylase) | 49 (478) | UL77 |
| M79 | (Unknown) | 49 (246) | UL79 |
| M87 | (Unknown) | 59 (408) | UL87 |
| M89 | Exon 2 (DNA cleavage protein) | 65 (673) | UL89 |
| M92 | (Unknown) | 50 (199) | UL92 |
| M105 | Helicase, helicase-primase subunit | 43 (861) | UL105 |

Example 9

Confirming Antigen-Specific CD8+ T Cell Responses

Once the members of the minimal cross-strain-protective DNA pool have been identified by screening above, it is important to confirm that each of the DNAs generates a antigen-specific CD8+ T cell response. With the exception of M100 (gM), protection elicited by the conserved MCMV genes above would likely be mediated by CD8+ T cells as they likely encode nonstructural antigens. The levels of antigen-specific CD8+ T cells elicited by immunization with each of the protective DNAs comprising the minimal pool may be quantified. In addition, the levels of CD8+ T cells specific for these MCMV genes may be measured following MCMV infection in order to determine whether these antigens are part of the natural CD8+ T cell repertoire. It is quite possible that these conserved genes elicit CD8+ T responses after DNA immunization but not MCMV infection due to the virus misdirecting the response in order for it to persist and establish latency.

The CD8+ T cell responses may be quantified by a modified ICS assay that uses transfected cells as stimulators (94) For example, 4 mice per group are i.d. immunized with either empty DNA vector or each of the protective DNAs of the minimal pool. In addition, a group of mice is i.p. infected with TC-MCMV. Ten days after MCMV infection or the last DNA immunization, splenocytes are isolated and stimulated in culture with syngeneic, highly transfectable cell lines (e.g. K41 H-$2^b$, BALB SV40 H-$2^d$, etc.) that were transfected with either empty vector or the protective DNA. Following stimulation, splenocytes are stained with fluorescent CD8− and IFN-gamma-specific antibodies and enumerated by flow cytometry as above. Because the transfected cells express the full-length ORF, all the possible epitopes that can be naturally generated in the proteasome and loaded onto MHC Class I complexes may be presented, eliminating the need to immediately define the minimal MHC Class I epitope of each antigen. Using this method the majority of the ORFs of MCMV strain Smith were screened for the generation of antigen-specific CD8+ T cells in C57BL/6 mice following MCMV infection (94). Taking the ICS assay data from the DNA immunized and MCMV infected mice together, one can quickly assess the immunological basis of the observed protection across the mouse haplotypes as well as address the question of whether infection with wild-type MCMV is able to suppress the priming of naïve CD8+ T cells that are specific for these otherwise protective antigens during infection. As described above, M84 is found to be the prototypical CD8+ T cell antigen of MCMV that is highly antigenic and protective following DNA immunization, but minimally antigenic during MCMV infection.

Example 10

Identifying Nonstructural E Genes that Elicit a CD8+ T Cell Response

In this example, nonstructural early genes that elicit a CD8+ T cell response were identified, the present example also demonstrates that antigen-specific CD8+ T cell responses may be obtained using methods of the present invention.

Mice, Cells, and Viruses, and Viral Purification.

Three- to 4-week old specific pathogen-free female BALB/c mice were purchased from Harlan Sprague Dawley, Inc. and housed in microisolator covered cages in the Pacific Hall vivarium, University of California, San Diego. Mice were allowed to acclimate at least one week prior to immunization or MCMV infection.

NIH 3T3 (ATCC CRL 1658), COS-7 (ATCC CRL 1651), and BALB/c mouse embryonic cells (MECs) were propagated as previously described (24). BALB SV40 cells, an SV40 transformed H-2" cell line (95), were grown in COS-7 media.

Salivary gland-derived MCMV strain K181 (SG-MCMV) was propagated in BALB/c mice and tissue culture-derived MCMV strain K181 (TC-MCMV) was prepared in MECs as previously described (96, 15). The titers of these stocks were determined by plaque assay on NIH 3T3 cells (27). The $LD_{50}$ of this SG-MCMV stock in BALB/c mice used in this study was $8\times10^5$ PFU (63).

Plasmid Construction and Expression.

Construction of pc3Δneo-pp 89, expressing the cDNA of IE1-pp 89 was described previously (89). Cloning of the M54, M70, and M105 genes of MCMV MW97.01, a virus derived from a bacterial artificial chromosome of Smith strain MCMV, into pcDNA3.1/V5-His-TOPO (Invitrogen Life Technologies) has also been described (97). For the studies reported here, the complete sequences of the 3 cloned ORFs were determined (Eton Biosciences, Inc., San Diego, Calif.) and compared with the published sequence of MCMV Smith (71), GenBank accession number U68299 (GI|21716071; NC004065). The coding sequences of the M54 and M105 ORFs were identical to the published sequence. The sequence of the M70 ORF was identical to the Smith strain sequence except for a single T insertion between the 3' end of the MCMV-encoded ORF and the vector-encoded epitope tag sequences: a mutation that resulted in an immediate termination codon. This mutation yielded a complete, wild-type, but untagged, coding sequence for the M70 protein. Confirmation of complete, continuous reading frames were provided by coupled in vitro transcription-translation (TNT T7 Quick Coupled Transcription/Translation System, Promega Corporation) using [$^{35}$S]methionine, sodium dodecyl sulfate-polyacrylamide gel electrophoresis (SDS-PAGE), and autoradiography following manufacturer's recommendations. To facilitate subsequent Western blot analysis of expression in transiently transfected COS-7 cells, the extraneous T of the M70 clone was deleted by QuikChange site-directed mutagenesis (Stratagene, Inc.) following the manufacturer's recommendations, and the resulting clone was verified by DNA sequencing.

Protein expression was confirmed by transient transfection of COS-7 cells using Effectene (Qiagen) followed by Western blot analysis. At 48 h posttransfection, cell lysates were made in reducing SDS sample buffer, solubilized at 42° C., resolved by SDS-PAGE, and proteins were transferred to nitrocellulose membranes. Plasmid expressed MCMV proteins were detected with a mouse anti-V5 tag-specific monoclonal antibody (Invitrogen) and SuperSignal West Pico reagent (Pierce) according to manufacturers' recommendations.

For i.d. immunization, plasmids were purified using Qiagen Endo-Free Mega or Giga columns and resuspended to approximately 2 mg of DNA per ml of endotoxin-free 10 mM Tris-HCl (pH 8).

Immunization, Virus Challenge, and Virus Titration.

Plasmids were diluted immediately before injection in endotoxin-free 10 mM Tris-HCl (pH 8) buffered saline. Mice were i.d. injected with 30 µl of diluted plasmid either into 3 sites (10 µl per site) in the shaved flank near the base of the tail or into one i.d. site in the tail approximately 1.5 to 2 cm from the base. Mice were injected 3 times within 2 weeks and challenged 2 or 3 weeks after the last injection by i.p. injection with 0.5 ml of Dulbecco's phosphate buffered saline (DPBS) containing various sublethal doses of SG-MCMV.

On day 6 post i.p. challenge, mice were sacrificed and the spleens were aseptically removed and washed with DPBS. Spleens were homogenized in Dulbecco's modified Eagle medium containing 10% heat inactivated-newborn calf serum (Invitrogen Life Technologies) and 10% DMSO using 7 ml Tenbröeck homogenizers and homogenates were aliquotted and stored at −80° C. until titration. The titer of infectious MCMV was determined by plaque assay of clarified homogenates using NIH 3T3 cells in 24-well dishes as previously described (27). The limit of sensitivity for this initial assay was 100 PFU per spleen. If the viral titer of a spleen was less than or equal to 5 times the detection limit (≦500 PFU per spleen), 100 µl of clarified homogenate from another aliquot of homogenate was used in a more sensitive plaque assay on NIH 3T3 cells in 10 cm dishes as previously described (63, 64), except the concentration of heat-inactivated newborn calf serum in the media was increased to 10%. The limit of sensitivity of this assay was empirically confirmed to be 10 PFU per spleen. The $Log_{10}$ was taken of the individual viral titers in each group and the mean of the $Log_{10}$ values was calculated.

Intracellular Cytokine Staining (ICS) Assay.

Levels of specific CD8 T cells elicited by DNA immunization were measured by ICS assay using transfected stimulator cells as described previously (97). For comparative purposes, CD8 T cell levels resulting from MCMV infection were measured in 3 BALB/c mice per group that were i.p. infected with 1.2×10$^5$ PFU of TC-MCMV 2 or 4 weeks prior to assay. Two to 3 weeks after the last pDNA immunization, 3 mice from each immunization or infection group were sacrificed for ICS assay. Briefly, BALB SV40 (H-2$^d$) cells were seeded into 96-well tissue culture plates and one day later, cells (ca. 60-75% confluent) were transfected with 0.5 µg of plasmid DNA and 1.25 µl of FuGene 6 (Roche) per well. Two days posttransfection, splenocytes were harvested, the erythrocytes were lysed (BD Pharm Lyse, BD Biosciences), and 8×10$^5$ splenocytes from the immunized or infected mice were added to duplicate wells of transfected BALB SV40 cells in the presence of brefeldin A (GolgiPlug, BD Pharmingen). For peptide stimulation, duplicate wells containing 2×10$^6$ splenocytes each were stimulated with 1 µM of the L$^d$-restricted nonapeptide epitope of IE1 ($^{168}$YPH-FMPTNL$^{176}$) in the presence of brefeldin A. Peptide stimulated splenocytes served as gating controls for CD8 and IFN-γ. staining. After 8 h stimulation at 37° C. and 7% $CO_2$, duplicate wells of splenocytes were combined into 1 well of a 96-well round-bottom plate for staining. Splenocytes were surface stained overnight with phycoerythrin-Cy5 (PE-Cy5) conjugated anti-mouse CD8a (Ly-2) antibody clone 53-6.7 (eBioscience) and, following fixation and permeabilization (BD Cytofix/Cytoperm, BD Biosciences), splenocytes were stained with a fluorescein isothiocyanate (FITC) conjugated anti mouse IFN-γ antibody clone XMG1.2 (eBioscience). The lymphocytes were gated and the dual stained splenocytes were enumerated on a BD FACSCanto flow cytometer (BD Biosciences) with BD FACSDiva software at the Research Flow Cytometry Core Facility, VA Medical Center, La Jolla, Calif.

For the measurement of secondary CD8 T responses, DNA immunized or TC-MCMV infected mice were i.p. infected with 1.2×10$^5$ PFU of SG-MCMV, and on day 5 postinfection, splenocytes were harvested and analyzed by ICS assay as above.

Statistical Analysis.

One-way analysis of variance (ANOVA) tests were used to compare MCMV titers or CD8 T cell levels, and Fisher's protected least significant difference test (PLSD) was used as the post-hoc test for pairwise comparisons. Analyses were performed using StatView 4.51 software for Macintosh (Abacus Concepts, Inc.) and statistical significance was achieved when P<0.05.

Cloning, Sequencing, and Expression of MCMV DNA pol (M54), Primase (M70), and Helicase (M105).

Figure 3:
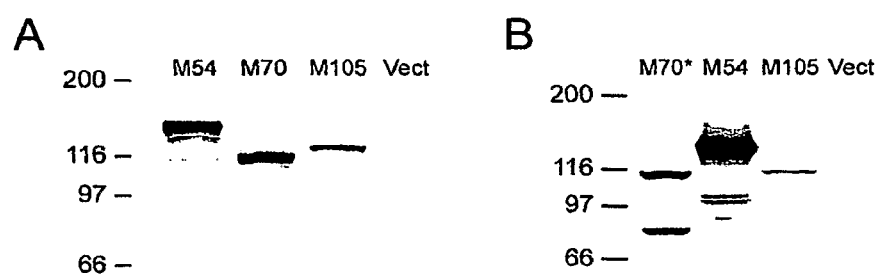
FIG. 3 In vitro and in vivo expression of the MCMV homologs of HCMV DNA polymerase (M54), primase (M70), and helicase (M105). A) The MCMV ORFs, cloned into pcDNA3.1/V5-His-TOPO, were expressed using the T7 promoter by coupled in vitro transcription/translation reactions (i.e. TNT T7 Quick) with [$^{35}$S]methionine. A portion of each reaction was subjected to reducing SDS-PAGE on a 7% polyacrylamide gel and the labeled proteins were detected by autoradiography. Numbers and lines on the left indicate the positions and relative molecular weights (in kDa) of the proteins in the marker. Vect indicates the TNT reaction performed with the DNA vector alone. Predicted molecular masses for the encoded proteins are: M54, 128.8 kDa; M70 (untagged), 109.6 kDa; and M105, 111.4 kDa. B) After mutating the M70 clone to yield the V5- and 6×His-tagged M70*, plasmids were transiently transfected into COS-7 cells and whole cells were lysed and solubilized in reducing SDS-PAGE sample buffer 48 h posttransfection. Lysate proteins were resolved by SDS-PAGE as above and electroblotted to a nitrocellulose membrane that was subsequently probed with a mouse-anti-V5 monoclonal antibody. Numbers at left are as in (A), and Vect indicates the lysate from cells transfected with empty plasmid vector. The predicted molecular mass for the M70* protein is 114.7 kDa.

The M54, M70, and M105 genes were cloned from MCMV MW97.01, a Smith strain derived bacterial artificial chromosome, into pcDNA3.1/V5-His-TOPO—a vector that provides carboxyterminal V5 epitope and 6×His tags (97). The complete sequences of the cloned M54 and M105 ORFs were identical to the published sequence (71) of MCMV strain Smith. The sequence of the cloned M70 ORF was identical to MCMV Smith except for a single T insertion between the 3' end of the M70 ORF and the vector-encoded epitope tag sequences. This mutation resulted in an immediate termination codon and thus a complete, but untagged, coding sequence for the M70 protein. Confirmation of complete, continuous reading frames for M54, M70, and M105 was provided by coupled in vitro transcription-translation (TNT T7 Quick) reactions and [$^{35}$S]methionine labeling (FIG. 3A). By SDS-PAGE and autoradiography, each of the plasmids was found to express a single labeled polypeptide with the predicted relative molecular mass: 128.8 kDa for M54, 109.6 kDa for the untagged M70, and 111.4 kDa for M105. Large-scale, endotoxin-free preparations of these DNA clones were prepared for i.d. immunization of mice.

To facilitate subsequent Western blot analysis following in vivo expression, the extraneous T at the 3' end of the M70 ORF was deleted by site-directed mutagenesis. The DNA sequence of the resulting M70 clone (designated M70*) was found to be identical to the parent except for the T deletion (data not shown). The M54, M70*, and M105 plasmids were transiently transfected into COS-7 cells and whole cell lysates were prepared in reducing SDS-PAGE sample buffer at 48 h posttransfection for Western blot analysis using a V5 tag-specific monoclonal antibody. Expression of M70* in COS-7 cells yielded a band corresponding to the predicted 114.7 kDA as well as a faster migrating band of equal intensity that may represent a proteolytic degradation product (FIG. 3B). No anti-V5 reactive band was observed following Western blot analysis of COS-7 cells transfected with the original mutant M70 clone. In addition, the predominant bands seen in the M54 and M105 lanes were of the expected sizes observed following expression in vitro (FIG. 3B). Duplicate blots were probed with a mouse-anti-MCMV hyperimmune serum, but no seroreactive bands were detectable. Taken together, these results demonstrate that the plasmids express the full-length, tagged ORFs, but that the encoded MCMV antigens do not elicit detectable antibody responses following repeated infection of BALB/c mice.

DNA Immunization with the M54 and M105, but not M70, Genes Elicits Protective Responses in BALB/c Mice.

The next inquiry was whether protective prophylactic responses could be generated using any of the three conserved, essential genes in BALB/c mice. Because the gene products of M54, M70, and M105 and their respective HCMV homologs are not likely to be part of the viral envelope, any protective responses elicited following DNA immunization using these genes would likely be from cell-mediated, not neutralizing antibody, responses. To test for the protective efficacies of these plasmid DNAs, 4 BALB/c female mice per group were i.d. immunized in the shaved flank with either 1) pc3 Δneo vector alone (20 μg) or with 10 μg of pc3Δneo plus 10 μg of either 2) IE1 (pp 89), 3) M54, 4) M70, or 5) M105. Two weeks after the last immunization, mice were i.p. challenged with 1 of 3 sublethal doses of SG-MCMV: $0.25 \times LD_{50}$ ($2 \times 10^5$ PFU), $0.50 \times LD_{50}$ ($4 \times 10^5$ PFU), or $0.75 \times LD_{50}$ ($6 \times 10^5$ PFU). The spleens were harvested on day 6 postchallenge for MCMV titer determination.

In addition to the positive control IE1 DNA, the DNAs encoding M54, and M105 were protective against viral replication in the spleen following all of the i.p. challenge doses (FIG. 1). Following challenge with the low dose of MCMV, the mean reductions in titer provided by immunization with the M54 and M105 DNAs were comparable to that in the IE1 group (12- to 15-fold relative to vector alone immunized mice.) While the virus titer reductions in the spleens of the M54 and M105 immunized mice were not as high as those in the IE1 immunized mice following the intermediate challenge dose, following the high challenge dose, both IE1 and M54 immunization resulted in greater than 600-fold reductions in viral titers, and M105 resulted in a 60-fold reduction. Compared with their respective vector DNA alone immunized controls, titer reductions in the spleens of the M54 or M105 DNA immunized mice were statistically significantly except for the M105 group after the high dose ($0.75 \times LD_{50}$) challenge (P=0.13). Finally, the M70 DNA, which interestingly has the lowest percent amino acid identity to its HCMV homolog, was not protective at any challenge dose level. These results identify M54 and M105 as protective members of a new class of protective antigens: the highly conserved, essential genes.

Figure 2:
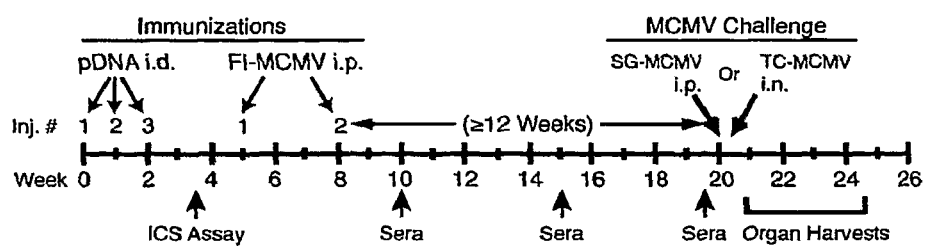
FIG. 2 is an example of a timeline of immunization and challenge infection.
Figure 4:
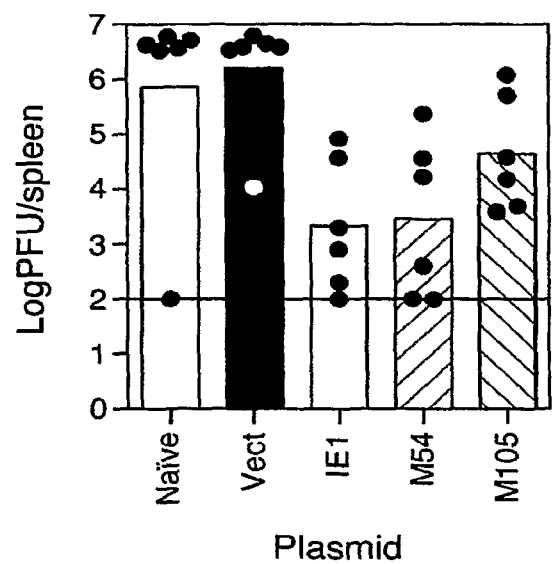
FIG. 4 Protection against virus replication in the spleen elicited by M54 and M105 in an independent experiment. Six BALB/c group were either left untreated (Naïve) or immunized as in FIG. 2. Three weeks after the last immunization, mice were i.p. challenged with 0.5×$LD_{50}$ of SG-MCMV, and on day 6 postchallenge, spleens were harvested and titered as in FIG. 2. Bars, circles, and the horizontal line are described in FIG. 2.

An independent experiment was performed to confirm the protective efficacies of the M54 and M105 DNAs. Groups of BALB/c mice were either left untreated (Nave) or i.d. immunized in the tail 3 times in 2 weeks with 50 μg of vector DNA (Vect), IE1, M54, or M105 DNA. Three weeks after the last immunization, mice were i.p. challenged with $0.50 \times LD_{50}$ ($4 \times 10^5$ PFU) of SG-MCMV and spleens were harvested on day 6 postchallenge for viral titer determination. As in FIG. 2, immunization with the IE1 or M54 DNAs resulted in mean viral titer reductions in the spleen of greater than 700- and 500-fold, respectively, relative to the vector DNA alone immunized controls, with more variability in the levels of protection in individual mice in this experiment (FIG. 4). The viral titer reductions elicited by either of these plasmids were statistically significant (P<0.002 compared with Vect). In this experiment, immunization with the M105 DNA resulted in a more modest reduction in viral titers, with a mean level approximately 40-fold lower than the Vect group (P=0.059). Taken together, immunization with the M54 DNA provided a high level of protection similar to that elicited by the immunodominant IE1 DNA, while immunization with the M105 DNA elicited more moderate virus titer reductions.

Immunization with M54 or M105 Elicits Specific CD8 T Responses that Rapidly Increase Following Viral Challenge.

Protective responses elicited by DNA immunization with the conserved, essential genes encoding DNA modifying enzymes would likely be due to specific adaptive cell-mediated immune responses, i.e. CD8 or CD4 T lymphocyte responses. DNA immunization with IE1 or M84 expressing plasmids, injected either alone or in combination, elicit strong CD8 T cell responses and protection against viral replication in the spleen after sublethal i.p. challenge (62, 89). Enumeration of pM84-specific CD8 T cells in DNA immunized or MCMV infected mice by ICS assay resulted in consistently higher numbers of IFN-γ+ CD8+ T cells following stimulation of splenocytes with cells expressing full-length M84 protein compared with the epitope peptide defined by Holtappels et al. (37, 88). These results led to the measurement of cell-mediated responses against the full-length protective M54 and M105 gene products rather than an attempt to map all of the $H-2^d$ restricted epitopes of these gene products and possibly overlook some of the protective specificities. An ICS assay was used in which splenocyte stimulation was mediated by BALB SV40 cells, a highly transfectable SV40 transformed $H-2^d$ cell line (95), that were previously transfected with DNAs expressing full-length MCMV ORFs. This technique was recently used to characterize the specificities of the CD8 T cell repertoire of MCMV infected C57BL/6 mice using plasmids encoding all 170 of the known MCMV ORFs (97).

Figure 5:
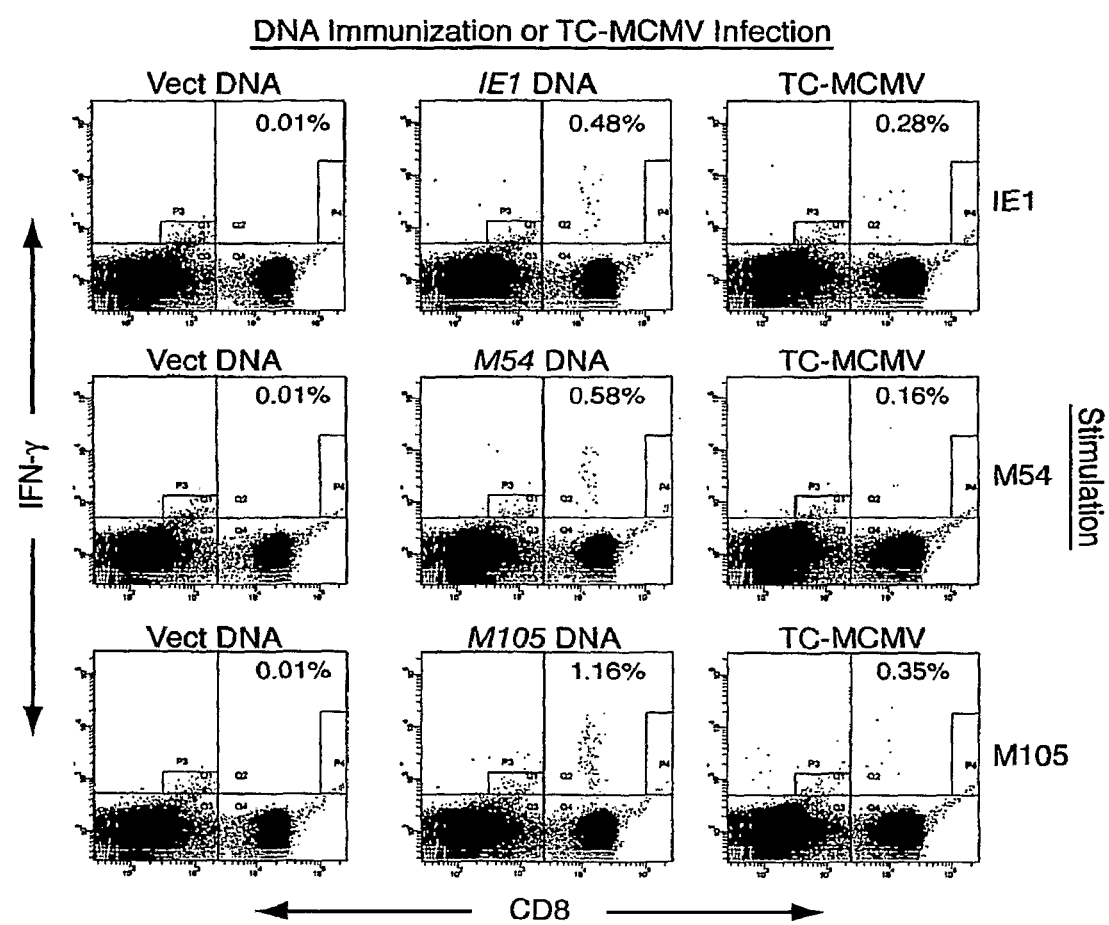
FIG. 5 Flow cytometric analyses of the CD8 T cell responses in BALB/c mice immunized with DNAs expressing IE1, M54, or M105 using transiently transfected stimulator cells. Mice were i.d. immunized 4 times with either empty plasmid vector (Vect DNA) or plasmid DNA expressing IE1, M54, or M105. To measure CD8 T responses elicited by MCMV infection, another group of mice was i.p. infected with 1.2□10$^5$ PFU of TC-MCMV. Two weeks after the last DNA immunization or MCMV infection, mice were sacrificed for ICS assay. As described in the Examples, splenocytes were prepared, counted, and incubated in the presence of brefeldin A with BALB SV40 (H-2$^d$) stimulator cells that were transfected 48 h earlier with plasmid DNA expressing either IE1, M54, or M105 as shown (Stimulation). After stimulation, splenocytes were surface stained with a PE-Cy5-anti-mouse-CD8a, fixed, stained intracellularly with FITC-anti-mouse-IFNγ antibodies, and analyzed by flow cytometry. The scatter plot for 1 mouse per immunization/infection and stimulation group is shown, arbitrarily chosen as Mouse #2. Percentages shown are the percentage of CD8+ T cells that were IFN-γ+ after stimulation, with the cell number for CD8 and IFN-γ double positive cells calculated as the cell number in quadrant Q2 minus the background staining in gate P4.

For measurement of specific CD8 T responses in DNA immunized mice, 7 week old female BALB/c mice were i.d. immunized in the tail with 25 μg of either empty plasmid vector (Vect) or plasmid DNA expressing IE1, M54, or M105. Mice were immunized 3 times in 2 weeks, and an additional booster was given either 2 (FIG. 6A) or 3 weeks (FIG. 6B) prior to ICS assay. Additional groups of mice were i.p. infected with $1.2 \times 10^5$ PFU of TC-MCMV either 2 weeks (FIG. 5A) or 4 weeks (FIG. 5B) prior to ICS assay in order to compare the specific CD8 T cell levels of DNA immunized with MCMV infected mice. For the ICS assay, SV40 BALB stimulator cells in 96-well dishes were transfected with either IE1, M54, or M105 DNA 48 h prior to harvesting the splenocytes from DNA immunized or MCMV infected mice. To monitor transfection efficiency of the stimulator cells, additional wells were transfected with either IE1 DNA or a DNA expressing the enhanced green fluorescent protein (EGFP), pcDNA3-EGFP. Erythrocyte depleted splenocytes from 3 mice per group were incubated with stimulator cells in the presence of brefeldin A for 8 h prior to overnight surface staining with anti-CD8 antibody, intracellular staining with anti-IFN-γ antibody, and analysis by flow cytometry. FIG. 4 shows the flow cytometric results for one representative mouse (Mouse 2) per immunization of infection group. Background staining of splenocytes from the vector immunized mice was very low, between 0.01% to 0.02% of the CD8+ T cells stained IFN-γ positive regardless of the DNA used to transfect the stimulator cells.

Figure 6:
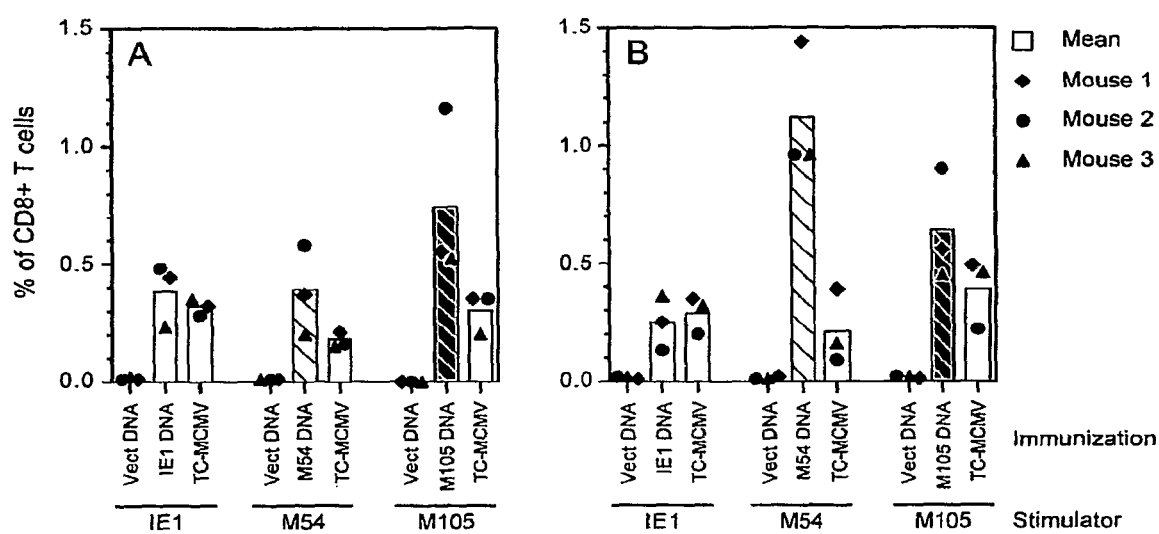
FIG. 6 CD8 T cell responses in BALB/c mice immunized with DNAs expressing IE1, M54, or M105. Groups of mice were DNA immunized or MCMV infected as in FIG. 4. A) Two weeks after the last DNA immunization or MCMV infection, 3 mice per group were sacrificed for ICS assay. The complete data for the experiment in FIG. 4 is shown, with bars representing the group mean percentages of CD8+ T cells that were IFN-γ+ for each vaccine group and symbols representing the individual values for each mouse in the group. Note that splenocytes from the same 3 TC-MCMV infected mice were tested with each of the 3 stimulator groups. B) Same as in (A) except that the ICS assay was performed on mice 3 weeks after the last DNA immunization or 4 weeks postinfection with TC-MCMV.

FIG. 6A shows the resulting CD8 T cell levels in the mice at 2 weeks after the last DNA immunization or 2 weeks after MCMV infection. Levels of IE1-specific CD8 T cells in IE1 DNA immunized or MCMV infected mice were comparable, with mean levels of 0.38% and 0.32%, respectively. Overall, these levels are lower than those obtained when splenocytes are stimulated with the dominant IE1 epitope peptide, most likely resulting from the lower probability of a primed CD8 T cell coming into contact with a stimulator cell presenting the single IE1 epitope compared with splenocytes bathed in a large excess of only the stimulating peptide. At the time of stimulation, transfected stimulator cells were routinely 85-100% confluent and 60-70% of cells were transfected as measured either by direct fluorescence of EGFP transfected cells or by immunofluorescent staining of IE1 transfected cells (data not shown). Nevertheless, the levels of IE1-specific CD8 T cells in DNA immunized or MCMV infected mice were statistically significantly higher than vector immunized mice (P=0.001 and 0.003, respectively). All mice immunized with M54 DNA or infected with MCMV had M54-specific CD8 T cells detectable after stimulation with M54 transfected stimulator cells, with the DNA immunized mice having slightly higher, but more variable, levels (mean 0.39%, range 0.20%-0.58%) relative to the MCMV infected mice (mean 0.18%, range 0.15-0.21%) (FIG. 6A). The responses in the M54 immunized mice were significantly higher than in vector immunized controls (P=0.006) but not the MCMV infected mice (P=0.06). The M54-specific responses in the MCMV infected mice also were not statistically higher than vector controls (P=0.12). Immunization with M105 DNA or MCMV infection elicited M105-specific CD8 T cells, with DNA immunization again eliciting high but variable levels (mean 0.74%, range 0.52-1.16%) compared with MCMV infection (mean 0.30%, range 0.20-0.35%). Similar to the M54 test groups above, the CD8 T cell responses in the M105 DNA immunized mice were significantly higher than vector immunized mice (P=0.006), while the responses in the MCMV infected mice were not statistically different than the controls (P=0.15). However, the M105-specific responses to DNA immunization and MCMV infection were significantly different in this group (P=0.045).

The CD8 T cell levels were subsequently tested in mice that were rested an additional week after the last DNA immunization (3 weeks total) or 2 weeks after MCMV infection (4 weeks total). Overall, these results (FIG. 6B) were very similar to those obtained above. The most notable exception is that the M54-specific CD8 T responses in the M54 DNA immunized mice were significantly increased relative to the MCMV infected mice (P<0.001). The mean M54-specific CD8 T responses in the MCMV infected mice were comparable between the 2 experiments (0.18% and 0.21%), suggesting that the increases observed in the M54 DNA immunized mice may have resulted from slower kinetics of the CD8 response to M54 DNA compared with the IE1 or M105 DNAs. In this experiment, the M105-specific CD8 T cell levels in the MCMV infected mice were significantly higher than vector immunized controls (P=0.03), but not statistically different than the M105 DNA immunized mice (P=0.11). Taken together, the results from these two experiments demonstrate that the M54 and M105 DNAs elicit antigen-specific CD8 T cell responses, with perhaps the response to the M54 DNA having slower kinetics. M54- and M105-specific CD8 T cell responses were also detectable following acute i.p. infection with MCMV, although only the responses to M105 at 4 weeks pi were statistically higher than vector controls. There was also a strong trend for the M54 and M105 DNAs to elicit higher levels of CD8 T cell levels than those resulting from MCMV infection, with MCMV infection eliciting statistically significant CD8 T cell levels against M54 or M105 in 1 of 2 experiments.

The secondary response to the M54 and M105 gene products was measured to determine how the CD8 T cells primed by DNA immunization responded to viral challenge. MCMV infection does not prime significant levels of IE1- or M84-specific CD8 T cells in vector alone immunized mice by 5 d postchallenge (89). In contrast, CD8 T cells in IE1 or M84 DNA immunized mice were able to respond vigorously by this early timepoint, indicating that a secondary response had occurred. Whether the low M54- or M105-specific CD8 T cell levels primed by MCMV infection would increase following subsequent viral challenge or whether these antigens' subdominance during infection hinders expansion of the primed CD8 T cells was also a goal of this example. To this end, 3 DNA immunized mice per group were i.p. challenged with $1.2 \times 10^5$ PFU of SG-MCMV on week 7 after the last immunization, while 3 of the MCMV infected mice were similarly re-infected with SG-MCMV 6 w after primary MCMV infection. On d 5 postchallenge or reinfection, splenocytes were isolated and analyzed by ICS assay as above.

Figure 7:
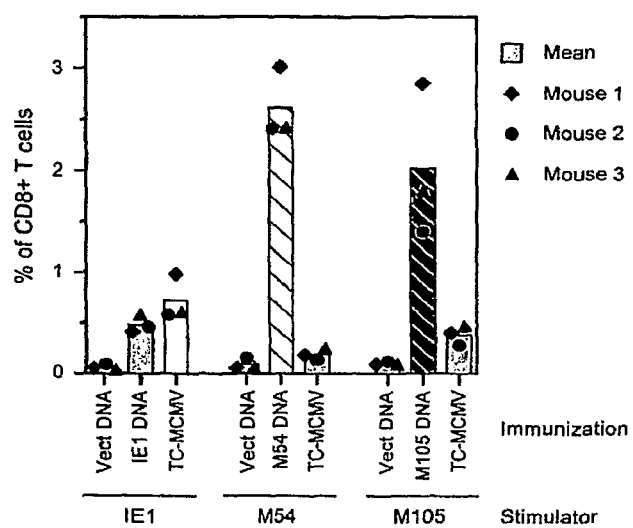
FIG. 7 CD8 T responses in DNA immunized or TC-MCMV infected mice on d 5 postchallenge with SG-MCMV. Three BALB/c mice were immunized 3 times in 2 weeks with either empty vector or plasmid DNA expressing either IE1, M54, or M105. Another group of mice was i.p. infected with TC-MCMV as in FIG. 4. Seven weeks after the last DNA immunization or 6 weeks after MCMV infection, mice were i.p. challenged with $1.2 \times 10^5$ PFU of SG-MCMV, and the ICS assay was performed on the splenocytes of these mice on day 5 postchallenge as above. Bars and symbols are as in FIG. 5.

The mean levels of specific CD8 T cells in the vector alone immunized mice on d 5 postchallenge were 0.06%, 0.09%, and 0.10% when stimulated with cells expressing the IE1, M54, or M105 DNAs, respectively (FIG. 7). These results indicate that primary responses to these antigens were low overall at this time postinfection and show the magnitude of their possible contribution to the levels in the DNA immunized or MCMV infected mice. The mean percentage of IE1-specific CD8 T cells in the IE1 DNA immunized mice was 0.48% (FIG. 7). This value was slightly higher that the peak level observed prechallenge (0.38%, FIG. 6A). By comparison, the mean in the MCMV infected mice post-reinfection was 0.73%, which was at least 2-fold higher than the peak prechallenge level of 0.32% (FIG. 6A).

The CD8 T cell levels in the mice that were MCMV challenged on week 7 after the last immunization with M54 or M105 DNA were also 2- to 3-fold higher than their respective peak levels prechallenge. In contrast, in the mice previously infected with MCMV, the postchallenge levels of CD8 T cells specific for M54 and M105 were almost identical to their respective prechallenge levels. Although it is not known what the levels of specific CD8 T cells to M54 and M105 in this group of DNA immunized mice would have been without restimulation with challenge virus, IE1 or M84 DNA immunized mice had CD8 T cell levels that either decreased or stayed the same after 2 weeks post-last immunization (89). More specifically, the level of IE1 peptide-specific CD8 T cells was 5.2% at week 2 after the last immunization and then declined to 1.7% at week 4, while the level of M84 peptide-specific CD8 T cells was 1.1% at week 2 and 1.0% at week 4. Taken together, our data showed that the M54- and M105-specific CD8 T cells in the DNA immunized mice were able to rapidly respond to viral challenge with increasing levels of IFN-γ+ cells, while the IFN-γ secreting M54- and M105- specific cells in MCMV infected mice, unlike the IE1-specific CD8 T cells, were not stimulated by subsequent reinfection.

In this example, protective CD8 T cell targets of MCMV on the E genes were identified whose homologs in HCMV have been found to be essential for viral replication in cultured cells. HCMV UL54 and UL105 were demonstrated to be essential for oriLyt-dependent DNA replication in a transient transfection system (98), and their requirement for viral replication in vivo has been confirmed by the independent mutagenesis studies by Dunn et al. and Yu et al. (12, 90). UL54 encodes the DNA polymerase catalytic subunit, and based on aa homology with the HSV-1 helicase protein encoded by UL5, HCMV UL105 is believed to contain the helicase activity of the proposed helicase-primase complex (UL70-UL102-UL105). Thus, it is unlikely that MCMV would be able to severely down regulate or abrogate expression of M54 and M105 in vivo in a productive infection in the face of cognate effector CD8 T cells. However, it remains a possibility that MCMV could down regulate the expression of M54 or M105 in infected tissues to a level that promotes a slower rate of replication and reduced pathogenicity but avoids the surface presentation of sufficient M54- or M105-derived peptides to be recognized by their cognate CD8 T cells. The similar protective abilities of the IE1 and M54 DNAs shown by our protection assay of acute-phase splenic viral replication following relatively high-dose systemic challenge with infectious virus does not illustrate a qualitative difference between the net protective abilities of IE1- and M54-specific CD8 T cells, but work is in progress to determine if there are any differential antiviral effects of these cells during chronic or latent infection.

DNA immunization with M54 or M105 consistently elicited CD8 T cell responses capable of IFN-γ secretion upon short-term incubation with transfected $H-2^d$ stimulator cells. Thus, there exists at least one $H-2^d$-restricted antigenic peptide within each polypeptide sequences. It also appeared that the peak response to M54 may be delayed relative to M105. This is consistent with the previous finding that the kinetics of IE1- and M84-specific CD8 T cell responses also differed slightly (89).

When it was examined whether MCMV infection generated CD8 T cell responses to either M54 or M105, it was found that the acute infection also primed specific responses to these antigens, but the response to M105 reached statistical significance in only 1 of 2 experiments. M54-specific responses to acute MCMV infection in individual mice were between 9- to 39-fold over background levels in 2 experiments, while M105-specific responses in these experiments ranged between 20- and 49-fold over background. MCMV infection may therefore elicit specific CD8 T cell responses to antigenic peptide(s) of both M54 and M105, the variability in this response or in the assay used to detect these cells makes achieving statistical significance difficult with the group sizes, variability, and level of increases. Although the mean and individual CD8 T cell responses that were specific for M105 and IE1 were similar for the MCMV infected mice within each of the 2 experiments shown (FIGS. 6A and 6B), the assay has not been rigorously optimized for each antigen. However, because the M54 and M105 DNAs were able to each elicit strong peak responses to their encoded antigens in each experiment relative to those elicited by MCMV infection (unlike the IE1 responses), further analyses would likely classify M54 and M105 among the subdominant antigens of MCMV in BALB/c mice. While acute MCMV infection may not prime high levels of specific CD8 T cells to M54 and M105, the efficacy of the CD8 T cells primed by DNA immunization demonstrates that M54- and M105-derived antigenic peptides are indeed presented by infected splenocytes in vivo.

Sylwester et al. and Munks et al. have comprehensively documented the repertoires of CD8 T cell immunity to HCMV and MCMV infection, respectively. In the case of HCMV, of the 33 seropositive subjects, only 3 (9%) had detectable UL54 peptide-specific CD8 T cell responses, and the levels were less than 1% (99), suggesting that UL54 encodes subdominant HLA-restricted antigenic peptides. UL105 was recognized by CD8 T cells in these subjects at a slightly higher frequency, as 6 of 33 subjects (18%) had detectable UL105-specific CD8 T cell responses, but only 0.1 subject had a level of that was greater than 1%.

In a pool of 3 acutely infected C57BL/6 mice, the CD8 T cell repertoire included a low, but >5-fold above background, response to M54 (ca. 0.2% of CD8 T cells). However, there was no measurable response to M105 (97). In experiments with acutely infected BALB/c mice using the same methodology as used in the C57BL/6 study, similar mean responses were found to M54 of 0.2% of CD8 T cells, but higher levels of M105-specific CD8 T cells of 0.3-0.4%. While these responses primed to M54 and M105 during acute MCMV were low, it remained to be determined whether reinfection with MCMV would increase these CD8 T cell levels or whether the mechanism(s) that govern the apparent subdominance of these antigens during infection would prevent an increased secondary response. Upon reinfection of mice that the levels of M54- and M105-specific CD8 T cells (FIG. 7) were not appreciably higher than their respective levels in the acutely infected mice at 4 weeks postinfection (FIG. 6B). However, it is possible that there were further declines in CD8 T cell levels between week 4 (the last timepoint measured before reinfection) and week 6 (when mice were reinfected) post primary infection, and that subsequent reinfection resulted in increases of CD8 T cell responses back to their week 4 levels. In any event, the responses to M54 and M105 in the reinfected mice contrasted with the IE1-specific CD8 T cell levels that increased at least 2-fold upon reinfection with MCMV on the time points measured. Thus, if preexisting immunity to MCMV in the infected mice had prevented the subsequent infecting virus (or viral antigen) from entering the splenic compartment to restimulate secondary responses to M54 or M105, the secondary response to IE1 was not similarly abrogated. The generation of a secondary response to IE1 likely has a temporal advantage over the M54 and M105 E proteins, and thus increases in the IE1-specific CD8 T cells, which are highly protective, may have precluded sufficient E gene expression in infected splenocytes to restimulate the CD8 T cells primed against M54 and M105 epitopes. It is not known whether an increased dose of challenge virus would overcome the lack of secondary responses against M54 and M105, as secondary responses to these antigens in the DNA immunized mice were clearly observed. The secondary responses in the IE1 DNA immunized mice were not as high as those observed previously in ICS assays using the immunodominant IE1 $L^d$-restricted epitope peptide (24), possibly due to differences in the ICS assays used.

Having found that the responses to 2 of the 3 conserved, essential E genes of MCMV tested were protective against viral replication it remains to be found whether the CD8 T response to MCMV infection is purposely skewed by the virus to limit the responses to these antigens. The skewing in favor of an immunodominant, but ultimately ineffective, CD8 T response has been demonstrated with the lack of viral control in immunoablated C57BL/6 mice reconstituted with M45-specific CD8 T cells (7). It was shown that the $D^b$-restricted M45 peptide is very effective at priming a specific CD8 T cell response, presumably through cross presentation of M45 protein in uninfected dendritic cells, but that the MHC Class I presentation of this peptide in the infected tissues is sufficiently blocked by the immunoevasin m152 to limit effector mechanisms of viral control. A mechanism by which negative skewing of the primary CD8 T response to viral antigens is not easily explained given the existing state of knowledge of T cell priming. However, the CMVs have successfully coevolved with and spread among their respective hosts over the last ~70 million years since the time of the mammalian radiation. Undoubtedly, the selective immune pressures of the host have helped to shape immunodominance hierarchy and the balance of the virus and host to establish a lifelong, persistent infection that is normally not pathogenic. A benefit of using DNA immunization to elicit virus specific CD8 T cells is that responses can be generated in the absence of the immunoevasins or antigenic competition between $\geq 170$ viral proteins expressed during viral replication.

Example 11

Determining Whether the Minimal Pool of Combined DNAs Together Elicit CD8+ T Cell Responses that are at Least as Protective in all 3 Mouse Strains as are the Individual DNAs Experiments with DNA immunization against MCMV in BALB/c mice have shown that a combination of multiple plasmids that are each protective when used alone results in increased, and sometimes synergistic, protection levels (62-64, 89). However, before proceeding with the next experiments in which mice are primed with the minimal DNA pool, boosted with FI-MCMV, and challenged by mucosal and systemic routes, it may first be confirmed whether the DNAs in the pool negatively affect the protective responses. This possibility may conflict with results that indicate that individually protective pDNAs when mixed with other protective or nonprotective plasmids remain fully protective. Nevertheless, the duration of the experiments that employ boosting with FI-MCMV as well as the need for immunizing 3 mouse strains justify the need for performing an additional relatively short-term experiment. As an added measure, this experiment provides the best opportunity to characterize the combined immune responses by comparing the CD8+ T responses to each antigen in the minimal DNA pool when injected alone or as a pool. Notably, although coimmunization with the IE1 and M84 DNAs typically results in lower levels of IE1-specific CD8+ T cells and higher levels of M84-specific CD8+ T cells when compared with immunization with each of the pDNAs alone, coimmunization consistently provides a synergistic level of protection (89). Thus, when interpreting the CD8+ T cell data from the mice immunized with the minimal DNA pool, as long as protection is increased or maintained relative to single DNA immunization, decreases in individual CD8+ T cell levels will not constitute a suboptimal vaccine.

To measure the CD8+ T cell and protective responses of the minimal DNA pool, an experiment may be conducted in each of the 3 mouse strains above, with experiments staggered to reduce the daily workload. Sixteen mice per group will be i.d. immunized with the empty vector (pcDNA3) DNA, the minimal DNA pool, or each of the 2 or 3 individually protective DNAs that comprise the pool. Furthermore, if it is found that inclusion of the gB or gH/gL plasmid(s) augments protection, the minimal DNA pool will also contain these plasmids. Seven to 10 days after the last immunization, 4 mice from each group will be sacrificed and splenocytes will be prepared for the ICS assay as above. Splenocytes will be stimulated with the appropriate syngeneic cell line transfected with either the empty pcDNA3 vector or one of the MCMV DNAs that was used for the injection. Splenocytes from the vector alone- and minimal DNA pool-immunized mice will both be stimulated with empty vector and each MCMV DNA expressing transfectant individually, while the splenocytes from the mice immunized with each individual component of the pool will be stimulated with cells transfected with either the empty vector or the DNA used for immunization.

Two weeks after the last immunization, mice will be i.p: challenged with a single dose of SG-MCMV shown in the screening experiments above to provide the optimal protection level for the DNAs in the minimal pool, and spleens will be harvested as above for MCMV titer determination. These results should quickly characterize the interaction the plasmids in the minimal DNA pool with regard to the resultant levels of CD8+ T cells and protection.

Example 12

Determining Whether Prime-Boost Vaccination with the Minimal DNA Pool and Attenuated Live or Inactivated MCMV Provide Complete Long-Term Protection in all 3 Mouse Strains Against Mucosal and Systemic Challenge The efficacy of the minimal DNA pool defined above when it is used as a priming step prior to boosting with attenuated live or inactivated MCMV may be evaluated. Because of the importance of the mucosal route for transmission of virus, the prime-boost vaccine's efficacy against i.n. challenge may be measured.

Experiments may be performed in each of the MCMV sensitive BALB/c ($H-2^d$), CBA ($H-2^k$), and 129/J ($H-2^b$) strains. Using the standard vaccination schedule (see FIG. 2 for timeline), 52 mice per group will be immunized by either 1) i.d. priming with pcDNA3 vector and i.p. boosting with PBS+alum or 2) i.d. priming with the minimal DNA pool and i.p. boosting with attenuated live or inactivatedFI-MCMV. In the event that the experiment of Example 2 shows that immunization with the minimal DNA pool alone results in undetectable levels of virus in the spleens of all of the 3 strains of mice tested, a third immunization group that is primed with the minimal DNA pool and boosted with PBS+alum in order to further characterize the DNA-mediated protection may be included. Seven to 10 days after the last i.d. DNA immunization, an ICS assay will be performed on 4 mice from each immunization group in order to measure the levels of CD8+ T cells specific for each antigen in the DNA pool. Eleven to 12 weeks after the last i.p. boost, blood samples to be collected retro-orbitally for virion-specific IgG and virus neutralizing antibody quantification, and then 12 weeks after the last i.p. boost, mice will be challenged either i.n with TC-MCMV or i.p. with SG-MCMV. On days 3, 6, 10, 14, 21, and 32, 4 mice per immunization group will be sacrificed and the spleen, liver, lungs, and salivary glands will be removed for determining the viral load over the course of the acute infection.

Example 13

Determining Whether the Attenuated or Inactivated Virus, or Challenge Virus in the Minimal DNA-Primed/Attenuated Live or Inactivated MCMV Boosted Mice Establish Latency Reactivation of latent HCMV in immunosuppressed individuals such as solid organ or bone marrow transplant recipients, as well as in AIDS patients, is a serious problem and often leads to graft failure and severe CMV disease (67).

To examine the ability of the challenge virus to establish latency, as defined by the presence of viral DNA and reactivatable virus in the absence of infectious virus, 2 groups of 48 BALB/c female mice per group will receive either A) no vaccination or B) i.d. injection of vector DNA and i.p. injection of PBS/alum. Additionally, 1 group of 52 mice will be immunized with C) i.d. injection of the minimal DNA pool and i.p. injection of attenuated live or inactivated, such as FI-MCMV/alum (see table below for immunization groups). In this experiment, published methods (61) may be used to construct an MCMV with a loxP site in intron 3 of ie1 to use for formalin inactivation and immunization in order to distinguish its genome from that of the challenge virus. Tagging only the immunizing virus with a 35 bp loxP site in intron 3 of ie1 will allow the use of a highly-sensitive PCR protocol (61) for detecting and differentiating ie1 sequences derived from genomic DNA from wild-type K181 (challenge virus) and from inactivated vaccine MCMV, while maintaining the antigenicity and growth characteristics of the virus.

Eight weeks after the last immunization, 12 mice per group will be challenged either i.n. or i.p. with 1 of 2 sublethal doses of TC-MCMV or SG-MCMV, respectively (see table for routes and doses). These challenge conditions will allow for the determination of latency establishment following mucosal or parenteral challenge with a low dose or high dose of virus. In addition, 4 mice in the optimized pDNA pool/attenuated live or FI-MCMV/alum immunization group will be left unchallenged as a control for the PCR-based detection of genomic ie1 sequences from the FI-MCMV.

TABLE 2

Latency - Experimental Group Summary (number of mice)

| Vaccination (# of mice) | Challenge route (#) | Challenge dose | Protection in lung/SG | Confirm latency | Co cultivation and PCR |
|---|---|---|---|---|---|
| None (48) | i.p. (12) | $0.5 \times LD_{50}$ | (4) | (2) | (6) |
| | i.p. (12) | $0.05 \times LD_{50}$ | (4) | (2) | (6) |
| | i.n. (12) | $5 \times 10^5$ PFU | (4) | (2) | (6) |
| | i.n. (12) | $5 \times 10^4$ PFU | (4) | (2) | (6) |
| Vector DNA + | i.p. (12) | $0.5 \times LD_{50}$ | (4) | (2) | (6) |
| PBS/alum (48) | i.p. (12) | $0.05 \times LD_{50}$ | (4) | (2) | (6) |
| | i.n. (12) | $5 \times 10^5$ PFU | (4) | (2) | (6) |
| | i.n. (12) | $5 \times 10^4$ PFU | (4) | (2) | (6) |
| Minimal DNA | i.p. (12) | $0.5 \times LD_{50}$ | (4) | (2) | (6) |
| pool + | i.p. (12) | $0.05 \times LD_{50}$ | (4) | (2) | (6) |
| FI-MCMV/alum | i.n. (12) | $5 \times 10^5$ PFU | (4) | (2) | (6) |
| (52) | i.n. (12) | $5 \times 10^4$ PFU | (4) | (2) | (6) |
| | None (4) | None | (0) | (0) | (4) |

Ten days postchallenge, 4 mice per each of the 4 combinations of i.p. or i.n. challenge route and low or high challenge dose will be sacrificed for MCMV titer determination in the lungs and salivary glands to confirm that complete protection was achieved. The remaining mice will be housed for at least 4 months to resolve the acute and persistent infection and allow the establishment of latency. Two mice per challenge route and challenge dose will be sacrificed to confirm the absence of infectious virus by titering homogenates of their salivary glands with a sensitive plaque assay. After confirmation of latency establishment, the remaining mice will be sacrificed for determination of: 1) the absence of infectious virus, 2) the relative level of latent viral DNA, and 3) the level of reactivatable latent virus. Briefly, spleens, salivary glands, liver, and lungs will be harvested and each divided into three fractions. One fraction will be Dounce homogenized for confirmation of the absence of infectious virus by plaque assay. Genomic DNA will be purified from the second tissue fraction and subjected to nested PCR for the amplification of the ie1 genomic region. This method reliably detects as little as a single copy of target DNA in a background of 1 µg tissue DNA and semi-quantitatively assesses the relative load of latent viral DNA (61). To confirm that the genomic DNAs are undegraded and free of PCR inhibitors, β-actin sequences are amplified from the same DNA dilutions negative for MCMV DNA. In addition, tissues from the immunized but unchallenged mice will be processed in parallel to determine whether the viral DNA derived from the attenuated live or inactivated MCMV is still detectable. In any event, one can differentiate the ie1 sequences in FI-MCMV and live challenge viruses in 2 ways: 1) the PCR product from the nested reaction will be 310 bp in the challenge virus and ca. 350 bp in the attenuated live or inactivated MCMV, and 2) a labeled oligonucleotide probe specific for the loxP site in the attenuated live or inactivated MCMV will be able to detect by Southern blot any attenuated live or inactivated MCMV sequences contributing to the PCR product. Furthermore, the 188 bp PCR product that would result from amplification of IE1 cDNA is clearly distinguishable from genomic ie1 sequences in the inactivated or challenge virus. Finally, the remaining tissues harvested from the latent mice will be co cultivated on MECs to detect the presence of reactivatable virus (58). Thus, while the PCR will provide the most sensitive measure of the total load of latent viral DNA, the relative frequencies of MCMV reactivation by co cultivation will demonstrate the level of viral DNA that can potentially reactivate and cause recurrent disease or viral transmission.

Example 14

Determining Whether Prime-Boost Vaccination with the Minimal DNA Pool and Attenuated Live or Inactivated MCMV Provide Complete Protection Against Acute and Latent MCMV Infection in an Outbred Population A vaccine's ability to provide sterilizing immunity against systemic and mucosal infection represents the gold standard for vaccination against CMV, as it guarantees that there is no persistent or reactivated virus that can be transmitted to the fetus in utero. To achieve this goal in humans, the vaccine must be effective in the outbred population. In the experiments above, it may be demonstrated that priming of mice from each of the 3 mouse haplotypes—$H-2^d$, $H-2^k$, and H-2%—with the minimal pool of conserved MCMV genes and boosting with FI-MCMV resulted in complete cross-strain protection. However, these experiments will have been conducted only in MCMV sensitive strains in order more unambiguously identify the protective conserved genes in the absence of strong, early NK responses. In addition, the MCMV sensitive strains provide the most stringent test of the ability of the DNA prime/FI-MCMV boost to provide sterilizing immunity, as any virus able to break through the vaccine-induced immunity is more efficiently replicated to detectable levels when compared to the innately resistant strains.

An immunization experiment in Swiss Webster outbred mice to determine whether the optimal prime-boost vaccine is completely protective against both acute and latent MCMV infection following systemic or mucosal challenge may be performed. To optimize the challenge conditions in this strain, Swiss Webster mice are immunized with either 1)

vector DNA prime plus PBS/alum boost or 2) minimal DNA pool prime plus an attenuated live or inactivated virus, such as FI-MCMV/alum boost. Blood samples will be collected as above to determine the levels of virus-specific IgG and neutralizing antibody. Twelve weeks after the last boost, mice will be i.n. or i.p. challenged and target organs will be analyzed as to assess the level of protection following short-term challenge. The remainder of the challenged mice will then be housed and analyzed to confirm the establishment of viral latency and to quantify the levels of latent viral DNA load and reactivatable virus in the controls and the DNA primed/FI-MCMV boosted mice.

If one or more of the protective pools found in the initial screen of the conserved essential genes is not protective in all 3 mouse strains, a follow-up immunization experiment will be performed, with priority being given to the pools that protect 2 strains rather than only one. Therefore, a pool from the first screen that is protective in 2 strains will be subdivided to determine whether a single plasmid is responsible for the observed protection in the 2 strains. If a single plasmid is found to protect both mouse strains protected in the first screen, it will be added to the master pool. Once the master pool contains a minimum number of plasmids that cross-protect all 3 mouse strains, the immune responses and protection elicited by this pool will be evaluated in the numbered experiments above.

If the results from the second screen using individual plasmids show that the protection in the 2 strains was mediated by more than one plasmid, the protective plasmids will be ranked first by the number of strains they protect and then on the basis of the levels of protection they confer. Thus, the most complex master pool will consist of 3 of the conserved essential MCMV genes, each that protects only one H-2 haplotype, while the pool of intermediate complexity would contain 2 plasmids that together are capable of protecting all 3 strains (i.e. Plasmid 1—H-$2^d$ and H-$2^k$ strains and Plasmid 2—H-$2^b$ and H-$2^k$ strains).

If a master pool of the conserved essential genes above that cross-protects all 3 mouse strains cannot be constructed due to the lack of protection in one or more mouse strains, other MCMV ORFs may be systematically cloned and screened in pools of 15 different MCMV genes, with priority given to the most conserved genes and those in the IE, E, and E/L classes. Intradermal immunization with IE1 and M84 DNA vectors in a pool of 10 additional plasmids that are individually nonprotective is able to significantly reduce virus titers in the spleen following i.p. viral challenge. As little as one IE1 protective plasmid in a pool equivalent to 50 nonprotective plasmids provides full protection.

4 mice per group may be injected with each pool of 15 DNA vaccine candidates (2 μg of each plasmid), over a 14 to 20 day period. As a negative control one group will be injected with vector backbone alone. As in the screens above, boosts with formalin-inactivated virus will not be given so that one can more easily identify the protection provided by the DNA immunization. Two weeks post-vaccination, the mice will be challenged i.p. with 1 of 3 different sublethal doses of SG-MCMV. MCMV titers in the spleen will be determined, and if a pool of ORFs is found to be protective, then it will be subdivided into 3 pools of 5 ORFs, which will then be tested as above. If one of these subpools is protective, then each of the ORFs will be tested individually. Once the minimal pool of cross-strain protecting plasmids is defined, the numbered experiments above can be performed with this pool.

Example 15

Optimization of the Route of DNA Immunization for Protective Immunity Against Mucosal and Systemic Challenge Mucosal areas are important entry sites for the initial CMV infection. If priming with the protective DNAs and boosting with attenuated live or inactivated MCMV is not completely protective against mucosal challenge, methods may be determined for administering the protective DNAs that results in the optimal protection against mucosal infection. Parenteral administration of both the DNA (i.d.) and attenuated live or inactivated MCMV (i.p.), such as FI-MCMV, provides complete protection in the spleen, liver, and salivary glands of the majority of immunized mice following i.n. challenge (93). In addition, MCMV titers in the lungs of DNA primed/FI-MCMV boosted mice were reduced by greater than 3 Logs at peak times of replication when compared to controls. Thus, the dual parenteral immunization did allow for breakthrough of viral replication at the mucosal site of entry, but almost completely prevented viral dissemination to the other target organs. In addition, mice that were only primed with a trivalent DNA cocktail containing gB, gB, and M84 showed some protection in the lungs following i.p. challenge as well as a more rapid induction of virus-specific IgA in the lungs after i.n. challenge (93). These results suggest that the immunity provided by the DNAs and FI-MCMV is protective in the lungs, but that the choice of DNA-encoded antigens and their route of administration may be optimized to protect against mucosal infection.

Mice were i.n. immunized with FI-MCMV in order to augment the protection in the lungs following i.n. challenge. While i.n. immunization with FI-MCMV conferred protection in the lungs following i.n. challenge, the protection was identical to that following i.p. immunization with FI-MCMV and did not extend into other organs. Because mucosal responses are generally poor to protein antigens following i.n. immunization, groups of mice were i.n. immunized with FI-MCMV together with either one or both of two potent and commonly used mucosal adjuvants: cholera toxin (CT) and immunostimulatory CpG DNA (CpG) (33, 83). However, not only did neither or both adjuvants together with FI-MCMV augment virus-specific salivary IgA levels compared to FI-MCMV alone, the 'sublethally' i.p. and i.n. challenged mice that received these i.n. adjuvants with FI-MCMV had abnormally high viral titers in the liver, morbidity, and even mortality not observed in mice receiving the adjuvant(s) alone.

The efficacy of immunizing by i.n. or oral delivery of the DNA and by i.p. boosting with the attenuated live or inactivated virus, such as FI-MCMV, may be determined. The following methods of mucosal immunization may, for example, be used. The first method involves i.n. immunization with viral genes and plasmids encoding macrophage inflammatory protein 1 alpha and 2 (MIP-1 alpha and MIP-2) (19). It has been shown that this mode of immunization with a DNA plasmid encoding HSV glycoprotein gB gene enhanced mucosal and systemic Th-1 type immune responses and provided protection from HSV that was administered through the vagina. In these experiments, BALB/c mice are immunized 3 times at 5-day intervals with 100 μg of a plasmid pool encoding the protective DNA (together with gB and/or gH/gL if found to augment protection) along with 200 μg of plasmids encoding chemokines MIP-1 alpha and MIP-2. As controls, a group of mice will be immunized with the protective DNA (without chemokine DNAs) by i.d. route and another group will be i.n. immunized with empty DNA vector plus MIP-1 alpha and MIP-2 DNAs. The i.n. primed mice will be subsequently i.p. boosted with FI-MCMV+alum. Because the sequence of DNA priming and heterologous boost has been shown to affect the subsequent levels of mucosal and systemic immunity and protection (18), a fourth group of mice will be immunized first by i.p. injections of FI-MCMV+ alum and then by i.n. administration of the MCMV ORF and MIP plasmids. Immunized mice will be i.n. or i.p. challenged with MCMV, and viral titers in the mucosal (lungs and salivary glands) and abdominal (spleen and liver) organs will be determined as above to assess the levels of mucosal and systemic protection, respectively.

Similar to coadministration with the MIP-1 alpha and MIP-2 chemokine plasmids, mucosal immunization with plasmids expressing the cytokines IL-2, IL-12, and IL-15 have been used to enhance Th1-mediated immunity and protection against mucosal viral challenge. While all three cytokines promote the development of CD8+ T responses, IL-15 has been found to enhance the proliferation of memory CD8+ T cells, making the latter an attractive genetic adjuvant for long-term protection (83). Intradermal coadministration of an IL-2 plasmid with suboptimally protective MCMV genes was able to increase the level of protection against i.p. MCMV challenge, suggesting that this approach may also be effective at enhancing plasmid-mediated mucosal protection. In experiments similar to those above, mice will be i.n. immunized with the protective DNA pool together with either IL-2, IL-12, or IL-15 DNAs prior to or subsequently after i.p. immunization with FI-MCMV. Protection against either i.n. or i.p. viral challenge will be measured as above.

The last method is based on a study showing that mucosal and systemic immune responses and protection against rotavirus infection was elicited following oral administration of plasmids encoding rotavirus genes in the form of encapsulated microparticles formed by poly (D,L-lactic-co-glycolic acid) (PLGA) (9, 32, 82). More recently, it has been demonstrated that oral administration of PLGA-encapsulated IL-2 DNA 2 days after an oral prime-boost vaccination with HIV env-gp160 DNA and recombinant vaccinia virus augmented gp160 specific serum antibodies, serum neutralizing antibodies, mucosal IgA, and systemic env-specific CTLs (86). Mice may be inoculated orally by gavage with 0.5 ml of the PLGA encapsulated plasmid DNA (100 μg/ml).

If the optimal DNA pool contains the gH and/or gH/gL plasmids, retro-orbital blood will be collected 4 weeks after the last oral immunization for examination of serum IgA, total IgG against gB and gH and virus structural proteins, and the $IgG_{2a}/IgG_1$ ratio. At the same time, vaginal IgA levels and complement-dependent neutralization titers will be determined. If the results are negative or borderline, the sera of the mice may be tested after an additional 2 weeks and then i.p. boost the mice with the attenuated live or inactivated MCMV. Four weeks later, the mice will be boosted i.p. with attenuated live or inactivated MCMV. Five weeks following the boost, retro-orbital blood will again be analyzed. The levels of vaginal, fecal, and nasal IgA will also be determined. The mice will be allowed to recover for 3 weeks, i.p. or i.n. challenged, and the MCMV titers in target organs will be determined.

Example 16

Eliciting a CD8+ T Cell Response Against Herpes Simplex Virus 2

All references cited in this Example refer to reference numbers, within this Example.

CD8 T cells specific for an immunodominant MCMV antigen are ineffective at limiting viral replication (33). Conversely, DNA immunization using a viral antigen that is scarcely immunogenic during infection elicits highly protective CD8 T cell responses (94, 95). Taken together, immunodominance during infection does not invariably correlate with protection, herpesviruses may skew the host T cell response to make dominant the specificities that favor viral persistence rather than clearance. The essential, nonstructural proteins that are highly conserved among the herpesviruses may represent a novel class of T cell targets. The rationale is that these genes must be expressed for viral replication, and the high amino acid conservation needed for maintaining protein activity limits immune escape by mutation. Of note, immunological studies of T cell specificities primed by infection with human CMV, MCMV, and HSV-2 have shown this class of targets to be largely subdominant (35, 42, 63, 84). This example provides three sets of assays to identify the conserved, essential HSV-2 genes that are protective using DNA vaccination, to determine the appropriate combinations of those genes, and to determine an appropriate prime/boost protocol, as summarized in the following three Aims:

Aim A. Identification of the conserved, essential HSV-2 genes that are protective in mice by prophylactic DNA vaccination. Using the mouse lethal challenge model, DNA vaccines that express each of the HSV-2 conserved, essential genes will be tested. The genes will be tested both alone and in combination with DNA encoding secreted glycoprotein D2 (gD2), a major target of neutralizing antibodies. The protective genes will be then tested in combination with each other either in the presence or the absence of the gD2 DNA to identify the most protective DNA vaccine combination.

Aim B. Determination in the guinea pig model of the immunity and protection elicited by the optimal combination of conserved, essential HSV-2 genes. The combination will be tested by itself and in the presence of the gD2 plasmid DNA. The protective efficacy of the optimized pDNA vaccine both alone and in combination with DNA expressing gD2 will be evaluated in the more human relevant guinea pig model, and the protection will be compared to that generated by a subunit protein vaccine containing the gD2 protein in MPL/alum, which has been shown to be a partially, but significantly, protective vaccine in clinical testing.

Aim C. Determination of the immunity and protection in guinea pigs following prime-boost immunization with the optimized plasmid DNA vaccine and whole, killed HSV-2 plus MPL/alum. Whether the DNA mediated protection is augmented by boosting with a novel combination of whole, killed virus plus MPL/alum adjuvants that will likely elicit virus specific Th1 responses and neutralizing antibodies to gD2 as well as other viral envelope glycoproteins will be tested in a guinea pig model. Immune correlates of protection and the effect of the vaccine on latent viral DNA loads will be studied.

Aim A. Identification of the conserved, essential HSV-2 genes that are protective in mice by prophylactic DNA vaccination. The genes will be tested alone and in combination with DNA encoding secreted glycoprotein D2 (gD2). The protective conserved genes will then be tested in combination with each other in the presence and absence of gD2 DNA to identify the most protective DNA combination.

During infection, naïve CD8 T cells may not be primed against conserved, nonstructural essential proteins (see table below), as the virus cannot sustain mutations in these proteins to evade immune responses. Thus, to provide sterilizing immunity, the herpesvirus vaccine induced CD8+ T cell responses may need to include specificities to essential viral proteins that do not prime the CD8 T cells during the viral infection. Of note, immunological studies of T cell specificities primed by infection with human CMV, MCMV, and HSV-2 have shown this class of targets to be largely subdominant (35, 42, 63, 84). As described above, our preliminary results lend support to this hypothesis.

While clearance of HSV-2 lesions has been shown to correlate with CD8+ and CD4+ T cell immunity, prophylactic antibody responses to recombinant gD2 plus 3-d-monophosphoryl lipid A (3-d-MPL)/alum have been shown to provide significant protection in HSV-1 and -2 seronegative women (82). An optimal vaccine, therefore, should prime both protective cell mediated and humoral immunity. Plasmid DNA vaccines expressing various forms of gD2 (full-length, secreted, and intracellular) have been evaluated in the mouse and guinea pig models (83). Immunization of mice with DNA encoding either the full-length or secreted gD2 was protective against lethal intravaginal challenge, while immunization with a secreted gD2 pDNA (and to a lesser extent full-length gD2) was found in guinea pigs to significantly reduce acute phase lesion scores, but not viral shedding, after intravaginal challenge, and provided a modest, but statistically significant, reduction in recurrent lesions (83). In addition, several studies have shown that protection and/or immunity from gD2 or gB1 pDNA immunization can be augmented by boosting with attenuated vaccinia (20) or MVA (55) vectors or possibly with soluble gD2 protein. It is important to note that while the delivery of gD2 and/or gB2 soluble antigens or plasmids to mice and guinea pigs has shown statistically significant reductions in lethality, acute phase virus replication, and incidence and severity of acute phase lesions, the resultant responses still allow significant levels of acute phase viral replication, recurrent viral shedding, and latent viral genome load. Thus, even in these animal models of HSV-2 vaccine efficacy, there is a significant window for measuring increased protective responses that may be elicited by cell-mediated immunity to the conserved, essential HSV-2 genes. Moreover, inclusion of a secreted gD2 expression plasmid with conserved, essential HSV-2 genes may provide qualitatively enhanced protection, especially after subsequent boosting with a heterologous delivery method of gD2 and other virion structural proteins (see Aim C).

Choice of Genes and Construction of DNA Expression Vectors

To test whether our successful immunization strategy using the conserved, essential MCMV genes is also applicable to HSV-2, the HSV-2 genes that are essential and highly conserved with their respective HCMV homologs (see table) will be cloned and tested by DNA immunization. Many of these are early genes that encode proteins that contribute to viral DNA synthesis and are conserved with other herpesviruses. Because the PCR-based methods for cloning herpesvirus genes have previously been optimized and streamlined in the laboratory, the cloning of the HSV-2 ORFs should be straightforward. The PCR product will be ligated into an eukaryotic expression vector (pcDNA3) such that a carboxy terminal Flag tag is added to facilitate protein detection. Resultant transformants will be screened for the presence of insert in the correct orientation by restriction analysis, and the 5' and 3' ends of each ORF will be sequenced. Expression of each protein will be demonstrated in an in vivo transient expression assay or in an in vitro transcription/translation reaction. The HSV-2 ORFs (see table) to clone and test in vivo will be prioritized based on 1) their amino acid conservation with the CMVs and other herpesviruses and 2) their amino acid conservation with HSV-1. A plasmid expressing a secreted form of gD2 will be similarly constructed except that an untagged gD2 lacking the transmembrane and intracellular domains will be amplified (31).

TABLE 3

Conserved, Essential Genes of HSV-2 Strain HG52 and Their HCMV AD169 Homologs

| HSV-2 ORF | Protein | HCMV ORF | % Identity (aa overlap length) | FastA Scores* of HCMV ORF vs. EBV/VZV/HSV-1 |
|---|---|---|---|---|
| UL5 | HP complex protein | UL105 | 39% (753) | 704/642/598 |
| UL6 | DNA cleavage-packaging | UL104 | 30% (521) | 357/375/309 |
| UL8 | HP complex protein | UL102 | 35% (40) | Pos†/Pos/Pos |
| UL15 | Terminase, DNA packaging | UL89 | 41% (674) | 1181/1104/1206 |
| UL17 | DNA packaging | UL93 | 14% (433) | Pos/Pos/Pos |
| UL29 | ICP8, ssDNA binding protein | UL57 | 25% (503) | 352/220/298 |
| UL30 | DNA polymerase | UL54 | 38% (955) | 343/326/423 |
| UL32 | DNA packaging | UL52 | 20% (397) | 138/179/207 |
| UL33 | DNA packaging | UL51 | 22% (126) | Pos/97/106 |
| UL34 | Egress | UL50 | 24% (230) | Pos/Pos/Pos |
| UL42 | DNA pol processivity | UL44 | 15% (53) | ND |
| UL52 | HP complex protein | UL70 | 29% (771) | 293/302/305 |

*FastA Scores >100 considered significant

†Pos, positionally conserved only;

HP, helicase-primase; ND, not determined

Initial Screening of DNA Vectors

The initial screening experiments will be performed in the mouse model of lethal intravaginal infection for the most rapid evaluation of our novel approach. Due to the number of conserved, essential genes to test, two screening experiments will be conducted. Eight 6- to 8-week old BALB/c female mice per group will be i.d. immunized 3 times in 2 weeks with 50 μg of pDNA in the tail near the base. There will be two groups for each conserved gene. To test the protective efficacy of the conserved gene alone, one group will receive 25 μg of a conserved, essential gene pDNA plus 25 μg of empty vector. To determine if the conserved gene can enhance gD2 pDNA-mediated protection, the second group will receive 25 μg of a conserved, essential gene pDNA plus 25 μg of secreted gD2 pDNA. There will be two control groups. One control group will receive secreted gD2 pDNA plus empty vector as a control for gD2 pDNA-mediated protection alone. As a negative control, the second group will be immunized with only empty plasmid vector.

On days 14 and 20 after the last immunization, mice will be injected subcutaneously with 3 mg of medroxyprogesterone acetate (Depo-Provera) to synchronize the estrus cycle and to increase susceptibility to vaginal HSV infection, and on day 21, mice will be intravaginally challenged with $5\times10^5$ PFU of HSV-2 strain 333 as described elsewhere (83). Mice will be scored daily for 21 days for the severity of vaginal inflammation from 0 (no vaginitis), 1 (mild swelling or redness only), 2 (moderate swelling or erosions), 3 (severe genital maceration), or 4 (central nervous system involvement or death). To confirm vaginal viral replication and measure shedding, vaginal swab samples will be collected on days 1, 3, and 5 postchallenge and stored at −80° C. in Vero cell medium containing antibiotics until titration by plaque assay on Vero cell monolayers. To measure the efficacies of the pDNA immunizations with conserved, essential genes with or without gD2 pDNA, statistical analyses (2-tailed) will be performed on 1) infection and mortality rates (Fisher's exact test), 2) daily lesion scores (Kruskal Wallis nonparametric analysis of variance plus pairwise comparison tests), and 3) levels of vaginal viral shedding (1-way analysis of variance plus pairwise Fisher's Least Significant Difference tests). Together, these analyses should identify any protective responses elicited by each of the conserved, essential HSV-2 genes. By using a combination of parameters to assess protection, differences in protection can be discerned and antigens that contribute weakly can be identified. Additionally, even if these protection levels are low when compared with the gD2 alone control, any responses to the conserved, essential genes that augment the gD2 pDNA-mediated protection may be identified.

RESULT 1—One or more of the conserved, essential genes provides prophylactic protection against primary vaginal HSV-2 infection and/or disease.

Based on the results above, the plasmids of the HSV-2 conserved, essential genes will be ranked first according to their levels of protective efficacy alone and subsequently according to their levels of augmentation of gD2 pDNA-mediated protection. This ranking will be used to prioritize the subsequent experiment to determine the minimal combination of pDNAs that provides the highest level of protection. If only one conserved, essential gene of HSV-2 has a protective effect (either alone or by augmenting gD2 pDNA), this plasmid will be tested in the guinea pig model Aim B.

RESULT 2—None of the conserved, essential genes provides significant protection following plasmid DNA immunization by itself or augments gD2 pDNA protection.

Because the selection of this novel group of antigens is based upon their potential to generate protective cell-mediated (CD4+ or CD8+ T) responses, it is important to consider that the antigens' putative MHC Class I epitopes may be restricted to Class I alleles not present in the BALB/c (H-$2^d$) model. Rather than repeat the immunization experiments in another mouse strain, which may have a different MHC restriction, the pDNAs would be tested, as in Aim B, directly in the guinea pig model of infection and disease. Results from this model would be more highly relevant to human infection, but because of the associated increase in cost and labor, the guinea pigs would be immunized with one of four pools of 3 conserved, essential gene pDNAs plus or minus gD2 pDNA in order to first demonstrate proof-of-concept before identifying which gene or genes is protective. As in the mouse experiments above, each pool of conserved, essential gene pDNAs will be tested in two groups. One group will receive the pool of conserved essential gene pDNAs alone. The second group will receive the pool of conserved essential gene pDNAs in combination with gD2 pDNA so that augmentation of gD2 pDNA-mediated protection can be measured. Having identified one or more protective HSV-2 genes, the remaining time and funds on the grant would be spent on identifying the minimal pDNA combination that provides optimal protection in the guinea pig by immunizing groups with one or more of the protective pDNAs. If only one conserved, essential gene is found to be protective and if there is sufficient time remaining, it will be tested together with gD2 plasmid in Aim C to determine whether this resulting immunity and protection can be augmented by heterologous boosting of pDNA primed guinea pigs with whole, killed HSV-2 and MPL/alum.

Determination of Minimal Number of Protective Conserved, Essential Gene pDNAs that Provides the Optimal Level of Protection in Mice Against Intravaginal HSV-2 Challenge Using the mouse model of MCMV immunity, immunization with two individually protective pDNAs can elicit CD8+ T cells specific for both antigens and provide a synergistic level of protection as measured by the reduction of challenge virus replication in the spleen (60). In addition, immunization of mice with a combined pool of 13 pDNAs expressing both individually protective and nonprotective plasmids resulted in the highest level of protection: a 10,000-fold reduction of challenge virus titers in the spleen compared with vector alone immunized controls (62). These results illustrate in a herpesvirus protection model that synergistic levels of pDNA-induced cell-mediated immunity and protection can be achieved by an optimized combination of plasmids. Additionally, it may be that an HSV-2 vaccine that is broadly protective across an outbred population would need to prime CD4+ and/or CD8+ T cells to more than one HSV antigen as the protective epitopes of each antigen may only associate with one or few HLA types. By the same reasoning, protective plasmids may express antigens that each contains epitopes that are presented in the same HLA context. In this case, immunization with a combined plasmid pool may result in a competition for the restricting HLA molecule and the resulting protective efficacy may not be increased, and characterization of an unnecessarily complex vaccine would be more laborious. Finally, it is possible that the cell-mediated immunity to a conserved, essential gene may provide protection against primary, but not recurrent, disease. Thus, it may be necessary to combine protective plasmids to achieve optimal protection against all phases of infection.

In this experiment, groups of eight BALB/c mice will be i.d. immunized as above with either 1) empty vector alone or 2) secreted gD2 pDNA+empty vector. Results from the above experiment should show whether coimmunization with gD2 pDNA affects the protection elicited by the conserved, essential gene pDNAs and also the relative levels of protection elicited by the conserved gene pDNAs and gD2 pDNA. The remaining mouse groups will be i.d. immunized with one or more protective conserved, essential gene pDNAs such that each pDNA will be retested alone or tested in combination with each of the other protective pDNAs. In addition, these combinations will be tested together with gD2 pDNA in order to measure the ability of each conserved gene pDNA combination to augment gD2 pDNA-mediated protection. If more than 3 pDNAs are protective, the ranking of their individual protective efficacies will be used to prioritize their testing in all possible combinations in order to maintain the groups at a manageable number. Immunized mice will be intravaginally challenged as above and infection and mortality rates, daily lesion scores, and levels of vaginal viral shedding will be determined and analyzed as in the experiment above. These data will be used to quickly identify the simplest pDNA vaccine combination that provides the highest level of protection against intravaginal HSV-2 challenge such that it can be further evaluated in the guinea pig model.

Aim B—Determination in the guinea pig model of prophylaxis of the immunity and protection elicited by the optimal combination of conserved, essential HSV-2 genes.

Results from Aim A will have rapidly identified the best vaccine candidates and demonstrated proof-of-concept of using the conserved, essential genes of HSV-2 as novel targets for T cell immunity. In order to more rigorously test its protective potential, the optimized pDNA combination will be further evaluated in the guinea pig model of genital HSV-2 infection. The guinea pig model more closely mimics human disease, allowing for the testing of the vaccine for its efficacy in protecting against both primary and recurrent infection and disease (80, 81). In addition, the immunity and protection of the optimized pDNA vaccine will be compared with the most successful vaccination strategy in clinical trials to date, subunit vaccination with gD2 protein/MPL/alum. While gD2 protein/MPL/alum has shown significant protection against primary infection and disease, this vaccine appears to be ultimately limited in its ability to be protective in men or in HSV seropositive individuals, and it does not protect against infection (82). In Aim B, guinea pigs will be immunized with the optimized combination of HSV-2 conserved, essential genes (both in the presence and absence of secreted gD2 pDNA) and the resultant levels of immunity and protection with those elicited by subunit vaccination with gD2 protein with MPL/alum will be compared.

Experimental Design

Female Hartley guinea pigs will be purchased from Charles River and immunized at 4- to 6-weeks of age (300-400 g). Ten guinea pigs per group will be immunized 3 times in 6 weeks with 50 µg of pDNA i.d. in each flank (100 µg total). A negative control group will receive empty vector. One test group will receive the optimized combination of the protective conserved, essential genes alone, and the second test group will receive the optimized combination of the protective conserved, essential genes together with gD2 pDNA. An additional group will receive gD2 pDNA (plus empty vector) alone to serve as a control for any augmentation of the gD2 pDNA-mediated responses by the conserved, essential genes. As a positive control for protection and reference for immune response levels, a group will be immunized on days 0 and 32 by bilateral injection in the quadriceps with a total of 125 µl containing 5 µg of truncated, secreted gD2 protein plus 12.5 µg of MPL (Sigma) and 125 µg of alum (Pierce), as this has been shown to provide significant protection against both primary and recurrent disease in guinea pigs (11). Secreted gD2 protein will be purified from the conditioned media of stably transfected CHO cells by lentil lectin and immunoaffinity chromatography as previously described (66). Finally, a mock subunit control group will be immunized with MPL and alum adjuvants only.

To measure antibody levels in immunized animals, blood will be obtained by toenail clip one day prior to challenge (week 9) and sera stored at −20° C. Sera will be tested for 1) gD2-specific IgG by ELISA using the purified gD2 protein above and 2) complement-independent virus neutralizing antibody by plaque reduction assay on Vero cells using 50-100 PFU of HSV-2 as described previously (34).

Three weeks after the last pDNA immunization and 5 weeks after the second subunit immunization, anesthetized guinea pigs will be intravaginally challenged as previously described (9). Briefly, the guinea pigs will be inoculated with virus by rupture of the vaginal closure membrane with a moistened calcium alginate tipped swab and by instillation of 0.1 ml of virus suspension containing 5.7 log 10 PFU of HSV-2 strain 333 into the vaginal vault by means of a plastic catheter. Animals will be scored daily for lesion development based on a severity scale of 0 (no lesions), 1 (erythema only), 2 (single or few vesicles), 3 (large or fused vesicles), or 4 (ulcerated lesions). Lesions will be scored for up to 60 days by researchers blinded to the identity of the vaccine group in order to assess both acute phase and recurrent lesions. In addition, viral shedding in the vagina will be measured on days 2, 5, 7, and 10 postchallenge. Vaginal swabs will be placed into 1 ml of Vero cell medium containing antibiotics and stored at −80° C. until titration by plaque assay on Vero cell monolayers. At the conclusion of the experiment, lumbrosacral ganglia from each guinea pig (6 to 8 per animal) will be dissected, pooled, rinsed with PBS and stored at −20° C. for the future extraction of DNA and real-time PCR quantification of latent HSV-2 DNA. In order to quantify the loads of latent HSV-2 DNA, cellular and viral DNA will be extracted using the DNeasy Tissue Kit (Qiagen) and subjected to real-time quantitative PCR using the ABI Prism 7000 detection system (Applied Biosystems). The HSV-2 primers and probe will be designed against a viral gene that is not present in the pDNA vaccine, and input DNA will be normalized using primers and a probe specific for the guinea pig lactalbumin gene (64).

Protection in the DNA immunized guinea pigs will be assessed by statistical analyses (as in Aim A) of 1) infection rates, 2) lesion scores through day 14 postchallenge (primary infection), 3) levels of vaginal virus through day 10 postchallenge (primary infection), 4) cumulative lesion scores through day 60 postchallenge (recurrent infection), and 5) quantity of latent HSV-2 DNA in the ganglia. The data from the conserved, essential pDNA combinations used either alone or plus gD2 pDNA will be compared with the gD2/MPL/alum subunit group to determine the protection elicited by the optimal pDNA combination relative to the current subunit strategy.

RESULT 1—The pDNA vaccine that was optimized in the mouse experiments also significantly protects guinea pigs against intravaginal HSV-2 challenge.

In this case, in Aim C, whether the protection elicited by the optimized pDNA can be augmented by subsequent boosting with a novel combination of whole, killed HSV-2 together with MPL and alum adjuvants will be examined.

RESULT 2—The pDNA vaccine that proved optimal in the mouse experiments does not significantly protect guinea pigs.

In this case, there will already be evidence in mice that the antigens are capable of priming CD8 T cells that can recognize loaded MHC complexes in infected tissues. One potential problem might be that the DNA vaccine-mediated priming of CD8 T cells may be suboptimal in the larger rodent. The next step would be to optimize the DNA delivery by immunizing guinea pigs with each pDNA pool adsorbed to polylactic coglycolide (PLG) microparticles. This delivery method has been shown in a variety of animal models, including guinea pigs and non-human primates, to enhance antibody or cellular responses to DNA vaccines by targeting the DNA to dendritic cells (for review, see (65). In addition, the same PLG formulation can simultaneously deliver several plasmids.

RESULT 3—DNA immunization of guinea pigs with the pools of conserved, essential genes shows no protective effect alone and does not augment gD2 pDNA protection.

In this case, the priority would be to proceed to Aim C and test whether the protection elicited by the gD2 pDNA could be enhanced by subsequent boosting of guinea pigs with whole, killed HSV-2 together with the Th1 promoting adjuvant MPL and alum. In addition, guinea pigs may be are immunized with the pools of conserved, essential gene pDNAs adsorbed to PLG particles as above in Result 2.

Aim C—Determination of the immunity and protection in guinea pigs following prime-boost immunization with the optimized plasmid DNA vaccine and whole, killed HSV-2 plus MPL/alum While the priming of mice with an MCMV gB pDNA before boosting with formalin killed MCMV results in greater protection when compared with that from killed virion alone (61), prime-boost augmentation of protection using the conserved, essential genes of HSV-2 and gD2 pDNA may need to be tested specifically in the guinea pig model of HSV-2 disease. Whole, formalin killed virus preparations have been previously evaluated in clinical trials for prophylaxis or treatment of recurrent HSV infection, but these early studies suffered from methodological deficiencies, including the lack of objective measures of protection and the absence of a placebo groups in many cases (for review, see (41). In addition, trials using either whole, killed virus or detergent extracted glycoproteins did not utilize the highly immunogenic adjuvants that are available today, so it is not surprising that low or inconsistent antibody responses (and likely no cell mediated responses) were generated and that protection was not significant. More recently, the lipopolysaccharide derivative MPL has been shown to be a powerful adjuvant for Th1 type responses, and together with alum, a gD2 subunit vaccine has been shown to provide protection against symptomatic genital disease in HSV seronegative women (82). By itself, however, this subunit vaccine was able to provide only limited protection (46% and 39%) against HSV-2 infection in two phase 3 trials. Additional antibody specificities to other HSV-2 envelope glycoproteins (present in the virion particles) may be needed for optimal virus neutralization and protection. For example, immunization of guinea pigs with the defective HSV-2 mutant dl5-29 elicited significantly higher levels of neutralizing antibodies compared with soluble gD2 protein, despite dl5-29 immunization eliciting significantly lower levels of gD2-specific IgG (34). In addition to containing more neutralizing antibody targets, presentation of the HSV-2 glycoproteins in the context of the viral envelope may also elicit protective antibody responses to nonlinear epitopes that may not be present in soluble, subunit vaccines. Taken together, optimal protection against genital infection and disease may depend on the presence of both cell mediated and antibody responses. To this end, the combined efficacy of priming with the optimized combination of protective conserved, essential genes and gD2 pDNA followed by boosting with whole, killed HSV-2 plus MPL/alum will be tested.

Experimental Design

HSV-2 is propagated in Vero or BHK cells, and after CPE reaches 100%, extracellular virus will be purified from clarified supernatant by sucrose gradient ultracentrifugation using standard methods as described (68). In order to control for the unlikely possibility that DNA from the killed HSV-2 vaccine could be detectable by subsequent PCR of vaginal swabs or lumbrosacral ganglia, the virus used for the vaccine will be a lacZ-tagged HSV-2 Strain 333 (77) so that lacZ-specific primers and probe can be used to differentiate between the vaccine and challenge viruses. Briefly, the infectious virus bands will be diluted in buffer, pelleted, and resuspended in order to measure infectivity and protein content. The preparation is expected to have a purity of ~$10^9$ PFU per 5 μg of protein. This preparation will be inactivated by formalin and confirmed to be inactive by infectivity assay as described previously (62).

Fourteen female Hartley guinea pigs per group will be pDNA primed as in Aim B (3 i.d. injections in 6 weeks) and on weeks 9 and 13, mock i.m. boosted or i.m. boosted with whole, formalin killed HSV-2 plus MPL/alum. Specifically, groups will receive the following prime-boost combinations: 1) prime with empty vector pDNA and boost with MPL/alum (vehicle control); 2) prime with empty vector pDNA and boost with 5 μg of killed HSV-2 plus 12.5 μg of MPL (Sigma) and 125 μg of alum (Pierce); 3) prime with the optimized conserved, essential pDNA combination plus gD2 pDNA and boost with MPL/alum; 4) prime with the optimized conserved, essential pDNA combination and boost with killed HSV-2 as in group 2; 5) prime with gD2 pDNA and boost with killed HSV-2; and 6) prime with the optimized conserved, essential pDNA combination plus gD2 pDNA and boost with killed HSV-2. As a positive control and reference for both protection and immunity, group 7 will be primed and boosted as in Aim B with the gD2/MPL/alum protein subunit vaccine.

Blood samples will be collected one day prior to each of the two boosts as well as one day prior to challenge and sera stored for quantification of HSV-2 specific IgG and virus neutralizing antibodies as in Aim B. To demonstrate antigen-specific T cell mediated (CD4+ T) immunity generated by the pDNA prime and protein boost, delayed-type hypersensitivity (DTH) responses will be measured in guinea pigs three days prior to the first killed HSV-2 boost (in guinea pigs set aside for DTH measurement) and three days prior to challenge (in animals to be challenged). Four guinea pigs per group will be i.d. injected in each ear with 10 μg of clarified, UV-inactivated Vero cell lysate from either uninfected or HSV-2 infected cells, and 24, 48, and 72 h later, the diameter of the induration will be measured by microcaliper to quantify the level of cellular infiltrate (38, 90). The responses to total HSV-2 cellular antigen will be calculated as the diameter differences between the indurations in the HSV-2 and negative control ears (background). Alternatively, to measure T cell responses to individual HSV-2 antigens, ears will be i.d. injected with lysates from 293T cells 48 h posttransfection with either empty vector (background control) or one of the conserved, essential gene pDNAs that comprises the pDNA priming combination (39). The magnitude of the inflammation will be measured and calculated as above. If the background from the untransfected cell lysate is too high, the conserved, essential gene product will be enriched by an anti-FLAG single-step immunoaffinity purification from larger scale transfections.

Four weeks after the last killed HSV-2 boost, the remaining guinea pigs will be intravaginally challenged and infection and disease will be measured as in Aim B. Because of the importance of a vaccine candidate in reducing viral reactivation and shedding in order to limit viral transmission, both lesion scores and viral shedding into the genital tract will be assessed in the guinea pigs through day 90 postchallenge. Vaginal swabs collected from the guinea pigs will be stored at −80° C. until DNAs are extracted and analyzed by real-time quantitative PCR. The HSV-2 primers and probe will be designed against a viral gene that is not present in the pDNA prime. As described above, lacZ-specific primers and probe will also be used in the PCR analyses to confirm that the viral DNA detected in the vaginal swabs is from challenge virus and not from the killed virus vaccine. Reactivating virus shedding in the control and vaccine groups will be compared with respect to incidence, frequency (mean number of days that viral DNA was isolated), and magnitude (number of viral genome equivalents) as previously described (11). At the conclusion of the experiment, lumbrosacral ganglia from each guinea pig (6 to 8 per animal) will be dissected, pooled, rinsed with PBS and stored at −20° C. In order to quantify the loads of latent HSV-2 DNA, cellular and viral DNA will be extracted and subjected to real-time quantitative PCR as above. Input DNA will be normalized using primers and a probe specific for the guinea pig lactalbumin gene (64).

Although formalin killed MCMV may be used as a boost following pDNA immunization for the complete protection of mice against viral replication following systemic challenge (61, 62), it is possible that the same success may not be achieved using killed HSV-2 whole virion. It is possible that the concentrations of gD2 and gB2 protein in the envelope, the major targets of neutralizing antibodies, are not sufficient to elicit an optimal protective antibody response, and that only a minor contribution to protection is provided by other envelope glycoproteins. Thus, in a boosting strategy may be employed that is more focused on the gD2 and gB2 proteins. A potential strategy would be to deliver these antigens by modified vaccinia virus Ankara (MVA) in a repeat experiment designed as outlined above. MVA is a highly attenuated vaccinia virus that has been safely used as a vaccine against smallpox and more recently as a vaccine vector. MVA can deliver one or more foreign genes into most human and mammalian cells and induce both humoral and cell mediated responses, even in a host with preexisting poxvirus immunity (91). As described above, heterologous prime-boost methods continue to show great promise in providing enhanced immunity compared to repeated boosts with the same antigen delivery method, and MVA vector-based experimental vaccines (used alone or in combination with DNA vaccines) against HIV and malaria are currently in phase I clinical trials.

BIBLIOGRAPHY AND REFERENCES CITED IN EXAMPLE 16

1. Allen, E. M., J. P. Weir, S. Martin, C. Mercadal, and B. T. Rouse. 1990. Role of coexpression of IL-2 and herpes simplex virus proteins in recombinant vaccinia virus vectors on levels of induced immunity. Viral Immunol. 3:207-215.
2. Ashley, R., G. J. Mertz, and L. Corey. 1987. Detection of asymptomatic herpes simplex virus infections after vaccination. J. Virol. 61:264-268.
3. Aurelian, L. 2004. Herpes simplex virus type 2 vaccines: new ground for optimism? Clin. Diagn Lab. Immunol. 11:437-445.
4. Aurelian, L., H. Kokuba, and C. C. Smith. 1999. Vaccine potential of a herpes simplex virus type 2 mutant deleted in the PK domain of the large subunit of ribonucleotide reductase (ICP10). Vaccine 17:1951-1963.
5. Aurelian, L., C. C. Smith, M. Wachsman, and E. Paoletti. 1991. Immune responses to herpes simplex virus in guinea pigs (footpad model) and mice immunized with vaccinia virus recombinants containing herpes simplex virus glycoprotein D. Rev. Infect. Dis. 13 Suppl 11:S924-934.
6. Bernstein, D. I. 2000. Effect of route of vaccination with vaccinia virus expressing HSV-2 glycoprotein D on protection from genital HSV-2 infection. Vaccine 18:1351-1358.
7. Blaney, J. E., E. Nobusawa, M. A. Brehm, R. H. Bonneau, L. M. Mylin, T. M. Fu, Y. Kawaoka, and S. S. Tevethia. 1998. Immunization with a single major histocompatibility complex class I-restricted cytotoxic T-lymphocyte recognition epitope of herpes simplex virus type 2 confers protective immunity. J. Virol. 72:9567-9574.
8. Bosnjak, L., M. Miranda-Saksena, D. M. Koelle, R. A. Boadle, C. A. Jones, and A. L. Cunningham. 2005. Herpes Simplex Virus Infection of Human Dendritic Cells Induces Apoptosis and Allows Cross-Presentation via Uninfected Dendritic Cells. J. Immunol. 174:2220-2227.
9. Bourne, N., F. J. Bravo, M. Francotte, D. I. Bernstein, M. G. Myers, M. Slaoui, and L. R. Stanberry. 2003. Herpes simplex virus (HSV) type 2 glycoprotein D subunit vaccines and protection against genital HSV-1 or HSV-2 disease in guinea pigs. J. Infect. Dis. 187:542-549.
10. Bourne, N., G. N. Milligan, M. R. Schleiss, D. I. Bernstein, and L. R. Stanberry. 1996. DNA immunization confers protective immunity on mice challenged intravaginally with herpes simplex virus type 2. Vaccine 14:1230-1234.
11. Bourne, N., G. N. Milligan, L. R. Stanberry, R. Stegall, and R. B. Pyles. 2005. Impact of immunization with glycoprotein D2/AS04 on herpes simplex virus type 2 shedding into the genital tract in guinea pigs that become infected. J Infect Dis 192:2117-23.
12. Bourne, N., L. R. Stanberry, D. I. Bernstein, and D. Lew. 1996. DNA immunization against experimental genital herpes simplex virus infection. J. Infect. Dis. 173:800-807.
13. Boursnell, M. E., C. Entwisle, D. Blakeley, C. Roberts, I. A. Duncan, S. E. Chisholm, G. M. Martin, R. Jennings, D. N. Challanain, I. Sobek, S. C. Inglis, and C. S. McLean. 1997. A genetically inactivated herpes simplex virus type 2 (HSV-2) vaccine provides effective protection against primary and recurrent HSV-2 disease. J. Infect. Dis. 175:16-25.
14. Bruyn, G. d., M. Vargas-Cortez, T. Warren, S. K. Tyring, K. H. Fife, J. Lalezari, R. C. Brady, M. Shahmanesh, G. Kinghorn, K. R. Beutner, R. Patel, M. A. Drehobl, P. Horner, T. O. Kurtz, S. McDermott, A. Wald, and L. Corey. 2006. A randomized controlled trial of a replication defective (gH deletion) herpes simplex virus vaccine for the treatment of recurrent genital herpes among immunocompetent subjects. Vaccine 24:914-920.
15. Cappel, R., S. Sprecher, F. D. Cuyper, and J. D. Braekeleer. 1985. Clinical efficacy of a herpes simplex subunit vaccine. J. Med. Virol. 16:137-145.
16. Casanova, G., R. Cancela, L. Alonzo, R. Benuto, C. M. Magana, D. R. Hurley, E. Fishbein, C. Lara, T. Gonzalez, R. Ponce, J. W. Burnett, and G. J. Calton. 2002. A double-blind study of the efficacy and safety of the ICP10PK vaccine against recurrent genital HSV-2 infections. Cutis 70.
17. Corey, L., A. G. Langenberg, R. Ashley, R. E. Sekulovich, A. E. Izu, J. M. Douglas, H. H. Handsfield, T. Warren, L. Marr, S. Tyring, R. DiCarlo, A. A. Adimora, P. Leone, C. L. Dekker, R. L. Burke, W. P. Leong, and S. E. Straus. 1999. Recombinant glycoprotein vaccine for the prevention of genital HSV-2 infection: two randomized controlled trials. Chiron HSV Vaccine Study Group. JAMA 282:331-340.
18. Cranmer, L. D., C. L. Clark, C. S. Morello, H. E. Farrell, W. D. Rawlinson, and D. H. Spector. 1996. Identification, analysis, and evolutionary relationship of the putative murine cytomegalovirus homologues of the human cytomegalovirus UL82 (pp 71) and UL83 (pp 65) matrix phosphoproteins. J. Virol. 70:7929-7939.
19. Dudek, T., and D. M. Knipe. 2006. Replication-defective viruses as vaccines and vaccine vectors. Virol. 344:230-239.
20. Eo, S. K., M. Gierynska, A. A. Kamar, and B. T. Rouse. 2001. Prime-boost immunization with DNA vaccine: mucosal route of administration changes the rules. J Immunol 166:5473-9.
21. Estcourt, M. J., A. J. Ramsay, A. Brooks, S. A. Thomson, C. J. Medveckzy, and I. A. Ramshaw. 2002. Prime-boost immunization generates a high frequency, high-avidity CD8(+) cytotoxic T lymphocyte population. Int. Immunol. 14:31-37.
22. Farrell, H. E., C. S. McLean, C. Harley, S. Efstathiou, S. Inglis, and A. C. Minson. 1994. Vaccine potential of a herpes simplex virus type 1 mutant with an essential glycoprotein deleted. J. Virol. 68:927-932.
23. Fleck, M., J. Podlech, K. Weise, and D. Falke. 1994. A vaccinia virus—herpes simplex virus (HSV) glycoprotein B1 recombinant or an HSV vaccine overcome the HSV type 2 induced humoral immunosuppression and protect against vaginal challenge in BALB/c mice. Med. Microbiol. Immunol. 183:87-94.
24. Fruh, K., K. Ahn, H. Djaballah, P. Sempe, P. v. Endert, R. Tampe, P. Peterson, and Y. Yang. 1995. A viral inhibitor of peptide transporters for antigen presentation. Nature 375:415-418.
25. Gallichan, W. S., D. C. Johnson, F. L. Graham, and K. L. Rosenthal. 1993. Mucosal immunity and protection after intranasal immunization with recombinant adenovirus expressing herpes simplex virus glycoprotein B. J. Infect. Dis. 168:622-629.
26. Goel, N., Q. Rong, D. Zimmerman, and K. S. Rosenthal. 2003. A L.E.A.P.S. heteroconjugate vaccine containing a T cell epitope from HSV-1 glycoprotein D elicits Th1 responses and protection. Vaccine 21:4410-4420.
27. Gold, M. C., M. W. Munks, M. Wagner, U. H. Koszinowski, A. B. Hill, and S. P. Fling. 2002. The murine cytomegalovirus immunomodulatory gene m152 prevents recognition of infected cells by M45-specific CTL but does not alter the immunodominance of the M45-specific CD8 T cell response in vivo. J. Immunol. 169:359-365.
28. Gonzalez Armas, J. C., C. S. Morello, L. D. Cranmer, and D. H. Spector. 1996. DNA immunization confers protection against murine cytomegalovirus infection. J. Virol. 70:7921-7928.
29. Gurunathan, S., D. M. Klinman, and R. A. Seder. 2000. DNA Vaccines: Immunology, Application, and Optimization. Annu. Rev. Immunol. 18:927-994.
30. Haynes, J. R., J. Arrington, L. Dong, R. P. Braun, and L. G. Payne. 2006. Potent protective cellular immune responses generated by a DNA vaccine encoding HSV-2 ICP27 and the *E. coli* heat labile enterotoxin. Vaccine 24:5016-5026.
31. Higgins, T. J., K. M. Herold, R. L. Arnold, S. P. McElhiney, K. E. Shroff, and C. J. Pachuk. 2000. Plasmid DNA-expressed secreted and nonsecreted forms of herpes simplex virus glycoprotein D2 induce different types of immune responses. J Infect Dis 182:1311-20.
32. Hill, A., P. Jugovic, I. York, G. Russ, J. Bennink, J. Yewdell, H. Ploegh, and D. Johnson. 1995. Herpes simplex virus turns off the TAP to evade host immunity. Nature 375:411-415.
33. Holtappels, R., J. Podlech, M. F. Pahl-Seibert, M. Julch, D. Thomas, C. O. Simon, M. Wagner, and M. J. Reddehase. 2004. Cytomegalovirus misleads its host by priming of CD8 T cells specific for an epitope not presented in infected tissues. J. Exp. Med. 199:131-136.
34. Hoshino, Y., S. K. Dalai, K. Wang, L. Pesnicak, T. Y. Lau, D. M. Knipe, J. I. Cohen, and S. E. Straus. 2005. Comparative efficacy and immunogenicity of replication-defective, recombinant glycoprotein, and DNA vaccines for herpes, simplex virus 2 infections in mice and guinea pigs. J Virol 79:410-8.
35. Hosken, N., P. McGowan, A. Meier, D. M. Koelle, P. Sleath, F. Wagener, M. Elliott, K. Grabstein, C. Posavad, and L. Corey. 2006. Diversity of the CD8+ T-Cell Response to Herpes Simplex Virus Type 2 Proteins among Persons with Genital Herpes. J. Virol. 80:5509-5515.
36. Jones, C. A., and A. L. Cunningham. 2003. Development of prophylactic vaccines for genital and neonatal herpes. Expert Rev. Vaccines 2:541-549.
37. Jones, C. A., M. Fernandez, K. Herc, L. Bosnjak, M. Miranda-Saksena, R. A. Boadle, and A. Cunningham. 2003. Herpes simplex virus type 2 induces rapid cell death and functional impairment of murine dendritic cells in vitro. J. Virol. 77:11139-11149.
38. Kawahara, M., K. Matsuo, and M. Honda. 2006. Intradermal and oral immunization with recombinant *Mycobacterium bovis* BCG expressing the simian immunodeficiency virus Gag protein induces long-lasting, antigen-specific immune responses in guinea pigs. Clin Immunol 119:67-78.
39. Khabiri, A. R., F. Bagheri, M. H. Alimohammadian, M. Assmar, and S. R. Nadaf. 2005. Leishmanin skin test in guinea pig with a single purified protein of *Leishmania major*. Exp Parasitol 111:239-43.
40. Koelle, D. M., H. B. Chen, M. A. Gavin, A. Wald, W. W. Kwok, and L. Corey. 2001. CD8 CTL from genital herpes simplex lesions: recognition of viral tegument and immediate early proteins and lysis of infected cutaneous cells. J. Immunol. 166:4049-4058.
41. Koelle, D. M., and L. Corey. 2003. Recent progress in herpes simplex virus immunobiology and vaccine research. Clin. Microbiol. Rev. 16:96-113.
42. Koelle, D. M., Z. Liu, C. L. McClurkan, R. C. Cevallos, J. Vieira, N. A. Hosken, C. A. Meseda, D. C. Snow, A. Wald, and L. Corey. 2003. Immunodominance among herpes simplex virus-specific CD8 T cells expressing a tissue-specific homing receptor. Proc. Natl. Acad. Sci. USA. 100: 12899-12904.
43. Koelle, D. M., Z. Liu, C. M. Mcaurkan, M. S. Topp, S. R. Riddell, E. G. Pamer, A. S. Johnson, A. Wald, and L. Corey. 2002. Expression of cutaneous lymphocyte-associated antigen by CD8(+) T cells specific for a skin-tropic virus. J. Clin. Invest. 110:537-548.
44. Koelle, D. M., C. M. Posavad, G. R. Barnum, M. L. Johnson, J. M. Frank, and L. Corey. 1998. Clearance of HSV-2 from recurrent genital lesions correlates with infiltration of HSV-specific cytotoxic T lymphocytes. J. Clin. Invest. 101:1500-1508.
45. Kriesel, J. D., S. L. Spruance, R. A. Daynes, and B. A. Araneo. 1996. Nucleic acid vaccine encoding gD2 protects mice from herpes simplex virus type 2 disease. J. Infect. Dis. 173:536-541.
46. Liu, M. A. 2003. DNA vaccines: a review. J. Intern. Med. 253:402-410.
47. Manickan, E., M. Francotte, N. Kuklin, M. Dewerchin, C. Molitor, D. Gheysen, M. Slaoui, and B. T. Rouse: 1995. Vaccination with recombinant vaccinia viruses expressing ICP27 induces protective immunity against herpes simplex virus through CD4+Th1+ T cells. J Virol 69:4711-6.
48. Manickan, E., Z. Yu, R. J. Rouse, W. S. Wire, and B. T. Rouse. 1995. Induction of protective immunity against herpes simplex virus with DNA encoding the immediate early protein ICP 27. Viral Immunol 8:53-61.
49. Maria, A. D., P. Tundo, A. Romano, and P. Grima. 1995. Anti-HSV-1 herpes vaccination by LUPIDON H: preliminary results. Adv. Exp. Med. Biol. 371B:1599-1600.
50. McClements, W. L., M. E. Armstrong, R. D. Keys, and M. A. Liu. 1996. Immunization with DNA vaccines encoding glycoprotein D or glycoprotein B, alone or in combination, induces protective immunity in animal models of herpes simplex virus-2 disease. Proc. Natl. Acad. Sci. USA. 93:11414-11420.
51. McClements, W. L., M. E. Armstrong, R. D. Keys, and M. A. Liu. 1997. The prophylactic effect of immunization with DNA encoding herpes simplex virus glycoproteins on HSV-induced disease in guinea pigs. Vaccine 15:857-860.
52. McConkey, S. J., W. H. Reece, V. S. Moorthy, D. Webster, S. Dunachie, G. Butcher, J. M. Vuola, T. J. Blanchard, P. Gothard, K. Watkins, C. M. Hannan, S. Everaere, K. Brown, K. E. Kester, J. Cummings, J. Williams, D. G. Heppner, A. Pathan, K. Flanagan, N. Arulanantham, M. T. Roberts, M. Roy, G. L. Smith, J. Schneider, T. Peto, R. E. Sinden, S. C. Gilbert, and A. V. Hill. 2003. Enhanced T-cell immunogenicity of plasmid DNA vaccines boosted by recombinant modified vaccinia virus Ankara in humans. Nat. Med. 9:729-735.
53. McDermott, M. R., F. L. Graham, T. Hanke, and D. C. Johnson. 1989. Protection of mice against lethal challenge with herpes simplex virus by vaccination with an adenovirus vector expressing HSV glycoprotein B. Virology 169: 244-247.
54. Mertz, G. J., R. Ashley, R. L. Burke, J. Benedetti, C. Critchlow, C. C. Jones, and L. Corey. 1990. Double-blind, placebo-controlled trial of a herpes simplex virus type 2 glycoprotein vaccine in persons at high risk for genital herpes infection. J. Infect. Dis. 161:653-660.
55. Meseda, C. A., K. L. Elkins, M. J. Merchlinsky, and J. P. Weir. 2002. Prime-boost immunization with DNA and modified vaccinia virus ankara vectors expressing herpes simplex virus-2 glycoprotein D elicits greater specific antibody and cytokine responses than DNA vaccine alone. J. Infect. Dis. 186:1065-1073.
56. Meseda, C. A., R. R. Stout, and J. P. Weir. 2006. Evaluation of a needle-free delivery platform for prime-boost immunization with DNA and modified vaccinia virus ankara vectors expressing herpes simplex virus 2 glycoprotein D. Viral Immunol. 19:250-259.
57. Mester, J. C., T. A. Twomey, E. T. Tepe, and D. I. Bernstein. 1999. Immunity induced by DNA immunization with herpes simplex virus type 2 glycoproteins B and C. Vaccine 18:875-883.
58. Mikloska, Z., M. Ruckholdt, I. Ghadiminejad, H. Dunckley, M. Denis, and A. L. Cunningham. 2000. Monophosphoryl lipid A and QS21 increase CD8 T lymphocyte cytotoxicity to herpes simplex virus-2 infected cell proteins 4 and 27 through IFN-gamma and IL-12 production. J. Immunol. 164:5167-5176.
59. Morello, C. S., L. D. Cranmer, and D. H. Spector. 1999. In vivo replication, latency, and immunogenicity of murine cytomegalovirus mutants with deletions in the M83 and M84 genes, the putative homologs of human cytomegalovirus pp 65 (UL83). J. Virol. 73:7678-7693.
60. Morello, C. S., L. D. Cranmer, and D. H. Spector. 2000. Suppression of murine cytomegalovirus replication with a DNA vaccine encoding the MCMV early nonstructural protein M84 (a homolog of human cytomegalovirus pp 65). J. Virol. 74:3696-3708.
61. Morello, C. S., M. Ye, S. Hung, L. A. Kelley, and D. H. Spector. 2005. Systemic priming-boosting immunization with a trivalent plasmid DNA and inactivated murine cytomegalovirus (MCMV) vaccine provides long-term protection against viral replication following systemic or mucosal MCMV challenge. J Virol 79:159-75.
62. Morello, C. S., M. Ye, and D. H. Spector. 2002. Development of a vaccine against murine cytomegalovirus (MCMV), consisting of plasmid DNA and formalin-inactivated MCMV, that provides long-term, complete protection against viral replication. J. Virol. 76:4822-4835.
63. Munks, M. W., M. C. Gold, A. L. Zajac, C. M. Doom, C. S. Morello, D. H. Spector, and A. B. Hill. 2006. Genome-wide analysis reveals a highly diverse CD8 T cell response to murine cytomegalovirus. J Immunol 176:3760-6.
64. Natuk, R. J., D. Cooper, M. Guo, P. Calderon, K. J. Wright, F. Nasar, S. Witko, D. Pawlyk, M. Lee, J. DeStefano, D. Tummolo, A. S. Abramovitz, S. Gangolli, N. Kalyan, D. K. Clarke, R. M. Hendry, J. H. Eldridge, S. A. Udem, and J. Kowalski. 2006. Recombinant vesicular stomatitis virus vectors expressing herpes simplex virus type 2 gD elicit robust CD4+ Th1 immune responses and are protective in mouse and guinea pig models of vaginal challenge. J. Virol. 80:4447-4457.
65. O'Hagan, D. T., M. Singh, and J. B. Ulmer. 2004. Microparticles for the delivery of DNA vaccines. Immunol. Rev. 199:191-200.
66. Pachl, C., R. L. Burke, L. L. Stuve, L. Sanchez-Pescador, G. Van Nest, F. Masiarz, and D. Dina. 1987. Expression of cell-associated and secreted forms of herpes simplex virus type 1 glycoprotein gB in mammalian cells. J Virol 61:315-25.
67. Pollara, G., D. R. Katz, and B. M. Chain. 2004. The host response to herpes simplex virus infection. Curr. Opin. Infect. Dis. 17:199-203.
68. Powell, K. L., and D. H. Watson. 1975. Some structural antigens of herpes simplex virus type 1. J Gen Virol 29:167-78.
69. Prichard, M. N., R. Kaiwar, W. T. Jackman, D. C. Quenelle, D. J. Collins, E. R. Kern, G. M. Kemble, and R. R. Spaete. 2005. Evaluation of AD472, a live attenuated recombinant herpes simplex virus type 2 vaccine in guinea pigs. Vaccine 23:5424-5431.
70. Roizman, B., and D. M. Knipe. 2001. Herpes Simplex Viruses and their replication, p. 2399-2459. In D. M. Knipe and P. M. Howley (ed.), Fields Virology, Fourth ed, vol. 2. Lippincott Williams & Wilkins, Philadelphia.
71. Sin, J., J. J. Kim, C. Pachuk, C. Satishchandran, and D. B. Weiner. 2000. DNA vaccines encoding interleukin-8 and RANTES enhance antigen-specific Th1-type CD4(+) T-cell-mediated protective immunity against herpes simplex virus type 2 in vivo. J. Virol. 74:11173-11180.
72. Sin, J. J. Kim, R. L. Arnold; K. E. Shroff, D. McCallus, C. Pachuk, S. P. McElhiney, M. W. Wolf, S. J. P.-d. Bruin, T. J. Higgins, R. B. Ciccarelli, and D. B. Weiner. 1999. IL-12 gene as a DNA vaccine adjuvant in a herpes mouse model: IL-12 enhances Th1-type CD4+ T cell-mediated protective immunity against herpes simplex virus-2 challenge. J. Immunol. 162:2912-29211.
73. Sin, J. I., J. J. Kim, D. Zhang, and D. B. Weiner. 2001. Modulation of cellular responses by plasmid CD40L: CD40L plasmid vectors enhance antigen-specific helper T cell type 1 CD4+ T cell-mediated protective immunity against herpes simplex virus type 2 in vivo. Hum. Gene Ther. 12:1091-1102.
74. Skinner, G. R., C. G. Fink, M. Cowan, A. Buchan, A. Fuller, C. E. Hartley, J. Durham, C. Wiblin, and J. Melling. 1987. Follow-up report on 50 subjects vaccinated against herpes genitalis with Skinner vaccine. Med. Microbiol. Immunol. 176:161-168.
75. Skinner, G. R., C. Woodman, C. Hartley, A. Buchan, A. Fuller, C. Wiblin, G. Wilkins, and J. Melling. 1982. Early experience with "antigenoid" vaccine Ac NFU1(S−) MRC towards prevention or modification of herpes genitalis. Dev. Biol. Stand. 52:333-344.
76. Skinner, G. R., C. B. Woodman, C. E. Hartley, A. Buchan, A. Fuller, J. Durham, M. Synnott, J. C. Clay, J. Melling, C. Wiblin, and J. Wilkins. 1982. Preparation and immunogenicity of vaccine Ac NFU1 (S−) MRC towards the prevention of herpes genitalis. Br J Vener Dis. 58:381-386.
77. Smith, T. J., L. A. Morrison, and D. A. Leib. 2002. Pathogenesis of herpes simplex virus type 2 virion host shutoff (vhs) mutants. J. Virol. 76:2054-2061.
78. Stanberry, L. R. 2004. Clinical trials of prophylactic and therapeutic herpes simplex virus vaccines. Herpes 11 Suppl. 3:161 A-169A.
79. Stanberry, L. R., D. I. Bernstein, R. L. Burke, C. Pachl, and M. G. Myers. 1987. Vaccination with recombinant herpes simplex virus glycoproteins: protection against initial and recurrent genital herpes. J. Infect. Dis. 155:914-920.
80. Stanberry, L. R., E. R. Kern, J. T. Richards, T. M. Abbott, and J. C. Overall, Jr. 1982. Genital herpes in guinea pigs:

pathogenesis of the primary infection and description of recurrent disease. J Infect Dis 146:397-404.

81. Stanberry, L. R., E. R. Kern, J. T. Richards, and J. C. Overall, Jr. 1985. Recurrent genital herpes simplex virus infection in guinea pigs. Intervirology 24:226-31.

82. Stanbeny, L. R., S. L. Spruance, A. L. Cunningham, D. I. Bernstein, A. Mindel, S. Sacks, S. Tyring, F. Y. Aoki, M. Slaoui, M. Denis, P. Vandepapeliere, G. Dubin, and G. H. V. E. S. Group. 2002. Glycoprotein-D-adjuvant vaccine to prevent genital herpes. N. Engl. J. Med. 347:1652-1661.

83. Strasser, J. E., R. L. Arnold, C. Pachuk, T. J. Higgins, and D. I. Bernstein. 2000. Herpes simplex virus DNA vaccine efficacy: effect of glycoprotein D plasmid constructs. J Infect Dis 182:1304-10.

84. Sylwester, A. W., B. L. Mitchell, J. B. Edgar, C. Taormina, C. Pelte, F. Ruchti, P. R. Sleath, K. H. Grabstein, N. A. Hosken, F. Kern, J. A. Nelson, and L. J. Picker. 2005. Broadly targeted human cytomegalovirus-specific CD4+ and CD8+ T cells dominate the memory compartments of exposed subjects. J Exp Med 202:673-85.

85. Tengvall, S., A. Lundqvist, R. J. Eisenberg, G. H. Cohen, and A. M. Harandi. 2006. Mucosal administration of CpG oligodeoxynucleotide elicits strong CC and CXC chemokine responses in the vagina and serves as a potent Th1-tilting adjuvant for recombinant gD2 protein vaccination against genital herpes. J. Virol. 80:5283-5291.

86. Tigges, M. A., D. Koelle, K. Hartog, R. E. Sekulovich, L. Corey, and R. L. Burke. 1992. Human CD8+ herpes simplex virus-specific cytotoxic T-lymphocyte clones recognize diverse virion protein antigens. J. Virol. 66:1622-1634.

87. Tigges, M. A., S. Leng, D. C. Johnson, and R. L. Burke. 1996. Human herpes simplex virus (HSV)-specific CD8+ CTL clones recognize HSV-2-infected fibroblasts after treatment with IFN-gamma or when virion host shutoff functions are disabled. J. Immunol. 156:3901-3910.

88. Tomazin, R., N. E. G. v. Schoot, K. Goldsmith, P. Jugovic, P. Sempe, K. Flub, and D. C. Johnson. 1998. Herpes simplex virus type 2 ICP47 inhibits human TAP but not mouse TAP. J. Virol. 72:2560-2563.

89. Ulmer, J. B., B. Wahren, and M. A. Liu. 2006. Gene-based vaccines: recent technical and clinical advances. Trends Mol. Med. 12:216-222.

90. Wachsman, M., L. Aurelian, C. C. Smith, M. E. Perkus, and E. Paoletti. 1989. Regulation of expression of herpes simplex virus (HSV) glycoprotein D in vaccinia recombinants affects their ability to protect from cutaneous HSV-2 disease. J Infect Dis 159:625-34.

91. Wang, Z., C. La Rosa, R. Maas, H. Ly, J. Brewer, S. Mekhoubad, P. Daftarian, J. Longmate, W. J. Britt, and D. J. Diamond. 2004. Recombinant modified vaccinia virus Ankara expressing a soluble form of glycoprotein B causes durable immunity and neutralizing antibodies against multiple strains of human cytomegalovirus. J Virol 78:3965-76.

92. Whitley, R. J. 2001. Herpes Simplex Viruses, p. 2461-2509. In D. M. Knipe and P. M. Howley (ed.), Fields Virology, Fourth ed, vol. 2. Lippincott Williams & Wilkins, Philadelphia.

93. Woodland, D. L. 2004. Jump-starting the immune system: prime-boosting comes of age. Trends Immunol. 25:98-104.

94. Ye, M., C. S. Morello, and D. H. Spector. 2004. Multiple epitopes in the murine cytomegalovirus early gene product M84 are efficiently presented in infected primary macrophages and contribute to strong CD8+-T-lymphocyte responses and protection following DNA immunization. J Virol 78:11233-45.

95. Ye, M., C. S. Morello, and D. H. Spector. 2002. Strong CD8 T-cell responses following coimmunization with plasmids expressing the dominant pp 89 and subdominant M84 antigens of murine cytomegalovirus correlate with long-term protection against subsequent viral challenge. J Virol 76:2100-12.

96. Zhao, X., E. Deak, K. Soderberg, M. Linehan, D. Spezzano, J. Zhu, D. M. Knipe, and A. Iwasaki. 2003. Vaginal submucosal dendritic cells, but not Langerhans cells, induce protective Th1 responses to herpes simplex virus-2. J. Exp. Med. 197:153-162.

REFERENCES

The following reference numbers are for use in the present application for sections other than Example 16.

1. Bening a, J., B. Kropff, and M. Mach. 1995. Comparative analysis of fourteen individual human cytomegalovirus proteins for helper T cell response. Journal of General Virology 76:153-160.

2. BenMohamed, L., R. Krishnan, C. Auge, J. F. Primus, and D. J. Diamond. 2002. Intranasal, administration of a synthetic lipopeptide without adjuvant induces systemic immune responses. Immunology 106:113-121.

3. Boeckh, M., W. G. Nichols, G. Papanicolaou, R. Rubin, J. R. Wingard, and J. Zaia. 2003. Cytomegalovirus in hematopoietic stem cell transplant recipients: Current status, known challenges, and future strategies. Biol. Blood Marrow Transplant. 9:543-558.

4. Boppana, S. B., L. B. Rivera, K. B. Fowler, M. Mach, and W. J. Britt. 2001; Intrauterine transmission of cytomegalovirus to infants of women with preconceptional immunity. N. Engl. J. Med. 344:1366-1371.

5. Borysiewicz, L. K., J. K. Hickling, S. Graham, J. Sinclair, M. P. Cranage, G. L. Smith, and J. G. P. Sissons. 1988. Human cytomegalovirus-specific cytotoxic T cells. Relative frequency of stage-specific CTL recognizing the 72 lcD immediate early protein and glycoprotein B expressed by recombinant vaccinia viruses. Journal of Experimental Medicine 168:919-931.

6. Britt, W. J., and M. Mach. 1996. Human cytomegalovirus glycoproteins. Intervirology 39:401-412.

7. Brown, M. G., A. O. Dokun, J. W. Heusel, H. R. C. Smith, D. L. Beckman, E. A. Blattenberger, C. E. Dubbelde, L. R. Stone, A. A. Scalzo, and W. Yokoyama. 2001. Vital involvement of a natural killer cell activation receptor in resistance to viral infection. Science 292:934-937.

8. Bukowski, J. F., J. F. Warner, G. Dennert, and R. M. Welsh. 1985. Adoptive transfer studies demonstrating the antiviral effect of natural killer cells in vivo. Journal of Experimental Medicine 161:40-52.

9. Chen, S. C., D. H. Jones, E. F. Fynan, G. H. Farrar, J. C. Clegg, H. B. Greenberg, and J. E. Herrmann. 1998. Protective immunity induced by oral immunization with a rotavirus DNA vaccine encapsulated in microparticles. Journal of Virology 72:5757-5761.

10. Cranmer, L., C. Clark, and D. H. Spector. 1994. Cloning, characterization and expression of the murine cytomegalovirus homologue of the human cytomegalovirus 28 kDa matrix phosphoprotein (UL99). Virology 205:417-429.

11. Cranmer, L. D., C. L. Clark, C. S. Morello, H. E. Farrell, W. D. Rawlinson, and D. H. Spector. 1996. Identification, analysis, and evolutionary relationships of the putative murine cytomegalovirus homologs of the human cytomegalovirus UL82 (pp 71) and UL83 (pp 65) matrix phosphoproteins. J. Virol. 70:7929-7939.
12. Dunn, W., C. Chou, H. Li, R. Hai, D. Patterson, V. Stoic, H. Zhu, and F. Liu. 2003. Functional profiling of a human cytomegalovirus genome. Proc. natl. Acad. Sci. USA 100: 14223-14228.
13. Ebeling, A., G. M. Keil, E. Knust, and U. H. Koszinowski. 1983. Molecular cloning and physical mapping of murine cytomegalovirus DNA. Journal of Virology 47:421-433.
14. Elkington, R., S. Walker, T. Crough, M. Menzies, J. Tellam, M. Bharadwaj, and R. Khanna. 2003. Ex vivo profiling of CD8 T-cell responses to human cytomegalovirus reveals broad and multispecific reactivities in healthy virus carriers. J. Virol. 77:5226-5240.
15. Elliott, R., C. Clark, D. Jaquish, and D. H. Spector. 1991. Transcription analysis and sequence of the putative murine cytomegalovirus DNA polymerase gene. Virology 185: 169-186.
16. Endresz, V., K. Burian, K. Berencsi, Z. Gyulai, L. Kari, H. Horton, D. Virok, C. Meric, S. A. Plotkin, and E. Gonczol. 2001. Optimization of DNA immunization against human cytomegalovirus. Vaccine 19:3972-3980.
17. Endresz, V., L. Kari, K. Berencsi, C. Kari, Z. Gyulai, C. Jeney, S. Pincus, U. Rodeck, C. Meric, S. A. Plotkin, and E. Gonczol. 1999. Induction of human cytomegalovirus (HCMV)-glycoprotein B (gB)-specific neutralizing antibody and phosphoprotein 65 (pp 65)-specific cytotoxic T lymphocyte responses by naked DNA immunization. Vaccine 17:50-58.
18. Eo, S. K., M. Gierynska, A. A. Kamar, and B. T. Rouse. 2001. Prime-boost immunization with DNA vaccine: mucosal route of administration changes the rules. J. Immunol. 166:5473-5479.
19. Eo, S. K., S. Lee, S. Chun, and B. T. Rouse. 2001. Modulation of immunity against herpes simplex virus infection via mucosal genetic transfer of plasmid DNA encoding chemokines. Journal of Virology 75:569-578.
20. Estcourt, M. J., A. J. Ramsay, A. Brooks, S. A. Thomson, C. J. Medveckzy, and I. A. Ramshaw. 2002. Prime-boost immunization generates a high frequency, high-avidity CD8(+) cytotoxic T lymphocyte population. Int. Immunol. 14:31-37.
21. Fowler, K. B., S. Stagno, and R. F. Pass. 2003. Maternal immunity and prevention of congenital cytomegalovirus infection. J. Amer. Med. Assoc. 289:1008-1011.
22. Fynan, E. F., R. G. Webster, D. H. Fuller, J. R. Haynes, J. C. Santoro, and H. L. Robinson. 1993. DNA vaccines: protective immunizations by parenteral, mucosal, and gene-gun inoculations. Proceedings of the National Academy of Sciences USA 90:11478-11482.
23. Gilbert, M. J., S. R. Riddell, C.-R. Li, and P. D. Greenberg. 1993. Selective interference with class I major histocompatibility complex presentation of the major immediate-early protein following infection with human cytomegalovirus. Journal of Virology 67:3461-3469.
24. Gold, M. C., M. W. Munks, M. Wagner, U. H. Koszinowski, A. B. Hill, and S. P. Fling. 2002. The murine cytomegalovirus immunomodulatory gene m152 prevents recognition of infected cells by M45-specific CTL but does not alter the immunodominance of the M45-specific CD8 T cell response in vivo. J. Immunol. 169:359-365.
25. Gold, M. C., M. W. Munks, M. Wagner, C. W. McMahon, A. Kelly, D. G. Kavanagh, M. K. Slifka, U. H. Koszinowski, D. H. Raulet, and A. B. Hill. 2004. Murine cytomegalovirus interference with antigen presentation has little effect on the size or the effector memory phenotype of the CD8 T cell response. J. Immunol. 172:6944-6953.
26. Gonczol, E., and S. Plotkin. 2001. Development of a cytomegalovirus vaccine: lessons from recent clinical trials. Expert Opin. Biol. Ther. 1:401-412.
27. González Armas, J. C., C. S. Morello, L. D. Cramer, and D. H. Spector. 1996. DNA immunization confers protection against murine cytomegalovirus infection. J. Virol. 70:7921-7928.
28. Greenberg, P. D., P. Reusser, J. M. Goodrich, and S. R. Riddell. 1991. Development of a treatment regimen for human cytomegalovirus (CMV) infection in bone marrow transplantation recipients by adoptive transfer of donor-derived CMV-specific T cell clones expanded in Annals of the New York Academy of Sciences 636:184-195.
29. Gurunathan, S., D. M. Klinman, and R. A. Seder. 2000. DNA Vaccines: Immunology, Application, and Optimization. Annual Reviews of Immunology 18:927-994.
30. Gyulai, Z., V. Endresz, K. Burian, S. Pincus, J. Toldi, W. I. Cox, C. Meric, S. Plotkin, E. Gonczol, and K. Berencsi. 2000. Cytotoxic T lymphocyte responses to HCMV pp 65, IElexon4, gB, pp 150, and pp 28 in healthy individuals: reevaluation of the prevalence of IE1-specific CTL. Journal of Infectious Diseases 181:1537-1546.
31. Heise, M. T., and H. W. Virgin. 1995. The T-cell-independent role of IFN-gamma and TNF-alpha in mcrophage activation during murine cytomegalovirus and herpes simplex virus infection. Journal of Virology 69:904-909.
32. Herrmann, J. E., S. C. Chen, D. H. Jones, A. Tinsley-Brown, E. F. Fynan, H. B. Greenberg, and G. H. Farrar. 1999. Immune responses and protection obtained by oral immunization with rotavirus VP4 and VP7 DNA vaccines encapsulated in microparticles. Virology 256:148-153.
33. Holmgren, J., C. Czerkinsky, K. Eriksson, and A. Mharandi. 2003. Mucosal immunisation and adjuvants: a brief overview of recent advances and challenges. Vaccine 21 Suppl 2:S89-95.
34. Holtappels, R., N. K. Grzimek, C. O, Simon, D. Thomas, D. Dreis, and M. J. Reddehase. 2002. Processing and presentation of murine cytomegalovirus pORFm164-derived peptide in fibroblasts in the face of all viral immunosubversive early gene functions. J. Virol. 76:6044-6053.
35. Holtappels, R., N. K. Grzimek, D. Thomas, and M. J. Reddehase. 2002. Early gene III18, a novel player in the immune response to murine cytomegalovirus. J. Gen. Virol. 83:311-316.
36. Holtappels, R., J. Podlech, N. K. Grzimek, D. Thomas, M. F. Pahl-Seibert, and M. J. Reddehase. 2001. Experimental preemptive immunotherapy of murine cytomegalovirus disease with CD8 T-cell lines specific for ppM83 and pM84, the two homologs of human cytomegalovirus tegument protein ppUL83 (pp 65). J. Virol. 75:6584-6600.
37. Holtappels, R., J. Podlech, M. F. Pahl-Seibert, M. Julch, D. Thomas, C. O, Simon, M. Wagner, and M. J. Reddehase. 2004. Cytomegalovirus misleads its host by priming of CD8 T cells specific for an epitope not presented in infected tissues. J. Exp. Med. 199:131-136.
38. Holtappels, R., D. Thomas, J. Podlech, G. Geginat, H. P. Steffens, and M. J. Reddehase. 2000. The putative natural killer decoy early gene m04 (gp34) of murine cytomegalovirus encodes an antigenic peptide recognized by protective antiviral CD8 T cells. J. Virol. 74:1871-1884.
39. Holtappels, R., D. Thomas, J. Podlech, and M. J. Reddehase. 2002. Two antigenic peptides from genes m123 and m164 of murine cytomegalovirus quantitatively dominate. CD8 T-cell memory in the H-2d haplotype. J. Virol. 76:151-164.

40. Holtappels, R., D. Thomas, and M. J. Reddehase. 2000. Identification of a K(d)-restricted antigenic peptide encoded by murine cytomegalovirus early gene M84. J. Gen. Virol. 81:3037-3042.
41. Jonjic, S., W. Mutter, F. Weiland, M. J. Reddehase, and U. B. Koszinowski. 1989. Site-restricted persistent cytomegalovirus infection after selective long-term depletion of CD4+T lymphocytes. J. Exp. Med. 169:1199-1212.
42. Kavanagh, D. G., M. C. Gold, M. Wagner, U. H. Koszinowski, and A. B. Hill. 2001. The multiple immune-evasion genes of murine cytomegalovirus are not redundant: m4 and m152 inhibit antigen presentation in a complementary and cooperative fashion. J. Exp. Med. 194:967-978.
43. Kern, F. I., L P. Surel, N. Faulhaber, C. Frommel, J. Schneider-Mergener, C. Schonemann, P. Reinke, and H.-D. Vold. 1999. Target structures of the CD8+-T Cell response to human cytomegalovirus: the 72-kilodalton major immediate-early protein revisited. Journal of Virology 73:8179-8184.
44. Kleijnen, M. F., J. B. Hupp, P. Lucin, S. Mukherjee, H. Farrell, A. E. Campbell, U. H. Koszinowski, A. B. Hill, and H. L. Ploegh. 1997. A mouse cytomegalovirus glycoprotein, gp34, forms a complex with folded class I MHC molecules in the ER is not retained but is transported to the cell surface. EMBO J. 16:685-694.
45. Krmpotic, A., M. Messerle, I. Crnkovic-Mertens, B. Polio, S. Jonjic, and U. H. Koszinowski. 1999. The immunoevasive function encoded by the mouse cytomegalovirus gene m152 protects the virus against T cell control in vivo. J. Exp. Med. 190:1285-1296.
46. La Rosa, C., Z. Wang, J. C. Brewer, S. F. Lacey, M. C. Villacres, R. Sharan, R. Krishnan, M. Crooks, S. Markel, R. Maas, and D. J. Diamond. 2002. Preclinical development of an adjuvant-free peptide vaccine with activity against CMV pp 65 in HLA transgenic mice. Blood 100: 3681-3689.
47. Lee, S. H., J. R. Webb, and S. M. Vidal. 2002. Innate immunity to cytomegalovirus: the Cmv1 locus and its role in natural killer cell function. Microbes Infect. 4:1491-1503.
48. LoPiccolo, D. M., M. C. Gold, D. G. Kavanagh, M. Wagner, U. H. Koszinowski, and A. B. Hill. 2003. Effective inhibition of K(b)- and D(b)-restricted antigen presentation in primary macrophages by murine cytomegalovirus. J. Virol. 77:301-308.
49. Lucie, P., J. Pavic, B. Folic, S. Jonjic, and U. H. Koszinowski. 1992. Gamma interferon-dependent clearance of cytomegalovirus infection in salivary glands. Journal of Virology 66:1977-1984.
50. Manley, T. J., L. Luy, T. Jones, M. Boeckh, H. Mutimer, and S. R. Riddell. 2004. Immune evasion proteins of human cytomegalovirus do not prevent a diverse CD8+ cytotoxic T-cell response in natural infection. Blood 104: 1075-1082.
51. Marks, J. A., and D. H. Spector. 1988. Replication of the murine cytomegalovirus genome: structure and role of the termini in the generation and cleavage of concatenates. Virology 162:98-107.
52. Marks, J. R., J. A. Mercer, and D. H. Spector. 1983. Transcription in mouse embryo cells permissively infected by murine cytomegalovirus. Virology 131:247-254.
53. Marks, J. R., and D. H. Spector. 1984. Fusion of the termini of the murine cytomegalovirus genome after infection. Journal of Virology 52:24-28.
54. McConkey, S. J., W. H. Reece, V. S. Moorthy, D. Webster, S. Dunachie, G. Butcher, J. M. Vuola, T. J. Blanchard, P. Gothard, K. Watkins, C. M. Hannan, S. Everaere, K. Brown, K. E. Kester, J. Cummings, J. Williams, D. G. Heppner, A. Pathan, K. Flanagan, N. Arulanantham, M. T. Roberts, M. Roy, a L. Smith, J. Schneider, T. Peto, R. E. Sinden, S. C. Gilbert, and A. V. Hill. 2003. Enhanced T-cell immunogenicity of plasmid DNA vaccines boosted by recombinant modified vaccinia virus Ankara in humans. Nat. Med. 9:729-735.
55. McLaughlin-Taylor, E., H. Pande, S. J. Forman, B. Tanamachi, C.-R. Li, J. A. Zaia, P. D. Greenberg, and S. R. Riddell. 1994. Identification of the major late human cytomegalovirus matrix protein pp 65 as a target antigen for CD8+ virus-specific cytotoxic T lymphocytes. Journal of Medical Virology 43:103-110.
56. Mercer, J. A., J. R. Marks, and D. H. Spector. 1983. Molecular cloning and restriction endonuclease mapping of the murine cytomegalovirus genome (Smith strain). Virology 129:94-106.
57. Mercer, J. A., and D. H. Spector. 1986. Pathogenesis of acute murine cytomegalovirus infection in resistant and susceptible strains of mice. J. Virol. 57:497-504.
58. Mercer, J. A., C. A. Wiley, and D. H. Spector. 1988. Pathogenesis of murine cytomegalovirus infection: identification of infected cells in the spleen during acute and latent infections. Journal of Virology 62:987-997.
59. Meyers, J. D. 1984. Cytomegalovirus infection following marrow transplantation: risk, treatment, and prevention. Birth Defects 20:101-117.
60. Mocarski, E. S., and C. T. Courcelle. 2001. Cytomegaloviruses and their replication, p. 2629-2673. In D. M. Knipe and P. M. Howley (ed.), Fields Virology, vol. 2. Lippincott Williams & Wilkins, Philadelphia.
61. Morello, C. S., L. D. Cranmer, and D. H. Spector. 1999. In vivo replication, latency, and immunogenicity of murine cytomegalovirus mutants with deletions in the M83 and M84 genes, the putative homologs of human cytomegalovirus pp 65 (UL83). J. Virol. 73:7678-7693.
62. Morello, C. S., L. D. Cranmer, and D. H. Spector. 2000. Suppression of murine cytomegalovirus (MCMV) replication with a DNA vaccine encoding MCMV M84 (a homolog of human cytomegalovirus pp 65). J. Virol. 74:3696-3708.
63. Morello, C. S., M. Ye, S. Hung, L. A. Kelley, and D. H. Spector. 2004'. Systemic prime-boost immunization with a trivalent plasmid DNA and inactivated murine cytomegalovirus (MCMV) vaccine provides long-term protection against viral replication following systemic or mucosal MCMV challenge. J. Virol. In press.
64. Morello, C. S., M. Ye, and D. H. Spector. 2002. Development of a vaccine against murine cytomegalovirus (MCMV), consisting of plasmid DNA and formalin-inactivated MCMV, that provides long-term, complete protection against viral replication. J. Virol. 76:4822-4835.
65. Orange, J. S., and C. A. Biron. 1996. Characterization of early IL-12, IFN-alpha/beta, and TNF effects on antiviral state and MK cell responses during murine cytomegalovirus infection. Journal of Immunology 156:4746-4756.
66. Orange, J. S., B. Wang, C. Terhorst, and C. A. Biron. 1995. Requirement for natural killer cell-produced interferon-in defense against murine cytomegalovirus infection and enhancement of this defense pathway by interleukin 12 administration. Journal of Experimental Medicine 182: 1045-1056.
67. Pass, R. F. 2001. Cytomegaloviruses, p. 2675-2706. In D. M. Knipe and P. M. Howley (ed.), Fields Virology, 4th ed. Lippincott-Raven, Philadelphia.
68. Pavic, I., B. Polic, I. Crnkovic, P. Lucin, S. Jonjic, and U. H. Koszinowski. 1993. Participation of endogenous 68. ~~tumour necrosis factor-alpha in host resistance to cytomegalovirus infection. Journal of General Virology 74:2215-2223.~~

69. Pepperl, S., J. Munster, M. Mach, J. R. Harris, and B. Plachter. 2000. Dense bodies of human cytomegalovirus induce both humoral and cellular immune responses in the absence of viral gene expression. J. Virol. 74:6132-6146.

70. Quinnan, G. J., N. Kirmani, A. H. Rook, J. F. Manischewitz, L. Jackson, G. Moreschi, G. W. Santos, R. Saral, and W. H. Burns. 1982. Cytotoxic T cells in cytomegalovirus infection: HLA-restricted T-lymphocyte and non-T-lymphocyte cytotoxic responses correlate with recovery from cytomegalovirus infection in bone-marrow-transplant recipients. New England Journal of Medicine 307:7-13.

71. Rawlinson, W. D., H. E. Farrell, and B. G. Barrell. 1996. Analysis of the complete DNA sequence of murine cytomegalovirus. J. Virol. 70:8833-8849.

72. Raz, E., D. A. Carson, S. E. Parker, T. B. Parr, A. M. Abai, G. Aichinger, S. H. Gromkowski, M. Singh, D. Lew, M. A. Yankauckas, S. M. Baird, and G. H. Rhodes. 1994. Interdermal gene immunization: the possible role of DNA uptake in the induction of cellular immunity to viruses. Proceedings of the National Academy of Sciences USA 91:9519-9123.

73. Reddehase, M. J. 2002. Antigens and immunoevasins: opponents in cytomegalovirus immune surveillance. Nat. Rev. Immunol. 2:831-844.

74. Reddehase, M. J. 2000. The immunogenicity of human and murine cytomegaloviruses. Curr. Opin. Immunol. 12:390-396.

75. Reddehase, M. J., G. M. Keil, and U. H. Koszinowski. 1984. The cytolytic T lymphocyte response to the murine cytomegalovirus. II. Detection of virus replication stage-specific antigens by separate populations of in vivo active cytolytic T lymphocyte precursors. Eur. J. Immunol. 14:56-61.

76. Reusch, U., W. Muranyi, P. Lucin, H. G. Burgert, H. Hengel, and U. H. Koszinowski. 1999. A cytomegalovirus glycoprotein re-routes MHC class I complexes to lysosomes for degradation. EMBO J. 18:1081-1091.

77. Riddell, S. R., and P. D. Greenberg. 2000. T-cell therapy of cytomegalovirus and human immunodeficiency virus infection. J. Antimicrob. Chemother. 45:35-43.

78. Riddell, S. R., M. Rabin, A. P. Geballe, W. J. Britt, and P. D. Greenberg. 1991. Class I MHC-restricted cytotoxic T lymphocyte recognition of cells infected with human cytomegalovirus does not require endogenous viral gene expression. Journal of Immunology 146:2795-2804.

79. Scalzo, A. A., P. A. Lyons, N. A. Fitzgeral, C. A. Forber, W. M. Yokoyama, and G. R. Shellam. 1995. Genetic mapping of Cmv1 in the region of mouse chromosome 6 encoding the NK gene complex-associated loci Ly49 and musNKR-P1. Genomics 27:435-441.

80. Schirmbeck, R., K. Bohm, K. Ando, F. V. Chisari, and J. Reimann. 1995. Nucleic acid vaccination primes Hepatitis B Virus surface antigen-specific cytotoxic T lymphocytes in nonresponder mice. Journal of Virology 69:5929-5934.

81. Tay, C. H., and R. M. Welsh. 1997. Distinct organ-dependent mechanisms for the control of murine cytomegalovirus infection by natural killer cells. J. Virol. 71:267-275.

82. Tinsley-Bown, A. M., R. Fretwell, A. B. Dowsett, S. L. Davis, and G. H. Farrar. 2000. Formulation of poly(D,L-lactic-co-glycolic acid) microparticles for rapid plasmid DNA delivery. J Control Release 66:229-241.

83. Toka, F. N., C. D. Pack, and B. T. Rouse. 2004. Molecular adjuvants for mucosal immunity. Immunol Rev 199:100-112.

84. Ulmer, J. B., J. J. Donnelly, S. E. Parker, G. H. Rhodes, P. L. Feigner, V. J. Dwarki, S. H. Gromkowski, R. R. Deck, C. M. DeWitt, A. Friedman, L. A. Hawe, K. R. Leander, D. Martinez, H. C. Perry, J. W. Shiver, D. L. Montgomery, and M. A. Liu. 1993. Heterologous protection against influenza by injection of DNA encoding a viral protein [see comments]. Science 259:1745-1749.

85. Wagner, M., A. Gutermann, J. Podlech, M. J. Reddehase, and U. H. Koszinowski. 2002. Major histocompatibility complex class I allele-specific cooperative and competitive interactions between immune evasion proteins of cytomegalovirus. J. Exp. Med. 196:805-816.

86. Wierzbicki, A., I. Kiszka, H. Kaneko, D. Kmieciak, T. J. Wasik, J. Gzyl, Y. Kaneko, and D. Kozbor. 2002. Immunization strategies to augment oral vaccination with DNA and viral vectors expressing HIV envelope glycoprotein. Vaccine 20:1295-1307.

87. Woodland, D. L. 2004. Jump-starting the immune system: prime-boosting comes of age. Trends Immunol. 25:98-104.

88. Ye, M., C. S. Morello, and D. H. Spector. 2004. Multiple epitopes in the murine cytomegalovirus early gene product M84 are efficiently presented in infected primary macrophages and contribute to strong CD8+ T-lymphocyte responses and protection following DNA immunization. J. Virol. In press.

89. Ye, M., C. S. Morello, and D. H. Spector. 2002. Strong CD8 T-cell responses following coimmunization with plasmids expressing the dominant gB and subdominant M84 antigens of murine cytomegalovirus correlate with long-term protection against subsequent viral challenge. J. Virol. 76:2100-2112.

90. Yu, D., M. C. Silva, and T. Shenk. 2003. Functional map of human cytomegalovirus AD169 defined by global mutational analysis. Proc. Natl. Acad. Sci. USA 100:12396-12401.

91. Zaia, J. A., G. Gallez-Hawkins, X. Li, Z. Q. Yao, N. Lomeli, K. Molinder, C. La Rosa, and D. J. Diamond. 2001. Infrequent occurrence of natural mutations in the pp 65(495-503) epitope sequence presented by the HLA A*0201 allele among human cytomegalovirus isolates. J. Virol. 75:2472-2474.

92. Ziegler, H., R. Thale, P. Lucin, W. Muranyi, T. Flohr, H. Hengel, H. Farrell, W. Rawlinson, and U. H. Koszinowski. 1997. A mouse cytomegalovirus glycoprotein retains MHC class I complexes in the ERGIC/cis-Golgi compartments. Immunity 6:57-66.

93. Morello C. S., M. Ye, S. Hung, L. A. Kelley, and D. H. Spector. 2005. Systemic priming-boosting immunization with a trivalent plasmid DNA and inactivated murine cytomegalovirus (MCMV) vaccine provides long-term protection against viral replication following systemic or mucosal MCMV challenge. J Virol. 79:159-175.

94. Munks, M. W., M. C. Gold, A. L. Zajac, C. M. Doom, C. S. Morello, D. H. Spector, and A. B. Hill. 2006. Genome-wide analysis reveals a highly diverse CD8 T Cell Response to Murine Cytomegalovirus. J. Immunol. 176:3760-3766.

95. Arase, H., E. S. Mocarski, A. E. Campbell, A. B. Hill, and L. L. Lanier. 2002. Direct recognition of cytomegalovirus by activating and inhibitory NK cell receptors. Science 296:1323-1326.

96. Brune, W., H. Hengel, and U. H. Koszinowski. 1999. A mouse model for cytomegalovirus infection, p. 19.17.11-

19.17.13. In J. E. Coligan, A. M. Kruisbeek, D. H. Margulies, E. M. Shevach, and W. Strober (ed.), Current Protocols In Immunology, vol. 4. John Wiley & Sons, Inc., New York.

97. Munks, M. W., M. C. Gold, A. L. Zajac, C. M. Doom, C. S. Morello, D. H. Spector, and A. B. Hill. 2006. Genome-wide analysis reveals a highly diverse CD8 T cell response to murine cytomegalovirus. J. Immunol. 176:3760-3766.

98. Pari, G. S., and D. G. Anders. 1993. Eleven loci encoding trans-acting factors are required for transient complementation of human cytomegalovirus oriLyt-dependent DNA replication. J. Virol. 67:6979-6988.

99. Sylvester, A. W., B. L. Mitchell, J. B. Edgar, C. Taormina, C. Pelte, F. Ruchti, P. R. Sleath, K. H. Grabstein, N. A. Hosken, F. Kern, J. A. Nelson, and L. J. Picker. 2005. Broadly targeted human cytomegalovirus-specific CD4+ and CD8+ T cells dominate the memory compartments of exposed subjects. J. Exp. Med. 202:673-685.

111. Hosken, N., P. McGowan, A. Meier, D. M. Koelle, P. Sleath, F. Wagener, M. Elliott, K. Grabstein, C. Posavad, and L. Corey. 2006. Diversity of the CD8+ T-Cell Response to Herpes Simplex Virus Type 2 Proteins among Persons with Genital Herpes. J. Virol. 80:5509-5515.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Singular forms "a", "an", and "the" include plural reference unless the context clearly dictates otherwise. Thus, for example, reference to "a subset" includes a plurality of such subsets, reference to "a nucleic acid" includes one or more nucleic acids and equivalents thereof known to those skilled in the art, and so forth. The term "or" is not meant to be exclusive to one or the terms it designates. For example, as it is used in a phrase of the structure "A or B" may denote A alone, B alone, or both A and B.

Unless defined otherwise, all technical and scientific terms used herein have the same meanings as commonly understood by one of ordinary skill in the art to which this invention belongs. Although any methods and systems similar or equivalent to those described herein can be used in the practice or testing of the present invention, the methods, devices, and materials are now described. All publications mentioned herein are incorporated herein by reference for the purpose of describing and disclosing the processes, systems, and methodologies that are reported in the publications which might be used in connection with the invention. Nothing herein is to be construed as an admission that the invention is not entitled to antedate such disclosure by virtue of prior invention.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

What is claimed is:

1. A vaccine composition comprising a DNA molecule comprising at least one herpes virus DNA sequence selected from the group consisting of UL54 or a homolog thereof, and UL105 or a homolog thereof.

2. The vaccine composition of claim 1, comprising UL54 or homolog thereof and UL105 or homolog thereof.

3. A kit comprising a first vaccine composition of claim 1 or claim 2, and a second vaccine composition comprising an attenuated live or an inactivated herpes virus.

4. A method of eliciting a CD8+ T-cell response in an individual, comprising administering to said individual the vaccine composition of claim 1 or claim 2.

5. The vaccine composition of claim 1 or claim 2, further comprising UL44 or homolog thereof, UL50 or homolog thereof, UL51 or homolog thereof, UL52 or homolog thereof, UL53 or homolog thereof, UL56 or homolog thereof, UL57 or homolog thereof, UL70 or homolog thereof, UL71 or homolog thereof, UL77 or homolog thereof, UL79 or homolog thereof, UL87 or homolog thereof, UL89 or homolog thereof, UL92 or homolog thereof, UL93 or homolog thereof, UL102 or homolog thereof, or UL104 or homolog thereof.

6. The vaccine composition of claim 1 or claim 2, further comprising gB, gH, or gL.

* * * * *

SEQUENCE LISTING

<160> NUMBER OF SEQ ID NOS: 93

<210> SEQ ID NO 1
<211> LENGTH: 433
<212> TYPE: PRT
<213> ORGANISM: Human cytomegalovirus

<400> SEQUENCE: 1

Met Asp Arg Lys Thr Arg Leu Ser Glu Pro Pro Thr Leu Ala Leu Arg
1               5                   10                  15

Leu Lys Pro Tyr Lys Thr Ala Ile Gln Gln Leu Arg Ser Val Ile Arg
            20                  25                  30

Ala Leu Lys Glu Asn Thr Thr Val Thr Phe Leu Pro Thr Pro Ser Leu
        35                  40                  45

Ile Leu Gln Thr Val Arg Ser His Cys Val Ser Lys Ile Thr Phe Asn
    50                  55                  60

Ser Ser Cys Leu Tyr Ile Thr Asp Lys Ser Phe Gln Pro Lys Thr Ile
65                  70                  75                  80

Asn Asn Ser Thr Pro Leu Leu Gly Asn Phe Met Tyr Leu Thr Ser Ser
                85                  90                  95

Lys Asp Leu Thr Lys Phe Tyr Val Gln Asp Ile Ser Asp Leu Ser Ala
            100                 105                 110

Lys Ile Ser Met Cys Ala Pro Asp Phe Asn Met Glu Phe Ser Ser Ala
            115                 120                 125

-continued

```
Cys Val His Gly Gln Asp Ile Val Arg Glu Ser Glu Asn Ser Ala Val
        130                 135                 140

His Val Asp Leu Asp Phe Gly Val Val Ala Asp Leu Leu Lys Trp Ile
145                 150                 155                 160

Gly Pro His Thr Arg Val Lys Arg Asn Val Lys Lys Ala Pro Cys Pro
                165                 170                 175

Thr Gly Thr Val Gln Ile Leu Val His Ala Gly Pro Pro Ala Ile Lys
            180                 185                 190

Phe Ile Leu Thr Asn Gly Ser Glu Leu Glu Phe Thr Ala Asn Asn Arg
        195                 200                 205

Val Ser Phe His Gly Val Lys Asn Met Arg Ile Asn Val Gln Leu Lys
210                 215                 220

Asn Phe Tyr Gln Thr Leu Leu Asn Cys Ala Val Thr Lys Leu Pro Cys
225                 230                 235                 240

Thr Leu Arg Ile Val Thr Glu His Asp Thr Leu Leu Tyr Val Ala Ser
                245                 250                 255

Arg Asn Gly Leu Phe Ala Val Glu Asn Phe Leu Thr Glu Glu Pro Phe
            260                 265                 270

Gln Arg Gly Asp Pro Phe Asp Lys Asn Tyr Val Gly Asn Ser Gly Lys
        275                 280                 285

Ser Arg Gly Gly Gly Gly Gly Gly Ser Leu Ser Ser Leu Ala Asn
    290                 295                 300

Ala Gly Gly Leu His Asp Asp Gly Pro Gly Leu Asp Asn Asp Leu Met
305                 310                 315                 320

Asn Glu Pro Met Gly Leu Gly Gly Leu Gly Gly Gly Gly Gly Gly Gly
                325                 330                 335

Gly Lys Lys His Asp Arg Gly Gly Gly Gly Ser Gly Thr Arg Lys
            340                 345                 350

Met Ser Ser Gly Gly Gly Gly Asp His Asp His Gly Leu Ser Ser
        355                 360                 365

Lys Glu Lys Tyr Glu Gln His Lys Ile Thr Ser Tyr Leu Thr Ser Lys
370                 375                 380

Gly Gly Ser Gly Gly Gly Gly Gly Gly Gly Gly Leu Asp Arg
385                 390                 395                 400

Asn Ser Gly Asn Tyr Phe Asn Asp Ala Lys Glu Glu Ser Asp Ser Glu
                405                 410                 415

Asp Ser Val Thr Phe Glu Phe Val Pro Asn Thr Lys Lys Gln Lys Cys
            420                 425                 430
Gly

<210> SEQ ID NO 2
<211> LENGTH: 1302
<212> TYPE: DNA
<213> ORGANISM: Artificial
<220> FEATURE:
<223> OTHER INFORMATION: Synthetic DNA sequence of GenBank accession
      NC_001347 region: 56142..57443

<400> SEQUENCE: 2
ctagccgcac ttttgcttct tggtgttagg gacgaactcg aacgttacag aatcctcgct      60
gtcgctctcc tctttcgcgt cgttgaagta attgccggag ttgcgatcca aaccgccgcc     120
tcctcctcct ccgccgccgc ccgatccacc tttggacgtc aggtagctgg tgatcttgtg     180
ctgctcgtat ttttccttgg aggaaagacc gtggtcgtga tcaccgccgc cgccaccgct     240
gctcattttc cgcgtaccgg aaccaccgcc gccaccgcgg tcgtgcttct tgccgccacc     300
```

-continued

```
gccgccacct cctcccagac cgccgagacc catgggctcg ttcatgagat cgttatccag   360
acccgggccg tcgtcatgca gaccgccggc attggccagc gaagagaggc tgccgccacc   420
accgccgccg ccacgcgact tgccgctgtt cccgacgtaa ttttgtcga agggatcgcc    480
acgctggaaa ggttcctcgg tgagaaaatt ctccacggcg aacagaccgt tgcggctggc   540
cacgtacaac agcgtgtcgt gctccgtaac tatacgcaac gtgcacggca gtttggtgac   600
ggcgcaattg agcagcgtct ggtagaagtt cttcagctgc acgttgatac gcatgttttt   660
cacgccgtgg aaactgacgc ggttattggc tgtgaattcc agctcgctgc cgttggtcag   720
gataaacttg atggccggtg gaccggcgtg caccagaatc tgcacggtgc cgtagggca    780
gggcgctttt ttaacgttac gcttgacgcg gtatgcggc ccgatccact taagcaggtc    840
ggccaccacg ccgaaatcta gatccacgtg cacggccgaa ttctcgcttt cgcgcacaat   900
gtcttggccg tgcacgcagg ccgagctgaa ctccatattg aaatcgggcg cgcacatgga   960
gatcttggcc gacaggtccg agatgtcctg cacgtagaac ttggtcaggt ccttgctgga   1020
agtcaggtac atgaaattac ccagcagcgg cgtggaattg ttaatggtct tgggctgaaa   1080
cgacttgtca gtgatgtaga ggcatgagct gttaaaagtg attttgaca cgcagtgact     1140
gcgtaccgtt tgcaagataa cgacggcgt gggcaagaag gtaaccgtgg tgttctcctt    1200
gagcgcacgg atcacagatc gcagctgctg gatagccgtc ttgtacggct tcagccgcag   1260
cgccagcgtc ggcggctccg agaggcgcgt cttgcgatcc at                      1302
```

<210> SEQ ID NO 3
<211> LENGTH: 397
<212> TYPE: PRT
<213> ORGANISM: Human cytomegalovirus

<400> SEQUENCE: 3

```
Met Glu Met Asn Lys Val Leu His Gln Asp Leu Val Gln Ala Thr Arg
1               5                   10                  15

Arg Ile Leu Lys Leu Gly Pro Ser Glu Leu Arg Val Thr Asp Ala Gly
            20                  25                  30

Leu Ile Cys Lys Asn Pro Asn Tyr Ser Val Cys Asp Ala Met Leu Lys
        35                  40                  45

Thr Asp Thr Val Tyr Cys Val Glu Tyr Leu Leu Ser Tyr Trp Glu Ser
    50                  55                  60

Arg Thr Asp His Val Pro Cys Phe Ile Phe Lys Asn Thr Gly Cys Ala
65                  70                  75                  80

Val Ser Leu Cys Cys Phe Val Arg Ala Pro Val Lys Leu Val Ser Pro
                85                  90                  95

Ala Arg His Val Gly Glu Phe Asn Val Leu Lys Val Asn Glu Ser Leu
            100                 105                 110

Ile Val Thr Leu Lys Asp Ile Glu Glu Ile Lys Pro Ser Ala Tyr Gly
        115                 120                 125

Val Leu Thr Lys Cys Val Val Arg Lys Ser Asn Ser Ala Ser Val Phe
    130                 135                 140

Asn Ile Glu Leu Ile Ala Phe Gly Pro Glu Asn Glu Gly Glu Tyr Glu
145                 150                 155                 160

Asn Leu Leu Arg Glu Leu Tyr Ala Lys Lys Ala Ala Ser Thr Ser Leu
                165                 170                 175

Ala Val Arg Asn His Val Thr Val Ser Ser His Ser Gly Ser Pro
            180                 185                 190

Ser Leu Trp Arg Ala Arg Met Ser Ala Ala Leu Thr Arg Thr Ala Gly
        195                 200                 205
```

```
Lys Arg Ser Ser Arg Thr Ala Ser Pro Pro Pro Pro Arg His Pro
    210                 215                 220
Ser Cys Ser Pro Thr Met Val Ala Ala Gly Ala Ala Ala Gly Pro
225                 230                 235                 240
Arg Pro Pro Pro Pro Met Ala Ala Gly Ser Trp Arg Leu Cys Arg
                245                 250                 255
Cys Glu Ala Cys Met Gly Arg Cys Gly Cys Ala Ser Glu Gly Asp Ala
            260                 265                 270
Asp Glu Glu Glu Glu Glu Leu Leu Ala Leu Ala Gly Glu Gly Lys Ala
        275                 280                 285
Ala Ala Ala Ala Ala Gly Gln Asp Val Gly Gly Ser Ala Arg Arg Pro
    290                 295                 300
Leu Glu Glu His Val Ser Arg Arg Gly Val Ser Thr His His Arg
305                 310                 315                 320
His Pro Pro Ser Pro Pro Cys Ala Pro Ser Leu Glu Arg Thr Gly Tyr
                325                 330                 335
Arg Trp Ala Pro Ser Ser Trp Trp Arg Ala Arg Ser Gly Pro Ser Arg
            340                 345                 350
Pro Gln Ser Gly Pro Trp Leu Pro Ala Arg Phe Ala Thr Leu Gly Pro
        355                 360                 365
Leu Val Leu Ala Leu Leu Leu Val Leu Ala Leu Leu Trp Arg Gly His
    370                 375                 380
Gly Gln Ser Ser Ser Pro Thr Arg Ser Ala His Arg Asp
385                 390                 395

<210> SEQ ID NO 4
<211> LENGTH: 1194
<212> TYPE: DNA
<213> ORGANISM: Artificial
<220> FEATURE:
<223> OTHER INFORMATION: Synthetic DNA sequence of GenBank accession
      NC_001347 region: 73000..74193

<400> SEQUENCE: 4
tcagtcgcgg tgtgcggagc gtgtcggaga cgacgactgg ccatgaccgc gccacagcag     60
agccagcacc agcagaagag ccagcaccag cgggcccaga gtcgcaaagc gcgcgggcag    120
ccacggccca gactgcggtc gcgatggccc ggagcgcgct cgccaccacg atgacggtgc    180
ccaacgataa ccagtccgct ccaaggacgg cgcgcacggc ggagacggcg gatgacggtg    240
atgggtcgac acccctcgcc gacgactcac gtgctcctcc agaggccgac gcgcggaccc    300
tccgacgtcc tggcccgccg ctgccgctgc cgccttccct tctcccgcca gagccagcaa    360
ctcctcctcc tcttcatcag cgtctccctc gcttgcgcat ccgcatcgtc ccatacaggc    420
ctcacaacga cacagccgcc acgaccccgc cgccatgggt ggcggcggcg gccgaggccc    480
ggcagcggcg ccgccagcgg cgaccatggt gggagagcaa ctcggatgac gaggaggagg    540
agggggagat gcggtccgag aggaccgctt ccccgccgtt cgcgtaagcg cggccgacat    600
gcgggcgcgc cacagggacg gaccgctgcc gctgtgactg cttacggtga cgtggttccg    660
gaccgccaac gacgtcgacg cggctttctt ggcgtacagc tcgcgcagca gattctcgta    720
ctcgccctcg ttttcgggtc cgaaggcgat gagctcgatg ttgaagaccg acgccgaatt    780
ggatttgcgc accacgcact cgtcagcac tccgtaggcc gagggcttga tctcctcgat    840
gtccttgagc gtgacgatga gcgactcgtt caccttaagc acattgaact cacctacgtg    900
gcgcgccggc gaaacgagct tgacgggcgc tcgtacaaaa cagcagaggg agacggcgca    960
```

```
gccagtgttt ttaaagataa aacaaggcac gtggtctgtg cggctctccc agtagctgag    1020
tagatactcg acacaataga ccgtgtctgt cttgagcatg cgtcgcaca ccgagtaatt    1080 ggggttttta cagatgaggc cggcatcggt gacgcgcagc tcgctgggac ccaacttgag    1140
gatacgccgc gtggcctgca ccagatcctg atggagaacc ttgttcatct ccat          1194
```

<210> SEQ ID NO 5
<211> LENGTH: 157
<212> TYPE: PRT
<213> ORGANISM: Human cytomegalovirus

<400> SEQUENCE: 5

```
Met Ser Trp Ala Lys Gln Arg Val Pro Phe Leu Asp Asp Asp Asp Gly
1               5                   10                  15

Glu Glu Glu Asn Asp Val Gln Asp Asp Val Asp Ser Pro Val Pro Thr
            20                  25                  30

Arg Pro Leu Val Ile Asp Glu Asp Ala Glu Pro Ala Ala Gly Thr Ser
        35                  40                  45

Gly Gly Leu Glu Gly Gly Gly Asp Glu Asp Gly Glu Asp Gly
    50                  55                  60

His Ala Leu Pro Asp Leu Asp Asp Leu Leu Gln Phe Glu Pro
65                  70                  75                  80

Met Leu Pro Arg Val Tyr Asp Leu Leu Leu Pro Ser Leu Asp Ala Arg
                85                  90                  95

Leu Asn Phe Val Asn Ala Gly Gln Lys Tyr Ala Ala Phe Leu Lys Tyr
            100                 105                 110

Val His Gly Asp Cys Ala Thr Cys Ser His Gly Glu Ile Leu Arg Glu
        115                 120                 125

Lys Thr Gln Leu Leu Thr Ala Ile Val Ser Lys Leu Met Asp Ile Asn
    130                 135                 140

Gly Ile Leu Glu Gly Lys Asp Glu Ser Ala Pro Gly Lys
145                 150                 155
```

<210> SEQ ID NO 6
<211> LENGTH: 474
<212> TYPE: DNA
<213> ORGANISM: Artificial
<220> FEATURE:
<223> OTHER INFORMATION: Synthetic DNA sequence of GenBank accession
      ND_001347 region: 74215..74688

<400> SEQUENCE: 6

```
ttatttaccc ggcgccgact cgtctttttcc ctccaggatt ccgttaatgt ccatgagctt    60
gctgacgatc gccgttaata gttgcgtctt ctcacggagg atctctccgt gactgcaggt    120
cgcgcagtcg ccgtgcacgt acttgaggaa ggcggcgtac ttctgacccg cgttcacgaa    180
atttaagcgc gcgtccagag agggcagcaa cagatcgtag acgcgcggca gcatcggctc    240
gaactgtaat agcagatcgt cgtcaagatc gggtagcgcg tgtccgtctt caccgtcctc    300
gtcgtcacca cctccccccct cgagcccacc gctcgtacca gccgcgggct ccgcgtcctc    360
gtcgatcacc agcggtcgcg tcggcaccgg agaatccacg tcatcctgca cgtcgttttc    420
ctcctctccg tcgtcatcgt ccagaaacgg cacccgctgc ttagcccagg acat          474
```

<210> SEQ ID NO 7
<211> LENGTH: 668
<212> TYPE: PRT
<213> ORGANISM: Human cytomegalovirus

<400> SEQUENCE: 7

```
Met Asn Pro Ser Thr His Val Ser Ser Asn Gly Pro Thr Pro Pro
1               5                   10                  15

His Gly Pro His Thr Thr Phe Leu Pro Pro Thr Ser Pro Ala Pro Ser
            20                  25              30

Thr Ser Ser Val Ala Ala Ala Thr Leu Cys Ser Pro Gln Arg Gln Ala
        35                  40                  45

Val Ser Arg Tyr Ser Gly Trp Ser Thr Glu Tyr Thr Gln Trp His Ser
50                  55                  60

Asp Leu Thr Thr Glu Leu Leu Trp His Ala His Pro Arg Gln Val Pro
65              70                  75                  80

Met Asp Glu Ala Leu Ala Ala Ala Ala Ala Ser Tyr Gln Val Asn
                85                  90                  95

Pro Gln His Pro Ala Asn Arg Tyr Arg His Tyr Glu Phe Gln Thr Leu
                100                 105                 110

Ser Leu Gly Thr Ser Glu Val Asp Glu Leu Leu Asn Cys Cys Ala Glu
            115                 120                 125

Glu Thr Thr Cys Gly Gly Thr Gln Ser Thr Val Leu Thr Asn Ala Thr
        130                 135                 140

Asn Thr Thr Ser Cys Gly Gly Ala Val Ala Gly Ser Ser Asn Val Gly
145                 150                 155                 160

Pro Ala Gly Ala Ser Ala Ala Cys Asp Leu Asp Ala Glu Leu Ala Gly
                165                 170                 175

Leu Glu Thr Ser Ala Ala Asp Phe Glu Gln Leu Arg Arg Leu Cys Ala
            180                 185                 190

Pro Leu Ala Ile Asp Thr Arg Cys Asn Leu Cys Ala Ile Ile Ser Ile
        195                 200                 205

Cys Leu Lys Gln Asp Cys Asp Gln Ser Trp Leu Leu Glu Tyr Ser Leu
    210                 215                 220

Leu Cys Phe Lys Cys Ser Tyr Ala Pro Arg Ala Ala Leu Ser Thr Leu
225                 230                 235                 240

Ile Ile Met Ser Glu Phe Thr His Leu Leu Gln Gln His Phe Ser Asp
                245                 250                 255

Leu Arg Ile Asp Asp Leu Phe Arg His His Val Leu Thr Val Phe Asp
            260                 265                 270

Phe His Leu His Phe Phe Ile Asn Arg Cys Phe Glu Lys Gln Val Gly
        275                 280                 285

Asp Ala Val Asp Asn Glu Asn Val Thr Leu Asn His Leu Ala Val Val
    290                 295                 300

Arg Ala Met Val Met Gly Glu Asp Thr Val Pro Tyr Asn Lys Pro Arg
305                 310                 315                 320

Arg His Pro Gln Gln Lys Gln Lys Asn Asn Pro Tyr His Val Glu Val
                325                 330                 335

Pro Gln Glu Leu Ile Asp Asn Phe Leu Glu His Ser Ser Pro Ser Arg
            340                 345                 350

Asp Arg Phe Val Gln Leu Leu Phe Tyr Met Trp Ala Gly Thr Gly Val
        355                 360                 365

Met Ser Thr Thr Pro Leu Thr Glu Leu Thr His Thr Lys Phe Ala Arg
    370                 375                 380

Leu Asp Ala Leu Ser Thr Ala Ser Glu Arg Glu Asp Ala Arg Met Met
385                 390                 395                 400

Ile Glu Glu Glu Glu Asp Glu Glu Gly Glu Lys Gly Gly Asp Asp
                405                 410                 415

Pro Gly Arg His Asn Gly Gly Gly Thr Ser Gly Gly Phe Ser Glu Ser
```

Thr Leu Lys Lys Asn Val Gly Pro Ile Tyr Leu Cys Pro Val Pro Ala
    420                 425                 430
            435                 440                 445

Phe Phe Thr Lys Asn Gln Thr Ser Thr Val Cys Leu Leu Cys Glu Leu
            450                 455                 460

Met Ala Cys Ser Tyr Tyr Asp Asn Val Val Leu Arg Glu Leu Tyr Arg
465                 470                 475                 480

Arg Val Val Ser Tyr Cys Gln Asn Asn Val Lys Met Val Asp Arg Ile
                485                 490                 495

Gln Leu Val Leu Ala Asp Leu Leu Arg Glu Cys Thr Ser Pro Leu Gly
            500                 505                 510

Ala Ala His Glu Asp Val Ala Arg Cys Gly Leu Glu Ala Pro Thr Ser
            515                 520                 525

Pro Gly Gly Asp Ser Asp Tyr His Gly Leu Ser Gly Val Asp Gly Ala
    530                 535                 540

Leu Ala Arg Pro Asp Pro Val Phe Cys His Val Leu Arg Gln Ala Gly
545                 550                 555                 560

Val Thr Gly Ile Tyr Lys His Phe Phe Cys Asp Pro Gln Cys Ala Gly
                565                 570                 575

Asn Ile Arg Val Thr Asn Glu Ala Val Leu Phe Gly Arg Leu His Pro
            580                 585                 590

His His Val Gln Glu Val Lys Leu Ala Ile Cys His Asp Asn Tyr Tyr
            595                 600                 605

Ile Ser Arg Leu Pro Arg Arg Val Trp Leu Cys Ile Thr Leu Phe Lys
            610                 615                 620

Ala Phe Gln Ile Thr Lys Arg Thr Tyr Lys Gly Lys Val His Leu Ala
625                 630                 635                 640

Asp Phe Met Arg Asp Phe Thr Gln Leu Leu Glu Ser Cys Asp Ile Lys
                645                 650                 655

Leu Val Asp Pro Thr Tyr Val Ile Asp Lys Tyr Val
            660                 665

<210> SEQ ID NO 8
<211> LENGTH: 2007
<212> TYPE: DNA
<213> ORGANISM: Artificial
<220> FEATURE:
<223> OTHER INFORMATION: Synthetic DNA sequence of GenBank accession
      NC_001347 region: 74727..76733

<400> SEQUENCE: 8
atgaatccga gtacccacgt gagcagtaac ggcccaacga ctcccctca cgggccccac      60 accacgtttc ttccccgac cagcccggcc ccgtccacca gctccgtcgc cgccgctacc     120
ttgtgcagtc cgcaacgaca ggccgtttcg cgttacagcg gctggagcac cgagtacacc     180
cagtggcact cggacttgac aactgagctg ctatggcacg cgcacccgcg tcaagtacct     240
atggacgaag cgctggccgc cgcggcggcc gcctcatacc aggtaaatcc tcaacacccc     300
gccaaccgtt accgtcatta cgaattccag acgctcagcc tcggcacctc ggaggtagac     360
gaactgctca actgttgtgc ggaagaaacc acgtgcggcg gcacgcaatc caccgtactc     420
accaatgcga ccaacaccac tagctgcggc ggagccgtcg ccggcagtag caacgtagga     480
cccgccggcg cttcggccgc ctgcgaccta gatgcagaac tggccggcct cgaaacctcg     540
gcggccgact tgaacaact gcggcgactg tgcgcgccgc tggccatcga cacgcgctgt     600
aacctatgcg ccatcatcag catctgcctc aaacaggact cgaccagag ctggctcctc     660

```
gagtacagct tgctgtgctt caaatgcagt tacgcgcccc gtgcggcgct cagcacgctc      720
atcatcatgt ccgagtttac gcatctgctg cagcagcact tttccgatct gcgcatcgac      780
gacctgttcc gacaccacgt tctcacggtc ttcgatttcc acctgcactt tttcatcaat      840
cgttgctttg aaaacaagt gggcgacgcg gttgataacg agaatgtcac cctgaaccat       900
ctggccgtgg tgcgggccat ggtcatgggt gaagacacgg tgccttacaa caagcctcgg      960
cgccacccgc aacagaagca aaaaacaac ccttatcacg tcgaagtgcc gcaagaactg      1020
atcgacaact ttctagaaca cagctcacct agccgcgacc gcttcgtgca gctgcttttc     1080
tatatgtggg ccggcaccgg cgtcatgagc accacgccac tcacggaact cacgcacact     1140
aagttcgcgc gactagacgc gttatccacg gcctcggaaa agaagacgc aaggatgatg      1200
atagaagaag aggaggatga agaaggagga gaaaaggag gagacgatcc gggccgtcac       1260
aacggcggtg gcaccagcgg ggggttcagc gagagcacgc taaaaaaaaa cgtgggtccc     1320
atttacctat gtcccgtacc cgctttttt accaagaacc aaaccagtac cgtgtgtctg       1380
ctgtgcgaac tcatggcctg ctcctattac gataacgtcg tcctgcgcga gctgtaccgc     1440
cgcgtcgtct cgtattgtca gaacaatgtg aagatggtgg accgcattca gctggtattg     1500
gccgatctgt tgcgcgaatg cacgtcgccg ctcggcgcgg cacacgagga cgtggcgcgc     1560
tgtggactcg aagcacccac ctcgcccgga ggcgactcgg actaccacgg cctgagcggc     1620
gtcgacggcg cactggcgcg acccgacccg gtattttgcc acgtcctgcg tcaggcaggc     1680
gtcacgggca tctacaagca ctttttctgc gaccccgcagt gcgccggcaa catccgcgtc    1740
accaacgagg ccgtgctctt cggacgcctg caccccacc acgtccagga ggtgaaactg      1800
gccatctgtc acgacaatta ctatataagt cgacttccgc gacgtgtgtg gctctgcatc     1860
acactcttca aggcctttca gattacaaaa cgcacctaca aaggcaaagt gcacctggcg     1920
gactttatgc gcgatttcac gcagctgttg gagagttgcg acatcaagct ggtggaccc     1980
acgtacgtga tagacaagta tgtctag                                          2007
```

<210> SEQ ID NO 9
<211> LENGTH: 376
<212> TYPE: PRT
<213> ORGANISM: Human cytomegalovirus

<400> SEQUENCE: 9

Met Ser Ser Val Ser Gly Val Arg Thr Pro Arg Glu Arg Arg Ser Ala
1               5                   10                  15

Leu Arg Ser Leu Leu Arg Lys Arg Gln Arg Glu Leu Ala Ser Lys
            20                  25                  30

Val Ala Ser Thr Val Asn Gly Ala Thr Ser Ala Asn Asn His Gly Glu
        35                  40                  45

Pro Pro Ser Pro Ala Asp Ala Arg Pro Arg Leu Thr Leu His Asp Leu
    50                  55                  60

His Asp Ile Phe Arg Glu His Pro Glu Leu Glu Lys Tyr Leu Asn
65                  70                  75                  80

Met Met Lys Met Ala Ile Thr Gly Lys Glu Ser Ile Cys Leu Pro Phe
                85                  90                  95

Asn Phe His Ser His Arg Gln His Thr Cys Leu Asp Ile Ser Pro Tyr
            100                 105                 110

Gly Asn Glu Gln Val Ser Arg Ile Ala Cys Thr Ser Cys Glu Asp Asn
        115                 120                 125

Arg Ile Leu Pro Thr Ala Ser Asp Ala Met Val Ala Phe Ile Asn Gln
    130                 135                 140

```
Thr Ser Asn Ile Met Lys Asn Arg Asn Phe Tyr Tyr Gly Phe Cys Lys
145                 150                 155                 160

Ser Ser Glu Leu Leu Lys Leu Ser Thr Asn Gln Pro Pro Ile Phe Gln
                165                 170                 175

Ile Tyr Tyr Leu Leu His Ala Ala Asn His Asp Ile Val Pro Phe Met
            180                 185                 190

His Ala Glu Asp Gly Arg Leu His Met His Val Ile Phe Glu Asn Pro
        195                 200                 205

Asp Val His Ile Pro Cys Asp Cys Ile Thr Gln Met Leu Thr Ala Ala
    210                 215                 220

Arg Glu Asp Tyr Ser Val Thr Leu Asn Ile Val Arg Asp His Val Val
225                 230                 235                 240

Ile Ser Val Leu Cys His Ala Val Ser Ala Ser Ser Val Lys Ile Asp
                245                 250                 255

Val Thr Ile Leu Gln Arg Lys Ile Asp Glu Met Asp Ile Pro Asn Asp
                260                 265                 270

Val Ser Glu Ser Phe Glu Arg Tyr Lys Glu Leu Ile Gln Glu Leu Cys
            275                 280                 285

Gln Ser Ser Gly Asn Asn Leu Tyr Glu Glu Ala Thr Ser Ser Tyr Ala
        290                 295                 300

Ile Arg Ser Pro Leu Thr Ala Ser Pro Leu His Val Val Ser Thr Asn
305                 310                 315                 320

Gly Cys Gly Pro Ser Ser Ser Gln Ser Thr Pro Pro His Leu His
                325                 330                 335

Pro Pro Ser Gln Ala Thr Gln Pro His His Tyr Ser His His Gln Ser
            340                 345                 350

Gln Ser Gln Gln His His Arg Pro Gln Ser Pro Pro Pro Leu
        355                 360                 365

Phe Leu Asn Ser Ile Arg Ala Pro
    370                 375

<210> SEQ ID NO 10
<211> LENGTH: 1131
<212> TYPE: DNA
<213> ORGANISM: Artificial
<220> FEATURE:
<223> OTHER INFORMATION: Synthetic DNA sequence of GenBank accession
      NC_001347 region: 76726..77856

<400> SEQUENCE: 10
atgtctagcg tgagcggcgt gcgcacgccg cgcgaacgac gctcggcctt gcgctccctg      60
ctccgcaagc gccgccaacg cgagctggcc agcaaagtgg cgtcgacggt gaacggcgct     120
acgtcggcca caaccacgg cgaaccgccg tcgccggccg acgcgcgccc gcgcctcacg      180
ctgcacgacc tgcacgacat cttccgcgag caccccgaac tggagctcaa gtaccttaac     240
atgatgaaga tggccatcac gggcaaagag tccatctgct tacccttcaa tttccactcg     300
caccggcagc acacctgcct cgacatctcg ccgtacggca cgagcaggt ctcgcgcatc      360 gcctgcacct cgtgcgagga caaccgcatc ctgcccaccg cctccgacgc catggtggcc     420
ttcatcaatc agacgtccaa catcatgaaa aatagaaact tttattacgg gttctgtaag     480
agcagcgagc tactcaagct ctccaccaac cagccgccca tcttccaaat ttattacctg     540
ctgcacgccg ccaaccacga catcgtgccc tttatgcacg ccgaggacgg ccggttgcac     600
atgcacgtca tcttcgaaaa ccccgacgtg cacatcccct gcgactgcat cacgcagatg     660
ctcacggcgg cgcgcgaaga ctacagcgtc acgctcaaca tcgtgcgcga ccacgtcgtt     720
```

-continued

```
atcagcgtgc tgtgtcacgc cgtctcggcc agcagcgtca agatcgacgt gactattttg    780
caacgcaaga ttgacgagat ggacattccc aacgacgtga gcgagtcctt tgagcgctac    840
aaagagctca ttcaggagct gtgtcagtcc agcggcaaca acctatacga ggaggccacg    900
tcgtcctacg cgatacggtc tcccttaacc gcgtcgccgt tgcacgtagt ttccaccaac    960
ggctgcggcc cctcctcctc gtcccagtcc acgccgcctc atctccaccc gccgtcgcag    1020
gcgacgcagc cccaccacta ctctcaccac cagtctcagt ctcagcagca tcatcaccgt    1080
ccccagtcac caccgccgcc gctgtttctc aacagcattc gtgcgccttg a            1131
```

<210> SEQ ID NO 11
<211> LENGTH: 1242
<212> TYPE: PRT
<213> ORGANISM: Human cytomegalovirus

<400> SEQUENCE: 11

```
Met Phe Phe Asn Pro Tyr Leu Ser Gly Gly Val Thr Gly Gly Ala Val
1               5                   10                  15

Ala Gly Gly Arg Arg Gln Arg Ser Gln Pro Gly Ser Ala Gln Gly Ser
            20                  25                  30

Gly Lys Arg Pro Pro Gln Lys Gln Phe Leu Gln Ile Val Pro Arg Gly
        35                  40                  45

Val Met Phe Asp Gly Gln Thr Gly Leu Ile Lys His Lys Thr Gly Arg
    50                  55                  60

Leu Pro Leu Met Phe Tyr Arg Glu Ile Lys His Leu Leu Ser His Asp
65                  70                  75                  80

Met Val Trp Pro Cys Pro Trp Arg Glu Thr Leu Val Gly Arg Val Val
                85                  90                  95

Gly Pro Ile Arg Phe His Thr Tyr Asp Gln Thr Asp Ala Val Leu Phe
            100                 105                 110

Phe Asp Ser Pro Glu Asn Val Ser Pro Arg Tyr Arg Gln His Leu Val
        115                 120                 125

Pro Ser Gly Asn Val Leu Arg Phe Phe Gly Ala Thr Glu His Gly Tyr
    130                 135                 140

Ser Ile Cys Val Asn Val Phe Gly Gln Arg Ser Tyr Phe Tyr Cys Glu
145                 150                 155                 160

Tyr Ser Asp Thr Asp Arg Leu Arg Glu Val Ile Ala Ser Val Gly Glu
                165                 170                 175

Leu Val Pro Glu Pro Arg Thr Pro Tyr Ala Val Ser Val Thr Pro Ala
            180                 185                 190

Thr Lys Thr Ser Ile Tyr Gly Tyr Gly Thr Arg Pro Val Pro Asp Leu
        195                 200                 205

Gln Cys Val Ser Ile Ser Asn Trp Thr Met Ala Arg Lys Ile Gly Glu
    210                 215                 220

Tyr Leu Leu Glu Gln Gly Phe Pro Val Tyr Glu Val Arg Val Asp Pro
225                 230                 235                 240

Leu Thr Arg Leu Val Ile Asp Arg Arg Ile Thr Thr Phe Gly Trp Cys
                245                 250                 255

Ser Val Asn Arg Tyr Asp Trp Arg Gln Gln Gly Arg Ala Ser Thr Cys
            260                 265                 270

Asp Ile Glu Val Asp Cys Asp Val Ser Asp Leu Val Ala Val Pro Asp
        275                 280                 285

Asp Ser Ser Trp Pro Arg Tyr Arg Cys Leu Ser Phe Asp Ile Glu Cys
    290                 295                 300
```

-continued

```
Met Ser Gly Glu Gly Gly Phe Pro Cys Ala Glu Lys Ser Asp Asp Ile
305                 310                 315                 320

Val Ile Gln Ile Ser Cys Val Cys Tyr Glu Thr Gly Gly Asn Thr Ala
            325                 330                 335

Val Asp Gln Gly Ile Pro Asn Gly Asn Asp Gly Arg Gly Cys Thr Ser
        340                 345                 350

Glu Gly Val Ile Phe Gly His Ser Gly Leu His Leu Phe Thr Ile Gly
    355                 360                 365

Thr Cys Gly Gln Val Gly Pro Asp Val Asp Val Tyr Glu Phe Pro Ser
370                 375                 380

Glu Tyr Glu Leu Leu Gly Phe Met Leu Phe Phe Gln Arg Tyr Ala
385                 390                 395                 400

Pro Ala Phe Val Thr Gly Tyr Asn Ile Asn Ser Phe Asp Leu Lys Tyr
                405                 410                 415

Ile Leu Thr Arg Leu Glu Tyr Leu Tyr Lys Val Asp Ser Gln Arg Phe
            420                 425                 430

Cys Lys Leu Pro Thr Ala Gln Gly Gly Arg Phe Phe Leu His Ser Pro
        435                 440                 445

Ala Val Gly Phe Lys Arg Gln Tyr Ala Ala Phe Pro Ser Ala Ser
450                 455                 460

His Asn Asn Pro Ala Ser Thr Ala Ala Thr Lys Val Tyr Ile Ala Gly
465                 470                 475                 480

Ser Val Val Ile Asp Met Tyr Pro Val Cys Met Ala Lys Thr Asn Ser
                485                 490                 495

Pro Asn Tyr Lys Leu Asn Thr Met Ala Glu Leu Tyr Leu Arg Gln Arg
                500                 505                 510

Lys Asp Asp Leu Ser Tyr Lys Asp Ile Pro Arg Cys Phe Val Ala Asn
            515                 520                 525

Ala Glu Gly Arg Ala Gln Val Gly Arg Tyr Cys Leu Gln Asp Ala Val
        530                 535                 540

Leu Val Arg Asp Leu Phe Asn Thr Ile Asn Phe His Tyr Glu Ala Gly
545                 550                 555                 560

Ala Ile Ala Arg Leu Ala Lys Ile Pro Leu Arg Arg Val Ile Phe Asp
                565                 570                 575

Gly Gln Gln Ile Arg Ile Tyr Thr Ser Leu Leu Asp Glu Cys Ala Cys
            580                 585                 590

Arg Asp Phe Ile Leu Pro Asn His Tyr Ser Lys Gly Thr Thr Val Pro
        595                 600                 605

Glu Thr Asn Ser Val Ala Val Ser Pro Asn Ala Ala Ile Ile Ser Thr
    610                 615                 620

Ala Ala Val Pro Gly Asp Ala Gly Ser Val Ala Ala Met Phe Gln Met
625                 630                 635                 640

Ser Pro Pro Leu Gln Ser Ala Pro Ser Ser Gln Asp Gly Val Ser Pro
                645                 650                 655

Gly Ser Gly Ser Asn Ser Ser Ser Val Gly Val Phe Ser Val Gly
                660                 665                 670

Ser Gly Ser Ser Gly Gly Val Gly Val Ser Asn Asp Asn His Gly Ala
            675                 680                 685

Gly Gly Thr Ala Ala Val Ser Tyr Gln Gly Ala Thr Val Phe Glu Pro
        690                 695                 700

Glu Val Gly Tyr Tyr Asn Asp Pro Val Ala Val Phe Asp Phe Ala Ser
705                 710                 715                 720

Leu Tyr Pro Ser Ile Ile Met Ala His Asn Leu Cys Tyr Ser Thr Leu
                725                 730                 735
```

```
Leu Val Pro Gly Gly Glu Tyr Pro Val Asp Pro Ala Asp Val Tyr Ser
            740                 745                 750

Val Thr Leu Glu Asn Gly Val Thr His Arg Phe Val Arg Ala Ser Val
            755                 760                 765

Arg Val Ser Val Leu Ser Glu Leu Leu Asn Lys Trp Val Ser Gln Arg
            770                 775                 780

Arg Ala Val Arg Glu Cys Met Arg Glu Cys Gln Asp Pro Val Arg Arg
785                 790                 795                 800

Met Leu Leu Asp Lys Glu Gln Met Ala Leu Lys Val Thr Cys Asn Ala
            805                 810                 815

Phe Tyr Gly Phe Thr Gly Val Val Asn Gly Met Met Pro Cys Leu Pro
            820                 825                 830

Ile Ala Ala Ser Ile Thr Arg Ile Gly Arg Asp Met Leu Glu Arg Thr
            835                 840                 845

Ala Arg Phe Ile Lys Asp Asn Phe Ser Glu Pro Cys Phe Leu His Asn
850                 855                 860

Phe Phe Asn Gln Glu Asp Tyr Val Val Gly Thr Arg Glu Gly Asp Ser
865                 870                 875                 880

Glu Glu Ser Ser Ala Leu Pro Glu Gly Leu Glu Thr Ser Ser Gly Gly
            885                 890                 895

Ser Asn Glu Arg Arg Val Glu Ala Arg Val Ile Tyr Gly Asp Thr Asp
            900                 905                 910

Ser Val Phe Val Arg Phe Arg Gly Leu Thr Pro Gln Ala Leu Val Ala
            915                 920                 925

Arg Gly Pro Ser Leu Ala His Tyr Val Thr Ala Cys Leu Phe Val Glu
            930                 935                 940

Pro Val Lys Leu Glu Phe Glu Lys Val Phe Val Ser Leu Met Met Ile
945                 950                 955                 960

Cys Lys Lys Arg Tyr Ile Gly Lys Val Glu Gly Ala Ser Gly Leu Ser
                    965                 970                 975

Met Lys Gly Val Asp Leu Val Arg Lys Thr Ala Cys Glu Phe Val Lys
            980                 985                 990

Gly Val Thr Arg Asp Val Leu Ser Leu Leu Phe Glu Asp Arg Glu Val
            995                1000                1005

Ser Glu Ala Ala Val Arg Leu Ser Arg Leu Ser Leu Asp Glu Val
        1010                1015                1020

Lys Lys Tyr Gly Val Pro Arg Gly Phe Trp Arg Ile Leu Arg Arg
        1025                1030                1035

Leu Val Gln Ala Arg Asp Asp Leu Tyr Leu His Arg Val Arg Val
        1040                1045                1050

Glu Asp Leu Val Leu Ser Ser Val Leu Ser Lys Asp Ile Ser Leu
        1055                1060                1065

Tyr Arg Gln Ser Asn Leu Pro His Ile Ala Val Ile Lys Arg Leu
        1070                1075                1080

Ala Ala Arg Ser Glu Glu Leu Pro Ser Val Gly Asp Arg Val Phe
        1085                1090                1095

Tyr Val Leu Thr Ala Pro Gly Val Arg Thr Ala Pro Gln Gly Ser
        1100                1105                1110

Ser Asp Asn Gly Asp Ser Val Thr Ala Gly Val Val Ser Arg Ser
        1115                1120                1125

Asp Ala Ile Asp Gly Thr Asp Asp Ala Asp Gly Gly Gly Val
        1130                1135                1140

Glu Glu Ser Asn Arg Arg Gly Gly Glu Pro Ala Lys Lys Arg Ala
```

Arg Lys Pro Pro Ser Ala Val Cys Asn Tyr Glu Val Ala Glu Asp
1160                1165                1170

Pro Ser Tyr Val Arg Glu His Gly Val Pro Ile His Ala Asp Lys
1175                1180                1185

Tyr Phe Glu Gln Val Leu Lys Ala Val Thr Asn Val Leu Ser Pro
1190                1195                1200

Val Phe Pro Gly Gly Glu Thr Ala Arg Lys Asp Lys Phe Leu His
1205                1210                1215

Met Val Leu Pro Arg Arg Leu His Leu Glu Pro Ala Phe Leu Pro
1220                1225                1230

Tyr Ser Val Lys Ala His Glu Cys Cys
1235                1240

<210> SEQ ID NO 12
<211> LENGTH: 3729
<212> TYPE: DNA
<213> ORGANISM: Artificial
<220> FEATURE:
<223> OTHER INFORMATION: Synthetic DNA sequence of GenBank accession
      NC_001347 region: 77834..81562

<400> SEQUENCE: 12
tcaacagcat tcgtgcgcct tgacactgta cggcagaaaa gccggctcca agtgcaagcg     60
ccgcggcagc accatgtgca aaaacttgtc cttgcgcgcg gtttcgccgc cgggaaagac    120
gggcgacagc acgttagtta cagccttgag aacctgctca agtacttgt cggcgtgaat    180 gggcacgccg tgctcgcgca cgtagctcgg atcttcggct acctcgtagt tgcacacggc    240
cgacggtggt tccgcgccc tcttctttgc cggctctcct cctctcctgt tgctctcctc    300
taccccgccg ccgtcagcgt cgtcgtccgt gccatcaatc gcgtccgacc gggaaaccac    360
gccggcggtt acagaatcac cgttgtcgga ggaaccctgc ggcgccgtcc ggacaccggg    420
cgccgtcaga acgtaaaaga cccgatcccc gaccgagggt agctcctcag aacgggccgc    480
caatcgctta tgacggcaa tgtgcggcag gttagattga cggtacagcg agatgtcctt    540
agagagcacc gacgaaagca ccaggtcctc gacacgcaca cggtgcaggt acagatcgtc    600
gcgggcctgc accaagcggc gtaagatacg ccagaaaccg cgtggcacgc cgtacttctt    660
gacttcatcg agtgagaggc gcgacaggcg cacggctgct tccgagacct cgcgatcctc    720
aaagagcagc gagaggacgt cacgcgtgac gcccttgacg aactcgcagg ccgtcttgcg    780
caccagatcc acgcccttca tgctcagacc cgaggcgccc tccactttgc cgatgtaacg    840
tttcttgcag atcatcataa gagagacgaa gacccttttca aactccagct tgacgggctc    900
cacaaaaaga caggccgtca cgtagtgcgc caggctgggc ccacgcgcca ccagagcctg    960
cggcgtcagg ccacgaaagc ggacaaacac gctgtccgtg tccccgtaga tgacccgcgc   1020
ctccacccgc cgttcgttcg agccccctga cgatgtttcg agccctccg gtaacgcgct   1080 gctctcctcc gaatcccct cccgcgttcc cactacatag tcttcctgat taaaaaatt    1140 gtgcaaaaaa cacggctctg aaaagttgtc tttgatgaac cgcgccgtgc gctctagcat   1200
gtcgcgaccg atgcgcgtga tgctggcggc gatgggcaga cacggcatca taccgttgac   1260
cacgccggta aaaccgtaga aagcgttgca cgttactttg agcgccatct gttccttgtc   1320
gagcagcata cggcgcacag ggtcttgaca ctcgcgcatg cattcgcgca cggcacgccg   1380
ctgcgaaacc cacttgttga gcagttccga gagcaccgag acgcgcaccg aagcacgcac   1440
aaagcggtgg gtcacgccgt tctctagcgt gacgctgtat acgtcggcgg ggtccacagg   1500

```
gtactcgcca cccggcacca gcagggtgga gtagcagagg ttgtgggcca tgatgatgga    1560
agggtagagg ctggcaaagt cgaacacggc cacggggtcg ttgtagtaac ccacctcggg    1620
ctcaaacacc gtggcgccct ggtacgaaac cgccggcgc cgtgattgtc                1680
gttggaaacg ccgacgccgc cactactgcc ggagccgacg ctgaaaacgc cgacgctgct    1740
actactgtta ctgccggagc cgggtgaaac gccgtcctga ctggacggcg cagattgcaa    1800
gggcggcgac atctgaaaca tagccgccac agaacccgcg tcgccgggca cagcggcggt    1860
agagatgata gcagcgttag gtgacacagc aacgctattc gtttcgggca ccgtcgtacc    1920
tttgctgtag tggttgggca ggataaaatc gcggcaggcg cactcgtcca gcagcgaggt    1980
gtagatacgg atctgctgtc cgtcaaagat gacacgccgc aacgaatttt agccagccg     2040
cgcgatggcc ccggcctcgt agtgaaaatt aatggtgttg aacagatcgc gcaccaatac    2100
ggcgtcctgc agacagtaac ggcctacctg ggcgcggccc tcggcattag ccacgaaaca    2160
acgcgggatg tccttgtaag acaggtcatc cttgcgttgc cgcaggtaaa gctcggccat    2220
agtgttgagc ttatagttgg gcgagttagt cttggccatg catacagggt acatgtcgat    2280
aaccaccgaa cccgcaatat acaccttggt ggcggccgtg ctggccggat gttgtgaga    2340
agccgaggga aaagcggcgg cgtactgccg cttaaaaccc acggcggggc tgtgtaaaaa    2400
gaaacgccg ccctgcgccg taggcaactt gcagaagcgc tgcgagtcca ccttatacag    2460
gtactcgaga cgcgtgagga tgtacttcaa gtcaaaagag ttgatgttgt aaccggtcac    2520
aaaggccggc gcgtaccgtt gaaagaaaag cataaagccc agcagcagct cgtattcgga    2580
agggaactcg tagacgtcca cgtctgggcc cacctgcccg caggtgccga tcgtaaagag    2640
atgaagaccc gagtgcccaa agatcacacc ctccgaagtg cagccccgac catcgttccc    2700
gtttgggatc ccctgatcca cggcggtgtt tccccccgtc tcgtagcaca cgcacgagat    2760
ctgaatgaca atgtcatcgg acttctcggc gcagggaaaa ccaccctcgc cgctcatgca    2820
ctcgatatcg aaggacaggc atcgatagcg cggccacgag ctgtcgtcgg gcacagccac    2880
caggtcagag acatcgcagt ctacctcgat atcacaagtc gacgcgcgac cctgctgccg    2940
ccagtcgtaa cgattcacgg agcaccagcc gaacgtggtg atccgccgat cgatgaccaa    3000
acgcgtcagc ggatccacac ggacctcgta cacgggaaaa ccctgctcca gcagatactc    3060
gccgattttt ctggccatgg tccagttgct gatagacaca cactgcaaat cgggcacggg    3120
tcgcgtcccg tacccataga tggaggtctt ggtggccggc gtgacagaca cggcgtatgg    3180
cgtccgcggt tcgggcacta gttcgcccac gctggcaatg acctcacgca gcctatcggt    3240
gtcgctgtac tcacagtaaa agtagctgcg ctgcccgaaa acgttgacgc agatactgta    3300
gccgtgttct gtggccccga agaaacgcaa cacgttcccc gaaggcacca gatgctgacg    3360
atagcgcggc gacacgtttt cgggcgagtc gaagaagagc acggcgtccg tctgatcgta    3420
ggtgtgaaaa cgaataggtc ccaccacgcg acccaccagg gtctcgcgcc aaggacacgg    3480
ccaaaccatg tcatgactca acaaatgttt aatctctcga tagaacatga gaggcagccg    3540
tcccgtctta tgcttgatca accccgtctg accgtcgaac atgacacctc gcggcacgat    3600
ctgcaaaaac tgtttctgtg gcggccgctt gcccgagccc tgcgcggagc cgggctgcga    3660
acgctgacgc cggccacccg cgaccgcacc gccggtcacg ccgccgctca gatacgggtt    3720
gaaaaacat                                                           3729

<210> SEQ ID NO 13
<211> LENGTH: 906
```

```
<212> TYPE: PRT
<213> ORGANISM: Human cytomegalovirus

<400> SEQUENCE: 13

Met Glu Ser Arg Ile Trp Cys Leu Val Cys Val Asn Leu Cys Ile
1               5                   10                  15

Val Cys Leu Gly Ala Ala Val Ser Ser Ser Thr Ser His Ala Thr
                20                  25                  30

Ser Ser Thr His Asn Gly Ser His Thr Ser Arg Thr Thr Ser Ala Gln
            35                  40                  45

Thr Arg Ser Val Tyr Ser Gln His Val Thr Ser Ser Glu Ala Val Ser
        50                  55                  60

His Arg Ala Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Ile Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
130                 135                 140

Lys Val Leu Thr Phe Arg Arg Ser Tyr Ala Tyr Ile Tyr Thr Thr Tyr
145                 150                 155                 160

Leu Leu Gly Ser Asn Thr Glu Tyr Val Ala Pro Pro Met Trp Glu Ile
                165                 170                 175

His His Ile Asn Lys Phe Ala Gln Cys Tyr Ser Ser Tyr Ser Arg Val
            180                 185                 190

Ile Gly Gly Thr Val Phe Val Ala Tyr His Arg Asp Ser Tyr Glu Asn
        195                 200                 205

Lys Thr Met Gln Leu Ile Pro Asp Asp Tyr Ser Asn Thr His Ser Thr
210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Leu Thr Ile Thr Thr
                245                 250                 255

Ala Arg Ser Lys Tyr Pro Tyr His Phe Phe Ala Thr Ser Thr Gly Asp
            260                 265                 270

Val Val Tyr Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
290                 295                 300

Ile Val Ser Asp Phe Gly Arg Pro Asn Ala Ala Pro Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
370                 375                 380

Ser Asp Ser Ala Leu Asp Cys Val Arg Asp Glu Ala Ile Asn Lys Leu
385                 390                 395                 400
```

```
Gln Gln Ile Phe Asn Thr Ser Tyr Asn Gln Thr Tyr Glu Lys Tyr Gly
                405                 410                 415
Asn Val Ser Val Phe Glu Thr Ser Gly Gly Leu Val Val Phe Trp Gln
            420                 425                 430
Gly Ile Lys Gln Lys Ser Leu Val Glu Leu Glu Arg Leu Ala Asn Arg
        435                 440                 445
Ser Ser Leu Asn Ile Thr His Arg Thr Arg Arg Ser Thr Ser Asp Asn
    450                 455                 460
Asn Thr Thr His Leu Ser Ser Met Glu Ser Val His Asn Leu Val Tyr
465                 470                 475                 480
Ala Gln Leu Gln Phe Thr Tyr Asp Thr Leu Arg Gly Tyr Ile Asn Arg
                485                 490                 495
Ala Leu Ala Gln Ile Ala Glu Ala Trp Cys Val Asp Gln Arg Arg Thr
            500                 505                 510
Leu Glu Val Phe Lys Glu Leu Ser Lys Ile Asn Pro Ser Ala Ile Leu
        515                 520                 525
Ser Ala Ile Tyr Asn Lys Pro Ile Ala Ala Arg Phe Met Gly Asp Val
    530                 535                 540
Leu Gly Leu Ala Ser Cys Val Thr Ile Asn Gln Thr Ser Val Lys Val
545                 550                 555                 560
Leu Arg Asp Met Asn Val Lys Glu Ser Pro Gly Arg Cys Tyr Ser Arg
                565                 570                 575
Pro Val Val Ile Phe Asn Phe Ala Asn Ser Ser Tyr Val Gln Tyr Gly
            580                 585                 590
Gln Leu Gly Glu Asp Asn Glu Ile Leu Leu Gly Asn His Arg Thr Glu
        595                 600                 605
Glu Cys Gln Leu Pro Ser Leu Lys Ile Phe Ile Ala Gly Asn Ser Ala
    610                 615                 620
Tyr Glu Tyr Val Asp Tyr Leu Phe Lys Arg Met Ile Asp Leu Ser Ser
625                 630                 635                 640
Ile Ser Thr Val Asp Ser Met Ile Ala Leu Asp Ile Asp Pro Leu Glu
                645                 650                 655
Asn Thr Asp Phe Arg Val Leu Glu Leu Tyr Ser Gln Lys Glu Leu Arg
            660                 665                 670
Ser Ser Asn Val Phe Asp Leu Glu Glu Ile Met Arg Glu Phe Asn Ser
        675                 680                 685
Tyr Lys Gln Arg Val Lys Tyr Val Glu Asp Lys Val Val Asp Pro Leu
    690                 695                 700
Pro Pro Tyr Leu Lys Gly Leu Asp Asp Leu Met Ser Gly Leu Gly Ala
705                 710                 715                 720
Ala Gly Lys Ala Val Gly Val Ala Ile Gly Ala Val Gly Gly Ala Val
                725                 730                 735
Ala Ser Val Val Glu Gly Val Ala Thr Phe Leu Lys Asn Pro Phe Gly
            740                 745                 750
Ala Phe Thr Ile Ile Leu Val Ala Ile Ala Val Val Ile Ile Thr Tyr
        755                 760                 765
Leu Ile Tyr Thr Arg Gln Arg Arg Leu Cys Thr Gln Pro Leu Gln Asn
    770                 775                 780
Leu Phe Pro Tyr Leu Val Ser Ala Asp Gly Thr Thr Val Thr Ser Gly
785                 790                 795                 800
Ser Thr Lys Asp Thr Ser Leu Gln Ala Pro Pro Ser Tyr Glu Glu Ser
                805                 810                 815
Val Tyr Asn Ser Gly Arg Lys Gly Pro Gly Pro Pro Ser Ser Asp Ala
            820                 825                 830
```

```
Ser Thr Ala Ala Pro Pro Tyr Thr Asn Glu Gln Ala Tyr Gln Met Leu
            835                 840                 845

Leu Ala Leu Ala Arg Leu Asp Ala Glu Gln Arg Ala Gln Gln Asn Gly
        850                 855                 860

Thr Asp Ser Leu Asp Gly Gln Thr Gly Thr Gln Asp Lys Gly Gln Lys
865                 870                 875                 880

Pro Asn Leu Leu Asp Arg Leu Arg His Arg Lys Asn Gly Tyr Arg His
                885                 890                 895

Leu Lys Asp Ser Asp Glu Glu Glu Asn Val
            900                 905

<210> SEQ ID NO 14
<211> LENGTH: 2721
<212> TYPE: DNA
<213> ORGANISM: Artificial
<220> FEATURE:
<223> OTHER INFORMATION: Synthetic DNA sequence of GenBank accession
      NC_001347 region: 81703..84423

<400> SEQUENCE: 14
```

| | | | | | |
|---|---|---|---|---|---|
| tcagacgttc | tcttcttcgt | cggagtcttt | caagtgtctg | tagccgtttt | tgcgatgtcg | 60 |
| cagccggtct | agcaggttag | gcttctgtcc | cttgtcctgc | gtgccagtct | gtccgtccaa | 120 |
| agaatctgta | ccgttctgct | gcgctcgctg | ctctgcgtcc | agacgggcca | gggccagaag | 180 |
| catctggtaa | gcctgctcgt | tggtgtaagg | cggagccgcc | gtggatgcat | cagacgacgg | 240 |
| tggtcccggt | cctttgcgac | cagaattata | aacactttcc | tcgtaggaag | gcggagcctg | 300 |
| taacgacgtg | tctttggtgc | tgcccgacgt | cacggtggtc | ccgtcggcgg | acaccagata | 360 |
| gggaaagagg | ttctgcagcg | gctgcgtgca | cagacgccgc | tgtcgagtat | agatcaaata | 420 |
| agtgataatg | actacggcta | tggccacgag | gatgatggtg | aaggctccga | aggggttttt | 480 |
| gaggaaggtg | gcaacgcctt | cgaccacgga | ggccaccgcg | ccacccacgg | ccccaatggc | 540 |
| tacgccaacg | gcctttcccg | cggcgcccag | gccgctcatg | aggtcgtcca | gacccttgag | 600 |
| gtagggcggt | agcgggtcga | ctaccttgtc | ctccacgtac | tttacccgct | gcttgtacga | 660 |
| gttgaattcg | cgcatgatct | cttcgaggtc | aaaaacgttg | ctggaacgca | gctctttctg | 720 |
| cgagtaaagt | tccagtaccc | tgaagtcggt | attttccagc | gggtcgatat | ccagggcgat | 780 |
| catgctgtcg | acggtggaga | tactgctgag | gtcaatcatg | cgtttgaaga | ggtagtccac | 840 |
| gtactcgtag | gccgagttcc | cggcgatgaa | gatcttgagg | ctgggaagct | gacattcctc | 900 |
| agtgcggtgg | ttgcccaaca | ggatttcgtt | gtcctcgccc | agttgaccgt | actgcacgta | 960 |
| cgagctgttg | gcgaaattaa | agatgaccac | gggtcgtgag | tagcagcgtc | ctggcgattc | 1020 |
| cttcacgttc | atatcacgca | gcaccttgac | gctggtttgg | ttgatggtca | cgcagctggc | 1080 |
| caggcccaag | acatcaccca | tgaaacgcgc | ggcaatcggt | ttgttgtaaa | tggccgagag | 1140 |
| aatggctgac | gggttgatct | tgctgagttc | cttgaagacc | tctagggtgc | gccgttgatc | 1200 |
| cacacaccag | gcttctgcga | tttgcgccag | cgcccggttg | atgtaaccgc | gcaacgtgtc | 1260 |
| ataggtgaac | tgcagctggg | cgtagaccag | attgtgcacc | gattccatgc | tggacaaatg | 1320 |
| agttgtatta | ttgtcactcg | tacttcttct | ggtcctatga | gtgatattca | gactggatcg | 1380 |
| attggccaaa | cgttccaatt | ccaccaaaga | tttttgcttg | atgccttgcc | agaacaccac | 1440 |
| cagaccgccg | ctggtttcga | agacggacac | gttccgtat | ttttcatatg | tttgattgta | 1500 |
| tgaagtattg | aaaatctgct | gtaacttatt | tatagcctca | tcacgtacgc | agtccagcgc | 1560 |
| ggagtcggac | atgttcactt | cttgtttctt | agacagaaaa | gttgcagtca | ttttggcaga | 1620 |

```
agaaaagtgg tacgagtctt cggcttcgga acggatagta cgttccgagg cttcccagaa     1680
ggtgagctgg caggtgacat tcttctcgtc ctgtatatcc aagagatca ccgagtcggc      1740 acgttcgaga aaagccacca acctatgggt ttctggcgca cgttgggtc ttccaaagtc      1800 ggaaacgatg gtgtagttcg ggaaaatgaa aaacttgtcg gcgttttctc caaagtagct    1860
ggcattgcga ttggttccgt tgtagaaagg agaaatgtaa accacatcac ccgtggaagt    1920
tgcaaaaaaa tgataaggat acttggagcg cgcagtagtg atggtcagca tacagttcag    1980
attacaggtc tcacgataga gccaggtgct gccgcggctg tgccactgat ccttgaccgt    2040
cacgtaacgg gtactgtggg tgttggaata atcgtcggga attaattgca tggttttgtt    2100
ttcataactg tccctatgat atgccacgaa aaccgtgcct cctataacgc ggctgtagga    2160
actgtagcat tgagcaaact tgttgatgtg atgaatctcc cacataggag gcgccacgta    2220
ttccgtattg ctgcccagca gataagtggt gtagatgtaa gcgtagctac gacgaaacgt    2280
caaaaccttt tggtagaccc gtaccttaaa ggtgtgcgcc acgatgttgc gcttgtagac    2340
caccatgatg ccctcatcca agtcttcatt gataggcttc atcgaggtgc agatgatatt    2400
acgttcaaag cgaataagat ccgtaccctg ggccatagaa cacacgcgat aggggtactt    2460
ggtagtgttg actcccacca catctccgta cttgagggta gtgttgtaga tagtctcgtt    2520
ggctctatga ctgacggctt cagaagacgt tacgtgttga aatagactg accgggtttg      2580 agcagacgtc gtacgagaag tatggcttcc attgtgagta aagaagttg catgggaagt      2640 actagaagag gaaaccgcag cacccagaca gacgatacac aggttaacgc agactaccag    2700
gcaccagatc ctggattcca t                                                2721

<210> SEQ ID NO 15
<211> LENGTH: 850
<212> TYPE: PRT
<213> ORGANISM: Human cytomegalovirus

<400> SEQUENCE: 15

Met Glu Met Asn Leu Leu Gln Lys Leu Cys Val Cys Ser Lys Cys
1               5                   10                  15

Asn Glu Tyr Ala Met Glu Leu Glu Cys Leu Lys Tyr Cys Asp Pro Asn
                20                  25                  30

Val Leu Leu Ala Glu Ser Thr Pro Phe Lys Arg Asn Ala Ala Ala Ile
            35                  40                  45

Val Tyr Leu Tyr Arg Lys Ile Tyr Pro Glu Val Ala Gln Asn Arg
        50                  55                  60

Thr Gln Ser Ser Leu Leu Thr Leu Tyr Leu Glu Met Leu Leu Lys Ala
65                  70                  75                  80

Leu His Glu Asp Thr Ala Leu Leu Asp Arg Ala Leu Met Ala Tyr Ser
                85                  90                  95

Arg Gln Pro Asp Arg Ala Ala Phe Tyr Arg Thr Val Leu Arg Leu Asp
                100                 105                 110

Arg Cys Asp Arg His His Thr Val Glu Leu Gln Phe Thr Asp Asn Val
            115                 120                 125

Arg Phe Ser Val Ser Leu Ala Thr Leu Asn Asp Ile Glu Arg Phe Leu
        130                 135                 140

Cys Lys Met Asn Tyr Val Tyr Gly Ile Leu Ala Pro Glu Ala Gly Leu
145                 150                 155                 160

Glu Val Cys Ala Gln Leu Leu Gly Leu Leu Arg Arg Leu Cys Gly Ile
                165                 170                 175
```

```
Ser Pro Val Ala Arg Gln Glu Val Tyr Val Glu Gly Thr Thr Cys Ala
            180                 185                 190
Gln Cys Tyr Glu Glu Leu Thr Ile Ile Pro Asn Gln Gly Arg Ser Leu
        195                 200                 205
Asn Lys Arg Leu Gln Gly Leu Leu Cys Asn His Ile Ala Val His Arg
    210                 215                 220
Pro Ser Ser Gln Ser Asp Val Asn Ile Gln Thr Val Glu Gln Asp Leu
225                 230                 235                 240
Leu Asp Leu Thr Thr Arg Ile Pro His Leu Ala Gly Val Leu Ser Ala
                245                 250                 255
Leu Lys Ser Leu Phe Ser Ser Ser Ala Tyr His Ser Tyr Ile Gln
            260                 265                 270
Glu Ala Glu Ala Leu Arg Glu Tyr Asn Leu Phe Thr Asp Ile Pro
        275                 280                 285
Glu Arg Ile Tyr Ser Leu Ser Asp Phe Thr Tyr Trp Ser Arg Thr Ser
290                 295                 300
Glu Val Ile Val Lys Arg Val Gly Ile Thr Ile Gln Gln Leu Asn Val
305                 310                 315                 320
Tyr His Gln Leu Cys Arg Ala Leu Met Asn Gly Ile Ser Arg His Leu
                325                 330                 335
Tyr Gly Glu Asp Val Glu Asp Ile Phe Val Leu Gly Glu Lys Ala Leu
            340                 345                 350
Asp Gly Glu Glu Arg Met Phe Val Gly Ser Val Phe Ala Ala Pro Asn
        355                 360                 365
Arg Ile Ile Asp Leu Ile Thr Ser Leu Ser Ile Gln Ala Phe Glu Asp
    370                 375                 380
Asn Pro Val Phe Asn Lys Leu His Glu Ser Asn Glu Met Tyr Thr Lys
385                 390                 395                 400
Ile Lys His Ile Leu Glu Glu Ile Arg Arg Pro Leu Pro Asp Gly Thr
                405                 410                 415
Gly Gly Asp Gly Pro Glu Gly Glu Ala Ile His Leu Arg Gly Arg Glu
            420                 425                 430
Ala Met Ser Gly Thr Gly Thr Thr Leu Met Thr Ala Ser Asn Ser Ser
        435                 440                 445
Asn Ser Ser Thr His Ser Gln Arg Asn Asn Gly Gly Gly Gly Arg Ala
    450                 455                 460
Arg Gly Gly Gly Lys Lys Val Val Gly Gly Val Asn Gly Gln Asp
465                 470                 475                 480
Gly Asp Gly Ser Glu Asn Gly Leu Arg Val Arg Asn Cys Asp Glu His
                485                 490                 495
Glu Ala Leu Asp Leu Val Asp Ala Arg Ser Arg Ile His Asn Val Thr
            500                 505                 510
Arg Glu Val Asn Val Arg Lys Arg Ala Tyr Leu Gln Lys Val Ser Glu
        515                 520                 525
Val Gly Tyr Gly Lys Val Ile Arg Cys Ile Lys Thr Gln Glu Arg Leu
    530                 535                 540
Thr Ser Lys Leu Ile Asp Val Asn Leu Val Gly Pro Leu Cys Leu Asp
545                 550                 555                 560
Phe Ile Ser Lys Leu Met Asn Gly Phe Leu Tyr Arg Ser Gln Tyr His
                565                 570                 575
Gln Asp Gln Asp Val Val Asp Val Gly Asp Gln Phe Thr Tyr Asp Glu
            580                 585                 590
His Leu Tyr Val Val Asn Asn Leu Ile His Lys Ser Leu Pro Val Glu
        595                 600                 605
```

Ser Leu Pro Leu Leu Gly Gln Gln Ile Tyr Glu Leu Cys Asn Gly Pro
    610                 615                 620

Leu Phe Thr His Cys Thr Asp Arg Tyr Pro Leu Ser His Asn Val Asp
625                 630                 635                 640

Met Ala Tyr Ala Cys Asp Asn Ala Gly Val Leu Pro His Val Lys Asp
                645                 650                 655

Asp Leu Val Lys Cys Ala Glu Gly Thr Val Tyr Pro Ser Glu Trp Met
            660                 665                 670

Val Val Lys Tyr Met Gly Phe Phe Asn Phe Ser Asp Cys Gln Asp Leu
        675                 680                 685

Asn Val Leu Gln Lys Glu Met Trp Met His Val Arg Glu Leu Val Leu
    690                 695                 700

Ser Val Ala Leu Tyr Asn Glu Thr Phe Gly Lys Gln Leu Ser Ile Ala
705                 710                 715                 720

Cys Leu Arg Asp Glu Leu His Pro Asp Arg Asp Val Ile Leu Thr Tyr
                725                 730                 735

Asn Lys Glu Trp Pro Leu Leu Arg His Glu Gly Ser Leu Tyr Lys
            740                 745                 750

Ser Lys Asp Leu Tyr Leu Leu Tyr Arg His Leu Ser Arg Pro Asp
        755                 760                 765

Glu Ser Gly Asp Val Pro Thr Ala Pro Val Ala Lys Pro Ser Thr Leu
    770                 775                 780

Thr Ala Ala Ala Val Ser Gly Val Phe Arg Glu Pro Asp Arg Pro
785                 790                 795                 800

Trp Leu Pro Ser Pro Tyr Pro Ser Ser Ser Thr Ala Gly Val Ser Arg
                805                 810                 815

Arg Val Arg Ala Thr Arg Lys Arg Pro Arg Arg Ala Ser Ser Leu Leu
            820                 825                 830

Asp Leu Ala Arg Asp Glu His Gly Ile Gln Asp Leu Val Pro Gly Ser
        835                 840                 845

Leu Arg
    850

<210> SEQ ID NO 16
<211> LENGTH: 2553
<212> TYPE: DNA
<213> ORGANISM: Artificial
<220> FEATURE:
<223> OTHER INFORMATION: Synthetic DNA sequence of GenBank accession
      NC_001347 region 84386..86938

<400> SEQUENCE: 16
ttaacgcaga ctaccaggca ccagatcctg gattccatgt tcgtcgcggg ccaaatccag      60
cagcgatgag gcgcgtcgtg gtctcttgcg tgtcgcgcgg accctccggg aaacacccgc     120
agtcgaggag gagggatacg gacttggcag ccaaggtcgg tccggctccc tgaagacacc     180
cgagacggcc gcggcggccg tcagggtgga gggcttggcc acgggagctg ttggcacgtc     240
gccactctca tccggtctgg acagatgcct gtagaggagg agatatagat ctttggactt     300
ataaagactt ccttcgtgac gaagcagcag cggccactct ttgttatacg tgagaatcac     360
atctctgtcc gggtgcagtt cgtcgcgcag gcacgcgatc gagagttgtt cccgaaagt     420 ttcattatat agtgcgacgg agagcacgag ctcccgcacg tgcatccaca tctccttctg     480
cagcacgttt aggtcctgac agtccgaaaa attgaaaaaa cccatatact tcaccaccat     540
ccactcactg ggatacacgg taccttccgc gcatttgacc aaatcgtcct tgacgtgggg     600

```
tagtacgccc gcgttgtcgc aggcataggc catgtccaca ttgtgagaga ggggataacg    660
atcggtgcag tgggtgaaga ggggcccgtt acacaactcg tagatctgct gacccagtag    720
cgggagggat tccacaggca gactcttgtg gatcaggtta ttgaccacat acaggtgctc    780
atcgtaggtg aactgatcac ccacgtccac cacgtcttgg tcctggtggt attggctgcg    840
gtacagaaac ccattcatga gcttagagat aaagtccaga cacaagggcc ccactagatt    900
gacatcgatg agcttgctag tcagacgctc ctgcgttttg atgcaacgga tcaccttgcc    960
atagcccacc tccgagacct tctgcaggta ggcgcgtttg cgcacgttca cctcgcgagt   1020
gacgttgtgg atgcgggagc gcgcgtccac caagtcgaga gcctcgtgtt cgtcgcagtt   1080
gcgcacccgt aagccgttct cgctgccgtc gccgtcctgc ccattcaccc ctccccctac   1140
cactttcttg cctcctccac gagcccggcc gccgccaccg ttattcctct gactgtgagt   1200
actgctgttg ctgctgttgc tggccgtcat caaagtcgta cccgtccccg acatcgcctc   1260
ccgtccacgc aggtgaatag cctcgccctc ggggccgtcg cccccgtgc catctggcag    1320
cggacgtcga atctcctcga gaatatgctt gattttggtg tacatctcgt tgctttcgtg   1380
gagcttgttg aacaccgggt tgtcctcgaa agcttgaatg ctgagggatg tgatgaggtc   1440
gatgatcctg ttgggggcgg caaagaccga ccccacgaac atgcgctcct ccccgtccaa   1500
cgccttttcc ccgagcacga agatgtcctc cacgtcctcc ccgtacagat ggcgactgat   1560
gccgttcatg agcgcccggc acagctggtg atacacattt agctgctgga tggtgatgcc   1620
cacccgcttg acgataacct ccgaggtacg ggaccagtag gtaaaatccg acaaggaata   1680
tattcgttcc ggtatatccg taaacaggtt gtactccctc agcgcctcct ccgcctcctg   1740
gatgtagctg tggtaggccg atgaagaaga gaataggctt ttgagggccg aaaggactcc   1800
agccaagtgg gggatgcgcg ttgtcaggtc cagcaggtcc tgctccaccg tctggatatt   1860
cacatcggac tggcttgacg gacggtggac cgctatatgg ttgcacagca agccctgcag   1920
ccgcttgttc agcgagcggc cctgattcgg gatgatggtc agctcctcgt agcatgggc    1980
gcatgtcgtc ccttcgacgt acacttcctg acgcgccacc ggcgagatgc cgcataggcg   2040
acggaggagc tccagcaact gcgcgcagac ctccaggccg gcctccggcg ccaggatccc   2100
gtacacgtag ttcattttgc acaggaagcg ctcgatgtcg ttgagtgtgg ccagactgac   2160
gctgaaacgg acgttgtccg taaactggag ctccacggtg tgatggcgat cgcagcgatc   2220
caaacggagg acggtacggt agaaggccgc ccggtccggc tggcgcgagt aggccatcag   2280
cgcccgatcc agcaaagccg tatcctcgtg cagcgccttc agcagcatct ccaggtagag   2340
cgtcagcaac gaactctgcg tacgattctg cgccaccacc tccgggtaga tcttccggta   2400
cagatacact atagccgccg cgtttctctt gaacggcgtg gactccgcca gtaacacgtt   2460
cggatcgcag tactttagac actccagctc catggcgtat tcgttgcatt tcgaacacac   2520
tacgcatagt ttctgtaaca aattcatctc cat                                2553
```

<210> SEQ ID NO 17
<211> LENGTH: 1235
<212> TYPE: PRT
<213> ORGANISM: Human cytomegalovirus

<400> SEQUENCE: 17

Met Ser His Glu Glu Leu Thr Ala Leu Ala Pro Val Gly Pro Ala Ala
1               5                   10                  15

Phe Leu Tyr Phe Ser Arg Leu Asn Ala Glu Thr Gln Glu Ile Leu Ala
            20                  25                  30

```
Thr Leu Ser Leu Cys Asp Arg Ser Ser Val Val Ile Ala Pro Leu
        35                  40                  45

Leu Ala Gly Leu Thr Val Glu Ala Asp Phe Gly Val Ser Val Arg Thr
 50                  55                  60

Pro Val Leu Cys Tyr Asp Gly Val Leu Thr Lys Val Thr Ser Phe
 65              70                  75                  80

Cys Pro Phe Ala Leu Tyr Phe His His Thr Gln Gly Ile Val Ala Phe
                 85                  90                  95

Thr Glu Asp His Gly Asp Val His Arg Leu Cys Glu Asp Ala Arg Gln
                100                 105                 110

Lys Tyr Ala Leu Glu Ala Tyr Met Pro Glu Ala Asp Arg Val Pro Thr
                115                 120                 125

Asp Leu Ala Ala Leu Cys Ala Ala Val Gly Cys Gln Ala Ser Glu Thr
130                 135                 140

Thr Val His Val Val Gly Asn Gly Leu Lys Glu Phe Leu Phe Ala
145                 150                 155                 160

Gly Gln Leu Ile Pro Cys Val Glu Glu Ala Thr Thr Val Arg Leu His
                165                 170                 175

Gly Gly Glu Ala Val Arg Val Pro Leu Tyr Pro Pro Thr Leu Phe Asn
                180                 185                 190

Ser Leu Gln Leu Asp Ala Glu Ala Asp Glu Val Ser Leu Asp Ala Arg
                195                 200                 205

Ser Ala Phe Val Glu Ala Arg Gly Leu Tyr Val Pro Ala Val Ser Glu
210                 215                 220

Thr Leu Phe Tyr Tyr Val Tyr Thr Ser Trp Cys Gln Ser Leu Arg Phe
225                 230                 235                 240

Ser Glu Pro Arg Val Leu Ile Glu Ala Ala Leu Arg Gln Phe Val His
                245                 250                 255

Asp Ser Gln Gln Ser Val Lys Leu Ala Pro His Lys Arg Tyr Leu Gly
                260                 265                 270

Tyr Met Ser Gln Arg Leu Ser Ser Leu Glu Lys Asp His Leu Met Leu
                275                 280                 285

Ser Asp Ala Val Val Cys Glu Leu Ala Phe Ser Phe Ala Ser Val Phe
290                 295                 300

Phe Asp Ser Ala Tyr Gln Pro Ala Glu Ser Met Leu Phe Ser Glu Trp
305                 310                 315                 320

Pro Leu Val Thr Asn Ala Thr Asp His Arg Asp Leu Ile Arg Ala Leu
                325                 330                 335

Thr Glu Leu Lys Leu His Leu Ser Thr His Val Ala Ala Leu Val Phe
                340                 345                 350

Ser Ala Asn Ser Val Leu Tyr Gln His Arg Leu Val Tyr Leu Gln Ser
                355                 360                 365

Ser Ala Arg His Pro Ser Ala Gly Gly Thr Ala Ser Gln Glu Thr Leu
370                 375                 380

Leu Lys Ala Ile Gln Phe Thr Asn Gly Leu Ser Ala Ala Cys Glu Asp
385                 390                 395                 400

Val Tyr Asn Asp Ala Arg Lys Val Leu Lys Phe Gln Gly Ala Pro Leu
                405                 410                 415

Lys Asp Glu Arg Tyr Gly Pro Gln His Leu Ala Leu Val Cys Gly Thr
                420                 425                 430

Cys Pro Gln Leu Val Ser Gly Phe Val Trp Tyr Leu Asn Arg Val Ser
                435                 440                 445

Val Tyr Asn Thr Gly Leu Ser Gly Ser Ser Thr Leu Thr Asn His Leu
450                 455                 460
```

```
Val Gly Cys Ala Ala Gly Leu Cys Glu Ala Cys Gly Thr Cys Cys
465                 470                 475                 480

His Thr Cys Tyr Gln Thr Ala Phe Val Arg Val Arg Thr Arg Leu Pro
                485                 490                 495

Val Val Pro Lys Gln Pro Lys Lys Glu Pro Cys Val Ile Thr Val Gln
            500                 505                 510

Ser Arg Phe Leu Asn Asp Val Asp Ile Leu Gly Ser Phe Gly Arg Arg
        515                 520                 525

Tyr Asn Val Asp Ala Lys Asp Gly Gly Leu Asp Gly Lys Gly Asp Asp
530                 535                 540

Gly Val Pro Gly Gly Gly Ala Gly Gly Gly Gly Arg Asp Val Ser
545                 550                 555                 560

Gly Gly Pro Ser Asp Gly Leu Gly Gly Arg Gly Gly Gly Gly
                565                 570                 575

Gly Asp Ser Gly Gly Met Met Gly Arg Gly Gly Arg Met Leu Gly Ala
                580                 585                 590

Ser Val Asp Arg Thr Tyr Arg Leu Asn Arg Ile Leu Asp Tyr Cys Arg
            595                 600                 605

Lys Met Arg Leu Ile Asp Pro Val Thr Gly Glu Asp Thr Phe Ser Ala
610                 615                 620

His Gly Lys Ser Asp Phe Val Ala Val Phe Ser Ala Leu Asn Lys Phe
625                 630                 635                 640

Val Asp Asp Glu Ala Leu Gly Phe Val Ser Glu Val Arg Leu Lys Ser
                645                 650                 655

Ser Arg Asp Glu Val Ala Gly Ala Thr Gln Ala Phe Asn Leu Asp Leu
            660                 665                 670

Asn Pro Tyr Ala Val Ala Phe Gln Pro Leu Leu Ala Tyr Ala Tyr Phe
        675                 680                 685

Arg Ser Val Phe Tyr Val Ile Gln Asn Val Ala Leu Ile Thr Ala Thr
690                 695                 700

Ser Tyr Ile Val Asp Asn Pro Leu Thr Thr Asn Leu Val Ser Lys Trp
705                 710                 715                 720

Met Thr Gln His Phe Gln Ser Ile His Gly Ala Phe Ser Thr Thr Ser
                725                 730                 735

Ser Arg Lys Gly Phe Leu Phe Thr Lys Gln Ile Lys Ser Ser Lys Asn
            740                 745                 750

Ser Asp His Asp Arg Leu Leu Asp Phe Arg Leu Tyr Ala Gln Gly Thr
        755                 760                 765

Tyr Ala Val Val Pro Met Glu Ile Lys Leu Ser Arg Leu Ser Val Pro
770                 775                 780

Thr Leu Ile Met Val Arg Val Lys Asn Arg Pro Ile Tyr Arg Ala Gly
785                 790                 795                 800

Lys Gly Asn Ala Gly Ser Val Phe Phe Arg Arg Asp His Val Pro Arg
                805                 810                 815

Arg Asn Pro Ala Lys Gly Cys Leu Gly Phe Leu Leu Tyr Arg His His
            820                 825                 830

Glu Arg Leu Phe Pro Glu Cys Gly Leu Pro Cys Leu Gln Phe Trp Gln
        835                 840                 845

Lys Val Cys Ser Asn Ala Leu Pro Lys Asn Val Pro Ile Gly Asp Met
850                 855                 860

Gly Glu Phe Asn Ala Phe Val Lys Phe Leu Val Ala Val Thr Ala Asp
865                 870                 875                 880

Tyr Gln Glu His Asp Leu Leu Asp Val Ala Pro Asp Cys Val Leu Ser
```

```
                885                 890                 895
Tyr Val Glu Ser Arg Phe His Asn Lys Phe Leu Cys Tyr Tyr Gly Phe
                900                 905                 910

Lys Asp Tyr Ile Gly Ser Leu His Gly Leu Thr Thr Arg Leu Thr Thr
                915                 920                 925

Gln Asn His Ala Gln Phe Pro His Val Leu Gly Ala Ser Pro Arg Phe
                930                 935                 940

Ser Ser Pro Ala Glu Phe Ala Leu His Val Lys Gly Leu Lys Thr Ala
945                 950                 955                 960

Gly Val Pro Ala Pro Met Ala Ala Thr Val Ala Arg Glu Ser Leu Val
                965                 970                 975

Arg Ser Val Phe Glu His Arg Ser Leu Val Thr Val Pro Val Ser Val
                980                 985                 990

Glu Lys Tyr Ala Gly Ile Asn Asn  Ser Lys Glu Ile Tyr  Gln Phe Gly
                995                 1000                1005

Gln Ile  Gly Tyr Phe Ser Gly  Asn Gly Val Glu Arg  Ser Leu Asn
    1010                1015                1020

Val Ser  Ser Met Ser Gly Gln  Asp Tyr Arg Phe Met  Arg Gln Arg
    1025                1030                1035

Tyr Leu  Leu Ala Thr Arg Leu  Ala Asp Val Leu Ile  Lys Arg Ser
    1040                1045                1050

Arg Arg  Glu Asn Val Leu Phe  Asp Ala Asp Leu Ile  Lys Asn Arg
    1055                1060                1065

Val Met  Leu Ala Leu Asp Ala  Glu Asn Leu Asp Cys  Asp Pro Glu
    1070                1075                1080

Val Met  Ala Val Tyr Glu Ile  Leu Ser Val Arg Glu  Glu Ile Pro
    1085                1090                1095

Ala Ser  Asp Asp Val Leu Phe  Phe Val Asp Gly Cys  Glu Ala Leu
    1100                1105                1110

Ala Ala  Ser Leu Met Asp Lys  Phe Ala Ala Leu Gln  Glu Gln Gly
    1115                1120                1125

Val Glu  Asp Phe Ser Leu Glu  Asn Leu Arg Arg Val  Leu Asp Ala
    1130                1135                1140

Asp Ala  Gln Arg Leu Thr Asp  Ala Ala Gly Gly Glu  Val His Asp
    1145                1150                1155

Leu Ser  Ala Leu Phe Ala Pro  Ser Gly Val Gly Ala  Ala Ser Gly
    1160                1165                1170

Val Gly  Gly Gly Gly Leu Leu  Leu Gly Glu Ser Val  Ala Gly Asn
    1175                1180                1185

Ser Ile  Cys Phe Gly Val Pro  Gly Glu Thr Gly Gly  Gly Cys Phe
    1190                1195                1200

Leu Val  Asn Ala Gly Glu Asp  Glu Ala Gly Gly Val  Gly Gly Ser
    1205                1210                1215

Ser Gly  Gly Gly Gly Gly Ser  Gly Leu Leu Pro Ala  Lys Arg Ser
    1220                1225                1230

Arg Leu
    1235

<210> SEQ ID NO 18
<211> LENGTH: 3708
<212> TYPE: DNA
<213> ORGANISM: Artificial
<220> FEATURE:
<223> OTHER INFORMATION: Synthetic DNA sequence of GenBank accession
      NC_001347 region: 87505..91212
```

<400> SEQUENCE: 18

```
ttacaaccgg ctgcgtttgg ccggcaataa cccgctgccc ccgccgcccc cgctgctccc      60
gccgacgccg ccagcctcgt cttcgccggc gttcacgaga aagcagccac ctcccgtctc     120
gccgggcacg ccgaagcaaa tggagttgcc cgcgacggac tcgccgagaa gaagaccgcc     180
accccgacg ccggacgccg cgccgacgcc actgggcgcg aagagcgccg acaggtcgtg      240
cacctccccc ccggcggcgt ccgttaatcg ctgggcgtcg gcgtccagca cgcgtcgcaa     300
gttctccagc gaaaagtcct ccacgccctg ctcctgcaac gcggcaaact tgtccatcag     360
cgacgcggcc agcgcctcgc agccatccac gaagaagagc acatcgtcgg acgcggggat     420
ctcctcgcgc acgctcagaa tctcgtacac ggccatcact tcggggtcgc aatccaagtt     480
ctcggcgtcc agcgccagca tgacgcggtt ttttataaga tccgcgtcaa aaagcacgtt     540
ctcgcggcgc gagcgtttga tgagcacgtc ggccagacgc gtagccaaga ggtagcgctg     600
gcgcatgaaa cgataatctt ggccgctcat agagctcacg ttaaggctgc gttccacacc     660
gttgcccgaa aagtagccga tctgcccaaa ctgatagatc tccttgctgt tgttgatacc     720
cgcatatttt tccacgctca cgggcacggt caccaaggaa cgatgctcaa aaacgctccg     780
taccaacgat tcacgcgcca cagtggcggc catgggcgcc ggcacgcctg cggtcttcaa     840
gcccttgaca tgcaacgcaa attcggcggg cgacagaaac cgcggactag cacctaacac     900
gtgaggaaac tgcgcgtggt tctgcgtcgt taagcgcgtc gtcaacccgt gcagcgagcc     960
gatgtagtct ttgaagccat aatagcagag gaatttgtta tggaaacggc tttccacgta    1020
actcagcaca cagtctggcg ccacatccag cagatcgtgc tcctgatagt cagccgtcac    1080
agccaccaga aatttgacga aagcattgaa ctcgcccatg tcacctatgg gcacattctt    1140
gggcaacgcg ttggaacaga ccttctgcca aaactgtaag caggggagac cacattcagg    1200
aaagagtcgc tcgtgatgtc gatacagcag aaatcccaag cagcccttag ccggattacg    1260
acgcggaacg tgatcgcggc gaaaaaacac gctacccgcg ttgcccttgc ccgcgcggta    1320
gatgggtcgg tttttcaccc gcaccatgat caacgtgggt accgacagcc gcgagagctt    1380
gatctccatg ggcaccacgg cgtacgtgcc ctgcgcgtac agcctaaagt ccagcaggcg    1440
gtcgtgatcc gaattcttgg acgacttgat ctgcttggtg aagagaaagc ccttgcgcga    1500
cgacgtggtg gagaacgcgc cgtgaatgga ttgaaaatgc tgcgtcatcc atttggatac    1560
caagttggtg gtcaacggat tgtccacaat gtatgaggta gcggtaataa gcgccacgtt    1620
ctggatcacg taaagacgg atctgaaata ggcgtaggct agcagcggct ggaaggccac     1680
ggcgtaggga ttcagatcca ggttgaaggc ctgcgtggcg cccgccacct cgtcgcggct    1740
gctcttgagg cgcacctccg aaacgaaacc cagggcctcg tcgtccacaa acttgttgag    1800
cgccgaaaag acggccacaa agtcgctttt gccgtgcgcg ctaaaggtat cctcgcccgt    1860
cacggggtcg atgagccgca tcttgcggca gtaatccaag atgcgattga gccgataggt    1920
acggtccacg ctagcgccca acatgcgacc gccgcgcccc atcattcccc cggaatcccc    1980
accaccccca ccaccacgac cgccaccccag accgtcgctc gggcccccgc tcacgtctcg    2040
tccaccaccc ccgccagcac cgccgcccgg aaccccgtcg tcacctttgc cgtccaaacc    2100
cccgtccttg gcgtcgacgt tgtaacgccg accgaagctg cccaaaatat ccacgtcgtt    2160
gagaaaacgc gactgcacgg tgatcacgca gggctccttc ttgggctgct tgggcaccac    2220
gggcaagcgg gtgcgcaccc gcacgaaggc cgtctgataa cacgtgtggc aacaagtacc    2280
cccacaggcc tcgcacagcc ccgcggcgca gcccaccagg tgattcgtga gcgtcgacga    2340
```

-continued

```
acccgacaag cccgtgttgt acaccgagac acgattcaga taccagacga agcccgaaac    2400
tagctgcgga cacgtgccac acaccaacgc caaatgctgc ggcccatagc gttcgtcctt    2460
gagcggcgcg ccctgaaact tgagcacctt gcgcgcgtcg ttgtagacgt cttcgcaggc    2520
cgccgacaac ccgttggtga actgaatagc cttgagcaac gtctcctgac tggccgtacc    2580
gccggcgctg ggatgccgcg ccgacgactg gagatacacc agcctgtgct ggtagagcac    2640
cgaattagcg ctgaagacca aggcggccac gtgcgtcgag agatgcaact tgagctcggt    2700
cagcgcgcgg atcagatcgc ggtgatcggt tgcgttggtc actaaaggcc actcggaaaa    2760
gagcatagat tcggcaggtt ggtaagccga atcgaaaaat accgaggcaa aactgaaggc    2820
caactcgcaa accaccgcgt cactcagcat cagatgatcc ttttccagac tgctgagtcg    2880
ctggctcatg taccccaagt agcgcttatg tggcgccagc ttcaccgact gctgactgtc    2940
gtgcacaaac tgccgcaacg ccgcctcgat cagcacacgc ggctccgaga agcgcagcga    3000
ttgacaccat gacgtgtaca cgtagtagaa aagcgtctcg cttacggccg gcacgtagag    3060
ccctcgcgcc tccacaaaag cgctgcgcgc atccagcgag acctcgtcgg cttcggcgtc    3120
aagctgcaac gaattaaaga gcgtaggcgg gtacaacggc acgcgcaccg cctcgccgcc    3180
gtgcagtcgc accgtggtcg cctcctccac gcatggaatc agctgaccgg caaagagaaa    3240
ctccttcaag ccgttgccca ccaccacgtg cacagtcgtc tcggacgcct acagcccac     3300 cgccgcgcac aacgccgcca gatcggtagg cacgcgatcc gcctcgggca tgtaagcctc    3360
caacgcgtac ttctggcggg cgtcctcgca cagccgatgc acgtctccgt gatcctcggt    3420
aaaagccacg atgccttgcg tatgatgaaa gtagagcgca aaaggacaga aggacgtgac    3480
tttcgtgagc accccgccgt cgtaacaaag cacaggcgtg cgcacagaga cgccgaaatc    3540
cgcctccacc gtgagccccg ccaacaaagg agcgatcacc acgctcgagg aacggtcgca    3600
tagcgagaga gtggccagaa tctcctgcgt ttctgcgttc aacctgctga agtagagaaa    3660
agccgcgggc cccaccggcg ctagcgcggt tagttcctcg tggctcat                 3708
```

<210> SEQ ID NO 19
<211> LENGTH: 946
<212> TYPE: PRT
<213> ORGANISM: Human cytomegalovirus

<400> SEQUENCE: 19

```
Met Thr Leu Val Leu Phe Ala Thr Glu Tyr Asp Ser Ala His Ile Val
1               5                   10                  15

Ala Asn Val Leu Ser Gln Thr Pro Thr Asp His Cys Val Phe Pro Leu
            20                  25                  30

Leu Val Lys His Gln Val Ser Arg Arg Val Tyr Phe Cys Leu Gln Thr
        35                  40                  45

Gln Lys Cys Ser Asp Ser Arg Arg Val Ala Pro Val Phe Ala Val Asn
    50                  55                  60

Asn Glu Thr Leu Gln Leu Ser Arg Tyr Leu Ala Ala Arg Gln Pro Ile
65                  70                  75                  80

Pro Leu Ser Ala Leu Ile Ala Ser Leu Asp Glu Ala Glu Thr Gln Pro
                85                  90                  95

Leu Tyr Arg His Leu Phe Arg Thr Pro Val Leu Ser Pro Glu His Gly
            100                 105                 110

Gly Glu Val Arg Glu Phe Lys His Leu Val Tyr Phe His His Ala Ala
        115                 120                 125

Val Leu Arg His Leu Asn Gln Val Phe Leu Cys Pro Thr Ser Pro Ser
    130                 135                 140
```

-continued

```
Trp Phe Ile Ser Val Phe Gly His Thr Glu Gly Gln Val Leu Leu Thr
145                 150                 155                 160

Met Ala Tyr Tyr Leu Phe Glu Gly Gln Tyr Ser Thr Ile Ser Thr Val
                165                 170                 175

Glu Glu Tyr Val Arg Ser Phe Cys Thr Arg Asp Leu Gly Thr Ile Ile
            180                 185                 190

Pro Thr His Ala Ser Met Gly Glu Phe Ala Arg Leu Leu Leu Gly Ser
        195                 200                 205

Pro Phe Arg Gln Arg Val Ser Ala Phe Val Ala Tyr Ala Val Ala Arg
    210                 215                 220

Asn Arg Arg Asp Tyr Thr Glu Leu Glu Gln Val Asp Thr Gln Ile Asn
225                 230                 235                 240

Ala Phe Arg Glu Arg Ala Arg Leu Pro Asp Thr Val Cys Val His Tyr
                245                 250                 255

Val Tyr Leu Ala Tyr Arg Thr Ala Leu Ala Arg Ala Arg Leu Leu Glu
            260                 265                 270

Tyr Arg Arg Val Val Ala Tyr Asp Ala Asp Ala Ala Pro Glu Ala Gln
        275                 280                 285

Cys Thr Arg Glu Pro Gly Phe Leu Gly Arg Arg Leu Ser Thr Glu Leu
    290                 295                 300

Leu Asp Val Met Gln Lys Tyr Phe Ser Leu Asp Asn Phe Leu His Asp
305                 310                 315                 320

Tyr Val Glu Thr His Leu Leu Arg Leu Asp Glu Ser Pro His Ser Ala
                325                 330                 335

Thr Ser Pro His Gly Leu Gly Leu Ala Gly Tyr Gly Gly Arg Ile Asp
            340                 345                 350

Gly Thr His Leu Ala Gly Phe Phe Gly Thr Ser Thr Gln Leu Ala Arg
        355                 360                 365

Gln Leu Glu Arg Ile Asn Thr Leu Ser Glu Ser Val Phe Ser Pro Leu
    370                 375                 380

Glu Arg Ser Leu Ser Gly Leu Leu Arg Leu Cys Ala Ser Leu Arg Thr
385                 390                 395                 400

Ala Gln Thr Tyr Thr Thr Gly Thr Leu Thr Arg Tyr Ser Gln Arg Arg
                405                 410                 415

Tyr Leu Leu Pro Glu Pro Ala Leu Ala Pro Leu Leu Glu Arg Pro Leu
            420                 425                 430

Pro Val Tyr Arg Val His Leu Pro Asn Asp Gln His Val Phe Cys Ala
        435                 440                 445

Val Ala Ser Glu Thr Trp His Arg Ser Leu Phe Pro Arg Asp Leu Leu
    450                 455                 460

Arg His Val Pro Asp Ser Arg Phe Ser Asp Glu Ala Leu Thr Glu Thr
465                 470                 475                 480

Val Trp Leu His Asp Asp Val Ala Ser Thr Ser Pro Glu Thr Gln
                485                 490                 495

Phe Tyr Tyr Thr Arg His Glu Val Phe Asn Glu Arg Leu Pro Val Phe
            500                 505                 510

Asn Phe Val Ala Asp Phe Asp Leu Arg Leu Arg Asp Gly Val Ser Gly
        515                 520                 525

Leu Ala Arg His Thr Val Phe Glu Leu Cys Arg Gly Leu Arg Arg Val
    530                 535                 540

Trp Met Thr Val Trp Ala Ser Leu Phe Gly Tyr Thr His Pro Asp Arg
545                 550                 555                 560

His Pro Val Tyr Phe Phe Lys Ser Ala Cys Pro Pro Asn Ser Val Pro
```

```
                       565                 570                 575

Val Asp Ala Ala Gly Ala Pro Phe Asp Asp Asp Tyr Leu Asp Tyr
                580                 585                 590

Arg Asp Glu Arg Asp Thr Glu Glu Asp Glu Asp Gly Lys Glu Asp Lys
            595                 600                 605

Asn Asn Val Pro Asp Asn Gly Val Phe Gln Lys Thr Thr Ser Ser Val
            610                 615                 620

Asp Thr Ser Pro Pro Tyr Cys Arg Cys Lys Gly Lys Leu Gly Leu Arg
625                 630                 635                 640

Ile Ile Thr Pro Phe Pro Ala Cys Thr Val Ala Val His Pro Ser Val
                645                 650                 655

Leu Arg Ala Val Ala Gln Val Leu Asn His Ala Val Cys Leu Asp Ala
                660                 665                 670

Glu Leu His Thr Leu Leu Asp Pro Ile Ser His Pro Glu Ser Ser Leu
            675                 680                 685

Asp Thr Gly Ile Tyr His His Gly Arg Ser Val Arg Leu Pro Tyr Met
            690                 695                 700

Tyr Lys Met Asp Gln Asp Asp Gly Tyr Phe Met His Arg Arg Leu Leu
705                 710                 715                 720

Pro Leu Phe Ile Val Pro Asp Ala Tyr Arg Glu His Pro Leu Gly Phe
                725                 730                 735

Val Arg Ala Gln Leu Asp Leu Arg Asn Leu Leu His His Pro Pro
                740                 745                 750

His Asp Leu Pro Ala Leu Pro Leu Ser Pro Pro Arg Val Ile Leu
            755                 760                 765

Ser Val Arg Asp Lys Ile Cys Pro Ser Thr Glu Ala Asn Phe Ile Glu
770                 775                 780

Thr Arg Ser Leu Asn Val Thr Arg Tyr Arg Arg Gly Leu Thr Glu
785                 790                 795                 800

Val Leu Ala Tyr His Leu Tyr Gly Gly Asp Gly Ala Thr Ala Ala Ala
                805                 810                 815

Ile Ser Asp Thr Asp Leu Gln Arg Leu Val Val Thr Arg Val Trp Pro
            820                 825                 830

Pro Leu Leu Glu His Leu Thr Gln His Tyr Glu Pro His Val Ser Glu
            835                 840                 845

Gln Phe Thr Ala Pro His Val Leu Leu Phe Gln Pro His Gly Ala Cys
            850                 855                 860

Cys Val Ala Val Lys Arg Arg Asp Gly Ala Arg Thr Arg Asp Phe Arg
865                 870                 875                 880

Cys Leu Asn Tyr Thr His Arg Asn Pro Gln Glu Thr Val Gln Val Phe
                885                 890                 895

Ile Asp Leu Arg Thr Glu His Ser Tyr Ala Leu Trp Ala Ser Leu Trp
            900                 905                 910

Ser Arg Cys Phe Thr Lys Lys Cys His Ser Asn Ala Lys Asn Val His
            915                 920                 925

Ile Ser Ile Lys Ile Arg Pro Pro Asp Ala Pro Val Pro Pro Ala Thr
930                 935                 940

Ala Val
945

<210> SEQ ID NO 20
<211> LENGTH: 2841
<212> TYPE: DNA
<213> ORGANISM: Artificial
<220> FEATURE:
```

<223> OTHER INFORMATION: Synthetic DNA sequence of GenBank accession
      NC_001347 region: 101464..104304

<400> SEQUENCE: 20

| | | | | | |
|---|---|---|---|---|---|
| tcagacggcg | gtcgccggcg | gcacgggcgc | gtcgggcggt | ctgattttga tggaaatgtg | 60 |
| gacgttttg | gcgttggagt | gacacttttt | ggtgaaacag | cggctccaga ggctggccca | 120 |
| gagcgcgtag | ctgtgctcgg | tgcgcaggtc | gatgaacacc | tgcacggtct cttgcgggtt | 180 |
| gcggtgcgtg | tagttgagac | agcgaaaatc | ccgcgtgcgc | gcgccgtcgc gccgcttgac | 240 |
| ggccacgcag | caggcgccgt | ggggctgaaa | gaggaggacg | tggggcgcgg taaactgctc | 300 |
| gctgacgtgc | ggttcgtagt | gttgcgtgag | gtgctcgagc | agcggcggcc acacgcgggt | 360 |
| gacgacgagc | cgctgcaagt | ccgtgtcgga | aatcgcagcg | gcagtggcgc cgtcgccacc | 420 |
| gtacaggtga | taggcgagca | cctcggtgag | accgcggcgt | cgataacgcg tcacgttaag | 480 |
| cgagcgcgtc | tcgataaagt | tggcttcggt | cgaggggcag | attttgtcgc gtacgctgag | 540 |
| aatgacgcgt | ggcggcggcg | acaggggcaa | cgcgggcagg | tcgtgcggcg ggtggtggtg | 600 |
| aagcaggtta | cgcagatcca | gttgggcgcg | cacaaagcct | agcgggtgtt cgcggtaggc | 660 |
| gtcgggcacg | atgaacagcg | gcaacagacg | gcgatgcatg | aaatagccgt cgtcttggtc | 720 |
| cattttatac | atgtagggca | gacgtacaga | gcgtccatgg | tggtagatgc ctgtgtctag | 780 |
| gctgctctcg | ggatgcgaga | tggggtccag | cagcgtgtgc | agttcggcgt cgagacagac | 840 |
| ggcgtgattg | agcacctgcg | ccacggcgcg | taaaacgctg | gggtgtacgg cgacggtgca | 900 |
| ggcggggaac | ggcgtgatga | tgcgcagccc | cagtttgccc | ttgcagcggc agtaagggg | 960 |
| tgacgtgtca | acggaggacg | ttgttttttg | gaaaacgccg | ttatccggga cgttattttt | 1020 |
| atcctctttc | ccgtcttcgt | cttcctctgt | gtcgcgctcg | tcccggtaat cgagatagtc | 1080 |
| gtcgtcatcg | aaaggcgcgc | cggccgcgtc | cacgggcacg | ctgttgggtg ggcacgcgct | 1140 |
| tttgaagaaa | tagaccgggt | gccggtcggg | gtgcgtgtag | ccaaagaggc tcgcccatac | 1200 |
| ggtcatccag | acgcgtcgta | gtccgcgaca | tagctcaaag | acggtgtgtc gcgccagacc | 1260 |
| ggagacgccg | tcgcgcagcc | gtaaatcaaa | gtcggccaca | aaattgaaga cgggcagacg | 1320 |
| ttcgttgaag | acttcgtgtc | gcgtgtagta | gaactgtgtc | tcggggctgg tgctggccac | 1380 |
| gtcgtcgtc | tgtagccaca | cggtctcggt | cagggcctcg | tccgagaaac ggctgtcggg | 1440 |
| tacgtgacgg | agcaggtcac | gcggaaagag | gctgcgatgc | caggtttcgg aggccacggc | 1500 |
| gcagaagacg | tgctggtcat | tgggcaggtg | tacgcggtag | acgggcagcg gtcgctccag | 1560 |
| cagcggtgcc | agcgcgggct | cgggtagcag | gtagcgacgt | tgcgagtaac gcgttagcgt | 1620 |
| gccggtggtg | taagtctggg | ctgtgcgtag | cgaggcgcat | agacgtaaca agccggacag | 1680 |
| ggagcgttcc | agcggggaga | agacagactc | ggaaagcgtg | ttgatgcgtt cgagctggcg | 1740 |
| cgccagctgc | gtggaggtgc | cgaagaagcc | cgccaggtgc | gtgccgtcga tcggccgcc | 1800 |
| gtagccggcc | agccccaagc | cgtgcgggct | ggtcgccgag | tgggggatt cgtcgagacg | 1860 |
| cagtaggtgc | gtctccacgt | agtcgtgtag | aaagttgtcg | agcagagaagt attttttgcat | 1920 |
| gacgtccagc | agctcggtgg | aaagccggcg | gcccagaaaa | cccggttcgc gcgtgcactg | 1980 |
| cgcttcgggc | gccgcgtcag | cgtcgtaagc | caccacgcgc | cggtactcga gcaaccgcgc | 2040 |
| gcgtgccagc | gccgtgcggt | aggccaggta | gacgtagtgc | acgcagaccg tgtcgggcag | 2100 |
| acgcgcacgt | tcgcggaacg | cgttgatctg | cgtgtccacc | tgctctagct cggtgtagtc | 2160 |
| gcggcggttg | cgcgcgacgg | cgtacgccac | gaaagcggac | acgcgctgac ggaagggcga | 2220 |
| gcccagtagc | agacgcgcga | actcgcccat | ggaggcgtgc | gtgggatga tggtgcccag | 2280 |

```
gtcgcgcgtg cagaagctgc gcacgtactc ctccacggtg agatggtgc tgtactggcc      2340 ctcgaatagg tagtaggcca tggtcagcag cacctggccc tcggtgtgcc cgaagacgct      2400
gatgaaccac gagggcgagg tggggcagag gaagacctgg ttgagatgac gtagcacggc      2460
cgcgtggtga agtacaccca ggtgcttgaa ttcgcgcacc tcgccgccgt gttcgggcga      2520
gagcacgggc gtgcggaaaa gatgccggta gagcggttgc gtctcggcct cgtccagact      2580
ggcgatgagc gccgagaggg ggatgggctg gcgcgcggcc aggtagcgcg agagctgcag      2640
cgtttcgttg ttcacggcga agacgggcgc caccgccgc gagtccgagc acttttgcgt       2700
ctgtaggcag aagtaaacac gtcgcgagac ctggtgtttg accagcaggg ggaagacgca      2760
gtggtccgtc ggtgtctgcg agagtacgtt ggcgactata tgagcagaat catactctgt      2820
tgcgaacaga acgagcgtca t                                               2841

<210> SEQ ID NO 21
<211> LENGTH: 361
<212> TYPE: PRT
<213> ORGANISM: Human cytomegalovirus

<400> SEQUENCE: 21

Met Gln Leu Ala Gln Arg Leu Cys Glu Leu Met Cys Arg Arg Lys
1               5                   10                  15

Ala Ala Pro Val Ala Asp Tyr Val Leu Leu Gln Pro Ser Glu Asp Val
                20                  25                  30

Glu Leu Arg Glu Leu Gln Ala Phe Leu Asp Glu Asn Phe Lys Gln Leu
            35                  40                  45

Glu Ile Thr Pro Ala Asp Leu Arg Thr Phe Ser Arg Asp Thr Asp Val
        50                  55                  60

Val Asn His Leu Leu Lys Leu Leu Pro Leu Tyr Arg Gln Cys Gln Ser
65                  70                  75                  80

Lys Cys Ala Phe Leu Lys Gly Tyr Leu Ser Glu Gly Cys Leu Pro His
                85                  90                  95

Thr Arg Pro Ala Ala Glu Val Glu Cys Lys Lys Ser Gln Arg Ile Leu
            100                 105                 110

Glu Ala Leu Asp Ile Leu Ile Leu Lys Leu Val Val Gly Glu Phe Ala
        115                 120                 125

Met Ser Glu Ala Asp Ser Leu Glu Met Leu Leu Asp Lys Phe Ser Thr
130                 135                 140

Asp Gln Ala Ser Leu Val Glu Val Gln Arg Val Met Gly Leu Val Asp
145                 150                 155                 160

Met Asp Cys Glu Lys Ser Ala Tyr Met Leu Glu Ala Gly Ala Ala Ala
                165                 170                 175

Thr Val Ala Pro Leu Thr Pro Pro Ala Val Val Gln Gly Glu Ser Gly
            180                 185                 190

Val Arg Glu Asp Gly Glu Thr Val Ala Ala Val Ser Ala Phe Ala Cys
        195                 200                 205

Pro Ser Val Ser Asp Ser Leu Ile Pro Glu Glu Thr Gly Val Thr Arg
    210                 215                 220

Pro Met Met Ser Leu Ala His Ile Asn Thr Val Ser Cys Pro Thr Val
225                 230                 235                 240

Met Arg Phe Asp Gln Arg Leu Leu Glu Glu Gly Asp Glu Glu Asp Glu
                245                 250                 255

Val Thr Val Met Ser Pro Ser Pro Glu Pro Val Gln Gln Gln Pro Pro
            260                 265                 270
```

```
Val Glu Pro Val Gln Gln Pro Gln Gly Arg Gly Ser His Arg Arg
        275                 280                 285

Arg Tyr Lys Glu Ser Ala Pro Gln Glu Thr Leu Pro Thr Asn His Glu
        290                 295                 300

Arg Glu Ile Leu Asp Leu Met Arg His Ser Pro Asp Val Pro Arg Glu
305                 310                 315                 320

Ala Val Met Ser Pro Thr Met Val Thr Ile Pro Pro Gln Ile Pro
                325                 330                 335

Phe Val Gly Ser Ala Arg Glu Leu Arg Gly Val Lys Lys Lys Pro
                340                 345                 350

Thr Ala Ala Ala Leu Leu Ser Ser Ala
        355                 360

<210> SEQ ID NO 22
<211> LENGTH: 1086
<212> TYPE: DNA
<213> ORGANISM: Artificial
<220> FEATURE:
<223> OTHER INFORMATION: Synthetic DNA sequence of GenBank accession
      NC_001347 region: 104320..105405

<400> SEQUENCE: 22
atgcagctgg cccagcgcct gtgcgagctg ctgatgtgcc gtcgcaaagc cgcgcctgtg     60
gccgattacg tgctgctgca gcctagcgag gacgtggagc tgcgcgagct gcaggcgttt    120
ctggacgaga actttaagca gctggagatc accccggccg acctgcgaac cttttctcgc    180
gacacggacg tggtgaacca cctgctgaag ctgctgccgc tctataggca atgccagagc    240
aagtgcgcgt tcctcaaggg ctatctctcg gagggctgtt tgcctcacac gcggccggcg    300
gccgaggtgg agtgcaagaa tcgcagcgt atcctagagg ccctggacat tctcatcctc    360
aaactggtgg tgggcgagtt tgccatgtcc gaggccgaca gcctggagat gttgctggac    420
aagttctcca cggatcaggc ctcgctggtg gaggtgcagc gcgttatggg cctggtggac    480
atggactgcg agaaaagcgc gtacatgctc gaggccggcg cggctgcgac ggttgcgcca    540
ctgacgccac cggcggtcgt tcaggggaaa gcggcgtcc gcgaggacgg ggaaacggtt    600
gccgccgtgt cggccttttgc ctgtccctcg gtttcggact cgctgatccc cgaggaaacg    660
gggtcacgc gtcctatgat gagtttggct cacattaaca ccgtctcctg tcctaccgtt    720
atgaggttcg accagcggct gctggaagag ggcgacgagg aggatgaagt gaccgtgatg    780
tcgccgtcac ccgagcccgt gcaacagcag ccgccggtcg agcccgtgca gcagcagccc    840
cagggacgcg ggtctcaccg tcggcgctac aaggagtcgg cgccgcaaga gacgctgcct    900
acgaatcacg aacgcgagat tttggatctc atgcgacaca gccccgacgt gcctcgggag    960
gcggtgatgt caccgaccat ggtcaccata cctcctcccc agataccctt tgtgggttcc   1020
gcgcgtgaac tcagggcgt gaagaaaaag aaacccacgg cggcggcctt gctgtcctcc   1080
gcgtga                                                              1086

<210> SEQ ID NO 23
<211> LENGTH: 642
<212> TYPE: PRT
<213> ORGANISM: Human cytomegalovirus

<400> SEQUENCE: 23

Met Ser Leu Leu His Thr Phe Trp Arg Leu Pro Val Ala Val Phe Phe
1               5                   10                  15

Glu Pro His Glu Glu Asn Val Leu Arg Cys Pro Glu Arg Val Leu Arg
            20                  25                  30
```

```
Arg Leu Leu Glu Asp Ala Ala Val Thr Met Arg Gly Gly Gly Trp Arg
            35                  40                  45

Glu Asp Val Leu Met Asp Arg Val Arg Lys Arg Tyr Leu Arg Gln Glu
 50                  55                  60

Leu Arg Asp Leu Gly His Arg Val Gln Thr Tyr Cys Glu Asp Leu Glu
 65                  70                  75                  80

Gly Arg Val Ser Glu Ala Glu Ala Leu Leu Asn Gln Gln Cys Glu Leu
                85                  90                  95

Asp Glu Gly Pro Ser Pro Arg Thr Leu Leu Gln Pro Pro Cys Arg Pro
            100                 105                 110

Arg Ser Ser Ser Pro Gly Thr Gly Val Ala Gly Ala Ser Ala Val Pro
            115                 120                 125

His Gly Leu Tyr Ser Arg His Asp Ala Ile Thr Gly Pro Ala Ala Ala
            130                 135                 140

Pro Ser Asp Val Val Ala Pro Ser Asp Ala Val Ala Ala Ser Ala Ala
145                 150                 155                 160

Ala Gly Ala Ser Ser Thr Trp Leu Ala Gln Cys Ala Glu Arg Pro Leu
                165                 170                 175

Pro Gly Asn Val Pro Ser Tyr Phe Gly Ile Thr Gln Asn Asp Pro Phe
            180                 185                 190

Ile Arg Phe His Thr Asp Phe Arg Gly Glu Val Asn Thr Met Phe
            195                 200                 205

Glu Asn Ala Ser Thr Trp Thr Phe Ser Phe Gly Ile Trp Tyr Tyr Arg
            210                 215                 220

Leu Lys Arg Gly Leu Tyr Thr Gln Pro Arg Trp Lys Arg Val Tyr His
225                 230                 235                 240

Leu Ala Gln Met Asp Asn Phe Ser Ile Ser Gln Glu Leu Leu Leu Gly
                245                 250                 255

Val Val Asn Ala Leu Glu Asn Val Thr Val Tyr Pro Thr Tyr Asp Cys
            260                 265                 270

Val Leu Ser Asp Leu Glu Ala Ala Cys Leu Leu Ala Ala Tyr Gly
            275                 280                 285

His Ala Leu Trp Glu Gly Arg Asp Pro Asp Ser Val Ala Thr Val
            290                 295                 300

Leu Gly Glu Leu Pro Gln Leu Leu Pro Arg Leu Ala Asp Asp Val Ser
305                 310                 315                 320

Arg Glu Ile Ala Ala Trp Glu Gly Pro Val Ala Ala Gly Asn Asn Tyr
                325                 330                 335

Tyr Ala Tyr Arg Asp Ser Pro Asp Leu Arg Tyr Tyr Met Pro Leu Ser
            340                 345                 350

Gly Gly Arg His Tyr His Pro Gly Thr Phe Asp Arg His Val Leu Val
            355                 360                 365

Arg Leu Phe His Lys Arg Gly Val Ile Gln His Leu Pro Gly Tyr Gly
            370                 375                 380

Thr Ile Thr Glu Glu Leu Val Gln Glu Arg Leu Ser Gly Gln Val Arg
385                 390                 395                 400

Asp Asp Val Leu Ser Leu Trp Ser Arg Arg Leu Leu Val Gly Lys Leu
                405                 410                 415

Gly Arg Asp Val Pro Val Phe Val His Glu Gln Gln Tyr Leu Arg Ser
            420                 425                 430

Gly Leu Thr Cys Leu Ala Gly Leu Leu Leu Leu Trp Lys Val Thr Asn
            435                 440                 445

Ala Asp Ser Val Phe Ala Pro Arg Thr Gly Lys Phe Thr Leu Ala Asp
```

```
                    450                 455                 460
Leu Leu Gly Ser Asp Ala Val Ala Gly Gly Leu Pro Gly Gly Arg
465                 470                 475                 480

Ala Gly Gly Glu Glu Glu Gly Tyr Gly Arg His Gly Arg Val Arg
                485                 490                 495

Asn Phe Glu Phe Leu Val Arg Tyr Tyr Ile Gly Pro Trp Tyr Ala Arg
                500                 505                 510

Asp Pro Ala Val Thr Leu Ser Gln Leu Phe Pro Gly Leu Ala Leu Leu
                515                 520                 525

Ala Val Thr Glu Ser Val Arg Ser Gly Trp Asp Pro Ser Arg Arg Glu
530                 535                 540

Asp Ser Ala Gly Gly Gly Asp Gly Gly Ala Val Leu Met Gln Leu
545                 550                 555                 560

Ser Lys Ser Asn Pro Val Ala Asp Tyr Met Phe Ala Gln Ser Ser Lys
                565                 570                 575

Gln Tyr Gly Asp Leu Arg Arg Leu Glu Val His Asp Ala Leu Leu Phe
                580                 585                 590

His Tyr Glu His Gly Leu Gly Arg Leu Leu Ser Val Thr Leu Pro Arg
                595                 600                 605

His Arg Val Ser Thr Leu Gly Ser Ser Leu Phe Asn Val Asn Asp Ile
                610                 615                 620

Tyr Glu Leu Leu Tyr Phe Leu Val Leu Gly Phe Leu Pro Ser Val Ala
625                 630                 635                 640

Val Leu

<210> SEQ ID NO 24
<211> LENGTH: 1929
<212> TYPE: DNA
<213> ORGANISM: Artificial
<220> FEATURE:
<223> OTHER INFORMATION: Synthetic DNA sequence of GenBank accession
      NC_001347 region: 111838..113766

<400> SEQUENCE: 24
atgagtctgt tgcacacctt ttggcggcta cccgtcgccg tcttcttcga accgcacgag    60
gaaaacgtgc tgcgctgccc cgagcgcgtg cttcggcggt tgctggagga cgcggcggtg   120
acaatgcgcg gcgggggctg cgcgcaggac gtgctcatgg accgggtgcg caaacggtat   180
ctgcgtcagg agctcaggga tctgggtcac agggtgcaga cttactgcga ggatctcgaa   240
gggcgcgtgt ccgaggcgga ggcgctgttg aaccagcagt gcgagctcga cgaaggaccg   300
tcgccgcgga cgctgctaca accaccgtgt cgtccgcgtt cttcgtcccc agggaccggc   360
gtggcaggag cttctgccgt cccacacggt ctttatagtc ggcacgatgc catcacggga   420
cccgccgccg ccccgtctga cgtggtcgcc ccgtctgacg cggtcgccgc gtcagcggcc   480
gccggtgctt cttctacctg gctggcgcag tgcgccgagc ggccgttgcc gggaacgta    540 cctagctact ttggaatcac gcagaacgat cccttatcc gctttcacac cgattttcgc    600
ggcgaggtgg tcaacaccat gttcgagaat gcctctactt ggactttctc ctttggtatc   660
tggtactatc ggctcaagcg ggggttgtac acgcaaccac ggtggaaacg agtgtaccat   720
ctggcgcaga tggacaactt ttccatttcg caggagctgc tgctcggcgt ggtcaacgct   780
ttggaaaacg tgacggtgta ccgacgtac gactgtgtac tctccgattt ggaagccgcc   840
gcctgtctgc tggccgccta cggacatgcg ctttgggagg ccgcgatcc gccggactcc   900 gtggcgacgg tgttgggtga gctccctcag ctgttgccgc gtctggccga cgacgtgagt   960
```

```
cgtgagattg ccgcttggga aggccccgtc gccgcgggta caactatta gcgtatcgc       1020 gactcgcccg atctacgcta ctacatgccc ctaagcggtg gtcgtcacta tcacccgggc     1080
acttttgatc gtcacgtgct ggtgcggctt ttccacaaac gcggcgttat tcagcatttg     1140
ccgggctacg ggacgataac ggaggagctg gtgcaagagc gtctgtcggg ccaggtgcgc     1200
gacgacgtgc tttctctctg gagtcgacgt ctgctggtcg gcaagctggg tcgcgacgtg     1260
cccgtctttg tgcacgaaca gcaatatctg cgttcgggcc tgacctgcct ggctggcctg     1320
ctgttgttgt ggaaggtgac caacgcggat agcgtcttcg ctccgcgcac gggcaaattt     1380
acgttggccg acctgctggg ttcggatgcc gtagccggcg gcgggttgcc cggggggcgc     1440
gcgggcggcg aagaggaggg ctacggggga cggcacgggc gggtacgtaa ctttgagttt     1500
ctggtacggt actacatcgg gccgtggtac gcgcgcgacc ccgcggtcac gctgtcgcag     1560
ctctttcccg gcctggctct gttggccgtg accgagagcg tgcgcagcgg ctgggatccc     1620
tcacgtcgcg aggacagcgc cggaggtggc gacggcggcg gcgccgtgct catgcagctc     1680
agcaagagca accccgtggc cgactacatg ttcgcgcaga gctccaaaca gtacggcgat     1740
ttacgtcgct tagaggtaca cgatgccctg ctctttcact acgaaacacgg gctagggcgg     1800 ctgttgtcag tgaccctgcc gcgtcaccgt gtgtccactc tgggctcgtc cctctttaac     1860
gtcaacgata tttacgaact gttgtacttt ttagtgttgg ggtttcttcc gagcgtggcg     1920
gtgttgtaa                                                              1929
```

<210> SEQ ID NO 25
<211> LENGTH: 295
<212> TYPE: PRT
<213> ORGANISM: Human cytomegalovirus

<400> SEQUENCE: 25

```
Met Met Ala Arg Asp Glu Glu Asn Pro Ala Val Pro Arg Val Arg Thr
1               5                   10                  15

Gly Lys Phe Ser Phe Thr Cys Ala Asn His Leu Ile Leu Gln Ile Ser
                20                  25                  30

Glu Lys Met Ser Arg Gly Gln Pro Leu Ser Ser Leu Arg Leu Glu Glu
            35                  40                  45

Leu Lys Ile Val Arg Leu Ile Cys Val Leu Leu Phe His Arg Gly Leu
        50                  55                  60

Glu Thr Leu Leu Leu Arg Glu Thr Met Asn Asn Leu Gly Val Ser Asp
65                  70                  75                  80

His Ala Val Leu Ser Arg Lys Thr Pro Gln Pro Tyr Trp Pro His Leu
                85                  90                  95

Tyr Arg Glu Leu Arg Gln Ala Phe Pro Gly Leu Asp Phe Glu Ala Ala
                100                 105                 110

Val Phe Asp Glu Thr Arg Ala Ala Arg Leu Ser Gln Arg Leu Cys His
            115                 120                 125

Pro Arg Leu Ser Gly Gly Leu Leu Thr Arg Phe Val Gln Arg His Thr
        130                 135                 140

Gly Leu Pro Val Val Phe Pro Glu Asp Leu Ala Arg Asn Gly Asn Ile
145                 150                 155                 160

Leu Phe Ser Leu Gly Thr Leu Tyr Gly His Arg Leu Phe Arg Leu Ala
                165                 170                 175

Ala Phe Phe Thr Arg His Trp Gly Ala Glu Ala Tyr Glu Pro Leu Ile
                180                 185                 190

Arg Ile Ile Cys Gln Lys Met Trp Tyr Phe Tyr Leu Ile Gly Thr Gly
            195                 200                 205
```

Lys Met Arg Ile Thr Pro Asp Ala Phe Glu Ile Gln Arg Ser Arg His
    210                 215                 220

Glu Thr Gly Ile Phe Thr Phe Ile Met Glu Asp Tyr Arg Thr Phe Ala
225                 230                 235                 240

Gly Thr Leu Ser Arg His Pro His Arg Pro His Pro Gln Gln Gln Gln
                245                 250                 255

His His His Pro Gly Pro Pro His Pro Pro Leu Ser His Pro Ala Ser
            260                 265                 270

Ser Cys Leu Ser Pro Glu Ala Val Leu Ala Ala Arg Ala Leu His Met
        275                 280                 285

Pro Thr Leu Ala Asn Asp Val
    290                 295

<210> SEQ ID NO 26
<211> LENGTH: 888
<212> TYPE: DNA
<213> ORGANISM: Artificial
<220> FEATURE:
<223> OTHER INFORMATION: Synthetic DNA sequence of GenBank accession
      NC_001347 region: 115205..116092

<400> SEQUENCE: 26
tcacacgtcg ttagccagcg tcggcatatg aagggcgcgg gcggccagta cggcctctgg      60
gctgagacag gacgaggcag ggtgagaaag aggaggatgg gggggaccgg ggtggtggtg     120
ctgctgctgt tgtgggtgcg gacggtgcgg gtgccgggac agcgtgccgg cgaacgttct     180
gtaatcttcc ataataaaag taaaaatgcc cgtctcgtgt cgactccgct ggatctcgaa     240
ggcgtcgggg gtaatgcgca tcttgccggt gccgatgaga taaaagtacc acatttttg      300 acagatgatg cgaatcaagg gttcgtacgc ttcggcaccc cagtggcgcg tgaagaaggc     360
cgccagacga acaagcggt gtccgtagag cgtgcctagg gagaagagga tgttgccgtt      420
gcgcgccagg tcttcgggga aaacgaccgg caggccggtg tggcgctgca caaagcgcgt     480
cagcagtccg ccgctcaagc gcgggtgaca caggcgctgg ctgagacggg cggcgcgcgt     540
ttcatcgaac acggccgcct caaagtccag ccccgggaag gcctggcgca gttcgcggta     600
cagatgaggc cagtagggtt gcggcgtctt gcgactaagc acggcgtggt ccgagacacc     660
caggttgttc atggtttcgc gcagtagcag cgtttcgaga ccgcggtgaa agaggaggac     720
gcagatgagg cgtacgatct tgagttcttc caaacgcagc gagctcagcg gctgtccgcg     780
cgacatcttc tcgctaatct gtaatattag atgattggcg caagtaaagg agaatttgcc     840
cgtgcggacc cgcgggacgg cgggttctc ttcgtcgcgg gccatcat                   888

<210> SEQ ID NO 27
<211> LENGTH: 941
<212> TYPE: PRT
<213> ORGANISM: Human cytomegalovirus

<400> SEQUENCE: 27

Met Ala Gly Ala Ala Pro Arg Arg Leu Gly Cys Asp Ala Leu Ile Val
1               5                   10                  15

Val Gly Gly Ser Ala Met Pro Arg Arg Val Leu His Val Pro Val His
            20                  25                  30

Val Arg Ala Cys Asn Leu Thr Gln Glu Leu Ser Thr Gly Glu Asp Ala
        35                  40                  45

Arg Phe Cys Arg Pro Arg Pro Val Asn Val Glu Arg Val Arg Ala Val
    50                  55                  60

```
Phe Ala Ala Leu Tyr Arg Ala Cys Pro Ile His Val Arg Thr Glu Pro
 65                  70                  75                  80

Glu Arg Val Lys Leu Val Leu Gly Arg Leu Leu Gly Pro Val Ala
                 85                  90                  95

Val Pro Cys Phe Cys Asp Gly Val Glu Gly His Gly Glu His Leu
            100                 105                 110

Val Pro Thr Thr Gln Phe Cys Arg Gly Pro Leu Leu Tyr Val His Arg
            115                 120                 125

Arg Cys Cys Cys Gly Ser Val Thr Ala Gly Arg Ala Leu Ser Tyr His
        130                 135                 140

Val Leu Glu Asn His Val Ala Thr His Val Leu Arg Gly Leu Leu Ser
145                 150                 155                 160

Leu Thr Glu Trp Asn Arg Glu Leu Pro Ser Leu Phe Cys Asp Cys Pro
                165                 170                 175

Gly Gly Gly Gly Ala Ser Gly Thr Glu Glu Arg Tyr Ala Met Ala Cys
            180                 185                 190

Leu Pro Arg Asp Leu Ser Leu His Leu Asp Asp Tyr Pro Tyr Leu Met
        195                 200                 205

Val Glu Ile Gly Arg Val Leu Ser Val Ser Glu Val Asp Asp Tyr Val
210                 215                 220

Thr Ala Val Ser Gly Tyr Leu Gly Ala Ala Ala Pro Arg Ile Gln
225                 230                 235                 240

Val His Tyr Lys Leu Leu Phe Gly Leu Asn Val Arg Pro Gln Ala Pro
                245                 250                 255

Cys Ala Leu Asp Ala Thr Arg Asp Phe Phe Leu Leu Glu Leu Gln Lys
            260                 265                 270

Leu Trp Leu Gly Val Glu Tyr His His Glu Val Thr Ser Glu Phe Phe
        275                 280                 285

Gly Arg Val Leu Ala Gln Leu His Arg Asp Arg Ala Arg Val Met Met
        290                 295                 300

Ala Leu Arg Leu Pro Glu Gln Thr Val Cys His Leu Ser Thr Phe Val
305                 310                 315                 320

Leu Ser Arg Phe Lys Arg Gln Val Leu Tyr Phe Lys Leu Gln Val Ser
                325                 330                 335

Tyr Gly Lys Cys Arg Thr Gly His Ala Asp Arg Ser Gly Gly Gly Gly
            340                 345                 350

Asn Gly Gly Asn Gln Gly His His Asn Leu Leu Cys Tyr Arg Arg Leu
        355                 360                 365

Ser Val Thr Phe Ala Asp Thr Asp Thr Val Trp Arg Asn Leu Phe Tyr
370                 375                 380

Val Tyr Tyr Glu Leu Ala Arg Asp Leu Gly Ser His Gly Thr Glu Asp
385                 390                 395                 400

Arg Pro Val Ser Arg Gly Tyr Gly Val Ser Cys Ala Ser Arg Thr Ser
                405                 410                 415

Arg Leu Ser Pro Ser Glu Ser Thr Val Val Ser Ala Asn Gly His Ala
            420                 425                 430

Leu Ser Ser Thr Ala Leu Pro Thr Thr Ser Ala Gly His Lys Leu Ser
        435                 440                 445

Leu Pro Arg Asp Pro Ala Ala Asp Arg Val Arg Arg Tyr Val Cys Ile
450                 455                 460

Ile Ser Arg Leu Met Tyr Ala Arg Tyr Gly Glu Arg Trp Lys His
465                 470                 475                 480

Cys Gln Arg Arg Ser Glu Thr Gly Glu Glu Glu Glu Glu Thr Leu
                485                 490                 495
```

```
Glu Ser Gly Glu Thr Asp Ala Thr Pro Pro Phe Asp Phe Thr Gly Gln
            500                 505                 510

Gln Leu Arg Arg Ala Tyr Gln Glu His Arg Arg Lys His Leu Ala
            515                 520                 525

Val Gln Arg Tyr Ala Pro Cys Arg Arg Lys Leu Ile Gly Gly Met Glu
            530                 535                 540

Phe Ala Glu Val Thr Gly Val Ser Leu Asp Arg Ile Ala Val Asn Ala
545                 550                 555                 560

Phe Asn Thr Asn Arg Val Ile Asn Met Lys Ala Ala Leu Ser Ser Ile
            565                 570                 575

Ala Ala Ser Gly Leu Gly Val Arg Ala Pro Arg Leu Pro Lys Asn Met
            580                 585                 590

Thr His Ser Phe Val Met Tyr Lys His Thr Phe Lys Glu Pro Ala Cys
            595                 600                 605

Thr Val Ser Thr Phe Val Ser Asn Asp Ala Val Tyr Ile Asn Ser Leu
            610                 615                 620

Asn Val Asn Ile Arg Gly Ser Tyr Pro Glu Phe Leu Tyr Ser Leu Gly
625                 630                 635                 640

Val Tyr Arg Leu His Val Asn Ile Asp His Phe Leu Pro Ala Val
            645                 650                 655

Val Cys Asn Ser Asn Ser Ser Leu Asp Val His Gly Leu Glu Asp Gln
            660                 665                 670

Ala Val Ile Arg Ser Glu Arg Ser Lys Val Tyr Trp Thr Thr Asn Phe
            675                 680                 685

Pro Cys Met Ile Ser His Thr Asn Asn Val Asn Val Gly Trp Phe Lys
            690                 695                 700

Ala Ala Thr Ala Ile Val Pro Arg Val Ser Gly Ala Asp Leu Glu Ala
705                 710                 715                 720

Ile Leu Leu Lys Glu Leu Ser Cys Ile Lys Asn Met Arg Asp Val Cys
            725                 730                 735

Ile Asp Tyr Gly Leu His Arg Val Phe Thr Gln Leu Glu Leu Arg Asn
            740                 745                 750

Ser Tyr Gln Ile Pro Phe Leu Ala Lys Gln Leu Val Leu Phe Leu Arg
            755                 760                 765

Ala Cys Leu Leu Lys Leu His Gly Arg Glu Lys Arg Leu Gln Leu Asp
            770                 775                 780

Arg Leu Val Phe Glu Ala Ala Gln Arg Gly Leu Phe Asp Tyr Ser Lys
785                 790                 795                 800

Asn Leu Thr Ala His Thr Lys Ile Lys His Thr Cys Ala Leu Ile Gly
            805                 810                 815

Ser Arg Leu Ala Asn Asn Val Pro Lys Ile Leu Ala Arg Asn Lys Lys
            820                 825                 830

Val Lys Leu Asp His Leu Gly Arg Asn Ala Asn Val Leu Thr Val Cys
            835                 840                 845

Arg His Val Glu Ala His Lys Ile Pro Arg Thr Arg Leu Lys Val Leu
            850                 855                 860

Val Glu Val Leu Gly Ala Leu Gln Ser Ile Ser Gly Thr Pro His Thr
865                 870                 875                 880

Arg Glu Val Ile His Gln Thr Leu Phe Arg Leu Cys Ser Ala Ala Ala
            885                 890                 895

Ala Thr Ser Gly Leu Cys Ser Pro Pro Leu Cys Val Ser Ser
            900                 905                 910

Ser Ser Ser Val Pro Ser Val Pro Thr Ser Val Ser Val Asp Gly Ser
```

```
                915                 920                 925
Ser Glu Pro Thr Ser Pro Arg Ala Arg Phe Ala Ser Arg
    930                 935                 940

<210> SEQ ID NO 28
<211> LENGTH: 2826
<212> TYPE: DNA
<213> ORGANISM: Artificial
<220> FEATURE:
<223> OTHER INFORMATION: Synthetic DNA sequence of GenBank accession
      NC_001347 region: 129286..132111

<400> SEQUENCE: 28
atggccggcg ctgcgccgcg ccgcctcggc tgtgacgctc taatagtcgt tggcggctcc      60
gctatgccgc gccgggtttt acacgtcccc gtgcacgttc gcgcctgcaa cctcaccccaa    120 gagctatcga cgggcgagga cgcccgcttt tgtcgtccgc gacccgttaa cgtcgaacgg    180
gtgcgcgctg tttttgcggc tctctaccgt gcctgtccga tacacgtgag gaccgagccc    240
gagcgtgtca agctggtact gggtcgtctg ttactgggac ccgtggccgt accctgttt    300 tgcgacggtg aagtggaggg ccacggtgaa catctggtac ctacgacgca gttttgtcgc    360
gggccgctgc tctacgtgca ccgacgttgt tgttgcggat ccgtgaccgc cgggcgcgcg    420
ctgtcctacc acgttctcga aaccacgtg gccacgcatg tgctacgcgg attgctctcg    480
ctgacggaat ggaatcgaga attgccgagc ctcttttgcg actgtcctgg cggcggtggc    540
gcctcgggaa ccgaggaacg ctacgctatg gcctgcctgc cgcgcgacct cagcctgcac    600
ctggacgact atccttacct gatggtggaa atcggacgcg tactcagtgt cagcgaggta    660
gacgactacg taaccgccgt ctccggctac ctgggcgagg ccgcggcgcc gcgcatccag    720
gttcactaca agctgctctt tggactcaac gtgcgtccgc aagcgccgtg cgcgttggac    780
gctacacgcg actttttttct gctggagctg caaaagcttt ggctgggcgt tgaatatcac    840
cacgaagtca cgtcggagtt tttcggtcgc gtactggctc agctgcatcg cgaccgcgcc    900
cgcgtcatga tggcgcttcg cttgcccgag cagacggtgt gccacctgag caccttcgtt    960
ctcagtcgct tcaagcgaca ggtactgtac ttcaagctac aggtgagcta cggcaagtgc   1020
cggactggtc acgctgacag aagtggggga gggggaacg gtggaaatca gggacaccac   1080
aacctactgt gttatcgacg ccttagcgtc acatttgccg acacagacac ggtgtggaga   1140 aacctttttct acgtttatta cgaactagct cgggatctgg ggtcccatgg gacggaggac   1200
cgacccgtaa gccgcggtta cggtgtttct tgcgcttcga ggacgtcgcg actgtcaccg   1260
tcagaatcga cggtggtttc ggcgaacgga cacgcgctgt cttccaccgc gctcccgacg   1320
acgagcgcgg tcacaagct gtcactgccg cgcgacccgg ccgcagatcg cgttcgacgt   1380
tacgtatgca ttatctcgcg tctcatgtac gctcggtacg gggagagatg gcgtaaacac   1440
tgtcaacggc ggtcggagac gggagaagag gaggaggaag agacgctgga atcggggag    1500 actgacgcca cgccgccatt tgactttacg gggcagcagc tgcgccgggc ctatcaggaa   1560
caccgacgtc gtaaacatct agccgtgcag cgttacgcgc cgtgccgtcg taagctcatc   1620
ggcgggatgg agtttgccga ggtgacgggc gtgagtctag accgcatcgc cgtcaacgct   1680
ttcaacacca accgcgttat caatatgaag gctgcgctct cgtccatcgc cgcgtcgggt   1740
ctcggcgtac gcgcgccgcg gcttcccaag aacatgaccc acagttttgt gatgtacaag   1800 cacacccttta aggagcccgc ttgcaccgtc agcacttttg tttccaacga cgccgtctac   1860
atcaactcgc tcaacgtcaa tattcgcggt tcctaccccg agtttctgta ctcgctgggc   1920
```

```
gtgtaccggc tgcacgttaa tatcgatcac ttttttctgc cggccgtggt gtgcaacagc    1980
aactcctcgc tggacgtgca tgggctggag gaccaggcgg tgattcgctc ggagcgcagc    2040
aaggtgtact ggaccaccaa ctttccgtgc atgatctcgc atactaacaa cgtcaacgtg    2100
ggctggttca aagcggctac ggccattgtg ccgcgcgtct cgggcgccga cctggaagcc    2160
attctgctca agaactctc gtgcatcaag aacatgcgcg acgtgtgcat cgattacggt    2220
ctgcaccgtg ttttcacgca actagagctg cgcaattcgt accagatccc cttcctggcc    2280
aagcagttag tgctgttttct gcgtgcttgc ctgctcaagc tgcacggtcg agagaagcgg    2340
ctgcagttgg accgcctagt atttgaggcg gcacagcggg gtctctttga ctacagcaag    2400
aacctcacgg cgcacaccaa gatcaagcac acttgtgcgc tcatcggcag tcgtctagcc    2460
aacaacgtgc ccaagatcct ggcccggaac aaaaaagtca aattggatca cctgggccgg    2520
aacgccaacg tgctgacggt gtgtcggcac gtggaagccc acaagatccc tcgcacgcgc    2580
ctcaaagtgt tagtcgaggt gctgggcgcg ttgcagagta tcagcggtac gccgcacacg    2640
cgcgaagtga tccaccagac gttgtttcga ttgtgctcgg cggccgcagc cacatcgggc    2700
ctgtgttcat cccctccccc attgtgtgtg tcctcatctt cctccgtccc ttctgtccca    2760
acctccgtca gcgttgacgg cagttctgaa cccacgtcgc gcgagcgcg gtttgcatca    2820 cgatga                                                              2826
```

<210> SEQ ID NO 29
<211> LENGTH: 674
<212> TYPE: PRT
<213> ORGANISM: Human cytomegalovirus

<400> SEQUENCE: 29

```
Met Leu Arg Gly Asp Ser Ala Ala Lys Ile Gln Glu Arg Tyr Ala Glu
1               5                   10                  15

Leu Gln Lys Arg Lys Ser His Pro Thr Ser Cys Ile Ser Thr Ala Phe
            20                  25                  30

Thr Asn Val Ala Thr Leu Cys Arg Lys Arg Tyr Gln Met Met His Pro
        35                  40                  45

Glu Leu Gly Leu Ala His Ser Cys Asn Glu Ala Phe Leu Pro Leu Met
    50                  55                  60

Ala Phe Cys Gly Arg His Arg Asp Tyr Asn Ser Pro Glu Glu Ser Gln
65                  70                  75                  80

Arg Glu Leu Leu Phe His Glu Arg Leu Lys Ser Ala Leu Asp Lys Leu
                85                  90                  95

Thr Phe Arg Pro Cys Ser Glu Glu Gln Arg Ala Ser Tyr Gln Lys Leu
            100                 105                 110

Asp Ala Leu Thr Glu Leu Tyr Arg Asp Pro Gln Phe Gln Gln Ile Asn
        115                 120                 125

Asn Phe Met Thr Asp Phe Lys Lys Trp Leu Asp Gly Gly Phe Ser Thr
    130                 135                 140

Ala Val Glu Gly Asp Ala Lys Ala Ile Arg Leu Glu Pro Phe Gln Lys
145                 150                 155                 160

Asn Leu Leu Ile His Val Ile Phe Phe Ile Ala Val Thr Lys Ile Pro
                165                 170                 175

Val Leu Ala Asn Arg Val Leu Gln Tyr Leu Ile His Ala Phe Gln Ile
            180                 185                 190

Asp Phe Leu Ser Gln Thr Ser Ile Asp Ile Phe Lys Gln Lys Ala Thr
        195                 200                 205

Val Phe Leu Val Pro Arg Arg His Gly Lys Thr Trp Phe Ile Ile Pro
```

-continued

```
                210                 215                 220
Ile Ile Ser Phe Leu Leu Lys His Met Ile Gly Ile Ser Ile Gly Tyr
225                 230                 235                 240

Val Ala His Gln Lys His Val Ser Gln Phe Val Leu Lys Glu Val Glu
                245                 250                 255

Phe Arg Cys Arg His Thr Phe Ala Arg Asp Tyr Val Val Glu Asn Lys
                260                 265                 270

Asp Asn Val Ile Ser Ile Asp His Arg Gly Ala Lys Ser Thr Ala Leu
                275                 280                 285

Phe Ala Ser Cys Tyr Asn Thr Asn Ser Ile Arg Gly Gln Asn Phe His
                290                 295                 300

Leu Leu Leu Val Asp Glu Ala His Phe Ile Lys Lys Glu Ala Phe Asn
305                 310                 315                 320

Thr Ile Leu Gly Phe Leu Ala Gln Asn Thr Thr Lys Ile Ile Phe Ile
                325                 330                 335

Ser Ser Thr Asn Thr Thr Ser Asp Ser Thr Cys Phe Leu Thr Arg Leu
                340                 345                 350

Asn Asn Ala Pro Phe Asp Met Leu Asn Val Val Ser Tyr Val Cys Glu
                355                 360                 365

Glu His Leu His Ser Phe Thr Glu Lys Gly Asp Ala Thr Ala Cys Pro
370                 375                 380

Cys Tyr Arg Leu His Lys Pro Thr Phe Ile Ser Leu Asn Ser Gln Val
385                 390                 395                 400

Arg Lys Thr Ala Asn Met Phe Met Pro Gly Ala Phe Met Asp Glu Ile
                405                 410                 415

Ile Gly Gly Thr Asn Lys Ile Ser Gln Asn Thr Val Leu Ile Thr Asp
                420                 425                 430

Gln Ser Arg Glu Glu Phe Asp Ile Leu Arg Tyr Ser Thr Leu Asn Thr
                435                 440                 445

Asn Ala Tyr Asp Tyr Phe Gly Lys Thr Leu Tyr Val Tyr Leu Asp Pro
                450                 455                 460

Ala Phe Thr Thr Asn Arg Lys Ala Ser Gly Thr Gly Val Ala Ala Val
465                 470                 475                 480

Gly Ala Tyr Arg His Gln Phe Leu Ile Tyr Gly Leu Glu His Phe Phe
                485                 490                 495

Leu Arg Asp Leu Ser Glu Ser Ser Glu Val Ala Ile Ala Glu Cys Ala
                500                 505                 510

Ala His Met Ile Ile Ser Val Leu Ser Leu His Pro Tyr Leu Asp Glu
                515                 520                 525

Leu Arg Ile Ala Val Glu Gly Asn Thr Asn Gln Ala Ala Ala Val Arg
                530                 535                 540

Ile Ala Cys Leu Ile Arg Gln Ser Val Gln Ser Ser Thr Leu Ile Arg
545                 550                 555                 560

Val Leu Phe Tyr His Thr Pro Asp Gln Asn His Ile Glu Gln Pro Phe
                565                 570                 575

Tyr Leu Met Gly Arg Asp Lys Ala Leu Ala Val Glu Gln Phe Ile Ser
                580                 585                 590

Arg Phe Asn Ser Gly Tyr Ile Lys Ala Ser Gln Glu Leu Val Ser Tyr
                595                 600                 605

Thr Ile Lys Leu Ser His Asp Pro Ile Glu Tyr Leu Leu Glu Gln Ile
                610                 615                 620

Gln Asn Leu His Arg Val Thr Leu Ala Glu Gly Thr Thr Ala Arg Tyr
625                 630                 635                 640
```

```
Ser Ala Lys Arg Gln Asn Arg Ile Ser Asp Asp Leu Ile Ile Ala Val
                645                 650                 655

Ile Met Ala Thr Tyr Leu Cys Asp Asp Ile His Ala Ile Arg Phe Arg
        660                 665                 670

Val Ser

<210> SEQ ID NO 30
<211> LENGTH: 5927
<212> TYPE: DNA
<213> ORGANISM: Artificial
<220> FEATURE:
<223> OTHER INFORMATION: Synthetic DNA sequence of GenBank accession
      NC_001347 region: 133394..139320

<400> SEQUENCE: 30
```

| | | | | | |
|---|---|---|---|---|---|
| ctagctgacc | ctgaaacgga | tggcgtgtat | atcgtcacac | aggtaggtgg | ccatgatgac | 60 |
| ggcgatgata | agatcgtccg | agatacgatt | ctggcgcttg | gccgagtaac | gcgccgtcgt | 120 |
| gccttcggcc | agcgtgacgc | ggtgcaggtt | ctgaatctgc | tccagaagat | actcgatggg | 180 |
| gtcgtggctc | agcttgatgg | tgtaggagac | gagctcttgc | gaggctttga | tgtagcccga | 240 |
| gttgaaacgc | gagatgaact | gttccacggc | cagcgccttg | tcgcggccca | tgaggtagaa | 300 |
| gggctgttcg | atgtggttct | ggtcgggcgt | gtggtagaag | agcacgcgga | tgagcgtgct | 360 |
| gctctgcacg | ctctgtcgga | tgaggcaggc | gatgcgcacg | gccgccgcct | ggttggtgtt | 420 |
| gccctccacg | gcgatgcgca | gttcgtccag | gtaagggtgc | aggctcagca | ccgagatgat | 480 |
| catgtgcgcc | gcgcactcgg | cgatggctac | ctcagaactc | tcgagaggt | gcgcaaaaa | 540 |
| gaaatgctct | aggccgtaaa | tgagaaactg | gtgtcggtag | gcgcctacgg | ccgccacgcc | 600 |
| cgtgcccgag | gccttgcggt | tggtggtgaa | ggcgggtcc | agatacacgt | aaagcgtctt | 660 |
| gccgaaataa | tcgtaggcgt | tggtgttgag | cgtgctgtaa | cgcaaaatat | cgaactcttc | 720 |
| gcggctctgg | tccgtgatga | gcacggtgtt | ctgcgagatt | ttattggtac | cgccgatgat | 780 |
| ctcgtccatg | aaagcgcccg | gcataaacat | gttggccgtc | ttgcgcactt | gcgagttgag | 840 |
| gctgatgaag | gtgggcttgt | gcagtcggta | gcaaggacac | gccgtggcgt | cgcccttctc | 900 |
| cgtgaagctg | tgcaggtgct | cttcgcacac | gtaagagacc | acgttgagca | tgtcaaaggg | 960 |
| cgcattgtta | aggcgcgtca | agaaacacgt | ggagtcactg | gtagtgttgg | tggacgatat | 1020 |
| gaagatgatc | ttggtggtat | tctgggccag | gaaccccaga | atggtgttga | aggcctcttt | 1080 |
| cttgatgaag | tgcgcctcgt | ccaccagcag | caagtggaag | ttttgtcctc | ggatgctctg | 1140 |
| tgtagagagg | agacagaaaa | gggactctta | tgattacgca | cgctcgactg | gaagcctaca | 1200 |
| gagtcggggt | ggggccggac | aggtgagcca | ggtgagccgc | caggtgaggc | gggatcgccg | 1260 |
| tgtgccaacc | gggctgcgac | ctgaaaaccg | gaaccaatcc | gccgacaccg | cgccgcgtg | 1320 |
| acgcgcgccc | ataaaaacga | aagtgtcgtc | gtcgcgaccc | gccacagccg | ccatgaactc | 1380 |
| gttgctggcg | gaactcaacc | gactaggggt | cgcgcacgcc | actacggagg | atgtttttat | 1440 |
| ctttgtcgac | cgcctctttc | aacactttc | cttccttttc | caggccgagg | agtcaggccc | 1500 |
| gcgccgcttg | gaactggtcg | cgtccgtgtt | cgagcacctg | acggtggagt | gcgttaacga | 1560 |
| catcctggac | gcctgcagtc | acccggacgt | gaacgtcgcg | gagacaagca | acacctgtcg | 1620 |
| tccctgccct | tctcctgttc | cctccgcccc | caaaactgtc | agcggcgctc | agacgtcatg | 1680 |
| tgcgacgcct | cgggcgccct | tgacatgagg | cacgtccaga | acgcgtttac | cgaggagatc | 1740 |
| cagttacact | cgctctacgc | gtgcacgcgc | tgctttcgca | cgcacctgtg | tgatctgggc | 1800 |
| agcggctgcg | cgctcgtctc | cacgctcgag | ggctccgtct | gcgtcaagac | gggcctggta | 1860 |

```
tacgaggctc tctatccggt ggcgcgtagc cacctgttgg aacccatcga ggaggccgca   1920
ctggacgacg tcaacatcat cagcgccgtg ctcagcggcg tgtacagcta cctcatgacg   1980
cacgccggcc gttacgccga cgtgatccag gaggtggtcg agcgcgaccg cctcaaaaag   2040
caggtggagg acagtattta cttcaccttt aataaggttt tccgttctat gcataacgtc   2100
aaccgtattt cggtgcccgt catcagccaa cttttattc agcttatcat cggtatctac    2160
tcaaagcaga ccaagtacga cgcgtgtgtc atcaaggtta gtcgtaagaa gcgcgaggac   2220
gcgcttctga acagatgcg ttccgaatat ggaaacgcac ctgtattcgg atctggcgtt    2280
tgaagcgcgg ttcgctgacg atgagcaatt gcctctacac ttggtgctcg accaggaggt   2340
gttgagtaac gaggaggccg agacgctgcg ctacgtctac tatcgtaatg tagacagcgc   2400
tggccgatcc acgggccgcg ctccaggcgg agatgaggac gacgcaccgg cctccgacga   2460
cgccgaggac gccgtgggcg gcgatcgcgc ttttgaccgc gagcggcgga cttggcagcg   2520
ggcctgtttt cgtgtactac cgcgcccact ggagttgctc gattacctac gtcaaagcgg   2580
tctcactgtg acgttagaga aagagcagcg cgtgcgcatg ttctatgccg tcttcactac   2640
gttgggtctg cgctgccccg ataatcggct ctcaggcgcg cagacgctac acctgagact   2700
ggtctggccc gacggcagct atcgtgactg ggagttttta gcgcgtgacc tgttacgaga   2760
agaaatggaa gcgaataagc gcgaccggca gcaccagttg gccacgacca cgaatcaccg   2820
tcggcggggc ggactgcgta ataacttaga caatgggtcg gatcgccgtt tgcccgaagc   2880
ggctgtggct tctctggaga cggccgtcag tactccattt ttgaaattc gaacggagc    2940 aggaacctcc tccgcgaacg gcgacggcag attcagtaac ctggagcagc gggtagcgcg   3000
tttgttgcgc ggcgacgagg aattcatcta tcacgcgggt ccattggagc cgccttccaa   3060
gatacgcggt catgagttgg tgcagctgcg cctggacgta aatccagacc tcatgtacgc   3120
caccgatccg cacgaccgcg acgaggtcgc gcgtacggac gagtggaagg gtgccggtgt   3180
ctcgcgtctt cgcgaggtct gggatgtgca gcatcgcgtg cgcctccgtg tgctgtggta   3240
cgtcaattcc ttttggcgca gtcgcgagct gagctacgat gaccacgaag tcgaactata   3300
ccgggcgttg gacgcttatc gggcgcgcat cgccgtcgag tacgtgctga ttcgcgccgt   3360
gcgcgacgag atctacgctg tactacgacg ggacggcggc gcgttgccac agcgtttcgc   3420
ctgccacgtg tcacggaaca tgtcctggcg cgttgtttgg gaactttgcc gtcatgcctt   3480
ggcgctctgg atggattggg cggacgtgcg tagctgtatt attaaggcgc taacgcctcg   3540
tctgagccgg ggtgccgccg ctgccgctca gcgagctcgt cgccagcgcg agcgctcggc   3600
gcccaaaccg caggagctgc ttttcgggcc gcggaacgag agcggtccgc ccgccgaaca   3660
gacttggtac gctgacgtgg tgcgctgcgt tcgcgcgcaa gtggatttgg gcgtggaagt   3720
gcgcgcggcg cgttgtcctc gcaccgggct ttggatcgtc cgtgatcgcc gcggacgcct   3780
gcgacgttgg ctctcgcagc ccgaggtgtg cgtgctgtac gtcacgccag acttggactt   3840
ttactgggtg ctgccggcg gctttgccgt ctcttcgcgc gtcactcttc atggcttggc    3900
gcagcgggct ttgcgagacc gattccagaa ctttgaagca gttcttgcaa gaggaatgca   3960
tgtggaagct ggtcggcaag agccggaaac accgcgagta tcgggccgtc gcttgccgtt   4020
cgacgatctt tagtccggag gacgacagct cgtgtatctt atgccagttg ctgttgctct   4080
accgcgacgg cgaatggatc atctgttttt gctgcaacgg ccgttatcaa ggccactatg   4140
gcgtgaacca cgtacatcgg cgtcgtcgac gcatctgtca tctacctacc ttgtaccaac   4200
tgagcttcgg aggtcctttg ggtccagcca gcatcgattt cttgccaagc tttagccagg   4260
```

```
tgaccagcag tatgacgtgc gatggtatta cgcccgacgt gatttacgag gtctgcatgt    4320
tggtgcccca ggatgaagcc aagcgtatcc tggtcaaggg tcacggtgcc atggacctga    4380
cctgtcagaa ggcagtgacg ctaggcggcg ccggcgcctg gttgctgccg cgtcccgaag    4440
gctacacgct tttcttttac attctgtgtt acgacctgtt tacctcatgc ggcaatcggt    4500
gcgatatccc ttccatgacg cgcctcatgg cggcggccac ggcctgcggg caggcgggtt    4560
gcagcttttg cacggatcac gagggacacg tagatcccac tggcaattac gtgggttgca    4620
cccccgatat gggccgctgt ctttgttacg tgccctgtgg gcccatgacg cagtcgctca    4680
tccacaacga ggaacccgcg actttttttct gtgagagcga tgacgccaag tacctatgcg    4740
ccgtaggttc taagaccgcg gcgcaggtca cactgggaga cggcctggat tatcacatcg    4800
gtgttaagga ttctgagggc cgatggctgc ccgtcaagac cgatgtgtgg gacctggtca    4860
aggtagagga acctgtgtca cgtatgatag tgtgttcctg tccggtgctt aagaacctag    4920
tgcactaacg gggtctgaca gttcacgggg agaagaaaca agaaacaaca aaaaaaagga    4980
ggacatggac tcgccacggt ttgtggcaag gcgtatgtta tcatcatgga gctactcacg    5040
ttggtgttgt agcaactggc aaaaagcgcc gtgctcttgg cgccgcggtg gtcgatgctg    5100
atcacgttgt ccttgttctc gaccacgtag tcgcgcgcga aggtgtggcg gcagcggaac    5160
tcgacctctt tgagcacaaa ctgcgacacg tgcttttggt gcgccacgta gccgatgctg    5220
atgccgatca tgtgcttaag cagaaacgag ataatgggga tgatgaacca agtcttgccg    5280
tgacgtcgcg gcaccaggaa cacggtggct ttctgcttaa agatgtcgat ggaggtctgc    5340
gagaggaagt cgatctggaa ggcgtggatg aggtactgca gcacgcgatt ggccagcacg    5400
gggatcttgg tcacggctat aaaaaagatg acgtgtatca ataaattctt ttgaaacggt    5460
tcgagtcgga tggcttttgc gtcgccctcg acggcggtac tgaagccgcc gtcgagccac    5520
tttttaaagt cggtcatgaa gttgttgatc tgctgaaact gcggatcgcg gtagagctcg    5580
gtcaacgcgt ccagcttctg gtaggaggcg cgctgctcct cggagcacgg gcgaaacgtc    5640
agtttatcga gcgcgctctt gaggcgctcg tgaaacagca gctcgcgctg ctttcctcg     5700 ggcgagttgt agtcgcggtg gcggccgcag aaggccatga gcggcaggaa ggcctcgttg    5760
cacgagtggg ccagcccgag ttcggggtgc atcatctggt agcgcttgcg gcacagcgtc    5820
gccacattgg tgaaggccgt ggagatgcag gaggtggggt ggctcttgcg cttctgcagc    5880
tccgcgtagc gctcctggat cttggcggcc gagtctccgc gcaacat                  5927

<210> SEQ ID NO 31
<211> LENGTH: 201
<212> TYPE: PRT
<213> ORGANISM: Human cytomegalovirus

<400> SEQUENCE: 31

Met Cys Asp Ala Ser Gly Ala Cys Asp Met Arg His Val Gln Asn Ala
1               5                   10                  15

Phe Thr Glu Glu Ile Gln Leu His Ser Leu Tyr Ala Cys Thr Arg Cys
            20                  25                  30

Phe Arg Thr His Leu Cys Asp Leu Gly Ser Gly Cys Ala Leu Val Ser
        35                  40                  45

Thr Leu Glu Gly Ser Val Cys Val Lys Thr Gly Leu Val Tyr Glu Ala
    50                  55                  60

Leu Tyr Pro Val Ala Arg Ser His Leu Leu Glu Pro Ile Glu Glu Ala
65                  70                  75                  80
```

```
Ala Leu Asp Asp Val Asn Ile Ile Ser Ala Val Leu Ser Gly Val Tyr
            85                  90                  95

Ser Tyr Leu Met Thr His Ala Gly Arg Tyr Ala Asp Val Ile Gln Glu
            100                 105                 110

Val Val Glu Arg Asp Arg Leu Lys Lys Gln Val Glu Asp Ser Ile Tyr
            115                 120                 125

Phe Thr Phe Asn Lys Val Phe Arg Ser Met His Asn Val Asn Arg Ile
            130                 135                 140

Ser Val Pro Val Ile Ser Gln Leu Phe Ile Gln Leu Ile Ile Gly Ile
145                 150                 155                 160

Tyr Ser Lys Gln Thr Lys Tyr Asp Ala Cys Val Ile Lys Val Ser Arg
            165                 170                 175

Lys Lys Arg Glu Asp Ala Leu Leu Lys Gln Met Arg Ser Glu Tyr Gly
            180                 185                 190

Asn Ala Pro Val Phe Gly Ser Gly Val
            195                 200

<210> SEQ ID NO 32
<211> LENGTH: 606
<212> TYPE: DNA
<213> ORGANISM: Artificial
<220> FEATURE:
<223> OTHER INFORMATION: Synthetic DNA sequence of GenBank accession
      NC_001347 region: 135071..135676

<400> SEQUENCE: 32
atgtgcgacg cctcgggcgc ctgtgacatg aggcacgtcc agaacgcgtt taccgaggag      60
atccagttac actcgctcta cgcgtgcacg cgctgctttc gcacgcacct gtgtgatctg     120
ggcagcggct gcgcgctcgt ctccacgctc gagggctccg tctgcgtcaa gacgggcctg     180
gtatacgagg ctctctatcc ggtggcgcgt agccaccgtg tggaacccat cgaggaggcc     240
gcactggaca cgtcaacat catcagcgcc gtgctcagcg gcgtgtacag ctacctcatg     300
acgcacgccg gccgttacgc cgacgtgatc caggaggtgg tcgagcgcga ccgcctcaaa     360
aagcaggtgg aggacagtat ttacttcacc tttaataagg ttttccgttc tatgcataac     420
gtcaaccgta tttcggtgcc cgtcatcagc caactttttta ttcagcttat catcggtatc     480
tactcaaagc agaccaagta cgacgcgtgt gtcatcaagg ttagtcgtaa gaagcgcgag     540
gacgcgcttc tgaaacagat gcgttccgaa tatggaaacg cacctgtatt cggatctggc     600
gtttga                                                                606

<210> SEQ ID NO 33
<211> LENGTH: 531
<212> TYPE: PRT
<213> ORGANISM: Human cytomegalovirus

<400> SEQUENCE: 33

Met Met Ala Ala Ala Val Val Arg Ala Glu Val Arg Arg Gln Arg Arg
1               5                   10                  15

Glu Glu Arg Lys Lys Met Ala Ala Ala Arg Thr Thr Glu Asp Pro Pro
            20                  25                  30

Glu Asn His Val Val Ala Asp Val Ala Arg Gly Thr Gly Ala Val Thr
            35                  40                  45

Arg Ser Ser Ser Ser Ser Leu Val Ser Ser Ser Ser Ala Ser Gly
        50                  55                  60

Ser Asp Glu Ser Ser Ser Ala Ser Pro Leu Ser Phe Pro Val Ser Ser
65                  70                  75                  80
```

-continued

```
Pro Ser Thr Ala Val Arg Ser Pro Gly Ser Ala Gly Val Ser Thr Ser
                85                  90                  95
Leu Cys Ser Val Glu Arg Met Val Glu Leu Ser Ala Gln Ser Pro Ala
            100                 105                 110
Ala Asp Phe Ser Val Ser Glu Ala Trp Arg Phe Glu Glu Ala Val Asn
        115                 120                 125
Met Ala Leu Val Ala Cys Glu Ala Val Ser Pro Tyr Asp Arg Phe Arg
    130                 135                 140
Leu Ile Glu Thr Pro Asp Glu Asn Phe Leu Leu Val Thr Asn Val Ile
145                 150                 155                 160
Pro Arg Glu Ser Ala Glu Val Pro Val Leu Asp Ser Ser Ser Ser Gly
                165                 170                 175
Gly Asp Ser Gly Pro Glu Asp Lys Lys Lys Asn Val Gly Asn Lys Thr
            180                 185                 190
Ala Gly Glu Lys Asn Gly Gly Ser Arg Ala Lys Arg Arg Arg Arg
        195                 200                 205
Arg Arg Ala Pro Lys Asn Asp Ala Ala Thr Pro Ser Phe Leu Arg Arg
    210                 215                 220
His Asp Val Leu Glu Arg Phe Ala Ala Ala Lys Pro Leu Pro Ser
225                 230                 235                 240
Leu Cys Val Arg Asp Tyr Ala Leu Arg Asn Ala Asp Arg Val Thr Tyr
                245                 250                 255
Asp Gly Glu Leu Ile Tyr Gly Ser Tyr Leu Leu Tyr Arg Lys Ala His
            260                 265                 270
Val Glu Leu Ser Leu Ser Ser Asn Lys Val Gln His Val Glu Ala Val
        275                 280                 285
Leu Arg Gln Val Tyr Thr Pro Gly Leu Leu Asp His His Asn Val Cys
    290                 295                 300
Asp Val Glu Ala Leu Leu Trp Leu Leu Tyr Cys Gly Pro Arg Ser Phe
305                 310                 315                 320
Cys Ala Arg Asp Thr Cys Phe Gly Arg Glu Lys Asn Gly Cys Pro Phe
                325                 330                 335
Pro Ala Leu Leu Pro Lys Leu Phe Tyr Glu Pro Val Arg Asp Tyr Met
            340                 345                 350
Thr Tyr Met Asn Leu Ala Glu Leu Tyr Val Phe Val Trp Tyr Arg Gly
        355                 360                 365
Tyr Glu Phe Pro Ala Pro Thr Pro Gln Ala Thr Thr Ala Gly Gly Gly
    370                 375                 380
Gly Gly Ser Gly Gly Gly Gly Ala Gly Cys Ala Val Glu Thr
385                 390                 395                 400
Ser Ala Ser Ala Gly Arg Val Asp Asp Ala Gly Asp Glu Val His Leu
                405                 410                 415
Pro Leu Lys Pro Val Ser Leu Asp Arg Leu Arg Glu Val Leu Gln Ala
            420                 425                 430
Val Arg Gly Arg Phe Ser Gly Arg Glu Val Pro Ala Trp Pro Ala Ser
        435                 440                 445
Ser Arg Thr Cys Leu Leu Cys Ala Leu Tyr Ser Gln Asn Arg Leu Cys
    450                 455                 460
Leu Asp Leu Ala Arg Asp Glu Ala Arg Thr Val Ser Tyr Ser Pro Ile
465                 470                 475                 480
Val Ile Gln Asp Cys Ala Ala Ala Val Thr Asp Val Thr Leu Ser His
                485                 490                 495
Ile Leu Pro Gly Gln Ser Thr Val Ser Leu Phe Pro Val Tyr His Val
            500                 505                 510
```

Gly Lys Leu Leu Asp Ala Leu Ser Leu Asn Asp Ala Gly Leu Ile Thr
        515                 520                 525

Leu Asn Leu
    530

<210> SEQ ID NO 34
<211> LENGTH: 1596
<212> TYPE: DNA
<213> ORGANISM: Artificial
<220> FEATURE:
<223> OTHER INFORMATION: Synthetic DNA sequence of GenBank accession
      NC_001347 region: 139319..140914

<400> SEQUENCE: 34
atgatggcgg cggcggtggt gcgagcggag gttaggcggc agcggcgaga ggagaggaaa      60
aagatggcgg ccgcgaggac gacggaggat ccacccgaaa accacgttgt tgcggacgtg     120
gctcgtggga cgggcgccgt cactcgttcg tcttcgtcgt ccctagtggt gtcgtcttcc     180
tcggcgtcag gctcggacga atcttcctcc gcctctcctc tcagtttccc cgtctcctcc     240
ccctcaactg ccgtcaggtc tccggggtcc gccgggggttt caacgtccct gtgctcggtg     300
gaacggatgg tcgagctgtc ggcgcagtct ccggccgccg atttctcggt ctccgaggct     360
tggcgcttcg aggaggccgt aaatatggcg ctggtggcct gcgaggccgt gtcaccttac     420
gatcgctttc gcctaattga aacgcccgac gagaatttct tgttggtcac caacgtaatt     480
ccgcgcgaat cggccgaggt gccggtgttg gatagcagta gcagcggtgg cgatagcggg     540
ccggaggaca aaagaaaaa cgtcgggaat aaaaccgcgg gggaaaagaa cggcggtggg     600
tctcgggcca aacgccgtcg tagacgacgc gctccgaaaa acgacgccgc cacgccgtct     660
tttctacgtc gacacgacgt gctggagcgt ttcgcggccg cggctaagcc tttgccgtcg     720 cttttgtgtgc gtgattatgc gttacgcaat gctgaccgtg ttacctacga cggcgaatta     780
atctacggca gttacctgtt gtatcgcaag gctcacgtgg agctgtcact ctccagcaac     840
aaggtgcaac acgtggaagc cgtgctgcga caggtgtaca cgccgggctt gttagatcat     900
cacaacgtgt gcgacgtgga ggccctgctg tggctgctgt actgtggacc gcgcagcttt     960
tgcgcgcgtg acacttgttt cggtcgcgaa aagaacggtt gtccttcccc cgcgttgttg    1020
cccaaactct tttacgaacc cgtgcgggac tatatgacct acatgaatct ggctgagctg    1080
tacgtctttg tttggtatcg cggctacgaa ttccctgcgc cgacgccgca ggcgacgacg    1140
gcgggtggtg gtggtggtag tggtggcggc ggcggggccg cgcttgtgc ggtcgagacg    1200 agcgcgtcag caggccgggt cgatgacgcc ggcgacgagg tgcatttgcc tttaaagccc    1260
gtctcgctgg accgtctcag agaggtgttg caggcggtgc gcggccgctt ctcgggggcgc    1320 gaggtgcccg cctggccggc ctcgtcgcgc acctgtttgt tgtgcgcgct ctacagtcag    1380
aaccgtctct gtttagatct cgcgcgtgac gaggcgcgga ccgtgagtta tagccccatc    1440
gttatccaag actgcgccgc ggctgtcacc gacgtcactt tgagccacat cttgcccggc    1500
cagagcaccg tctcgctttt ccccgtctac cacgtcggca agttgctgga cgctctctcg    1560
ctgaacgacg cgggtctcat cacgttgaat ctatga                              1596

<210> SEQ ID NO 35
<211> LENGTH: 584
<212> TYPE: PRT
<213> ORGANISM: Human cytomegalovirus

<400> SEQUENCE: 35

```
Met Trp Gly Val Ser Ser Leu Asp Tyr Asp Asp Glu Glu Leu Thr
1               5                   10                  15

Arg Leu Leu Ala Val Trp Asp Asp Glu Pro Leu Ser Leu Phe Leu Met
            20                  25                  30

Asn Thr Phe Leu Leu His Gln Glu Gly Phe Arg Asn Leu Pro Phe Thr
        35                  40                  45

Val Leu Arg Leu Ser Tyr Ala Tyr Arg Ile Phe Ala Lys Met Leu Arg
50                  55                  60

Ala His Gly Thr Pro Val Ala Glu Asp Phe Met Thr Arg Val Ala Ala
65                  70                  75                  80

Leu Ala Arg Asp Glu Gly Leu Arg Asp Ile Leu Gly Gln Arg His Ala
                85                  90                  95

Ala Glu Ala Ser Arg Ala Glu Ile Ala Glu Ala Leu Glu Arg Val Ala
            100                 105                 110

Glu Arg Cys Asp Asp Arg His Gly Gly Ser Asp Asp Tyr Val Trp Leu
            115                 120                 125

Ser Arg Leu Leu Asp Leu Ala Pro Asn Tyr Arg Gln Val Glu Leu Phe
        130                 135                 140

Gln Leu Leu Glu Lys Glu Ser Arg Gly Gln Ser Arg Asn Ser Val Trp
145                 150                 155                 160

His Leu Leu Arg Met Asp Thr Val Ser Ala Thr Lys Phe Tyr Glu Ala
                165                 170                 175

Phe Val Ser Gly Cys Leu Pro Gly Ala Ala Ala Asp Gly Ser Gly
            180                 185                 190

Gly Gly Gly Ser His Tyr Thr Gly Ser Arg Ala Gly Val Ser Pro Gly
        195                 200                 205

Ile Gln Phe Gly Ile Lys His Glu Gly Leu Val Lys Thr Leu Val Glu
210                 215                 220

Cys Tyr Val Met His Gly Arg Glu Pro Val Arg Asp Gly Leu Gly Leu
225                 230                 235                 240

Leu Ile Asp Pro Thr Ser Gly Leu Leu Gly Ala Ser Met Asp Leu Cys
            245                 250                 255

Phe Gly Val Leu Lys Gln Gly Ser Gly Arg Thr Leu Leu Val Glu Pro
            260                 265                 270

Cys Ala Arg Val Tyr Glu Ile Lys Cys Arg Tyr Lys Tyr Leu Arg Lys
            275                 280                 285

Lys Glu Asp Pro Phe Val Gln Asn Val Leu Arg Arg His Asp Ala Ala
        290                 295                 300

Ala Val Ala Ser Leu Leu Gln Ser His Pro Pro Gly Val Glu Phe
305                 310                 315                 320

Arg Gly Glu Arg Glu Thr Pro Ser Ala Arg Glu Phe Leu Leu Ser His
            325                 330                 335

Asp Ala Ala Leu Phe Arg Ala Thr Leu Lys Arg Ala Arg Pro Leu Lys
            340                 345                 350

Pro Pro Glu Pro Leu Arg Glu Tyr Leu Ala Asp Leu Leu Tyr Leu Asn
        355                 360                 365

Lys Ala Glu Cys Ser Glu Val Ile Val Phe Asp Ala Lys His Leu Ser
370                 375                 380

Asp Asp Asn Ser Asp Gly Asp Ala Thr Ile Thr Ile Asn Ala Ser Leu
385                 390                 395                 400

Gly Leu Ala Ala Gly Asp Gly Ala Gly Gly Ala Asp His His Leu
            405                 410                 415

Arg Gly Ser Pro Gly Asp Ser Pro Pro Ile Pro Phe Glu Asp Glu
            420                 425                 430
```

Asn Thr Pro Glu Leu Leu Gly Arg Leu Asn Val Tyr Glu Val Ala Arg
            435                 440                 445

Phe Ser Leu Pro Ala Phe Val Asn Pro Arg His Gln Tyr Tyr Phe Gln
        450                 455                 460

Met Leu Ile Gln Gln Tyr Val Leu Ser Gln Tyr Tyr Ile Lys Lys His
465                 470                 475                 480

Pro Asp Pro Glu Arg Ile Asp Phe Arg Asp Leu Pro Thr Val Tyr Leu
                485                 490                 495

Val Ser Ala Ile Phe Arg Glu Arg Glu Ser Glu Leu Gly Cys Glu
            500                 505                 510

Leu Leu Ala Gly Gly Arg Val Phe His Cys Asp His Ile Pro Leu Leu
        515                 520                 525

Leu Ile Val Thr Pro Val Val Phe Asp Pro Gln Phe Thr Arg His Ala
        530                 535                 540

Val Ser Thr Val Leu Asp Arg Trp Ser Arg Asp Leu Ser Arg Lys Thr
545                 550                 555                 560

Asn Leu Pro Ile Trp Val Pro Asn Ser Ala Asn Glu Tyr Val Ser
                565                 570                 575

Ser Val Pro Arg Pro Val Ser Pro
            580

```
<210> SEQ ID NO 36
<211> LENGTH: 1755
<212> TYPE: DNA
<213> ORGANISM: Artificial
<220> FEATURE:
<223> OTHER INFORMATION: Synthetic DNA sequence of GenBank accession
      NC_001347 region: 143632..145386

<400> SEQUENCE: 36
atgtggggcg tctcgagttt ggactacgac gacgatgagg agctcacccg gctgctggcg      60
gtttgggacg atgagcccct cagtctgttt ctcatgaaca cctttttgct gcaccaggag     120
ggcttccgta atctgccctt tacggtgctg cgtctgtctt acgcctaccg catcttcgcc     180
aagatgctgc gggcccacgg tacgccagta gccgaggact tatgacgcg cgtggccgcg     240 ctggctcgcg acgagggtct gcgcgacatt ttgggtcagc ggcacgccgc cgaagcttcg     300
cgcgccgaga tcgccgaggc cctggagcgc gtggccgagc ggtgcgacga ccggcacggc     360
ggctcggacg actacgtgtg gctcagccgg ttgctggatt tagcgcccaa ctatcggcag     420
gtcgagctct tccagttgct ggaaaaggaa tcgcgcggac agtcgcgcaa tcggtgtgg     480 catctgttgc gtatggacac ggtctcggcc accaagttct acgaggcctt cgtcagcggc     540
tgtctgccgg cgccgcggc ggcggacggt tcgggtggcg gcggctcgca ctacacgggt     600
tcgcgcgccg gcgtctcgcc gggcatccag ttcggtatca acacgagggg cttagtcaaa     660
acgctggtgg aatgttacgt gatgcacgga cgcgagccgg tgcgcgacgg cctcggtctg     720
ctcatcgacc ccacgtcggg gctgctgggc gcttccatgg acctgtgctt cggcgtgctc     780
aagcagggta gcgttcgcac cttgctggtg gaaccgtgtg cgcgcgtcta cgagatcaag     840
tgccgctaca atatttgcg caaaaaggag gacccctttg tgcagaacgt gctgcggagg     900
cacgacgcgg cggccgtggc ctcgctgttg cagtcacacc cggtgccggg cgtggagttt     960
cgcggtgaac gcgagacccc gtcggcacgc gagtttctgc tttcgcacga cgcggcgctc    1020
ttcagggcca cgctcaagcg cgcgcgcccg ctcaagccgc cgaaccgct gcgcgagtac    1080 ctggccgatc tgctgtatct caataaggcc gagtgttcgg aagtgatcgt gtttgacgcc    1140
```

```
aagcacctga gtgacgacaa cagcgacggg gacgccacga tcactattaa cgcgagtctc    1200
ggcctagccg cgggcgacgg cgctggcggc ggcgctgatc accacctgcg ggcagcccg     1260 ggcgattcgc cgccgccgat acctttcgag gacgaaaaca cgcccgagct gctgggccgg    1320
ctcaacgtgt acgaggtagc cgcttttca ctgccggctt ttgtcaatcc cgtcaccag     1380 tattactttc agatgctcat tcagcagtac gtgctcagcc aatactatat aaagaagcat    1440
ccggacccgg agcggatcga tttcgcgac ctgcctaccg tctacctggt ctcggccatc     1500
ttccgcgagc gcgaggaaag cgaactgggc tgcgagttgc tggccggcgg tcgcgttttc    1560
cactgcgacc acatcccgct cctgctcatc gtcacgcccg tggtctttga ccctcagttt    1620
acgcgccatg ccgtctctac cgtgctagac cgttggagtc gcgacctgtc ccgcaagacg    1680
aacctaccga tatgggtgcc gaactctgca acgaatatg ttgtgagttc ggtaccacgc     1740
ccggtgagcc cctga                                                     1755

<210> SEQ ID NO 37
<211> LENGTH: 372
<212> TYPE: PRT
<213> ORGANISM: Human cytomegalovirus

<400> SEQUENCE: 37

Met Ala Pro Ser His Val Asp Lys Val Asn Thr Arg Thr Trp Ser Ala
1               5                   10                  15

Ser Ile Val Phe Met Val Leu Thr Phe Val Asn Val Ser Val His Leu
                20                  25                  30

Val Leu Ser Asn Phe Pro His Leu Gly Tyr Pro Cys Val Tyr Tyr His
            35                  40                  45

Val Val Asp Phe Glu Arg Leu Asn Met Ser Ala Tyr Asn Val Met His
        50                  55                  60

Leu His Thr Pro Met Leu Phe Leu Asp Ser Val Gln Leu Val Cys Tyr
65                  70                  75                  80

Ala Val Phe Met Gln Leu Val Phe Leu Ala Val Thr Ile Tyr Tyr Leu
                85                  90                  95

Val Cys Trp Ile Lys Ile Ser Met Arg Lys Asp Lys Gly Met Ser Leu
                100                 105                 110

Asn Gln Ser Thr Arg Asp Ile Ser Tyr Met Gly Asp Ser Leu Thr Ala
            115                 120                 125

Phe Leu Phe Ile Leu Ser Met Asp Thr Phe Gln Leu Phe Thr Leu Thr
        130                 135                 140

Met Ser Phe Arg Leu Pro Ser Met Ile Ala Phe Met Ala Ala Val His
145                 150                 155                 160

Phe Phe Cys Leu Thr Ile Phe Asn Val Ser Met Val Thr Gln Tyr Arg
                165                 170                 175

Ser Tyr Lys Arg Ser Leu Phe Phe Ser Arg Leu His Pro Lys Leu
            180                 185                 190

Lys Gly Thr Val Gln Phe Arg Thr Leu Ile Val Asn Leu Val Glu Val
        195                 200                 205

Ala Leu Gly Phe Asn Thr Thr Val Val Ala Met Ala Leu Cys Tyr Gly
    210                 215                 220

Phe Gly Asn Asn Phe Phe Val Arg Thr Gly His Met Val Leu Ala Val
225                 230                 235                 240

Phe Val Val Tyr Ala Ile Ile Ser Ile Ile Tyr Phe Leu Leu Ile Glu
                245                 250                 255

Ala Val Phe Phe Gln Tyr Val Lys Val Gln Phe Gly Tyr His Leu Gly
            260                 265                 270
```

```
Ala Phe Phe Gly Leu Cys Gly Leu Ile Tyr Pro Ile Val Gln Tyr Asp
            275                 280                 285

Thr Phe Leu Ser Asn Glu Tyr Arg Thr Gly Ile Ser Trp Ser Phe Gly
        290                 295                 300

Met Leu Phe Phe Ile Trp Ala Met Phe Thr Thr Cys Arg Ala Val Arg
305                 310                 315                 320

Tyr Phe Arg Gly Arg Gly Ser Gly Ser Val Lys Tyr Gln Ala Leu Ala
                325                 330                 335

Thr Ala Ser Gly Glu Glu Val Ala Val Leu Ser His His Asp Ser Leu
            340                 345                 350

Glu Ser Arg Arg Leu Arg Glu Glu Asp Asp Asp Asp Glu Asp
            355                 360                 365

Phe Glu Asp Ala
        370

<210> SEQ ID NO 38
<211> LENGTH: 1119
<212> TYPE: DNA
<213> ORGANISM: Artificial
<220> FEATURE:
<223> OTHER INFORMATION: Synthetic DNA sequence of GenBank accession
      NC_001347 region: 146157..147275

<400> SEQUENCE: 38
ttaagcgtcc tcgaagtctt catcatcgtc gtcgtcctct tcttcgcgga ggcgacggct      60
ttccaagctg tcgtggtgac tgagcacagc gacttcttcg ccggaggctg tggccagcgc    120
ctggtacttg acactgccgc taccgcgtcc gcgaaagtag cggacggcgc gacacgtcgt    180
aaacatggcc catatgaaaa agagcatgcc gaacgaccag ctgatgccgg tgcggtattc    240
gttgctgagg aaggtatcgt actgcacgat ggggtagatg aggccgcaga gtccaaagaa    300
ggcgcccagg tggtagccga attgcacctt gacgtattga aaaagacgg cctcgatcag    360 taaaaagtag atgatggaga tgatagcgta gaccacgaag acggctaaca ccatgtggcc    420
tgtacgcacg aaaaagttgt ttccgaagcc gtagcacagg gccatggcta ccacggtggt    480
gttgaaacca agcgctacct ctaccaggtt gacgatgagc gtgcggaact gcaccgtacc    540
tttgagcttg gggtgcagac gcgagaagaa aaagagtgag cgtttgtagc tgcggtactg    600
cgtgaccatg ctcacgttga aaatggtcag gcagaaaaag tgcacggcgg ccatgaaggc    660
gatcatgctg ggcagccgaa atgacatggt cagtgtgaat agttggaacg tgtccatgct    720
gagaatgaag aggaaggctg tgaggctgtc gcccatgtac gaaatgtcgc gtgtcgactg    780
gtttaggctc atgcctttgt ccttgcgcat gctgatcttg atccagcata ccaggtagta    840
gatggtcacg gctaaaaaga cgagctgcat gaacacggcg tagcacacca actgcaccga    900
gtctaagaaa agcataggcg tgtgcaggtg cattacgttg taggccgaca tgttgagcct    960
ttcaaagtcc acgacgtgat agtagacgca ggggtagccc aggtgcggaa aattgctcag   1020
cactagatgc acgctgacgt tgacaaaagt cagcaccatg aaaacgatag aagcgctcca   1080
tgtccgtgta ttcaccttat ccacgtgcga ggggccat                           1119

<210> SEQ ID NO 39
<211> LENGTH: 873
<212> TYPE: PRT
<213> ORGANISM: Human cytomegalovirus

<400> SEQUENCE: 39

Met Thr Ala Gln Pro Pro Leu His His Arg His His Pro Tyr Thr Leu
```

-continued

```
1               5                   10                  15
Phe Gly Thr Ser Cys His Leu Ser Trp Tyr Gly Leu Leu Glu Ala Ser
                20                  25                  30

Val Pro Ile Val Gln Cys Leu Phe Leu Asp Leu Gly Gly Arg Ala
                35                  40                  45

Glu Pro Arg Leu His Thr Phe Val Arg Gly Asp Arg Leu Pro Pro
    50                  55                  60

Ala Glu Val Arg Ala Val His Arg Ala Ser Tyr Ala Ala Leu Ala Ser
65                  70                  75                  80

Ala Val Thr Thr Asp Ala Asp Glu Arg Arg Gly Leu Glu Gln Arg
                85                  90                  95

Ser Ala Val Leu Ala Arg Val Leu Leu Glu Gly Ser Ala Leu Ile Arg
                100                 105                 110

Val Leu Ala Arg Thr Phe Thr Pro Val Gln Ile Gln Thr Asp Ala Ser
                115                 120                 125

Gly Val Glu Ile Leu Glu Ala Ala Pro Ala Leu Gly Val Glu Thr Ala
                130                 135                 140

Ala Leu Ser Asn Ala Leu Ser Leu Phe His Val Ala Lys Leu Val Val
145                 150                 155                 160

Ile Gly Ser Tyr Pro Glu Val His Glu Pro Arg Val Val Thr His Thr
                165                 170                 175

Ala Glu Arg Val Ser Glu Glu Tyr Gly Thr His Ala His Lys Lys Leu
                180                 185                 190

Arg Arg Gly Tyr Tyr Ala Tyr Asp Leu Ala Met Ser Phe Arg Val Gly
                195                 200                 205

Thr His Lys Tyr Val Leu Glu Arg Asp Asp Glu Ala Val Leu Ala Arg
    210                 215                 220

Leu Phe Glu Val Arg Glu Val Cys Phe Leu Arg Thr Cys Leu Arg Leu
225                 230                 235                 240

Val Thr Pro Val Gly Phe Val Ala Val Ala Val Thr Asp Glu Gln Cys
                245                 250                 255

Cys Leu Leu Leu Gln Ser Ala Trp Thr His Leu Tyr Asp Val Leu Phe
                260                 265                 270

Arg Gly Phe Ala Gly Gln Pro Pro Leu Arg Asp Tyr Leu Gly Pro Asp
                275                 280                 285

Leu Phe Glu Thr Gly Ala Ala Arg Ser Phe Phe Pro Gly Phe Pro
    290                 295                 300

Pro Val Pro Val Tyr Ala Val His Gly Leu His Thr Leu Met Arg Glu
305                 310                 315                 320

Thr Ala Leu Asp Ala Ala Ala Glu Val Leu Ser Trp Cys Gly Leu Pro
                325                 330                 335

Asp Ile Val Gly Ser Ala Gly Lys Leu Glu Val Glu Pro Cys Ala Leu
                340                 345                 350

Ser Leu Gly Val Pro Glu Asp Glu Trp Gln Val Phe Thr Glu Ala
    355                 360                 365

Gly Gly Gly Ala Val Arg Leu Asn Ala Thr Ala Phe Arg Glu Arg Pro
    370                 375                 380

Ala Gly Gly Asp Arg Arg Trp Leu Leu Pro Pro Leu Pro Arg Asp Asp
385                 390                 395                 400

Gly Asp Gly Glu Asn Asn Val Val Glu Val Ser Ser Thr Gly Gly
                405                 410                 415

Ala His Pro Pro Ser Asp Asp Ala Thr Phe Thr Val His Val Arg Asp
                420                 425                 430
```

```
Ala Thr Leu His Arg Val Leu Ile Val Asp Leu Val Glu Arg Val Leu
        435                 440                 445

Ala Lys Cys Val Arg Ala Arg Asp Phe Asn Pro Tyr Val Arg Tyr Ser
450                 455                 460

His Arg Leu His Thr Tyr Ala Val Cys Glu Lys Phe Ile Glu Asn Leu
465                 470                 475                 480

Arg Phe Arg Ser Arg Ala Phe Trp Gln Ile Gln Ser Leu Leu Gly
                485                 490                 495

Tyr Ile Ser Glu His Val Thr Ser Ala Cys Ser Ala Gly Leu Leu
                500                 505                 510

Trp Val Leu Ser Arg Gly His Arg Glu Phe Tyr Val Tyr Asp Gly Tyr
            515                 520                 525

Ser Gly His Gly Pro Val Ser Ala Glu Val Cys Val Arg Thr Val Val
530                 535                 540

Asp Cys Tyr Trp Arg Lys Leu Phe Gly Gly Asp Pro Gly Pro Thr
545                 550                 555                 560

Cys Arg Val Gln Glu Ser Ala Pro Gly Val Leu Val Trp Gly Asp
                565                 570                 575

Glu Arg Leu Val Gly Pro Phe Asn Phe Phe Tyr Gly Asn Gly Gly Ala
                580                 585                 590

Gly Gly Ser Pro Leu His Gly Val Gly Gly Phe Ala Ala Gly His
            595                 600                 605

Cys Gly Gly Ala Cys Cys Ala Gly Cys Val Val Thr His Arg His Ser
610                 615                 620

Ser Gly Gly Gly Gly Ser Gly Val Gly Asp Ala Asp His Ala Ser Gly
625                 630                 635                 640

Gly Gly Leu Asp Ala Ala Ala Gly Ser Gly His Asn Gly Gly Ser Asp
                645                 650                 655

Arg Val Ser Pro Ser Thr Pro Pro Ala Ala Leu Gly Gly Cys Cys Cys
                660                 665                 670

Ala Ala Gly Gly Asp Trp Leu Ser Ala Val Gly His Val Leu Gly Arg
            675                 680                 685

Leu Pro Ala Leu Leu Arg Glu Arg Val Ser Val Ser Glu Leu Glu Ala
        690                 695                 700

Val Tyr Arg Glu Ile Leu Phe Arg Phe Val Ala Arg Arg Asn Asp Val
705                 710                 715                 720

Asp Phe Trp Leu Leu Arg Phe Gln Pro Gly Glu Asn Glu Val Arg Pro
                725                 730                 735

His Ala Gly Val Ile Asp Cys Ala Pro Phe His Gly Val Trp Ala Glu
            740                 745                 750

Gln Gly Gln Ile Ile Val Gln Ser Arg Asp Thr Ala Leu Ala Ala Asp
        755                 760                 765

Ile Gly Tyr Gly Val Tyr Val Asp Lys Ala Phe Ala Met Leu Thr Ala
    770                 775                 780

Cys Val Glu Val Trp Ala Arg Glu Leu Leu Ser Ser Thr Ala Ser
785                 790                 795                 800

Thr Thr Ala Cys Ser Ser Ser Val Leu Ser Ser Ala Leu Pro Ser
                805                 810                 815

Val Thr Ser Ser Ser Gly Thr Ala Thr Val Ser Pro Pro Ser Cys
                820                 825                 830

Ser Ser Ser Ala Thr Trp Leu Glu Glu Arg Asp Glu Trp Val Arg
        835                 840                 845

Ser Leu Ala Val Asp Ala Gln His Ala Ala Lys Arg Val Ala Ser Glu
        850                 855                 860
```

Gly Leu Arg Phe Phe Arg Leu Asn Ala
865                 870

<210> SEQ ID NO 40
<211> LENGTH: 2622
<212> TYPE: DNA
<213> ORGANISM: Artificial
<220> FEATURE:
<223> OTHER INFORMATION: Synthetic DNA sequence of GenBank accession
      NC_001347 region: 147453..150074

<400> SEQUENCE: 40

| | | | | | |
|---|---|---|---|---|---|
| atgaccgctc | agccgccgct | gcaccaccgc | caccacccgt | acaccctgtt | cgggaccagc | 60 |
| tgtcatctca | gctggtacgg | ccttctagag | gcctcggtgc | ctatcgtaca | atgtctgttt | 120 |
| ttggatctgg | gtggcggccg | tgccgagccg | cggcttcaca | cgttcgtggt | gcgcggtgac | 180 |
| cgtctaccgc | cggctgaggt | gcgtgctgtg | catcgcgcca | gctacgctgc | gctggcctcg | 240 |
| gccgtgacta | cggacgccga | tgagcgtcgg | cgcggcctag | agcagcgtag | cgccgtgttg | 300 |
| gcgcgcgtgt | tgctagaagg | cagcgcgtta | atccgcgtgt | tggcgcgcac | cttcacgccg | 360 |
| gtgcagattc | agacggacgc | tagtggcgtg | gagattttgg | aggccgcacc | ggcactgggc | 420 |
| gtggaaaccg | cagcgctgtc | gaacgcgctt | agtcttttcc | acgtagccaa | gctagtggtc | 480 |
| atcggctcgt | atcccgaagt | gcacgagccg | cgtgtggtca | cgcataccgc | ggaacgcgtc | 540 |
| tccgaagagt | atggcaccca | cgcgcacaaa | aaattgcgtc | gcggttacta | cgcctacgat | 600 |
| ttggccatgt | cgtttcgcgt | cggcactcac | aagtatgtgc | tggagcgcga | cgacgaggcc | 660 |
| gtcctggcac | gcctctttga | ggtgcgcgag | gtgtgttttt | tgcgcacctg | tctgcgtctg | 720 |
| gtcacgcctg | tcggtttcgt | ggccgtggca | gtgaccgacg | agcagtgttg | tttattgctg | 780 |
| cagtcggcct | ggactcacct | ttacgacgtg | cttttccgtg | gtttcgctgg | gcagccgccg | 840 |
| ctacgcgact | acctggggcc | ggacctcttt | gagacgggcg | ccgcccgttc | tttctttttt | 900 |
| cccggtttcc | cgcccgtgcc | cgtctacgcg | gtccacggtc | tgcacacgtt | aatgcgcgag | 960 |
| acggcgttgg | acgcggcggc | tgaggtgctc | tcgtggtgcg | gcctgcccga | catcgtgggc | 1020 |
| tcggccggca | agctggaggt | ggaaccctgc | gcgctctcgc | tcggcgtgcc | cgaggatgag | 1080 |
| tggcaggtct | tcggtaccga | ggccggcggc | ggcgccgtgc | gtctcaatgc | cacggctttt | 1140 |
| cgcgagcgac | cggccggcgg | cgatcgtcgc | tggctgttgc | cgccgctgcc | acgtgacgac | 1200 |
| ggcgacggtg | aaaacaacgt | cgtggaagtc | agcagcagca | ccggcggtgc | gcacccgccg | 1260 |
| agcgacgacg | ccactttcac | cgtgcacgtt | cgcgacgcca | cgctacatcg | agtgctcatc | 1320 |
| gtggatttgg | tcgagcgcgt | gctggccaag | tgtgtacgcg | cgcgcgactt | caatccctac | 1380 |
| gtgcgttata | gtcatcgact | ccacacttat | gcggtttgtg | aaaagtttat | tgagaatctg | 1440 |
| cgttttcgct | cgcgacgcgc | tttctggcag | atccagagtc | tgctgggcta | catctccgag | 1500 |
| cacgttacgt | cagcctgcgc | ttcggccggc | cttttgtggg | ttctgtcgcg | cggccaccgc | 1560 |
| gagtttatg | tctacgacgg | ctattcgggt | cacggacccg | tctcggccga | agtgtgcgtg | 1620 |
| cggactgtgg | tcgactgtta | ttggcgcaaa | cttttggcg | cgacgatcc | gggtcccacc | 1680 |
| tgtcgtgttc | aagagagcgc | gcccggcgtg | ctgttggtct | ggggcgacga | gcggttggtg | 1740 |
| ggtcccttca | acttcttcta | cggcaacggc | ggcgccggtg | gtagtccgct | ccacggggtg | 1800 |
| gtgggtggtt | tcgcgcgggg | acattgcggt | ggcgcttgtt | gcgcgggctg | cgtcgtcact | 1860 |
| caccgccatt | ctagcggcgg | cggtggtagt | ggcgtgggcg | acgcggacca | cgcgagtggc | 1920 |
| ggcggtctag | atgccgctgc | cgggagtggt | cataacggcg | gtagtgatcg | ggtttctccc | 1980 |

```
tccacgccgc cgcggcgtt aggtggctgt tgctgcgcag ccggtggcga ctggctctcg    2040
gccgtgggtc atgtcctggg ccggctgccg gcgctgttac gggagcgcgt gagcgtgtcc    2100
gagctggaag ccgtgtaccg cgagatcctc tttcgtttcg tggctcgccg caacgacgtg    2160
gacttttggt tactgcgctt ccagcccggt gaaaacgaag taaggccgca cgctggggtg    2220
attgactgcg cgcccttcca cggcgtgtgg gccgagcagg gccagatcat cgtacagtca    2280
cgcgatacgg cgttggcggc cgatatcggc tacggcgtct atgtggacaa ggcctttgcc    2340
atgctcacgg cttgcgtgga ggtctgggcg cgagagttat tgtcgtcctc caccgcttcc    2400
accaccgctt gttcttcttc ttccgttctc tcctccgcct gccgtccgt cacttcgtcc    2460 tcttcgggca cggcgacggt gtctcctccg tcttgttctt cttcgtcggc gacttggctc    2520
gaggagcgcg acgagtgggt gcgctcgctg gcggttgacg cgcaacacgc tgctaagcgg    2580
gtggcttccg agggcctgcg gttttccgg ctcaacgctt aa                         2622
```

<210> SEQ ID NO 41
<211> LENGTH: 697
<212> TYPE: PRT
<213> ORGANISM: Human cytomegalovirus

<400> SEQUENCE: 41

```
Met Glu Arg Asn His Trp Asn Glu Lys Ser Ser Gly Ala Lys Arg Ser
  1               5                  10                  15

Arg Glu Arg Asp Leu Thr Leu Ser Thr Ile Arg Ser Ile Leu Ala Ala
             20                  25                  30

Asp Glu Arg Leu Arg Ile Lys Ala Ser Ser Tyr Leu Gly Val Gly Arg
         35                  40                  45

Gly Val Asp Asp Glu Ala Val Ile Asp Ile Phe Pro Thr Gly Gln Thr
     50                  55                  60

Met Ser Phe Leu Arg Leu Leu His Gly Phe Leu Gly Thr Cys Arg Gly
 65                  70                  75                  80

Gln Ser Met His Gln Val Leu Arg Asp Pro Cys Val Leu Arg Lys Gln
                 85                  90                  95

Leu Leu Tyr Gly Val Cys Lys Thr Leu Phe Asp Thr Ile Thr Val Arg
            100                 105                 110

Arg Val Ala Glu Glu Trp Lys Leu His Ala Ala Leu Phe Pro Tyr Arg
        115                 120                 125

Ala Leu Asp Glu Glu Asp Leu Glu Gln Tyr Leu Leu Val Trp Ser Ala
    130                 135                 140

Ser Leu Arg Gln Ser Val Gln Thr Gly Val Leu Gly Gly Leu Arg Asp
145                 150                 155                 160

Ile Leu Tyr Gln Tyr Ala Asp Asn Asp Asp Tyr Gly Leu Tyr Val Asp
                165                 170                 175

Trp Cys Val Thr Val Gly Leu Val Pro Leu Leu Asp Val Lys Thr Lys
            180                 185                 190

Pro Ser Glu Ala Ala Glu Arg Ala Gln Phe Val Arg Ala Ala Val Gln
        195                 200                 205

Arg Ala Thr Glu Thr His Pro Leu Ala Gln Asp Leu Leu Gln Ala Asn
    210                 215                 220

Leu Ala Leu Leu Leu Gln Val Ala Glu Arg Leu Gly Ala Val Arg Val
225                 230                 235                 240

Ala Asn Ala Pro Glu Val Arg Val Phe Lys Lys Val Arg Ser Glu Arg
                245                 250                 255

Leu Glu Ala Gln Leu Arg Gly Lys His Ile Arg Leu Tyr Val Ala Ala
```

```
                260             265             270
Glu Pro Leu Ala Tyr Glu Arg Asp Lys Leu Leu Phe Thr Thr Pro Val
            275             280             285

Ala His Leu His Glu Glu Ile Leu Arg Tyr Asp Gly Leu Cys Arg His
            290             295             300

Gln Lys Ile Cys Gln Leu Leu Asn Thr Phe Pro Val Lys Val Val Thr
305             310             315             320

Ala Ser Arg His Glu Leu Asn Cys Lys Lys Leu Val Glu Met Met Glu
            325             330             335

Gln His Asp Arg Gly Ser Asp Ala Lys Lys Ser Ile Met Lys Phe Leu
            340             345             350

Leu Asn Val Ser Asp Ser Lys Ser Arg Ile Gly Ile Glu Asp Ser Val
            355             360             365

Glu Ser Phe Leu Gln Asp Leu Thr Pro Ser Leu Val Asp Gln Asn Arg
            370             375             380

Leu Leu Pro Ala Arg Gly Pro Gly Gly Pro Gly Val Val Gly Pro Gly
385             390             395             400

Gly Ala Val Val Gly Gly Pro Ala Gly His Val Gly Leu Leu Pro Pro
            405             410             415

Pro Pro Gly Pro Ala Ala Pro Glu Arg Asp Ile Arg Asp Leu Phe Lys
            420             425             430

Lys Gln Val Ile Lys Cys Leu Glu Gln Ile Gln Ser Gln Val Asp
            435             440             445

Glu Ile Gln Asp Leu Arg Thr Leu Asn Gln Thr Trp Glu Asn Arg Val
            450             455             460

Arg Glu Leu Arg Asp Leu Leu Thr Arg Tyr Ala Ser Arg Arg Glu Asp
465             470             475             480

Ser Met Ser Leu Gly Ala Arg Asp Ala Glu Leu Tyr His Leu Pro Val
            485             490             495

Leu Glu Ala Val Arg Lys Ala Arg Asp Ala Ala Pro Phe Arg Pro Leu
            500             505             510

Ala Val Glu Asp Asn Arg Leu Val Ala Asn Ser Phe Phe Ser Gln Phe
            515             520             525

Val Pro Gly Thr Glu Ser Leu Glu Arg Phe Leu Thr Gln Leu Trp Glu
            530             535             540

Asn Glu Tyr Phe Arg Thr Phe Arg Leu Arg Arg Leu Val Thr His Gln
545             550             555             560

Gly Ala Glu Glu Ala Ile Val Tyr Ser Asn Tyr Thr Val Glu Arg Val
            565             570             575

Thr Leu Pro Tyr Leu Cys His Ile Leu Ala Leu Gly Thr Leu Asp Pro
            580             585             590

Val Pro Glu Ala Tyr Leu Gln Leu Ser Phe Gly Glu Ile Val Ala Ala
            595             600             605

Ala Tyr Asp Asp Ser Lys Phe Cys Arg Tyr Val Glu Leu Ile Cys Ser
            610             615             620

Arg Glu Lys Ala Arg Arg Gln Met Ser Arg Glu Ala Ala Gly Gly
625             630             635             640

Val Pro Glu Arg Gly Thr Ala Ser Ser Gly Gly Pro Gly Thr Leu Glu
            645             650             655

Arg Ser Ala Pro Arg Arg Leu Ile Thr Ala Asp Glu Glu Arg Arg Gly
            660             665             670

Pro Glu Arg Val Gly Arg Phe Arg Asn Gly Gly Pro Asp Asp Pro Arg
            675             680             685
```

Arg Ala Gly Gly Pro Tyr Gly Phe His
    690                 695

<210> SEQ ID NO 42
<211> LENGTH: 2094
<212> TYPE: DNA
<213> ORGANISM: Artificial
<220> FEATURE:
<223> OTHER INFORMATION: Synthetic DNA sequence of GenBank accession
      NC_001347 region: 150936..153029

<400> SEQUENCE: 42

| | | | | |
|---|---|---|---|---|
| ctagtgaaat | ccgtatggac | ctccagcacg | ccgcggatca | tcagggcctc catttcgaaa | 60 |
| tcggccgaca | cgctctgggc | cgcgccgctc | ctcgtctgcc | gtgatcaagc ggcgcggcgc | 120 |
| ggacctttca | agtgttcctg | ggccgccgct | cgaggcagtt | ccccttctg gcactccgcc | 180 |
| cgccgcttcg | cggctcattt | ggcgccgacg | cgccttctcg | cggctgcaaa tcagctccac | 240 |
| gtatcggcaa | aacttgctgt | cgtcgtaggc | ggcggccacg | atctcgccga aggagagctg | 300 |
| caggtaggcc | tcgggtacgg | ggtccagcgt | gcccagcgcc | aggatgtgac acagataggg | 360 |
| cagggtcacg | cgctctaccg | tgtaattgga | gtagacgatg | gcctcttcgg cccttgatg | 420 |
| cgtgaccaga | cgccgtaggc | gaaaggtacg | gaaatactcg | ttttcccaca actgcgtgag | 480 |
| gaagcgttcc | agcgactcgg | tgccgggcac | gaactgcgag | aagaagctgt tggccaccag | 540 |
| gcggttgtct | tccaccgcca | gcggacggaa | gggcgccgcg | tcgcgcgcct tgcgcacggc | 600 |
| ctccaacacg | ggcaggtggt | agagttcggc | gtcgcgcgcg | cccaggctca tggagtcctc | 660 |
| gcgccgcgag | gcgtagcgcg | tgagcaggtc | gcgcagttcg | cgcacgcgat tctcccaggt | 720 |
| ctggttaagc | gtgcgcaggt | cctggatctc | gtccacctgc | gactggatct gctcctccag | 780 |
| gcacttgata | acctgcttct | taaacaggtc | gcggatgtcc | cgctcgggcg ccgccgggcc | 840 |
| gggtggcggc | ggcagcagcc | cgacgtggcc | cgcgggtcct | ccaccacgg cgccgccggg | 900 |
| tcccaccacg | ccgggtccgc | ccggaccacg | cgcgggtagt | agacggtttt ggtccaccag | 960 |
| cgaggggtc | aggtcctgca | gaaaggactc | gacgctgtcc | tcgatgccga tgcgcgattt | 1020 |
| gctgtccgag | acgttaagca | aaaacttcat | aatggacttt | ttggcgtcgc tgccccggtc | 1080 |
| gtgctgctcc | atcatctcca | ccagcttctt | gcagttgagc | tcgtggcggc tggcggtcac | 1140 |
| cactttcaca | ggaaaggtat | tgagcaactg | gcagatcttt | tggtggcggc agagcccgtc | 1200 |
| gtagcgcaga | atctcctcgt | gcaggtgtgc | caccggcgtg | gtgaacagca gcttgtcgcg | 1260 |
| ctcataagcc | agcggttcgg | ccgccacgta | caagcggatg | tgcttgccgc gcagctgcgc | 1320 |
| ctccagccgc | tccgagcgca | ccttcttgaa | gacgcgtacc | tcgggcgcgt tggctacgcg | 1380 |
| cacgcgcccc | aggcgctcgg | ccacctgcag | cagcagcgcc | aggttagcct gcagcaggtc | 1440 |
| ctgcgccagc | gggtgtgtct | cggtggcccg | ctgcacggcc | gcgcgtacaa attgcgcccg | 1500 |
| ctcggccgcc | tcgctcggct | tggtcttcac | gtccagcagc | ggtaccagtc ccaccgttac | 1560 |
| gcaccaatcc | acgtagagac | catagtcgtc | gttatcggcg | tactgatata aaatgtcgcg | 1620 |
| gaggccgccc | agcacgcccg | tttgcacgct | ctggcgcaac | gaggcgctcc acaccaacag | 1680 |
| atactgctcc | aggtcctctt | cgtccagcgc | gcggtaggga | aatagcgccg cgtgcaactt | 1740 |
| ccactcctcg | gccacgcgcc | gcaccgtgat | ggtgtcaaag | agcgttttgc acactccgta | 1800 |
| gagcagctgc | ttgcgcagca | cgcacgggtc | gcgcagcacc | tggtgcatgc tttggccgcg | 1860 |
| acacgtcccc | agaaagccgt | gcagcaacca | caggaagctc | atcgtctgcc ccgtggggaa | 1920 |
| aatgtcgatg | acggcctcgt | catccacgcc | gcggcccacg | cccaagtacg acgacgcctt | 1980 |

```
gatcctcaac ctctcgtcgg ccgccaagat cgaacggatc gtcgacaagg tcaagtccct    2040
ctcgcgcgag cgctttgcgc ccgaggattt ttcgttccag tggtttcgct ccat          2094
```

<210> SEQ ID NO 43
<211> LENGTH: 956
<212> TYPE: PRT
<213> ORGANISM: Human cytomegalovirus

<400> SEQUENCE: 43

| | | | | | | | | | | | | | | |
|---|---|---|---|---|---|---|---|---|---|---|---|---|---|---|
| Met | Ser | Met | Thr | Ala | Ser | Ser | Thr | Pro | Arg | Pro | Thr | Pro | Lys | Tyr |
| 1 | | | | 5 | | | | | 10 | | | | | 15 |
| Asp | Asp | Ala | Leu | Ile | Leu | Asn | Leu | Ser | Ser | Ala | Ala | Lys | Ile | Glu | Arg |
| | | | 20 | | | | | 25 | | | | | 30 | | |
| Ile | Val | Asp | Lys | Val | Lys | Ser | Leu | Ser | Arg | Glu | Arg | Phe | Ala | Pro | Glu |
| | | 35 | | | | | 40 | | | | | 45 | | | |
| Asp | Phe | Ser | Phe | Gln | Trp | Phe | Arg | Ser | Ile | Ser | Arg | Val | Glu | Arg | Thr |
| | 50 | | | | | 55 | | | | | 60 | | | | |
| Thr | Asp | Asn | Asn | Pro | Ser | Ala | Ala | Thr | Ala | Ala | Thr | Thr | Thr |
| 65 | | | | | 70 | | | | | 75 | | | | 80 |
| Val | His | Ser | Ser | Ala | Ser | Ser | Ala | Ala | Ala | Ala | Ser | Ser | Glu |
| | | | | 85 | | | | | 90 | | | | | 95 |
| Ala | Gly | Gly | Thr | Arg | Val | Pro | Cys | Val | Asp | Arg | Trp | Pro | Phe | Phe | Pro |
| | | | 100 | | | | | 105 | | | | | 110 | | |
| Phe | Arg | Ala | Leu | Leu | Val | Thr | Gly | Thr | Ala | Gly | Ala | Gly | Lys | Thr | Ser |
| | | 115 | | | | | 120 | | | | | 125 | | | |
| Ser | Ile | Gln | Val | Leu | Ala | Ala | Asn | Leu | Asp | Cys | Val | Ile | Thr | Gly | Thr |
| | 130 | | | | | 135 | | | | | 140 | | | | |
| Thr | Val | Ile | Ala | Ala | Gln | Asn | Leu | Ser | Ala | Ile | Leu | Asn | Arg | Thr | Arg |
| 145 | | | | | 150 | | | | | 155 | | | | | 160 |
| Ser | Ala | Gln | Val | Lys | Thr | Ile | Tyr | Arg | Val | Phe | Gly | Phe | Val | Ser | Lys |
| | | | | 165 | | | | | 170 | | | | | 175 | |
| His | Val | Pro | Leu | Ala | Asp | Ser | Ala | Val | Ser | His | Glu | Thr | Leu | Glu | Arg |
| | | | 180 | | | | | 185 | | | | | 190 | | |
| Tyr | Arg | Val | Cys | Glu | Pro | His | Glu | Glu | Thr | Thr | Ile | Gln | Arg | Leu | Gln |
| | | 195 | | | | | 200 | | | | | 205 | | | |
| Ile | Asn | Asp | Leu | Leu | Ala | Tyr | Trp | Pro | Val | Ile | Ala | Asp | Ile | Val | Asp |
| | 210 | | | | | 215 | | | | | 220 | | | | |
| Lys | Cys | Leu | Asn | Met | Trp | Glu | Arg | Lys | Ala | Ala | Ser | Ala | Ser | Ala | Ala |
| 225 | | | | | 230 | | | | | 235 | | | | | 240 |
| Ala | Ala | Ala | Ala | Ala | Cys | Glu | Asp | Leu | Ser | Glu | Leu | Cys | Glu | Ser | Asn |
| | | | | 245 | | | | | 250 | | | | | 255 | |
| Ile | Ile | Val | Ile | Asp | Glu | Cys | Gly | Leu | Met | Leu | Arg | Tyr | Met | Leu | Gln |
| | | | 260 | | | | | 265 | | | | | 270 | | |
| Val | Val | Val | Phe | Phe | Tyr | Tyr | Phe | Tyr | Asn | Ala | Leu | Gly | Asp | Thr | Arg |
| | | 275 | | | | | 280 | | | | | 285 | | | |
| Leu | Tyr | Arg | Glu | Arg | Arg | Val | Pro | Cys | Ile | Ile | Cys | Val | Gly | Ser | Pro |
| | 290 | | | | | 295 | | | | | 300 | | | | |
| Thr | Gln | Thr | Glu | Ala | Leu | Glu | Ser | Arg | Tyr | Asp | His | Tyr | Thr | Gln | Asn |
| 305 | | | | | 310 | | | | | 315 | | | | | 320 |
| Lys | Ser | Val | Arg | Lys | Gly | Val | Asp | Val | Leu | Ser | Ala | Leu | Ile | Gln | Asn |
| | | | | 325 | | | | | 330 | | | | | 335 | |
| Glu | Val | Leu | Ile | Asn | Tyr | Cys | Asp | Ile | Ala | Asp | Asn | Trp | Val | Met | Phe |
| | | | 340 | | | | | 345 | | | | | 350 | | |
| Ile | His | Asn | Lys | Arg | Cys | Thr | Asp | Leu | Asp | Phe | Gly | Asp | Leu | Leu | Lys |
| | | 355 | | | | | 360 | | | | | 365 | | | |

```
Tyr Met Glu Phe Gly Ile Pro Leu Lys Glu His Val Ala Tyr Val
    370             375             380

Asp Arg Phe Val Arg Pro Ser Ser Ile Arg Asn Pro Ser Tyr Ala
385             390             395             400

Ala Glu Met Thr Arg Leu Phe Leu Ser His Val Glu Val Gln Ala Tyr
            405             410             415

Phe Lys Arg Leu His Glu Gln Ile Arg Leu Ser Glu Arg His Arg Leu
            420             425             430

Phe Asp Leu Pro Val Tyr Cys Val Val Asn Asn Arg Ala Tyr Gln Glu
            435             440             445

Leu Cys Glu Leu Ala Asp Pro Leu Gly Asp Ser Pro Gln Pro Val Glu
    450             455             460

Leu Trp Phe Arg Gln Asn Leu Ala Arg Ile Ile Asn Tyr Ser Gln Phe
465             470             475             480

Val Asp His Asn Leu Ser Ser Glu Ile Thr Lys Glu Ala Leu Arg Pro
            485             490             495

Ala Ala Asp Val Val Ala Thr Asn Asn Ser Ser Val Gln Ala His Gly
            500             505             510

Gly Gly Gly Ser Val Ile Gly Ser Thr Gly Gly Asn Asp Glu Thr Ala
            515             520             525

Phe Phe Gln Asp Asp Thr Thr Thr Ala Pro Asp Ser Arg Glu Thr
    530             535             540

Leu Leu Thr Leu Arg Ile Thr Tyr Ile Lys Gly Ser Ser Val Gly Val
545             550             555             560

Asn Ser Lys Val Arg Ala Cys Val Ile Gly Tyr Gln Gly Thr Val Glu
            565             570             575

Arg Phe Val Asp Ile Leu Gln Lys Asp Thr Phe Ile Glu Arg Thr Pro
            580             585             590

Cys Glu Gln Ala Ala Tyr Ala Tyr Ser Leu Val Ser Gly Leu Leu Phe
    595             600             605

Ser Ala Met Tyr Tyr Phe Tyr Val Ser Pro Tyr Thr Thr Glu Glu Met
    610             615             620

Leu Arg Glu Leu Ala Arg Val Glu Leu Pro Asp Val Ser Ser Leu Cys
625             630             635             640

Ala Ala Ala Ala Ala Thr Ala Ala Ala Pro Ala Trp Ser Gly Gly Glu
            645             650             655

Asn Pro Ile Asn Asn His Val Asp Ala Asp Ser Ser Gln Gly Gly Gln
            660             665             670

Ser Val Pro Val Ser Gln Arg Met Glu His Gly Gln Glu Glu Thr His
            675             680             685

Asp Ile Pro Cys Leu Ser Asn His His Asp Asp Ser Asp Ala Ile Thr
            690             695             700

Asp Ala Glu Leu Met Asp His Thr Ser Leu Tyr Ala Asp Pro Phe Phe
705             710             715             720

Leu Lys Tyr Val Lys Pro Pro Ser Leu Ala Leu Ser Phe Glu Glu
            725             730             735

Thr Val His Met Tyr Thr Thr Phe Arg Asp Ile Phe Leu Lys Arg Tyr
            740             745             750

Gln Leu Met Gln Arg Leu Thr Gly Gly Arg Phe Ala Thr Leu Pro Leu
            755             760             765

Val Thr Tyr Asn Arg Arg Asn Val Val Phe Lys Ala Asn Cys Gln Ile
            770             775             780

Ser Ser Gln Thr Gly Ser Phe Val Gly Met Leu Ser His Val Ser Pro
```

```
                785                 790                 795                 800
Ala Gln Thr Tyr Thr Leu Glu Gly Tyr Thr Ser Asp Asn Val Leu Ser
            805                 810                 815

Leu Pro Ser Asp Arg His Arg Ile His Pro Glu Val Val Gln Arg Gly
        820                 825                 830

Leu Ser Arg Leu Val Leu Arg Asp Ala Leu Gly Phe Leu Phe Val Leu
    835                 840                 845

Asp Val Asn Val Ser Arg Phe Val Glu Ser Ala Gln Gly Lys Ser Leu
850                 855                 860

His Val Cys Thr Thr Val Asp Tyr Gly Leu Thr Ser Arg Thr Ala Met
865                 870                 875                 880

Thr Ile Ala Lys Ser Gln Gly Leu Ser Leu Glu Lys Val Ala Val Asp
            885                 890                 895

Phe Gly Asp His Pro Lys Asn Leu Lys Met Ser His Ile Tyr Val Ala
        900                 905                 910

Met Ser Arg Val Thr Asp Pro Glu His Leu Met Met Asn Val Asn Pro
    915                 920                 925

Leu Arg Leu Pro Tyr Glu Lys Asn Thr Ala Ile Thr Pro Tyr Ile Cys
930                 935                 940

Arg Ala Leu Lys Asp Lys Arg Thr Thr Leu Ile Phe
945                 950                 955

<210> SEQ ID NO 44
<211> LENGTH: 2871
<212> TYPE: DNA
<213> ORGANISM: Artificial
<220> FEATURE:
<223> OTHER INFORMATION: Synthetic DNA sequence of GenBank accession
      NC_001347 region: 152857..155727

<400> SEQUENCE: 44
atgtcgatga cggcctcgtc atccacgccg cggcccacgc ccaagtacga cgacgccttg      60
atcctcaacc tctcgtcggc cgccaagatc gaacggatcg tcgacaaggt caagtccctc     120
tcgcgcgagc gctttgcgcc cgaggatttt tcgttccagt ggtttcgctc catcagtcgc     180
gttgaacgaa cgacagataa caaccccctct gccgcaacta ccgccgcggc aacgacgacc     240
gttcactcct ccgcctcctc ttctgccgcc gctgccgctt cgtccgaggc cggcggcacg     300
cgcgtgccct gcgtcgaccg ttggcccttc tttcccttcc gcgcgctgct cgtcaccggc     360
acggcgggcg ccggcaagac ttccagcatc caggtgctgg cggccaatct agattgcgtg     420
atcaccggta ccacggtgat cgccgcgcag aacctcagcg cgatcctcaa ccgcactcgc     480
tcggcgcagg tcaagaccat ctaccgcgtc ttcggcttcg tcagcaagca cgtgccgctg     540
gctgacagcg ccgttagcca cgagacgctg aacgctacc gcgtgtgcga gccgcacgag      600
gagaccacca tccagcgcct gcagatcaac gatctgctcg cctactgcc ggtcatcgcc       660 gacatcgtgg acaaatgctt aaatatgtgg gagcgcaagg ccgcttcggc ctccgccgcg     720
gccgcagccg ccgcctgcga ggacctctcg gagctgtgcg agagcaatat catcgtcatc     780
gacgagtgcg gccttatgct gcgctacatg ctgcaggtgg tggtgttttt ttactacttt     840
tacaacgccc tgggcgacac gcgacttac cgcgaacgcc gcgtgccctg catcatctgc       900
gtcggttcgc ccacgcagac cgaggcgctg gagagccgct acgaccacta cacgcaaaac     960
aagagcgtgc gcaagggcgt tgacgtgctc tcggcgctga ttcagaacga ggtgctcatc    1020
aactactgcg acatcgccga caactgggtc atgtttattc acaacaagcg ttgcaccgac    1080
ctggactttg gcgacctgct caagtacatg gagttcggta tcccgctcaa ggaggagcac    1140
```

```
gtggcctacg tggatcgctt cgtgcggccg cccagctcca tccgcaaccc ctcgtacgcc   1200
gccgagatga cgcggctttt tctctcacac gtcgaggtgc aggcttactt caagcggctg   1260
cacgagcaga tccgcctgag cgagcgccac cgtctctttg atctgcccgt ctactgcgtg   1320
gtcaacaacc gcgcgtacca ggagctctgc gagctggccg acccgctggg cgactcgccg   1380
cagcccgtcg agctctggtt ccgccagaac ttggcgcgca tcattaacta ctcgcagttt   1440
gtcgaccaca acctctccag cgagatcacc aaggaggcgc tgcgcccgc ggccgacgtc   1500 gttgccacca caactcctc cgtccaggct cacggagggg gaggatctgt aatcgggagc   1560
accggcggca acgacgagac ggcgttttc caggacgatg ataccaccac tgcgcccgat   1620
agccgtgaga cgctgctcac cttgcgcatt acctacatca agggcagttc ggtgggagtc   1680
aactctaagg tgcgggcctg tgttatcgga taccagggca cggtcgaacg tttcgtggac   1740
atcttgcaaa aggacacgtt tatcgaacgc acgccctgcg agcaggcggc ctacgcctac   1800
tcgttagttt cgggcctgct cttctcggcc atgtactact ctacgtgtc gccctacacg   1860 accgaggaga tgttgcgtga ctggcgcgc gttgagctgc ccgacgtgag ttcgctctgc   1920
gccgctgccg ccgccacggc cgccgctccc gcttggagcg ggggagagaa tccgataaat   1980
aatcacgtcg acgcggattc ttctcagggc ggccagagcg tgccggtatc tcaacggatg   2040
gaacatggcc aagaggagac ccacgacatc ccctgcctgt ccaaccacca tgacgactcg   2100
gacgccatca cggacgccga actcatggat cacaccagtc tgtacgcgga tccctttttt   2160
ctcaaatacg tcaagccacc tagcctggcg ctgctttctt tcgaggagac ggtgcacatg   2220
tacactacct tccgcgacat ttttctcaag cgctaccagc tcatgcagcg tctcacgggc   2280
ggtcgcttcg ccacgttgcc gctcgttacc tacaatcgcc gtaacgtggt gttcaaggcc   2340
aactgtcaga tcagctcgca gaccggctcc ttcgtgggca tgctttcgca tgtgtcgccg   2400
gcgcagacgt acacgctcga gggctacacc agcgacaacg tgctcagtct gcccagtgac   2460
cgccaccgca tccaccccga ggtggtgcag cgcggccttt cgcggctggt gctacgcgat   2520
gcgcttgggt tcctctttgt gctcgacgtt aacgtttcgc gcttcgtcga gtcggcgcag   2580
ggcaagagtc tgcacgtgtg caccaccgtg gactacggcc tcacttcgcg cacggccatg   2640
accatcgcca agagtcaggg cctgtcgctc gagaaggtgg ccgtggactt tggggaccat   2700
cccaagaacc tcaagatgag ccacatctac gtggccatgt cgcgagtcac ggaccccgaa   2760
cacctcatga tgaacgttaa cccgttgcga ctgccctatg agaagaacac cgctatcacc   2820
ccctatatct gtcgcgcgct caaagacaaa cgcaccacgc ttattttttg a           2871
```

<210> SEQ ID NO 45
<211> LENGTH: 250
<212> TYPE: PRT
<213> ORGANISM: Human cytomegalovirus

<400> SEQUENCE: 45

```
Met Ala Leu Lys Gln Trp Met Leu Ala Asn Ile Ala Asp Asn Lys Gly
1               5                   10                  15

Ser Leu Leu Thr Pro Asp Glu Gln Ala Arg Val Phe Cys Leu Ser Ala
            20                  25                  30

Asp Trp Ile Arg Phe Leu Ser Leu Pro Asp His Asp Thr Val Leu Leu
        35                  40                  45

Arg Asp Thr Val Ala Ala Val Glu Gly Ala Arg Gln Leu Glu Met Val
    50                  55                  60

Tyr Pro Ala Pro Glu His Val His Arg Trp Ser Tyr Leu Cys Pro Pro
```

```
                65                  70                  75                  80
Glu Gln Val Arg Val Val Ile Val Gly Gln Asp Pro Tyr Cys Asp Gly
                    85                  90                  95

Ser Ala Ser Gly Leu Ala Phe Gly Thr Leu Ala Gly Arg Pro Pro Pro
            100                 105                 110

Pro Ser Leu Asn Asn Val Phe Arg Glu Leu Ala Arg Thr Val Asp Gly
        115                 120                 125

Phe Gln Arg Pro Ala Ser Gly Cys Leu Asp Ala Trp Ala Arg Arg Gly
    130                 135                 140

Val Leu Leu Leu Asn Thr Val Phe Thr Val Val His Gly Gln Pro Gly
145                 150                 155                 160

Ser His Arg His Leu Gly Trp Gln Thr Leu Ser Asn His Val Ile Arg
                165                 170                 175

Arg Leu Ser Glu Arg Arg Glu His Leu Val Phe Met Leu Trp Gly Ala
            180                 185                 190

Asp Ala His Thr Cys Glu Tyr Leu Ile Asp Arg Arg His Leu Val
        195                 200                 205

Leu Lys Ser Cys His Pro Ser Pro Arg Asn Thr Thr Arg Ala Phe Val
    210                 215                 220

Gly Asn Asp His Phe Ile Leu Ala Asn Ala Tyr Leu Asp Thr His Tyr
225                 230                 235                 240

Arg Glu Thr Met Asp Trp Arg Leu Cys Gly
                245                 250

<210> SEQ ID NO 46
<211> LENGTH: 753
<212> TYPE: DNA
<213> ORGANISM: Artificial
<220> FEATURE:
<223> OTHER INFORMATION: Synthetic DNA sequence of GenBank accession
      NC_001347 region: 163901..164653

<400> SEQUENCE: 46
tcacccacag agtcgccagt ccatggtctc tcggtaatgc gtgtccagat acgcgttggc      60
cagtataaaa tggtcgttgc ccacgaaggc gcgggtggtg ttgcgcggcg acgggtggca     120
ggacttgagt accaagtgcc gccgtcggtc gatcaggtac tcgcaggtgt gcgcgtcggc     180
gccccacagc atgaacacca gatgctcccg gcgctctgac agcctccgga tcacatggtt     240
actcagcgtc tgccagccta agtgacggtg agatccaggc tgtccgtgca ccacggtgaa     300
cacggtgttg agcagcagca cgccgcgtcg cgcccaggcg tccaggcaac ccgaggccgg     360
acgctgaaac ccgtccaccg tacgcgccag ttcgcgaaac acgttgttga gggagggcgg     420
cggcggtcgg cccgccagcg tgccgaaggc caggccgctg gcgctgccgt cgcagtacgg     480
gtcctggccc acgatcacca cgcgcacctg ctcgggcgga cacagatagc tccagcggtg     540
tacgtgctcg ggtgccgggt acaccatctc gagttgccgc gcgccctcca ccgccgccac     600
cgtgtcgcgc agcagcaccg tgtcgtggtc gggcaagctg aggaagcgga tccagtcggc     660
gctcagacaa aacacgcgag cctgctcgtc gggggttaac agagagcctt tattatcagc     720
aatgttagcg agcatccact gcttgagggc cat                                  753

<210> SEQ ID NO 47
<211> LENGTH: 316
<212> TYPE: PRT
<213> ORGANISM: Murine cytomegalovirus

<400> SEQUENCE: 47
```

Met Glu Ile Asp Lys Asn Val Gly Ala Asp Leu Ile Ser Asn Thr Arg
1               5                   10                  15

Arg Ile Leu Arg Leu Asp Glu Asn Glu Leu Arg Ile Thr Asp Thr Ala
                20                  25                  30

Leu Ile Cys Lys Asn Pro Asn Tyr Ser Leu Cys Asp Ala Met Leu Thr
            35                  40                  45

Thr Asp Ile Val Tyr Pro Val Glu Tyr Leu Leu Ser Tyr Trp Glu Cys
    50                  55                  60

Arg Ser Gly Arg Thr Ala Cys Phe Val Phe Lys Asn Thr Gly Cys Arg
65                  70                  75                  80

Val Ser Leu Ser Cys Tyr Ile Gly Phe Pro Glu Arg Leu Lys Asp Leu
                85                  90                  95

Lys Arg Val Cys Asp Phe Asn Phe Leu Ser Val Asn Glu Ala Leu Val
            100                 105                 110

Val Thr Leu Ala Asp Ile Glu Arg Ile Lys Pro Cys Asp Lys Gly Val
        115                 120                 125

Leu Thr Asn Cys Val Val Arg Lys Ser Asn Ser Gly Met Ser Tyr Asn
    130                 135                 140

Ile Glu Val Val Ala Phe Gly Pro Asp Asn Glu Ala Glu Tyr Gln Ala
145                 150                 155                 160

Leu Leu Arg Asp Ile Tyr Ala Arg Arg Met Thr Ser Val Pro Thr Asp
                165                 170                 175

Cys Gly Ser Leu Ile Cys Arg Arg Ala Arg Cys Leu Ala Ala Ala Pro
            180                 185                 190

Pro Arg Arg Pro Pro Pro Pro Pro Gly Gln Arg Trp Gly Ser
    195                 200                 205

Leu Arg Lys His Gly Pro Val Leu Thr Arg Arg Tyr Ala Gly Gly Gly
210                 215                 220

Gly Ala Ala Lys Asn Gln Pro Ala Ala Ala Ser Pro Thr Ser Thr Ser
225                 230                 235                 240

Thr Ser Ser Pro Ala Ala Pro Ser Arg Asp Gln Asp Gln Thr Gln Arg
            245                 250                 255

Pro Pro Pro Ala Gly Asp Thr Asn Val Thr Ala Ala Glu Thr Thr Tyr
            260                 265                 270

Ser Glu Arg Thr Ile Ser Phe Leu Thr Arg His Ala Asn Ala Ile His
    275                 280                 285

Cys Ala Leu Ile Leu Ala Ala Ala Ile Ala Leu Val Leu Leu Trp Leu
290                 295                 300

Leu Tyr Trp His Ala Ala Arg Ser Ala Gly His Pro
305                 310                 315

<210> SEQ ID NO 48
<211> LENGTH: 233
<212> TYPE: PRT
<213> ORGANISM: Murine cytomegalovirus

<400> SEQUENCE: 48

Met Leu Thr Ile Ala His Arg Leu Gln Arg Glu Ser Ile Ser Ser Gly
1               5                   10                  15

Arg His Ser Ser Arg Ile Ser Ala Val Phe Ser Ser Pro Ile Arg Ala
                20                  25                  30

Ser Ser Glu Ser Arg Ser Gln His Ala Ala Ser Ser Ser Ser Ser Ile
            35                  40                  45

Val Ser Arg Pro Glu Ser Val Asp Glu Asp Glu Glu Asp Gly Val
    50                  55                  60

-continued

Trp Pro Ser Val Thr Ser Gly Gly Val Leu Val Gly Cys Ala Cys Ser
65                  70                  75                  80

Asn Ser Ser Leu Thr Arg Asn Glu Ser Ile Val Val Ser Glu Gly Ser
                85                  90                  95

Gln Ala Leu Tyr Ile Ala Ser Ala Ala Thr Ala Met Asn Gly Asp Ser
            100                 105                 110

Val Arg Arg Arg Gly Gly Asp Ala Pro Asp Asp Glu Ala Ala Gly
        115                 120                 125

Ala Ala Pro Val Pro Ala Glu Glu Cys Asn Leu Asp Ala Leu Phe Glu
    130                 135                 140

Arg Phe Phe Gly Asp Gly Gly Ala Asp Ala Ile Arg Phe Glu Pro Met
145                 150                 155                 160

Leu Pro Arg Val Tyr Glu Leu Thr Leu Pro Ser Ile Asp Ser Arg Leu
                165                 170                 175

Asn Phe Ile Asn Val Gly Arg Arg His Ala Ala Phe Leu Arg His Val
            180                 185                 190

Tyr Gly Gly Cys Asp Arg Cys Glu His Ala Ala Val Leu Asn Glu Lys
        195                 200                 205

Met Lys Leu Phe Thr Ala Val Ile Thr Lys Leu Leu Asp Val Asn Gly
    210                 215                 220

Ile Leu Glu Arg Arg Glu Thr Thr Asp
225                 230

<210> SEQ ID NO 49
<211> LENGTH: 517
<212> TYPE: PRT
<213> ORGANISM: Murine cytomegalovirus

<400> SEQUENCE: 49

Met Tyr Arg Ala Trp Asp Pro Ser Leu Thr Thr Ile Asp Ser Phe Leu
1               5                   10                  15

Val Asn Glu Leu Leu His Ala His Pro Thr Lys Thr Pro Pro Glu
            20                  25                  30

Val Thr Glu Gly Gln Thr Pro Ser Ser Ser Ser Ser Ser Thr Asp
        35                  40                  45

Ser Gly Arg Glu Thr Met Leu Glu Glu Glu Ala Ala Cys Cys Asp
    50                  55                  60

Leu Asp Ser Glu Leu Ala Arg Ile Gly Asp Glu Asn Thr Ala Glu Ile
65                  70                  75                  80

Arg Glu Leu Cys Leu Pro Leu Gly Ile Asp Ser Arg Cys Asn Leu Cys
                85                  90                  95

Ala Ile Val Ser Ile Cys Leu Arg Arg Asp Pro Gln Gln Lys Trp Leu
            100                 105                 110

Leu Asp Tyr Cys Phe Leu Cys His Lys Cys Ala Ala Ala Pro Arg Thr
        115                 120                 125

Ala Met Ala Thr Leu Ile Val Ala Thr Glu Phe Leu His Leu Met Lys
    130                 135                 140

Leu His Phe Arg Asp Ile Ala Phe Asp Asn Ile Phe Lys Glu Arg Ile
145                 150                 155                 160

Val Thr Ile Phe Asp Phe His Ala His Phe Phe Ile Asn Arg Cys Tyr
                165                 170                 175

Thr Gln Arg Asp Glu His Pro Val Met Val Glu Asn Ile Thr Leu Ala
            180                 185                 190

His Met Ala Val Thr Arg Ala Leu Leu Thr Asp Asp Ala Val Pro
        195                 200                 205

```
Tyr Thr Lys Arg Arg Lys Ile Gln Tyr Lys Leu Pro Lys Pro Ala
    210                 215                 220

Pro Ala Glu Pro Glu Leu Arg Leu Leu Asp Lys Tyr Arg Arg Ala
225                 230                 235                 240

Thr Glu Gly Ser Phe Ala Arg Val Leu Phe Tyr Ile Trp Ser Gly Thr
                245                 250                 255

Asn Val Met Phe Asn Thr Thr Leu Thr Asp Leu Ala Ile Lys Lys Ser
                260                 265                 270

Lys Ala Leu Lys Ala Leu Lys Thr Arg Gln Ser Glu Ile Glu Pro Ser
            275                 280                 285

Val Gly Pro Val Phe Leu Ser Pro Ile Pro Thr Phe Arg Leu Arg Asn
            290                 295                 300

Ala Thr Thr Thr Val Cys Leu Leu Cys Glu Leu Met Ala Cys Ser Tyr
305                 310                 315                 320

Arg Asp Asn Val Phe Leu Gln Gln Leu Arg Glu Arg Ile Thr Asn Tyr
                325                 330                 335

Ser Arg Asn Asn Leu Lys Ile Ile Asp Arg Thr Gln Leu Thr Met Ala
                340                 345                 350

Glu Ile Leu Ser His Gly Arg Asn Ser Glu Phe Pro Gln Gln Leu Lys
            355                 360                 365

Asn Lys Asp Val Ser Ile Tyr Val Thr Ser Ser Pro Glu Thr Leu Ala
            370                 375                 380

Ala Ala Ser Arg Pro Gly Thr Glu Pro Phe Glu Leu Ser Ala Leu
385                 390                 395                 400

Thr Tyr Leu Val Leu Arg Gln Val Gly Val Ile Gly Val Tyr Lys His
                405                 410                 415

Leu Phe Ala Asp Pro Leu Cys Ala Ala Asn Met Arg Ser Thr Asp Pro
            420                 425                 430

Asn Ile Leu Phe Phe Asp Val Pro Asn Glu Tyr Leu Asn Glu Ala Lys
            435                 440                 445

Leu Ala Ile Cys Ser Thr Asn Ala Tyr Pro Ser Arg Val Glu Arg Asp
450                 455                 460

Phe Trp Leu Tyr Ala His Met Phe Lys Ala Phe Gln Ile Ile Lys Arg
465                 470                 475                 480

Asn Phe Lys Thr Lys Thr Gln Leu Ser Asp Phe Leu Arg Asp Phe Ser
                485                 490                 495

Gln Val Leu Glu Ser His Asp Phe Ser Leu Val Asp Pro Ser Phe Thr
            500                 505                 510

Val Glu Lys Tyr Val
            515

<210> SEQ ID NO 50
<211> LENGTH: 333
<212> TYPE: PRT
<213> ORGANISM: Murine cytomegalovirus

<400> SEQUENCE: 50

Met Phe Arg Ser Pro Glu Gly Glu Arg Asp Ala Ala Asp Arg Glu
1               5                   10                  15

Glu Glu Glu Gly Gly Glu Ala Arg Arg Ser Arg Met Met Met Ser
            20                  25                  30

Pro Arg Arg Val Lys Arg Ala Arg His Arg Pro Ala Gly Ser Gly Leu
            35                  40                  45

Arg Thr Pro Leu Arg Ser Pro Ser Ala Cys Arg Cys Ser Ser Pro Ser
50                  55                  60
```

-continued

Pro Glu Arg Gln Trp Gln Gln Arg Arg Arg Ala Lys Arg Ser Thr
 65                  70                  75                  80

Thr Pro Thr Asp Pro Pro Pro Pro Lys Arg Ser Ala Ala Ser Ala
                 85                  90                  95

Ala Ala Gly Ala Ala Pro Glu Ser Glu Tyr Leu Asn Val Lys Leu
            100                 105                 110

Ser Glu Leu His Asp Val Phe Gln Arg His Pro Asp Leu Glu Gln Lys
        115                 120                 125

Tyr Leu Lys Ile Met Lys Leu Pro Ile Thr Gly Lys Glu Ser Ile Arg
    130                 135                 140

Leu Pro Phe Asp Phe Lys Ser His Arg Gln His Thr Cys Leu Asp Leu
145                 150                 155                 160

Ser Pro Tyr Gly Asn Asp Gln Val Ser Arg Ser Ala Cys Thr Thr Cys
                165                 170                 175

Lys Glu Thr Thr Arg Leu Pro Thr Ala Ser Asp Ser Met Val Ala Phe
            180                 185                 190

Ile Asn Gln Thr Ser Asn Val Met Lys His Arg Lys Phe Tyr Phe Gly
        195                 200                 205

Phe Arg Lys Asn Met Glu Leu Leu Lys Met Ala Ala Asn Gln Pro Gln
    210                 215                 220

Leu Phe Gln Ile Tyr Tyr Ile Val Gln Ser Cys Val Gln Glu Ile Val
225                 230                 235                 240

Pro Leu Ile Tyr Tyr Asp Arg Glu Met Ala His Met Gln Leu Ile Phe
                245                 250                 255

Glu Lys Glu Thr Val His Ile Pro Ser Gln Cys Ile Glu Gln Ile Leu
            260                 265                 270

Thr Val Ala Lys Asp Ala Tyr Gly Val Ser Leu Asp Ile Ala His Gln
        275                 280                 285

Arg Ile Thr Leu Thr Ala Arg Cys Leu Arg Leu Glu Ser Ser Ser Leu
    290                 295                 300

Arg Ile Asp Val Leu Met Leu Gln Arg Lys Val Asp Glu Leu Glu Ile
305                 310                 315                 320

Pro Asn Glu Thr Asn Glu Lys Phe Glu Ser Tyr Ser Leu
                325                 330

<210> SEQ ID NO 51
<211> LENGTH: 1097
<212> TYPE: PRT
<213> ORGANISM: Murine cytomegalovirus

<400> SEQUENCE: 51

Met Asp Thr Cys Val Glu Thr Phe Phe Asn Pro Tyr Leu Arg Arg Lys
1               5                   10                  15

Pro Arg Arg Asp Trp Arg Arg Cys Glu Asp Asn Asn Lys Asn Phe Leu
            20                  25                  30

Gln Val Val Pro Arg Gly Val Leu Tyr Asp Gly Ala Thr Gly Leu Ile
        35                  40                  45

Lys Val Gln Ser Gly Met Glu Pro Arg Met Phe Tyr Ala Glu Lys Glu
    50                  55                  60

Tyr Val Leu Asn Pro Asp Lys Pro Trp Pro Thr Leu Arg Thr Arg Gly
65                  70                  75                  80

Trp Cys Arg Gly Pro Tyr Ser Asp Glu Leu Arg Phe His Thr Tyr Asp
                85                  90                  95

Gln Val Val Asn Leu Val Leu Ala Asp Ser Asp Glu Gln Ile Ser Pro
            100                 105                 110

-continued

```
Arg Trp Lys His His Val Val Pro Ala Gly Asn Val Ile Arg Met Phe
            115                 120                 125
Gly Ala Thr Asp Glu Gly Val Ser Val Cys Val Asn Val Phe Gly Gln
        130                 135                 140
Lys Ala Tyr Phe Tyr Cys Glu Arg Met Gln Ser Glu Asp Leu Lys Asn
145                 150                 155                 160
Thr Val Tyr Asp Ile Ala Asp Lys Val Pro Glu Pro Cys Ser Pro Phe
                165                 170                 175
Ser Val Ser Ile Ser Pro Val Thr Lys Ser Ser Phe Tyr Gly Tyr Gly
            180                 185                 190
Leu Gly His Ile Pro Asn Leu Tyr Arg Leu Ser Phe Asn Asn Trp Asn
        195                 200                 205
Met Cys Arg Lys Ile Gly Lys Arg Met Leu Glu Glu Gly Arg Lys Val
    210                 215                 220
Tyr Glu Leu Gly Val Asp Pro Leu Ala Arg Phe Leu Ile Asp Arg Lys
225                 230                 235                 240
Ile Pro Ser Phe Gly Trp Cys Leu Ala Arg Arg Tyr Ser Val Arg Ala
                245                 250                 255
Ala Gly Tyr Val Ser Arg Ala Gln Leu Glu Ile Asp Cys Asp Val Ala
            260                 265                 270
Asp Ile Leu Pro Ile Glu Glu Gln Ser Asn Trp Pro Phe Tyr Arg Cys
        275                 280                 285
Leu Ser Phe Asp Ile Glu Cys Met Ser Gly Thr Gly Ala Phe Pro Ala
    290                 295                 300
Ala Glu Asn Val Asp Asp Ile Ile Gln Ile Ser Cys Val Cys Phe
305                 310                 315                 320
Gly Val Gly Glu Met Val His His Ala Tyr Asp Val His Ala Asp Leu
                325                 330                 335
Ser Thr Pro Ala Val Pro Glu Asn His Leu Phe Thr Ile Gly Pro Cys
            340                 345                 350
Ala Pro Ile Pro Asp Val Lys Ile Tyr Thr Phe Pro Ser Glu Tyr Glu
        355                 360                 365
Met Leu Arg Gly Phe Phe Ile Phe Leu Ser Trp Tyr Ser Pro Glu Phe
    370                 375                 380
Ile Thr Gly Tyr Asn Ile Asn Gly Phe Asp Ile Lys Tyr Ile Leu Thr
385                 390                 395                 400
Arg Ala Glu Lys Leu Tyr Lys Met Asp Val Gly Gln Phe Thr Lys Leu
                405                 410                 415
Arg Arg Gly Gly Arg Met Phe Val Phe Ser Pro Glu Lys Gly Lys Ala
            420                 425                 430
Gly Phe Gly Thr Ser Asn Thr Val Lys Val Phe Trp Ser Gly Ser Ile
        435                 440                 445
Val Leu Asp Met Tyr Pro Val Cys Thr Ala Lys Ala Ser Ser Pro Asn
    450                 455                 460
Tyr Lys Leu Asp Thr Met Ala Glu Ile Tyr Leu Lys Lys Lys Asp
465                 470                 475                 480
Asp Leu Ser Tyr Lys Glu Ile Pro Val Gln Phe Ser Ala Gly Asp Glu
                485                 490                 495
Gly Arg Ala Arg Val Gly Lys Tyr Cys Leu Gln Asp Ala Val Leu Val
            500                 505                 510
Arg Glu Leu Phe Glu Met Leu Ala Phe His Phe Glu Ala Ala Ala Ile
        515                 520                 525
Ala Arg Leu Ala Arg Ile Pro Leu Arg Lys Val Ile Phe Asp Gly Gln
    530                 535                 540
```

```
Gln Ile Arg Ile Tyr Thr Cys Leu Leu Glu Glu Cys Ser Gly Arg Asp
545                 550                 555                 560

Met Ile Leu Pro Asn Met Pro Ser Leu Gly His Glu Ala Ala Ala Ala
                565                 570                 575

Ile Glu Glu Ala Ala Gly Gly Glu Gly Asp Glu Thr Ser Glu Gly
            580                 585                 590

Glu Asn Ser Asn Asn Ser Arg Thr Val Gly Tyr Gln Gly Ala Thr Val
            595                 600                 605

Leu Glu Pro Glu Cys Gly Phe His His Val Pro Val Cys Val Phe Asp
            610                 615                 620

Phe Ala Ser Leu Tyr Pro Ser Ile Ile Met Ser Asn Asn Leu Cys Tyr
625                 630                 635                 640

Ser Thr Leu Leu Val Glu Gly Ser Pro Glu Val Pro Glu Lys Asp Val
                645                 650                 655

Leu Arg Val Glu Ile Gly Asp Gln Cys His Arg Phe Val Arg Glu Asn
                660                 665                 670

Val His Arg Ser Leu Leu Ala Glu Leu Leu Val Arg Trp Leu Thr Gln
            675                 680                 685

Arg Lys Leu Val Arg Glu Ala Met Lys Gln Cys Thr Asn Glu Met Gln
690                 695                 700

Arg Met Ile Met Asp Lys Gln Gln Leu Ala Leu Lys Val Thr Cys Asn
705                 710                 715                 720

Ala Phe Tyr Gly Phe Thr Gly Val Ala Ala Gly Met Leu Pro Cys Leu
                725                 730                 735

Pro Ile Ala Ala Ser Ile Thr Lys Ile Gly Arg Asp Met Leu Leu Ala
                740                 745                 750

Thr Ala Gly His Ile Glu Asp Arg Cys Asn Arg Pro Asp Phe Leu Arg
            755                 760                 765

Thr Val Leu Gly Leu Pro Pro Glu Ala Ile Asp Pro Glu Ala Leu Arg
            770                 775                 780

Val Lys Ile Ile Tyr Gly Asp Thr Asp Ser Val Phe Ala Ala Phe Tyr
785                 790                 795                 800

Gly Ile Asp Lys Glu Ala Leu Leu Lys Ala Val Gly Ala Leu Ala Ala
                805                 810                 815

Asn Val Thr Asn Ala Leu Phe Lys Glu Pro Val Arg Leu Glu Phe Glu
            820                 825                 830

Lys Met Phe Val Ser Leu Met Met Ile Cys Lys Lys Arg Tyr Ile Gly
                835                 840                 845

Lys Val His Gly Ser Gln Asn Leu Ser Met Lys Gly Val Asp Leu Val
            850                 855                 860

Arg Arg Thr Ala Cys Gly Phe Val Lys Ala Val Ser Asp Val Leu
865                 870                 875                 880

His Met Val Phe Asn Asp Glu Thr Val Ser Glu Gly Thr Met Lys Leu
                885                 890                 895

Ser Arg Met Thr Phe Asp Asp Leu Lys Lys Asn Gly Ile Pro Cys Glu
            900                 905                 910

Phe Gly Pro Val Val Ser Arg Leu Cys Arg Ala Arg Asp Asp Leu His
            915                 920                 925

Leu Lys Lys Val Pro Val Pro Glu Leu Thr Leu Ser Ser Val Leu Ser
            930                 935                 940

Gln Glu Leu Ser Cys Tyr Lys Gln Lys Asn Leu Pro His Leu Ala Val
945                 950                 955                 960

Ile Arg Arg Leu Ala Ala Arg Lys Glu Glu Leu Pro Ala Val Gly Asp
```

```
                         965                 970                 975
Arg Val Glu Tyr Val Leu Thr Leu Pro Asp Gly Cys Lys Lys Asn Val
                980                 985                 990

Pro Asn Tyr Glu Ile Ala Glu Asp Pro Arg His Val Val Glu Ala Lys
            995                1000                1005

Leu Ser Ile Asn Ala Glu Lys Tyr Tyr Glu Gln Val Val Lys Ala
       1010                1015                1020

Val Thr Asn Thr Leu Met Pro Val Phe Pro Arg Asp Met Pro Lys
   1025                1030                1035

Arg Glu Lys Phe Phe Ser Leu Val Val Pro Gln Arg Ile Tyr Ile
   1040                1045                1050

Pro Asp Gln Phe Leu His Leu Cys Gly Asn Val Asn Glu Leu Ala
   1055                1060                1065

Arg Gly Gly Asp Asp Ser Asp Gly Gly Asp Ser Glu Lys Glu Asn
   1070                1075                1080

Met Asp Thr Glu Arg Ser Ser His Glu Ala Met Glu Thr
   1085                1090                1095

<210> SEQ ID NO 52
<211> LENGTH: 937
<212> TYPE: PRT
<213> ORGANISM: Murine cytomegalovirus

<400> SEQUENCE: 52

Met Ser Arg Arg Asn Glu Arg Gly Cys Arg Ser Ser Trp Tyr Ala
1               5                  10                  15

Met Ser Thr Ala Leu Ala Val Thr Ile Trp Cys Leu Leu Ala Cys Thr
                20                  25                  30

Ser Glu Val Ile Ala Ala Ala Ser Thr Pro Gly Thr Thr Pro Lys Ala
            35                  40                  45

Lys Thr Asp Thr Ser Ser Glu Thr Ala Ser Ala Glu Thr Glu Thr Ala
    50                  55                  60

Thr Ser Gly Ala Ala Thr Gly Lys Lys Glu Ala Thr Pro Thr Gln Ala
65                  70                  75                  80

Ser Lys Ile Thr Gly Thr Thr Ile Val Pro Phe Val Asn Glu Thr Glu
                85                  90                  95

Asn Met Val Ser Val Asp Ile Asp Lys Tyr Pro Tyr Arg Val Cys Met
            100                 105                 110

Ser Val Ser Thr Asp Leu Val Arg Phe Gly Lys Ser Ile Asp Cys Ile
        115                 120                 125

Asn His Thr Pro Lys Thr Pro Val Gln Glu Gly Ile Met Ile Val Tyr
    130                 135                 140

Lys Gln Asn Ile Val Ala His Thr Phe Glu Val Ile Thr Tyr His Lys
145                 150                 155                 160

Asp Ala Ile Phe Gln Arg Ser Tyr Ala Asp Thr Thr Asn Tyr Phe
                165                 170                 175

Leu Gly Thr Ser Val Thr Lys Met Ala Phe Pro Val Trp Glu Leu Asp
            180                 185                 190

Glu Val Asn Arg Asn Asn Arg Cys Tyr Ser Ala Ala Ser Arg Ile Leu
        195                 200                 205

Asn Gly Glu Val Tyr Val Ala Tyr His Glu Asp Ser Tyr Arg Asn Tyr
    210                 215                 220

Thr Met Val Leu Val Glu Asp Asp Tyr Arg Ser Lys Asn Ser Lys Arg
225                 230                 235                 240

Tyr Val Thr Thr Lys Ser Arg Tyr His Lys Gly Ala Trp Thr Trp Arg
```

```
                        245                 250                 255
Tyr Thr Glu Ser Cys Asn Met Asn Cys Val Val Val Thr Lys Ala
                    260                 265                 270

Arg Ser Asn Thr Pro Tyr Glu Phe Phe Val Leu Ser Ser Gly Glu Val
                275                 280                 285

Val Glu Ile Ser Pro Phe Tyr Asp Gly Glu Asn Ser Glu Pro Phe Glu
            290                 295                 300

Glu Asp Thr Arg Asn Phe Trp Ile Arg Lys Asn Tyr Thr Met Lys Thr
305                 310                 315                 320

Tyr Phe Gly Glu Leu Ala Ala Pro Lys Lys Val Val Pro Leu Met Ala
                325                 330                 335

Phe Leu Glu Arg Glu Asp Met Thr Ile Gly Trp Glu Ile Phe Pro Lys
                340                 345                 350

Gln Asn Val Thr Cys Asp Trp Lys Lys Trp Gln Thr Val Ser Arg Ala
                355                 360                 365

Ile Arg Thr Asp Thr Asn Thr Ser Tyr His Phe Val Ser Lys Ser Leu
            370                 375                 380

Thr Ala Thr Phe Val Ala Ser Lys His Lys Ile Asp Tyr Asn Thr Thr
385                 390                 395                 400

Thr Glu Gly Lys Asn Tyr Asn Thr Phe Arg Cys Val Tyr Asp Glu Phe
                405                 410                 415

Val Glu Glu Val Asn Arg Val Phe Glu Asp Glu Tyr Asn Glu Thr His
                420                 425                 430

Val Lys Asp Gly Glu Leu Glu Met Tyr Arg Thr Thr Gly Gly Leu Ile
                435                 440                 445

Val Leu Trp Gln Gly Leu Lys Ala Lys Ser Leu His Asn Leu Glu Lys
                450                 455                 460

Phe Ala Ala Leu Asn Asn Val Ser Val Gly Thr Val Ser Pro Pro Val
465                 470                 475                 480

Thr Ser Ala Thr Glu Asn Gly Thr Thr Ala Ala Ser Val Ala Ala Arg
                485                 490                 495

Arg Lys Arg Ser Leu Asp His Ile Asp Asp Val Val Thr Asp Ile Thr
                500                 505                 510

Tyr Ala Gln Leu Gln Phe Thr Tyr Asp Val Leu Lys Asp Tyr Ile Asn
                515                 520                 525

Asp Ala Leu Arg Asn Ile Met Asp Ala Trp Cys Arg Asp Gln Lys Arg
                530                 535                 540

Thr Ala Glu Met Leu Lys Glu Leu Ser Lys Ile Asn Pro Ser Asn Ile
545                 550                 555                 560

Leu Ser Ala Ile Tyr Glu Arg Pro Val Thr Ala Lys Leu Ala Gly Asp
                565                 570                 575

Val Ile Ala Met Ser Glu Cys Val Lys Val Asp Gln Ser Ser Val Lys
                580                 585                 590

Val Leu Lys Asp Met Arg Ile Phe Gln Asp Gly Lys Val Val Asn Cys
                595                 600                 605

Tyr Ser Arg Pro Leu Val Val Phe Gln Phe Ile Asn Ser Thr Lys Leu
                610                 615                 620

Glu Ser Gly Gln Leu Gly Glu Asn Asn Glu Ile Met Leu Gly Thr Phe
625                 630                 635                 640

Arg Thr Glu Asn Cys Asp Thr Asn Ser Arg Lys Ile Phe Val Val Gly
                645                 650                 655

Thr Val Gly Tyr Glu Tyr Arg Asp Tyr Arg Phe Arg Asn Val Thr Ser
                660                 665                 670
```

-continued

```
Leu Glu His Ile Gln Leu Val Asp Thr Leu Ile Gly Leu Asp Ile Glu
            675                 680                 685

Pro Leu Glu Asn Thr Asp Phe Lys Val Leu Glu Leu Tyr Ser Lys Gly
        690                 695                 700

Glu Leu Arg Ala Ser Asn Val Phe Ser Leu Asp Glu Ile Met Arg Glu
705                 710                 715                 720

Tyr Asn Ser Gln Lys Gln His Ile Arg Thr Leu Ser Ala Lys Val Asn
                725                 730                 735

Asp Asn Thr Pro Ser Tyr Leu Leu Gly Leu Asp Thr Phe Met Gln Gly
            740                 745                 750

Leu Gly Val Ala Gly Lys Gly Ile Gly Val Ala Ile Gly Ala Val Gly
                755                 760                 765

Gly Ala Val Ser Ser Val Val Asn Ala Val Thr Gly Phe Leu Thr Asn
    770                 775                 780

Pro Phe Gly Gly Phe Thr Thr Ile Leu Leu Val Ile Gly Val Leu Ala
785                 790                 795                 800

Val Val Tyr Leu Ile Phe Thr Arg Gln Arg Ser Ala Ala Ala Arg Pro
                805                 810                 815

Val Glu Tyr Phe Phe Pro Tyr Ala Thr Gln Thr Ala Val Gln Tyr Ala
            820                 825                 830

Pro Pro Gly Gly Ala His Gly Gly Leu Glu Ser Gly Pro Pro Gly Ala
        835                 840                 845

Pro Gly Leu His Arg Arg Val Asn Ala Gly Gly Ser Asp Asp Ser Gly
    850                 855                 860

Lys Ala Trp Thr Ser Asp Lys Lys Gly Leu Glu Arg Thr Tyr Thr Glu
865                 870                 875                 880

Gln Asp Ala Leu Leu Ile Leu Arg Ala Leu Lys Gln Leu Asp Asp Ser
                885                 890                 895

Gln Arg Thr Glu Lys Ala Gln Gln Lys Ala Thr Arg Leu Pro Thr Gly
            900                 905                 910

Ile Leu Asp Arg Leu Lys Gly Asn Asp Thr Ser Gly Tyr Gln Arg Leu
        915                 920                 925

Pro Ala Glu Asp Ser Asp Phe Glu Tyr
    930                 935

<210> SEQ ID NO 53
<211> LENGTH: 798
<212> TYPE: PRT
<213> ORGANISM: Murine cytomegalovirus

<400> SEQUENCE: 53

Met Ala Met Asn Thr Leu Gln Lys Leu Cys Val Val Cys Ser Lys Cys
1               5                   10                  15

Asn Glu Cys Ala Met Asp Val Glu Cys Leu Lys Tyr Cys Asp Pro Asn
                20                  25                  30

Ile Val Ser Met Asp Ser Thr Ala Phe Arg Arg Asn Gly Val Met Val
            35                  40                  45

Ile His Leu Tyr Arg Thr Leu Tyr Pro Ala Leu Val Ser Gln Asn Ala
        50                  55                  60

Val Gln Thr Ser Val Leu Thr Leu Tyr Met Glu Met Leu Leu Gln Gly
65                  70                  75                  80

Leu Tyr Asp Thr Met Arg Glu Ile Asp Met Ala Leu Thr Asp Phe Gly
                85                  90                  95

Thr His Arg Asp Arg Gln Arg Tyr Arg Arg Val Leu Lys Leu Asp
            100                 105                 110
```

-continued

```
Ser Cys Asn Arg His Glu Ser Ile Thr Ile Thr Phe Ala Pro Glu Leu
        115                 120                 125

Ala Leu Thr Ile Asp Leu Ala Thr Leu Asn Asp Val Glu Arg Leu Leu
130                 135                 140

Cys Lys Ile Asn Cys Val Tyr Gly Ala Val Asp Ala Ser Gln Gly Val
145                 150                 155                 160

Ala Val Cys Arg Arg Leu Leu Ser Leu Leu Ala Arg Leu Cys Asp Ile
                165                 170                 175

Cys Pro Val Ala Gly Pro Glu Ile Tyr Arg Glu Thr Val Thr Cys Phe
                180                 185                 190

Gln Cys Tyr Glu Glu Leu Met Ala Val Pro Asn Gln Gly Arg Ser Ile
        195                 200                 205

Asn Arg Arg Met Gln Gly Leu Leu Cys Asp His Ile Thr Ile Lys Lys
        210                 215                 220

Val Leu Val Gln Leu Asp Met Asp Ala Gln Thr Val Glu Gln Asp Met
225                 230                 235                 240

Gly Asp Ile Ala Ile Arg Ala Pro Ser Val Lys Gly Ile Ile Arg Ala
                245                 250                 255

Ile Lys Ser Leu Ala Ser Phe Ser Pro Ala Ser Tyr Ala Tyr Ile Asn
                260                 265                 270

Asp Ala Glu Ala Leu Arg Gly Tyr Asn Leu Phe Ser Glu Ile Pro
                275                 280                 285

Asp Arg Ile Tyr Ser Leu Ser Asp Tyr Thr Tyr Trp Ser Lys Thr Ser
        290                 295                 300

Glu Ala Ile Val Arg His Val Gly Ile Thr Met Arg Gln Leu Asn Val
305                 310                 315                 320

Ser His Ser Leu Trp Lys Thr Leu Arg Thr Glu Leu Ser Arg Tyr His
                325                 330                 335

Tyr Gly Glu Asp Leu Glu Asp Val Phe Thr Leu Gly Glu Gly Arg Phe
                340                 345                 350

Gly Gly Asp Glu Arg Ile Tyr Val Gly Ser Ile Phe Ala Ala Pro Gly
        355                 360                 365

Lys Val Val Asp Met Ile Thr Ser Met Ser Ile Lys Ser Phe Glu Asn
        370                 375                 380

Asn Pro Leu Phe Asn Arg Leu His Glu Ser Asn Glu Ile Tyr Ala Lys
385                 390                 395                 400

Ile Lys Ser Leu Ile Glu Glu Ile Arg Gly Val Gly Asp Gly Pro Ala
                405                 410                 415

Ala Gly Ala Ala Ala Ser Arg Ala Glu Ala Ala Ser Gly Ala Gly Ala
                420                 425                 430

Gly Gly Glu Glu Gly Ala Gly Ala Ala Ala Gly Arg Gly Asn Thr Gly
        435                 440                 445

Gly Asp Glu Gly Ala Gly Thr Thr Thr Ala Met Ser Ser Ala Leu Glu
        450                 455                 460

Cys Gly Asp Pro Leu Leu Arg Val His Asp Val Asn Lys Glu Val Asn
465                 470                 475                 480

Val Arg Lys Arg Ala Tyr Leu Lys Lys Val Ser Glu Met Gly Tyr Asn
                485                 490                 495

Lys Val Met Ala Cys Ile Arg Asn Gln Glu His Leu Val Thr Lys Leu
                500                 505                 510

Val Asn Val Asn Leu Val Gly Thr Val Cys Leu Glu Ala Val Ser Lys
        515                 520                 525

Ile Met Asn Gly Phe Leu Ser Arg Gln Arg Ser Ile Thr Glu Ala Glu
        530                 535                 540
```

```
Thr Tyr Pro Asp Val Ala Glu Ser Leu Gly Tyr Asp Glu His Leu Tyr
545                 550                 555                 560

Val Ile Asn Asn Leu Val His Lys Arg Leu Pro Ser Glu Leu Leu Pro
                565                 570                 575

Gln Leu Gly Gln Gln Ile Tyr Arg Phe Ile Asn Gly Pro Met Phe Thr
            580                 585                 590

His Tyr Leu Asp Arg His Pro Leu Pro Tyr Asn Val Asn Met Ala Tyr
        595                 600                 605

Ala Cys Asp Asn Ala Gly Ile Leu Pro His Val Lys Glu Asp Leu Val
    610                 615                 620

Arg Cys Ala Asp Gly Thr Val Pro Ser Asp Trp Met Thr Val Gly
625                 630                 635                 640

Tyr Met Gly Phe Phe Arg Phe Ala Asp Ile Arg Glu Leu Asn Asp Leu
                645                 650                 655

Gln Lys Met Val Trp Ala His Ile Arg Glu Leu Val Leu Ser Val Ala
            660                 665                 670

Leu Tyr Asn Glu Thr Phe Gly Lys Gln Leu Ala Leu Trp Arg Val Glu
        675                 680                 685

Asp Gly Asp Glu Ile Gly Gly Ile Ile Leu Thr Tyr Asn Pro Glu
    690                 695                 700

Ser Pro Leu Ile Leu Arg Arg Gly Asp Arg Ser Tyr Arg Ser Arg Asp
705                 710                 715                 720

Leu Tyr Leu Leu Leu Tyr Lys His Leu Ser Val Asp Ser Glu Thr Leu
                725                 730                 735

Ala Asp Ala Gly Ser Arg Ala Ser Val Ala Asp Leu Cys Gln Val Glu
            740                 745                 750

Arg Pro Gly Pro Ile Ala Glu Gln Arg Ser Ser Thr Gln Asn Val Lys
        755                 760                 765

Lys Lys Arg Lys Arg Met Ser Leu Leu Glu Leu Val Arg Asp Val Asp
    770                 775                 780

Gly Ala Gly Gly Asp Asp Leu Val Pro Pro Cys Leu Tyr Lys
785                 790                 795

<210> SEQ ID NO 54
<211> LENGTH: 1191
<212> TYPE: PRT
<213> ORGANISM: Murine cytomegalovirus

<400> SEQUENCE: 54

Met Ala Asp Asp Asp Leu Ser Ser Leu Ala Pro Val Ala Pro Ala Val
1               5                   10                  15

Trp Met Phe Phe Leu Lys Lys Thr Arg Glu Leu Ala Asp Ile Val Ala
                20                  25                  30

Ala Met Ser Leu Cys Asp Lys Ala Thr Pro Val Val Ile Ala Pro Leu
            35                  40                  45

Leu Ile Asp Leu Thr Val Asp Arg Asp Phe Cys Gly Ala Val Arg Thr
        50                  55                  60

Pro Met Ser Thr Tyr Glu Gly Gly Val Leu Thr Lys Val Thr Ser Phe
65                  70                  75                  80

Cys Pro Phe Ala Phe Phe His Asn Thr Asp Glu Ile Leu Asp Val
                85                  90                  95

Val Glu Asp His Gly Asp Val Val His Leu Cys Asp Asp Ala Arg Arg
                100                 105                 110

Arg Phe Gly Val Gln Ala Phe Ser Pro Leu Ala Asn Arg Asp Arg Thr
            115                 120                 125
```

```
Asp Val Asp Val Leu Cys Asp Glu Leu Gly Ile Ala Pro Ala Glu Tyr
    130                 135                 140

Thr Gly His Val Val Cys Gly Asn Gly Leu Lys Glu Leu Leu Tyr Ala
145                 150                 155                 160

Gly Gln Leu Ile Pro Cys Pro Glu Glu Ala Val Lys Val Gln Val Gly
                165                 170                 175

Ala Val Asp Gly Val Lys Val Pro Leu Tyr Pro Tyr Thr Leu Phe Ser
            180                 185                 190

Gly Gly Ala Asp Ala Ala His Ala Asp Gly Ala Ser Ala Ala Val Ala
        195                 200                 205

Cys Asp Asp Pro Trp Val Leu Glu His Gly Phe Tyr Asp Pro Ala Leu
    210                 215                 220

Ser Glu Ala Leu Phe Tyr Phe Met Phe Thr Ser Trp Gly Gln Ser Leu
225                 230                 235                 240

Arg Val Cys Glu Thr Ser Arg Leu Ile Glu Ala Gly Leu Gln Gln Phe
                245                 250                 255

Val Glu Asp Thr Gln Gln Thr Val Lys Leu Thr Pro Phe Lys Lys Tyr
            260                 265                 270

His Gly Tyr Thr Ser Gln Lys Leu Thr Ala Val Glu Arg Asp Gln Leu
        275                 280                 285

Met Thr Val Asp Ala Val Cys Ser Glu Leu Ala Phe Ser Tyr Ala Ser
    290                 295                 300

Ile Tyr Leu Asp Ser Val Tyr Glu Phe Ser Thr Ala Ser Asn Phe Leu
305                 310                 315                 320

Glu Trp Pro Leu Val Lys Asn Ala Lys Thr His Ala Asp Leu Leu Asp
                325                 330                 335

Asn Leu Arg Asp Phe Gln Leu His Leu Ala Lys His Ile Ala Ala Leu
            340                 345                 350

Ile Phe Ser Ser Asn Ser Ile Leu Tyr Gln Thr Arg Ile Val Phe Val
        355                 360                 365

Pro Ser Ala Gly Lys Gly Ala Asn Ser Asn Pro Ser Ala Gln Asp Ser
    370                 375                 380

Leu Leu Lys Ser Ile Arg Phe Phe Asn Gly Leu Thr Gly Met Tyr Asp
385                 390                 395                 400

Asp Ile Leu Asn Asp Ala Lys Lys Thr Ile Arg Phe Glu Gly Ala Val
                405                 410                 415

Gly Arg Asp Glu Lys Tyr Ser Pro His His Leu Ala Tyr Phe Cys Gly
            420                 425                 430

Thr Ser Pro Gln Leu Phe Ser Thr Leu Met Trp Phe Phe Asn Arg Met
        435                 440                 445

Ser Ile Tyr Ser Thr Gly Val Thr Ser Gly Asp Thr Val Phe Ser His
    450                 455                 460

Ile Val Asn Ala Gly Ser Lys Leu Cys Gly Ala Cys Gly Gly Arg Cys
465                 470                 475                 480

Cys His Thr Cys Tyr Ala Thr Ser Phe Ile Arg Val Asn Thr Arg Leu
                485                 490                 495

Pro Gly Ile Pro Lys Gln Ile Lys Lys Glu Pro Val Val Thr Leu
            500                 505                 510

Leu Ser Arg Ala Phe Ala Asp Ala Asp Leu Leu Gly Asn Tyr Gly Lys
        515                 520                 525

Arg Tyr Gly Leu Glu Ser Arg Glu Ala Gly Asp Gly Gly Gly Gly
    530                 535                 540

Ala Gly Gly Arg Thr Asp Glu Val Ala Ala Gly Pro Pro Ala Gly Gly
```

```
              545                 550                 555                 560
        Ala Ser Gly Leu Asn Phe Val Ser Val Asp Arg Met Lys Tyr Leu Gly
                        565                 570                 575
        Gln Val Leu Asp Tyr Cys Lys Lys Asn Ser Leu Ile Asp Ala Ile Thr
                        580                 585                 590
        Gly Glu Asp Ile Ile Asn Val Arg Ser Lys Arg Asp Phe Val Ala Thr
                        595                 600                 605
        Val Thr Ala Leu Asn Gln Thr Ile Asp Asp Ala Val Cys Arg Phe Ala
                        610                 615                 620
        Met Asp Val Arg Arg Ser Gly His Gly Arg Asp Glu Ile Ser Gly Ser
        625                 630                 635                 640
        Thr Gln Ser Phe Asn Leu Asp Leu Ser Pro Tyr Ala Thr Ala Phe Ser
                        645                 650                 655
        Pro Val Leu Ser Phe Gln Tyr Arg Thr Met Phe Ser Ile Ile Gln
                        660                 665                 670
        Asn Leu Ala Leu Ile Asn Ala Ala Ser Tyr Val Val Asp Asn Pro Leu
                        675                 680                 685
        Thr Thr Ala Gln Ile Ser Lys Trp Val Ala Leu His Phe Gln Ser Ile
                        690                 695                 700
        Cys Gly Ala Phe Gly Thr Thr Pro Leu Lys Lys Gly Phe Leu Asn Val
        705                 710                 715                 720
        Lys Asp Thr Lys Asn Leu Lys Ser Val Glu Phe Glu Arg Ile Met Asp
                        725                 730                 735
        Phe Arg Ser Phe Gln Glu Thr Gly Arg Tyr Arg Lys Ile Ser Thr Glu
                        740                 745                 750
        Ile Lys Ser Cys Lys Met Ser Val Gln Ser Leu Lys Ser Cys Arg Ile
                        755                 760                 765
        Lys Asn Arg Pro Ile Ser Lys Thr Pro Gln Ser Ser Val Phe Phe Lys
        770                 775                 780
        Lys Gly Ala Leu Gln Arg Lys Asn Pro Ile Lys Gly Cys Leu Ser Phe
        785                 790                 795                 800
        Leu Leu Phe Arg Cys His Glu Lys Leu Phe Pro Ala Cys Gly Leu Ser
                        805                 810                 815
        Cys Leu Glu Phe Trp Gln Arg Val Leu Gln Asn Ser Leu Pro Arg Ser
                        820                 825                 830
        Val Asn Val Gly Lys Val Glu Asp Phe Asp Asn Leu Val Arg Phe Leu
                        835                 840                 845
        Leu Thr Val Thr Asp Asp Tyr Asp Glu Ser Asp Val Val Asp Ile Gln
                        850                 855                 860
        Pro Asp Cys Leu Leu Ser Tyr Val Glu Asn Arg Phe His Asn Lys Phe
        865                 870                 875                 880
        Leu Tyr Met Phe Gly Phe Arg Asp Tyr Met Ser Thr Ile Gln Gly Met
                        885                 890                 895
        Ser Thr Arg Leu Thr Pro Gln Asn His Ser Gln Phe Pro Cys Leu Leu
                        900                 905                 910
        Lys Asp Ala Pro Lys Phe Val Ser Ile Ala Glu Tyr Val Leu His Phe
                        915                 920                 925
        Lys Lys Met Lys Leu Asp Gly Val Lys Ala Pro Gln Val Ala Thr Ile
        930                 935                 940
        Thr Arg Glu Pro Val Leu Lys Asn Val Phe Asp Gly Arg Ser Leu Val
        945                 950                 955                 960
        Ser Val Ser Phe Ala Val Glu Lys Tyr Ser Ser Met Gly Thr Arg
                        965                 970                 975
```

```
Asp Val Phe Gln Phe Gly Gln Ile Gly Tyr Tyr Val Gly Ser Gly Val
            980                 985                 990

Asp Arg Ser Leu Asn Thr Gly Ser Met Gly Thr Gln Asp Tyr Arg Phe
        995                 1000                1005

Met Arg Tyr Arg Tyr Ile Ile Ala Thr Lys Leu Val Asp Val Leu
    1010                1015                1020

Ile Arg Arg Ser Arg Arg Glu Asn Val Met Tyr Asp Ala Asp Val
    1025                1030                1035

Val Arg Ser Arg Val Leu Ala Ala Leu Asp Ser Thr Gly Leu Asp
    1040                1045                1050

Val Asp Pro Glu Leu Ala Ala Ile Ala Glu Leu Met Glu Gly Arg
    1055                1060                1065

Asp Glu Gly Asp Ile Pro Glu Ile Asp Asp Ile Leu Phe Tyr Val
    1070                1075                1080

Asp Gln Gln Glu Tyr Ile Ala Arg Ser Met Tyr Arg Lys Met Arg
    1085                1090                1095

Ser Leu Ala Glu Arg Gly Val Thr Asp Phe Ser Leu Ala Ser Leu
    1100                1105                1110

Arg Glu Ala Thr Ala Thr Asn Ala Thr Ala Ala Gly Ser Ala Ala
    1115                1120                1125

Gly Gly Gly Gly Ser Ala Thr Glu Gly Gly Gly Gly Ala Ala Ala
    1130                1135                1140

Ala Asp Glu Ser Gly Pro Met Tyr Asp Phe Ser Ala Leu Phe Ser
    1145                1150                1155

Arg Arg Asp Glu Ala Glu Asp Val Asn Ala Gly Leu Ile Asn Gly
    1160                1165                1170

Asp Asp Val Arg Gly Asp Asp Glu Phe Glu Leu Pro Ser Lys Arg
    1175                1180                1185

Ser Arg Leu
    1190

<210> SEQ ID NO 55
<211> LENGTH: 964
<212> TYPE: PRT
<213> ORGANISM: Murine cytomegalovirus

<400> SEQUENCE: 55

Met Thr Val Val Leu Phe Ala Thr Glu Tyr Asp Thr Pro Asn Ile Val
1               5                   10                  15

Val Asn Met Leu Ser Glu Thr Pro Thr Glu His His Leu Phe Pro Leu
            20                  25                  30

Met Ile Lys Tyr Lys Pro Ser Asn Arg Ile Glu Phe Val Leu Gln Thr
        35                  40                  45

Gln Arg Cys Pro Asp Ser Thr Arg Val Arg Pro Val Phe Ile Cys Asp
    50                  55                  60

Ala Arg Arg Leu Ser Leu Ser Glu Tyr Val Ser Thr Asn Thr Pro Leu
65                  70                  75                  80

Pro Ala Arg Val Ile Cys Ala Gly Ile Asp Ala Asp Ala Thr Arg Glu
                85                  90                  95

Leu Tyr Glu His Leu Phe Asp Arg Lys Lys Asp Glu Thr Gly His Asp
            100                 105                 110

Glu Glu Asn Gly Ser Ala Gly Gly Asp Leu Phe Ser Asp Leu Thr Ser
        115                 120                 125

Thr Leu Lys Cys Leu Val His Tyr Asn Arg Ser Ala Ile Leu Arg Tyr
    130                 135                 140
```

```
Leu Asn Asn Thr Phe Leu Ser Pro Thr Ser Pro Ser Trp Phe Leu Ser
145                 150                 155                 160

Thr Tyr Gly Thr His Glu Gly Thr Leu Ile Leu Thr Met Ser Tyr Tyr
                165                 170                 175

Leu Phe Glu Arg Gln Tyr Ser Thr Ile Gln Thr Thr Arg Asp Tyr Thr
            180                 185                 190

Lys Cys Phe Thr Ala Asp Pro Gly Arg Asn Leu Phe Thr Tyr Ile Asn
        195                 200                 205

Met Arg Asp Phe Met Ala Thr Met Asn Gly Ser Arg Phe Arg Lys Gln
    210                 215                 220

Thr Ala Arg Phe Ala Ala Phe Ala Lys Ala Arg Asn Ala Arg Asp Arg
225                 230                 235                 240

Arg Glu Leu Glu Tyr Val Asp Ala Lys Ile Asn Ala Phe Arg Glu Glu
                245                 250                 255

Ser Arg Leu Ala Ala Asp Ser Cys Val Tyr Val Tyr Leu Ala Tyr
            260                 265                 270

Arg Thr Ala Leu Cys Arg Glu Lys Phe Leu Gln Tyr Cys Glu His Thr
        275                 280                 285

Ala Tyr Asp Lys Asn Leu Pro Asp Asp Gln Gln Cys Ala Ala Glu Glu
    290                 295                 300

Asn Tyr Leu Gly Arg Ser Leu Asp Ala Glu Leu Ile Ser Ile Met Asn
305                 310                 315                 320

Thr Tyr Phe Ser Val Glu Gly Tyr Phe Gly Ser Tyr Ile His Val Asp
                325                 330                 335

Arg Ala Lys Leu Ser Pro Pro His Ser Tyr Arg Gly Tyr Asp Trp Asn
            340                 345                 350

Thr Glu Ala Asp Thr Met Val Gly Tyr Ser Ser Thr Ala Thr Asn Leu
        355                 360                 365

Ala Ile Ser Leu Arg Lys Leu Asn Ser Thr Cys Glu Ser Leu Phe Ser
    370                 375                 380

Pro Leu Pro Pro Thr Leu Met Gly Leu Leu Lys Leu Cys Ala Ser Asp
385                 390                 395                 400

Arg Tyr Val Pro Arg Ala Glu Lys Ser Arg Lys Arg Thr Ser Gly Gly
                405                 410                 415

Arg Glu Lys Glu Asp Glu Thr Arg Val Cys Arg Arg Asn Tyr Leu Leu
            420                 425                 430

Asn Asp Thr Ser Arg Pro Ile Gly Pro Met Pro Val Phe Arg Val Glu
        435                 440                 445

Met Pro Glu Lys Arg His Val Phe Cys Ala Val Ser Ala Glu Asn Trp
    450                 455                 460

Thr Arg Arg Leu Leu Pro Lys Asp Leu Met Lys Asn Leu Pro Ser Glu
465                 470                 475                 480

Tyr Val Ser Asp Glu Cys Leu Thr Asp Ala Val Trp Leu Arg Glu Asp
                485                 490                 495

Ile Ala Ala Ser Cys Glu Val Gly Glu Gln Leu Tyr Arg Thr Arg His
            500                 505                 510

Glu Met Phe Asn Glu Asn Leu Pro Val Phe Asn Phe Val Gly Asp Val
        515                 520                 525

Asp Leu Lys Leu Arg Glu Asp Leu Gln Gly Leu Ser Arg Gln Glu Val
    530                 535                 540

Phe Asp Leu Cys Arg Ala Leu Arg Arg Thr Leu Ile Gly Ala Trp Arg
545                 550                 555                 560

His Leu Phe Pro Glu Val Asp Pro Asp Ser His Pro Val Phe Phe Phe
                565                 570                 575
```

```
Lys Ser Ala Cys Pro Gln Asn Ala Ala Gly Ala Ala Asp Glu Ala Met
            580                 585                 590

Leu Tyr Gly Gly Gly Tyr Asp Glu Asp Asp Pro Arg Pro Glu
        595                 600             605

His Ala Ala Val Val Asp Tyr Gly Asp Ala Val Arg Arg Pro Pro
610                 615                 620

Phe Cys Val Cys Arg Arg Lys Leu Gly Leu Arg Val Ile Ile Pro Phe
625                 630                 635                 640

Pro Pro Arg Thr Ala Ala Ile Gly Ala Gln Thr Leu Lys Arg Leu Ala
                645                 650                 655

Gly Ile Leu Asp His Thr Leu Cys Leu Asp Arg Asp Leu Val Cys Lys
                660                 665                 670

Leu Asn Ala Ile Ser His Pro Gly Glu Cys Phe Asp Thr Gly Ile Tyr
                675                 680                 685

Ser His Gly Arg Ser Ile Arg Met Pro Leu Met Tyr Lys Leu Asp Glu
            690                 695                 700

Ala Ser Gly Leu Met Leu His Ser Arg Leu Asn Pro Ile Phe Ile Val
705                 710                 715                 720

Pro Ala Gly Tyr Arg Asp Arg Pro Ala Glu Phe Val Leu Gln Gln Leu
                725                 730                 735

Cys Pro Gln Asn Leu Thr His His Gly Arg Pro Pro Arg Arg Asp Gly
                740                 745                 750

Ser Ala Asp Gln Leu Thr Glu Val Val Leu His Ile Thr Asp Arg Ala
            755                 760                 765

Cys Ala Asp Ser Asp Gly Asn Phe Leu Gln Ser Arg Ala Arg Arg Ala
770                 775                 780

Met Ser Arg Arg Leu Pro Leu Gly Pro Leu Leu Arg Ala His Leu
785                 790                 795                 800

Ser Leu Glu Ser Gly Gln Ser Ala Pro Ser Leu Pro Thr Leu Val Gly
                805                 810                 815

Arg Gly Gly Gly Gly Glu Gly Gly Ala Ser Ser Asp Tyr Glu Glu Glu
                820                 825                 830

Arg Ala Val Gly Ser Asp Glu Glu Asp Asp Asp Val Glu Asn
                835                 840                 845

Leu Gln Ala Phe Ala Arg Arg Ile Ala Trp Pro Ala Leu Leu Arg His
850                 855                 860

Thr Arg Asn His Tyr Arg Glu Glu Val Gln Gln Gln Leu Glu Ala Ala
865                 870                 875                 880

Thr Val Phe Thr Ala Val Gly Arg Thr Cys Val Ala Val Lys Arg Gly
                885                 890                 895

Leu Tyr Gly Arg Ala Arg Asp Phe Ser Cys Leu Ala Arg Glu His Tyr
                900                 905                 910

Thr Arg Gln Glu Thr Val Gln Val Phe Leu Asp Ile Arg Gly Asp Gln
            915                 920                 925

Arg Arg Asn Val Trp Ala Thr Leu Trp Ser Cys Phe Thr Arg Arg
930                 935                 940

Cys Asn Ser Asn Ala Lys Gln Thr His Leu Ser Leu Lys Ile Ser Leu
945                 950                 955                 960

Pro Ser Gln Tyr

<210> SEQ ID NO 56
<211> LENGTH: 299
<212> TYPE: PRT
<213> ORGANISM: Murine cytomegalovirus
```

```
<400> SEQUENCE: 56

Met Met Met Thr Asp Phe Gly Gly Gly Thr Gly Thr Ser Asn Ala
1               5                   10                  15

Arg Gly Gly Val Gly Gly Ala Ile Ala Ala Asp Asp Ala Gly
            20                  25                  30

Ala Ala Pro Pro Ser Cys Trp Arg Arg Met Leu Asp Phe Ala Leu Cys
            35                  40                  45

Arg Arg Thr Ile Arg Asp Gly Ser Glu Tyr Ile Val Leu Arg Ala Asp
50                  55                  60

Glu Asp Val Asp Met Ala Glu Leu Glu Gly Phe Leu Lys Asp Asn Phe
65                  70                  75                  80

Gly Asn Leu Gly Val Ser Ser Ala Asp Leu Ser Glu Ile Asp Arg Glu
                85                  90                  95

Ser Glu Val Thr Lys His Leu Leu Arg Leu Leu Pro Val Tyr Lys Arg
            100                 105                 110

Cys Val Arg Arg Gln Thr Arg Leu Asp Arg Leu Leu Ala Asn Gln Cys
            115                 120                 125

Arg Pro His Leu Arg Asn Ala Ala Glu Ile Glu Cys Gln Lys Ser Lys
130                 135                 140

Arg Val Met Gln Ala Leu Asp Ile Val Ile Leu Lys Leu Leu Val Gly
145                 150                 155                 160

Glu Phe Thr Leu Ser Asp Glu Asp Ser Val Glu Arg Leu Leu Glu Lys
                165                 170                 175

Phe Ser Val Asp Gln Ser Thr Leu Cys Glu Val Gly Arg Ile Val Arg
            180                 185                 190

Leu Ile Asp Met Asp Arg Glu Asn Thr Gln Arg Leu Val Asp Gly Arg
            195                 200                 205

Glu Glu Pro Ala Pro Pro Leu Cys Asp Leu Asn Gly Val Pro Ser Ser
210                 215                 220

Ser Ser Ser Ser Ser Tyr Ala Ala Thr Thr Thr Ile Ser Ser Ala Ser
225                 230                 235                 240

Asp Leu Leu Leu Arg Glu Leu Asp Asn Ala Pro Ala Ala Pro Asp His
                245                 250                 255

Leu Pro Gly Glu Ile Asp Glu Ile Leu Leu Arg Asp Glu Ala Thr Ser
            260                 265                 270

Gly Thr Gly Arg Leu His Asn Val Gly Arg Arg Arg Asp Leu Glu Glu
            275                 280                 285

Gln Lys Gln Gln His Gln Gln Met Ala Ala Leu
290                 295

<210> SEQ ID NO 57
<211> LENGTH: 628
<212> TYPE: PRT
<213> ORGANISM: Murine cytomegalovirus

<400> SEQUENCE: 57

Met Ser Arg Leu Lys Thr Phe His Asp Val Pro Cys Ile Val Ala Phe
1               5                   10                  15

Glu Ala His Arg Glu Asn Val Leu Val Phe Pro Arg Glu Lys Leu Ala
            20                  25                  30

Arg Leu Arg Asp Glu Ser Ala Leu Arg Leu Arg Gln Tyr Ala Asp Asp
            35                  40                  45

Leu Gly His Asp Ala Arg Leu Arg Arg Arg Ala Gly Glu Asp Leu Glu
50                  55                  60
```

```
Ser Leu Gly Lys Glu Leu Arg Asn Glu Cys Glu Arg Phe Arg Gly Arg
 65                  70                  75                  80

Ile Asp Gln Ala Glu Gln Leu Leu Ser Gly Pro Met Ser Asp Ile Leu
                 85                  90                  95

Gly Gly Gly Glu Gly Thr Glu Val Ala Gly Thr Ala Gly Asp Gly Gly
            100                 105                 110

Ser Val Asp Asn Ala Ser Gln Lys Asn Lys Arg Lys Lys Ala Gly Gly
        115                 120                 125

Gly Ala Ser Ala Ser Ser Cys Ser Ala Thr Gly Asp Gly Gly Gly Ser
130                 135                 140

Gly Val Gly Asp Asp Asp Ser Arg Gln Gln Cys Leu Trp Val Thr
145                 150                 155                 160

Pro Asn Asp Pro Pro Ile Ser Tyr Ser Thr Asp Phe Arg Gly Glu Leu
                165                 170                 175

Val Glu Thr Ile Phe Asn Val Ser Gln Ala Trp Thr Phe Ser Phe Gly
                180                 185                 190

Ser Trp Tyr Tyr Arg Leu Lys Arg Trp Leu Tyr Asn Gln Pro Arg Trp
            195                 200                 205

Arg Arg Val Tyr Arg Leu Thr Gln Ile Glu Ser Leu Ser Val Ser Gln
210                 215                 220

Glu Leu Leu Met Gly Val Leu Asn Ala Val Glu Gln Val Thr Val Tyr
225                 230                 235                 240

Pro Gly His Asp Thr Val Ser Asp Leu Glu Val Ala Ala Cys Leu
                245                 250                 255

Leu Ala Ala Tyr Gln Ala Ala Leu Asp Pro Arg Ala Ala Val Pro Thr
            260                 265                 270

Thr Val Glu Gly Val Leu Arg Asp Ser Gly Arg Val Leu Arg Ala Leu
        275                 280                 285

Ser Asp Asp Ile Ala Ala Glu Ile Ala Arg Arg Pro Ser Gly Gly Asn
290                 295                 300

Ala Phe Ala Tyr Lys Asp Pro Pro Gly Leu Arg Phe Tyr Ala Pro Val
305                 310                 315                 320

Gln Gln Gly Arg Arg Tyr Ala Ala Gly Thr Phe Asp Glu Asn Ala Leu
                325                 330                 335

Val Ala Val Leu Leu Arg Arg Gly Ala Ile Ala Gln Val Pro Gly Gly
            340                 345                 350

Ala Thr Gly Val Ala Ala Ala Ser Gly Gly Pro Gly Ser Ser Ala
        355                 360                 365

Ala Ala Ala Val Ala Ser Arg Glu Val Met Ser Arg Leu Ser Gly Ala
370                 375                 380

Val Ser Asp Asp Val Leu Ala Leu Trp Thr Leu Arg Leu Phe Gly Lys
385                 390                 395                 400

Arg Leu Ser Gly Val Val Pro Asn Leu Leu Gln Glu Gln His Tyr Leu
                405                 410                 415

Arg Ser Gly Leu Thr Ala Val Leu Cys Leu Leu Phe Leu Trp Lys Leu
            420                 425                 430

Leu Asn Ser Glu Ser Val Phe Ser Gly Arg Ala Gly Lys Phe Ser Leu
        435                 440                 445

Arg Asp Val Phe Pro Asp Leu Cys Gly Arg Asp Ala Pro Pro
450                 455                 460

Val Glu Arg Glu Glu Gly Phe Ala Gly Gly Cys Val Lys Asn Phe Glu
465                 470                 475                 480

Phe Met Met Glu Arg Tyr Val Val Pro Trp Tyr Ser Arg Asp Pro Ala
                485                 490                 495
```

```
Val Thr Val Ser Gln Leu Trp Pro Gly Leu Val Leu Leu Leu Tyr Cys
            500                 505                 510

Glu Ser His Arg Ser Gly Trp Asp Leu Ser Arg Arg Pro Phe Glu His
            515                 520                 525

Ala Thr Ala Asp Gly Val Ser Ala Ala Gly Val Leu His Val Gln
            530                 535             540

Ala Ser Arg Phe Asn Pro Leu Val Asp Tyr Met Leu Leu Gln Gln Thr
545                 550                 555                 560

Ala Ala Pro Asp Lys Asp Val Asp Arg Leu Ala Ala His Asp Phe Ala
                565                 570                 575

Leu Phe His Cys Glu Asn Gly Ile Gly Arg Leu Leu Ser Ile Thr Leu
                580                 585                 590

Pro Lys His Arg Val Leu Thr Leu Gly Gln Gln Phe Phe Asn Leu Gln
                595                 600                 605

Asn Val Tyr Asp Ser Met Tyr Phe Phe Val Leu Gly Phe Leu Pro Val
            610                 615                 620

Val Ser Val Thr
625

<210> SEQ ID NO 58
<211> LENGTH: 258
<212> TYPE: PRT
<213> ORGANISM: Murine cytomegalovirus

<400> SEQUENCE: 58

Met Val Lys Thr Ile Arg Val Gly Arg Phe Leu His Leu Ser Asp Asp
1               5                   10                  15

Asn His Leu Ile Leu His Ile Thr Thr Lys Leu Leu Ser Gly Gln Pro
            20                  25                  30

Leu Ser Ser Met Arg Leu Glu Glu Leu Lys Ile Ile Arg Leu Ala Cys
        35                  40                  45

Leu Leu Thr Leu Gly Arg Gly Ile Glu Leu Leu Ile Leu Arg Glu Thr
    50                  55                  60

Val Ala Asn Asn Gly Val Ser Asp Asn Thr Ile Leu Asn Arg Lys Ile
65                  70                  75                  80

Ser Pro Glu Phe Trp Arg Lys Met Tyr Glu Ala Met Arg Ala His Val
                85                  90                  95

Pro Thr Glu Thr Leu His Arg Ala Phe Ser Glu Arg Ser Ala Ala Ala
            100                 105                 110

Leu Ser Val Glu Ile Thr Gly Ser Arg Ala Cys Arg Ala Leu Val Ser
        115                 120                 125

His Leu Ile Arg Thr Glu Thr Gly Leu Ala Leu Ser Leu Pro Asp Glu
    130                 135                 140

Leu Leu Ser Asp Gly Asn Ile Phe Phe Ser Leu Gly Thr Val Tyr Gly
145                 150                 155                 160

His Arg Leu Phe Arg Leu Leu Arg Phe Phe Asn Arg His Trp Gly Lys
                165                 170                 175

Glu Ala His Glu Pro Ala Ile Arg Thr Ile Cys Gln Lys Val Trp Phe
            180                 185                 190

Phe Tyr Leu Ile Ala Trp Lys Lys Leu Thr Val Ser Pro Glu Ala Phe
        195                 200                 205

Ser Val Gln Arg Ser Asp His Glu Leu Gly Ile Phe Ser Phe Leu Ile
    210                 215                 220

Gln Asp Tyr Leu Thr Phe Thr Gly Thr Leu Arg Arg Ser Thr Pro Pro
225                 230                 235                 240
```

```
Met Asp Lys Lys Glu Glu Gly Val Ile Ala Asp Leu Leu Ser Gly Ala
                245                 250                 255

Leu Glu

<210> SEQ ID NO 59
<211> LENGTH: 926
<212> TYPE: PRT
<213> ORGANISM: Murine cytomegalovirus

<400> SEQUENCE: 59

Met Met Ser Ala Ser Asp Gly Ser Pro Ala Ser Leu Ser Cys Leu Asp
1               5                   10                  15

Pro Ala Leu Ile Val Lys Ser Pro Thr Ala Arg Val Lys Ser Ala Pro
                20                  25                  30

Val Cys Val Asn Ser Tyr Asn Leu Thr Arg Glu Ile Ser Pro Phe Glu
                35                  40                  45

Asp Ser Arg Leu Ser Gln Ala Val Thr Val Asp Glu Glu His Ile Ser
            50                  55                  60

Ser Ile Phe Arg Thr Leu Met Ala Ala Gly Pro Asp Pro Gly Ala Thr
65                  70                  75                  80

Asp Glu Asp Lys Ala Arg Val Val Leu Cys Arg Leu Leu Met Gly Pro
                85                  90                  95

Val Ala Val Pro Cys Tyr Cys Asp Glu Trp Asp Val Asp Tyr Leu
                100                 105                 110

Ala Lys Cys Ala Tyr Arg Cys Ser Gly Pro Ala Leu Tyr Val His Arg
                115                 120                 125

Ser Arg Cys Arg Cys Gly Ala Glu Gly Gly Thr Met Phe Thr Leu
            130                 135                 140

Leu His Asp His Tyr Thr Thr His Val Phe Arg Gly Leu Leu Ser Leu
145                 150                 155                 160

Ser Glu Trp Asn Val Arg Leu Thr Asp Val Phe Cys Ala Cys Asn Ala
                165                 170                 175

Phe Arg Ser Asp Arg Tyr Val Met Ala Val Leu Pro Lys His Gln Ser
                180                 185                 190

Val Phe Ile Glu Tyr Tyr Pro Tyr Phe Leu Val Cys Leu Ala Arg Tyr
                195                 200                 205

Leu Thr Val Pro Glu Ile Asp Asp Cys Ala Asn Ser Met Thr Ala His
            210                 215                 220

Leu Gly Pro Ala Ile Ala Ala Arg Val Gly Val His Tyr Lys Met Leu
225                 230                 235                 240

Phe Gly Ala Asn Ala Arg Pro Pro Arg Val Thr Glu Val Ala Arg Arg
                245                 250                 255

Ala Asn Tyr Asp Leu Phe Leu Leu Glu Leu Gln Lys Leu Trp Leu Asn
                260                 265                 270

Val Ser Tyr Arg Asn Ala Val Thr Arg Asp Phe Glu Thr Val Phe
                275                 280                 285

Ser Ala Phe His His Glu Thr Gly Lys Val Met Leu Ala Leu Arg Ser
            290                 295                 300

Pro Gly Arg Gln Pro Leu Phe Pro Arg Trp Ile Ser Met Ser Arg Phe
305                 310                 315                 320

Lys Lys Gln Val Leu Tyr Phe Glu Leu Glu Val Arg Cys Thr Lys Ser
                325                 330                 335

Arg Lys Asp Glu Leu Lys Asn Ala Leu Ile Phe Arg Lys Thr Ser Val
                340                 345                 350
```

```
Leu Phe Ala Asp His Asp Val Ile Trp Arg Asn Leu Phe Tyr Thr Tyr
        355                 360                 365

Tyr Ala Trp Cys Ala His Arg Gly Phe Gly Gly Glu Ser Arg Leu Trp
    370                 375                 380

Gly Pro Ser Gly Ser Gly Gly Ala Ala Thr Glu Ser Glu Arg Gly
385                 390                 395                 400

Gly Gly Val Arg Gly Arg Asp Gln Ala Thr Thr Ala Ser Ala Ala Ala
                405                 410                 415

Ala Ala Ala Ser Thr Asp Asp Ala Ser Ala Ser Thr Glu Ser
            420                 425                 430

Gly Val Ala Val Ser Ala Pro Ala Ala Ala Thr Ser Ala Ala Lys
        435                 440                 445

Ala His Pro His Ala Pro Ala Ala Pro Thr Val Val Gly Gly Gly Gln
    450                 455                 460

Gly Thr Ala Val Ser Ser Thr Ala Thr Gln Lys Tyr Val Lys Ile Val
465                 470                 475                 480

Asp Arg Leu Ala Leu Val Arg Leu Arg Phe Arg Glu Arg Leu Ala
            485                 490                 495

Ala Glu Ala Ala Val Gly Ser Gly Ser Gly Ser Val Glu Gly Ala Val
            500                 505                 510

Ala Gly Gly Thr Ser Gly Val Gln Thr Asp Val Lys Ala Asp Glu Pro
        515                 520                 525

Val Ala Val Pro Ser Phe Asp Phe Asp Pro Tyr Arg Cys Leu Val Arg
530                 535                 540

His Arg Ala Ala Glu Gly Val Arg Arg Glu Gly Glu Gly Ser Val Tyr
545                 550                 555                 560

Gly Ala Arg Lys Ile Ile Gly Gly Arg Glu Phe Ser Glu Met Thr Ala
                565                 570                 575

Val Ser Leu Asn Arg Val Ala Val Asn Ala Phe Asn Thr Asn Arg Val
            580                 585                 590

Ile Asn Leu Lys Ala Thr Ile Val Gln Thr Pro Arg Leu Ser Ala Phe
        595                 600                 605

Tyr Val Pro Arg Asn Met Thr His Ser Phe Val Met Tyr Lys His Thr
    610                 615                 620

Phe Lys Glu Pro Pro Tyr Thr Val Ser Thr Phe Val Ser Asn Asp Ala
625                 630                 635                 640

Ala His Thr Asn Ser Leu Asn Val Asn Ile Arg Gly Ser Tyr Gln Glu
                645                 650                 655

Phe Leu Tyr Ala Leu Ser Val Tyr Lys Leu Tyr Val Asn Ile Glu Asn
            660                 665                 670

Phe Phe Leu Pro Ala Ser Val Cys Asn Ser Asn Ser Ser Leu Asp Val
        675                 680                 685

His Gly Ile Glu Asp Gln Gly Val Ile Arg Ser Glu Arg Asp Lys Val
    690                 695                 700

Tyr Trp Thr Thr Asn Phe Pro Cys Met Ile Ser Asn Thr Asp Asn Ile
705                 710                 715                 720

Asn Val Gly Trp Phe Lys Ala Thr Ala Ile Ile Pro Lys Val Ser
                725                 730                 735

Gly Val Ala Leu Glu Asn Val Leu Leu Lys Glu Leu Ala Tyr Val Thr
            740                 745                 750

Ser Ile Asp Gln Leu Cys Val Asp Tyr Thr Leu His Arg Val Phe Thr
        755                 760                 765

Val Leu Glu Thr Arg Asn Cys Tyr Gln Ile Pro Phe Leu Ser Lys Gln
770                 775                 780
```

```
Phe Ile Leu Phe Val Arg Ile Met Met Leu Arg Ile Cys Gly Leu Glu
785                 790                 795                 800

His Arg Leu Ala Val Asp Arg Leu Ile Phe Arg Ala Ile Arg Gln Gly
            805                 810                 815

Val Phe Asp Tyr His Lys Asn Thr Val Ala His Thr Lys Ile Lys His
        820                 825                 830

Thr Cys Ala Leu Val Gly Thr Arg Leu Ala Asn Asn Val Pro Lys Val
        835                 840                 845

Leu Val Lys Asn Lys Lys Ile Lys Leu Asp Tyr Leu Gly Arg Asn Ala
850                 855                 860

Asn Leu Leu Thr Leu Cys Arg His Val Asp His Ala Cys Val Asp Ala
865                 870                 875                 880

His Arg Leu Glu Ala Leu Ile Gly Val Leu Asp Cys Leu Glu Lys Leu
            885                 890                 895

Thr Ser Ile Asp Arg Thr Lys Glu Ala Leu Thr Arg Ala Arg Val Arg
        900                 905                 910

Leu Cys Gly Gly Tyr Arg Pro Glu Ala Ala Thr Ser Arg Arg
        915                 920                 925

<210> SEQ ID NO 60
<211> LENGTH: 375
<212> TYPE: PRT
<213> ORGANISM: Murine cytomegalovirus

<400> SEQUENCE: 60

Met Ser Ile Arg Gly Gln Asn Phe Asn Leu Leu Ile Val Asp Glu Ala
1               5                   10                  15

His Phe Ile Lys Lys Glu Ala Phe Asn Thr Ile Leu Gly Phe Leu Ala
            20                  25                  30

Gln Asn Thr Thr Lys Ile Ile Phe Ile Ser Ser Thr Asn Thr Thr Ser
        35                  40                  45

Asp Ser Thr Cys Phe Leu Thr Lys Leu Thr Ser Ala Pro Phe Asp Met
    50                  55                  60

Leu Asn Val Val Ser Tyr Val Cys Glu Glu His Ile Gln Ala Phe Ser
65                  70                  75                  80

Glu Lys Gly Asp Ala Thr Ala Cys Pro Cys Tyr Arg Leu His Lys Pro
            85                  90                  95

Thr Phe Ile Thr Leu Asn Ser Asp Val Arg Lys Thr Ala Asn Met Phe
        100                 105                 110

Met Pro Gly Ser Phe Met Asp Glu Ile Met Gly Gly Thr Asn Lys Ile
        115                 120                 125

Asn Glu Glu Thr Val Leu Ile Thr Asp Glu Ser Arg Glu Glu Phe Asp
    130                 135                 140

Leu Phe Arg Tyr Ser Thr Thr Asn Pro Gln Phe His Pro His Leu Gly
145                 150                 155                 160

Ala Ile Leu Ser Val Tyr Val Asp Pro Ala Phe Thr Ser Asn Arg Arg
            165                 170                 175

Ala Ser Gly Thr Gly Val Ala Val Gly Thr Tyr Arg Asp Gln Phe
        180                 185                 190

Ile Val Tyr Gly Leu Glu His Tyr Phe Leu Lys Asp Leu Leu Asp Ser
        195                 200                 205

Ser Glu Thr Ser Ile Ala Asp Cys Val Ser His Met Leu Leu Ser Ile
    210                 215                 220

Leu Arg Leu His Pro Phe Leu Ser Gln Val Arg Val Thr Ile Glu Gly
225                 230                 235                 240
```

```
Asn Ser Asn Gln Ala Ala Val Arg Ile Ala Cys Asn Ile Lys His
            245                 250                 255

Asn Leu Leu Ser Ala His Ala Glu Thr Leu Phe Tyr His Ser Pro Asp
            260                 265                 270

Gln Asn Glu Ile Gln Gln Pro Phe Tyr Leu Met Asn Arg Asp Lys Arg
            275                 280                 285

Leu Ala Val Glu Asp Phe Ile Ala Lys Phe Asn Ser Ser Tyr Ile Lys
            290                 295                 300

Ala Ser Gln Glu Leu Ile Ser His Thr Ile Lys Leu Ser Tyr Asp Pro
305                 310                 315                 320

Val Glu Tyr Leu Leu Asp Gln Leu Arg His Ile Gln Arg Ile Thr Leu
                325                 330                 335

Asn Glu Tyr Val Thr Tyr Ser Ala Lys Arg Asn Asn Gln Ser Asp Asp
                340                 345                 350

Leu Val Val Ala Leu Ile Met Ala Val Tyr Met Cys Ser Pro Glu Arg
                355                 360                 365

Ser Phe Asn Phe Lys Pro Ile
            370                 375

<210> SEQ ID NO 61
<211> LENGTH: 230
<212> TYPE: PRT
<213> ORGANISM: Murine cytomegalovirus

<400> SEQUENCE: 61

Met Phe Ser His Gly Arg Asp Pro Arg Thr Gly Lys Pro Ile Ser Ala
1               5                   10                  15

Ala Gly Ala Arg Ala His Ala Arg Gly Gly Ser Gly Lys Cys Asp
            20                  25                  30

Gly Gly Gly Gly Cys Asp Met Arg Asn Leu Cys Asn Pro Leu Thr Gln
            35                  40                  45

Glu Leu Asn Leu Arg Asn Met Tyr Val Cys Val Arg Cys His Arg Thr
    50                  55                  60

His Leu Cys Asp Leu Arg His Asp Cys Val Val His Thr Gln Asp
65                  70                  75                  80

Gly Ser Val Cys Ile Lys Thr Gly Leu Thr Tyr Gly Ser Val Phe Pro
                85                  90                  95

Gly Gly Cys Val Ser Ala Leu Glu Pro Val Thr Glu Pro His Val Asp
            100                 105                 110

Glu Ile Asn Val Val Gly Val Ile Met Ser Tyr Val Tyr Thr Tyr Leu
            115                 120                 125

Thr Arg Asn Ala Asp His Tyr Ala Asp Val Ile Gly Ser Val Ile Glu
130                 135                 140

Gly Gly Trp Phe Asn Lys Pro Thr Glu Asn Ala Ile Tyr Phe Thr Phe
145                 150                 155                 160

Asn Arg Val Phe Lys Gln His Asn Ala Leu Gln Lys Val Pro Ile Ser
                165                 170                 175

Val Ile Gly Gln Leu Phe Val Gln Leu Val Ile Gly Val His Ala Arg
            180                 185                 190

Val Thr Lys Tyr Asp Ser Thr Val Ile Lys Val Ser Arg Arg Lys Arg
            195                 200                 205

Glu Asp Gly Leu Leu Lys Arg Met Arg Phe Glu Tyr Gly Asn Ala Pro
    210                 215                 220

Ser Phe Arg Thr Gly Arg
225                 230
```

<210> SEQ ID NO 62
<211> LENGTH: 417
<212> TYPE: PRT
<213> ORGANISM: Murine cytomegalovirus

<400> SEQUENCE: 62

Met Ala Thr Ala Ala Gly Gly Val Tyr Ala Gly Gly Glu Asp Gln Gln
1               5                   10                  15

Gln Gln Arg Pro Arg Ala Thr Asp Val Ser Thr Ala Leu Cys Asp Val
            20                  25                  30

Glu Ala Leu Ala Ala Val Glu Glu Gly Arg Val Ser Glu Ala Asp Val
        35                  40                  45

Asn Arg Tyr Arg Glu Ala Val Asp Ala Ala Leu Ile Ala Cys Glu Ala
    50                  55                  60

Ser Ser Pro Arg Asp Arg Phe Arg Leu Ile Glu Thr Ala Gly Gly Asn
65                  70                  75                  80

Phe Leu Leu Val Thr Asn Ala Leu Pro Lys Asp Arg Thr Glu Gln Gln
                85                  90                  95

Pro Pro Cys Val Leu Glu Gly Ser Gly Arg Ala Ser Ser Asn Asn Asn
            100                 105                 110

Tyr Glu Gly Ile Gly Thr Pro Ser Ala Gly Ser Gly Asn Ala Phe Asp
        115                 120                 125

Gly Leu Leu Ala Leu Glu Arg Gly Thr Ser Gly Gly Leu Thr Ala
    130                 135                 140

Thr Val Pro Ser Ala Pro Gly Tyr Val Ala Lys Ser Val Asn Thr Leu
145                 150                 155                 160

Ser Tyr Asp Gly Arg Leu Leu Ser Asn Ser Tyr Val Leu Tyr Thr Lys
                165                 170                 175

Glu Gln Leu Arg Lys Ser Leu Ser Pro Asp Lys Arg Ala Ile Val Glu
            180                 185                 190

Arg Ile Leu Arg Phe Val Asp Thr Pro Gly Ile Leu Asp His Asn Asn
        195                 200                 205

Val Gln Asp Val Glu Ala Val Leu Trp Leu Leu Phe Cys Gly Pro Gln
    210                 215                 220

Ser Val Cys Gln Asn Pro Thr Cys Phe Gly Arg Asp Arg Glu Cys Glu
225                 230                 235                 240

Val Ser Tyr Pro Val Leu Leu Pro Pro Val Phe Tyr Asp Pro Ile Thr
                245                 250                 255

Asp Tyr Ser Ala Tyr Ile Asn Leu Ala Glu Leu Tyr Val Tyr Val Trp
            260                 265                 270

Tyr Arg Asn Tyr Asp Phe Asp Ser Glu Pro Thr Arg Cys Tyr Glu Leu
        275                 280                 285

Gly Thr Val Ala Met Asp Arg Val Lys Lys Thr Leu Gln Ser Val Arg
    290                 295                 300

Gln Arg Phe Ser Asp Arg Ser Val Pro Val Trp Pro Val Ser Ser Arg
305                 310                 315                 320

Thr Cys Val Phe Cys Ala Leu Tyr Asn Gln Asn Arg Val Cys Leu Asp
                325                 330                 335

Leu Ala Lys Ser Asp Val Asp Val Thr Ser Tyr Ser Pro Ile Ile Ile
            340                 345                 350

Lys Asp Cys Arg Asp Ala Ala Thr Asn Val Thr Leu Ser His Val Leu
        355                 360                 365

Pro Gly Gln Arg Val Ala Ser Leu Phe Pro Val Tyr Asp Ile Gly Thr
    370                 375                 380

```
Leu Leu Arg Ala Leu Cys Asp Ser Asn Asp Gly Glu Glu Arg Lys
385                 390                 395                 400

Arg Met Arg Glu Thr Ile Asp Ser Ala Leu Ser Thr Thr Asp Asp Ala
                405                 410                 415

Val
```

<210> SEQ ID NO 63
<211> LENGTH: 561
<212> TYPE: PRT
<213> ORGANISM: Murine cytomegalovirus

<400> SEQUENCE: 63

```
Met Ala Thr Thr Val Leu Pro Pro Glu Ala Thr Ala Met Thr Thr Ile
1               5                   10                  15

Pro Arg Arg Ile Val Asp Asp Val Val Val Asp Asp Gly Gly Gly Phe
                20                  25                  30

Val Thr His Asn Ile Asp Ser Ala Phe Gly Gly Ser Glu Arg Asn Glu
            35                  40                  45

Cys Leu Val Phe Asp Gln Ser Glu Gln Cys Leu Ala Arg Val Phe Asp
50                  55                  60

Gly Leu Ser Ser Glu Ser Phe Asp Ile Tyr Cys Leu Tyr Asn Leu Leu
65                  70                  75                  80

Asp Ile Lys Glu Arg Val Ser Ser Val Pro Val Cys Ala Leu Arg Leu
                85                  90                  95

Ala Tyr Phe Arg Ser Val Phe Asn Lys Ile Asn Leu Thr His Asp Gly
            100                 105                 110

Pro Gly Leu Ala Thr Asn Phe Leu Ser Ile Val Asp Arg Glu Val Ser
        115                 120                 125

Asn Ala Gly Gly Glu Ser Thr Val Arg Asp Ala Val Gly Gly Val Glu
130                 135                 140

Gly Ala Gln Phe Ala Leu Ala Arg Ala Ile Phe Arg Leu Pro Ala Arg
145                 150                 155                 160

Arg Leu Leu Arg Val Met Lys Ala Ile Glu Arg Asp Ser Arg Gly Gln
                165                 170                 175

Ala Ala Asn Pro Val Trp His Ala Leu Arg Val Asp Thr Val Ser Ala
            180                 185                 190

Thr Arg Phe His Asp Val Leu Ala Thr Arg Lys Ile Ala Phe Arg Lys
        195                 200                 205

Asp Leu Asp Val Arg His Ser Ser Glu Ala Val Arg Phe Gly Met Gln
210                 215                 220

Cys Glu Ser Ala Ile Ala Gln Val Leu Arg Glu Phe Val Ala Glu Gly
225                 230                 235                 240

Arg Gly Gly Val Ser Asp Ile Gly Leu Leu Leu Asp Pro Ala Ser Gly
                245                 250                 255

Val Leu Gly Ala Ser Leu Asp Phe Cys Ser Gly Leu Ser Arg Asp Asp
            260                 265                 270

Asp Gly Leu Leu Val Val Ala Pro Gly Ala Ala Ile Phe Glu Ile Lys
        275                 280                 285

Cys Arg Phe Lys Tyr Leu Arg Ser Arg Asp Arg Ala Val Gln Gly
290                 295                 300

Leu Leu Asp Asp Pro Gly Leu Gln Ser Phe Ala Asp Phe Ile Leu Asp
305                 310                 315                 320

His His Thr Pro Ala Val Glu Phe Arg His Gln Gly Gln Leu Pro Thr
                325                 330                 335
```

Ser Arg Glu Cys Leu Val Ser Tyr Asp Arg Val Phe Arg Gln Ser Cys
            340                 345                 350

Lys Arg Arg Thr Gly Val Val Ser Glu Ser Leu Arg Leu Trp Ile
        355                 360                 365

Asp Gly Leu Ile Lys Glu Asn Ser Glu Val Leu Ser Thr Val Phe Val
370                 375                 380

Phe Asp Ala Arg Ala Ala Glu Gly Glu Thr Gly Ala Ala Thr Cys Val
385                 390                 395                 400

Gly Asp Asp Asp Glu Asp Phe Ile Leu Ser Ala Glu Arg Pro Pro Leu
            405                 410                 415

Tyr Leu Asp Leu Phe Leu Lys Ala Ala Phe Ala Ala Pro Val Phe Ala
        420                 425                 430

Asn Pro Arg His Pro Tyr Tyr Cys Gln Thr Leu Val Gln His Tyr Val
    435                 440                 445

Leu Ser Gln Tyr Tyr Ile Asn Ala His Arg Asp Pro Glu Arg Met Ser
450                 455                 460

Pro Asp Glu Leu Pro Ser Val Tyr Leu Val Ser Ala Ile Leu Arg Lys
465                 470                 475                 480

Arg Asp Glu Ser Glu Arg Gly Arg Val Ile Arg Ile Asn Gly His Arg
            485                 490                 495

Ser Asp Cys Asp Glu Val Pro Leu Cys Val Val Thr Pro Val Arg
        500                 505                 510

Leu Asp Pro His Phe Ala Arg Asp Ala Val Ser Ser Val Leu Asp Val
    515                 520                 525

Trp Glu Gly Asp Ile Gly Lys Lys Thr Gly Leu Ala Leu Trp Val Gln
530                 535                 540

Ser Ala Val Asn Ser Tyr Val Ala Ala Cys Ile Pro Thr Pro Arg Thr
545                 550                 555                 560

Pro

<210> SEQ ID NO 64
<211> LENGTH: 371
<212> TYPE: PRT
<213> ORGANISM: Murine cytomegalovirus

<400> SEQUENCE: 64

Met Leu Ser Leu Phe Asp Pro Pro Arg Arg Pro Arg Thr Arg Asp Thr
1               5                   10                  15

Cys Thr Met Ala Lys Ala Gly Val Met Thr Leu Ser His Val Asp Arg
            20                  25                  30

Met Asn Leu Arg Thr Trp Thr Met Ala Ile Ala Cys Cys Leu Leu Ser
        35                  40                  45

Phe Val Asn Ile Val Val Phe Ser Val Ala Ala His Phe Pro Gly Ile
    50                  55                  60

Gly Phe Pro Cys Tyr Tyr Pro Arg Ile Ile Asp Phe Asp Asn Met Asn
65              70                  75                  80

Leu Thr Met Tyr Asn Ala Ile His His Leu Thr Pro Gln Leu Phe Leu
            85                  90                  95

Asp Pro Val Gln Leu Ile Val Tyr Val Ile Phe Thr Glu Leu Ile Phe
        100                 105                 110

Phe Cys Val Leu Ser Tyr Tyr Ile Val Cys Trp Val Gln Ile Tyr Phe
    115                 120                 125

Arg Ser Glu His Gly Thr Gln Val Asn Gln Ser Thr Arg Asp Ile Asn
130                 135                 140

Phe Met Gly Asp Ser Ala Thr Cys Phe Thr Phe Val Leu Thr Met Asp

```
                145                 150                 155                 160
Thr Phe Gln Ile Phe Leu Leu Ser Leu Ser Phe Arg Leu Pro Ser Met
                165                 170                 175

Val Ala Phe Ser Lys Cys Met Tyr Phe Met Cys Leu Thr Ala Phe Val
            180                 185                 190

Val Thr Leu Val Thr His Tyr Glu Ser Arg Glu Arg Ser Ala Phe Ala
        195                 200                 205

Leu Ser Lys Ile His Pro Lys Leu Gln Gly Thr Ile Arg Tyr Arg Thr
    210                 215                 220

Ala Val Val Asn Leu Thr Gln Leu Ile Leu Gly Phe Ala Thr Met Val
225                 230                 235                 240

Leu Ala Met Ser Leu Ala Leu Gly Phe Gly Asn Ser Phe Phe Val Lys
                245                 250                 255

Thr Ala His Val Val Phe Gly Ala Met Val Ala Phe Ala Ile Val Ala
            260                 265                 270

Cys Val Tyr Phe Ser Ile Ile Glu Ser Val Leu Ser Arg Tyr Met Lys
        275                 280                 285

Val Gln Phe Gly Tyr His Ile Gly Thr Ile Leu Gly Val Cys Gly Ala
    290                 295                 300

Met Tyr Pro Ile Ile Arg Tyr Glu Ala Leu Asn Ala Ser Ser Tyr Ala
305                 310                 315                 320

Arg Asp Ile Asn Ile Gly Ile Thr Val Leu Leu Leu Cys Val Ala
                325                 330                 335

Phe Ser Val Ile Arg Thr Val Arg Phe Leu Leu Arg Arg Asn Lys Arg
            340                 345                 350

Tyr Arg Ala Leu Ala Leu Asp Asn Glu Glu Ile Arg Ala Leu Arg Ser
        355                 360                 365

Asp Ala Glu
    370

<210> SEQ ID NO 65
<211> LENGTH: 812
<212> TYPE: PRT
<213> ORGANISM: Murine cytomegalovirus

<400> SEQUENCE: 65

Met Glu Arg Arg Trp Arg Arg Gly Leu Pro Val His Leu Ser Ile Tyr
1               5                   10                  15

Ala Phe Leu Pro Glu Glu Asn Gln Ala Ile Leu Gln Cys Phe Phe Cys
            20                  25                  30

Glu Val Ala Asp Gly Asp Arg Val Val Thr Arg Leu Phe Val Phe Pro
        35                  40                  45

Val Asn Ile Pro Ala Glu Gly Glu Leu Arg Thr Tyr Leu Leu Ala Asn
    50                  55                  60

Tyr Thr Ser Ala Ile Val Ser Ser Ser Leu Asp Thr Ile Pro Asp Ser
65                  70                  75                  80

Thr Thr Ala Ala Asn Gly Ser Gly Val Gly Gly Glu Val Gly Gly Gly
                85                  90                  95

Gly Gly Ser Gly Asp Glu Cys Ala Asp Arg Val Ala Arg Ser Arg
            100                 105                 110

Ala Leu Ala Gln Ile Leu Met His Val Gly Pro Asp Phe Glu Pro Leu
        115                 120                 125

Thr Arg Phe Phe Thr Pro Val Glu Ile Phe Ser Asp Gly Val Glu Ile
    130                 135                 140

Leu Gly Ser Arg Arg Trp Glu Asn Val Arg Gly Ile Tyr Asn Ser Ile
```

```
                145                 150                 155                 160
Leu Gln Thr Leu Ala Ala Leu Thr Val Gly Arg Ile Arg Ala Ile Gly
                165                 170                 175
Ser Tyr His Gln Met Ala Asp Ala Val Ser Ile Glu Thr Ser Thr Ala
                180                 185                 190
Ile Gln Ser Ile Ile Ala Glu Gly Ala Thr Thr Glu Asp Ala Glu Asp
                195                 200                 205
Glu Cys Arg Tyr Arg Asn Thr His Ala Tyr Arg Lys Leu Arg Arg Gly
        210                 215                 220
Phe Val Ser Arg Asp Ile Thr Phe Ser Ile Arg Ile Gly Asn Lys Lys
225                 230                 235                 240
Phe Met Leu Ser Glu Pro Ser Ala Val Gly Ala Lys Phe Ser Val Ser
                245                 250                 255
Asp Val Phe Val Ile Gln Asp Val Lys Trp Arg Gly Lys Lys Leu Arg
                260                 265                 270
Leu Cys Phe Pro Arg Glu Phe Leu Ala Phe Val Phe Ser Asp Asp Gln
                275                 280                 285
Cys Leu Val Leu Leu Arg Asp Ala Met Gln Arg Leu Phe Lys Glu Val
        290                 295                 300
Tyr Gly Gly Phe Ser Gly Leu Tyr Pro Val Phe Asp Phe Gly Pro
305                 310                 315                 320
Asn Met Leu Arg Ser Gly Gly Pro Arg Ser Val Phe Phe Pro Gly Phe
                325                 330                 335
Pro Ala Val Ala Val Tyr Ser Val Pro Trp Arg Tyr Asp Met Asn Thr
                340                 345                 350
Glu Asn Gly Ala Asp Ala Ile Asn Glu Ile Arg Ser Leu Val Gly Leu
                355                 360                 365
Pro Asp Ile Val Gly Val Ala Gly Lys Val Pro Leu Val Pro Glu Pro
        370                 375                 380
Gly Asn Ala Val Asp Thr Leu Asp Ala Val Arg Met Tyr Asp Ile Asp
385                 390                 395                 400
Leu His Tyr Ala Asp Met Arg His Phe Arg Ile Asn Ala Arg Leu Cys
                405                 410                 415
Val Thr His Asp Met Gly Asp Ala Ala Leu Asp Asp Glu Ser Ser Val
                420                 425                 430
Ala His Ile Tyr Val Gly Val Gly Gly Val Cys Arg Ile Ser Ile Val
                435                 440                 445
Asp Leu Arg Phe Ala Val Leu Arg Met Cys Leu Pro Gly Pro Glu Phe
        450                 455                 460
Pro Phe Val Leu Ser Asp Val Ala Arg Arg Val Asp Arg Met Met Ile
465                 470                 475                 480
Asp Ala Phe Leu Gln Arg Leu Ala His Ser Ser Pro Arg Ile Phe Arg
                485                 490                 495
Arg Val Arg Ser Leu Glu Asn Tyr Ile Cys Lys Arg Val Met Asp Ala
                500                 505                 510
Cys Glu Asp Glu Gly Tyr Pro Trp Ile Leu Val Arg Asp Asp Cys Glu
                515                 520                 525
Ile Phe Val Arg Arg Pro Val Asp Cys Asp Gln Val Asn Phe Asp Thr
        530                 535                 540
Ile Val Arg Ala Asn Leu Ala Arg Val Trp Ala Glu Leu Phe Gly Leu
545                 550                 555                 560
Gln Tyr Leu Cys Pro Val Cys Arg Ile Thr Val Ala Met Ser Gly Val
                565                 570                 575
```

```
Leu Phe Ala Thr Gly Lys Tyr Leu Leu Ser Gly Phe Pro Asp Glu Gln
            580                 585                 590

Lys Tyr Phe Pro Thr Pro Gly Trp Val Gly Ala Thr Gly Arg Leu Leu
            595                 600                 605

Ser Glu Ala Val Phe Cys Ala Phe Gln Ser Pro Asp Trp Gly Ala Lys
            610                 615                 620

Asp Lys Ile Ile Arg Phe Met Ala Thr His Met Leu Arg Leu Ser Ala
625                 630                 635                 640

Arg Arg His Glu Thr Arg Phe Trp Ala Gln Arg Phe Ala Pro Gly Arg
                645                 650                 655

Asn Arg Val Gln Gln His Asp Gly Val Met Asp Ala Asn Glu Phe Cys
            660                 665                 670

Gly Ile His Val Cys Gly Arg Met Val Ala Val Gln Pro Leu Asp Gly
            675                 680                 685

Ala Leu His Asp Asn Ile Cys Tyr Asn Asp Tyr Val Lys Lys Thr Phe
            690                 695                 700

Glu Val Leu Arg Val Thr Leu Glu Lys Val Ile Val Leu Ser Gln
705                 710                 715                 720

Asp Gln Thr Asn Thr Ala Val Val Asn Asn Ser Thr Gly Glu Ile Asp
                725                 730                 735

Cys Val Ala Ile Lys Gln Glu Val Thr Asp Asp Ala Ile Val Ser Asp
                740                 745                 750

Thr Thr Gly Ser Asp Glu Leu Asp Ala Ala Leu Arg Ala Leu Arg Glu
            755                 760                 765

Thr Thr Ala Asn Thr Val Gly Met Val Val Glu Arg Thr Asp Thr His
770                 775                 780

Asn Leu Ile Glu Glu Phe Asn Asp Val Phe Gln Gln Thr Met Asp Phe
785                 790                 795                 800

Val Val Glu Arg Tyr Ser Ala Phe Phe Ser Met Asn
                805                 810

<210> SEQ ID NO 66
<211> LENGTH: 704
<212> TYPE: PRT
<213> ORGANISM: Murine cytomegalovirus

<400> SEQUENCE: 66

Met Trp Arg Asn Gln Ser Leu Tyr Arg Asp Ser Arg Glu Asn Arg Phe
1               5                   10                  15

Lys Ala Ser Asp Leu Thr Arg Ser Thr Ile Arg Ser Ile Phe Glu Ala
            20                  25                  30

Asp Asp Ile Phe Arg Thr Lys Met Leu Ser Tyr Leu Asp Asn Pro Pro
        35                  40                  45

Glu Pro Pro Ser Asp Pro Leu Phe Pro Thr Asp Ser Ser Leu Asp Leu
    50                  55                  60

Phe Ser Met Ile Asn Gly Thr Glu Gly Ala Cys Ile Gly Gln Thr Ile
65                  70                  75                  80

His Gln Ile Leu Arg Asp Pro Ser Val Phe Arg Lys Gln Ile Phe Tyr
                85                  90                  95

Ala Met Met Arg Phe Leu Leu Asn Gly Ile Ser Val Gly Glu Leu Ser
            100                 105                 110

Thr Ala Trp Ala Ser His Arg Arg Phe Val Arg Ala Glu Asp Glu
        115                 120                 125

Gly Gly Ala Ala Leu Glu Gln Phe Glu Ile Trp Ala Asp Ala Leu Lys
    130                 135                 140
```

```
His Thr Ile Val Asp Ser Ile Ala Ala Leu Leu Glu Lys Leu Ile Tyr
145                 150                 155                 160

Thr Tyr Ala Ala Asp Asp Arg Tyr Cys Arg Tyr Val Asp Trp Ile Val
            165                 170                 175

Ser Val Gly Val Pro Ile Ala Glu Val Arg Thr Ala Glu Arg Glu
        180                 185                 190

Lys Ala Val Asp Ala Ala Gln Arg Arg Phe Leu Ala Glu Val Ala Glu
        195                 200                 205

Cys His Leu Leu Asp Arg Pro Asp Pro Leu Arg Ala Arg Thr Leu Arg
        210                 215                 220

Ala Cys Val Ser Ala Leu Met Thr Arg Glu Val Pro Asn Val Pro Asp
225                 230                 235                 240

Ile Arg Ile His Arg Leu Lys Ser Asn Gly His Ile Glu Cys Phe Ser
                245                 250                 255

Gly Lys Arg Arg Leu Lys Arg Phe Ile Tyr Ala Glu Pro Thr Ile Leu
            260                 265                 270

Glu Glu Glu Arg Leu Ile Leu Thr Thr Pro Leu Ala Arg Ile Arg Tyr
            275                 280                 285

Glu Arg Lys Arg His Asn Glu Leu Arg Ile His Lys Lys Ile Cys Gln
290                 295                 300

Leu Leu Asn Thr Asn Pro Ile Lys Val Val Thr Thr Ser Arg His Glu
305                 310                 315                 320

Met Asn Thr Lys Arg Ile Val Glu Leu Met Glu Lys Arg Asp Arg Gln
                325                 330                 335

Val Asp Ala Lys Thr Ser Ile Val Lys Phe Leu Leu Asn Val Ser Asp
            340                 345                 350

Ser Lys Ser Lys Ile Gly Leu Glu Asp Ser Val Glu Ser Phe Leu Gln
        355                 360                 365

Asp Leu Thr Pro Ser Val Asp Gln Ala Arg Leu Leu Pro Ser Arg Ala
        370                 375                 380

Pro Leu Ile Gln Pro Ala Pro Ser Gly Ser Gly Ala Gln Asp Ile Arg
385                 390                 395                 400

Glu Leu Phe Arg Arg Gln Val Ile Arg Cys Leu Glu Asp Gln Ile Gln
                405                 410                 415

Asp His Val Glu Glu Ile Glu Asn Leu Lys Leu Leu Asn Lys Thr Trp
            420                 425                 430

Glu Ser Lys Thr Arg Glu Leu Arg Asp Ala Leu Asp Arg Tyr Glu Ser
        435                 440                 445

Glu Gly Arg Arg Gly Arg Gly Pro Pro Ala Phe Asp Leu Gln Thr Leu
        450                 455                 460

Asp Thr Val Asn Ala Leu Arg Arg Val Gln Gly Leu Pro Thr Ala Pro
465                 470                 475                 480

Val Thr Val Asp Asp Asn Arg Val Val Cys Asn Ser Phe Phe Ser Gln
                485                 490                 495

Phe Val Pro Asp Glu Arg Glu Ser Asp Glu Arg Leu Ser Arg Leu Trp
            500                 505                 510

Glu Gln Glu Tyr Phe Arg Cys Phe Lys Phe Arg Arg Asn Val Thr Asn
        515                 520                 525

Gln Gly Ala Glu Asp Ser Ile Ser Tyr Ser Asn Tyr Thr Ile Glu Arg
        530                 535                 540

Val Leu Leu Pro Phe Leu Thr Ala Val Ile Glu Phe Pro Met Leu Asp
545                 550                 555                 560

Ala Ile Pro Glu Glu Tyr Leu Phe Leu Ser Leu Ser Glu Leu Ala Asn
                565                 570                 575
```

```
Val Ile Tyr Glu Thr Ser Lys Leu Gln Arg Tyr Thr Asp Tyr Ile Arg
            580                 585                 590

Tyr Arg Glu Thr Ile Arg Val Gln Ala Phe Leu Glu Arg Glu Gln Ala
        595                 600                 605

Thr Ala Ala Ala Ala Ala Gly Ala Ala Thr Ala Ala Ala Pro
    610                 615                 620

Ser Glu Arg Ile Gly Arg Ala Pro Gly Gln Val Ser Gly Pro Pro Thr
625                 630                 635                 640

Lys Ile Arg Arg Leu Asp Glu Thr Thr Pro Gly Thr Ala Asn Tyr Arg
                645                 650                 655

Pro Gln Gln Lys Thr Ile Val Thr Thr Thr Pro Ile Gly Leu Pro Pro
                660                 665                 670

Pro Ser Ser Pro Ala Pro Glu Val Ser Pro Arg Phe Arg Ser Pro Gln
            675                 680                 685

Gln Lys Leu Glu Thr Leu Arg Asp Arg Asn Val Gln His Leu Asn Gly
690                 695                 700

<210> SEQ ID NO 67
<211> LENGTH: 900
<212> TYPE: PRT
<213> ORGANISM: Murine cytomegalovirus

<400> SEQUENCE: 67

Met Glu Lys Arg Ser Ser Asp Glu Ser Val Gly Asn Lys Gly Ser Asp
1               5                   10                  15

Gly Gly Ser Gly Gly Leu Ser Arg Tyr Asp Asn Ile Phe Val Leu Asn
            20                  25                  30

Met Ser Ser Ala Ser Lys Ile Glu Arg Ile Val Asp Arg Val Lys Ser
        35                  40                  45

Leu Ala Leu Lys Arg Phe Ser Arg Glu Ser Leu Tyr Lys Asp Trp Phe
    50                  55                  60

Arg His Met Leu Asp Pro Cys Ala Gly Leu Val Ala Pro Glu Leu Gly
65                  70                  75                  80

Asp Asp Gly Ser Ser Glu Gly Gly Gly Asn Ala Ala Met Ile Val Gly
                85                  90                  95

Asp Arg Glu Leu Ala Arg Arg Pro Pro Phe Leu Pro Phe Ser Cys Leu
            100                 105                 110

Leu Ile Thr Gly Thr Ala Gly Ala Gly Lys Thr Ser Ser Val Gln Val
        115                 120                 125

Leu Ala Ala Asn Leu Asp Cys Val Ile Thr Gly Ser Thr Val Ile Ser
    130                 135                 140

Ser Gln Ala Leu Ser Ser Ala Leu Asn Arg Ser Arg Ser Ala Gln Ile
145                 150                 155                 160

Lys Thr Ile Phe Arg Thr Phe Gly Phe Asn Ser Arg His Val Ala Leu
                165                 170                 175

Ala Asp Arg Val His Leu Arg Arg Arg Asp Val Ala Phe Asp Gly
            180                 185                 190

Asp Val Asp Pro Ile Cys Gln Gln Gln Trp Arg Asp Leu Ser Thr Tyr
        195                 200                 205

Trp Pro Val Val Ser Asp Ile Ala Ile Arg Ala Leu Asp Gly Gly Lys
    210                 215                 220

Gly Arg Lys Asp Thr Asp Asp Leu Cys Arg Ser Asn Ile Ile Val Ile
225                 230                 235                 240

Asp Glu Cys Gly Val Ile Leu Arg His Met Leu His Val Val Phe
                245                 250                 255
```

```
Phe Tyr Tyr Phe Tyr Asn Ala Leu Asn Asp Ser Glu Leu Tyr Arg Gln
            260                 265                 270

Arg Ala Ala Pro Cys Ile Val Cys Val Gly Ser Pro Thr Gln Ser Glu
        275                 280                 285

Ala Leu Glu Ser Arg Tyr Asp His Arg Thr Gln Asn Arg Asp Val Gln
    290                 295                 300

Arg Gly Met Asp Val Leu Ser Ala Leu Ile Ser Asp Pro Val Leu Ser
305                 310                 315                 320

Glu Tyr Cys Asp Val Ala His Asn Trp Val Met Phe Ile Asn Asn Lys
                325                 330                 335

Arg Cys Leu Asp Leu Glu Phe Gly Asp Leu Leu Lys His Ile Glu Phe
            340                 345                 350

Gly Leu Pro Leu Lys Ser Glu His Val Glu Tyr Leu Asp Arg Phe Val
        355                 360                 365

Arg Pro Ala Gly Leu Ile Arg Asp Pro Ala His Ala Ile Asp Val Thr
    370                 375                 380

Arg Leu Phe Ile Ser His Ala Glu Val Lys Arg Tyr Phe Thr Ala Leu
385                 390                 395                 400

His Asp Arg Val Arg Ile Tyr Ser Gln His Leu Ile Phe Glu Val Pro
                405                 410                 415

Val Tyr Cys Val Leu Asn Asn Ser Ala Phe His Glu Tyr Cys Ala Ser
            420                 425                 430

Met Cys Thr Gly Glu Pro Thr Pro Arg Pro Glu Thr Trp Phe Arg Lys
        435                 440                 445

Asn Leu Ala Arg Ile Ser Asn Tyr Ser Gln Phe Thr Asp His Asn Leu
    450                 455                 460

Ser Glu Asp Ile Gln Val Glu Leu Ala Gln Ser Cys Gly Gly Gly
465                 470                 475                 480

Gly Ala Gly Gly Asp Asp Asp Gly Phe Asp Leu Glu Glu Glu Met Ile
                485                 490                 495

Asn Glu Thr Leu Leu Thr Cys Arg Ile Thr Phe Ile Arg Asp Ser Ala
            500                 505                 510

Val Gly Val Thr Ala Lys Thr Lys Ala Cys Val Val Gly Tyr Thr Gly
        515                 520                 525

Thr Phe Asp Asp Phe Ala Glu Ile Leu Gln Lys Asp Leu Phe Ile Glu
    530                 535                 540

Arg Thr Pro Cys Glu Gln Ala Val Tyr Ala Tyr Ser Leu Ile Ser Gly
545                 550                 555                 560

Leu Leu Phe Ser Ala Met Tyr Leu Phe Tyr Ser Ser Pro Leu Thr Thr
                565                 570                 575

Pro Glu Ile Leu Arg Asp Leu Ser Glu Ile Pro Leu Pro Asp Ile Pro
            580                 585                 590

Thr Leu Val Ile Gly Ala Asn Gly Gly Asp Gly Ala Arg Asp Ser Asp
        595                 600                 605

Asp Asn Asp Glu Tyr Glu Glu Asp Leu Glu Gly Gly Cys Phe Asp
    610                 615                 620

Gly Val Ser Gly Gly Ser Gly Asn Gly Gly Glu Lys Tyr Arg
625                 630                 635                 640

Arg Arg Leu Thr Ser Asp Asp Glu Asp Phe Tyr Asp Leu Ser Tyr
                645                 650                 655

Val Asp Arg Gly Arg Gln Pro Glu Pro Pro Gln Leu Gln Pro Pro
            660                 665                 670

Gln Pro Gln Pro Gln Pro Arg Leu Thr Met Ser Ala Ala Leu Pro Pro
```

```
              675                 680                 685
Arg Gln Ile Asp Glu Glu Ile Ser Asp Val Glu Met Leu Cys Tyr Ser
        690                 695                 700

Asp Ile Tyr Thr Asp Lys Phe Phe Leu Lys Tyr Ser Ile Pro Pro Pro
705                 710                 715                 720

Val Ser Ser Ile Ser Phe Glu Glu Ile Val His Ile Tyr Thr Ile Phe
                725                 730                 735

Arg Asp Ile Phe Leu Ala Arg Tyr Arg Ile Met Gln Lys His Thr Lys
                740                 745                 750

Gly Ala Phe Gly Lys Thr Arg Leu Val Thr Tyr Asn Arg Arg Asn Val
                755                 760                 765

Trp Arg Arg Lys Asn Cys Glu Ile Glu Ser Gln Thr Gly Ser Phe Val
        770                 775                 780

Gly Met Leu Thr Phe Val Ser Pro Ser Asn Asn Tyr Val Leu Glu Gly
785                 790                 795                 800

Phe Thr Asn His Asn Val Phe Ile Met Asp Ala Glu Arg Asn Arg Ile
                805                 810                 815

His Arg Arg Ile Leu Glu Lys Gly Leu Pro Arg Leu Ile Val Arg Asp
                820                 825                 830

Ala Cys Gly Phe Leu Leu Ile Leu Asp Tyr Asn Val Ser Lys Phe Ser
                835                 840                 845

Asp Val Ile Asp Gly Lys Ser Val His Ile Cys Thr Met Val Asp Tyr
        850                 855                 860

Gly Val Thr Ser Arg Met Ala Met Thr Ile Ala Lys Ser Gln Gly Ile
865                 870                 875                 880

Gly Leu Glu Ser Val Ala Ile Asp Phe Gly Asp Asn Pro Lys Asn Leu
                885                 890                 895

Lys Met Ser Gln
        900

<210> SEQ ID NO 68
<211> LENGTH: 262
<212> TYPE: PRT
<213> ORGANISM: Murine cytomegalovirus

<400> SEQUENCE: 68

Met Ala Leu Arg Gln Trp Met Leu Arg His Ile Ala Val His Asp Val
1               5                   10                  15

Gly Ala Ala Ala Gly Ala Asp Val Ser Ala Asp Val Ile His Gln
                20                  25                  30

Gln Ala Glu Ala Leu Gly Ile His Glu Ala Trp Met Ser Phe Leu Lys
        35                  40                  45

Leu Ser Ala Thr Gln Ala Ser Gln Leu Val Arg Ile Thr Asp Arg Val
        50                  55                  60

Asp Gln Glu Arg Arg Met Cys Thr Ile Tyr Pro Glu Lys Ser Asp Val
65                  70                  75                  80

His Arg Trp Ser Arg Leu Cys Phe Pro Tyr Asp Val Arg Val Ile
                85                  90                  95

Leu Gly Gln Asp Pro Tyr His Asp Gly Ser Ala Cys Gly Leu Ala Phe
                100                 105                 110

Gly Thr Val Arg Asp Arg Pro Ala Pro Ser Leu Val Thr Val Phe
                115                 120                 125

Lys Glu Leu Arg Arg Ser Ile Pro Glu Phe Ser Met Pro Lys Cys Gly
        130                 135                 140

Cys Leu Asp Ala Trp Cys Arg Glu Gly Val Leu Leu Ile Asn Thr Val
```

-continued

```
            145                 150                 155                 160
Phe Thr Val Val Lys Gly Gln Pro Gly Ser His Glu Ala Leu Gly Trp
            165                 170                 175
Gln Ile Leu Ser Asp Arg Val Leu Gln Ala Leu Ser Glu Gln Arg Glu
            180                 185                 190
Gly Leu Val Phe Leu Leu Trp Gly Leu Gln Ala Gln Lys Lys Glu Tyr
            195                 200                 205
Leu Ile Asp Pro Arg Lys His Leu Ile Leu Arg Ser Ser His Pro Ser
            210                 215                 220
Pro Arg Ala Gln Gly Ala Arg Asn Pro Phe Val Gly Asn Asn His Phe
225                 230                 235                 240
Val Leu Ala Asn Glu Tyr Leu Ser Arg Gly Glu Arg Val Asp Trp
            245                 250                 255
Asn Val Leu Cys Ser Lys
            260

<210> SEQ ID NO 69
<211> LENGTH: 881
<212> TYPE: PRT
<213> ORGANISM: Herpes simplex virus 2

<400> SEQUENCE: 69

Met Ala Ala Ser Gly Gly Glu Gly Ser Arg Asp Val Arg Ala Pro Gly
1               5                   10                  15
Pro Pro Pro Gln Gln Pro Gly Ala Arg Pro Ala Val Arg Phe Arg Asp
            20                  25                  30
Glu Ala Phe Leu Asn Phe Thr Ser Met His Gly Val Gln Pro Ile Ile
            35                  40                  45
Ala Arg Ile Arg Glu Leu Ser Gln Gln Gln Leu Asp Val Thr Gln Val
            50                  55                  60
Pro Arg Leu Gln Trp Phe Arg Asp Val Ala Ala Leu Glu Val Pro Thr
65              70                  75                  80
Gly Leu Pro Leu Arg Glu Phe Pro Phe Ala Ala Tyr Leu Ile Thr Gly
            85                  90                  95
Asn Ala Gly Ser Gly Lys Ser Thr Cys Val Gln Thr Leu Asn Glu Val
            100                 105                 110
Leu Asp Cys Val Val Thr Gly Ala Thr Arg Ile Ala Ala Gln Asn Met
            115                 120                 125
Tyr Val Lys Leu Ser Gly Ala Phe Leu Ser Arg Pro Ile Asn Thr Ile
            130                 135                 140
Phe His Glu Phe Gly Phe Arg Gly Asn His Val Gln Ala Gln Leu Gly
145                 150                 155                 160
Gln His Pro Tyr Thr Leu Ala Ser Ser Pro Ala Ser Leu Glu Asp Leu
            165                 170                 175
Gln Arg Arg Asp Leu Thr Tyr Tyr Trp Glu Val Ile Leu Asp Ile Thr
            180                 185                 190
Lys Arg Ala Leu Ala Ala His Gly Gly Glu Asp Ala Arg Asn Glu Phe
            195                 200                 205
His Ala Leu Thr Ala Leu Glu Gln Thr Leu Gly Leu Gly Gln Gly Ala
            210                 215                 220
Leu Thr Arg Leu Ala Ser Val Thr His Gly Ala Leu Pro Ala Phe Thr
225                 230                 235                 240
Arg Ser Asn Ile Ile Val Ile Asp Glu Ala Gly Leu Leu Gly Arg His
            245                 250                 255
Leu Leu Thr Thr Val Val Tyr Cys Trp Trp Met Ile Asn Ala Leu Tyr
```

-continued

```
                  260                 265                 270
    His Thr Pro Gln Tyr Ala Gly Arg Leu Arg Pro Val Leu Val Cys Val
                275                 280                 285

Gly Ser Pro Thr Gln Thr Ala Ser Leu Glu Ser Thr Phe Glu His Gln
    290                 295                 300

Lys Leu Arg Cys Ser Val Arg Gln Ser Glu Asn Val Leu Thr Tyr Leu
    305                 310                 315                 320

Ile Cys Asn Arg Thr Leu Arg Glu Tyr Thr Arg Leu Ser His Ser Trp
                325                 330                 335

Ala Ile Phe Ile Asn Asn Lys Arg Cys Val Glu His Glu Phe Gly Asn
                340                 345                 350

Leu Met Lys Val Leu Glu Tyr Gly Leu Pro Ile Thr Glu Glu His Met
                355                 360                 365

Gln Phe Val Asp Arg Phe Val Val Pro Glu Ser Tyr Ile Thr Asn Pro
                370                 375                 380

Ala Asn Leu Pro Gly Trp Thr Arg Leu Phe Ser Ser His Lys Glu Val
    385                 390                 395                 400

Ser Ala Tyr Met Ala Lys Leu His Ala Tyr Leu Lys Val Thr Arg Glu
                405                 410                 415

Gly Glu Phe Val Val Phe Thr Leu Pro Val Leu Thr Phe Val Ser Val
                420                 425                 430

Lys Glu Phe Asp Glu Tyr Arg Arg Leu Thr Gln Gln Pro Thr Leu Thr
                435                 440                 445

Met Glu Lys Trp Ile Thr Ala Asn Ala Ser Arg Ile Thr Asn Tyr Ser
                450                 455                 460

Gln Ser Gln Asp Gln Asp Ala Gly His Val Arg Cys Glu Val His Ser
    465                 470                 475                 480

Lys Gln Gln Leu Val Val Ala Arg Asn Asp Ile Thr Tyr Val Leu Asn
                485                 490                 495

Ser Gln Val Ala Val Thr Ala Arg Leu Arg Lys Met Val Phe Gly Phe
                500                 505                 510

Asp Gly Thr Phe Arg Thr Phe Glu Ala Val Leu Arg Asp Asp Ser Phe
                515                 520                 525

Val Lys Thr Gln Gly Glu Thr Ser Val Glu Phe Ala Tyr Arg Phe Leu
                530                 535                 540

Ser Arg Leu Met Phe Gly Gly Leu Ile His Phe Tyr Asn Phe Leu Gln
    545                 550                 555                 560

Arg Pro Gly Leu Asp Ala Thr Gln Arg Thr Leu Ala Tyr Gly Arg Leu
                565                 570                 575

Gly Glu Leu Thr Ala Glu Leu Leu Ser Leu Arg Arg Asp Ala Ala Gly
                580                 585                 590

Ala Ser Ala Thr Arg Ala Ala Asp Thr Ser Asp Arg Ser Pro Gly Glu
                595                 600                 605

Arg Ala Phe Asn Phe Lys His Leu Gly Pro Arg Asp Gly Pro Asp
                610                 615                 620

Asp Phe Pro Asp Asp Leu Asp Val Ile Phe Ala Gly Leu Asp Glu
    625                 630                 635                 640

Gln Gln Leu Asp Val Phe Tyr Cys His Tyr Ala Leu Glu Glu Pro Glu
                645                 650                 655

Thr Thr Ala Ala Val His Ala Gln Phe Gly Leu Leu Lys Arg Ala Phe
                660                 665                 670

Leu Gly Arg Tyr Leu Ile Leu Arg Glu Leu Phe Gly Glu Val Phe Glu
                675                 680                 685
```

-continued

| Ser | Ala | Pro | Phe | Ser | Thr | Tyr | Val | Asp | Asn | Val | Ile | Phe | Arg | Gly | Cys |
| | | | | 690 | | | | 695 | | | | 700 | | | |

| Glu | Leu | Leu | Thr | Gly | Ser | Pro | Arg | Gly | Gly | Leu | Met | Ser | Val | Ala | Leu |
| 705 | | | | | 710 | | | | | 715 | | | | | 720 |

| Gln | Thr | Asp | Asn | Tyr | Thr | Leu | Met | Gly | Tyr | Thr | Tyr | Thr | Arg | Val | Phe |
| | | | | 725 | | | | | 730 | | | | | 735 | |

| Ala | Phe | Ala | Glu | Glu | Leu | Arg | Arg | His | Ala | Thr | Ala | Gly | Val | Ala |
| | | | 740 | | | | | 745 | | | | | 750 | |

| Glu | Phe | Leu | Glu | Glu | Ser | Pro | Leu | Pro | Tyr | Ile | Val | Leu | Arg | Asp | Gln |
| | | | 755 | | | | | 760 | | | | | 765 | | |

| His | Gly | Phe | Met | Ser | Val | Val | Asn | Thr | Asn | Ile | Ser | Glu | Phe | Val | Glu |
| | 770 | | | | | 775 | | | | | 780 | | | | |

| Ser | Ile | Asp | Ser | Thr | Glu | Leu | Ala | Met | Ala | Ile | Asn | Ala | Asp | Tyr | Gly |
| 785 | | | | | 790 | | | | | 795 | | | | | 800 |

| Ile | Ser | Ser | Lys | Leu | Ala | Met | Thr | Ile | Thr | Arg | Ser | Gln | Gly | Leu | Ser |
| | | | | 805 | | | | | 810 | | | | | 815 | |

| Leu | Asp | Lys | Val | Ala | Ile | Cys | Phe | Thr | Pro | Gly | Asn | Leu | Arg | Leu | Asn |
| | | | 820 | | | | | 825 | | | | | 830 | | |

| Ser | Ala | Tyr | Val | Ala | Met | Ser | Arg | Thr | Thr | Ser | Ser | Glu | Phe | Leu | His |
| | | | 835 | | | | | 840 | | | | | 845 | | |

| Met | Asn | Leu | Asn | Pro | Leu | Arg | Glu | Arg | His | Glu | Arg | Asp | Asp | Val | Ile |
| | 850 | | | | | 855 | | | | | 860 | | | | |

| Ser | Glu | His | Ile | Leu | Ser | Ala | Leu | Arg | Asp | Pro | Asn | Val | Val | Ile | Val |
| 865 | | | | | 870 | | | | | 875 | | | | | 880 |

| Tyr |

<210> SEQ ID NO 70
<211> LENGTH: 3404
<212> TYPE: DNA
<213> ORGANISM: Artificial
<220> FEATURE:
<223> OTHER INFORMATION: Synthetic DNA sequence of GenBank accession
NC_001798 region: 11846..15249

<400> SEQUENCE: 70

```
tttattgacc gttcgttcgc ccggcggtgc cgtcgccgcg cgcagaggga atatgcaagc      60
gggcggggtg gggaggaaag aaggtttcag gttccggggg ttgggtctgc gtcgtccagg     120
gtggggctga tctgaatttc ccgcagaacc tcgaccagta ggtctgttgt gtttgctggg     180
aactcgcccg ccgttgggga tacggggcg ggggtgtgg tcgggcggac gtccaggggt      240
gcgttatcgc accccgcgc cgcctcgggg gccgtccgt agatcgttgc ggtgatgtag      300
atggtgtccg gggtccacac caccgtcagg atgccggccg tcgcactccg gacgcttttcg    360
ccgtgcgatg agctgaccca ggagtcaaag gggtacgcgt acatatgggc gtcccaccag    420
cgctccagcc tctgggtact agcgcgtcct ataaagcggt atgcgcaaaa ttcggcacga    480
cagtcgataa tcaccagcag cccgatgggg gtgtgttgta tcaccacgcc tccgcggggc    540
aggcggtcct ggcgcgctcg accccgcgtc agaaccgcgc gcgtccctga ctcaaacacg    600
tgcaccacct gtgccgcgtc cggcagcgcg ctcgttagcg acgccctggg gtgatgtagg    660
ctgtacgcga tggtcgtctg ggggttcccc atgtctcggg ggggtggggg tgaatgtcac    720
ccggcccggg tgcggtggga acgcgaggga atggagggtt aatagacaat gaccacattc    780
ggatcgcgta gagcagatag tatgtgctcg ctaatgacgt catcgcgttc gtggcgctcc    840
cggagcgggt ttagattcat gtgcaggaac tcgatgaggg tggtgcggga catggctacg    900
tacgcgctgt ttaggcgcag gtttccgggc gtgaagcata tggcgacctt gtccagactg    960
```

```
agcccctggg agcgcgtgat ggtcatcgcg agtttggagc tgatgccgta gtcggcgttg   1020
atggccatgg ccagctccgt ggagtcgatc gactcgacaa actcactgat gttggtattg   1080
acgacagaca tgaagccgtg ctggtcccgc aggacgatgt agggcagggg ggactcctcc   1140
aagaactcgg ccacgccggc cgtcgcgtgc cgccgccgca gctcctccgc gaacgcgaac   1200
acccgggtgt acgtgtaccc catcagcgtg tagttgtccg tctgcagggc cacggacatc   1260 agcccccccgc gcggcgagcc ggtcagcagc tcgcagcccc ggaaaatgac attgtccacg   1320
taggtgctga aggggcgct ctcaaacacc tccccgaaga gctcccgtag gataaggtat   1380
cgccccagaa aggccctctt caggagccca aactgggcgt ggacggccgc ggtggtctca   1440
ggctcttcga gggcgtagtg gcagtagaac acgtccagct gctgttcgtc cagcccggcg   1500
aagataacgt caaggtcgtc gtcggggaag tcgtccgggc cccgtcccg cgggcccagg   1560 tgcttaaaat tgaacgcacg ctcccccgga gagcggtcgc tggtgtcggc ggccctggtt   1620
gccgatgcgc cggcggcgtc ccggcgtagc gacaggagtt ctgccgtcag ctcccctagg   1680
cggccgtagg ccagggtcct ctgggtcgcg tccaggccgg ggcgctggag aaagttgtaa   1740
aagtgaatca gcccgccgaa catgagccgc gacaggaacc ggtaggcgaa ctccaccgag   1800 gtctcccct gggtcttcac gaagctgtcg tcgcgcagca cagcctcgaa ggtccgaaac   1860
gtcccgtcga acccaaacac catctttcgg aggcgcgcgg tcaccgcgac ctggctgttg   1920
aggacgtacg tgatgtcgtt ccgggccacg actagctgtt gcttgctgtg cacctcacag   1980
cgcacgtgcc ccgcgtcctg gtcctgactc tgggagtagt tggtgatgcg actggcgttg   2040
gccgtgatcc actttttccat ggtcagcgtg ggttgctgcg tgagccgtcg atactcgtca   2100
aactctttga ccgacacaaa cgtgagcacg gggagggtaa acacaacaaa ctcccccctcg   2160 cgagtcacct ttaggtaggc gtggagcttg gccatgtacg cgctgacctc cttgtgggac   2220
gagaacagcc gcgtccaccc cggaaggttg gccgggttgg tgatgtaact ttccgggacg   2280
acaaagcggt ccacaaactg catgtgctcc tcggtgatgg gaaggccgta ctccagcacc   2340
ttcatgaggt tcccgaactc gtgctccaca catcgcttgt tgttaatgaa aatgggcccag   2400 ctgtgcgaga ggcgcgtgta ctcgcgtagg gtgcggttgc agatgaggta cgtgagcacg   2460 tttttcgctct gccggacgga gcatcgcagt ttttggtgtt cgaaggtgga ctccagcgag   2520
gccgtctggg tcggcgaccc cacgcacacc agcaccggcc gcaggcggcc cgcgtactgg   2580
ggggtgtggt acagggcgtt aatcatccac cagcaataca ccacggtcgt gagtaggtgc   2640
cgccccagga gcccggcctc gtcgatgacg ataatgttgc tgcgggtgaa agccggcagc   2700
gccccgtgtg tgaccgaggc caggcgcgtg agggcaccct ggcccagccc caaagtctgc   2760
tctagggcgg tgagggcgtg gaactcgttt cgcgcgtctt cgccccgtg cgccgccagg   2820 gcccgcttgg tgatgtcgag gatcacctcc cagtagtacg tcaggtctcg ccgctgcagg   2880
tcttccagcg aggcggggct gctggccagg gtgtacgggt gctgccccag ctgggcctgg   2940
acgtgattcc cgcgaaaccc gaactcgtga aagatggtgt tgatgggtcg actcagaaac   3000
gcccccgaga gcttaacgta catgttctgc gccgcgattc gcgtggcgcc cgtgaccacg   3060
cagtccagga cctcgttgag gtctgcacg cacgtactct ttccggatcc ggcgttgccg   3120
gtgatgagat acgccgcgaa cggaaactcc cggagcggca ggcggtcgg gacctccaag   3180 gccgccacgt cccggaacca ctgcaggcgc ggcacctgcg tgacgtcgag ctgctgctgc   3240
gagagctctc ggatgcgtgc gatgattggt tggaccccgt gcatggacgt aaaatttaaa   3300
aacgcctcgt ccctgaaccg cacggcgggt ctggccccgg gctgctgtgg gggcggacct   3360
```

```
ggtgcccgga cgtcccgcga gccctccccg ccggacgccg ccat              3404
```

<210> SEQ ID NO 71
<211> LENGTH: 678
<212> TYPE: PRT
<213> ORGANISM: Herpes simplex virus 2

<400> SEQUENCE: 71

```
Met Ala Ala Gln Arg Ala Arg Ala Pro Ala Met Arg Thr Arg Gly Gly
 1               5                  10                  15

Asp Ala Ala Leu Cys Ala Pro Glu Asp Gly Trp Val Lys Val His Pro
            20                  25                  30

Thr Pro Gly Thr Met Leu Phe Arg Glu Ile Leu Leu Gly Gln Met Gly
        35                  40                  45

Tyr Thr Glu Gly Gln Gly Val Tyr Asn Val Val Arg Ser Ser Glu Ala
    50                  55                  60

Ala Thr Arg Gln Leu Gln Ala Ala Ile Phe His Ala Leu Leu Asn Ala
65                  70                  75                  80

Thr Thr Tyr Arg Asp Leu Glu Glu Asp Trp Arg Arg His Val Val Ala
                85                  90                  95

Arg Gly Leu Gln Pro Gln Arg Leu Val Arg Arg Tyr Arg Asn Ala Arg
            100                 105                 110

Glu Gly Asp Ile Ala Gly Val Ala Glu Arg Val Phe Asp Thr Trp Arg
        115                 120                 125

Cys Thr Leu Arg Thr Thr Leu Leu Asp Phe Ala His Gly Val Val Asp
    130                 135                 140

Cys Phe Ala Pro Gly Gly Pro Ser Gly Pro Thr Ser Phe Pro Lys Tyr
145                 150                 155                 160

Ile Asp Trp Leu Thr Cys Leu Gly Leu Val Pro Ile Leu Arg Lys Thr
                165                 170                 175

Arg Glu Gly Glu Ala Thr Gln Arg Leu Gly Ala Phe Leu Arg Gln His
            180                 185                 190

Thr Leu Pro Arg Gln Leu Ala Thr Val Ala Gly Ala Ala Glu Arg Ala
        195                 200                 205

Gly Pro Gly Leu Leu Asp Leu Ala Val Ala Phe Asp Ser Thr Arg Met
    210                 215                 220

Ala Glu Tyr Asp Arg Val His Ile Tyr Tyr Asn His Arg Arg Gly Glu
225                 230                 235                 240

Trp Leu Val Arg Asp Pro Val Ser Gly Gln Arg Gly Glu Cys Leu Val
                245                 250                 255

Leu Cys Pro Pro Leu Trp Thr Gly Asp Arg Leu Val Phe Asp Ser Pro
            260                 265                 270

Val Gln Arg Leu Cys Pro Glu Ile Val Ala Cys His Ala Leu Arg Glu
        275                 280                 285

His Ala His Ile Cys Arg Leu Arg Asn Thr Ala Ser Val Lys Val Leu
    290                 295                 300

Leu Gly Arg Lys Ser Asp Ser Glu Arg Gly Val Ala Gly Ala Ala Arg
305                 310                 315                 320

Val Val Asn Lys Ala Leu Gly Glu Asp Asp Glu Thr Lys Ala Gly Ser
                325                 330                 335

Ala Ala Ser Arg Leu Val Arg Leu Ile Ile Asn Met Lys Gly Met Arg
            340                 345                 350

His Val Gly Asp Ile Asn Asp Thr Val Arg Ala Tyr Leu Asp Glu Ala
        355                 360                 365
```

```
Gly Gly His Leu Ile Asp Thr Pro Ala Val Asp His Thr Leu Pro Gly
        370                 375                 380

Phe Gly Lys Gly Gly Thr Gly Arg Gly Ser Arg Pro Gln Asp Pro Gly
385                 390                 395                 400

Ala Arg Pro Gln Gln Leu Arg Gln Ala Phe Gln Thr Ala Val Val Asn
                405                 410                 415

Asn Ile Asn Gly Met Leu Glu Gly Tyr Ile Asn Asn Leu Phe Gly Thr
            420                 425                 430

Ile Glu Arg Leu Arg Glu Thr Asn Ala Gly Leu Ala Thr Gln Leu Gln
        435                 440                 445

Ala Arg Asp Arg Glu Leu Arg Ala Gln Ala Gly Ala Leu Glu Arg
    450                 455                 460

Glu Gln Arg Ala Ala Asp Arg Ala Ala Gly Gly Ala Gly Arg Pro
465                 470                 475                 480

Ala Glu Ala Asp Leu Leu Arg Ala Asp Tyr Asp Ile Ile Asp Val Ser
                485                 490                 495

Lys Ser Met Asp Asp Thr Tyr Val Ala Asn Ser Phe Gln His Gln
            500                 505                 510

Tyr Ile Pro Ala Tyr Gly Gln Asp Leu Glu Arg Leu Ser Arg Leu Trp
        515                 520                 525

Glu His Glu Leu Val Arg Cys Phe Lys Ile Leu Arg His Arg Asn Lys
    530                 535                 540

Gln Gly Gln Glu Thr Ser Ile Ser Tyr Ser Ser Gly Ala Ile Ala Ser
545                 550                 555                 560

Phe Val Ala Pro Tyr Phe Glu Tyr Val Leu Arg Ala Pro Arg Ala Gly
                565                 570                 575

Ala Leu Ile Thr Gly Ser Asp Val Ile Leu Gly Glu Glu Leu Trp
            580                 585                 590

Glu Ala Val Phe Lys Lys Thr Arg Leu Gln Thr Tyr Leu Thr Asp Val
        595                 600                 605

Ala Ala Leu Phe Val Ala Asp Val Gln His Ala Ala Leu Pro Arg Pro
    610                 615                 620

Pro Ser Pro Thr Pro Ala Asp Phe Arg Ala Ser Ala Ser Pro Arg Gly
625                 630                 635                 640

Gly Ser Arg Ser Arg Thr Arg Thr Arg Ser Arg Ser Pro Gly Arg Thr
                645                 650                 655

Pro Arg Gly Ala Pro Asp Gln Gly Trp Gly Val Glu Arg Arg Asp Gly
            660                 665                 670

Arg Pro His Ala Arg Arg
        675

<210> SEQ ID NO 72
<211> LENGTH: 2916
<212> TYPE: DNA
<213> ORGANISM: Artificial
<220> FEATURE:
<223> OTHER INFORMATION: Synthetic DNA sequence of GenBank accession
      NC_001798 region: 15248..18163

<400> SEQUENCE: 72
atggccgcac agcgcgcgcg ggcgccggcg atgcggacgc ggggcggcga cgcggcgcta    60 tgcgccccg aggacggctg ggtgaaggtt caccccaccc ccgggacgat gttgttccgc   120
gagattctcc tcgggcagat ggggtacacc gagggtcagg gggtgtacaa cgtcgtccgg   180
tccagcgagg ccgccacccg acagctgcag gcggcgatct tccacgcgct cctcaacgcc   240
acgacgtacc gggacctgga ggaggactgg cgccgccacg tggtggcccg cggcctccag   300
```

| | |
|---|---|
| ccgcagcggc tggttcgcag gtaccggaac gcccgggagg gcgatatcgc cggggtggcc | 360 |
| gagcgggtgt tcgacacgtg gcgatgcacg ctcaggacga cgctgctgga ctttgcccac | 420 |
| ggggtggtag actgctttgc gccgggcggc ccaagcggac cgaccagctt ccccaaatat | 480 |
| atcgactggc tgacgtgtct ggggctggtt cccatattgc gcaagacgcg cgagggggag | 540 |
| gcgacgcagc gcctggggc gtttctcagg cagcacacgc tgccccggca gctggccacg | 600 |
| gtcgccgggg ccgcggagcg cgccggcccg gggcttctgg atctggccgt cgcgttcgac | 660 |
| tccacgcgca tggcggaata cgaccgcgtg cacatctact acaaccatcg ccgggggag | 720 |
| tggctggtgc gcgacccggt cagcgggcag cgcggcgagt gcctggtgct gtgcccccc | 780 |
| ctgtggaccg gcgaccgcct ggtcttcgat tcgcccgttc agcggctgtg ccccgagatc | 840 |
| gtcgcgtgcc acgccctccg ggaacacgcg cacatctgcc gtctgcgcaa caccgcgtcc | 900 |
| gtcaaggtgc tgttggggcg caagagcgac agcgagcgcg gggtggctgg cgccgcgcgg | 960 |
| gtcgtcaata aggcgctggg ggaggatgac gagacgaagg ccggctcggc cgcctcgcgt | 1020 |
| ctcgtgcggc tcatcatcaa catgaagggc atgcgccacg tgggcgacat caacgacacg | 1080 |
| gtacgcgcct acttggacga ggcgggggg cacctgatcg acaccccgc cgtcgaccac | 1140 |
| accctccctg ggttcggcaa gggcggcacc ggccgcgggt cgcgccccca ggacccgggg | 1200 |
| gcgcgaccgc agcagcttcg ccaggcgttt cagacgccg tggtcaacaa catcaacggc | 1260 |
| atgctggagg gctatatcaa taatctcttt ggaaccatag aacgcctgcg agagacgaac | 1320 |
| gcgggtctgg cgacccagct gcaggcgcgc gaccgcgagc tgcggcgcgc ccaggcgggg | 1380 |
| gcgctggagc gggagcagcg cgcggcggac cgggcggccg ggggaggcgc gggccgcccg | 1440 |
| gcggaggcgg atcttctccg ggccgactac gacattatcg acgtcagcaa gtccatggac | 1500 |
| gacgacacgt acgtggccaa cagtttccag caccagtaca tccccgcgta cggccaggac | 1560 |
| ctcgagcgcc tgtcgcgcct ctgggagcac gagctggtgc gctgcttcaa gattctgcgc | 1620 |
| caccgcaaca agcagggcca ggaaacgtcg atctcgtact ctagcgggc gatcgcctcc | 1680 |
| ttcgtggccc cgtatttcga gtacgtgctt cgcgccccc gagcgggcgc gctcatcacc | 1740 |
| ggctccgatg tcatcctagg ggaggaggag ttatgggagg cggtctttaa gaaaacccgc | 1800 |
| ctgcagacgt acctgacaga cgtcgcggcc ctgttcgtgg cggacgtaca gcacgcggct | 1860 |
| ctgccccggc ccccctcccc aaccccgcc gatttccggg cgagcgcgtc cccgcggggc | 1920 |
| gggtcccggt cccggacccg gacccgatcc cggtcgcccg ggagaacgcc gaggggtgcg | 1980 |
| ccggaccagg gctggggcgt cgaacgcagg gatggccgac cccacgcccg ccgatgaggg | 2040 |
| aacggccgcc gccatcctca aacaggccat cgccggggac cgcagtctgg tcgaggtggc | 2100 |
| ggagggatc agcaaccagg cgctgctgcg catggcctgc gaggtgcgcc aggtcagcga | 2160 |
| tcgccagccg cggtttaccg cgaccagcgt cctgcgcgtt gacgtcaccc ccagggggcg | 2220 |
| gttgcggttc gttctggacg ggagttccga cgacgcgtac gtggcgtcgg aggattactt | 2280 |
| taagcgctgc ggggaccagc cgacgtatcg cggttttgcg gtcgtcgtcc tcacggccaa | 2340 |
| cgaggaccac gtgcacagcc tggccgtgcc cccctcgtt ctgctgcacc ggctctcctt | 2400 |
| gtttcgcccc acggacctcc gggacttcga gctcgtctgc ctgctgatgt acctggagaa | 2460 |
| ctgtccccgg agccacgcca cgccctcgct gttcgtcaag gtgtcggcgt ggttgggggt | 2520 |
| cgtggcccgc cacgcgtctc ccttcgagcg cgtccgctgc cttctcctcc gcagctgcca | 2580 |
| ctggatcctg aacacgctaa tgtgcatggc gggcgtgaag cccttcgacg acgagctagt | 2640 |
| cctgccccac tggtacatgg cccactacct gctggccaac aatccgcccc cgtcctctc | 2700 |

```
ggccctgttt tgcgccaccc cgcagagctc tgcgttgcag ttgcccgggc ccgtcccccg    2760
cacggactgt gtggcctata acccggccgg cgtcatggga agctgctgga attccaagga    2820
cctgcgttcg gctctggtgt attggtggct ttcggggagc cccaaacgac ggacctcgtc    2880
gcttttctat cggttttgct aactccggaa aataaa                              2916
```

<210> SEQ ID NO 73
<211> LENGTH: 752
<212> TYPE: PRT
<213> ORGANISM: Herpes simplex virus 2

<400> SEQUENCE: 73

```
Met Glu Ala Pro Gly Ile Val Trp Val Glu Ser Val Ser Ala Ile
1               5                   10                  15

Thr Leu Tyr Ala Val Trp Leu Pro Pro Arg Thr Arg Asp Cys Leu His
            20                  25                  30

Ala Leu Leu Tyr Leu Val Cys Arg Asp Ala Ala Gly Glu Ala Arg Ala
        35                  40                  45

Arg Phe Ala Glu Val Ser Val Gly Ser Ser Asp Leu Gln Asp Phe Tyr
    50                  55                  60

Gly Ser Pro Asp Val Ser Ala Pro Gly Ala Val Ala Ala Arg Ala
65                  70                  75                  80

Ala Thr Ala Pro Ala Ala Ser Pro Leu Glu Pro Leu Gly Asp Pro Thr
                85                  90                  95

Leu Trp Arg Ala Leu Tyr Ala Cys Val Leu Ala Ala Leu Glu Arg Gln
            100                 105                 110

Thr Gly Arg Trp Ala Leu Phe Val Pro Leu Arg Leu Gly Trp Asp Pro
        115                 120                 125

Gln Thr Gly Leu Val Val Arg Val Glu Arg Ala Ser Trp Gly Pro Pro
    130                 135                 140

Ala Ala Pro Arg Ala Ala Leu Leu Asp Val Glu Ala Lys Val Asp Val
145                 150                 155                 160

Asp Pro Leu Ala Leu Ser Ala Arg Val Ala Glu His Pro Gly Ala Arg
                165                 170                 175

Leu Ala Trp Ala Arg Leu Ala Ala Ile Arg Asp Ser Pro Gln Cys Ala
            180                 185                 190

Ser Ser Ala Ser Leu Ala Val Thr Ile Thr Arg Thr Ala Arg Phe
        195                 200                 205

Ala Arg Glu Tyr Thr Thr Leu Ala Phe Pro Pro Thr Arg Lys Glu Gly
    210                 215                 220

Ala Phe Ala Asp Leu Val Glu Val Cys Glu Val Gly Leu Arg Pro Arg
225                 230                 235                 240

Gly His Pro Gln Arg Val Thr Ala Arg Val Leu Leu Pro Arg Gly Tyr
                245                 250                 255

Asp Tyr Phe Val Ser Ala Gly Asp Gly Phe Ser Ala Pro Ala Leu Val
            260                 265                 270

Ala Leu Phe Arg Gln Trp His Thr Thr Val His Ala Ala Pro Gly Ala
        275                 280                 285

Leu Ala Pro Val Phe Ala Phe Leu Gly Pro Gly Phe Glu Val Arg Gly
    290                 295                 300

Gly Pro Val Gln Tyr Phe Ala Val Leu Gly Phe Pro Gly Trp Pro Thr
305                 310                 315                 320

Phe Thr Val Pro Ala Ala Ala Ala Glu Ser Ala Arg Asp Leu Val
                325                 330                 335
```

-continued

```
Arg Gly Ala Ala Ala Thr His Ala Ala Cys Leu Gly Ala Trp Pro Ala
            340                 345                 350

Val Gly Ala Arg Val Val Leu Pro Arg Ala Trp Pro Ala Val Ala
        355                 360                 365

Ser Glu Ala Ala Gly Arg Leu Leu Pro Ala Phe Arg Glu Ala Val Ala
370                 375                 380

Arg Trp His Pro Thr Ala Thr Thr Ile Gln Leu Leu Asp Pro Ala
385                 390                 395                 400

Ala Val Gly Pro Val Trp Thr Ala Arg Phe Cys Phe Ser Gly Leu Gln
                405                 410                 415

Ala Gln Leu Leu Ala Ala Leu Ala Gly Leu Gly Glu Ala Gly Leu Pro
            420                 425                 430

Glu Ala Arg Gly Arg Ala Gly Leu Glu Arg Leu Asp Ala Leu Val Ala
        435                 440                 445

Ala Ala Pro Ser Glu Pro Trp Ala Arg Ala Val Leu Glu Arg Leu Val
    450                 455                 460

Pro Asp Ala Cys Asp Ala Cys Pro Ala Leu Arg Gln Leu Leu Gly Gly
465                 470                 475                 480

Val Met Ala Ala Val Cys Leu Gln Ile Glu Gln Thr Ala Ser Ser Val
                485                 490                 495

Lys Phe Ala Val Cys Gly Gly Thr Gly Ala Ala Phe Trp Gly Leu Phe
            500                 505                 510

Asn Val Asp Pro Gly Asp Ala Asp Ala Ala His Gly Ala Ile Gln Asp
        515                 520                 525

Ala Arg Arg Ala Leu Glu Ala Ser Val Arg Ala Val Leu Ser Ala Asn
    530                 535                 540

Gly Ile Arg Pro Arg Leu Ala Pro Ser Leu Ala Pro Glu Gly Val Tyr
545                 550                 555                 560

Thr His Val Val Thr Trp Ser Gln Thr Gly Ala Trp Phe Trp Asn Ser
                565                 570                 575

Arg Asp Asp Thr Asp Phe Leu Gln Gly Phe Pro Leu Arg Gly Ala Ala
            580                 585                 590

Tyr Ala Ala Ala Ala Glu Val Met Arg Asp Ala Leu Arg Arg Ile Leu
        595                 600                 605

Arg Arg Pro Ala Ala Gly Pro Pro Glu Glu Ala Val Cys Ala Ala Arg
    610                 615                 620

Gly Val Met Glu Asp Ala Cys Asp Arg Phe Val Leu Asp Ala Phe Gly
625                 630                 635                 640

Arg Arg Leu Asp Ala Glu Tyr Trp Ser Val Leu Thr Pro Pro Gly Glu
                645                 650                 655

Ala Asp Asp Pro Leu Pro Gln Thr Ala Phe Arg Gly Gly Ala Leu Leu
            660                 665                 670

Asp Ala Glu Gln Tyr Trp Arg Arg Val Val Arg Val Cys Pro Gly Gly
        675                 680                 685

Gly Glu Ser Val Gly Val Pro Val Asp Leu Tyr Pro Arg Pro Leu Val
    690                 695                 700

Leu Pro Pro Val Asp Cys Ala His His Leu Arg Glu Ile Leu Arg Glu
705                 710                 715                 720

Ile Gln Leu Val Phe Thr Gly Val Leu Glu Gly Val Trp Gly Glu Gly
                725                 730                 735

Gly Ser Phe Val Tyr Pro Phe Asp Glu Lys Ile Arg Phe Leu Phe Pro
            740                 745                 750
```

<210> SEQ ID NO 74

<211> LENGTH: 2273
<212> TYPE: DNA
<213> ORGANISM: Artificial
<220> FEATURE:
<223> OTHER INFORMATION: Synthetic DNA sequence of GenBank accession
      NC_001798 region: 18393..20665

<400> SEQUENCE: 74

```
tttattgacc aaattcaggg aaacagaaac cgaatctttt catcgaaagg gtacacaaag      60
ctcccgccct cgccccacac gccttccaga accccgtaa acaccagttg aatctcgcgc     120
aggatctcgc gcaggtgatg ggcgcagtcc acgggggga gcaccaaggg ccgcgggtac     180
agatccacgg ggacgccgac cgactccccg ccccggac atacgcgcac gacgcgtctc     240
cagtattgct ccgcgtccag cagggcgcct ccgcggaagg ccgtttgggg caggggtcg     300
tcggcctcgc ctggggggt cagaacgctc cagtactccg cgtccagacg cctcccgaag     360
gcatccagga caaagcgtc acaggcgtcc tccatgacgc cccgggccgc gcacacggcc     420
tcctccggcg ggcggcggc cggccgcggg aggattcgtc tcagcgcgtc gcgcataacc     480
tcggccgccg cggcgtacgc ggccccgcgg agaggaaatc cctgcaggaa gtcggtgtca     540
tcgcgggagt tccagaacca cgccccggtc tggctccagg tgacgacgtg ggtgtagacg     600
ccctctggcg ccagggaggg ggcgaggcgc gggcgtatgc cgttggccga aagtacggcg     660
cgcacggacg cctcgagggc ccggcgggcg tcctggatcg cgccgtgcgc ggcgtccgcg     720
tccccggggt ccacgttgaa cagcccccag aacgcagccc cggtgccgcc gcagaccgca     780
aacttcaccg agctggccgt ctgctcgatc tgcaggcaga cggcggccat gaccccgccg     840
agcagctgcc ggagcgcggg gcaggcgtcg cacgcgtccg gcaccaggcg ctccagcacg     900
gcccgggccc agggctccga gggggcggcc gccaccagcg cgtccagcct ttccaggccc     960
gcccgccccc gggcttccgg cagcccggcc tccccgaggc ccgcgagggc ggccaggagc    1020
tgggcctgga gcccggagaa acaaaaccgc gccgtccaga ccggcccgac ggccgccggg    1080
gggtcgagta gttggatggt ggtggccgtg gggtgccacc gcgcgaccgc ttcccgaaag    1140
gcgggcagga ggcggccggc cgcctccgag gccacggccg gccatgcccg cggggcagg    1200
acgaccctgg cgcccaccgc gggccaggcc cccaggcacg cggcatgggt ggccgcggcg    1260
ccccgcacca ggtcacgcgc cgactcggcg cggcggcgg ccggcacggt aaacgtgggc    1320
cagcccggaa atcccagcac ggcaaagtat tggacgggcc ctccccggac ctcaaacccg    1380
ggccccagaa aagcgaagac gggggccagg gctccggggg cggcgtggac cgtggtatgc    1440
cactgccgga agagggcgac cagcgccggg gcggagaacc cgtcgccggc gctcacgaag    1500
tagtcgtagc cgcgcggcag cagcaccccg gccgtgaccc gctgcgggtg tccgcggggc    1560
cgcaggccga cctcgcacac ctcgaccagg tccgcgaagg cgccctcctt cctggtcggc    1620
ggaaacgcca gggtggtgta ttcgcgcgca aaacgcgcgg tcctcgtcgt gatggtgacg    1680
gcgagcgagg cggaggacgc gcactggggg ctgtcgcgaa tggcggccag gcgcgcccac    1740
gccaaccgcg cgccggggtg ctcggcgacg cgcgcggaca gggccagcgg gtcgacgtcg    1800
accttggcct ccacgtccag gagggcggcg cgaggagcgg ccggcgggcc ccacgacgcc    1860
ctttcgaccc tcacgaccag acccgtctgc gggtccagc ccaggcgcag cgggacgaag    1920
agggcccacc ggcccgtctg gcgctccagg gccgccagaa cgcacgcata cagcgcccgc    1980
cacagggtcg ggtccccag gggctccagc ggggaggcgg ccggggccgt cgcggcgcgg    2040
gcggccgcga cggccccggg ggccgagacg tcggggagc cgtagaagtc ctgcaggtcg    2100
gacgaaccaa cggacaccctc cgcgaagcgc gcgcgcgcct ccccgcggc gtcgcgacag    2160
```

```
accagataca gcagggcgtg gaggcagtcg cgcgtgcgcg gggcagcca taccgcgtat    2220 agggtaatgg cgctgacgct ctcctccacc caaacgatgc cggggcttc cat            2273
```

<210> SEQ ID NO 75
<211> LENGTH: 734
<212> TYPE: PRT
<213> ORGANISM: Herpes simplex virus 2

<400> SEQUENCE: 75

```
Met Phe Gly Gln Gln Leu Ala Ser Asp Val Gln Gln Tyr Leu Glu Arg
1               5                   10                  15

Leu Glu Lys Gln Arg Gln Lys Val Gly Val Asp Glu Ala Ser Ala
            20                  25                  30

Gly Leu Thr Leu Gly Gly Asp Ala Leu Arg Val Pro Phe Leu Asp Phe
        35                  40                  45

Ala Thr Ala Thr Pro Lys Arg His Gln Thr Val Val Pro Gly Val Gly
50                  55                  60

Thr Leu His Asp Cys Cys Glu His Ser Pro Leu Phe Ser Ala Val Ala
65                  70                  75                  80

Arg Arg Leu Leu Phe Asn Ser Leu Val Pro Ala Gln Leu Arg Gly Arg
                85                  90                  95

Asp Phe Gly Gly Asp His Thr Ala Lys Leu Glu Phe Leu Ala Pro Glu
            100                 105                 110

Leu Val Arg Ala Val Ala Arg Leu Arg Phe Arg Glu Cys Ala Pro Glu
        115                 120                 125

Asp Ala Val Pro Gln Arg Asn Ala Tyr Tyr Ser Val Leu Asn Thr Phe
    130                 135                 140

Gln Ala Leu His Arg Ser Glu Ala Phe Arg Gln Leu Val His Phe Val
145                 150                 155                 160

Arg Asp Phe Ala Gln Leu Leu Lys Thr Ser Phe Arg Ala Ser Ser Leu
                165                 170                 175

Ala Glu Thr Thr Gly Pro Pro Lys Lys Arg Ala Lys Val Asp Val Ala
            180                 185                 190

Thr His Gly Gln Thr Tyr Gly Thr Leu Glu Leu Phe Gln Lys Met Ile
        195                 200                 205

Leu Met His Ala Thr Tyr Phe Leu Ala Ala Val Leu Leu Gly Asp His
    210                 215                 220

Ala Glu Gln Val Asn Thr Phe Leu Arg Leu Val Phe Glu Ile Pro Leu
225                 230                 235                 240

Phe Ser Asp Thr Ala Val Arg His Phe Arg Gln Arg Ala Thr Val Phe
                245                 250                 255

Leu Val Pro Arg Arg His Gly Lys Thr Trp Phe Leu Val Pro Leu Ile
            260                 265                 270

Ala Leu Ser Leu Ala Ser Phe Arg Gly Ile Lys Ile Gly Tyr Thr Ala
        275                 280                 285

His Ile Arg Lys Ala Thr Glu Pro Val Phe Asp Glu Ile Asp Ala Cys
    290                 295                 300

Leu Arg Gly Trp Phe Gly Ser Ser Arg Val Asp His Val Lys Gly Glu
305                 310                 315                 320

Thr Ile Ser Phe Ser Phe Pro Asp Gly Ser Arg Ser Thr Ile Val Phe
                325                 330                 335

Ala Ser Ser His Asn Thr Asn Gly Ile Arg Gly Gln Asp Phe Asn Leu
            340                 345                 350

Leu Phe Val Asp Glu Ala Asn Phe Ile Arg Pro Asp Ala Val Gln Thr
```

355                 360                 365
Ile Met Gly Phe Leu Asn Gln Ala Asn Cys Lys Ile Ile Phe Val Ser
    370                 375                 380

Ser Thr Asn Thr Gly Lys Ala Ser Thr Ser Phe Leu Tyr Asn Leu Arg
385                 390                 395                 400

Gly Ala Ala Asp Glu Leu Leu Asn Val Val Thr Tyr Ile Cys Asp Asp
                405                 410                 415

His Met Pro Arg Val Val Thr His Thr Asn Ala Thr Ala Cys Ser Cys
                420                 425                 430

Tyr Ile Leu Asn Lys Pro Val Phe Ile Thr Met Asp Gly Ala Val Arg
            435                 440                 445

Arg Thr Ala Asp Leu Phe Leu Pro Asp Ser Phe Met Gln Glu Ile Ile
        450                 455                 460

Gly Gly Gln Ala Arg Glu Thr Gly Asp Asp Arg Pro Val Leu Thr Lys
465                 470                 475                 480

Ser Ala Gly Glu Arg Phe Leu Tyr Arg Pro Ser Thr Thr Thr Asn
                485                 490                 495

Ser Gly Leu Met Ala Pro Glu Leu Tyr Val Tyr Val Asp Pro Ala Phe
                500                 505                 510

Thr Ala Asn Thr Arg Ala Ser Gly Thr Gly Ile Ala Val Val Gly Arg
            515                 520                 525

Tyr Arg Asp Asp Phe Ile Ile Phe Ala Leu Glu His Phe Phe Leu Arg
        530                 535                 540

Ala Leu Thr Gly Ser Ala Pro Ala Asp Ile Ala Arg Cys Val Val His
545                 550                 555                 560

Ser Leu Ala Gln Val Leu Ala Leu His Pro Gly Ala Phe Arg Ser Val
                565                 570                 575

Arg Val Ala Val Glu Gly Asn Ser Ser Gln Asp Ser Ala Val Ala Ile
                580                 585                 590

Ala Thr His Val His Thr Glu Met His Arg Ile Leu Ala Ser Ala Gly
            595                 600                 605

Ala Asn Gly Pro Gly Pro Glu Leu Leu Phe Tyr His Cys Glu Pro Pro
        610                 615                 620

Gly Gly Ala Val Leu Tyr Pro Phe Phe Leu Leu Asn Lys Gln Lys Thr
625                 630                 635                 640

Pro Ala Phe Glu Tyr Phe Ile Lys Lys Phe Asn Ser Gly Gly Val Met
                645                 650                 655

Ala Ser Gln Glu Leu Val Ser Val Thr Val Arg Leu Gln Thr Asp Pro
                660                 665                 670

Val Glu Tyr Leu Ser Glu Gln Leu Asn Asn Leu Ile Glu Thr Val Ser
            675                 680                 685

Pro Asn Thr Asp Val Arg Met Tyr Ser Gly Lys Arg Asn Gly Ala Ala
        690                 695                 700

Asp Asp Leu Met Val Ala Val Ile Met Ala Ile Tyr Leu Ala Ala Pro
705                 710                 715                 720

Thr Gly Ile Pro Pro Ala Phe Phe Pro Ile Thr Arg Thr Ser
                725                 730

<210> SEQ ID NO 76
<211> LENGTH: 5861
<212> TYPE: DNA
<213> ORGANISM: Artificial
<220> FEATURE:
<223> OTHER INFORMATION: Synthetic DNA sequence of GenBank accession
      NC_001798 region: 28969..34829

```
<400> SEQUENCE: 76
atgtttggcc agcagctggc gtccgacgtg cagcagtacc tggagcgcct ggagaaacag      60
aggcaacaga aggtgggcgt cgacgaggcg tcggcgggcc tgacgctcgg cggcgatgcg     120
ctgcgcgtcc cttttttgga ttttgccacc gcgacgccca agcgccacca gaccgtggtc     180
ccgggcgtcg ggacgctcca cgactgctgc gagcactcgc cgctcttctc ggccgtcgcg     240
cggcggttgc tgtttaatag cctggtgccg gcgcaactca gggggcgtga ctttgggggc     300
gaccacacgg ccaagctgga gttcctggcc cccgagctgg tgcgggcggt ggcgcgcctg     360
cggtttcggg agtgcgcgcc ggaggacgcc gtgccccaac gcaacgccta ctacagcgtc     420
ctgaacacgt tcaggcccct gcaccgctcc gaagcctttc ggcagttggt tcacttcgtg     480
cgggacttcg cccagttgtt gaaaacctcg ttccgggcct ctagtctcgc ggagactacg     540
ggccccccga agaaacgggc caaggtggac gtggccaccc acgggcagac gtacggcacc     600
ttggagctct tccagaaaat gatactaatg cacgcgacct actttctggc cgccgtgctg     660
ctcggggacc acgcggagca ggtcaacacg ttcctgcggc tcgtgttcga gatcccctg      720
tttagcgaca cggccgtgcg gcacttccgc cagcgcgcca ccgtgtttct agtccccagg     780
cgccacggaa agacctggtt tttggtgccc ctcatcgcgc tgtcgctcgc gtccttccgg     840
gggatcaaga taggctacac ggcccacatc cgcaaggcga ccgagcccgt gtttgatgag     900
atcgacgcct gcctgcgggg ctggtttggc tcgtcccggg tggaccacgt caaggggaa      960
accatctcgt tctcgttccc ggacggctcg cgcagcacga tcgtgtttgc ctccagccac    1020
aacacgaacg taagtacgcc ttcctcccgc ggtgcctgtt tccccggtgc cgccctcccc    1080
gagatcgacc gacagacaaa cacagccaga cgcgagtgtg ggacgacacg cccgcagccc    1140
ccccccccgcc atggcggggg ggaagcctta ctgtttatt gtaatcggac gatgaggctc    1200
tggccacggc ccgcgcgacc gcggggcagc tcgttgcaaa caggcggctg gtatacgatg    1260
acagaacgca gaggcgccac ccggcgctgg tcgggcggat gacgctttcc gcgccgtccc    1320
ggcccacgac gacctcgtgc aggtgggccg tgatgcgcgg gcggcgggtc gcctgccgca    1380
ggataaccgc gtccacgggg tgcccgaaga ggagctgaca caggctcgcg tcccccccgga   1440
cggccagggt gcgctgggcc atattggacc acatgcacgg ggcgacgcag ggacaggcct    1500
ccgccacggc ggggcgcgc cacagcgcgt tggcggaatc gatgtgggcc gtcggggcgc     1560
aggcgccgcc tcctcccggg gggtcggtaa tcctggatag cagccatcct aaatggcggg    1620
cccggctgcc cggggacag agcgacccca ggtcatcatc catggcccag cagtatatgc     1680
ggccgccggg gaggtgccac caggcccccg gacccagggc acagcacgcc ccggattcgg     1740
gggccgtgtc cgtgggtacc aggtaggcgc cgtcagctc gtgggccacg gctcgtccg      1800
cgagctgttc ggcggcgggg tcgggggttt cctccggggg ggaggcagct tccaggtggc    1860
cgaaggctag ggtgcacagc agcggggtcc ggggtgcgt tacgctgcgg aggtggacgg     1920
tggcgcagta gcggcgctcg cggttaaaga agaaaatggc aaagaacgtg ttcgaaggca    1980
ggcgcagcgc cttgggccgc gtcaggtaca ggaagatctc gcagaaaagg gcacgctcgg    2040
ggtcggggtc cggaagggcc acctggcaca gcggctcggt gaggaccgtg aggcaccgaa    2100
aaatcttaag ccgctcgtcc cccgaacga gcgccacac gaagacagag ttggcgatgc      2160
gcgcgacgag gtcggcttcg ggccccgggt cgggggcgcg cgcgtcgggg ggggcgcccc    2220
ggtgacccgg cggggccgcg gctcccgggg ggcctggcgt cgcctgggga cgccagagtg    2280
cccgctgtgc caggttggtg gtggggaagg gaccggagac gcaccaaaag cagaggggcc    2340
```

-continued

| | |
|---|---|
| agcgcgtgta tgagttgggg ggggggtggg tgagcggtgg aacaaaagca cgcgtcagcg | 2400 |
| gacaaggccg ggtcccgtag ccgccccgcg acagaaccgg agtccgacgg cacgcgcgac | 2460 |
| ggggtctgcg aggctgaggt acgccgcggt gttaatggta aacgcaaagc ctcccggaaa | 2520 |
| gaccactagc ccgcagaggc ggcgattgaa cccaaggcag aggtacgcgt agctctctcc | 2580 |
| cggaaggtat tgctcgcaga ccctgtgtgg ggcagtggag gggctgccct ccatgaagcg | 2640 |
| acatttactc tgctcgcgtc cattgacgtc accgtcaatc accactgcga ttggacggtt | 2700 |
| ggtgaggcgc agcgtgtctc cgctggtgct gtagtagtca aacgcgtagt gggcgtcgga | 2760 |
| gtcggcgaag cgggcgggga tgtcgtcgct gagagggacg agccgccgcc gccgcccccg | 2820 |
| accgccctgg ccgcccagat gcgccagcac ggccagggcg tacgcggtgt gaaagaacgc | 2880 |
| gtcggggcg gtcccctcga gggcgcgcat caggttctcc aggagcacgg ggaagcgccg | 2940 |
| cgtcacctcc cctagccact cgctctggtg ggggccaaag tcgtagcgca ggcgctggaa | 3000 |
| gatgcgcggg ccgccttgga gcgcggcccg gatagagtgg cccagggccc gcagacacgc | 3060 |
| gatctggatg cgcgcgacga aggccacctc ggccgcgatg tcaaagggct gcagcacggg | 3120 |
| gcgcgggtgg cgcaggggtc cctcgagcgc gggaaagcga cgcagcagcg ccgtctgggc | 3180 |
| cgcgggggac agctggtggg ggcgcacgac gcgctcggcg gcacaggcct ccgtcagggc | 3240 |
| cgtggccagc tcggaggaca gccgcggggg cgggcgcgt cgcccgcccc acgccaccga | 3300 |
| attctcgtag gagacgacga cgaagcgctg cttggtcccg tagtgatggc gcaggaccac | 3360 |
| ggagatggag cgacggctcc acagccagtc gggccggtcg ccgccggcca gagcttccca | 3420 |
| cccgcggtcc agccactcga ccagcgatcg cggcttggcg gtccccggca cgagggtgag | 3480 |
| cacgtcgttg aggacgtcct cgcccgcggc ccggggccc cccggctgg caaagcgccc | 3540 |
| cccgccgggc ggctccaggc ccgccagcac cgcctccgcg tccgacgcgc ccagggctcc | 3600 |
| cccgctgacg gcctggtgga ccagggcgcc ctggcggagc cccgaggcga cgccggaggc | 3660 |
| cgcgtgcttg gggcgcgcgc ggaccgggtg gcggcgggtg acgtcctgca cggcccgctg | 3720 |
| gaccagcgcg aggatctcct cgttctcttg cgtgatggac acgtcctccg cggtggccgt | 3780 |
| gtcgcctccc ggggccgtga gctgctcctc cggggagatg gggggtctg gggtgccgac | 3840 |
| aacggccggc ccggccccgc ccgagaccga ggacgcctgg ggagtggggg tgccgctttc | 3900 |
| ccccatcccc agggacaggt gggcgccgc ctccgtcgcg gcggcgggag ccgcggcccc | 3960 |
| cagccgcgcg acgtagcgac aaaagtggcg acagaggcgc atgaggcgcg cgccgtcggc | 4020 |
| cgcgtatcgc gtgtttggcg ggacgagctc gtcgtaactg aacaggagca cgcgggcaca | 4080 |
| ggtcgcccac gggccccacg ccaggcgcag cgccgcgacc gtgtacgggt cgtacacgcc | 4140 |
| ttgggcgtcg cacgcgaccg gcaggagac gaacagcccg cccgcgctgg ggacgcgcgg | 4200 |
| caggaggtcc gggtgcgccg ggatgacggg ggctaggatc gcccccaccg catccgccgg | 4260 |
| cacgtaggcg gcaaacgccg aacgccacgg ggtgcagtcg ccggtcgcgt gggcccgggt | 4320 |
| ctgggtttcg acccggaagt tcgcggccgc cccaccgtcg gggcggccgc gcacgagggc | 4380 |
| ggacagcggg accccgccg ccgccaggca ctcgctggag atgatgacgt gaatcagcga | 4440 |
| ggcggggctg ctcgggtccc gggtgagatc gtattggacc tcgttggcaa agtgcgcgtt | 4500 |
| catgccccgg ccgcggtgc gagcccttcc cggtgccgga aggggcgtgg gtgggggtg | 4560 |
| cgtgtgcgcg tcctcggggc ccgcgggcgc acgtgcgctt atacgctgtg tgtttcgtct | 4620 |
| gtccccaggg aatccgggc caggacttta acctgctttt cgtcgacgag gccaacttta | 4680 |
| ttcgcccgga tgcggtccag acgattatgg gctttctcaa tcaggccaac tgcaagatca | 4740 |

```
tcttcgtctc gtcgaccaac accgggaagg ccagcacgag cttttgtac aacctccgcg    4800
gggccgccga cgagctgctc aacgtggtca cctatatatg cgacgaccac atgccgcggg    4860
tggtgacgca caccaacgcc acggcctgtt cctgctatat cctgaacaaa cccgtgttta    4920
tcacgatgga cggcgccgtt cgccggacgg ccgatctgtt tctgcccgac tccttcatgc    4980
aggagatcat cggggggcag gcccgcgaga ccggcgacga ccggcccgtc ctaacaaagt    5040
cggcggggga gcggtttctg ctgtaccgcc cctccaccac caccaacagc ggcctgatgg    5100
cccccgagct gtacgtgtac gtggacccgg cgttcacggc caacacgcgc gcctccggca    5160
ccggcatcgc ggtcgtcggg aggtaccgcg acgatttcat tatcttcgcc ctggagcact    5220
ttttcctccg cgcgctcacg ggatcggccc ccgcggacat cgcccgctgc gtcgtgcaca    5280
gcctcgccca ggtgctggcg ctgcaccccg gggcgtttcg cagcgttcgc gtggcggtcg    5340
agggcaacag cagccaggac tcggccgtgg ccatcgccac acacgtgcat accgagatgc    5400
accgcatcct ggcctcggcg ggggccaacg gcccggggcc cgagctcctc ttctatcact    5460
gcgagccgcc cggcggcgcg gtattgtacc ccttcttcct gctcaacaaa cagaagacgc    5520
ccgccttcga atactttatc aaaaagttca actccggggg cgtcatggcg tcccaggagc    5580
tcgtctccgt gacggtgcgc ctgcagaccg accggtcga gtatctgtcc gagcagctca    5640
acaacctcat cgaaaccgtc tctcccaaca ccgacgtccg catgtactcc ggaaaacgca    5700
acggtgccgc ggacgaccctc atggtcgcgg tcatcatggc catttacctg gcggccccga    5760
ccggatccc cccggccttt tttccgatca cgcgcacgtc ttgagtcttt cttgccgttt    5820
cttttgtttc tctttctttc cccccctctc tccgcaataa a                      5861
```

<210> SEQ ID NO 77
<211> LENGTH: 702
<212> TYPE: PRT
<213> ORGANISM: Herpes simplex virus 2

<400> SEQUENCE: 77

Met Asn Ala His Phe Ala Asn Glu Val Gln Tyr Asp Leu Thr Arg Asp
1               5                   10                  15

Pro Ser Ser Pro Ala Ser Leu Ile His Val Ile Ile Ser Ser Glu Cys
            20                  25                  30

Leu Ala Ala Ala Gly Val Pro Leu Ser Ala Leu Val Arg Gly Arg Pro
        35                  40                  45

Asp Gly Gly Ala Ala Ala Asn Phe Arg Val Glu Thr Gln Thr Arg Ala
    50                  55                  60

His Ala Thr Gly Asp Cys Thr Pro Trp Arg Ser Ala Phe Ala Ala Tyr
65                  70                  75                  80

Val Pro Ala Asp Ala Val Gly Ala Ile Leu Ala Pro Val Ile Pro Ala
                85                  90                  95

His Pro Asp Leu Leu Pro Arg Val Pro Ser Ala Gly Gly Leu Phe Val
            100                 105                 110

Ser Leu Pro Val Ala Cys Asp Ala Gln Gly Val Tyr Asp Pro Tyr Thr
        115                 120                 125

Val Ala Ala Leu Arg Leu Ala Trp Gly Pro Trp Ala Thr Cys Ala Arg
    130                 135                 140

Val Leu Leu Phe Ser Tyr Asp Glu Leu Val Pro Pro Asn Thr Arg Tyr
145                 150                 155                 160

Ala Ala Asp Gly Ala Arg Leu Met Arg Leu Cys Arg His Phe Cys Arg
                165                 170                 175

Tyr Val Ala Arg Leu Gly Ala Ala Ala Pro Ala Ala Ala Thr Glu Ala

-continued

```
                180                 185                 190
Ala Ala His Leu Ser Leu Gly Met Gly Glu Ser Gly Thr Pro Thr Pro
            195                 200                 205

Gln Ala Ser Ser Val Ser Gly Gly Ala Gly Pro Ala Val Val Gly Thr
        210                 215                 220

Pro Asp Pro Pro Ile Ser Pro Glu Glu Gln Leu Thr Ala Pro Gly Gly
225                 230                 235                 240

Asp Thr Ala Thr Ala Glu Asp Val Ser Ile Thr Gln Glu Asn Glu Glu
                245                 250                 255

Ile Leu Ala Leu Val Gln Arg Ala Val Gln Asp Val Thr Arg Arg His
            260                 265                 270

Pro Val Arg Ala Arg Pro Lys His Ala Ala Ser Gly Val Ala Ser Gly
        275                 280                 285

Leu Arg Gln Gly Ala Leu Val His Gln Ala Val Ser Gly Gly Ala Leu
    290                 295                 300

Gly Ala Ser Asp Ala Glu Ala Val Leu Ala Gly Leu Glu Pro Pro Gly
305                 310                 315                 320

Gly Gly Arg Phe Ala Ser Arg Gly Gly Pro Arg Ala Ala Gly Glu Asp
                325                 330                 335

Val Leu Asn Asp Val Leu Thr Leu Val Pro Gly Thr Ala Lys Pro Arg
            340                 345                 350

Ser Leu Val Glu Trp Leu Asp Arg Gly Trp Glu Ala Leu Ala Gly Gly
        355                 360                 365

Asp Arg Pro Asp Trp Leu Trp Ser Arg Arg Ser Ile Ser Val Val Leu
    370                 375                 380

Arg His His Tyr Gly Thr Lys Gln Arg Phe Val Val Ser Tyr Glu
385                 390                 395                 400

Asn Ser Val Ala Trp Gly Gly Arg Arg Ala Arg Pro Pro Arg Leu Ser
                405                 410                 415

Ser Glu Leu Ala Thr Ala Leu Thr Glu Ala Cys Ala Ala Glu Arg Val
            420                 425                 430

Val Arg Pro His Gln Leu Ser Pro Ala Ala Gln Thr Ala Leu Leu Arg
        435                 440                 445

Arg Phe Pro Ala Leu Glu Gly Pro Leu Arg His Pro Arg Pro Val Leu
    450                 455                 460

Gln Pro Phe Asp Ile Ala Ala Glu Val Ala Phe Val Ala Arg Ile Gln
465                 470                 475                 480

Ile Ala Cys Leu Arg Ala Leu Gly His Ser Ile Arg Ala Ala Leu Gln
                485                 490                 495

Gly Gly Pro Arg Ile Phe Gln Arg Leu Arg Tyr Asp Phe Gly Pro His
            500                 505                 510

Gln Ser Glu Trp Leu Gly Glu Val Thr Arg Arg Phe Pro Val Leu Leu
        515                 520                 525

Glu Asn Leu Met Arg Ala Leu Glu Gly Thr Ala Pro Asp Ala Phe Phe
    530                 535                 540

His Thr Ala Tyr Ala Leu Ala Val Leu Ala His Leu Gly Gly Gln Gly
545                 550                 555                 560

Gly Arg Gly Arg Arg Arg Leu Val Pro Leu Ser Asp Asp Ile Pro
                565                 570                 575

Ala Arg Phe Ala Asp Ser Asp Ala His Tyr Ala Phe Asp Tyr Tyr Ser
            580                 585                 590

Thr Ser Gly Asp Thr Leu Arg Leu Thr Asn Arg Pro Ile Ala Val Val
        595                 600                 605
```

-continued

```
Ile Asp Gly Asp Val Asn Gly Arg Glu Gln Ser Lys Cys Arg Phe Met
610                 615                 620
Glu Gly Ser Pro Ser Thr Ala Pro His Arg Val Cys Glu Gln Tyr Leu
625                 630                 635                 640
Pro Gly Glu Ser Tyr Ala Tyr Leu Cys Leu Gly Phe Asn Arg Arg Leu
                645                 650                 655
Cys Gly Leu Val Val Phe Pro Gly Gly Phe Ala Phe Thr Ile Asn Thr
                660                 665                 670
Ala Ala Tyr Leu Ser Leu Ala Asp Pro Val Ala Arg Ala Val Gly Leu
            675                 680                 685
Arg Phe Cys Arg Gly Ala Ala Thr Gly Pro Gly Leu Val Arg
690                 695                 700
```

<210> SEQ ID NO 78
<211> LENGTH: 3330
<212> TYPE: DNA
<213> ORGANISM: Artificial
<220> FEATURE:
<223> OTHER INFORMATION: Synthetic DNA sequence of GenBank accession
      NC_001798 region: 30142..33471

<400> SEQUENCE: 78

```
tttatttgta atcggacgat gaggctctgg ccacggcccg cgcgaccgcg gggcagctcg      60
ttgcaaacag gcggctggta tacgatgaca gaacgcagag gcgccacccg cgctggtcg     120
ggcggatgac gctttccgcg ccgtcccggc ccacgacgac ctcgtgcagg tgggccgtga    180
tgcgcgggcg gcgggtcgcc tgccgcagga taaccgcgtc cacggggtgc ccgaagagga    240
gctgacacag gctcgcgtcc ccccggacgg ccagggtgcg ctgggccata ttggaccaca    300
tgcacggggc gacgcaggga caggcctccg ccacggcggg ggcgcgccac agcgcgttgg    360
cggaatcgat gtgggccgtc ggggcgcagg cgccgcctcc tcccgggggg tcggtaatcc    420
tggatagcag ccatcctaaa tggcgggccc ggctgcccgg ggacagagc gacccccaggt    480
catcatccat ggcccagcag tatatgcggc cgccggggag gtgccaccag ccccccggac    540
ccagggcaca gcacgccccg gattcggggg ccgtgtccgt gggtaccagg taggcgccgt    600
cgagctcgtg ggccacgggc tcgtccgcga gctgttcggc ggcggggtcg ggggtttcct    660
ccggggggga ggcagcttcc aggtggccga aggctagggt gcacagcagc ggggtccggg    720
ggtgcgttac gctgcggagg tggacggtgg cgcagtagcg gcgctcgcgg ttaaagaaga    780
aaatggcaaa gaacgtgttc gaaggcaggc gcagcgcctt gggccgcgtc aggtacagga    840
agatctcgca gaaaagggca cgctcggggt cggggtccgg aagggccacc tggcacagcg    900
gctcggtgag gaccgtgagg caccgaaaaa tcttaagccg ctcgtccccc gaacgacgc    960
gccacacgaa gacagagttg gcgatgcgcg cgacgaggtc ggcttcgggc cccgggtcgg   1020
gggcgcgcgc gtcgggggg gcgcccggt gacccggcgg ggccgcggct cccgggggc     1080
ctggcgtcgc ctggggacgc cagagtgccc gctgtgccag gttggtggtg gggaagggac   1140
cggagacgca ccaaaagcag aggggccagc gcgtgtatga gttggggggg ggtgggtga   1200
gcggtggaac aaaagcacgc gtcagcggac aaggccgggt cccgtagccg ccccgcgaca   1260
gaaccggagt ccgacggcac gcgcgacggg gtctgcgagg ctgaggtacg ccgcggtgtt   1320
aatggtaaac gcaaagcctc ccggaaagac cactagcccg cagaggcggc gattgaaccc   1380
aaggcagagg tacgcgtagc tctctcccgg aaggtattgc tcgcagaccc tgtgtggggc   1440
agtggagggg ctgccctcca tgaagcgaca tttactctgc tcgcgtccat tgacgtcacc   1500
gtcaatcacc actgcgattg gacggttggt gaggcgcagc gtgtctccgc tggtgctgta   1560
```

```
gtagtcaaac gcgtagtggg cgtcggagtc ggcgaagcgg gcggggatgt cgtcgctgag    1620
agggacgagc cgccgccgcc gccccgacc gccctggccg cccagatgcg ccagcacggc     1680
cagggcgtac gcggtgtgaa agaacgcgtc ggggggcggtc ccctcgaggg cgcgcatcag   1740
gttctccagg agcacgggga agcgccgcgt cacctcccct agccactcgc tctggtgggg   1800
gccaaagtcg tagcgcaggc gctggaagat gcgcggccg ccttggagcg cggcccggat    1860
agagtggccc agggcccgca gacacgcgat ctggatcgc gcgacgaagg ccacctcggc    1920
cgcgatgtca aagggctgca gcacggggcg cgggtggcgc aggggtccct cgagcgcggg   1980
aaagcgacgc agcagcgccg tctgggccgc gggggacagc tggtgggggc gcacgacgcg   2040
ctcggcggca caggcctccg tcagggccgt ggccagctcg gaggacagcc gcgggggggcg 2100 ggcgcgtcgc ccgccccacg ccaccgaatt ctcgtaggag acgacgacga agcgctgctt   2160
ggtcccgtag tgatggcgca ggaccacgga gatggagcga cggctccaca gccagtcggg   2220
ccggtcgccg ccgccagag cttcccaccc gcggtccagc cactcgacca gcgatcgcgg    2280
cttggcggtc cccggcacga gggtgagcac gtcgttgagg acgtcctcgc ccgcggcccg   2340 gggcccccc cggctggcaa agcgcccccc gccgggcggc tccaggcccg ccagcaccgc    2400
ctccgcgtcc gacgcgccca gggctccccc gctgacggcc tggtggacca gggcgccctg   2460
gcggagcccc gaggcgacgc cggaggccgc gtgcttgggg cgcgcgcgga ccgggtggcg   2520
gcgggtgacg tcctgcacgg cccgctggac cagcgcgagg atctcctcgt tctcttgcgt   2580
gatggacacg tcctccgcgg tggccgtgtc gcctcccggg gccgtgagct gctcctccgg   2640
ggagatgggg gggtctgggg tgccgacaac ggccggcccg gccccgcccg agaccgagga   2700
cgcctgggga gtgggggtgc cgcttttcccc catcccagg gacaggtggg ccgccgcctc    2760
cgtcgcggcg gcgggagccg cggcccccag ccgcgcgacg tagcgacaaa agtggcgaca   2820
gaggcgcatg aggcgcgcgc cgtcggccgc gtatcgcgtg tttggcggga cgagctcgtc   2880
gtaactgaac aggagcacgc gggcacaggt cgcccacggg cccacgcca ggcgcagcgc     2940 cgcgaccgtg tacgggtcgt acacgccttg ggcgtcgcac gcgaccggca gggagacgaa   3000
cagcccgccc gcgctgggga cgcgcggcag gaggtccggg tgcgccggga tgacggggc    3060 taggatcgcc cccaccgcat ccgccggcac gtaggcggca aacgccgaac gccacgggt    3120 gcagtcgccg gtcgcgtggg cccgggtctg ggtttcgacc cggaagttcg cggccgcccc   3180
accgtcgggg cggccgcgca cgagggcgga cagcgggacc cccgccgccg ccaggcactc   3240
gctggagatg atgacgtgaa tcagcgaggc ggggctgctc gggtcccggg tgagatcgta   3300
ttggacctcg ttggcaaagt gcgcgttcat                                   3330
```

<210> SEQ ID NO 79
<211> LENGTH: 1196
<212> TYPE: PRT
<213> ORGANISM: Herpes simplex virus 2

<400> SEQUENCE: 79

Met Asp Thr Lys Pro Lys Thr Thr Thr Val Lys Val Pro Pro Gly
1               5                   10                  15

Pro Met Gly Tyr Val Tyr Gly Arg Ala Cys Pro Ala Glu Gly Leu Glu
            20                  25                  30

Leu Leu Ser Leu Leu Ser Ala Arg Ser Gly Asp Ala Asp Val Ala Val
        35                  40                  45

Ala Pro Leu Ile Val Gly Leu Thr Val Glu Ser Gly Phe Glu Ala Asn
    50                  55                  60

```
Val Ala Ala Val Val Gly Ser Arg Thr Thr Gly Leu Gly Gly Thr Ala
 65                  70                  75                  80

Val Ser Leu Lys Leu Met Pro Ser His Tyr Ser Pro Ser Val Tyr Val
                 85                  90                  95

Phe His Gly Gly Arg His Leu Ala Pro Ser Thr Gln Ala Pro Asn Leu
            100                 105                 110

Thr Arg Leu Cys Glu Arg Ala Arg Pro His Phe Gly Phe Ala Asp Tyr
        115                 120                 125

Ala Pro Arg Pro Cys Asp Leu Lys His Glu Thr Thr Gly Asp Ala Leu
    130                 135                 140

Cys Glu Arg Leu Gly Leu Asp Pro Asp Arg Ala Leu Leu Tyr Leu Val
145                 150                 155                 160

Ile Thr Glu Gly Phe Arg Glu Ala Val Cys Ile Ser Asn Thr Phe Leu
                165                 170                 175

His Leu Gly Gly Met Asp Lys Val Thr Ile Gly Asp Ala Glu Val His
            180                 185                 190

Arg Ile Pro Val Tyr Pro Leu Gln Met Phe Met Pro Asp Phe Ser Arg
        195                 200                 205

Val Ile Ala Asp Pro Phe Asn Cys Asn His Arg Ser Ile Gly Glu Asn
    210                 215                 220

Phe Asn Tyr Pro Leu Pro Phe Phe Asn Arg Pro Leu Ala Arg Leu Leu
225                 230                 235                 240

Phe Glu Ala Val Val Gly Pro Ala Ala Val Ala Leu Arg Ala Arg Asn
                245                 250                 255

Val Asp Ala Val Ala Arg Ala Ala His Leu Ala Phe Asp Glu Asn
            260                 265                 270

His Glu Gly Ala Ala Leu Pro Ala Asp Ile Thr Phe Thr Ala Phe Glu
        275                 280                 285

Ala Ser Gln Gly Lys Pro Gln Arg Gly Ala Arg Asp Ala Gly Asn Lys
    290                 295                 300

Gly Pro Ala Gly Gly Phe Glu Gln Arg Leu Ala Ser Val Met Ala Gly
305                 310                 315                 320

Asp Ala Ala Leu Ala Leu Glu Ser Ile Val Ser Met Ala Val Phe Asp
                325                 330                 335

Glu Pro Pro Asp Ile Thr Thr Trp Pro Leu Leu Glu Gly Gln Glu
            340                 345                 350

Thr Pro Ala Ala Arg Ala Gly Ala Val Gly Ala Tyr Leu Ala Arg Ala
        355                 360                 365

Ala Gly Leu Val Gly Ala Met Val Phe Ser Thr Asn Ser Ala Leu His
    370                 375                 380

Leu Thr Glu Val Asp Asp Ala Gly Pro Ala Asp Pro Lys Asp His Ser
385                 390                 395                 400

Lys Pro Ser Phe Tyr Arg Phe Phe Leu Val Pro Gly Thr His Val Ala
                405                 410                 415

Ala Asn Pro Gln Leu Asp Arg Glu Gly His Val Val Pro Gly Tyr Glu
            420                 425                 430

Gly Arg Pro Thr Ala Pro Leu Val Gly Gly Thr Gln Glu Phe Ala Gly
        435                 440                 445

Glu His Leu Ala Met Leu Cys Gly Phe Ser Pro Ala Leu Leu Ala Lys
    450                 455                 460

Met Leu Phe Tyr Leu Glu Arg Cys Asp Gly Gly Val Ile Val Gly Arg
465                 470                 475                 480

Gln Glu Met Asp Val Phe Arg Tyr Val Ala Asp Ser Gly Gln Thr Asp
```

```
                485                 490                 495
Val Pro Cys Asn Leu Cys Thr Phe Glu Thr Arg His Ala Cys Ala His
            500                 505                 510

Thr Thr Leu Met Arg Leu Arg Ala Arg His Pro Lys Phe Ala Ser Ala
            515                 520                 525

Ala Arg Gly Ala Ile Gly Val Phe Gly Thr Met Asn Ser Ala Tyr Ser
            530                 535                 540

Asp Cys Asp Val Leu Gly Asn Tyr Ala Ala Phe Ser Ala Leu Lys Arg
545                 550                 555                 560

Ala Asp Gly Ser Glu Asn Thr Arg Thr Ile Met Gln Glu Thr Tyr Arg
                565                 570                 575

Ala Ala Thr Glu Arg Val Met Ala Glu Leu Glu Ala Leu Gln Tyr Val
            580                 585                 590

Asp Gln Ala Val Pro Thr Ala Leu Gly Arg Leu Glu Thr Ile Ile Gly
            595                 600                 605

Asn Arg Glu Ala Leu His Thr Val Val Asn Asn Ile Lys Gln Leu Val
            610                 615                 620

Asp Arg Glu Val Glu Gln Leu Met Arg Asn Leu Ile Glu Gly Arg Asn
625                 630                 635                 640

Phe Lys Phe Arg Asp Gly Leu Ala Glu Ala Asn His Ala Met Ser Leu
                645                 650                 655

Ser Leu Asp Pro Tyr Thr Cys Gly Pro Cys Pro Leu Leu Gln Leu Leu
            660                 665                 670

Ala Arg Arg Ser Asn Leu Ala Val Tyr Gln Asp Leu Ala Leu Ser Gln
            675                 680                 685

Cys His Gly Val Phe Ala Gly Gln Ser Val Glu Gly Arg Asn Phe Arg
            690                 695                 700

Asn Gln Phe Gln Pro Val Leu Arg Arg Arg Val Met Asp Leu Phe Asn
705                 710                 715                 720

Asn Gly Phe Leu Ser Ala Lys Thr Leu Thr Val Ala Leu Ser Glu Gly
                725                 730                 735

Ala Ala Ile Cys Ala Pro Ser Leu Thr Ala Gly Gln Thr Ala Pro Ala
            740                 745                 750

Glu Ser Ser Phe Glu Gly Asp Val Ala Arg Val Thr Leu Gly Phe Pro
            755                 760                 765

Lys Glu Leu Arg Val Lys Ser Arg Val Leu Phe Ala Gly Ala Ser Ala
            770                 775                 780

Asn Ala Ser Glu Ala Ala Lys Ala Arg Val Ala Ser Leu Gln Ser Ala
785                 790                 795                 800

Tyr Gln Lys Pro Asp Lys Arg Val Asp Ile Leu Leu Gly Pro Leu Gly
                805                 810                 815

Phe Leu Leu Lys Gln Phe His Ala Val Ile Phe Pro Asn Gly Lys Pro
            820                 825                 830

Pro Gly Ser Asn Gln Pro Asn Pro Gln Trp Phe Trp Thr Ala Leu Gln
            835                 840                 845

Arg Asn Gln Leu Pro Ala Arg Leu Leu Ser Arg Glu Asp Ile Glu Thr
            850                 855                 860

Ile Ala Phe Ile Lys Arg Phe Ser Leu Asp Tyr Gly Ala Ile Asn Phe
865                 870                 875                 880

Ile Asn Leu Ala Pro Asn Asn Val Ser Glu Leu Ala Met Tyr Tyr Met
                885                 890                 895

Ala Asn Gln Ile Leu Arg Tyr Cys Asp His Ser Thr Tyr Phe Ile Asn
            900                 905                 910
```

Thr Leu Thr Ala Val Ile Ala Gly Ser Arg Arg Pro Pro Ser Val Gln
    915                 920                 925

Ala Ala Ala Ala Trp Ala Pro Gln Gly Gly Ala Gly Leu Glu Ala Gly
    930                 935                 940

Ala Arg Ala Leu Met Asp Ser Leu Asp Ala His Pro Gly Ala Trp Thr
945                 950                 955                 960

Ser Met Phe Ala Ser Cys Asn Leu Leu Arg Pro Val Met Ala Ala Arg
                965                 970                 975

Pro Met Val Val Leu Gly Leu Ser Ile Ser Lys Tyr Tyr Gly Met Ala
            980                 985                 990

Gly Asn Asp Arg Val Phe Gln Ala  Gly Asn Trp Ala Ser  Leu Leu Gly
        995                 1000                1005

Gly Lys  Asn Ala Cys Pro Leu  Leu Ile Phe Asp Arg  Thr Arg Lys
    1010                1015                1020

Phe Val  Leu Ala Cys Pro Arg  Ala Gly Phe Val Cys  Ala Ala Ser
    1025                1030                1035

Ser Leu  Gly Gly Gly Ala His  Glu His Ser Leu Cys  Glu Gln Leu
    1040                1045                1050

Arg Gly  Ile Ile Ala Glu Gly  Gly Ala Val Ala  Ser Ser Val
    1055                1060                1065

Phe Val  Ala Thr Val Lys Ser  Leu Gly Pro Arg Thr  Gln Gln Leu
    1070                1075                1080

Gln Ile  Glu Asp Trp Leu Ala  Leu Leu Glu Asp Glu  Tyr Leu Ser
    1085                1090                1095

Glu Glu  Met Met Glu Phe Thr  Thr Arg Ala Leu Glu  Arg Gly His
    1100                1105                1110

Gly Glu  Trp Ser Thr Asp Ala  Ala Leu Glu Val Ala  His Glu Ala
    1115                1120                1125

Glu Ala  Leu Val Ser Gln Leu  Gly Ala Ala Gly Glu  Val Phe Asn
    1130                1135                1140

Phe Gly  Asp Phe Gly Asp Glu  Asp Asp His Ala Ala  Ser Phe Gly
    1145                1150                1155

Gly Leu  Ala Ala Ala Ala Gly  Ala Ala Gly Val Ala  Arg Lys Arg
    1160                1165                1170

Ala Phe  His Gly Asp Asp Pro  Phe Gly Glu Gly Pro  Pro Glu Lys
    1175                1180                1185

Lys Asp  Leu Thr Leu Asp Met  Leu
    1190                1195

<210> SEQ ID NO 80
<211> LENGTH: 3643
<212> TYPE: DNA
<213> ORGANISM: Artificial
<220> FEATURE:
<223> OTHER INFORMATION: Synthetic DNA sequence of GenBank accession
      NC_001798 region: 58805..62447

<400> SEQUENCE: 80
tttattttat acacaacacc aacctttcct tcgaccccc ccaccccgc ccctagagca      60 tatccaacgt caggtccttt ttctccggtg gtccctcccc aaacggatcg tcgccgtgaa    120
acgcccgctt tcgggcgacg ccggccgccc ccgccgccgc cgccaaaccg ccgaacgacg    180
ccgcgtggtc atcctcgtcg ccgaaatccc caaagttaaa cacctccccg gcggcgccga    240
gctggctgac cagggcctcc gctcgtgggg ccacctccag ggccgcgtcg gtcgaccact    300
cgccatgccc gcgctccagg gcgcgggtgg taaactccat catttcctcg ctcaggtact    360

-continued

```
cgtcctccag cagcgccagc cagtcctcga tctgcagctg ctgggtgcgg gggcccaggc    420
tcttgacggt cgccacaaac acgctgctgg cgaccgccgc cccgcccctcc gcaatgatgc   480 cccggagctg ctcgcacagc gaatgctcgt gggccccgcc cccgagactc gacgccgcgc   540
acacaaaccc ggccctgggg caggccagga caaacttgcg ggtgcggtca agatcagca    600 gcgggcacgc gttttttgccg cccagcaggc tggcccagtt cccggcctga acacgcggt    660 cgttgccggc catgccgtag tatttgctga tgctgaggcc cagcacgacc atcgggcgcg   720
cggccatcac gggccgcagc aggttgcagc tcgcgaacat ggacgtccag gcgccggggt   780
gcgcgtcgag ggagtccatc agcgcgcggg ccccggcctc caggcccgcg ccgccctgcg   840
gggcccaggc ggccgccgcc tgcacgctgg ggggacggcg ggacccggcg atgacggccg   900
tgagggtgtt tatgaagtac gtcgagtggt cgcagtacct caagatctgg ttggccatgt    960
agtacatggc cagttcgctc acgttattgg gggccaggtt gataaagtta atcgcgccgt   1020
agtccaggga gaacctctta atgaacgcga tggtctctat gtcctcgcgc gacaagagcc   1080
gggcggggag ctggttgcgc tggagggcgg tccagaacca ctgcgggttc ggctggttcg   1140 accccgggg cttgccgttg ggaaagatga ccgcgtggaa ctgcttcagc aggaagccca   1200
gcggtccgag gaggatgtcc acgcgcttgt cgggcttctg gtaggcgctc tggaggctgg   1260
cgacccgcgc cttggcggcc tcggacgcgt tggcgctcgc gccgcgaac aacacgcggc   1320 tcttgacgcg cagttccttg ggaaacccaa gggtcacgcg gcaacgtcg ccctcgaagc   1380 tgctctcggc gggggccgtc tggcggccg ttaggctggg ggcgcagata gccgcccct   1440 ccgagagcgc gaccgtcagc gtcttcgccg acaggaaccc gttgttgaac aggtccatga   1500
cgcgccgccg cagcaccggt tggaattgat tgcgaaagtt gcgcccctcg accgactgcc   1560
cggcgaacac cccgtggcac tggctcaggg ccaggtcctg gtacacggcg aggttggacc   1620
gccgcgcgag gagctgcagc agggggcacg gcccgcaggt gtacgggtcc agcgacagcg   1680
acatggcgtg gttggcctcg ccagaccgt cgcggaactt aaagttgcgc ccctcgatca   1740
ggttgcgcat cagctgttcc acctcgcgat ccaccagctg cttgatgttg ttcaccaccg   1800
tgtgcagggc ctcgcggttg ccgataatcg tctccagcct ccccagggcc gtgggcaccg   1860
cctggtccac gtactgcagg gcctcgagct cggccatgac gcgctcggtg gccgcgcggt   1920
acgtctcctg catgatggtc cgggtgttct cggacccgtc cgcgcgcttc agggccgaga   1980
aggcggcgta gttccccagc acgtcgcagt cgctgtacgc gctgttcatc gttccgaaga   2040
ccccaatggc cccccgggcg cgctcgcga acttggggtg gcgggccgc agccgcatca   2100 gcgtcgtgtg cgcgcaggcg tggcgggtct cgaaggtaca caggttgcag gcacgtcgg   2160 tctggcccga gtccgcgacg tagcgaaaca cgtccatctc ctggcgcccg acgatgactc   2220
cgccgtcgca gcgctccagg taaaacagca tcttggccag cagggccgga gagaacccgc   2280
acagcatggc caggtgctcg ccggcgaact cctgggttcc gccgacgagg ggcgccgtgg   2340
ggcgcccctc gtacccgggc accacgtggc cctcgcggtc cagctgcggg ttggccgcca   2400
cgtgcgtgcc gggcacgaga aagaagcggt aaaaggaggg cttgctgtgg tccttgggt    2460 ccgccggccc ggcgtcgtcc acctcggtca ggtggagggc cgaattggtg ctgaacacca   2520
tggcgcccac gaggcccgcg gcgcgcgcca ggtacgcccc gacggcgccg gcgcgggccg   2580
cgggcgtttc ctggcccctca agcaggggcc acgtggtgat gtcgggggc ggctcgtcaa   2640 agaccgccat cgacacgatg gactccaggg ccagggcggc gtcgcccgcc atcaccgagg   2700
ccaggcgctg ctcaaacccg cccgccgggc ccttgttccc ggcgtcgcgc gcgccccgct   2760
```

```
ggggcttacc ctggctggcc tcgaaggccg tgaacgtaat gtcggcgggg agggccgcgc    2820
cctcgtggtt ttcgtcgaac gccaggtggg cggccgcgcg ggccacggcg tccacgttcc    2880
gggcacgcag ggccacggcg gcgggcccga cgaccgcctc gaacagcagg cgggcgaggg    2940
ggcggttgaa aaacggaagg gggtagttga aattctcccc gatcgatcgg tggttgcagt    3000
taaacggatc ggcgatgacc cggctaaaat ccggcataaa catctgcagc ggatacacgg    3060
ggatgcggtg aacctccgcg tccccgatgg ttaccttgtc catcccgccc agatgcagga    3120
aggtgttgct gatgcacacg gcctcccgga agccctccgt gatcaccaga tacagcaagg    3180
cccggtccgg gtccagtccg agccgctcgc acagcgcgtc ccccgtcgtc tcgtgcttta    3240
ggtcgcaggg ccggggcgcg tagtccgcga agccaaaatg cgggcgcgcc cgctcgcaga    3300
gccgcgtcag gttgggggcc tgggtgctgg gggccaggtg gcggccgccg tgaaagacgt    3360
aaacggacgg gctgtagtgc gagggcataa gcttgaggga caccgcggtc ccccaaggc    3420 ccgtcgtgcg ggacccgacg accgcggcca cgttggcctc aaacccgctc tccacggtca    3480
ggccgacgat gaggggcgcg acggcgacgt ccgcgtcgcc gctgcgcgcc gacagtagcg    3540
acagcagctc caggccttcg gccggacagg cgcggccata cacgtacccc atcggccccg    3600
gaggaacctt gacggtggtc gtcgttttgg gcttggtgtc cat                      3643
```

<210> SEQ ID NO 81
<211> LENGTH: 1240
<212> TYPE: PRT
<213> ORGANISM: Herpes simplex virus 2

<400> SEQUENCE: 81

```
Met Phe Cys Ala Ala Gly Gly Pro Ala Ser Pro Gly Gly Lys Pro Ala
1               5                   10                  15

Ala Arg Ala Ala Ser Gly Phe Phe Ala Pro His Asn Pro Arg Gly Ala
                20                  25                  30

Thr Gln Thr Ala Pro Pro Pro Cys Arg Arg Gln Asn Phe Tyr Asn Pro
            35                  40                  45

His Leu Ala Gln Thr Gly Thr Gln Pro Lys Ala Leu Gly Pro Ala Gln
        50                  55                  60

Arg His Thr Tyr Tyr Ser Glu Cys Asp Glu Phe Arg Phe Ile Ala Pro
65                  70                  75                  80

Arg Ser Leu Asp Glu Asp Ala Pro Ala Glu Gln Arg Thr Gly Val His
                85                  90                  95

Asp Gly Arg Leu Arg Arg Ala Pro Lys Val Tyr Cys Gly Gly Asp Glu
            100                 105                 110

Arg Asp Val Leu Arg Val Gly Pro Glu Gly Phe Trp Pro Arg Arg Leu
        115                 120                 125

Arg Leu Trp Gly Gly Ala Asp His Ala Pro Glu Gly Phe Asp Pro Thr
    130                 135                 140

Val Thr Val Phe His Val Tyr Asp Ile Leu Glu His Val Glu His Ala
145                 150                 155                 160

Tyr Ser Met Arg Ala Ala Gln Leu His Glu Arg Phe Met Asp Ala Ile
                165                 170                 175

Thr Pro Ala Gly Thr Val Ile Thr Leu Leu Gly Leu Thr Pro Glu Gly
            180                 185                 190

His Arg Val Ala Val His Val Tyr Gly Thr Arg Gln Tyr Phe Tyr Met
        195                 200                 205

Asn Lys Ala Glu Val Asp Arg His Leu Gln Cys Arg Ala Pro Arg Asp
    210                 215                 220
```

```
Leu Cys Glu Arg Leu Ala Ala Ala Leu Arg Glu Ser Pro Gly Ala Ser
225                 230                 235                 240

Phe Arg Gly Ile Ser Ala Asp His Phe Glu Ala Val Val Glu Arg
                245                 250                 255

Ala Asp Val Tyr Tyr Glu Thr Arg Pro Thr Leu Tyr Tyr Arg Val
            260                 265                 270

Phe Val Arg Ser Gly Arg Ala Leu Ala Tyr Leu Cys Asp Asn Phe Cys
        275                 280                 285

Pro Ala Ile Arg Lys Tyr Glu Gly Val Asp Ala Thr Thr Arg Phe
    290                 295                 300

Ile Leu Asp Asn Pro Gly Phe Val Thr Phe Gly Trp Tyr Arg Leu Lys
305                 310                 315                 320

Pro Gly Arg Gly Asn Ala Pro Ala Gln Pro Arg Pro Thr Ala Phe
                325                 330                 335

Gly Thr Ser Ser Asp Val Glu Phe Asn Cys Thr Ala Asp Asn Leu Ala
            340                 345                 350

Val Glu Gly Ala Met Cys Asp Leu Pro Ala Tyr Lys Leu Met Cys Phe
            355                 360                 365

Asp Ile Glu Cys Lys Ala Gly Gly Glu Asp Leu Ala Phe Pro Val
    370                 375                 380

Ala Glu Arg Pro Glu Asp Leu Val Ile Gln Ile Ser Cys Leu Leu Tyr
385                 390                 395                 400

Asp Leu Ser Thr Thr Ala Leu Glu His Ile Leu Leu Phe Ser Leu Gly
            405                 410                 415

Ser Cys Asp Leu Pro Glu Ser His Leu Ser Asp Leu Ala Ser Arg Gly
        420                 425                 430

Leu Pro Ala Pro Val Val Leu Glu Phe Asp Ser Glu Phe Glu Met Leu
        435                 440                 445

Leu Ala Phe Met Thr Phe Val Lys Gln Tyr Gly Pro Glu Phe Val Thr
450                 455                 460

Gly Tyr Asn Ile Ile Asn Phe Asp Trp Pro Phe Val Leu Thr Lys Leu
465                 470                 475                 480

Thr Glu Ile Tyr Lys Val Pro Leu Asp Gly Tyr Gly Arg Met Asn Gly
                485                 490                 495

Arg Gly Val Phe Arg Val Trp Asp Ile Gly Gln Ser His Phe Gln Lys
            500                 505                 510

Arg Ser Lys Ile Lys Val Asn Gly Met Val Asn Ile Asp Met Tyr Gly
        515                 520                 525

Ile Ile Thr Asp Lys Val Lys Leu Ser Ser Tyr Lys Leu Asn Ala Val
530                 535                 540

Ala Glu Ala Val Leu Lys Asp Lys Lys Asp Leu Ser Tyr Arg Asp
545                 550                 555                 560

Ile Pro Ala Tyr Tyr Ala Ser Gly Pro Ala Gln Arg Gly Val Ile Gly
            565                 570                 575

Glu Tyr Cys Val Gln Asp Ser Leu Leu Val Gly Gln Leu Phe Phe Lys
            580                 585                 590

Phe Leu Pro His Leu Glu Leu Ser Ala Val Ala Arg Leu Ala Gly Ile
        595                 600                 605

Asn Ile Thr Arg Thr Ile Tyr Asp Gly Gln Gln Ile Arg Val Phe Thr
        610                 615                 620

Cys Leu Leu Arg Leu Ala Gly Gln Lys Gly Phe Ile Leu Pro Asp Thr
625                 630                 635                 640

Gln Gly Arg Phe Arg Gly Leu Asp Lys Glu Ala Pro Lys Arg Pro Ala
                645                 650                 655
```

```
Val Pro Arg Gly Glu Gly Glu Arg Pro Gly Asp Gly Asn Gly Asp Glu
            660                 665                 670

Asp Lys Asp Asp Glu Asp Gly Asp Glu Asp Gly Asp Glu Arg Glu
        675                 680                 685

Glu Val Ala Arg Glu Thr Gly Gly Arg His Val Gly Tyr Gln Gly Ala
        690                 695                 700

Arg Val Leu Asp Pro Thr Ser Gly Phe His Val Asp Pro Val Val
705                 710                 715                 720

Phe Asp Phe Ala Ser Leu Tyr Pro Ser Ile Ile Gln Ala His Asn Leu
                725                 730                 735

Cys Phe Ser Thr Leu Ser Leu Arg Pro Glu Ala Val Ala His Leu Glu
                740                 745                 750

Ala Asp Arg Asp Tyr Leu Glu Ile Glu Val Gly Gly Arg Arg Leu Phe
                755                 760                 765

Phe Val Lys Ala His Val Arg Glu Ser Leu Leu Ser Ile Leu Leu Arg
        770                 775                 780

Asp Trp Leu Ala Met Arg Lys Gln Ile Arg Ser Arg Ile Pro Gln Ser
785                 790                 795                 800

Thr Pro Glu Glu Ala Val Leu Leu Asp Lys Gln Gln Ala Ala Ile Lys
                805                 810                 815

Val Val Cys Asn Ser Val Tyr Gly Phe Thr Gly Val Gln His Gly Leu
                820                 825                 830

Leu Pro Cys Leu His Val Ala Ala Thr Val Thr Thr Ile Gly Arg Glu
                835                 840                 845

Met Leu Leu Ala Thr Arg Ala Tyr Val His Ala Arg Trp Ala Glu Phe
        850                 855                 860

Asp Gln Leu Leu Ala Asp Phe Pro Glu Ala Ala Gly Met Arg Ala Pro
865                 870                 875                 880

Gly Pro Tyr Ser Met Arg Ile Ile Tyr Gly Asp Thr Asp Ser Ile Phe
                885                 890                 895

Val Leu Cys Arg Gly Leu Thr Ala Ala Gly Leu Val Ala Met Gly Asp
                900                 905                 910

Lys Met Ala Ser His Ile Ser Arg Ala Leu Phe Leu Pro Pro Ile Lys
        915                 920                 925

Leu Glu Cys Glu Lys Thr Phe Thr Lys Leu Leu Leu Ile Ala Lys Lys
        930                 935                 940

Lys Tyr Ile Gly Val Ile Cys Gly Gly Lys Met Leu Ile Lys Gly Val
945                 950                 955                 960

Asp Leu Val Arg Lys Asn Asn Cys Ala Phe Ile Asn Arg Thr Ser Arg
                965                 970                 975

Ala Leu Val Asp Leu Leu Phe Tyr Asp Asp Thr Val Ser Gly Ala Ala
                980                 985                 990

Ala Ala Leu Ala Glu Arg Pro Ala Glu Glu Trp Leu Ala Arg Pro Leu
        995                 1000                1005

Pro Glu Gly Leu Gln Ala Phe Gly Ala Val Leu Val Asp Ala His
    1010                1015                1020

Arg Arg Ile Thr Asp Pro Glu Arg Asp Ile Gln Asp Phe Val Leu
    1025                1030                1035

Thr Ala Glu Leu Ser Arg His Pro Arg Ala Tyr Thr Asn Lys Arg
    1040                1045                1050

Leu Ala His Leu Thr Val Tyr Tyr Lys Leu Met Ala Arg Arg Ala
    1055                1060                1065

Gln Val Pro Ser Ile Lys Asp Arg Ile Pro Tyr Val Ile Val Ala
```

|  |  |  | 1070 |  |  |  | 1075 |  |  |  | 1080 |  |
|---|---|---|---|---|---|---|---|---|---|---|---|---|

Gln Thr Arg Glu Val Glu Glu Thr Val Ala Arg Leu Ala Ala Leu
     1085                1090                1095

Arg Glu Leu Asp Ala Ala Ala Pro Gly Asp Glu Pro Ala Pro Pro
1100                1105                1110

Ala Ala Leu Pro Ser Pro Ala Lys Arg Pro Arg Glu Thr Pro Ser
     1115                1120                1125

His Ala Asp Pro Pro Gly Gly Ala Ser Lys Pro Arg Lys Leu Leu
     1130                1135                1140

Val Ser Glu Leu Ala Glu Asp Pro Gly Tyr Ala Ile Ala Arg Gly
     1145                1150                1155

Val Pro Leu Asn Thr Asp Tyr Tyr Phe Ser His Leu Leu Gly Ala
     1160                1165                1170

Ala Cys Val Thr Phe Lys Ala Leu Phe Gly Asn Asn Ala Lys Ile
     1175                1180                1185

Thr Glu Ser Leu Leu Lys Arg Phe Ile Pro Glu Thr Trp His Pro
     1190                1195                1200

Pro Asp Asp Val Ala Ala Arg Leu Arg Ala Ala Gly Phe Gly Pro
     1205                1210                1215

Ala Gly Ala Gly Ala Thr Ala Glu Glu Thr Arg Met Leu His
     1220                1225                1230

Arg Ala Phe Asp Thr Leu Ala
     1235                1240

<210> SEQ ID NO 82
<211> LENGTH: 3762
<212> TYPE: DNA
<213> ORGANISM: Artificial
<220> FEATURE:
<223> OTHER INFORMATION: Synthetic DNA sequence of GenBank accession
      NC_001798 region: 63265..67026

<400> SEQUENCE: 82
atgttttgtg ccgcgggcgg cccggcttcc cccgggggga agccggcggc tcgggcggcg    60
tctgggtttt ttgcccccca caaccccccgg ggagccaccc agacggcacc gccgccttgc   120
cgccggcaga acttctacaa cccccacctc gctcagaccg aacgcagcc aaaggccctc    180 gggccggctc agcgccatac gtactacagc gagtgcgacg aatttcgatt tatcgccccg    240
cgttcgctgg acgaggacgc ccccgcggag cagcgcaccg ggtccacga cggccgcctc    300 cggcgcgccc ctaaggtgta ctgcgggggg gacgagcgcg acgtcctccg cgtgggcccg    360
gagggcttct ggccgcgtcg cttgcgcctg tggggcggtg cggaccatgc ccccgagggg    420 ttcgaccccca ccgtcaccgt cttccacgtg tacgacatcc tggagcacgt ggaacacgcg   480
tacagcatgc gcgccgccca gctccacgag cgatttatgg acgccatcac gcccgccggg   540
accgtcatca cgcttctggg tctgaccccc gaaggccatc gctcgccgt tcacgtctac    600 ggcacgcggc agtactttta catgaacaag gcggaggtgg atcggcacct gcagtgccgt   660
gccccgcgcg atctctgcga gcgcctggcg gcggccctgc gcgagtcgcc ggggcgtcg   720 ttccgcggca tctccgcgga ccacttcgag gcggaggtgg tggagcgcgc cgacgtgtac   780
tattacgaaa cgcgccccgac cctgtactac gcgcgtcttcg tgcgaagcgg gcgcgcgctg   840
gcctacctgt gcgacaactt tgccccgcg atcaggaagt acgagggggg cgtcgacgcc   900
accacccggt ttatcctgga caacccgggg tttgtcacct tcggctggta ccgcctcaag    960
cccggccgcg ggaacgcgcc ggcccaaccg cgccccccga cggcgttcgg aacctcgagc   1020

```
gacgtcgagt ttaactgcac ggcggacaac ctggccgtcg agggggccat gtgtgacctg   1080
ccggcctaca agctcatgtg cttcgatatc gaatgcaagg ccggggggga ggacgagctg   1140
gcctttccgg tcgcggaacg cccggaagac ctcgtcatcc agatctcctg tctgctctac   1200
gacctgtcca ccaccgccct cgagcacatc ctcctgtttt cgctcggatc ctgcgacctc   1260
cccgagtccc acctcagcga tctcgcctcc aggggcctgc cggcccccgt cgtcctggag   1320
tttgacagcg aattcgagat gctgctggcc ttcatgacct tcgtcaagca gtacggcccc   1380
gagttcgtga ccgggtacaa catcatcaac ttcgactggc ccttcgtcct gaccaagctg   1440
acggagatct acaaggtccc gctcgacggg tacgggcgca tgaacggccg gggtgtgttc   1500
cgcgtgtggg acatcggcca gagccacttt cagaagcgca gcaagatcaa ggtgaacggg   1560
atggtgaaca tcgacatgta cggcatcatc accgacaagg tcaaactctc cagctacaag   1620
ctgaacgccg tcgccgaggc cgtcttgaag gacaagaaga aggatctgag ctaccgcgac   1680
atccccgcct actacgcctc cgggcccgcg cagcgcgggg tgatcggcga gtattgtgtg   1740
caggactcgc tgctggtcgg gcagctgttc ttcaagtttc tgccgcacct ggagctttcc   1800
gccgtcgcgc gcctggcggg catcaacatc ccccgcacca tctacgacgg ccagcagatc   1860
cgcgtcttca cgtgcctcct gcgccttgcg ggccagaagg gcttcatcct gccggacacc   1920
caggggcggt ttcggggcct cgacaaggag gcgcccaagc gcccggccgt gcctcggggg   1980 gaagggagc ggccggggga cgggaacggg gacgaggata aggacgacga cgaggacggg   2040
gacgaggacg gggacgagcg cgaggaggtc gcgcgcgaga ccggggccg gcacgttggg   2100 taccaggggg cccgggtcct cgaccccacc tccgggtttc acgtcgaccc cgtggtggtg   2160
tttgactttg ccagcctgta ccccagcatc atccaggccc acaacctgtg cttcagtacg   2220
ctctccctgc ggcccgaggc cgtcgcgcac ctggaggcgg accgggacta cctggagatc   2280
gaggtggggg gccgacggct gttcttcgtg aaggcccacg tacgcgagag cctgctgagc   2340
atcctgctgc gcgactggct ggccatgcga aagcagatcc gctcgcggat cccccagagc   2400
accccccagg aggccgtcct cctcgacaag caacaggccg ccatcaaggt ggtgtgcaac   2460
tcggtgtacg ggttcaccgg ggtgcagcac ggtcttctgc cctgcctgca cgtggccgcc   2520
accgtgacga ccatcggccg cgagatgctc ctcgcgacgc gcgcgtacgt gcacgcgcgc   2580
tgggcggagt tcgatcagct gctggccgac ttttccggagg cggccggcat gcgcgccccc   2640
ggtccgtact ccatgcgcat catctacggg gacacggact ccatttttcgt tttgtgccgc   2700 ggcctcacgg ccgcgggcct ggtggccatg ggcgacaaga tggcgagcca catctcgcgc   2760
gcgctgttcc tcccccccgat caagctcgag tgcgaaaaaa cgttcaccaa gctgctgctc   2820
atcgccaaga aaaagtacat cggcgtcatc tgcgggggca agatgctcat caagggcgtg   2880
gatctggtgc gcaaaaacaa ctgcgcgttt atcaaccgca cctccagggc cctggtcgac   2940
ctgctgtttt acgacgatac cgtatccgga gcggccgccg cgttagccga cgcccccgca   3000
gaggagtggc tggcgcgacc cctgcccgag ggactgcagg cgttcggggc cgtcctcgta   3060
gacgcccatc ggcgcatcac cgacccgagg agggacatcc aggactttgt cctcaccgcc   3120
gaactgagca gacacccgcg cgcgtacacc aacaagcgcc tggcccacct gacggtgtat   3180
tacaagctca tggcccgccg cgcgcaggtc ccgtccatca aggaccggat cccgtacgtg   3240
atcgtggccc agacccgcga ggtagaggag acggtcgcgc ggctggccgc cctccgcgag   3300
ctagacgccg ccgccccagg ggacgagccc gccccccag cggccctgcc ctccccggcc   3360
aagcgccccc gggagacgcc gtcgcatgcc gaccccccgg gaggcgcgtc caagcccgc   3420
```

-continued

```
aagctgctgg tgtccgagct ggcggaggat cccgggtacg ccatcgcccg gggcgttccg    3480
ctcaacacgg actattactt ctcgcacctg ctggggcgg cctgcgtgac gttcaaggcc     3540
ctgtttggaa ataacgccaa gatcaccgag agtctgttaa agaggtttat tcccgagacg    3600
tggcaccccc cggacgacgt ggccgcgcgg ctcaggccg cggggttcgg gccggcgggg    3660
gccggcgcta cggcggagga aactcgtcga atgttgcata gagcctttga tactctagca    3720
tgagcccccc gtcgaagctg atgtcccgca tcttgcaata aa                        3762
```

<210> SEQ ID NO 83
<211> LENGTH: 598
<212> TYPE: PRT
<213> ORGANISM: Herpes simplex virus 2

<400> SEQUENCE: 83

```
Met Ala Thr Ser Ala Pro Gly Val Pro Ser Ala Ala Val Arg Glu
1               5                   10                  15

Glu Ser Pro Gly Ser Ser Trp Lys Glu Gly Ala Phe Glu Arg Pro Tyr
            20                  25                  30

Val Ala Phe Asp Pro Asp Leu Leu Ala Leu Asn Glu Ala Leu Cys Ala
        35                  40                  45

Glu Leu Leu Ala Ala Cys His Val Val Gly Val Pro Pro Ala Ser Ala
    50                  55                  60

Leu Asp Glu Asp Val Glu Ser Asp Val Ala Pro Ala Pro Pro Arg Pro
65                  70                  75                  80

Arg Gly Ala Ala Arg Glu Ala Ser Gly Gly Arg Gly Pro Gly Ser Ala
                85                  90                  95

Arg Gly Pro Pro Ala Asp Pro Thr Ala Glu Gly Leu Leu Asp Thr Gly
            100                 105                 110

Pro Phe Ala Ala Ala Ser Val Asp Thr Phe Ala Leu Asp Arg Pro Cys
        115                 120                 125

Leu Val Cys Arg Thr Ile Glu Leu Tyr Lys Gln Ala Tyr Arg Leu Ser
    130                 135                 140

Pro Gln Trp Val Ala Asp Tyr Ala Phe Leu Cys Ala Lys Cys Leu Gly
145                 150                 155                 160

Ala Pro His Cys Ala Ala Ser Ile Phe Val Ala Ala Phe Glu Phe Val
                165                 170                 175

Tyr Val Met Asp His His Phe Leu Arg Thr Lys Lys Ala Thr Leu Val
            180                 185                 190

Gly Ser Phe Ala Arg Phe Ala Leu Thr Ile Asn Asp Ile His Arg His
        195                 200                 205

Phe Phe Leu His Cys Cys Phe Arg Thr Asp Gly Gly Val Pro Gly Arg
    210                 215                 220

His Ala Gln Lys Gln Pro Arg Pro Thr Pro Ser Pro Gly Ala Ala Lys
225                 230                 235                 240

Val Gln Tyr Ser Asn Tyr Ser Phe Leu Ala Gln Ser Ala Thr Arg Ala
                245                 250                 255

Leu Ile Gly Thr Leu Ala Ser Gly Gly Asp Asp Gly Ala Gly Ala Gly
            260                 265                 270

Ala Gly Gly Gly Ser Gly Thr Gln Pro Ser Leu Thr Thr Ala Leu Met
        275                 280                 285

Asn Trp Lys Asp Cys Ala Arg Leu Leu Asp Cys Thr Glu Gly Lys Arg
    290                 295                 300

Gly Gly Gly Asp Ser Cys Cys Thr Arg Ala Ala Ala Arg Asn Gly Glu
305                 310                 315                 320
```

```
Phe Glu Ala Ala Ala Gly Ala Leu Ala Gln Gly Gly Glu Pro Glu Thr
                325                 330                 335

Trp Ala Tyr Ala Asp Leu Ile Leu Leu Leu Ala Gly Thr Pro Ala
        340                 345                 350

Val Trp Glu Ser Gly Pro Arg Leu Arg Ala Ala Asp Ala Arg Arg
    355                 360                 365

Ala Ala Val Ser Glu Ser Trp Glu Ala His Arg Gly Ala Arg Met Arg
370                 375                 380

Asp Ala Ala Pro Arg Phe Ala Gln Phe Ala Glu Pro Gln Pro Gln Pro
385                 390                 395                 400

Asp Leu Asp Leu Gly Pro Leu Met Ala Thr Val Leu Lys His Gly Arg
                405                 410                 415

Gly Arg Gly Arg Thr Gly Gly Glu Cys Leu Leu Cys Asn Leu Leu Leu
            420                 425                 430

Val Arg Ala Tyr Trp Leu Ala Met Arg Arg Leu Arg Ala Ser Val Val
        435                 440                 445

Arg Tyr Ser Glu Asn Asn Thr Ser Leu Phe Asp Cys Ile Val Pro Val
    450                 455                 460

Val Asp Gln Leu Glu Ala Asp Pro Glu Ala Gln Pro Gly Asp Gly Gly
465                 470                 475                 480

Arg Phe Val Ser Leu Leu Arg Ala Ala Gly Pro Glu Ala Ile Phe Lys
                485                 490                 495

His Met Phe Cys Asp Pro Met Cys Ala Ile Thr Glu Met Glu Val Asp
            500                 505                 510

Pro Trp Val Leu Phe Gly His Pro Arg Ala Asp His Arg Asp Glu Leu
        515                 520                 525

Gln Leu His Lys Ala Lys Leu Ala Cys Gly Asn Glu Phe Glu Gly Arg
    530                 535                 540

Val Cys Ile Ala Leu Arg Ala Leu Ile Tyr Thr Phe Lys Thr Tyr Gln
545                 550                 555                 560

Val Phe Val Pro Lys Pro Thr Ala Leu Ala Thr Phe Val Arg Glu Ala
                565                 570                 575

Gly Ala Leu Leu Arg Arg His Ser Ile Ser Leu Leu Ser Leu Glu His
            580                 585                 590

Thr Leu Cys Thr Tyr Val
        595

<210> SEQ ID NO 84
<211> LENGTH: 2789
<212> TYPE: DNA
<213> ORGANISM: Artificial
<220> FEATURE:
<223> OTHER INFORMATION: Synthetic DNA sequence of GenBank accession
      NC_001798 region: 66850..69638

<400> SEQUENCE: 84
tttattcccg agacgtggca ccccccggac gacgtggccg cgcggctcag ggccgcgggg      60
ttcgggccgg cggggccggc cgctacggcg gaggaaactc gtcgaatgtt gcatagagcc     120
tttgatactc tagcatgagc cccccgtcga agctgatgtc ccgcatcttg caataaatgt     180
ctgcggccga cacggtcgga atttccgcgt ccgctggttt ctctgcgttg cgtctgacca     240
cgagcacaaa cgtgctctgc cacacgtggg cggcgaaccg gtagccgggg cacgcggtca     300
gcatccgatc gatgagccgg tagtgcaggt gggccgacgt gccggggaag atgacgtaca     360
gcatgtggcc cccgtacgtg gggtccgggt aaaaagaaa ccgggggtcg cacgcccccc      420
ctccgcgcag gatcgtgtgc acgaaaaaga gctcgggctg gccgagcgta tcggccagga     480
```

-continued

```
ggtcctggag gggggtgctg tggcggtcgg ccagcacgac cagggaggcc agaaaggtgc    540
ggtgctcaaa gatcgtattg atctgctgca cgaaggccag gatgagggcc tcgcggctga    600
cggtggccag ccgcccgtcg cccgcgctgc acgcggggca gcagcccccg atccccaggt    660
agtagcccat gcccgagagg gtcaggcagt tgtcggccac ggtctggtcc aggctgaagg    720
ggagcgacac gggggtcgtc ttcaccaggg gcacggagag cgagcgcacg atggcgatct    780
cctcggaggg cgtctgggcg agggcggcga agaagccgcg gtagcgacgg cgctcgtgca    840
ggcagagctc cagcctgcgc gcgtgcgacg gcaggctctt gcgggaggcc cggcgctcca    900
cgccggggtt cccggcggcg gaaaagcgcg accgccgccg ggtcttgtcg cggccgggcc    960
cgggccggga ccggagcgac cgggggggcga tgtcatacat aggtacagag ggtgtgctcc   1020
agggacagga gagagatcga gtgtcgtctg agcagcgcgc cggcctcgcg gacaaatgtg   1080
gccagcgcgg tgggcttcgg cacaaatacc tggtacgtct tgaaggtgta gatgagggcc   1140
cgcagggcta tacagacccg cccctcgaac tcgttgccgc aggccaactt ggccttgtga   1200
agctgcagct cgtcgcgatg gtcggcgcgg gggtggccaa acaggaccca ggggtcgact   1260
tccatctccg tgatggcgca catcggatcg cagaacatgt gcttgaagat ggcctcgggg   1320
cccgcggccc gaagcaggct cacgaaccgg ccccgtccc cgggctgcgc ctcggggtcc    1380
gcctcgagct ggtccacgac cggcactatg cagtcgaaga ggctggtgtt gttctccgag   1440
tagcggacga cggacgccct caggcgtcgc atggccagcc agtaggcccg caccagcaac   1500
agattgcaca gcaggcattc cccgccgtg cgcccgcgcc cccggccgtg cttcagcacg    1560
gtggccatca gcgggcccag gtccaggtcg ggctggggct ggggctcggc gaactgcgca   1620
aaacgcgggg ccgcgtcgcg catgcgcgcc ccgcggtgcg cttcccagga ctcgctgacc   1680
gcggcgcggc gggcgtccgc ggcggcgcgc agccggggcc ccgactccca gacggcgggg   1740
gtgccggcga gcagcagcag gatcaggtcg gcgtacgccc acgtctccgg ctcaccccc    1800
tgcgccagcg ccccggcggc ggcctcgaac tccccgttgc gggcggcggc gcgcgtgcag   1860
cagctgtctc cgccccgcg cttgcccctcg gtgcagtcga gcaggcgggc gcagtccttc   1920
cagttcatca gggcggtggt gagggagggt tgcgttcccg agccccgcc cgcccccgcc    1980
cccgccccgt catcgccccc ggaggccagg gtcccgatga gggcccgggt tgcggactgc   2040
gcgaggaagg aatagttgga gtactgcacc ttggcggcgc ccggggaggg cgtcggcctg   2100
ggttgcttct gggcgtggcg cccgggcacc ccgccgtcgg tccggaagca gcagtggaga   2160
aagaaatgcc ggtggatgtc gttgatggtc agggcgaagc gcgcgaagga ccgacaagg    2220
gtcgccttct tggtgcgcag gaagtggtgg tccatgacgt agacgaactc gaaggcggcc   2280
acgaagatgc tcgcggcgca gtggggcgcg cccaggcact tggcgcagag gaacgcgtaa   2340
tcggccaccc actggggcga gaggcggtag gcctgcttgt acagctcgat ggtgcggcag   2400
accagacagg ggcggtccag cgcgaaggtg tcgacgacg ccgcggcgaa gggccccgtg    2460
tccaagagtc cctctgccgt ggggtctgcg ggcgggccgc gggcggaccc cggccccgc    2520
cccccgaag cctcgcgcgc ggccccgcgc ggccgcgggg gggcgggcgc gacgtcgctc    2580
tccacgtcct cgtcgagcgc gctcgcgggc ggcacgccta ccacgtgaca ggccgccagg   2640
agctcggcgc acagggcctc gttaagagcc agaaggtcgg gatcgaaggc cacatacgga   2700
cgctcgaacg cgccctcctt ccagctgctg cccggcgact cttcgcgcac ggcggcgctc   2760
gacggcaccc ccggggcgga cgtcgccat                                     2789
```

<210> SEQ ID NO 85
<211> LENGTH: 130
<212> TYPE: PRT
<213> ORGANISM: Herpes simplex virus 2

<400> SEQUENCE: 85

```
Met Ala Gly Arg Ala Gly Arg Thr Arg Pro Arg Thr Leu Arg Asp Ala
 1               5                  10                  15

Ile Pro Asp Cys Ala Leu Arg Ser Gln Thr Leu Glu Ser Leu Asp Ala
            20                  25                  30

Arg Tyr Val Ser Arg Asp Gly Ala Gly Asp Ala Ala Val Trp Phe Glu
        35                  40                  45

Asp Met Thr Pro Ala Glu Leu Glu Val Ile Phe Pro Thr Thr Asp Ala
    50                  55                  60

Lys Leu Asn Tyr Leu Ser Arg Thr Gln Arg Leu Ala Ser Leu Leu Thr
65                  70                  75                  80

Tyr Ala Gly Pro Ile Lys Ala Pro Asp Gly Pro Ala Ala Pro His Thr
                85                  90                  95

Gln Asp Thr Ala Cys Val His Gly Glu Leu Leu Ala Arg Lys Arg Glu
            100                 105                 110

Arg Phe Ala Ala Val Ile Asn Arg Phe Leu Asp Leu His Gln Ile Leu
        115                 120                 125

Arg Gly
    130
```

<210> SEQ ID NO 86
<211> LENGTH: 1833
<212> TYPE: DNA
<213> ORGANISM: Artificial
<220> FEATURE:
<223> OTHER INFORMATION: Synthetic DNA sequence of GenBank accession
      NC_001798 region: 69637..71469

<400> SEQUENCE: 86

| atggccggtc | gagcggggcg | cacgcgtccg | cgaacgttac | gggacgcgat | ccccgactgc | 60 |
| gcgctgcggt | cccagaccct | ggaaagtcta | gacgcgcgct | acgtctcgcg | agacggcgcg | 120 |
| ggggacgcgg | ccgtctggtt | cgaggacatg | accccgccg | aactagaggt | tatattcccg | 180 |
| accacggacg | ccaagctgaa | ctacctctcg | cggacgcagc | ggctggcctc | cctcctgacg | 240 |
| tacgccgggc | ctataaaagc | gcccgacggc | cccgccgccc | cacatacgca | ggacaccgcg | 300 |
| tgcgtgcacg | gcgagctgct | cgcccgaaag | cgcgaacggt | tcgcggcggt | cattaaccgg | 360 |
| ttcctggacc | tgcaccagat | cctgcggggc | tgacgcgcgc | ttcggcgggg | caccggcacc | 420 |
| gggaccgact | tgttttacat | aacagtaggg | ggtgggggaa | cgcgcaccct | tgcccggtcg | 480 |
| cgatggcggg | gatggggaag | ccctacggcg | gccgcccggg | ggacgcgttc | gagggtctcg | 540 |
| ttcagcgcat | caggctcatt | gttcccgcca | cgctgcgcgg | cggggtgtgg | gagtcgggcc | 600 |
| cctactcgcc | atccaacccg | ccctcgagat | gtgccttcca | gttccacggc | caggatgggt | 660 |
| ccgacgaggc | cttcccgatc | gagtacgtcc | tgcggctcat | gaacgactgg | gccgatgtgc | 720 |
| cctgcaaccc | ctacctgcgc | gtgcagaaca | ccggcgtttc | ggtgctgttt | cagggggtttt | 780 |
| ttaaccggcc | ccacggcgcc | cggggggggcg | cgatcacggc | ggagcagacc | aacgtgattc | 840 |
| tgcactccac | cgagacgacg | ggactgtccc | tcggagacct | ggacgacgtc | aaggggcgcc | 900 |
| tcggcctgga | cgccggccg | atgatggcca | gcatgtggat | cagctgcttt | gtgcgcatgc | 960 |
| cccgggtgca | gctcgcgttt | cggttcatgg | gccccgagga | cgccgttcgc | acgcggcgga | 1020 |
| tcctgtgtcg | cgccgccgag | caggccctcg | cccgtcgccg | ccggtccagg | cggtcccagg | 1080 |

-continued

```
atgactacgg ggcggtggtg gtggcggcgg cgcaccactc ttccggagcg cccgggccgg    1140
gggtcgccgc ctcgggcccg ccagcgccgc ccggacgggg accggcccgt ccgtggcatc    1200
aggccgtgca gttgttccgg gccccgcgtc cgggcccccc ggcgcttctg ttgctggcgg    1260
cggggctgtt tctgggggcc gctatctggt gggcggttgg cgcgcgccta tgaaaggggg    1320
cgagccaccg tccgcccgc cagtgcatcc cagacgcccg cgagccgcac atccctccg     1380 ctcccgcctc cggcccgatt cttacggcgc gacccaaggt cccgatggcc gccccgcagt   1440
ttcaccgccc cagcaccatt accgccgaca acgtccgggc gctcggcatg cgcgggctcg   1500
tgttggccac caacaacgct cagttcatca tggataacag ctaccccgcat ccgcacggaa  1560 cgcagggtgc ggtgcgagag tttcttcgcg ggcaggccgc ggcgctgacg gacctcgggg   1620
tgacccacgc caacaacacg ttcgcccccgc agcctatgtt cgcgggcgac gccgcggccg  1680
aatggctgcg gccctcgttc ggtcttaagc gcacgtattc cccctttgtc gttcgcgacc   1740
ccaagacccc cagcaccccg tgagtcctcg gcgggtccct ccgcggccgt ctctcgttgc   1800
ccccctttcc cccttcccgg gtggttcaat aaa                                1833
```

<210> SEQ ID NO 87
<211> LENGTH: 276
<212> TYPE: PRT
<213> ORGANISM: Herpes simplex virus 2

<400> SEQUENCE: 87

```
Met Ala Gly Met Gly Lys Pro Tyr Gly Gly Arg Pro Gly Asp Ala Phe
 1               5                  10                  15

Glu Gly Leu Val Gln Arg Ile Arg Leu Ile Val Pro Ala Thr Leu Arg
             20                  25                  30

Gly Gly Gly Gly Glu Ser Gly Pro Tyr Ser Pro Ser Asn Pro Pro Ser
         35                  40                  45

Arg Cys Ala Phe Gln Phe His Gly Gln Asp Gly Ser Asp Glu Ala Phe
     50                  55                  60

Pro Ile Glu Tyr Val Leu Arg Leu Met Asn Asp Trp Ala Asp Val Pro
 65                  70                  75                  80

Cys Asn Pro Tyr Leu Arg Val Gln Asn Thr Gly Val Ser Val Leu Phe
                 85                  90                  95

Gln Gly Phe Phe Asn Arg Pro His Gly Ala Pro Gly Gly Ala Ile Thr
            100                 105                 110

Ala Glu Gln Thr Asn Val Ile Leu His Ser Thr Glu Thr Thr Gly Leu
        115                 120                 125

Ser Leu Gly Asp Leu Asp Asp Val Lys Gly Arg Leu Gly Leu Asp Ala
    130                 135                 140

Arg Pro Met Met Ala Ser Met Trp Ile Ser Cys Phe Val Arg Met Pro
145                 150                 155                 160

Arg Val Gln Leu Ala Phe Arg Phe Met Gly Pro Glu Asp Ala Val Arg
                165                 170                 175

Thr Arg Arg Ile Leu Cys Arg Ala Ala Glu Gln Ala Leu Ala Arg Arg
            180                 185                 190

Arg Arg Ser Arg Arg Ser Gln Asp Asp Tyr Gly Ala Val Val Val Ala
        195                 200                 205

Ala Ala His His Ser Ser Gly Ala Pro Gly Pro Gly Val Ala Ala Ser
    210                 215                 220

Gly Pro Pro Ala Pro Pro Gly Arg Gly Pro Ala Arg Pro Trp His Gln
225                 230                 235                 240
```

```
Ala Val Gln Leu Phe Arg Ala Pro Arg Pro Gly Pro Ala Leu Leu
            245                 250                 255
Leu Leu Ala Ala Gly Leu Phe Leu Gly Ala Ala Ile Trp Trp Ala Val
        260                 265                 270
Gly Ala Arg Leu
        275

<210> SEQ ID NO 88
<211> LENGTH: 1351
<212> TYPE: DNA
<213> ORGANISM: Artificial
<220> FEATURE:
<223> OTHER INFORMATION: Synthetic DNA sequence of GenBank accession
      NC_001798 region: 70119..71469

<400> SEQUENCE: 88
atggcgggga tggggaagcc ctacggcggc cgcccggggg acgcgttcga gggtctcgtt      60
cagcgcatca ggctcattgt tcccgccacg ctgcgcggcg ggggtgggga gtcgggcccc     120
tactcgccat ccaacccgcc ctcgagatgt gccttccagt tccacggcca ggatgggtcc     180
gacgaggcct tcccgatcga gtacgtcctg cggctcatga cgactgggc cgatgtgccc     240
tgcaacccct acctgcgcgt gcagaacacc ggcgtttcgg tgctgtttca ggggtttttt     300
aaccggcccc acggcgcccc gggggcgcgc atcacggcgg agcagaccaa cgtgattctg     360
cactccaccg agacgacggg actgtccctc ggagacctgg acgacgtcaa ggggcgcctc     420
ggcctggacg cccggccgat gatggccagc atgtggatca gctgctttgt gcgcatgccc     480
cgggtgcagc tcgcgtttcg gttcatgggc cccgaggacg ccgttcgcac gcggcggatc     540
ctgtgtcgcg ccgccgagca ggccctcgcc cgtcgccgcc ggtccaggcg gtcccaggat     600
gactacgggg cggtggtggt ggcggcggcg caccactctt ccggagcgcc cgggccgggg     660
gtcgccgcct cgggcccgcc agcgccgccc ggacggggac cggcccgtcc gtggcatcag     720
gccgtgcagt tgttccgggc cccgcgtccg ggccccccgg cgcttctgtt gctggcggcg     780
gggctgtttc tggggccgc tatctggtgg gcggttggcg cgcgcctatg aaaggggcg     840
agccaccgtc ccgcccgcca gtgcatccca gacgcccgcg agccgcacat ccctccgct     900
cccgcctccg gcccgattct tacggcgcga cccaaggtcc cgatggccgc cccgcagttt     960
caccgcccca gcaccattac cgccgacaac gtccgggcgc tcggcatgcg cgggctcgtg    1020
ttggccacca caacgctca gttcatcatg ataacagct accgcatcc gcacggaacg    1080
cagggtgcgg tgcgagagtt tcttcgcggg caggccgcgg cgctgacgga cctcggggtg    1140
acccacgcca caacacgtt cgccccgcag cctatgttcg cgggcgacgc cgcggccgaa    1200
tggctgcggc cctcgttcgg tcttaagcgc acgtattccc cctttgtcgt tcgcgacccc    1260
aagaccccca gcacccgtg agtcctcggc gggtccctcc gcggccgtct ctcgttgccc    1320
cccttccccc ttcccgggt ggttcaataa a                                   1351

<210> SEQ ID NO 89
<211> LENGTH: 470
<212> TYPE: PRT
<213> ORGANISM: Herpes simplex virus 2

<400> SEQUENCE: 89

Met Ala His Leu Pro Gly Gly Ala Ala Ala Pro Leu Ser Glu Asp
1               5                   10                  15
Ala Ile Pro Ser Pro Arg Glu Arg Thr Glu Asp Trp Pro Pro Cys Gln
            20                  25                  30
```

```
Ile Val Leu Gln Gly Ala Glu Leu Asn Gly Ile Leu Gln Ala Phe Ala
             35                  40                  45

Pro Leu Arg Thr Ser Leu Leu Asp Ser Leu Leu Val Val Gly Asp Arg
 50                  55                  60

Gly Ile Leu Val His Asn Ala Ile Phe Gly Glu Gln Val Phe Leu Pro
 65                  70                  75                  80

Leu Asp His Ser Gln Phe Ser Arg Tyr Arg Trp Gly Gly Pro Thr Ala
                     85                  90                  95

Ala Phe Leu Ser Leu Val Asp Gln Lys Arg Ser Leu Leu Ser Val Phe
                 100                 105                 110

Arg Ala Asn Gln Tyr Pro Asp Leu Arg Arg Val Glu Leu Thr Val Thr
             115                 120                 125

Gly Gln Ala Pro Phe Arg Thr Leu Val Gln Arg Ile Trp Thr Thr Ala
130                 135                 140

Ser Asp Gly Glu Ala Val Glu Leu Ala Ser Glu Thr Leu Met Lys Arg
145                 150                 155                 160

Glu Leu Thr Ser Phe Ala Val Leu Leu Pro Gln Gly Asp Pro Asp Val
                 165                 170                 175

Gln Leu Arg Leu Thr Lys Pro Gln Leu Thr Lys Val Val Asn Ala Val
             180                 185                 190

Gly Asp Glu Thr Ala Lys Pro Thr Thr Phe Glu Leu Gly Pro Asn Gly
         195                 200                 205

Lys Phe Ser Val Phe Asn Ala Arg Thr Cys Val Thr Phe Ala Ala Arg
     210                 215                 220

Glu Glu Gly Ala Ser Ser Thr Ser Ala Gln Val Gln Ile Leu Thr
225                 230                 235                 240

Ser Ala Leu Lys Lys Ala Gly Gln Ala Ala Asn Ala Lys Thr Val
                 245                 250                 255

Tyr Gly Glu Asn Thr His Arg Thr Phe Ser Val Val Asp Asp Cys
             260                 265                 270

Ser Met Arg Ala Val Leu Arg Arg Leu Gln Val Gly Gly Thr Leu
         275                 280                 285

Lys Phe Phe Leu Thr Ala Asp Val Pro Ser Val Cys Val Thr Ala Thr
     290                 295                 300

Gly Pro Asn Ala Val Ser Ala Val Phe Leu Leu Lys Pro Gln Arg Val
305                 310                 315                 320

Cys Leu Asn Trp Leu Gly Arg Ser Pro Gly Ser Ser Thr Gly Ser Leu
                 325                 330                 335

Ala Ser Gln Asp Ser Arg Ala Gly Pro Thr Asp Ser Gln Asp Ser Ser
             340                 345                 350

Ser Glu Pro Asp Ala Gly Asp Arg Gly Ala Pro Glu Glu Gly Leu
         355                 360                 365

Glu Gly Gln Ala Arg Val Pro Pro Ala Phe Pro Glu Pro Gly Thr
     370                 375                 380

Lys Arg Arg His Pro Gly Ala Glu Val Val Pro Ala Asp Asp Ala Thr
385                 390                 395                 400

Lys Arg Pro Lys Thr Gly Val Pro Ala Pro Thr Arg Ala Glu Ser
                 405                 410                 415

Pro Pro Leu Ser Ala Arg Tyr Gly Pro Glu Ala Ala Glu Gly Gly Gly
             420                 425                 430

Asp Gly Gly Arg Tyr Ala Cys Tyr Phe Arg Asp Leu Gln Thr Gly Asp
         435                 440                 445
```

Ala Ser Pro Ser Pro Leu Ser Ala Phe Arg Gly Pro Gln Arg Pro Pro
    450                 455                 460

Tyr Gly Phe Gly Leu Pro
465                 470

<210> SEQ ID NO 90
<211> LENGTH: 1487
<212> TYPE: DNA
<213> ORGANISM: Artificial
<220> FEATURE:
<223> OTHER INFORMATION: Synthetic DNA sequence of GenBank accession
      NC_001798 region: 93769..95255

<400> SEQUENCE: 90

| | |
|---|---|
| atggctcatc ttcccggcgg tgcggccgcc gcccccttt cggaggacgc gatcccgtcg | 60 |
| ccgcgcgagc ggacggaaga ctggccgccc tgccagatag tgctgcaggg cgccgagctg | 120 |
| aacgggatcc tgcaggcctt gcgccgctt cgcacgagcc ttttggactc gctcctggtc | 180 |
| gtgggcgacc gaggcatcct tgtacataac gcgattttcg gcgagcaggt gtttctgccc | 240 |
| ctcgaccatt cgcagttcag tcgctatcga tggggcggac ccaccgcggc gttcctgtct | 300 |
| ctcgtgacc agaagcgatc cctgctgagc gtgtttcgcg ccaaccagta ccctgacctg | 360 |
| cggcgggtgg agctgacggt cacgggccag gccccgtttc gcacgctggt gcagcgcata | 420 |
| tggacgaccg cgtccgacgg agaggccgtg gagcttgcca gcgagacgct catgaaacgc | 480 |
| gagttgacga gcttcgcggt actactcccc cagggcgacc ccgacgtcca gctgcgcctc | 540 |
| acgaagcccc agctcacgaa ggtggtgaac gccgtcgggg acgagaccgc caaacccacc | 600 |
| acgttcgagc tcggccccaa cggcaagttt ccgtgtttta acgcgcgcac ctgcgtcacc | 660 |
| tttgccgccc gcgaggaggg cgcgtcgtcc agcaccagcg cccaggtcca gattctgacc | 720 |
| agcgcgctga agaaggcggg ccaagcggcc gccaacgcca agacggtcta cggggaaaac | 780 |
| acacaccgca cattctcggt ggtcgtcgac gactgcagca tgcgggcggt cctccggcgg | 840 |
| ctccaggtcg gcgggggac cctcaagttc ttcctcacgg ccgacgtccc cagcgtgtgt | 900 |
| gtcaccgcca ccgccccaa cgcggtgtcg gcggtgtttc ttttaaaacc ccagcgggtc | 960 |
| tgcctgaact ggctcggccg gagcccgggt tcctcgaccg ggagcttggc gtcccaggac | 1020 |
| tctcgggccg gcccgaccga cagccaggac tcctcctccg agccggacgc gggcgaccgc | 1080 |
| ggcgccccag aagaagaagg cctcgagggc caggcccggg taccgcccgc gttcccggaa | 1140 |
| ccgccgggaa ccaagcggag caccccgggg ccgaagttg tccccgcgga cgacgccacc | 1200 |
| aagcgcccga gacgggcgt gcccgccgcc cccacgcgag ccgagtcgcc cccctctcc | 1260 |
| gcgagatacg gacccgaggc ggcggagggt ggtggggacg gcggccgcta cgcgtgctac | 1320 |
| tttcgcgacc tccagaccgg cgacgcgagc cccagccccc tctccgcctt ccggggtccc | 1380 |
| caaagacccc catacggctt tgggttgccc tgacggcaac gggtggtggc cgaacgcctc | 1440 |
| accgcgcccg ggcacgcggg gtgcgttgtg ttaaaaaat aaataaa | 1487 |

<210> SEQ ID NO 91
<211> LENGTH: 1066
<212> TYPE: PRT
<213> ORGANISM: Herpes simplex virus 2

<400> SEQUENCE: 91

Met Gly Thr Glu Asp Cys Asp His Glu Gly Arg Ser Val Ala Ala Pro
1               5                   10                  15

Val Glu Val Thr Ala Leu Tyr Ala Thr Asp Gly Cys Val Ile Thr Ser
            20                  25                  30

```
Ser Leu Ala Leu Leu Thr Asn Cys Leu Leu Gly Ala Glu Pro Leu Tyr
         35                  40                  45

Ile Phe Ser Tyr Asp Ala Tyr Arg Ser Asp Ala Pro Asn Gly Pro Thr
 50                  55                  60

Gly Ala Pro Thr Glu Gln Glu Arg Phe Glu Gly Ser Arg Ala Leu Tyr
 65                  70                  75                  80

Arg Asp Ala Gly Gly Leu Asn Gly Asp Ser Phe Arg Val Thr Phe Cys
                 85                  90                  95

Leu Leu Gly Thr Glu Val Gly Val Thr His His Pro Lys Gly Arg Thr
             100                 105                 110

Arg Pro Met Phe Val Cys Arg Phe Glu Arg Ala Asp Asp Val Ala Val
         115                 120                 125

Leu Gln Asp Ala Leu Gly Arg Gly Thr Pro Leu Leu Pro Ala His Val
     130                 135                 140

Thr Ala Thr Leu Asp Leu Glu Ala Thr Phe Ala Leu His Ala Asn Ile
145                 150                 155                 160

Ile Met Ala Leu Thr Val Ala Ile Val His Asn Ala Pro Ala Arg Ile
                 165                 170                 175

Gly Ser Gly Ser Thr Ala Pro Leu Tyr Glu Pro Gly Glu Ser Met Arg
             180                 185                 190

Ser Val Val Gly Arg Met Ser Leu Gly Gln Arg Gly Leu Thr Thr Leu
         195                 200                 205

Phe Val His His Glu Ala Arg Val Leu Gly Ala Tyr Arg Arg Ala Tyr
     210                 215                 220

Tyr Gly Ser Ala Gln Ser Pro Phe Trp Phe Leu Ser Lys Phe Gly Pro
225                 230                 235                 240

Asp Glu Lys Ser Leu Val Leu Ala Ala Arg Tyr Tyr Leu Leu Gln Ala
                 245                 250                 255

Pro Arg Leu Gly Gly Ala Gly Ala Thr Tyr Asp Leu Gln Ala Val Lys
             260                 265                 270

Asp Ile Cys Ala Thr Tyr Ala Ile Pro His Asp Pro Arg Pro Asp Thr
         275                 280                 285

Leu Ser Ala Ala Ser Leu Thr Ser Phe Ala Ala Ile Thr Arg Phe Cys
     290                 295                 300

Cys Thr Ser Gln Tyr Ser Arg Gly Ala Ala Ala Gly Phe Pro Leu
305                 310                 315                 320

Tyr Val Glu Arg Arg Ile Ala Ala Asp Val Arg Glu Thr Gly Ala Leu
                 325                 330                 335

Glu Lys Phe Ile Ala His Asp Arg Ser Cys Leu Arg Val Ser Asp Arg
             340                 345                 350

Glu Phe Ile Thr Tyr Ile Tyr Leu Ala His Phe Glu Cys Phe Ser Pro
         355                 360                 365

Pro Arg Leu Ala Thr His Leu Arg Ala Val Thr Thr His Asp Pro Ser
     370                 375                 380

Pro Ala Ala Ser Thr Glu Gln Pro Ser Pro Leu Gly Arg Glu Ala Val
385                 390                 395                 400

Glu Gln Phe Phe Arg His Val Arg Ala Gln Leu Asn Ile Arg Glu Tyr
                 405                 410                 415

Val Lys Gln Asn Val Thr Pro Arg Glu Thr Ala Leu Ala Gly Asp Ala
             420                 425                 430

Ala Ala Ala Tyr Leu Arg Ala Arg Thr Tyr Ala Pro Ala Leu Thr
         435                 440                 445

Pro Ala Pro Ala Tyr Cys Gly Val Ala Asp Ser Ser Thr Lys Met Met
     450                 455                 460
```

```
Gly Arg Leu Ala Glu Ala Glu Arg Leu Leu Val Pro His Gly Trp Pro
465                 470                 475                 480

Ala Phe Ala Pro Thr Thr Pro Gly Asp Asp Ala Gly Gly Gly Thr Ala
                485                 490                 495

Ala Pro Gln Thr Cys Gly Ile Val Lys Arg Leu Leu Lys Leu Ala Ala
            500                 505                 510

Thr Glu Gln Gln Gly Thr Thr Pro Pro Ala Ile Ala Ala Leu Met Gln
        515                 520                 525

Asp Ala Ser Val Gln Thr Pro Leu Pro Val Tyr Arg Ile Thr Met Ser
    530                 535                 540

Pro Thr Gly Gln Ala Phe Ala Ala Ala Arg Asp Asp Trp Ala Arg
545                 550                 555                 560

Val Thr Arg Asp Ala Arg Pro Pro Glu Ala Thr Val Val Ala Asp Ala
                565                 570                 575

Ala Ala Ala Pro Glu Pro Gly Ala Leu Gly Arg Arg Leu Thr Arg Arg
            580                 585                 590

Ile Cys Ala Arg Gly Pro Ala Leu Pro Pro Gly Gly Leu Ala Val Gly
        595                 600                 605

Gly Gln Met Tyr Val Asn Arg Asn Glu Ile Phe Asn Ala Ala Leu Ala
610                 615                 620

Val Thr Asn Ile Ile Leu Asp Leu Asp Ile Ala Leu Lys Glu Pro Val
625                 630                 635                 640

Pro Phe Pro Arg Leu His Glu Ala Leu Gly His Phe Arg Arg Gly Ala
                645                 650                 655

Leu Ala Ala Val Gln Leu Leu Phe Pro Ala Ala Arg Val Asp Pro Asp
            660                 665                 670

Ala Tyr Pro Cys Tyr Phe Phe Lys Ser Ala Cys Arg Pro Arg Ala Pro
        675                 680                 685

Pro Val Cys Ala Gly Asp Gly Pro Ser Ala Gly Gly Asp Asp Gly Asp
690                 695                 700

Gly Asp Trp Phe Pro Asp Ala Gly Gly Pro Gly Asp Glu Glu Trp Glu
705                 710                 715                 720

Glu Asp Thr Asp Pro Met Asp Thr Thr His Gly Pro Leu Pro Asp Asp
                725                 730                 735

Glu Ala Ala Tyr Leu Asp Leu Leu His Glu Gln Ile Pro Ala Ala Thr
            740                 745                 750

Pro Ser Glu Pro Asp Ser Val Val Cys Ser Cys Ala Asp Lys Ile Gly
        755                 760                 765

Leu Arg Val Cys Leu Pro Val Pro Ala Pro Tyr Val His Gly Ser
770                 775                 780

Leu Thr Met Arg Gly Val Ala Arg Val Ile Gln Gln Ala Val Leu Leu
785                 790                 795                 800

Asp Arg Asp Phe Val Glu Ala Val Gly Ser His Val Lys Asn Phe Leu
                805                 810                 815

Leu Ile Asp Thr Gly Val Tyr Ala His Gly His Ser Leu Arg Leu Pro
            820                 825                 830

Tyr Phe Ala Lys Ile Gly Pro Asp Gly Ser Ala Cys Gly Arg Leu Leu
        835                 840                 845

Pro Val Phe Val Ile Pro Pro Ala Cys Glu Asp Val Pro Ala Phe Val
850                 855                 860

Ala Ala His Ala Asp Pro Arg Arg Phe His Phe His Ala Pro Pro Met
865                 870                 875                 880

Phe Ser Ala Ala Pro Arg Glu Ile Arg Val Leu His Ser Leu Gly Gly
                885                 890                 895
```

Asp Tyr Val Ser Phe Phe Glu Lys Lys Ala Ser Arg Asn Ala Leu Glu
            900                 905                 910

His Phe Gly Arg Arg Glu Thr Leu Thr Glu Val Leu Gly Arg Tyr Asp
        915                 920                 925

Val Arg Pro Asp Ala Gly Glu Thr Val Glu Gly Phe Ala Ser Glu Leu
930                 935                 940

Leu Gly Arg Ile Val Ala Cys Ile Glu Ala His Phe Pro Glu His Ala
945                 950                 955                 960

Arg Glu Tyr Gln Ala Val Ser Val Arg Arg Ala Val Ile Lys Asp Asp
                965                 970                 975

Trp Val Leu Leu Gln Leu Ile Pro Gly Arg Gly Ala Leu Asn Gln Ser
            980                 985                 990

Leu Ser Cys Leu Arg Phe Lys His  Gly Arg Ala Ser Arg  Ala Thr Ala
        995                 1000                1005

Arg Thr  Phe Leu Ala Leu Ser  Val Gly Thr Asn Asn  Arg Leu Cys
    1010                1015                1020

Ala Ser  Leu Cys Gln Gln Cys  Phe Ala Thr Lys Cys  Asp Asn Asn
    1025                1030                1035

Arg Leu  His Thr Leu Phe Thr  Val Asp Ala Gly Thr  Pro Cys Ser
    1040                1045                1050

Arg Ser  Ala Pro Ser Ser Thr  Ser Arg Pro Ser Ser  Ser
    1055                1060                1065

<210> SEQ ID NO 92
<211> LENGTH: 4440
<212> TYPE: DNA
<213> ORGANISM: Artificial
<220> FEATURE:
<223> OTHER INFORMATION: Synthetic DNA sequence of GenBank accession
      NC_001798 region: 109875..114314

<400> SEQUENCE: 92
atggggacgg aagactgcga tcacgaaggg cggtcggttg cggctcccgt ggaggttacg      60
gcgctgtatg cgaccgacgg gtgcgttatc acctcctcgc tcgccctcct cacaaactgc    120
ctgctggggg ccgagccgtt gtatatattc agctacgacg cgtaccggtc cgatgcgccc    180
aatggcccca cgggcgcgcc caccgaacag gagaggttcg aggggagccg ggcgctctac    240
cgggatgcgg gggggctaaa tggcgattca tttcgggtga ccttttgttt attggggacg    300
gaagtgggcg tgacccacca cccgaaaggg cgcacccggc ccatgtttgt gtgccgcttc    360
gagcgagcgg acgacgtcgc cgtgctccaa gacgccctgg gccgcgggac cccattgctc    420
ccggcccacg tcacagcaac tctggacttg gaggcgacgt ttgcgctcca cgctaacatc    480
atcatggctc tcaccgtggc catcgtccac aacgcccccg cccgcatcgg cagcggcagc    540
accgcccccc tgtatgagcc cggcgaatcg atgcgctcgg tcgtcgggcg catgtccctg    600
gggcagcgcg gcctcaccac gctgttcgtg caccacgagg cgcgcgtgct gggggcgtac    660
cgccgggcgt attatgggag cgcccaaagc ccctttttggt ttctgagcaa attcggcccg    720
gacgaaaaga gcctggtgct ggccgctagg tactacctac tccaggctcc gcgcttgggg    780
ggcgccggag ccacgtacga tctgcaggcc gtgaaagaca tctgcgcgac ctacgcaatc    840
ccccacgacc cacgccccga cacccctcagt gccgcgtcct tgacctcgtt cgccgccatc    900
actcggttct gttgcacgag ccagtactcc cgcggggccg cggccgctgg gtttccgctg    960
tatgtggagc gccgcatcgc cgccgacgta cgcgagaccg cgcgctgga gaagttcatc   1020 gcccacgatc gcagctgcct cgcgcgtgtcc gaccgggaat tcattacgta catctacctg   1080

```
gcccactttg agtgcttcag ccccccgcgc ctggccacgc atctccgggc cgtgaccacc   1140
cacgacccca gccccgcggc cagcacggag cagccctcgc ccctgggtcg ggaggcggtg   1200
gaacagttct tccggcacgt gcgcgcccag ctgaacatcc gcgagtacgt aaagcaaaac   1260
gtcaccccca gggaaaccgc cctggcggga gacgcggccg ccgcctacct gcgcgcgcgc   1320
acgtatgccc cggcggccct cacgcccgcc cccgcgtact gcggggtcgc agactcgtcc   1380
accaaaatga tgggacgtct ggcggaagca gaaaggctcc tagtccccca cggctggccc   1440
gcgttcgcac caacaacccc cggggacgac gcgggggggcg gcactgccgc ccccagacc   1500 tgcggaatcg tcaagcgcct cctcaagctg gccgccacgg agcagcaggg cacgacgccc   1560
ccggcgatcg cggctctcat gcaggacgcg tcggtccaaa ccccctgcc cgtgtacagg    1620 attaccatgt ccccgaccgg ccaggcgttt gccgcggcgg cgcgggacga ctgggcccgc   1680
gtgacgcggg acgcgcgccc gccggaagcg accgtggtcg cggacgcggc ggcggcgccc   1740
gagcccggcc cgctcggccg gcggctcacg cgccgcattt gcgcccgggg ccccgcgctc   1800
cccccgggcg gcctggccgt cggggggcag atgtacgtga accgcaacga gatcttcaac   1860
gccgcgctgg ccgttacgaa catcatcctg gatctggaca tcgccctgaa ggagcccgtc   1920 cccttttcccc ggctccacga ggccctgggt cactttaggc gcggggcgct ggcggcggtt   1980
cagctgttgt ttcccgcggc ccgcgtagac cccgacgcct atccctgtta ttttttcaaa   2040
agcgcctgtc ggccccgcgc gccgcccgtc tgtgcgggcg acgggccctc ggccggtggc   2100
gacgacggcg acggggactg gttccccgac gccggtggtc ccggcgacga ggagtgggag   2160
gaggacacgg accccatgga cacgacccac ggcccctcc cggacgacga ggccgcgtac   2220
ctcgacctgc tacacgaaca gataccagcg gcgacgccca gcgaaccgga ctccgtcgtg   2280
tgttcctgcg ccgacaagat cgggctgcgc gtgtgcctac cggtccccgc cccgtacgtt   2340
gtgcacggct ccctgacgat gcgtggggtg gcgagggtga tccagcaggc ggtgctgttg   2400
gaccgcgact tcgtggaggc cgtagggagc cacgtaaaga acttttttgct gatcgatacg   2460 ggcgtgtacg cccacggcca cagcctgcgc ttgccgtatt tcgccaagat cggccccgac   2520
ggctccgcgt gcggccggtt attgcccgtc ttcgtgatcc cccccgcgtg cgaggacgtt   2580
ccggcgttcg tcgccgcgca cgccgacccg cggcgcttcc actttcacgc cccgcccatg   2640
ttttccgcgg ccccgcggga gatccgcgtc ctccacagcc tgggcgggga ctatgtcagc   2700
tttttcgaga agaaggcgtc gcgcaacgcc ctggagcact tgggcgacg cgagaccctg   2760 acggaggttc tgggccgcta cgatgtgcgg cccgacgccg gggagaccgt ggaggggttc   2820
gcgtcagaac tgctggggcg aatagtcgcg tgcatcgagg ctcactttcc cgagcacgcg   2880
cgggaatatc aggccgtgtc cgttcgccgg ccgtcatta aggacgactg ggtcctgctg   2940
cagctgatcc ccggccgcgg cgccctgaac caaagcctct cgtgtctgcg cttcaagcac   3000
ggcagggcaa gtcgcgcgac ggcccggacc tttctcgcgc tgagcgtcgg gaccaacaac   3060
cgcctatgcg cgtccctgtg tcagcagtgc tttgccacta aatgcgataa caaccgcctg   3120
cacacgctgt ttaccgtcga tgcgggcacg ccatgctcgc ggtccgctcc ctccagcacc   3180
tcacgaccgt catcttcata acggcctacg gcctcgtgct cgcgtggtac atcgtctttg   3240
gtgccagtcc gctccaccga tgtatttacg cggtgcgccc cgcggggcg cacaacgata   3300 ccgccctcgt gtggatgaag ataaaccaga cgctgttgtt tctgggcccg ccgaccgccc   3360
cccccggcgg ggcatggacc ccccacgccc gcgtctgcta cgccaatatc atcgaaggtc   3420
gggccgtgtc cctcccggcc atccccggcg ccatgagccg ccgggtcatg aacgtgcacg   3480
```

```
aggccgtaaa ctgcttggag gccctctggg acacccagat gcgcctggtg gtcgtcggtt    3540
ggtttctgta tctagcgttc gtcgcccttc accaacgacg atgcatgttc ggcgtcgtga    3600
gtcccgcgca cagcatggtg gccccggcga cctatctttt gaactacgcc ggccgcatag    3660
tgtcgagcgt gttcttgcaa taccoctaca cgaaaatcac ccgcctcctc tgcgagctat    3720
ccgttcaacg ccagaccctg gtgcagctgt tcgaggcgga tccggtcacc ttcttgtacc    3780 accgccggc cattggcgtc atcgtgggct gcgagctgct gctccgcttc gtggccctcg    3840
gtctcatcgt cggcaccgct ctcatctccc ggggcgcctg cgcgatcaca caccccctgt    3900
ttctaacaat caccacctgg tgtttcgtgt ccatcatcgc cctgacggag ctgtatttca    3960
tcctgcggcg gggctcggcc cccaaaaacg cggaaccagc ggccccagg gggcgctcca    4020 aagggtggtc gggcgtctgc gggcgctgct gttccatcat cctctccggt atcgccgtgc    4080
gcctgtgcta tatcgccgtc gtggccgggg tggtgctcgt ggcgcttcgc tacgaacagg    4140
agattcagcg gcgcctgttt gatctgtgac gtaacgcctc ttccgttgga agaggcggac    4200
ccagtcgccc atacaaatta aatacacgac ccgcctcggg cctacgcacc ctcgcacgtc    4260
gcatgcaaat taaaatcgtg cacagagccg atccggcctc gggtctgctt gcccctcccc    4320
cggcccagca caggcaggct cgtccgactt ccgcatacac cccaccctac cgcgtgcttc    4380 cgcaccccg cctacgcgtg tacgcgaagg cggacccaga cctgccgtat gctaattaaa    4440
```

<210> SEQ ID NO 93
<211> LENGTH: 411
<212> TYPE: PRT
<213> ORGANISM: Murine cytomegalovirus

<400> SEQUENCE: 93

```
Met Glu Gly Gly Arg Lys Val Arg Glu His Glu Pro Pro Thr Leu Ala
1               5                   10                  15

Phe Arg Leu Lys Ser Tyr Lys Thr Ala Ile Gln Gln Leu Arg Cys Val
                20                  25                  30

Val Arg Ser Leu Lys Glu Asn Thr Thr Val Ser Phe Leu Pro Thr Pro
            35                  40                  45

Ala Leu Ile Val Gln Thr Val Lys Asn Gln Phe Ile Ala Lys Ile Val
        50                  55                  60

Phe Asn Ser Ser Cys Leu Tyr Ile Thr Asp Lys Ser Phe Ser Ala Lys
65                  70                  75                  80

Thr Ile Asn Asn Ser Ile Pro Leu Leu Gly Asn Leu Met Tyr Met Thr
                85                  90                  95

Ser Ser Arg Asp Leu Thr Lys Phe Thr Val Gln Asp Thr Ser Asp Leu
                100                 105                 110

Ser Ala Lys Val Cys Met Ser Ala Pro Asp Tyr Asn Met Glu Phe Ser
            115                 120                 125

Ser Ala Cys Val His Asn Gln Asp Ile Ile Arg Glu Thr Gly Asp Ser
        130                 135                 140

Ala Ala Arg Val Asp Leu Asp Ser Ala Val Val Gly Glu Leu Ile Arg
145                 150                 155                 160

Trp Ile Ala Pro Asn Ile Arg Pro Lys Arg Asn Ser Lys Lys Gln Ser
                165                 170                 175

Thr Ser Ser Ser Thr Val Gln Ile Thr Leu His Ala Asn Pro Pro Thr
                180                 185                 190

Val Lys Phe Ser Leu Gly Cys Asn Ser Glu Leu Glu Phe Thr Ala Ser
            195                 200                 205
```

-continued

```
Asn Arg Ile Ala Phe His Glu Val Lys Asn Leu Arg Ile Thr Val Gln
    210                 215                 220

Ala Lys Asn Leu His Gln Ala Leu Cys Asn Cys Val Val Thr Lys Leu
225                 230                 235                 240

Ala Cys Thr Leu Arg Val Met Thr Asp His Glu Thr Met Leu Tyr Val
            245                 250                 255

Ala Ser Lys Asn Ala Asn Phe Thr Ile Glu Asn Phe Leu Ser Glu Glu
                260                 265                 270

Pro Phe Val Arg Gly Asp Val Gly Phe Asp Arg Met Pro Val Ala Asn
            275                 280                 285

Ser Asn Asn Tyr Gln Asn Ser Ser Ser Ala Gly Asp Asp Phe Ala
    290                 295                 300

Ala Cys Val Asp Gln Val Ile Asp Asn Cys Thr Lys Lys His Glu Arg
305                 310                 315                 320

Val Ser Arg Lys Ala Gly Gly Gly Gly Gly Gly Gly Gly Val Val
                325                 330                 335

Val Asn Asp Asp His Gln Gly Gly Gly Ser Gly Lys Asp Asn Lys
            340                 345                 350

Tyr Asp Gln His Lys Ile Thr Ser Phe Met Val Ser Lys Gly Ala Val
            355                 360                 365

Gly Gly Gly Ala Gly Gly Gly Ser Asp Arg Gly Gly Tyr Phe Asn
    370                 375                 380

Asp Thr Lys Glu Glu Ser Asp Ser Glu Asp Ser Val Thr Phe Glu Tyr
385                 390                 395                 400

Thr Pro Asn Thr Lys Lys Gln Lys Cys Ala Ala
                405                 410
```